(12) United States Patent
Feng et al.

(10) Patent No.: US 11,041,009 B2
(45) Date of Patent: Jun. 22, 2021

(54) GLUCOSE RESPONSIVE INSULIN COMPRISING A TRI-VALENT SUGAR CLUSTER FOR TREATMENT OF DIABETES

(71) Applicant: Merck Sharp & Dohme Corp., Rahway, NJ (US)

(72) Inventors: Danqing Feng, Green Brook, NJ (US); Pei Huo, Millburn, NJ (US); Ahmet Kekec, Hoboken, NJ (US); Songnian Lin, Holmdel, NJ (US); Christopher R. Moyes, Westfiled, NJ (US); Ravi Nargund, Skillman, NJ (US); Brenda Pipik, Edison, NJ (US); Dmitri A. Pissarnitski, Scotch Plains, NJ (US); Lin Yan, East Brunswick, NJ (US); Yuping Zhu, Basking Ridge, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/495,703

(22) PCT Filed: Mar. 19, 2018

(86) PCT No.: PCT/US2018/023052
§ 371 (c)(1),
(2) Date: Sep. 19, 2019

(87) PCT Pub. No.: WO2018/175272
PCT Pub. Date: Sep. 27, 2018

(65) Prior Publication Data
US 2020/0087375 A1    Mar. 19, 2020

Related U.S. Application Data

(60) Provisional application No. 62/475,252, filed on Mar. 23, 2017.

(51) Int. Cl.
*C07K 14/62* (2006.01)
*A61K 47/61* (2017.01)
*A61K 47/54* (2017.01)
*A61K 38/00* (2006.01)

(52) U.S. Cl.
CPC ............ *C07K 14/62* (2013.01); *A61K 47/549* (2017.08); *A61K 47/61* (2017.08); *A61K 38/00* (2013.01)

(58) Field of Classification Search
None
See application file for complete search history.

(56) References Cited

U.S. PATENT DOCUMENTS

| 4,145,410 A | 3/1979 | Sears |
| 4,348,387 A | 9/1982 | Brownlee et al. |
| 5,304,473 A | 4/1994 | Belagaje et al. |
| 5,830,506 A | 11/1998 | Taylor |
| 5,902,603 A | 5/1999 | Chen et al. |
| 6,410,053 B1 | 6/2002 | Taylor |
| 6,630,348 B1 | 10/2003 | Lee et al. |
| 7,105,314 B2 | 9/2006 | Kjeldsen |
| 9,050,370 B2 | 6/2015 | Zion et al. |
| 9,427,475 B2 * | 8/2016 | Lin ........................... A61P 3/10 |
| 2004/0202719 A1 | 10/2004 | Zion et al. |
| 2008/0057004 A1 | 3/2008 | Bell et al. |
| 2009/0170750 A1 | 7/2009 | Kjeldsen et al. |
| 2011/0301083 A1 | 12/2011 | Zion et al. |
| 2013/0131310 A1 | 5/2013 | Kane et al. |
| 2014/0256622 A1 | 9/2014 | Zion et al. |
| 2016/0251407 A1 | 9/2016 | Lin |
| 2016/0303244 A1 | 10/2016 | Lin |

FOREIGN PATENT DOCUMENTS

| WO | 1995016708 A1 | 6/1995 |
| WO | 9634882 A1 | 11/1996 |
| WO | 2005054291 A1 | 6/2005 |
| WO | 2006097521 A1 | 9/2006 |
| WO | 2007096332 A1 | 8/2007 |
| WO | 2007/104737 A1 | 9/2007 |
| WO | 2007/104738 A2 | 9/2007 |
| WO | 2007104734 A1 | 9/2007 |
| WO | 2007104736 A2 | 9/2007 |
| WO | 2009099763 A1 | 8/2009 |
| WO | 2009132129 A2 | 10/2009 |
| WO | 2010080606 A1 | 7/2010 |
| WO | 2010080607 A1 | 7/2010 |
| WO | 2010080609 A1 | 7/2010 |

(Continued)

OTHER PUBLICATIONS

Han, Zhenfu, Structure-Based Drug Design and Optimization of Mannoside Bacterial FimH Antagonists, Journal of Medicinal Chemistry, 2010, 4779-4792, 53.
Hayes, Wayne, One-pot synthesis of multivalent arrays of mannose mono- and disaccharides, Tetrahedron, 2003, 7983-7996, 59.
Hietanen, Ari, Applying Biocatalysis to the Synthesis of Diastereomerically Enriched Cyanohydrin Mannosides, Eur. J. Org. Chem., 2010, 6974-6980, 36.
John E. Gerich M.D., Novel Insulins: Expanding Options in Diabetes Management, The American Journal of Medicine, 2002, 308-316, vol. 113.

(Continued)

*Primary Examiner* — Dale R Miller
(74) *Attorney, Agent, or Firm* — Julie M. Lake; Catherine D. Fitch

(57) ABSTRACT

An insulin conjugate comprising or consisting of a tri-valent sugar cluster is described. In particular aspects, the insulin conjugate displays a pharmacokinetic (PK) and/or pharmacodynamic (PD) profile that is responsive to the systemic concentrations of a saccharide such as glucose or alpha-methylmannose even when administered to a subject in need thereof in the absence of an exogenous multivalent saccharide-binding molecule such as Con A.

6 Claims, 11 Drawing Sheets

Specification includes a Sequence Listing.

(56) References Cited

FOREIGN PATENT DOCUMENTS

| WO | 2010088294 A1 | 8/2010 |
|----|---------------|--------|
| WO | 2015051052 A2 | 4/2015 |

OTHER PUBLICATIONS

Kristensen et al., A single-chain insulin-like growth factor I/insulin hybrid binds with high affinity to the insulin receptor, Biochem. J., 1995, pp. 981-986, 305.
Micklitsch, Christopher M., Unnatural multidentate metal ligating alpha-amino acids, Tetrahedron Letters, 2006, 6277-6280, 47.
Miroslav Baudys et al., Extending Insulin Action in vivo by Conjugation to Carboxymethyl Dextran, Bioconjugate Chem., 1998, 176-183, 9.
Robert Sardzik et al., Preparation of Aminoethyl Glycosides for Glycoconjugation, Beilstein Journal of Organic Chemistry, 2010, 699-703, 6.
Stephen Crotty et al., The New Insulins, Pediatric Emergency Care, 2007, 903-908, 23(12).
R. Yang et al., A glucose-responsive insulin therapy protects animals again hypoglycemia, JCI Insight, 2018, 1-14, 3(1).

* cited by examiner

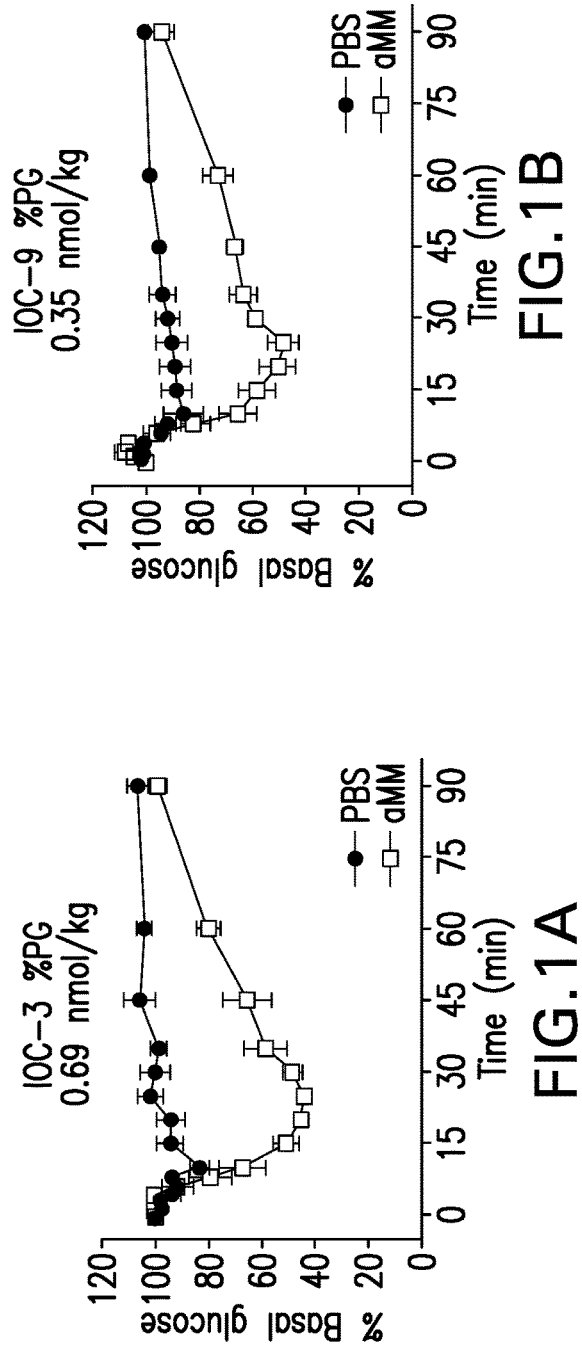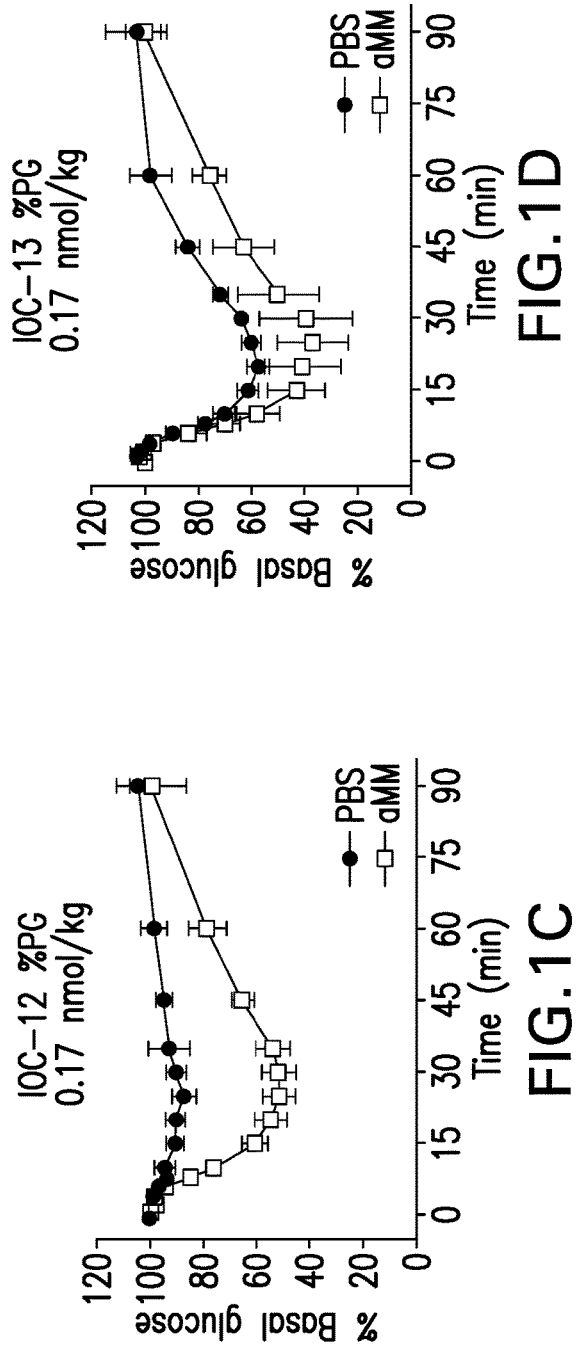

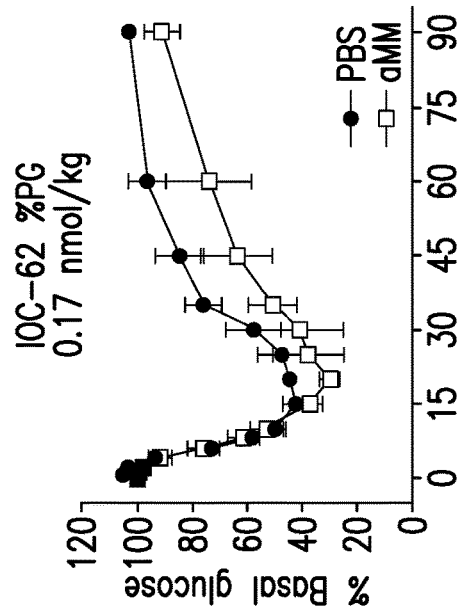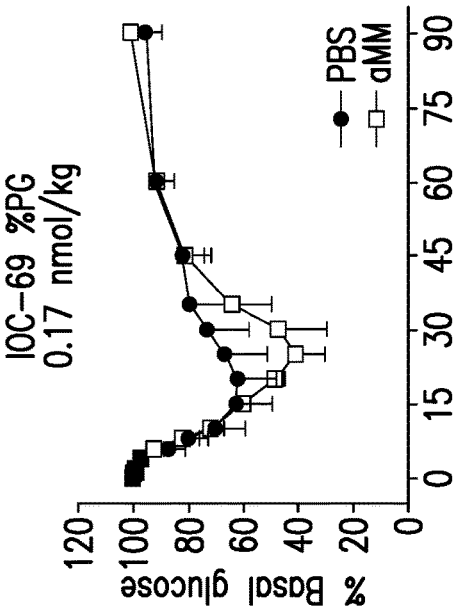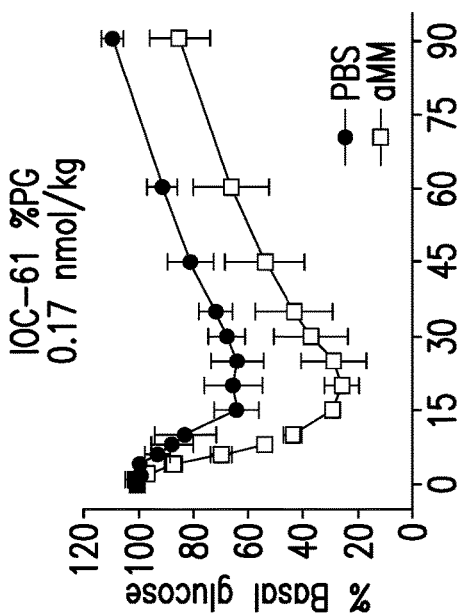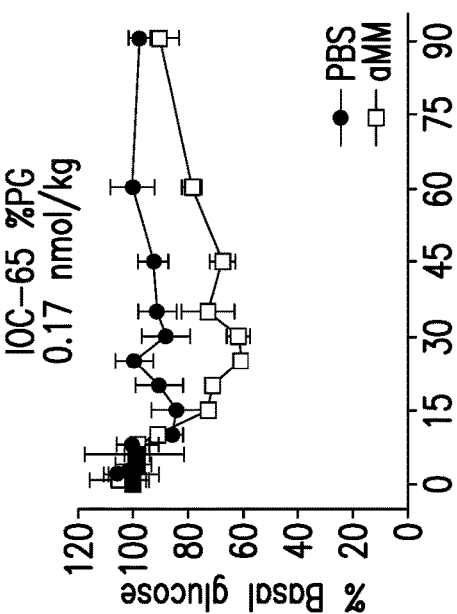

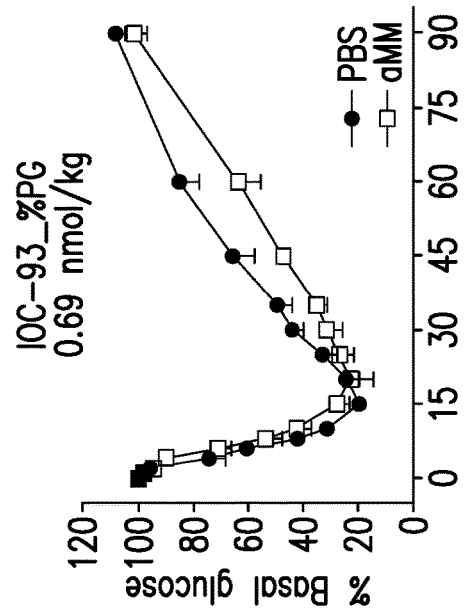
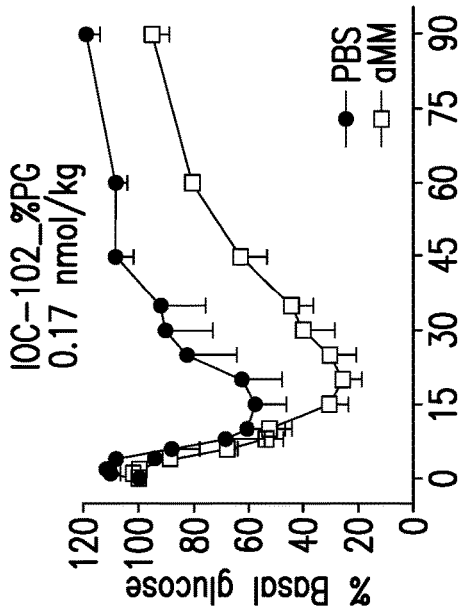
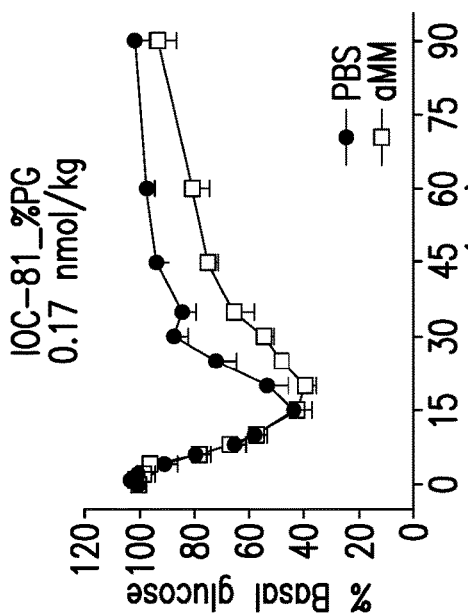
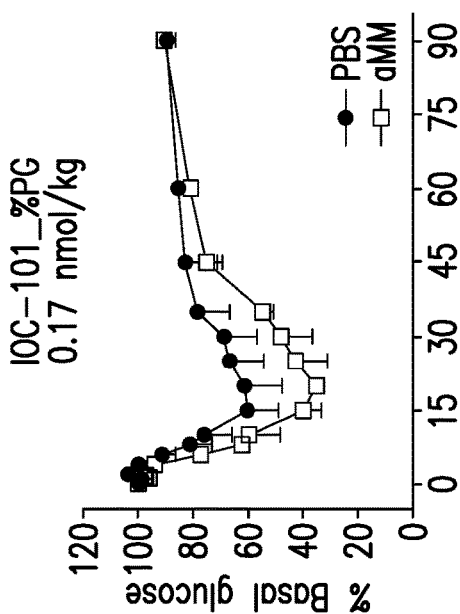

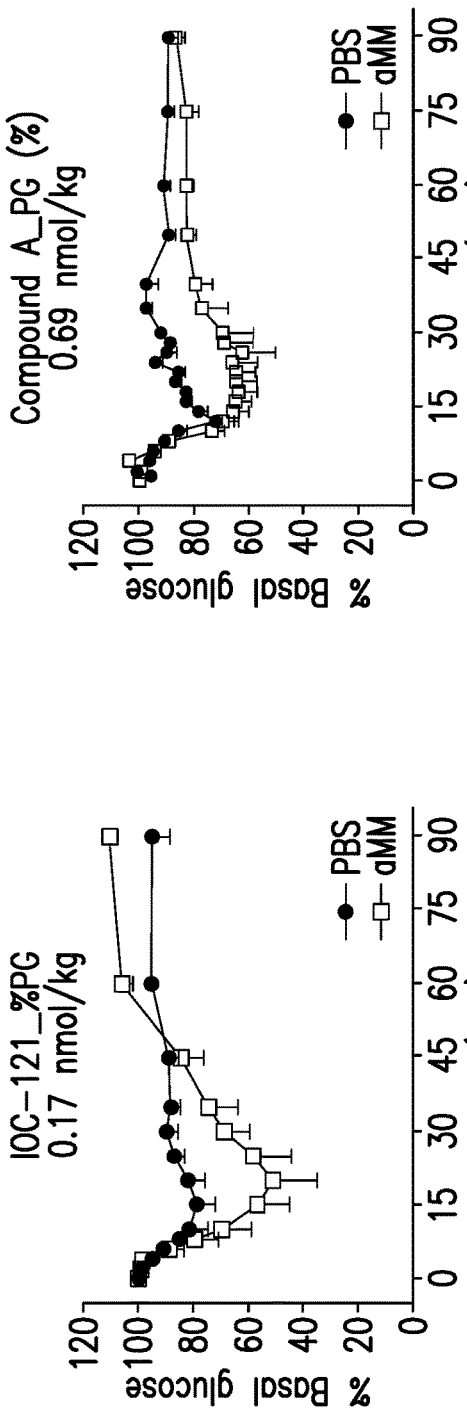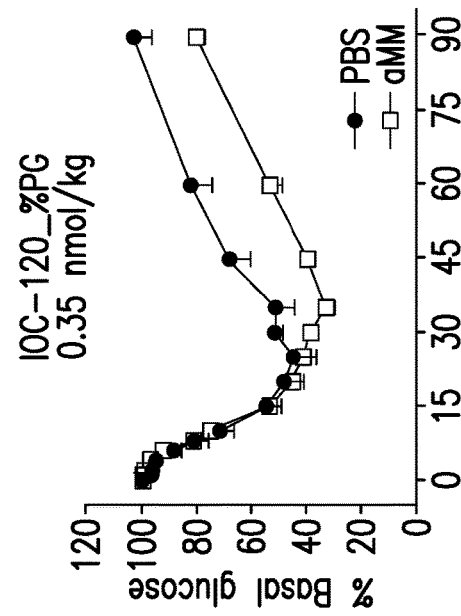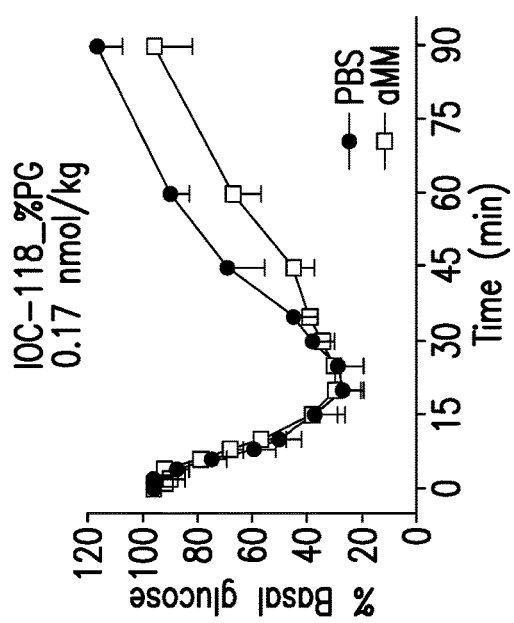
FIG. 11A  FIG. 11B  FIG. 11C  FIG. 11D

SEQUENCE LISTING

```
<160> NUMBER OF SEQ ID NOS: 10

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2
```

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 30
<212> TYPE: PRT
<213> ORGANISM: artificial sequence
<220> FEATURE:
<223> OTHER INFORMATION: Insulin lispro B-chain

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 4
<211> LENGTH: 30
<212> TYPE: PRT
<213> ORGANISM: artificial sequence
<220> FEATURE:
<223> OTHER INFORMATION: Insulin aspart B-chain

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 5
<211> LENGTH: 30
<212> TYPE: PRT
<213> ORGANISM: artificial sequence
<220> FEATURE:
<223> OTHER INFORMATION: Insulin glulisine B-chain

<400> SEQUENCE: 5

Phe Val Lys Gln His Leu Cys Gly Ser His Leu Val Glu Ala Leu Tyr
1               5                   10                  15

Leu Val Cys Gly Glu Arg Gly Phe Phe Tyr Thr Asn Lys Thr
            20                  25                  30

<210> SEQ ID NO 6
<211> LENGTH: 21
<212> TYPE: PRT
<213> ORGANISM: artificial sequence
<220> FEATURE:
<223> OTHER INFORMATION: Insulin glargine A-chain

<400> SEQUENCE: 6

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 7
<211> LENGTH: 32
<212> TYPE: PRT
<213> ORGANISM: artificial sequence
<220> FEATURE:
<223> OTHER INFORMATION: Insulin glargine B-chain

<400> SEQUENCE: 7
```

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 8
<211> LENGTH: 21
<212> TYPE: PRT
<213> ORGANISM: artificial sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is threonine or histidine
<220> FEATURE:
<221> NAME/KEY: MISC_FEATURE
<222> LOCATION: (21)..(21)
<223> OTHER INFORMATION: Xaa at position 21 is asparagine, glycine,
      alanine, glutamine, glutamate, threonine, or serine
<220> FEATURE:
<221> NAME/KEY: MISC_FEATURE
<222> LOCATION: (21)..(21)
<223> OTHER INFORMATION: Xaa is asparagine, glycine, alanine, glutamine,
      glutamate, threonine, or serine

<400> SEQUENCE: 8

Gly Ile Val Glu Gln Cys Cys Xaa Ser Ile Cys Ser Leu Tyr Gln Leu
1               5                   10                  15

Glu Asn Tyr Cys Xaa
            20

<210> SEQ ID NO 9
<211> LENGTH: 21
<212> TYPE: PRT
<213> ORGANISM: artificial sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (6)..(6)
<223> OTHER INFORMATION: Xaa is histidine, aspartic acid, glutamic acid,
      homocysteic acid or cysteic acid

<400> SEQUENCE: 9

Xaa Leu Cys Gly Xaa Xaa Leu Val Glu Ala Leu Tyr Leu Val Cys Gly
1               5                   10                  15

Glu Arg Gly Phe Phe
            20

<210> SEQ ID NO 10
<211> LENGTH: 32
<212> TYPE: PRT
<213> ORGANISM: artificial sequence
<220> FEATURE:
<223> OTHER INFORMATION: Analog of the insulin B chain
<220> FEATURE:
```

```
<221> NAME/KEY: MISC_FEATURE
<222> LOCATION: (1)..(1)
<223> OTHER INFORMATION: Xaa at position 1 is phenylalanine or
      desamino-phenylalanine
<220> FEATURE:
<221> NAME/KEY: MISC_FEATURE
<222> LOCATION: (5)..(5)
<223> OTHER INFORMATION: Xaa at position 5 is histidine and threonine
<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa is histidine, aspartic acid, glutamic acid,
      homocysteic acid or cysteic acid
<220> FEATURE:
<221> NAME/KEY: MISC_FEATURE
<222> LOCATION: (28)..(29)
<223> OTHER INFORMATION: Xaa for position 28 and Xaa for position 29 are
      selected from aspartate-lysine, lysine-proline, and a
      proline-lysine, respectively
<220> FEATURE:
<221> NAME/KEY: MISC_FEATURE
<222> LOCATION: (30)..(30)
<223> OTHER INFORMATION: Xaa is threonine or alanine
<220> FEATURE:
<221> NAME/KEY: MISC_FEATURE
<222> LOCATION: (31)..(32)
<223> OTHER INFORMATION: Xaa at positions 31-32 are either each arginine
      or each absent when position 30 is threonine

<400> SEQUENCE: 10

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr Xaa Xaa Xaa Xaa Xaa
            20                  25                  30
```

GLUCOSE RESPONSIVE INSULIN COMPRISING A TRI-VALENT SUGAR CLUSTER FOR TREATMENT OF DIABETES

CROSS-REFERENCE TO RELATED APPLICATIONS

This application is a National Stage application of International Patent Application No. PCT/US2018/023052, filed Mar. 19, 2018, which claims priority to U.S. Provisional Patent Application No. 62/475,252, filed Mar. 23, 2017.

FIELD OF THE INVENTION

The present invention relates to an insulin conjugate comprising or consisting of a tri-valent sugar cluster. In particular aspects, the insulin conjugate that displays a pharmacokinetic (PK) and/or pharmacodynamic (PD) profile that is responsive to the systemic concentrations of a saccharide such as glucose or alpha-methylmannose even when administered to a subject in need thereof in the absence of an exogenous multivalent saccharide-binding molecule such as Con A.

BACKGROUND OF THE INVENTION

The majority of "controlled-release" drug delivery systems known in the prior art (e.g., U.S. Pat. No. 4,145,410 to Sears, which describes drug release from capsules that are enzymatically labile) are incapable of providing drugs to a patient at intervals and concentrations which are in direct proportion to the amount of a molecular indicator (e.g., a metabolite) present in the human body. The drugs in these prior art systems are thus not literally "controlled," but simply provided in a slow release format which is independent of external or internal factors. The treatment of diabetes mellitus with injectable insulin is a well-known and studied example where uncontrolled, slow release of insulin is undesirable. In fact, it is apparent that the simple replacement of the hormone is not sufficient to prevent the pathological sequelae associated with this disease. The development of these sequelae is believed to reflect an inability to provide exogenous insulin proportional to varying blood glucose concentrations experienced by the patient. To solve this problem several biological and bioengineering approaches to develop a more physiological insulin delivery system have been suggested (e.g., see U.S. Pat. No. 4,348,387 to Brownlee et al.; U.S. Pat. Nos. 5,830,506, 5,902,603, and 6,410,053 to Taylor et al. and U.S. Patent Application Publication No. 2004-0202719 to Zion et al.).

Each of these systems relies on the combination of a multivalent glucose binding molecule (e.g., the lectin Con A) and a sugar based component that is reversibly bound by the multivalent glucose binding molecule. Unfortunately, Con A and many of the other readily available lectins have the potential to stimulate lymphocyte proliferation. By binding to carbohydrate receptors on the surfaces of particular types of lymphocytes, these so-called "mitogenic" lectins can potentially induce the mitosis of lymphocytes and thereby cause them to proliferate. Most mitogenic lectins including Con A are selective T-cell mitogens. A few lectins are less selective and stimulate both T-cells and B-cells. Local or systemic in vivo exposure to mitogenic lectins can result in inflammation, cytotoxicity, macrophage digestion, and allergic reactions including anaphylaxis. In addition, plant lectins are known to be particularly immunogenic, giving rise to the production of high titers of anti-lectin specific antibodies. It will be appreciated that mitogenic lectins cannot therefore be used in their native form for in vivo methods and devices unless great care is taken to prevent their release. For example, in U.S. Pat. No. 5,830,506, Taylor highlights the toxic risks that are involved in using Con A and emphasizes the importance and difficulty of containing Con A within a drug delivery device that also requires glucose and insulin molecules to diffuse freely in and out of the device. The risks and difficulties that are involved with these and other in vivo uses of lectins could be significantly diminished if an alternative controlled drug delivery system could be provided that did not require lectins.

SUMMARY OF THE INVENTION

The present invention provides insulin conjugates comprising a tri-valent sugar cluster. These insulin conjugates may display a pharmacokinetic (PK) and/or pharmacodynamic (PD) profile that is responsive to the systemic concentrations of a saccharide such as glucose or alpha-methylmannose when administered to a subject in need thereof in the absence of an exogenous multivalent saccharide-binding molecule such as Con A. In general, the conjugates comprise an insulin or insulin analog molecule covalently attached at its A1, B1, B29, or B28 amino acid to a linker having a tri-valent sugar cluster thereon.

In particular embodiments, a conjugate may have a polydispersity index of one and a MW of less than about 20,000 Da. In particular embodiments, the conjugate is long acting (i.e., exhibits a PK profile that is more sustained than soluble recombinant human insulin (RHI)).

The conjugates disclosed herein may display a pharmacodynamic (PD) or pharmacokinetic (PK) profile that is sensitive to the serum concentration of a serum saccharide when administered to a subject in need thereof in the absence of an exogenous saccharide binding molecule. In particular aspects, the serum saccharide is glucose or alpha-methylmannose. In further aspects, the conjugate binds an endogenous saccharide binding molecule at a serum glucose concentration of 60 or 70 mg/dL or less when administered to a subject in need thereof. The binding of the conjugate to the endogenous saccharide binding molecule is sensitive to the serum concentration of the serum saccharide. In a further aspect, the conjugate is capable of binding the insulin receptor at a serum saccharide concentration greater than 60, 70, 80, 90, or 100 mg/dL. At serum saccharide concentration at 60 or 70 mg/dL, the conjugate preferentially binds the endogenous saccharide binding molecule over the insulin receptor, and, as the serum concentration of the serum saccharide increases from 60 or 70 mg/dL, the binding of the conjugate to the endogenous saccharide binding molecule decreases, and the binding of the conjugate to the insulin receptor increases.

The present invention provides a conjugate comprising an insulin or insulin analog molecule covalently attached to at least one tri-valent sugar cluster wherein the tri-valent sugar cluster is provided by a tri-dentate linker having three arms wherein each arm of the tri-dentate linker is independently covalently linked to a ligand comprising or consisting of a saccharide such as a monosaccharide, bisaccharide, trisaccharide, tetrasaccharide, or branched trisaccharide, with the proviso that the conjugate does not have the structure of IOC-212, IOC-213, IOC-224 or Compound A or a structure selected from the group consisting of

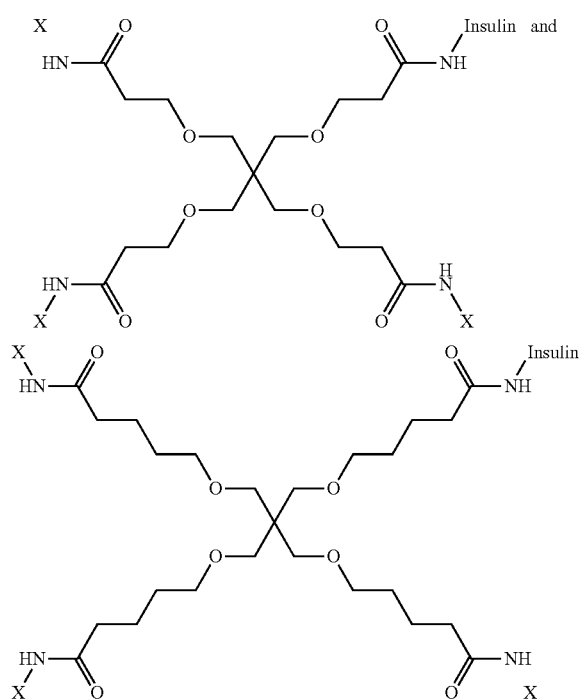

wherein each X is independently a ligand comprising or consisting of a monosaccharide, bisaccharide, trisaccharide, tetrasaccharide, or branched trisaccharide.

In particular embodiments of the conjugate, the conjugate comprises an insulin or insulin analog molecule conjugated to at least two tri-valent sugar clusters. In a further embodiment, the conjugate comprises an insulin or insulin analog molecule conjugated to at least three tri-valent sugar clusters.

The present invention provides a conjugate comprising an insulin or insulin analog molecule covalently attached to one tri-valent sugar cluster wherein the tri-valent sugar cluster is provided by a tri-dentate linker having three arms wherein each arm of the tri-dentate linker is independently covalently linked to a ligand comprising or consisting of a saccharide such as a monosaccharide, bisaccharide, trisaccharide, tetrasaccharide, or branched trisaccharide, with the proviso that the conjugate does not have the structure of IOC-212, IOC-213, IOC-224 or Compound A or a structure selected from the group consisting of

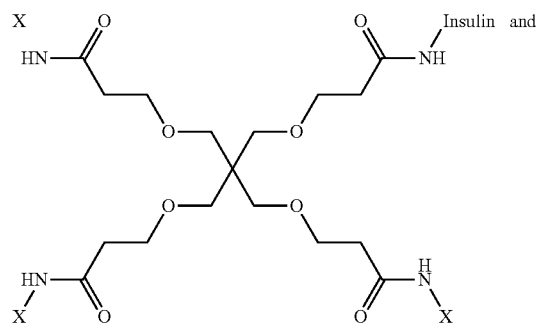

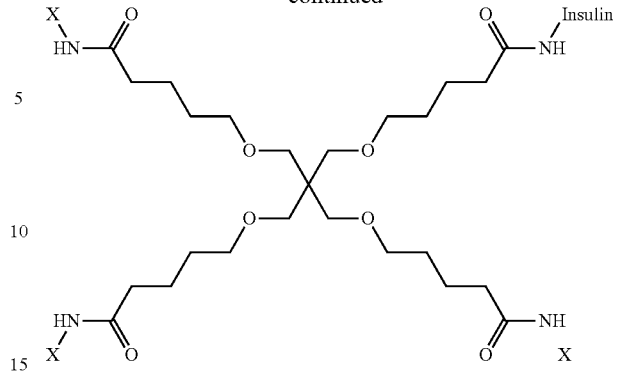

wherein each X is independently a ligand comprising or consisting of a monosaccharide, bisaccharide, trisaccharide, tetrasaccharide, or branched trisaccharide.

The present invention provides a conjugate comprising an insulin or insulin analog molecule covalently attached to two tri-valent sugar clusters wherein each tri-valent sugar cluster is provided by a tri-dentate linker having three arms wherein each arm of the tri-dentate linker is independently covalently linked to a ligand comprising or consisting of a saccharide such as a monosaccharide, bisaccharide, trisaccharide, tetrasaccharide, or branched trisaccharide, with the proviso that the conjugate does not have the structure of IOC-212, IOC-213, IOC-224 or Compound A or a structure selected from the group consisting of

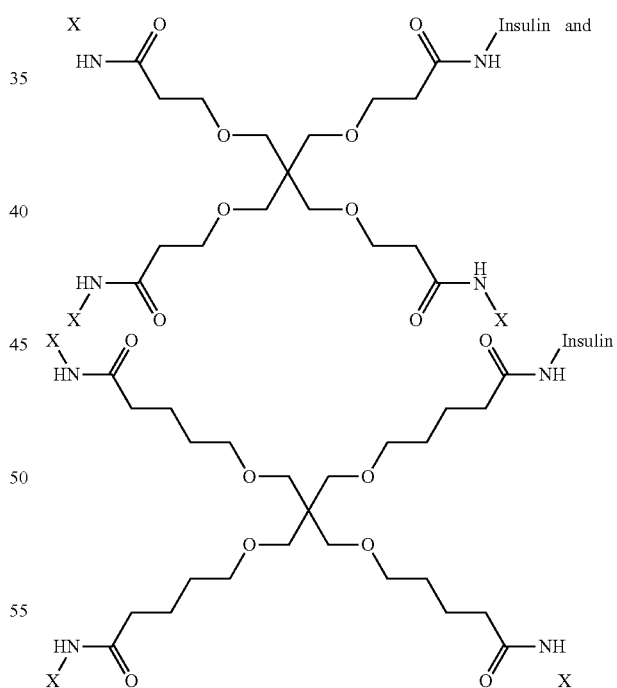

wherein each X is independently a ligand comprising or consisting of a monosaccharide, bisaccharide, trisaccharide, tetrasaccharide, or branched trisaccharide.

The present invention provides a conjugate comprising an insulin or insulin analog molecule covalently attached to three tri-valent sugar clusters wherein each tri-valent sugar cluster is provided by a tri-dentate linker having three arms wherein each arm of the tri-dentate linker is independently covalently linked to a ligand comprising or consisting of a saccharide such as a monosaccharide, bisaccharide, trisaccharide, tetrasaccharide, or branched trisaccharide, with the proviso that the conjugate does not have the structure of IOC-212, IOC-213, IOC-224 or Compound A or a structure selected from the group consisting of

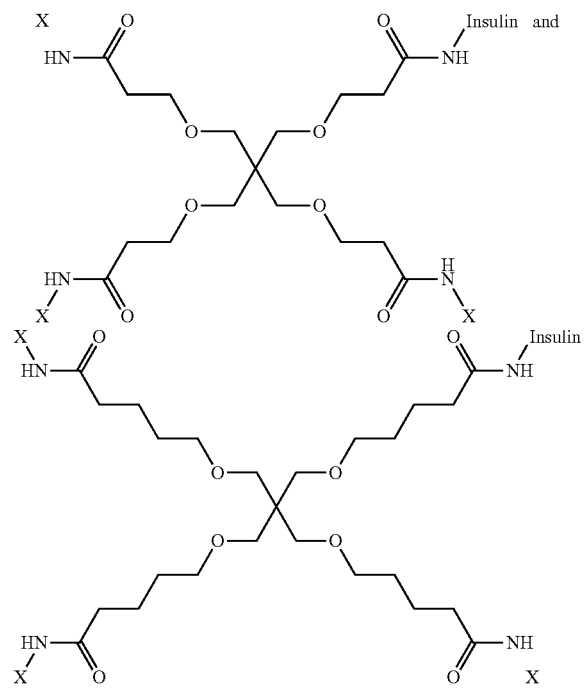

wherein each X is independently a ligand comprising or consisting of a monosaccharide, bisaccharide, trisaccharide, tetrasaccharide, or branched trisaccharide.

In particular embodiments of the conjugate, the ligand comprises or consists of a saccharide selected from the group consisting of fucose, mannose, glucosamine, glucose, bimannose, trimannose, tetramannose, or branched trimannose.

In particular embodiments, the ligand comprises or consists of a saccharide and ethyl group. In particular embodiments, the saccharide and amine group are separated by a $C_1$-$C_6$ alkyl group, e.g., a $C_1$-$C_3$ alkyl group.

In particular embodiments, the ligand comprises or consists of a saccharide selected from the group consisting of aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF). In particular embodiments, the saccharide is of the "D" configuration and in other embodiments, the saccharide is of the "L" configuration.

In particular embodiments of the conjugate, the tri-valent sugar cluster is covalently linked to the amino acid at position A1 of the insulin or insulin analog molecule; position B1 of the insulin or insulin analog molecule; position B29 of the insulin or insulin molecule; position B28 of the insulin analog molecule; or position B3 of the insulin analog molecule.

In particular embodiments of the conjugate, the insulin analog is insulin lispro, insulin glargine, insulin aspart, insulin detemir, or insulin glulisine.

In particular embodiments of the conjugate, the conjugate displays a pharmacodynamic (PD) and/or pharmacokinetic (PK) profile that is sensitive to the serum concentration of a serum saccharide when administered to a subject in need thereof in the absence of an exogenous saccharide binding molecule.

In particular embodiments of the conjugate, the serum saccharide is glucose or alpha-methylmannose.

In particular embodiments of the conjugate, the conjugate binds an endogenous saccharide binding molecule at a serum glucose concentration of 60 mg/dL or less when administered to a subject in need thereof.

In particular embodiments of the conjugate, the endogenous saccharide binding molecule is human mannose receptor 1.

In particular embodiments of the conjugate, the conjugate has the general formula (I):

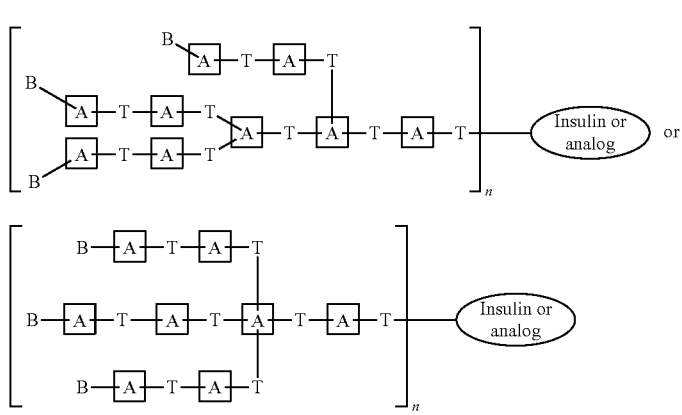

wherein:

each occurrence of (A−T)

represents a potential repeat within a branch of the conjugate;

(ii) each occurrence of A is independently a covalent bond, a carbon atom, a heteroatom, or an optionally substituted group selected from the group consisting of acyl, aliphatic, heteroaliphatic, aryl, heteroaryl, and heterocyclic;

(iii) each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;

(iv) each occurrence of R is independently hydrogen, a suitable protecting group, or an acyl moiety, arylalkyl moiety, aliphatic moiety, aryl moiety, heteroaryl moiety, or heteroaliphatic moiety;

(v) -B is -T-$L^B$-X, wherein each occurrence of X is independently the ligand and each occurrence of $L^B$ is independently a covalent bond or a group derived from the covalent conjugation of a T with an X; and, (vi) n is 1, 2, or 3.

In further embodiments of the conjugate, the conjugate comprises or consists of the structure of conjugate I wherein the insulin or onsulin analog is conjugated to a tri-valent linker selected from the group consisting of

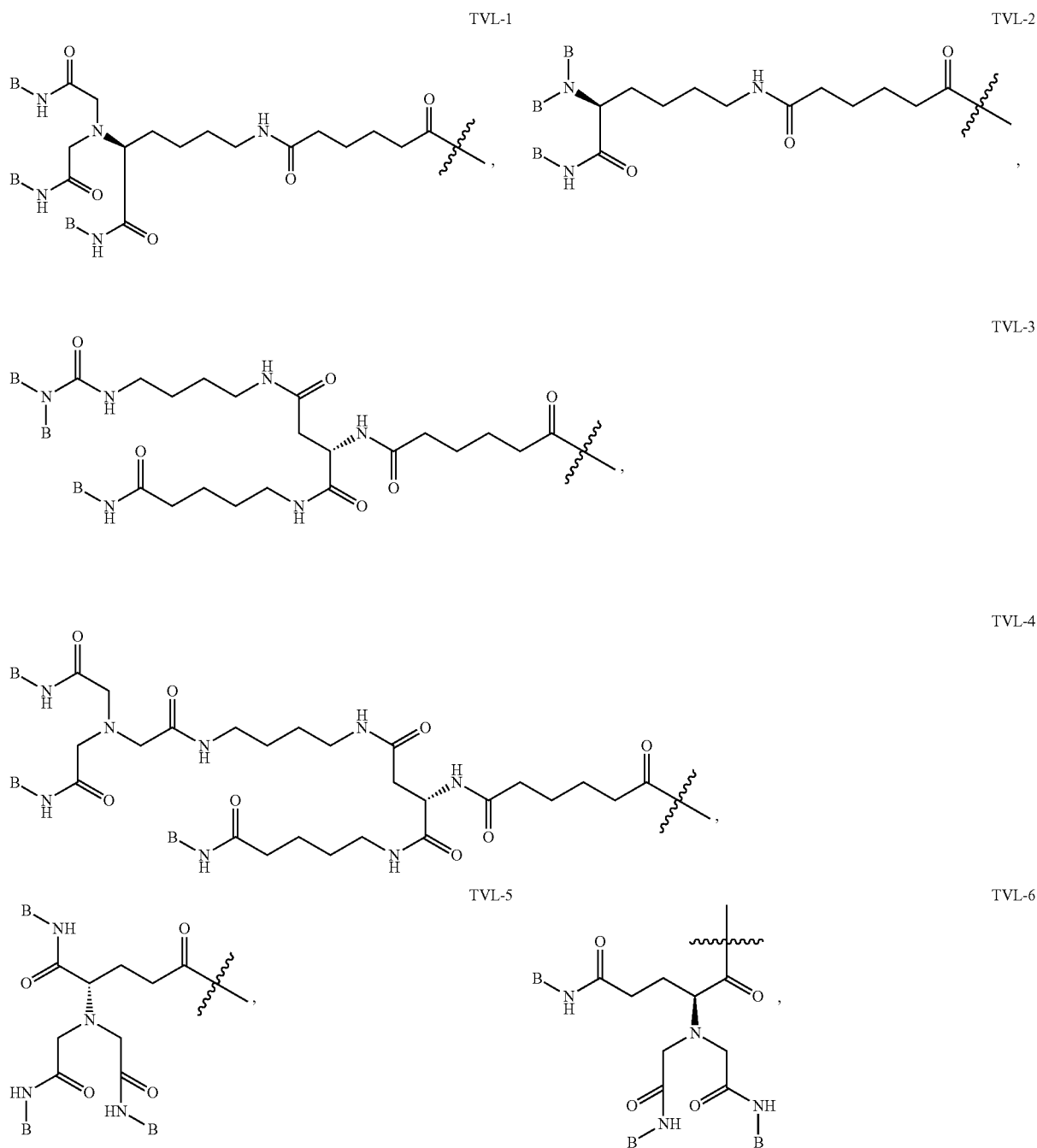

TVL-7
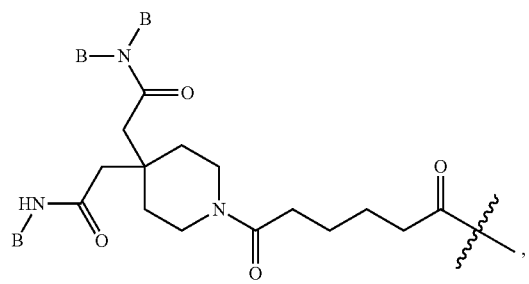
TVL-8
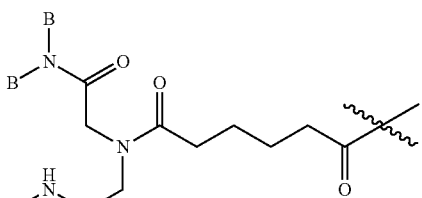
TVL-9
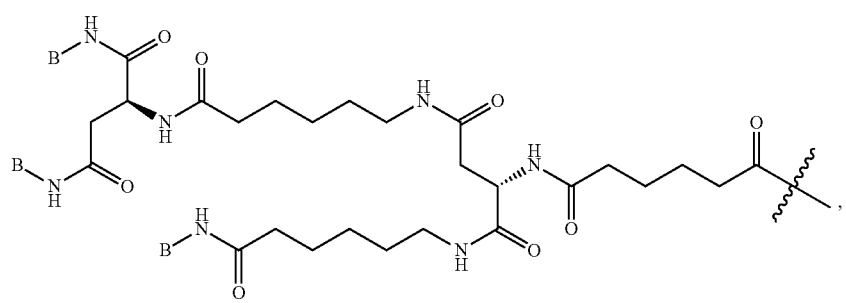
TVL-10
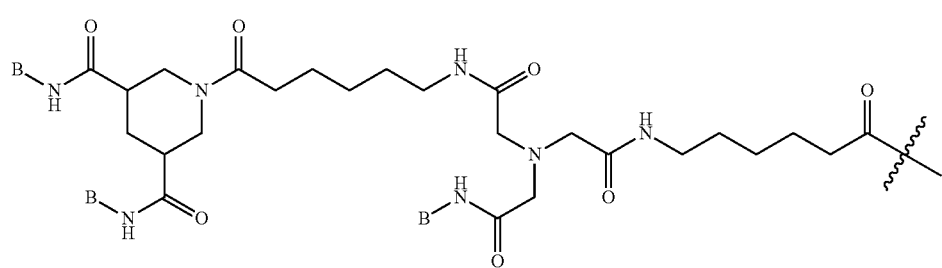
TVL-11
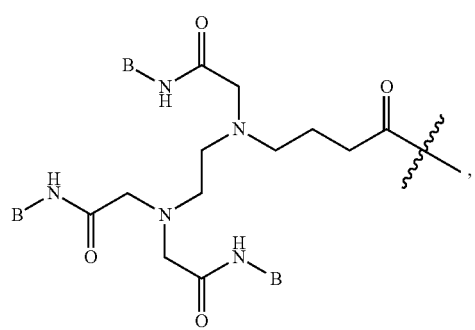
TVL-12
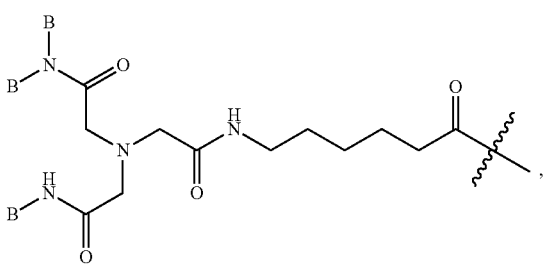
TVL-13
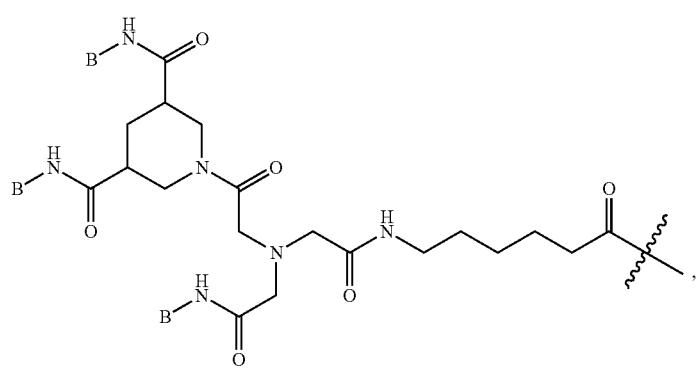

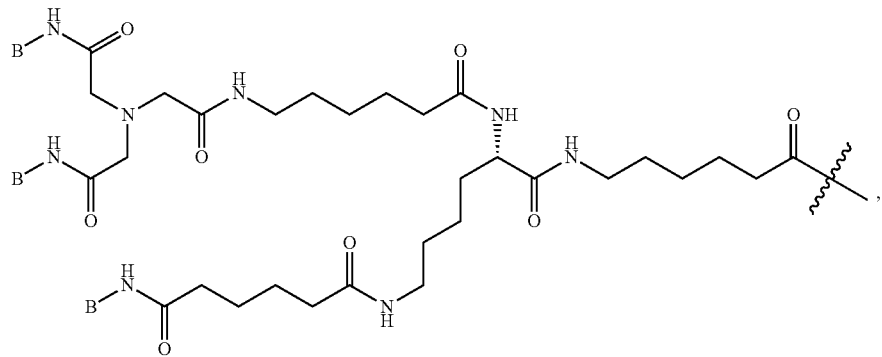
TVL-14
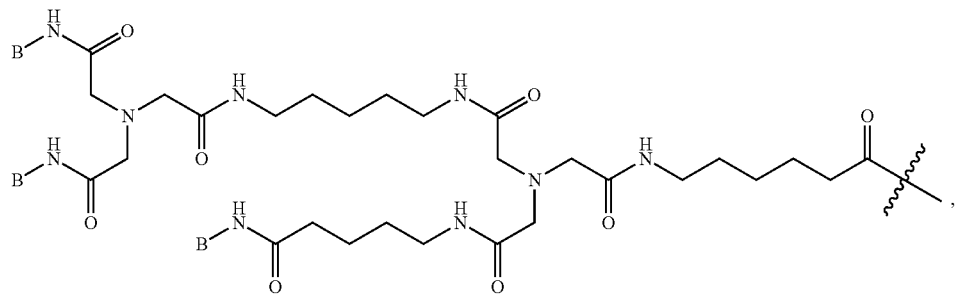
TVL-15
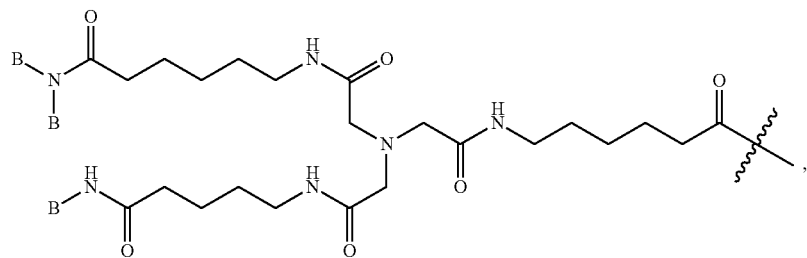
TVL-16
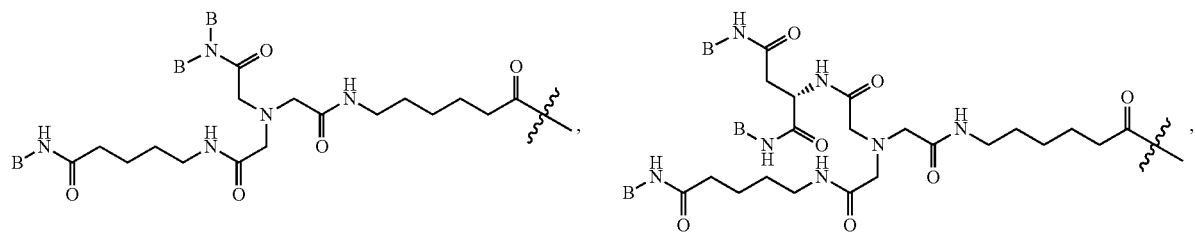
TVL-17, TVL-18
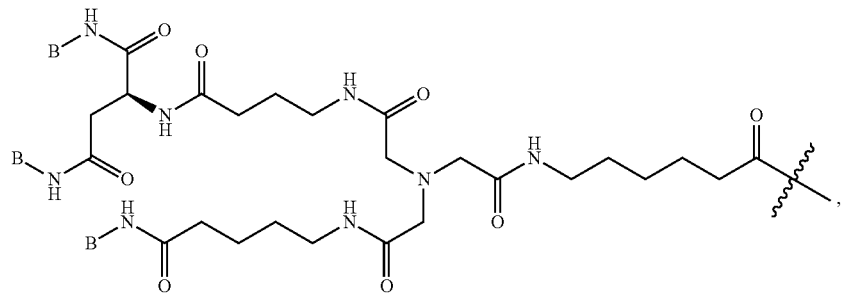
TVL-19

-continued

TVL-20
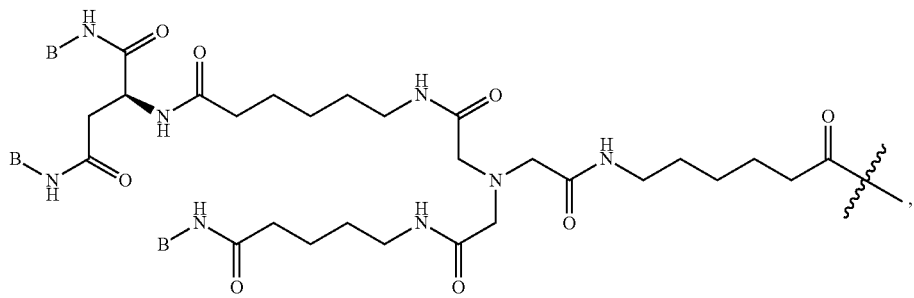

TVL-21
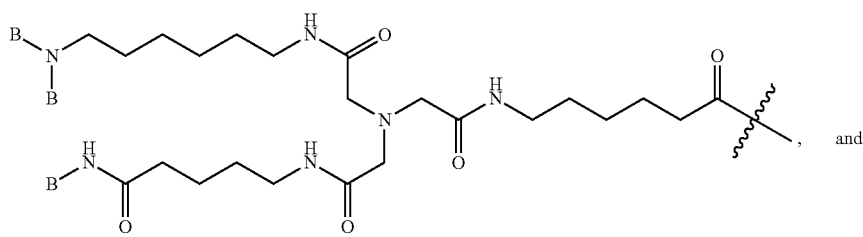
and

TVL-22
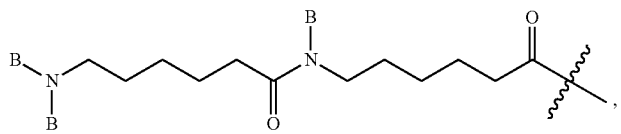

or the conjugate comprises the structure of conjugate II wherein the insulin or insulin analog is conjugated to a tri-valent linker selected from the group consisting of TVL-23
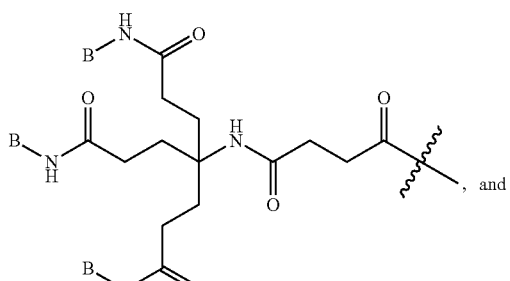
and TVL-24
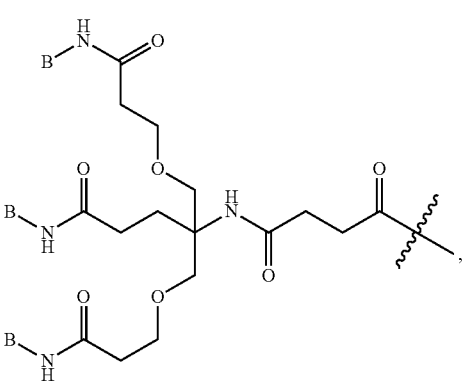

wherein the wavy line indicates the bond between the proximal end of the linker arm and amino acid on the insulin or insulin analog and wherein each B is independently -T-$L^B$-X, wherein each occurrence of X is independently the ligand and each occurrence of $L^B$ is independently a covalent bond or a group derived from the covalent conjugation of a T with an X.

The present invention further provides a conjugate comprising an insulin or insulin analog is conjugated to a tri-valent sugar cluster comprises a structure selected from the group consisting of ML-1, ML-2, ML-3, ML-4, ML-5, ML-6, ML-7, ML-8, ML-9, ML-10, ML-11, ML-12, ML-13, ML-14, ML-15, ML-16, ML-17, ML-18, ML-19, ML-20, ML-21, ML-22, ML-23, ML-24, ML-25, ML-26, ML-27, ML-28, ML-29, ML-30, ML-31, ML-32, ML-33, ML-34, ML-35, ML-36, ML-37, ML-38, ML-39, ML-40, ML-41, ML-42, ML-43, ML-44, ML-45, ML-46, ML-47, ML-48, ML-49, ML-50, ML-51, ML-52, ML-53, ML-54, ML-55, ML-56, ML-57, ML-58, ML-59, ML-60, ML-61, ML-62, ML-63, and ML-64.

In particular embodiments of the conjugate, the conjugate is selected from the group consisting of IOC-1, IOC-2, IOC-3, IOC-4, IOC-5, IOC-6, IOC-7, IOC-8, IOC-9, IOC-10, IOC-11, IOC-12, IOC-13, IOC-14, IOC-15, IOC-16, IOC-17, IOC-18, IOC-19, IOC-20, IOC-21, IOC-22, IOC-23, IOC-24, IOC-25, IOC-26, IOC-27, IOC-28, IOC-29, IOC-30, IOC-31, IOC-32, IOC-33, IOC-34, IOC-35, IOC-36, IOC-37, IOC-38, IOC-39, IOC-40, IOC-41, IOC-42, IOC-43, IOC-44, IOC-45, IOC-46, IOC-47, IOC-48, IOC-49, IOC-50, IOC-51, IOC-52, IOC-53, IOC-54, IOC-55, IOC-56, IOC-57, IOC-58, IOC-59, IOC-60, IOC-61, IOC-62, IOC-63, IOC-64, IOC-65, IOC-66, IOC-67, IOC-68, IOC-69, IOC-70, IOC-71, IOC-72, IOC-73, IOC-74, IOC-75, IOC-76, IOC-77, IOC-78, IOC-79, IOC-80, IOC-81, IOC-82, IOC-83, IOC-84, IOC-85, IOC-86, IOC-87, IOC-88, IOC-89, IOC-90, IOC-91, IOC-92, IOC-93, IOC-94, IOC-95, IOC-96, IOC-97, IOC-98, IOC-99, IOC-100, IOC-101, IOC-102, IOC-103, IOC-104, IOC-105, IOC-106, IOC-107, IOC-108, IOC-109, IOC-110, IOC-111, IOC-112, IOC-113, IOC-114, IOC-115, IOC-116, IOC-117, IOC-118, IOC-119, IOC-120, and IOC-121.

The present invention provides a composition comprising an insulin or insulin analog molecule covalently attached to at least one tri-valent sugar cluster wherein the tri-valent sugar cluster is provided by a tri-dentate linker having three arms wherein each arm of the tri-dentate linker is independently covalently linked to a ligand comprising or consisting of a monosaccharide, bisaccharide, trisaccharide, tetrasaccharide, or branched trisaccharide, with the proviso that the conjugate does not have the structure of IOC-212, IOC-213, IOC-224 or Compound A or a structure selected from the group consisting of

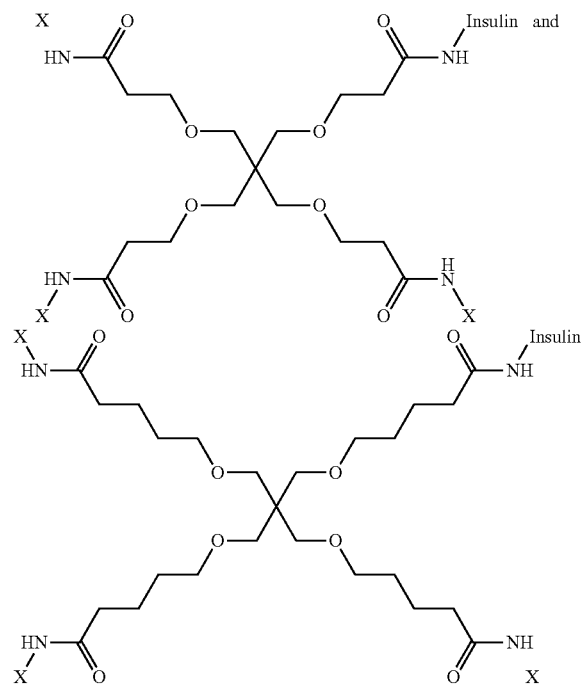

wherein each X is independently a ligand comprising or consisting of a monosaccharide, bisaccharide, trisaccharide, tetrasaccharide, or branched trisaccharide, and a pharmaceutically acceptable carrier.

In particular embodiments of the composition, the ligand is selected from the group consisting of fucose, mannose, glucosamine, glucose, bimannose, trimannose, tetramannose, or branched trimannose.

In particular embodiments of the composition, the tri-valent sugar cluster is covalently linked to the amino acid at position A1 of the insulin or insulin analog molecule; position B1 of the insulin or insulin analog molecule; position B29 of the insulin or insulin molecule; position B28 of the insulin analog molecule; or position B3 of the insulin analog molecule.

In particular embodiments of the composition, the insulin analog is insulin lispro, insulin glargine, insulin aspart, insulin detemir, or insulin glulisine.

In particular embodiments of the composition, the conjugate displays a pharmacodynamic (PD) and/or pharmacokinetic (PK) profile that is sensitive to the serum concentration of a serum saccharide when administered to a subject in need thereof in the absence of an exogenous saccharide binding molecule.

In particular embodiments of the composition, the serum saccharide is glucose or alpha-methylmannose.

In particular embodiments of the composition, the conjugate binds an endogenous saccharide binding molecule at a serum glucose concentration of 60 mg/dL or less when administered to a subject in need thereof.

In particular embodiments of the composition, the endogenous saccharide binding molecule is human mannose receptor 1.

In particular embodiments of the composition, the conjugate has the general formula (I):

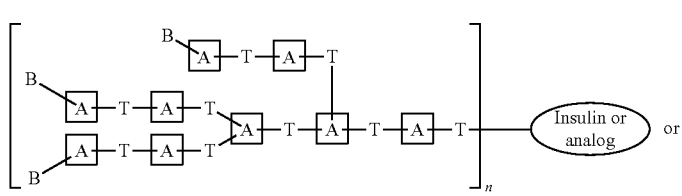

I

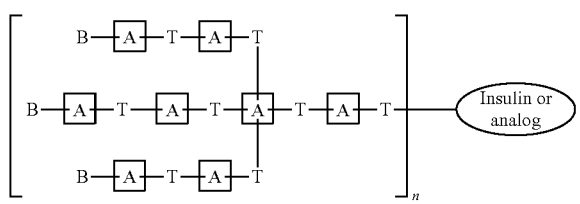

II wherein:
(i) each occurrence of

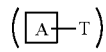

represents a potential repeat within a branch of the conjugate;

(ii) each occurrence of [A] is independently a covalent bond, a carbon atom, a heteroatom, or an optionally substituted group selected from the group consisting of acyl, aliphatic, heteroaliphatic, aryl, heteroaryl, and heterocyclic;

(iii) each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;

(iv) each occurrence of R is independently hydrogen, a suitable protecting group, or an acyl moiety, arylalkyl moiety, aliphatic moiety, aryl moiety, heteroaryl moiety, or heteroaliphatic moiety;

(v) -B is -T-$L^B$-X, wherein each occurrence of X is independently a ligand and each occurrence of $L^B$ is independently a covalent bond or a group derived from the covalent conjugation of a T with an X; and, (vi) n is 1, 2, or 3.

In particular embodiments of the composition, the insulin or insulin analog is conjugated to a tri-valent sugar cluster comprises a structure selected from the group consisting of ML-1, ML-2, ML-3, ML-4, ML-5, ML-6, ML-7, ML-8, ML-9, ML-10, ML-11, ML-12, ML-13, ML-14, ML-15, ML-16, ML-17, ML-18, ML-19, ML-20, ML-21, ML-22, ML-23, ML-24, ML-25, ML-26, ML-27, ML-28, ML-29, ML-30, ML-31, ML-32, ML-33, ML-34, ML-35, ML-36, ML-37, ML-38, ML-39, ML-40, ML-41, ML-42, ML-43, ML-44, ML-45, ML-46, ML-47, ML-48, ML-49, ML-50, ML-51, ML-52, ML-53, ML-54, ML-55, ML-56, ML-57, ML-58, ML-59, ML-60, ML-61, ML-62, ML-63, and ML-64.

In particular embodiments of the composition, the conjugate is selected from the group consisting of IOC-1, IOC-2, IOC-3, IOC-4, IOC-5, IOC-6, IOC-7, IOC-8, IOC-9, IOC-10, IOC-11, IOC-12, IOC-13, IOC-14, IOC-15, IOC-16, IOC-17, IOC-18, IOC-19, IOC-20, IOC-21, IOC-22, IOC-23, IOC-24, IOC-25, IOC-26, IOC-27, IOC-28, IOC-29, IOC-30, IOC-31, IOC-32, IOC-33, IOC-34, IOC-35, IOC-36, IOC-37, IOC-38, IOC-39, IOC-40, IOC-41, IOC-42, IOC-43, IOC-44, IOC-45, IOC-46, IOC-47, IOC-48, IOC-49, IOC-50, IOC-51, IOC-52, IOC-53, IOC-54, IOC-55, IOC-56, IOC-57, IOC-58, IOC-59, IOC-60, IOC-61, IOC-62, IOC-63, IOC-64, IOC-65, IOC-66, IOC-67, IOC-68, IOC-69, IOC-70, IOC-71, IOC-72, IOC-73, IOC-74, IOC-75, IOC-76, IOC-77, IOC-78, IOC-79, IOC-80, IOC-81, IOC-82, IOC-83, IOC-84, IOC-85, IOC-86, IOC-87, IOC-88, IOC-89, IOC-90, IOC-91, IOC-92, IOC-93, IOC-94, IOC-95, IOC-96, IOC-97, IOC-98, IOC-99, IOC-100, IOC-101, IOC-102, IOC-103, IOC-104, IOC-105, IOC-106, IOC-107, IOC-108, IOC-109, IOC-110, IOC-111, IOC-112, IOC-113, IOC-114, IOC-115, IOC-116, IOC-117, IOC-118, IOC-119, IOC-120, and IOC-121.

The present invention further provides a method for treating diabetes comprising administering to an individual in need thereof a therapeutically effective amount of the conjugate or composition herein to treat the diabetes. In particular aspects, the diabetes is type I diabetes, type II diabetes, or gestational diabetes.

The present invention further provides for the use of the conjugate or composition herein for the treatment of diabetes. In particular aspects, the diabetes is type I diabetes, type II diabetes, or gestational diabetes.

Definitions

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987.

Acyl—As used herein, the term "acyl," refers to a group having the general formula —C(=O)R$^{X1}$, —C(=O)OR$^{X1}$, —C(=O)—O—C(=O)$_R$$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Aliphatic—As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments, aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Alkenyl—As used herein, the term "alkenyl" denotes an optionally substituted monovalent group derived from a straight- or branched-chain aliphatic moiety having at least one carbon-carbon double bond by the removal of a single hydrogen atom. In particular embodiments, the alkenyl group employed in the invention contains 2-6 carbon atoms. In particular embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

Alkyl—As used herein, the term "alkyl" refers to optionally substituted saturated, straight- or branched-chain hydrocarbon radicals derived from an aliphatic moiety containing between 1-6 carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl—As used herein, the term "alkynyl" refers to an optionally substituted monovalent group derived from a straight- or branched-chain aliphatic moiety having at least one carbon-carbon triple bond by the removal of a single hydrogen atom. In particular embodiments, the alkynyl group employed in the invention contains 2-6 carbon atoms. In particular embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

Aryl—As used herein, the term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In particular embodiments of the present invention, "aryl" refers to an aromatic ring system that includes, but not limited to, phenyl, biphenyl, naphthyl, anthracyl and the like, which may bear one or more substituents.

Arylalkyl—As used herein, the term "arylalkyl" refers to an alkyl group substituted with an aryl group (e.g., an aromatic or heteroaromatic group).

Bivalent hydrocarbon chain—As used herein, the term "bivalent hydrocarbon chain" (also referred to as a "bivalent alkylene group") is a polymethylene group, i.e., $-(CH_2)_z-$, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below for a substituted aliphatic group.

Carbonyl—As used herein, the term "carbonyl" refers to a monovalent or bivalent moiety containing a carbon-oxygen double bond. Non-limiting examples of carbonyl groups include aldehydes, ketones, carboxylic acids, ester, amide, enones, acyl halides, anhydrides, ureas, carbamates, carbonates, thioesters, lactones, lactams, hydroxamates, isocyanates, and chloroformates.

Cycloaliphatic—As used herein, the terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

Fucose—refers to the D or L form of fucose and may refer to an oxygen or carbon linked glycoside.

Halogen—As used herein, the terms "halo" and "halogen" refer to an atom selected from fluorine (fluoro, —F), chlorine (chloro, —Cl), bromine (bromo, —Br), and iodine (iodo, —I).

Heteroaliphatic—As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

Heteroaralkyl—As used herein, the term "heteroaralkyl" refers to an alkyl group substituted by a heteroaryl, wherein the alkyl and heteroaryl portions independently are optionally substituted.

Heteroaryl—As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Unsaturated—As used herein, the term "unsaturated", means that a moiety has one or more double or triple bonds.

Partially unsaturated—As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Optionally substituted—As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in particular embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$, which may be substituted with $R°$; —CH=CHPh, which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR—$, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched)alkylene)O—$N(R°)_2$; or —$(C_{1-4}$ straight or branched)alkylene)C(O)O—$N(R°)_2$, wherein each $R°$ may be substituted as defined below and is independently hydrogen, $C_{1-6}$ aliphatic, —$CH_2Ph$, —$O(CH_2)_{0-1}Ph$, or a 5- to 6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3- to 12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^•$, -(halo$R^•$), —$(CH_2)_{0-2}OH$, —$(CH_2)_{0-2}R^•$, —$(CH_2)_{0-2}CH(OR^•)_2$; —O(halo$R^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)O$R^•$, or —$SSR^•$ wherein each $R^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5- to 6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic that may be substituted as defined below, or an unsubstituted 5- or 6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic, which may be substituted as defined below, or an unsubstituted 5- to 6-membered saturated, partially unsaturated, or aryl ring having 0-4 heteroatoms independently selected from nitrogen, oxygen, or sulfur.

Suitable substituents on the aliphatic group of R* include halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic that may be substituted as defined below, unsubstituted —OPh, or an unsubstituted 5- to 6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

Suitable protecting group—As used herein, the term "suitable protecting group," refers to amino protecting groups or hydroxyl protecting groups depending on its location within the compound and includes those described in detail in *Protecting Groups in Organic Synthesis*, T. W. Greene and P. G. M. Wuts, 3$^{rd}$ edition, John Wiley & Sons, 1999.

In any case where a chemical variable (e.g., an R group) is shown attached to a bond that crosses a bond of the ring, this means that one or more such variables are optionally attached to the ring having the crossed bond. Each R group on such a ring can be attached at any suitable position on the ring, this is generally understood to mean that the group is attached in place of a hydrogen atom on the parent ring. This includes the possibility that two R groups can be attached to the same ring atom. Furthermore, when more than one R group is present on a ring, each may be the same or different than other R groups attached thereto, and each group is defined independently of other groups that may be attached elsewhere on the same molecule, even though they may be represented by the same identifier.

Exogenous—As used herein, an "exogenous" molecule is one that is not present at significant levels in a patient unless administered to the patient. In particular embodiments the patient is a mammal, e.g., a human, a dog, a cat, a rat, a minipig, etc. As used herein, a molecule is not present at significant levels in a patient if normal serum for that type of patient includes less than 0.1 mM of the molecule. In particular embodiments, normal serum for the patient may include less than 0.08 mM, less than 0.06 mM, or less than 0.04 mM of the molecule.

Treat—As used herein, the term "treat" (or "treating", "treated", "treatment", etc.) refers to the administration of a conjugate of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition. For example, as used herein the term "treating diabetes" will refer in general to maintaining glucose blood levels near normal levels and may include increasing or decreasing blood glucose levels depending on a given situation.

Pharmaceutically acceptable carrier—as used herein, the term includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

Effective or therapeutically effective amount—as used herein refers to a nontoxic but sufficient amount of an insulin analog to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

Parenteral—as used herein, the term means not through the alimentary canal but by some other route such as intranasal, inhalation, subcutaneous, intramuscular, intraspinal, or intravenous.

Insulin—as used herein, the term means the active principle of the pancreas that affects the metabolism of carbohydrates in the animal body and is of value in the treatment of diabetes mellitus. The term includes synthetic and biotechnologically derived products that are the same as, or similar to, naturally occurring insulins in structure, use, and intended effect and are of value in the treatment of diabetes mellitus.

Insulin or insulin molecule—the term is a generic term that designates the 51 amino acid heterodimer comprising the A-chain peptide having the amino acid sequence shown in SEQ ID NO: 1 and the B-chain peptide having the amino acid sequence shown in SEQ ID NO: 2, wherein the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

Insulin analog or analogue—the term as used herein includes any heterodimer analogue or single-chain analogue that comprises one or more modification(s) of the native A-chain peptide and/or B-chain peptide. Modifications include but are not limited to substituting an amino acid for the native amino acid at a position selected from A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, and B30; deleting any or all of positions B1-4 and B26-30; adding any or all of terminal positions A1, B1, A21, and B30; or conjugating directly or by a polymeric or non-polymeric linker one or more acyl, polyethylglycine (PEG), or saccharide moiety (moieties); or any combination thereof. As exemplified by the N-linked glycosylated insulin analogues disclosed herein, the term further includes any insulin heterodimer and single-chain analogue that has been modified to have at least one N-linked glycosylation site and in particular, embodiments in which the N-linked glycosylation site is linked to or occupied by an N-glycan. Examples of insulin analogues include but are not limited to the heterodimer and single-chain analogues disclosed in published international application WO20100080606, WO2009/099763, and WO2010080609, the disclosures of which are incorporated herein by reference. Examples of single-chain insulin analogues also include but are not limited to those disclosed in published International Applications WO9634882, WO95516708, WO2005054291, WO2006097521, WO2007104734, WO2007104736, WO2007104737, WO2007104738, WO2007096332, WO2009132129; U.S. Pat. Nos. 5,304,473 and 6,630,348; and Kristensen et al., Biochem. J. 305: 981-986 (1995), the disclosures of which are each incorporated herein by reference.

The term further includes single-chain and heterodimer polypeptide molecules that have little or no detectable activity at the insulin receptor but that have been modified to include one or more amino acid modifications or substitutions to have an activity at the insulin receptor that has at least 1%, 10%, 50%, 75%, or 90% of the activity at the insulin receptor as compared to native insulin and that further includes at least one N-linked glycosylation site. In particular aspects, the insulin analogue is a partial agonist that has from 2× to 100× less activity at the insulin receptor as does native insulin. In other aspects, the insulin analogue has enhanced activity at the insulin receptor, for example, the IGF$^{B16B17}$ derivative peptides disclosed in published international application WO2010080607 (which is incorporated herein by reference). These insulin analogues, which have reduced activity at the insulin growth hormone receptor and enhanced activity at the insulin receptor, include both heterodimers and single-chain analogues.

Single-chain insulin or single-chain insulin analog—as used herein, the term encompasses a group of structurally-related proteins wherein the A-chain peptide or functional analogue and the B-chain peptide or functional analogue are covalently linked by a peptide or polypeptide of 2 to 35 amino acids or non-peptide polymeric or non-polymeric linker and which has at least 1%, 10%, 50%, 75%, or 90% of the activity of insulin at the insulin receptor as compared to native insulin. The single-chain insulin or insulin analogue further includes three disulfide bonds: the first disulfide bond is between the cysteine residues at positions 6 and 11 of the A-chain or functional analogue thereof, the second disulfide bond is between the cysteine residues at position 7 of the A-chain or functional analogue thereof and position 7 of the B-chain or functional analogue thereof, and the third disulfide bond is between the cysteine residues at position 20 of the A-chain or functional analogue thereof and position 19 of the B-chain or functional analogue thereof.

Connecting peptide or C-peptide—as used herein, the term refers to the connection moiety "C" of the B-C-A polypeptide sequence of a single chain preproinsulin-like molecule. Specifically, in the natural insulin chain, the C-peptide connects the amino acid at position 30 of the B-chain and the amino acid at position 1 of the A-chain. The term can refer to both the native insulin C-peptide, the monkey C-peptide, and any other peptide from 3 to 35 amino acids that connects the B-chain to the A-chain thus is meant to encompass any peptide linking the B-chain peptide to the A-chain peptide in a single-chain insulin analogue (See for example, U.S. Published application Nos. 20090170750 and 20080057004 and WO9634882) and in insulin precursor molecules such as disclosed in WO9516708 and U.S. Pat. No. 7,105,314.

Amino acid modification—as used herein, the term refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

Amino acid substitution—as used herein refers to the replacement of one amino acid residue by a different amino acid residue.

Conservative amino acid substitution—as used herein, the term is defined herein as exchanges within one of the following five groups:
  I. Small aliphatic, nonpolar or slightly polar residues: Ala, Ser, Thr, Pro, Gly;
  II. Polar, negatively charged residues and their amides: Asp, Asn, Glu, Gln, cysteic acid and homocysteic acid;
  III. Polar, positively charged residues: His, Arg, Lys; Ornithine (Orn)
  IV. Large, aliphatic, nonpolar residues: Met, Leu, Ile, Val, Cys, Norleucine (Nle), homocysteine
  V. Large, aromatic residues: Phe, Tyr, Trp, acetyl phenylalanine Tridentate linker—a linker comprising a linker arm having a proximal end and a distal end wherein the proximal end is covalently linked to an amino acid on an insulin molecule and the distal end is covalently linked at or near the distal end to three ligand arms, each ligand arm having a distal end and a proximal end wherein the distal end is covalently linked to a ligand and the proximal end is covalently linked to the linker arm at or near the distal end of the linker arm.

As used herein, "plasma glucose" is usually 10-12% higher than "blood glucose" (considering blood glucose to be plasma+all blood cells).

BRIEF DESCRIPTION OF THE DRAWINGS

FIG. 1A shows plasma glucose depression curves in non-diabetic male Yucatan minipigs equipped with dual vascular access ports (n=3 per study) following i.v. injection of conjugate IOC-3 at 0.69 nmol/kg under conditions of PBS infusion or i.v. alpha methyl mannose (αMM) infusion.

FIG. 1B shows plasma glucose depression curves in non-diabetic male Yucatan minipigs equipped with dual vascular access ports (n=3 per study) following i.v. injection of conjugate IOC-9 at 0.35 nmol/kg under conditions of PBS infusion or i.v. alpha methyl mannose (αMM) infusion.

FIG. 1C shows plasma glucose depression curves in non-diabetic male Yucatan minipigs equipped with dual vascular access ports (n=3 per study) following i.v. injection of conjugate IOC-12 at 0.17 nmol/kg under conditions of PBS infusion or i.v. alpha methyl mannose (αMM) infusion.

FIG. 1D shows plasma glucose depression curves in non-diabetic male Yucatan minipigs equipped with dual vascular access ports (n=3 per study) following i.v. injection of conjugate IOC-13 at 0.17 nmol/kg under conditions of PBS infusion or i.v. alpha methyl mannose (αMM) infusion.

FIG. 6A shows plasma glucose depression curves in non-diabetic male Yucatan minipigs equipped with dual vascular access ports (n=3 per study) following i.v. injection of conjugate IOC-61 at 0.17 nmol/kg under conditions of PBS infusion or i.v. alpha methyl mannose (αMM) infusion.

FIG. 6B shows plasma glucose depression curves in non-diabetic male Yucatan minipigs equipped with dual vascular access ports (n=3 per study) following i.v. injection of conjugate IOC-62 at 0.17 nmol/kg under conditions of PBS infusion or i.v. alpha methyl mannose (αMM) infusion.

FIG. 6C shows plasma glucose depression curves in non-diabetic male Yucatan minipigs equipped with dual vascular access ports (n=3 per study) following i.v. injection of conjugate IOC-65 at 0.17 nmol/kg under conditions of PBS infusion or i.v. alpha methyl mannose (αMM) infusion.

FIG. 6D shows plasma glucose depression curves in non-diabetic male Yucatan minipigs equipped with dual vascular access ports (n=3 per study) following i.v. injection of conjugate IOC-69 at 0.17 nmol/kg under conditions of PBS infusion or i.v. alpha methyl mannose (αMM) infusion.

FIG. 8A shows plasma glucose depression curves in non-diabetic male Yucatan minipigs equipped with dual vascular access ports (n=3 per study) following i.v. injection of conjugate IOC-81 at 0.17 nmol/kg under conditions of PBS infusion or i.v. alpha methyl mannose (αMM) infusion.

FIG. 8B shows plasma glucose depression curves in non-diabetic male Yucatan minipigs equipped with dual vascular access ports (n=3 per study) following i.v. injection of conjugate IOC-93 at 0.69 nmol/kg under conditions of PBS infusion or i.v. alpha methyl mannose (αMM) infusion.

FIG. 8C shows plasma glucose depression curves in non-diabetic male Yucatan minipigs equipped with dual vascular access ports (n=3 per study) following i.v. injection of conjugate IOC-101 at 0.17 nmol/kg under conditions of PBS infusion or i.v. alpha methyl mannose (αMM) infusion.

FIG. 8D shows plasma glucose depression curves in non-diabetic male Yucatan minipigs equipped with dual vascular access ports (n=3 per study) following i.v. injection of conjugate IOC-102 at 0.17 nmol/kg under conditions of PBS infusion or i.v. alpha methyl mannose (αMM) infusion.

FIG. 11A shows plasma glucose depression curves in non-diabetic male Yucatan minipigs equipped with dual vascular access ports (n=3 per study) following i.v. injection of conjugate IOC-118 at 0.17 nmol/kg under conditions of PBS infusion or i.v. alpha methyl mannose (αMM) infusion.

FIG. 11B shows plasma glucose depression curves in non-diabetic male Yucatan minipigs equipped with dual vascular access ports (n=3 per study) following i.v. injection of conjugate IOC-120 at 0.35 nmol/kg under conditions of PBS infusion or i.v. alpha methyl mannose (αMM) infusion.

FIG. 11C shows plasma glucose depression curves in non-diabetic male Yucatan minipigs equipped with dual vascular access ports (n=3 per study) following i.v. injection of conjugate IOC-121 at 0.17 nmol/kg under conditions of PBS infusion or i.v. alpha methyl mannose (αMM) infusion.

FIG. 11D shows plasma glucose depression curves in non-diabetic male Yucatan minipigs equipped with dual vascular access ports (n=3 per study) following i.v. injection of Compound A at 0.69 nmol/kg under conditions of PBS infusion or i.v. alpha methyl mannose (αMM) infusion.

DETAILED DESCRIPTION OF THE INVENTION

Figure 2A:
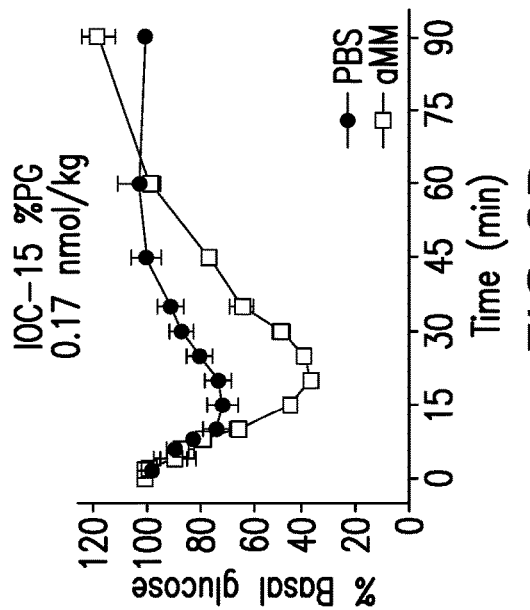
FIG. 2A shows plasma glucose depression curves in non-diabetic male Yucatan minipigs equipped with dual vascular access ports (n=3 per study) following i.v. injection of conjugate IOC-14 at 0.17 nmol/kg under conditions of PBS infusion or i.v. alpha methyl mannose (αMM) infusion.

The present invention provides methods for controlling the pharmacokinetic (PK) and/or pharmacodynamic (PD) profiles of insulin in a manner that is responsive to the systemic concentrations of a saccharide such as glucose. The methods are based in part on the discovery disclosed in U.S. Published Application No. 2011/0301083 that when particular insulin conjugates are modified to include high affinity saccharide ligands such as branched trimannose, they could be made to exhibit PK/PD profiles that responded to saccharide concentration changes even in the absence of an exogenous multivalent saccharide-binding molecule such as the lectin Concanavalin A (Con A).

In general, the insulin conjugates of the present invention comprise an insulin or insulin analog molecule covalently attached to a tri-valent sugar cluster at the A1, B1, B29, or B28 amino acid of insulin or insulin analog. In particular embodiments, the tri-valent sugar cluster is capable of competing with a saccharide (e.g., glucose or alpha-methylmannose) for binding to an endogenous saccharide-binding molecule such as the Macrophage Mannose Receptor 1. In particular embodiments, the tri-valent sugar cluster is capable of competing with glucose or alpha-methylmannose for binding to Con A. In particular embodiments, the linker is non-polymeric or highly branched. In particular embodiments, the conjugate may have a polydispersity index of one and a MW of less than about 20,000 Da. In particular embodiments, the conjugate is of formula (I) or (II) as defined and described herein. In particular embodiments, the conjugate is long acting (i.e., exhibits a PK profile that is more sustained than soluble recombinant human insulin (RHI)).

Insulin Conjugates

In one aspect, the present invention provides an insulin or insulin analog molecule conjugated to at least one tri-valent sugar cluster wherein the tri-valent sugar cluster is provided by a branched linker having three arms (tri-dentate linker) wherein each arm of the tri-dentate linker is independently covalently linked to a ligand comprising or consisting of a monosaccharide, bisaccharide, trisaccharide, tetrasaccharide, or branched trisaccharide. Thus, as used herein a tri-valent sugar cluster comprises or consists of three ligands conjugated to a single amino acid on the insulin or insulin analog molecule. In particular embodiments, the amino acid is the amino acid at the N-terminus of the A-chain polypeptide or the B-chain polypeptide or the Lys residue at position B3, B29, or B28 of the B-chain polypeptide.

In particular aspects, the insulin or insulin analog molecule is conjugated to one, two, or three tri-dentate linkers wherein each arm of each tri-dentate linker is independently covalently linked to a ligand comprising or consisting of a saccharide. In particular aspects, each ligand independently comprises or consists of a monosaccharide, bisaccharide, trisaccharide, tetrasaccharide, or branched trisaccharide. In particular aspects, each ligand comprises or consists of a monomannose, bimannose, trimannose, tetramannose, or branched trimannose. In particular aspects, at least one ligand is fucose. In particular aspects, at least one ligand is a branched trimannose. In particular aspects, at least one ligand is a bimannose. In particular aspects, at least one ligand is mannose. In particular aspects, at least two ligands are fucose, branched mannose, bimannose, or mannose. In particular aspects, all three ligands are fucose, branched mannose, bimannose, or mannose.

In particular aspects, the insulin or insulin analog molecule is conjugated to two tri-dentate linkers wherein each arm of each tri-dentate linker is independently covalently linked to a ligand comprising or consisting of a saccharide. In particular aspects, each ligand independently comprises or consists of a monosaccharide, bisaccharide, trisaccharide, tetrasaccharide, or branched trisaccharide. In particular aspects, each ligand comprises or consists of a monomannose, bimannose, trimannose, tetramannose, or branched trimannose. In particular aspects, at least one ligand is fucose. In particular aspects, at least one ligand is a branched trimannose. In particular aspects, at least one ligand is a bimannose. In particular aspects, at least one ligand is mannose. In particular aspects, at least two ligands are fucose, branched mannose, bimannose, or mannose. In particular aspects, all three ligands are fucose, branched mannose, bimannose, or mannose.

In particular aspects, the insulin or insulin analog molecule is conjugated to three tri-dentate linkers wherein each arm of each tri-dentate linker is independently covalently linked to a ligand comprising or consisting of a saccharide. In particular aspects, each ligand independently comprises or consists of a monosaccharide, bisaccharide, trisaccharide, tetrasaccharide, or branched trisaccharide. In particular aspects, each ligand comprises or consists of a monomannose, bimannose, trimannose, tetramannose, or branched trimannose. In particular aspects, at least one ligand is fucose. In particular aspects, at least one ligand is a branched trimannose. In particular aspects, at least one ligand is a bimannose. In particular aspects, at least one ligand is mannose. In particular aspects, at least two ligands are fucose, branched mannose, bimannose, or mannose. In particular aspects, all three ligands are fucose, branched mannose, bimannose, or mannose.

In particular aspects, the insulin or insulin analog molecule of the insulin conjugate disclosed herein is conjugated to a tri-dentate linker wherein each arm of each tri-dentate linker is independently covalently linked to a ligand comprising or consisting of a saccharide and is covalently attached to a linear linker linked to one ligand comprising or consisting of a saccharide. In particular aspects, each ligand independently comprises or consists of a monosaccharide, bisaccharide, trisaccharide, tetrasaccharide, or branched trisaccharide. In particular aspects, each ligand comprises or consists of a monomannose, bimannose, trimannose, tetramannose, or branched trimannose. In particular aspects, at least one ligand is fucose. In particular aspects, at least one ligand is a branched trimannose. In particular aspects, at least one ligand is a bimannose. In particular aspects, at least one ligand is mannose. In particular aspects, at least two ligands are fucose, branched mannose, bimannose, or mannose. In particular aspects, all three ligands are fucose, branched mannose, bimannose, or mannose.

In particular aspects, the insulin or insulin analog molecule of the insulin conjugate disclosed herein is conjugated to a tri-dentate linker wherein each arm of each tri-dentate linker is independently covalently linked to a ligand comprising or consisting of a saccharide and is covalently attached to a linker having two arms, each arm independently covalently linked to a ligand comprising or consisting of a saccharide. In particular aspects, each ligand independently comprises or consists of a monosaccharide, bisaccharide, trisaccharide, tetrasaccharide, or branched trisaccharide. In particular aspects, each ligand comprises or consists of a monomannose, bimannose, trimannose, tetramannose, or branched trimannose. In particular aspects, at least one ligand is fucose. In particular aspects, at least one ligand is a branched trimannose. In particular aspects, at least one ligand is a bimannose. In particular aspects, at least one ligand is mannose. In particular aspects, at least two ligands are fucose, branched mannose, bimannose, or mannose. In particular aspects, all three ligands are fucose, branched mannose, bimannose, or mannose.

When the insulin conjugate is administered to a mammal at least one pharmacokinetic or pharmacodynamic property of the conjugate is sensitive to the serum concentration of a saccharide. In particular embodiments, the PK and/or PD properties of the conjugate are sensitive to the serum concentration of an endogenous saccharide such as glucose. In particular embodiments, the PK and/or PD properties of the conjugate are sensitive to the serum concentration of an exogenous saccharide, e.g., without limitation, mannose, fucose, N-acetyl glucosamine and/or alpha-methyl mannose.

PK and PD Properties

In various embodiments, the pharmacokinetic and/or pharmacodynamic behavior of the insulin conjugate may be modified by variations in the serum concentration of a saccharide. For example, from a pharmacokinetic (PK) perspective, the serum concentration curve may shift upward when the serum concentration of the saccharide (e.g., glucose) increases or when the serum concentration of the saccharide crosses a threshold (e.g., is higher than normal glucose levels).

In particular embodiments, the serum concentration curve of a conjugate disclosed herein is substantially different when administered to the mammal under fasted and hyperglycemic conditions. As used herein, the term "substantially different" means that the two curves are statistically different as determined by a student t-test ($p<0.05$). As used herein, the term "fasted conditions" means that the serum concentration curve was obtained by combining data from five or more fasted non-diabetic individuals. In particular embodiments, a fasted non-diabetic individual is a randomly selected 18-30 year old human who presents with no diabetic symptoms at the time blood is drawn and who has not eaten within 12 hours of the time blood is drawn. As used herein, the term "hyperglycemic conditions" means that the serum concentration curve was obtained by combining data from five or more fasted non-diabetic individuals in which hyperglycemic conditions (glucose $C_{max}$ at least 100 mg/dL above the mean glucose concentration observed under fasted conditions) were induced by concurrent administration of conjugate and glucose. Concurrent administration of conjugate and glucose simply requires that the glucose $C_{max}$ occur during the period when the conjugate is present at a detectable level in the serum. For example, a glucose injection (or ingestion) could be timed to occur shortly before, at the same time or shortly after the conjugate is administered. In particular embodiments, the conjugate and glucose are administered by different routes or at different locations. For example, in particular embodiments, the conjugate is administered subcutaneously while glucose is administered orally or intravenously.

In particular embodiments, the serum $C_{max}$ of the conjugate is higher under hyperglycemic conditions as compared to fasted conditions. Additionally or alternatively, in particular embodiments, the serum area under the curve (AUC) of the conjugate is higher under hyperglycemic conditions as compared to fasted conditions. In various embodiments, the serum elimination rate of the conjugate is slower under hyperglycemic conditions as compared to fasted conditions. In particular embodiments, the serum concentration curve of the conjugates can be fit using a two-compartment bi-exponential model with one short and one long half-life. The long half-life appears to be particularly sensitive to glucose concentration. Thus, in particular embodiments, the long half-life is longer under hyperglycemic conditions as compared to fasted conditions. In particular embodiments, the fasted conditions involve a glucose $C_{max}$ of less than 100 mg/dL (e.g., 80 mg/dL, 70 mg/dL, 60 mg/dL, 50 mg/dL, etc.). In particular embodiments, the hyperglycemic conditions involve a glucose $C_{max}$ in excess of 200 mg/dL (e.g., 300 mg/dL, 400 mg/dL, 500 mg/dL, 600 mg/dL, etc.). It will be appreciated that other PK parameters such as mean serum residence time (MRT), mean serum absorption time (MAT), etc. could be used instead of or in conjunction with any of the aforementioned parameters.

The normal range of glucose concentrations in humans, dogs, cats, and rats is 60 to 200 mg/dL. One skilled in the art will be able to extrapolate the following values for species with different normal ranges (e.g., the normal range of glucose concentrations in miniature pigs is 40 to 150 mg/dl). Glucose concentrations below 60 mg/dL are considered hypoglycemic. Glucose concentrations above 200 mg/dL are considered hyperglycemic. In particular embodiments, the PK properties of the conjugate may be tested using a glucose clamp method, and the serum concentration curve of the conjugate may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Additionally or alternatively, the serum $T_{max}$, serum $C_{max}$, mean serum residence time (MRT), mean serum absorption time (MAT) and/or serum half-life may be substantially different at the two glucose concentrations. As discussed below, in particular embodiments, 100 mg/dL and 300 mg/dL may be used as comparative glucose concentrations. It is to be understood, however, that the present disclosure encompasses each of these embodiments with an alternative pair of comparative glucose concentrations including, without limitation, any one of the following pairs: 50 and 200 mg/dL, 50 and 300 mg/dL, 50 and 400 mg/dL, 50 and 500 mg/dL, 50 and 600 mg/dL, 100 and 200 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc.

Thus, in particular embodiments, the $C_{max}$ of the conjugate is higher when administered to the mammal at the higher of the two glucose concentrations (e.g., 300 vs. 100 mg/dL glucose). In particular embodiments, the $C_{max}$ of the conjugate is at least 50% (e.g., at least 100%, at least 200% or at least 400%) higher when administered to the mammal at the higher of the two glucose concentrations (e.g., 300 vs. 100 mg/dL glucose).

In particular embodiments, the AUC of the conjugate is higher when administered to the mammal at the higher of the two glucose concentrations (e.g., 300 vs. 100 mg/dL glucose). In particular embodiments, the AUC of the conjugate is at least 50% (e.g., at least 100%, at least 200% or at least 400%) higher when administered to the mammal at the higher of the two glucose concentrations (e.g., 300 vs. 100 mg/dL glucose).

In particular embodiments, the serum elimination rate of the conjugate is slower when administered to the mammal at the higher of the two glucose concentrations (e.g., 300 vs. 100 mg/dL glucose). In particular embodiments, the serum elimination rate of the conjugate is at least 25% (e.g., at least 50%, at least 100%, at least 200%, or at least 400%) faster when administered to the mammal at the lower of the two glucose concentrations (e.g., 100 vs. 300 mg/dL glucose).

In particular embodiments the serum concentration curve of conjugates may be fit using a two-compartment bi-exponential model with one short and one long half-life. The long half-life appears to be particularly sensitive to glucose concentration. Thus, in particular embodiments, the long half-life is longer when administered to the mammal at the higher of the two glucose concentrations (e.g., 300 vs. 100 mg/dL glucose). In particular embodiments, the long half-life is at least 50% (e.g., at least 100%, at least 200% or at least 400%) longer when administered to the mammal at the higher of the two glucose concentrations (e.g., 300 vs. 100 mg/dL glucose).

In particular embodiments, the present disclosure provides a method in which the serum concentration curve of a conjugate is obtained at two different glucose concentrations (e.g., 300 vs. 100 mg/dL glucose); the two curves are fit using a two-compartment bi-exponential model with one short and one long half-life; and the long half-lives obtained under the two glucose concentrations are compared. In particular embodiments, this method may be used as an assay for testing or comparing the glucose sensitivity of one or more conjugates.

In particular embodiments, the hyperglycemic conditions involve a glucose $C_{max}$ in excess of 200 mg/dL (e.g., 300 mg/dL, 400 mg/dL, 500 mg/dL, 600 mg/dL, etc.). In particular embodiments, the fasted conditions involve a glucose $C_{max}$ of less than 100 mg/dL (e.g., 80 mg/dL, 70 mg/dL, 60 mg/dL, 50 mg/dL, etc.). It will be appreciated that any of the aforementioned PK parameters such as serum $T_{max}$, serum $C_{max}$, AUC, mean serum residence time (MRT), mean serum absorption time (MAT) and/or serum half-life could be compared.

From a pharmacodynamic (PD) perspective, the bioactivity of the conjugate may increase when the glucose concentration increases or when the glucose concentration crosses a threshold, e.g., is higher than normal glucose levels. In particular embodiments, the bioactivity of a conjugate is lower when administered under fasted conditions as compared to hyperglycemic conditions. In particular embodiments, the fasted conditions involve a glucose $C_{max}$ of less than 100 mg/dL (e.g., 80 mg/dL, 70 mg/dL, 60 mg/dL, 50 mg/dL, etc.). In particular embodiments, the hyperglycemic conditions involve a glucose $C_{max}$ in excess of 200 mg/dL (e.g., 300 mg/dL, 400 mg/dL, 500 mg/dL, 600 mg/dL, etc.).

In particular embodiments, the PD properties of the conjugate may be tested by measuring the glucose infusion rate (GIR) required to maintain a steady glucose concentration. According to such embodiments, the bioactivity of the conjugate may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Thus, in particular embodiments, the bioactivity of the conjugate is higher when administered to the mammal at the higher of the two glucose concentrations (e.g., 300 vs. 100 mg/dL glucose). In particular embodiments, the bioactivity of the conjugate is at least 25% (e.g., at least 50% or at least 100%) higher when administered to the mammal at the higher of the two glucose concentrations (e.g., 300 vs. 100 mg/dL glucose).

In general, it will be appreciated that any of the PK and PD characteristics discussed in this section can be determined according to any of a variety of published pharmacokinetic and pharmacodynamic methods (e.g., see Baudys et al., Bioconjugate Chem. 9:176-183, 1998 for methods suitable for subcutaneous delivery). It is also to be understood that the PK and/or PD properties may be measured in any mammal (e.g., a human, a rat, a cat, a minipig, a dog, etc.). In particular embodiments, PK and/or PD properties are measured in a human. In particular embodiments, PK and/or PD properties are measured in a rat. In particular embodiments, PK and/or PD properties are measured in a minipig. In particular embodiments, PK and/or PD properties are measured in a dog.

Ligand(s)

In general, a ligand comprises or consists of a monosaccharide, bisaccharide, trisaccharide, tetrasaccharide, or branched trisaccharide. In particular aspects, the ligand comprises or consists of a monomannose, bimannose, trimannose, tetramannose, or branched trimannose. In particular aspects, the ligand comprises or consists of fucose, glucose, or N-glucosamine.

In particular embodiments, the three ligands comprising a tri-valent sugar cluster are capable of competing with a saccharide (e.g., glucose, alpha-methylmannose, or mannose) for binding to an endogenous saccharide-binding molecule (e.g., without limitation surfactant proteins A and D or members of the selectin family). In particular embodiments, the ligands are capable of competing with glucose or alpha-methylmannose for binding to the human macrophage mannose receptor 1 (MRC1). In particular embodiments, the ligands are capable of competing with a saccharide for binding to a non-human lectin (e.g., Con A). In particular embodiments, the ligands are capable of competing with glucose, alpha-methylmannose, or mannose for binding to a non-human lectin (e.g., Con A). Exemplary glucose-binding lectins include calnexin, calreticulin, N-acetylglucosamine receptor, selectin, asialoglycoprotein receptor, collectin (mannose-binding lectin), mannose receptor, aggrecan, versican, Pisum sativum agglutinin (PSA), Vicia faba lectin, lens culinaris lectin, soybean lectin, peanut lectin, lathyrus ochrus lectin, sainfoin lectin, Sophora japonica lectin, bowringia milbraedii lectin, concanavalin A (Con A), and pokeweed mitogen.

In particular embodiments, one or more of the three ligands may have the same chemical structure as glucose or may be a chemically related species of glucose, e.g., glucosamine. In various embodiments, it may be advantageous for one or more of the three ligands to have a different chemical structure from glucose, e.g., in order to fine tune the glucose response of the conjugate. For example, in particular embodiments, one might use a ligand that includes glucose, mannose, fucose or derivatives of these (e.g., alpha-L-fucopyranoside, mannosamine, beta-linked N-acetyl mannosamine, methylglucose, methylmannose, ethylglucose, ethylmannose, propylglucose, propylmannose, etc.) and/or higher order combinations of these (e.g., a bimannose, linear and/or branched trimannose, etc.).

In particular embodiments, a ligand includes a monosaccharide. In particular embodiments, a ligand includes a disaccharide. In particular embodiments, a ligand includes a trisaccharide. In some embodiments, the ligand comprises or consists of a saccharide and one or more amine groups. In some embodiments, the ligand comprises or consists of a saccharide and ethyl group. In particular embodiments, the saccharide and amine group are separated by a $C_1$-$C_6$ alkyl group, e.g., a $C_1$-$C_3$ alkyl group. In some embodiments, the ligand is aminoethylglucose (AEG). In some embodiments, the ligand is aminoethylmannose (AEM). In some embodiments, the ligand is aminoethylbimannose (AEBM). In some embodiments, the ligand is aminoethyltrimannose (AETM). In some embodiments, the ligand is β-aminoethyl-N-acetylglucosamine (AEGA). In some embodiments, the ligand is aminoethylfucose (AEF). In particular embodiments, the saccharide is of the "D" configuration and in other embodiments, the saccharide is of the "L" configuration. Below are the structures of exemplary saccharides having an amine group separated from the saccharide by a $C_2$ ethyl group wherein R may be hydrogen or a carbonyl group of the linker. Other exemplary ligands will be recognized by those skilled in the art.

AEG

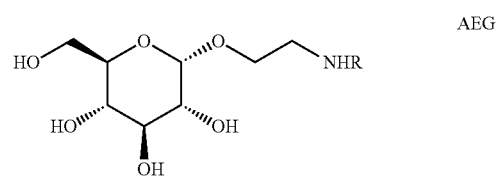

AEM

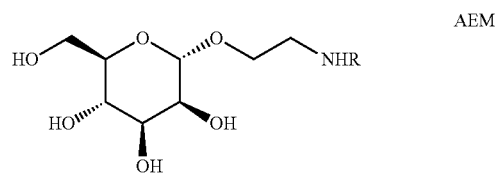

AEBM

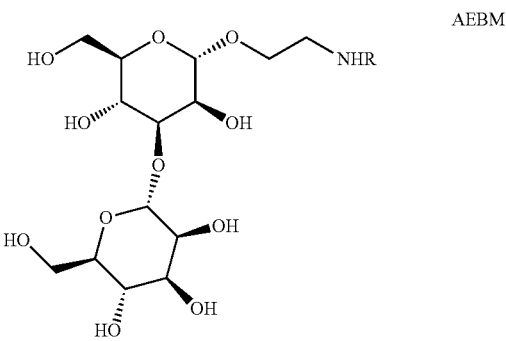

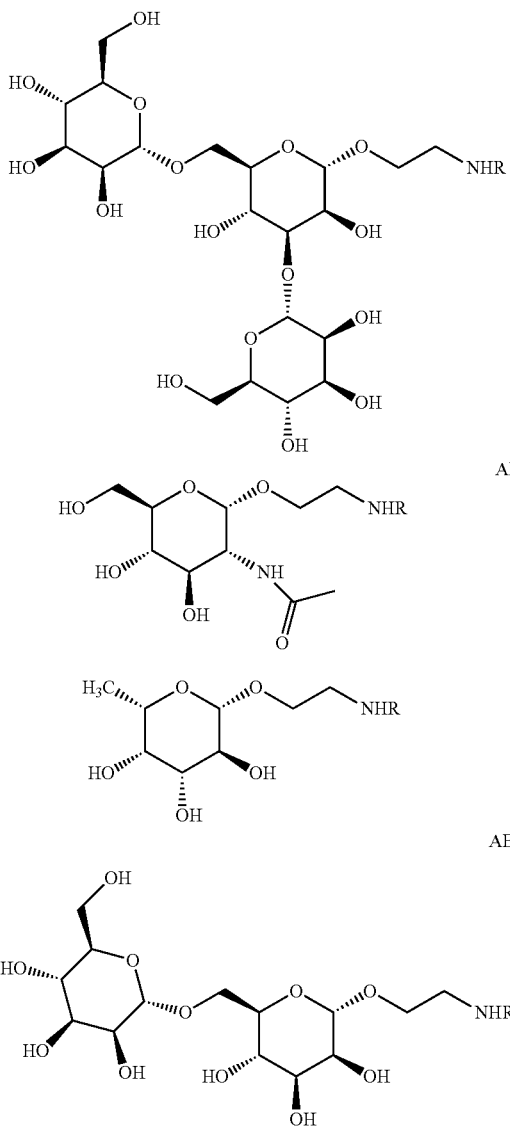

Insulin

As used herein, the term "insulin" or "insulin molecule" encompasses all salt and non-salt forms of the insulin molecule. It will be appreciated that the salt form may be anionic or cationic depending on the insulin molecule. By "insulin" or "an insulin molecule", we intend to encompass both wild-type insulin and modified forms of insulin as long as they are bioactive (i.e., capable of causing a detectable reduction in glucose when administered in vivo). Wild-type insulin includes insulin from any species whether in purified, synthetic or recombinant form (e.g., human insulin, porcine insulin, bovine insulin, rabbit insulin, sheep insulin, etc.). A number of these are available commercially, e.g., from Sigma-Aldrich (St. Louis, Mo.). A variety of modified forms of insulin are known in the art (e.g. see Crotty and Reynolds, *Pediatr. Emerg. Care.* 23:903-905, 2007 and Gerich, *Am. J. Med.* 113:308-16, 2002 and references cited therein). Modified forms of insulin (insulin analogs) may be chemically modified (e.g., by addition of a chemical moiety such as a PEG group or a fatty acyl chain as described below) and/or mutated (i.e., by addition, deletion or substitution of one or more amino acids).

In particular embodiments, an insulin molecule of the present disclosure will differ from a wild-type insulin by 1-10 (e.g., 1-9, 1-8, 1-7, 1-6, 1-5, 1-4, 1-3, 1-2, 2-9, 2-8, 2-7, 2-6, 2-5, 2-4, 2-3, 3-9, 3-8, 3-7, 3-6, 3-5, 3-4, 4-9, 4-8, 4-7, 4-6, 4-5, 5-9, 5-8, 5-7, 5-6, 6-9, 6-8, 6-7, 7-9, 7-8, 8-9, 9, 8, 7, 6, 5, 4, 3, 2, or 1) amino acid substitutions, additions and/or deletions. In particular embodiments, an insulin molecule of the present disclosure will differ from a wild-type insulin by amino acid substitutions only. In particular embodiments, an insulin molecule of the present disclosure will differ from a wild-type insulin by amino acid additions only. In particular embodiments, an insulin molecule of the present disclosure will differ from wild-type insulin by both amino acid substitutions and additions. In particular embodiments, an insulin molecule of the present disclosure will differ from a wild-type insulin by both amino acid substitutions and deletions.

In particular embodiments, amino acid substitutions may be made on the basis of similarity in polarity, charge, solubility, hydrophobicity, hydrophilicity, and/or the amphipathic nature of the residues involved. In particular embodiments, a substitution may be conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine. In particular embodiments, the hydrophobic index of amino acids may be considered in choosing suitable mutations. The importance of the hydrophobic amino acid index in conferring interactive biological function on a polypeptide is generally understood in the art. Alternatively, the substitution of like amino acids can be made effectively on the basis of hydrophilicity. The importance of hydrophilicity in conferring interactive biological function of a polypeptide is generally understood in the art. The use of the hydrophobic index or hydrophilicity in designing polypeptides is further discussed in U.S. Pat. No. 5,691,198.

The wild-type sequence of human insulin (A-chain and B-chain) is shown below.

```
A-Chain (SEQ ID NO: 1):
GIVEQCCTSICSLYQLENYCN

B-Chain (SEQ ID NO: 2):
FVNQHLCGSHLVEALYLVCGERGFFYTPKT
```

In various embodiments, an insulin molecule of the present disclosure is mutated at the B28 and/or B29 positions of the B-peptide sequence. For example, insulin lispro) (HUMALOG®) is a rapid acting insulin mutant in which the penultimate lysine and proline residues on the C-terminal end of the B-peptide have been reversed ($Lys^{B28}Pro^{B29}$-human insulin) (SEQ ID NO:3). This modification blocks the formation of insulin multimers. Insulin aspart (NOVOLOG®) is another rapid acting insulin mutant in which proline at position B28 has been substituted with aspartic acid ($Asp^{B28}$-human insulin) (SEQ ID NO:4). This mutant also prevents the formation of multimers. In some embodiments, mutation at positions B28 and/or B29 is accompanied by one or more mutations elsewhere in the insulin polypeptide. For example, insulin glulisine (APIDRA®) is yet another rapid acting insulin mutant in which aspartic acid at position B3 has been replaced by a lysine residue and lysine at position B29 has been replaced with a glutamic acid residue (Lys$^{B3}$Glu$^{B29}$-human insulin) (SEQ ID NO:5).

In various embodiments, an insulin molecule of the present disclosure has an isoelectric point that is shifted relative to human insulin. In some embodiments, the shift in isoelectric point is achieved by adding one or more arginine residues to the N-terminus of the insulin A-peptide and/or the C-terminus of the insulin B-peptide. Examples of such insulin polypeptides include Arg$^{A0}$-human insulin, Arg$^{B31}$Arg$^{B32}$-human insulin, Gly$^{A21}$Arg$^{B31}$Arg$^{B32}$-human insulin, Arg$^{A0}$Arg$^{B31}$Arg$^{B32}$-human insulin, and Arg$^{A0}$Gly$^{A21}$Arg$^{B31}$Arg$^{B32}$-human insulin. By way of further example, insulin glargine (LANTUS®) is an exemplary long acting insulin mutant in which Asp$^{A21}$ has been replaced by glycine (SEQ ID NO:6), and two arginine residues have been added to the C-terminus of the B-peptide (SEQ ID NO:7). The effect of these changes is to shift the isoelectric point, producing a solution that is completely soluble at pH 4. Thus, in some embodiments, an insulin molecule of the present disclosure comprises an A-peptide sequence wherein A21 is Gly and B-peptide sequence wherein B31 and B32 are Arg-Arg. It is to be understood that the present disclosure encompasses all single and multiple combinations of these mutations and any other mutations that are described herein (e.g., Gly$^{A21}$-human insulin, Gly$^{A21}$Arg$^{B31}$-human insulin, Arg$^{B31}$Arg$^{B32}$-human insulin, Arg$^{B31}$-human insulin).

In various embodiments, an insulin molecule of the present disclosure is truncated. For example, in particular embodiments, a B-peptide sequence of an insulin polypeptide of the present disclosure is missing B1, B2, B3, B26, B27, B28, B29 and/or B30. In particular embodiments, combinations of residues are missing from the B-peptide sequence of an insulin polypeptide of the present disclosure. For example, the B-peptide sequence may be missing residues B(1-2), B(1-3), B(29-30), B(28-30), B(27-30) and/or B(26-30). In some embodiments, these deletions and/or truncations apply to any of the aforementioned insulin molecules (e.g., without limitation to produce des(B30)-insulin lispro, des(B30)-insulin aspart, des(B30)-insulin glulisine, des(B30)-insulin glargine, etc.).

In some embodiments, an insulin molecule contains additional amino acid residues on the N- or C-terminus of the A or B-peptide sequences. In some embodiments, one or more amino acid residues are located at positions A0, A21, B0 and/or B31. In some embodiments, one or more amino acid residues are located at position A0. In some embodiments, one or more amino acid residues are located at position A21. In some embodiments, one or more amino acid residues are located at position B0. In some embodiments, one or more amino acid residues are located at position B31. In particular embodiments, an insulin molecule does not include any additional amino acid residues at positions A0, A21, B0 or B31.

In particular embodiments, an insulin molecule of the present disclosure is mutated such that one or more amidated amino acids are replaced with acidic forms. For example, asparagine may be replaced with aspartic acid or glutamic acid. Likewise, glutamine may be replaced with aspartic acid or glutamic acid. In particular, Asn$^{A18}$, Asn$^{A21}$, or Asn$^{B3}$, or any combination of those residues, may be replaced by aspartic acid or glutamic acid. Gln$^{A15}$ or Gln$^{B4}$, or both, may be replaced by aspartic acid or glutamic acid. In particular embodiments, an insulin molecule has aspartic acid at position A21 or aspartic acid at position B3, or both.

One skilled in the art will recognize that it is possible to mutate yet other amino acids in the insulin molecule while retaining biological activity. For example, without limitation, the following modifications are also widely accepted in the art: replacement of the histidine residue of position B10 with aspartic acid (His$^{B10}$→Asp$^{B10}$); replacement of the phenylalanine residue at position B1 with aspartic acid (Phe$^{B1}$→Asp$^{B1}$); replacement of the threonine residue at position B30 with alanine (Thr$^{B30}$→Ala$^{B30}$); replacement of the tyrosine residue at position B26 with alanine (Tyr$^{B26}$→Ala$^{B26}$); and replacement of the serine residue at position B9 with aspartic acid (Ser$^{B9}$→Asp$^{B9}$).

In various embodiments, an insulin molecule of the present disclosure has a protracted profile of action. Thus, in particular embodiments, an insulin molecule of the present disclosure may be acylated with a fatty acid. That is, an amide bond is formed between an amino group on the insulin molecule and the carboxylic acid group of the fatty acid. The amino group may be the alpha-amino group of an N-terminal amino acid of the insulin molecule, or may be the epsilon-amino group of a lysine residue of the insulin molecule. An insulin molecule of the present disclosure may be acylated at one or more of the three amino groups that are present in wild-type human insulin or may be acylated on lysine residue that has been introduced into the wild-type human insulin sequence. In particular embodiments, an insulin molecule may be acylated at position B 1. In particular embodiments, an insulin molecule may be acylated at position B29. In particular embodiments, the fatty acid is selected from myristic acid (C14), pentadecylic acid (C15), palmitic acid (C16), heptadecylic acid (C17) and stearic acid (C18). For example, insulin detemir (LEVEMIR®) is a long acting insulin mutant in which Thr$^{B30}$ has been deleted, and a C14 fatty acid chain (myristic acid) has been attached to Lys$^{B29}$.

In some embodiments, the N-terminus of the A-peptide, the N-terminus of the B-peptide, the epsilon-amino group of Lys at position B29 or any other available amino group in an insulin molecule of the present disclosure is covalently linked to a fatty acid moiety of general formula:

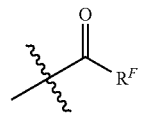

wherein $R^F$ is hydrogen or a $C_{1-30}$ alkyl group. In some embodiments, $R^F$ is a $C_{1-20}$ alkyl group, a $C_{3-19}$ alkyl group, a $C_{5-18}$ alkyl group, a $C_{6-17}$ alkyl group, a $C_{8-16}$ alkyl group, a $C_{10-15}$ alkyl group, or a $C_{12-14}$ alkyl group. In particular embodiments, the insulin polypeptide is conjugated to the moiety at the A1 position. In particular embodiments, the insulin polypeptide is conjugated to the moiety at the B1 position. In particular embodiments, the insulin polypeptide is conjugated to the moiety at the epsilon-amino group of Lys at position B29. In particular embodiments, position B28 of the insulin molecule is Lys and the epsilon-amino group of Lys$^{B28}$ is conjugated to the fatty acid moiety. In particular embodiments, position B3 of the insulin molecule is Lys and the epsilon-amino group of Lys$^{B3}$ is conjugated to the fatty acid moiety. In some embodiments, the fatty acid chain is 8-20 carbons long. In some embodiments, the fatty acid is octanoic acid (C8), nonanoic acid (C9), decanoic acid (C10), undecanoic acid (C11), dodecanoic acid (C12), or tridecanoic acid (C13). In particular embodiments, the fatty acid is myristic acid (C14), pentadecanoic acid (C15), palmitic acid (C16), heptadecanoic acid (C17), stearic acid (C18), nonadecanoic acid (C19), or arachidic acid (C20).

In various embodiments, an insulin molecule of the present disclosure includes the three wild-type disulfide bridges (i.e., one between position 7 of the A-chain and position 7 of the B-chain, a second between position 20 of the A-chain and position 19 of the B-chain, and a third between positions 6 and 11 of the A-chain). In particular embodiments, an insulin molecule is mutated such that the site of mutation is used as a conjugation point, and conjugation at the mutated site reduces binding to the insulin receptor (e.g., $Lys^{A3}$). In particular other embodiments, conjugation at an existing wild-type amino acid or terminus reduces binding to the insulin receptor (e.g., $Gly^{A1}$). In some embodiments, an insulin molecule is conjugated at position A4, A5, A8, A9, or B30. In particular embodiments, the conjugation at position A4, A5, A8, A9, or B30 takes place via a wild-type amino acid side chain (e.g., $Glu^{A4}$). In particular other embodiments, an insulin molecule is mutated at position A4, A5, A8, A9, or B30 to provide a site for conjugation (e.g., $Lys^{A4}$, $Lys^{A5}$, $Lys^{A8}$, $Lys^{A9}$, or $Lys^{B30}$).

Methods for conjugating insulin molecules are described below. In particular embodiments an insulin molecule is conjugated to a tri-valent sugar cluster via the A1 amino acid residue. In particular embodiments the A1 amino acid residue is glycine. It is to be understood however, that the present disclosure is not limited to N-terminal conjugation and that in particular embodiments an insulin molecule may be conjugated via a non-terminal A-chain amino acid residue. In particular, the present disclosure encompasses conjugation via the epsilon-amine group of a lysine residue present at any position in the A-chain (wild-type or introduced by site-directed mutagenesis). It will be appreciated that different conjugation positions on the A-chain may lead to different reductions in insulin activity. In particular embodiments, an insulin molecule is conjugated to the tri-valent sugar cluster via the B1 amino acid residue. In particular embodiments the B1 amino acid residue is phenylalanine. It is to be understood however, that the present disclosure is not limited to N-terminal conjugation and that in particular embodiments an insulin molecule may be conjugated via a non-terminal B-chain amino acid residue. In particular, the present disclosure encompasses conjugation via the epsilon-amine group of a lysine residue present at any position in the B-chain (wild-type or introduced by site-directed mutagenesis). For example, in particular embodiments an insulin molecule may be conjugated via the B29 lysine residue. In the case of insulin glulisine, conjugation to the at least one tri-valent sugar cluster via the B3 lysine residue may be employed. It will be appreciated that different conjugation positions on the B-chain may lead to different reductions in insulin activity.

In particular embodiments, the tri-valent sugar cluster is conjugated to more than one conjugation point on the insulin molecule. For example, an insulin molecule can be conjugated at both the A1 N-terminus and the B29 lysine. In some embodiments, amide conjugation takes place in carbonate buffer to conjugate at the B29 and A1 positions, but not at the B1 position. In other embodiments, an insulin molecule can be conjugated at the A1 N-terminus, the B1 N-terminus, and the B29 lysine. In yet other embodiments, protecting groups are used such that conjugation takes place at the B1 and B29 or B1 and A1 positions. It will be appreciated that any combination of conjugation points on an insulin molecule may be employed. In some embodiments, at least one of the conjugation points is a mutated lysine residue, e.g., $Lys^{A3}$.

Exemplary Insulin Conjugates

In various embodiments, the insulin conjugate of the present disclosure comprises an insulin or insulin analog molecule conjugated one tri-valent sugar cluster wherein the tri-valent sugar cluster is provided by a branched linker having three arms (tri-dentate linker) wherein each arm of the tri-dentate linker is independently covalently linked to a ligand comprising or consisting of a monosaccharide, bisaccharide, trisaccharide, tetrasaccharide, or branched trisaccharide. In particular embodiments, the ligands are independently selected from the group consisting of aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF). In particular embodiments, the insulin molecule is conjugated via the A1 amino acid residue. In particular embodiments, the insulin molecule is conjugated via the B1 amino acid residue. In particular embodiments, the insulin molecule is conjugated via the epsilon-amino group of $Lys^{B29}$. In particular embodiments, the insulin molecule is an analog that comprises a lysine at position B28 ($Lys^{B28}$) and the insulin molecule is conjugated via the epsilon-amino group of $Lys^{B28}$, for example, insulin lispro conjugated via the epsilon-amino group of $Lys^{B28}$. In particular embodiments, the insulin molecule is an analog that comprises a lysine at position B3 ($Lys^{B3}$) and the insulin molecule is conjugated via the epsilon-amino group of $Lys^{B3}$, for example, insulin glulisine conjugated via the epsilon-amino group of $Lys^{B3}$.

In particular embodiments, the insulin or insulin molecule of the above insulin conjugate may be conjugated to one or more additional linkers attached to one or more ligands, each ligand independently selected from aminoethylglucose (AEG), aminoethylmannose (AEM), aminoethylbimannose (AEBM) ligands, aminoethyltrimannose (AETM) ligands, β-aminoethyl-N-acetylglucosamine (AEGA), and aminoethylfucose (AEF). The additional linkers may be linear, bi-dentate, tri-dentate, quadri-dentate, etc. wherein each arm of the linker comprises a ligand, which may independently be selected from aminoethylglucose (AEG), aminoethylmannose (AEM), aminoethylbimannose (AEBM) ligands, aminoethyltrimannose (AETM) ligands, β-aminoethyl-N-acetylglucosamine (AEGA), and aminoethylfucose (AEF).

Thus, in particular embodiments, the insulin conjugate may comprise or consist of a tri-valent sugar cluster conjugated to the amino group at position A1 of the insulin or insulin analog; or the amino group at position B1 of the insulin or insulin analog; or the amino group at position B3 of the insulin analog; or the amino group at position B28 of the insulin analog; or the amino group at position B29 of the insulin or insulin analog.

In particular embodiments, the insulin conjugate may comprise or consist of two tri-valent sugar clusters (a first sugar cluster and a second sugar cluster) wherein each ligand comprising the first tri-valent sugar cluster is independently a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position A1 and wherein each ligand comprising the second tri-valent sugar cluster is independently a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B1, B3, B28, or B29.

In particular embodiments, the insulin conjugate may comprise or consist of two tri-valent sugar clusters (a first sugar cluster and a second sugar cluster) wherein each ligand comprising the first tri-valent sugar cluster is independently a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B1 and wherein each ligand comprising the second tri-valent sugar cluster is independently a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position A1, B3, B28, or B29.

In particular embodiments, the insulin conjugate may comprise or consist of two tri-valent sugar clusters (a first sugar cluster and a second sugar cluster) wherein each ligand comprising the first tri-valent sugar cluster is independently a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B3 and wherein each ligand comprising the second tri-valent sugar cluster is independently a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position A1, B1, B28, or B29.

In particular embodiments, the insulin conjugate may comprise or consist of two tri-valent sugar clusters (a first sugar cluster and a second sugar cluster) wherein each ligand comprising the first tri-valent sugar cluster is independently a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B28 and wherein each ligand comprising the second tri-valent sugar cluster is independently a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B1, B3, or A1.

In particular embodiments, the insulin conjugate may comprise or consist of two tri-valent sugar clusters (a first sugar cluster and a second sugar cluster) wherein each ligand comprising the first tri-valent sugar cluster is independently a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B29 and wherein each ligand comprising the second tri-valent sugar cluster is independently a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B1, B3, or A1.

In particular embodiments, the insulin conjugate may comprise or consist of three tri-valent sugar clusters (a first sugar cluster a second sugar cluster, and a third sugar cluster) wherein each ligand comprising the first tri-valent sugar cluster is independently a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B29; wherein each ligand comprising the second tri-valent sugar cluster is independently a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position B1 and wherein each ligand comprising the third tri-valent sugar cluster is independently a ligand selected from aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF) is conjugated to the amino group at position A1.

In particular embodiments, the insulin or insulin analog molecule further includes an acyl group covalently linked to the A1 or both A1 and B1 N-terminal amino groups. In particular embodiments, the insulin or insulin analog molecule further includes a urea group covalently linked to the A1 and B1 N-terminal amino groups.

Insulin Conjugates

This section describes some exemplary insulin or insulin analog conjugates.

In various embodiments, the conjugates may have the general formula (I):

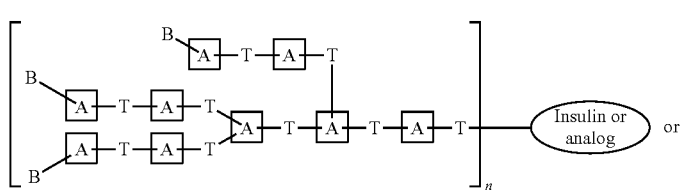

wherein each occurrence of

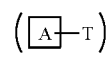

represents a potential repeat within a branch of the conjugate;

each occurrence of [A] is independently a covalent bond, a carbon atom, a heteroatom, or an optionally substituted group selected from the group consisting of acyl, aliphatic, heteroaliphatic, aryl, heteroaryl, and heterocyclic; each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;

each occurrence of R is independently hydrogen, a suitable protecting group, or an acyl moiety, arylalkyl moiety, aliphatic moiety, aryl moiety, heteroaryl moiety, or heteroaliphatic moiety;

-B is -T-L$^B$-X;

each occurrence of X is independently a ligand;

each occurrence of L$^B$ is independently a covalent bond or a group derived from the covalent conjugation of a T with an X; and, wherein n is 1, 2, or 3, with the proviso that the insulin is conjugated to at least one linker in which one of the ligands is fucose.

In particular embodiments, the insulin or insulin analog conjugate may have the general formula (II):

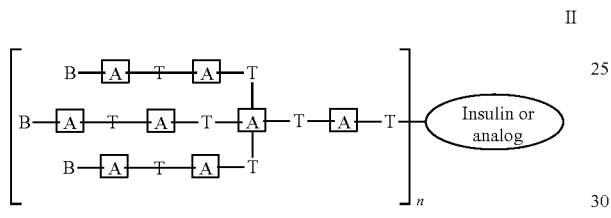

II wherein each occurrence of

represents a potential repeat within a branch of the conjugate;

each occurrence of ▣ is independently a covalent bond, a carbon atom, a heteroatom, or an optionally substituted group selected from the group consisting of acyl, aliphatic, heteroaliphatic, aryl, heteroaryl, and heterocyclic;

each occurrence of T is independently a covalent bond or a bivalent, straight or branched, saturated or unsaturated, optionally substituted C$_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;

each occurrence of R is independently hydrogen, a suitable protecting group, or an acyl moiety, arylalkyl moiety, aliphatic moiety, aryl moiety, heteroaryl moiety, or heteroaliphatic moiety;

-B1 is -T-L$^{B1}$-Fucose
wherein L$^{B1}$ is a covalent bond or a group derived from the covalent conjugation of a T with an X;

-B2 is -T-L$^{B2}$-X
wherein X is a ligand comprising a saccharide, which may be fucose, mannose, or glucose; and L$^{B2}$ is a covalent bond or a group derived from the covalent conjugation of a T with an X; and, wherein n is 1, 2, or 3.

Description of Exemplary Groups

▣ (Node)

In particular embodiments, each occurrence of ▣ is independently an optionally substituted group selected from the group consisting of acyl, aliphatic, heteroaliphatic, aryl, heteroaryl, and heterocyclic. In some embodiments, each occurrence of ▣ is the same. In some embodiments, the central ▣ is different from all other occurrences of ▣. In particular embodiments, all occurrences of ▣ are the same except for the central ▣.

In some embodiments, ▣ is an optionally substituted aryl or heteroaryl group. In some embodiments, ▣ is a 2-, 3, 4, 6, or 8-membered aryl or heteroaryl group. In some embodiments, ▣ is a 5- or 6-membered heterocyclic group. In particular embodiments, ▣ is a heteroatom selected from N, O, or S. In some embodiments, ▣ is nitrogen atom. In some embodiments, ▣ is an oxygen atom. In some embodiments, ▣ is sulfur atom. In some embodiments, ▣ is a carbon atom. In some embodiments, ▣ is the structure

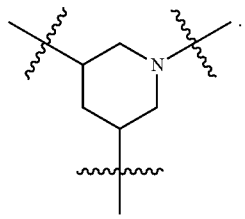 [SMILES: *C1CC(*)CN(*)C1]

T (Spacer)

In particular embodiments, each occurrence of T is independently a bivalent, straight or branched, saturated or unsaturated, optionally substituted C$_{1-20}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group. In particular embodiments, one, two, three, four, or five methylene units of T are optionally and independently replaced. In particular embodiments, T is constructed from a C$_{1-10}$, C$_{1-8}$, C$_{1-6}$, C$_{1-4}$, C$_{2-12}$, C$_{4-12}$, C$_{6-12}$, C$_{8-12}$, or C$_{10-12}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group. In some embodiments, one or more methylene units of T is replaced by a heterocyclic group. In some embodiments, one or more methylene units of T is replaced by a triazole moiety. In particular embodiments, one or more methylene units of T is replaced by —C(O)—. In particular embodiments, one or more methylene units of T is replaced by —C(O)N(R)—. In particular embodiments, one or more methylene units of T is replaced by —O—.

In particular embodiments of the conjugate, the conjugate comprises or consists of the structure of conjugate I wherein the insulin or onsulin analog is conjugated to a tri-valent linker selected from the group consisting of TVL-1
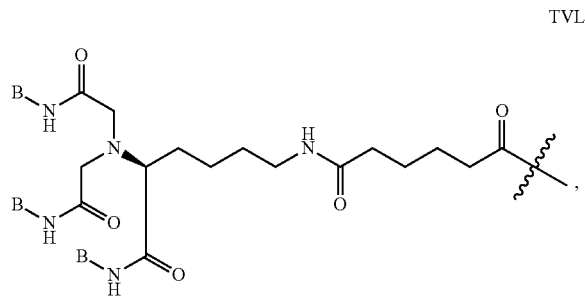
TVL-2
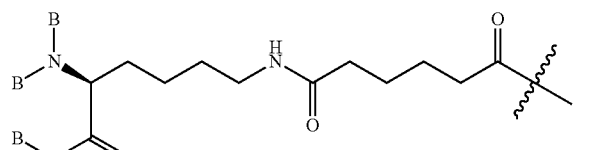
TVL-3
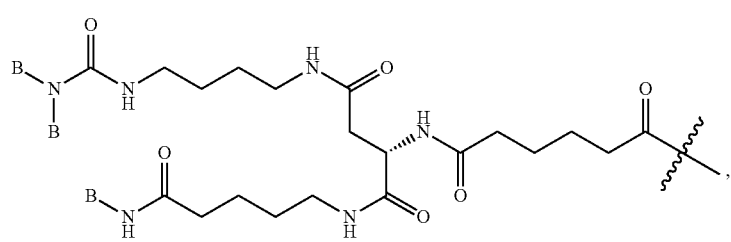
TVL-4
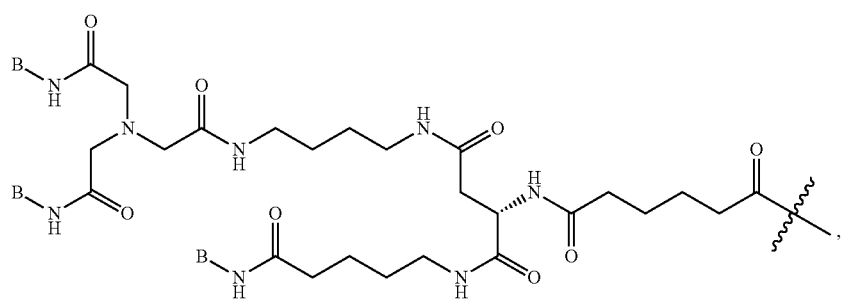
TVL-5
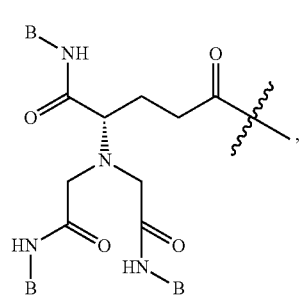
TVL-6
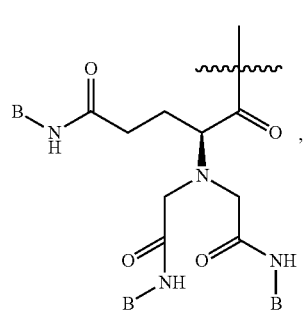
TVL-7
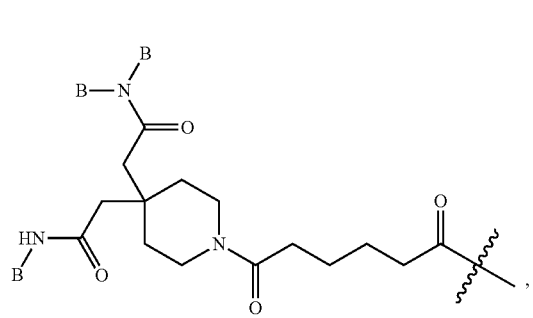
TVL-8
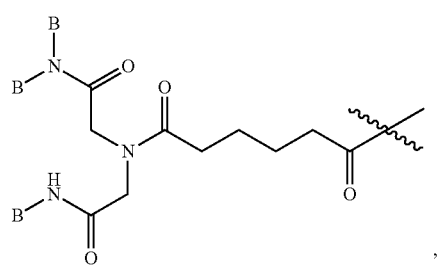

-continued
TVL-9
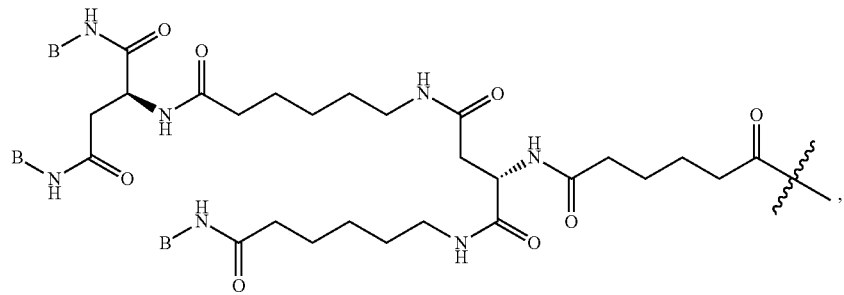
TVL-10
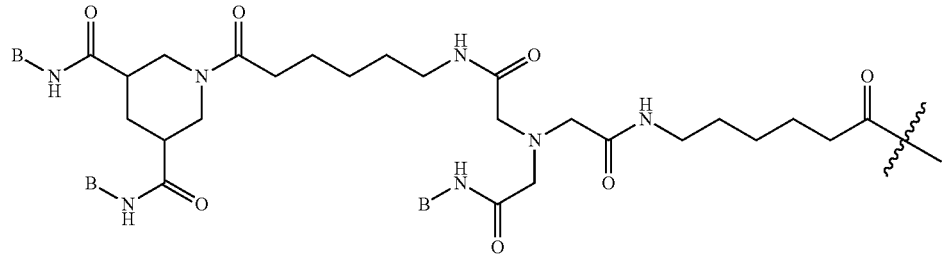
TVL-11
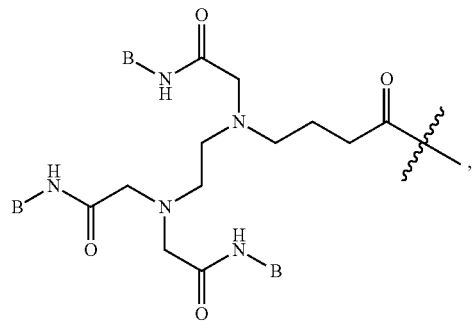
TVL-12
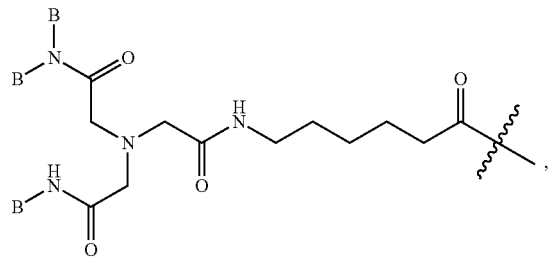
TVL-13
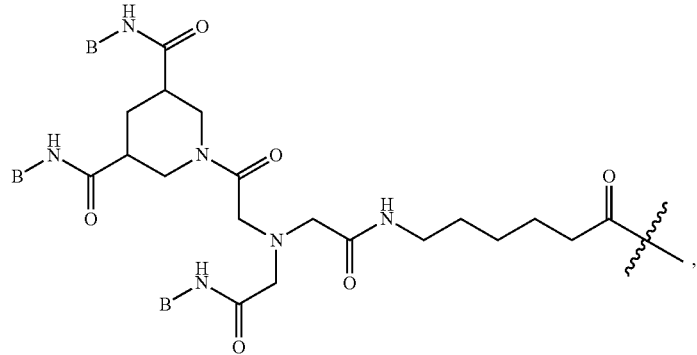
TVL-14
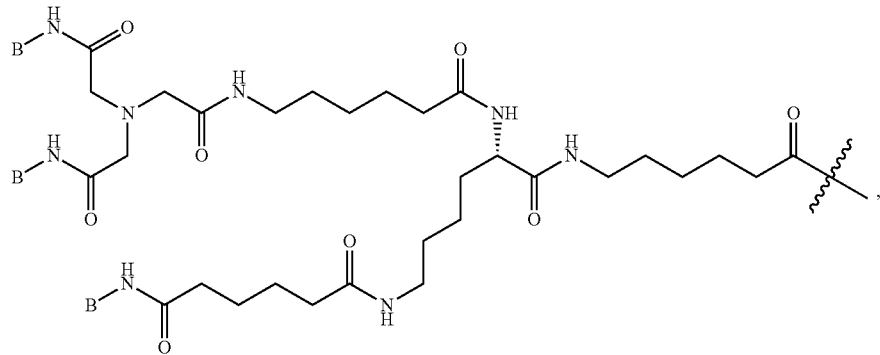

-continued
TVL-15
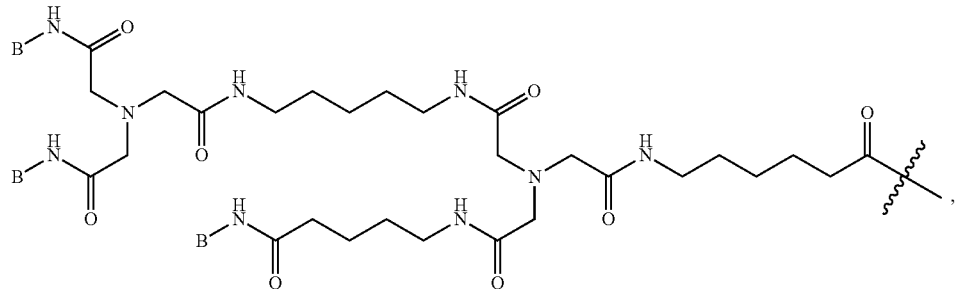
TVL-16
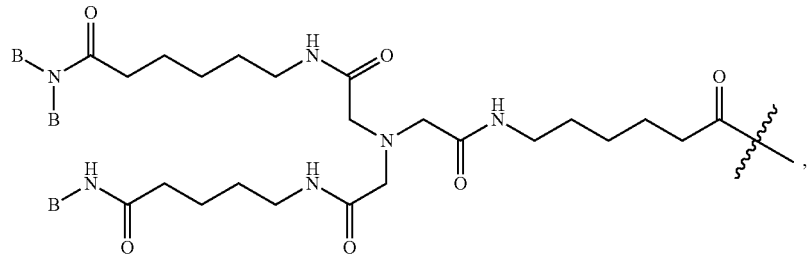
TVL-17
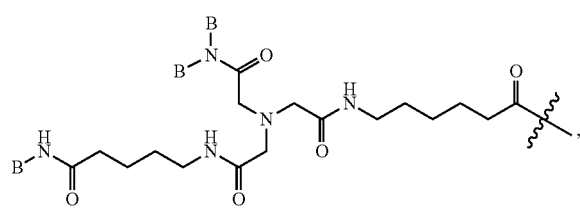
TVL-18
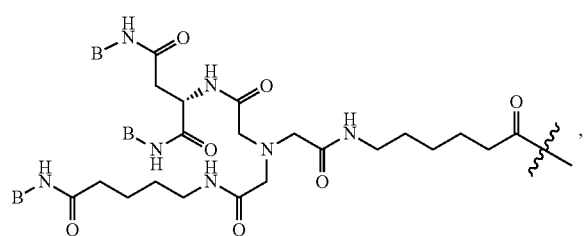
TVL-19
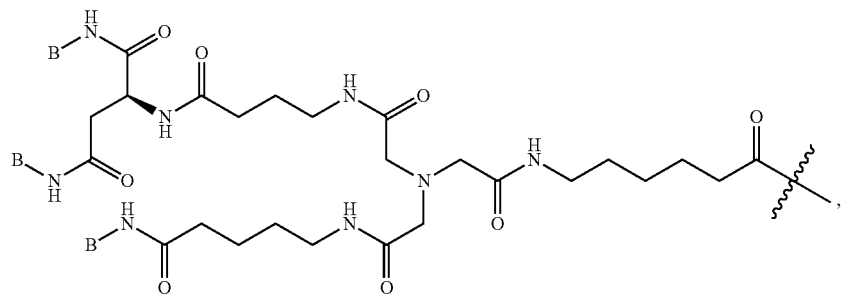
TVL-20
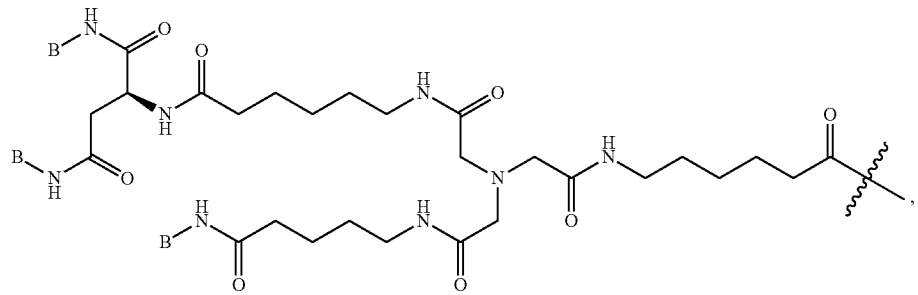

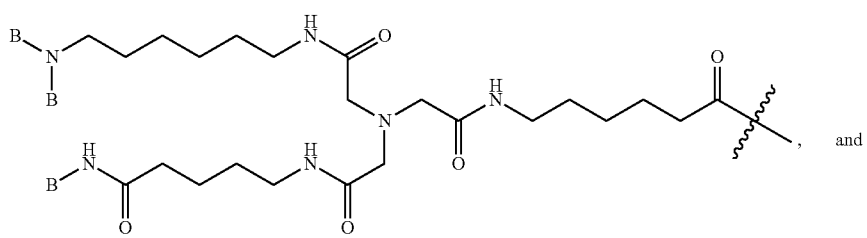
TVL-21

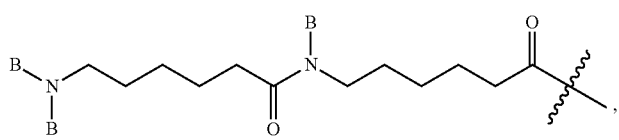
TVL-22 or the conjugate comprises the structure of conjugate II wherein the insulin or insulin analog is conjugated to a tri-valent linker selected from the group consisting of

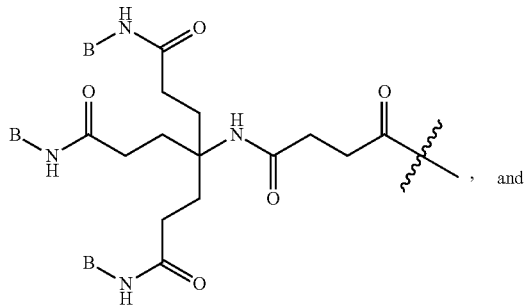
TVL-23

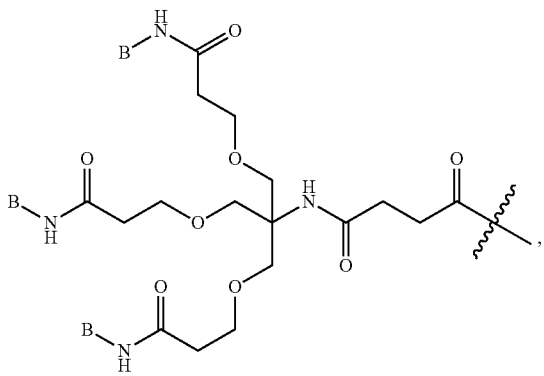
TVL-24 wherein the wavy line indicates the bond between the proximal end of the linker arm and amino acid on the insulin or insulin analog and wherein each B is independently -T-$L^B$-X, wherein each occurrence of X is independently the ligand and each occurrence of $L^B$ is independently a covalent bond or a group derived from the covalent conjugation of a T with an X.

In particular embodiments, the insulin analog may comprise an A chain sequence comprising a sequence of GIVEQCCX$_1$SICSLYQLENYCX$_2$ (SEQ ID NO: 8); and a B chain sequence comprising a sequence of X$_3$LCGX$_4$X$_5$LVEALYLVCG ERGFF (SEQ ID NO: 9) or X$_8$VNQX$_3$LCGX$_4$X$_5$LVEALYLVCGERGFFYTX$_6$ X$_7$ (SEQ ID NO: 10) wherein X$_1$ is selected from the group consisting of threonine and histidine;

X$_2$ is asparagine or glycine;

X$_3$ is selected from the group consisting of histidine and threonine;

X$_4$ is selected from the group consisting of alanine, glycine and serine;

X$_5$ is selected from the group consisting of histidine, aspartic acid, glutamic acid, homocysteic acid and cysteic acid;

X$_6$ is aspartate-lysine dipeptide, a lysine-proline dipeptide, or a proline-lysine dipeptide;

X$_7$ is threonine, alanine, or a threonine-arginine-arginine tripeptide; and

X$_8$ is selected from the group consisting of phenylalanine and desamino-phenylalanine.

In particular embodiments, the A-chain may have the amino acid sequence set forth in SEQ ID NO:1 or SEQ ID NO:6 and the B-chain may have the amino acid sequence set forth in SEQ ID NO:2, SEQ ID NO:3, SEQ ID NO:4, or SEQ ID NO:5. In particular embodiments, the insulin analog is a des B30 insulin analog, a des B29-B30 insulin analog, a des B28-B30 insulin analog, a des B27-B30 insulin analog, or a des B26-B30 insulin analog.

In particular embodiments, the insulin or insulin analog is conjugated to one, two, or three tri-valent sugar clusters selected from the group consisting of ML-1, ML-2, ML-3, ML-4, ML-5, ML-6, ML-7, ML-8, ML-9, ML-10, ML-11, ML-12, ML-13, ML-14, ML-15, ML-16, ML-17, ML-18, ML-19, ML-20, ML-21, ML-22, ML-23, ML-24, ML-25, ML-26, ML-27, ML-28, ML-29, ML-30, ML-31, ML-32, ML-33, ML-34, ML-35, ML-36, ML-37, ML-38, ML-39, ML-40, ML-41, ML-42, ML-43, ML-44, ML-45, ML-46, ML-47, ML-48, ML-49, ML-50, ML-51, ML-52, ML-53, ML-54, ML-55, ML-56, ML-57, ML-58, ML-59, ML-60, ML-61, ML-62, ML-63, and ML-64.

Exemplary human insulin oligosaccharide conjugates (IOCs) of the present invention include the IOCs having the following structures:

IOC-1
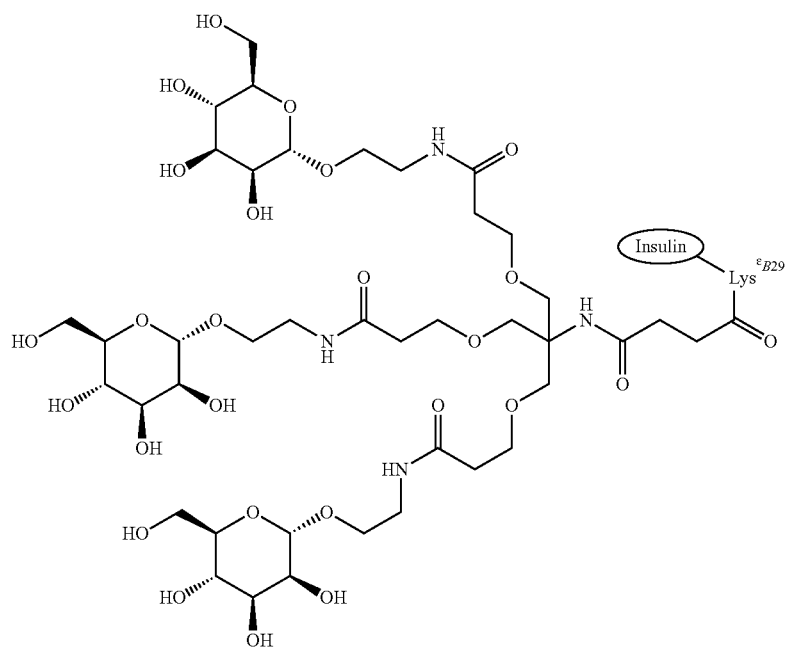
IOC-2
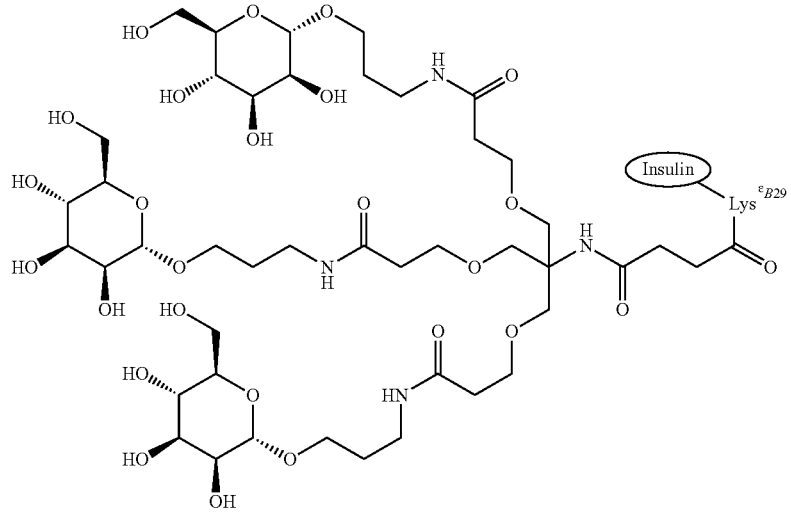

IOC-3
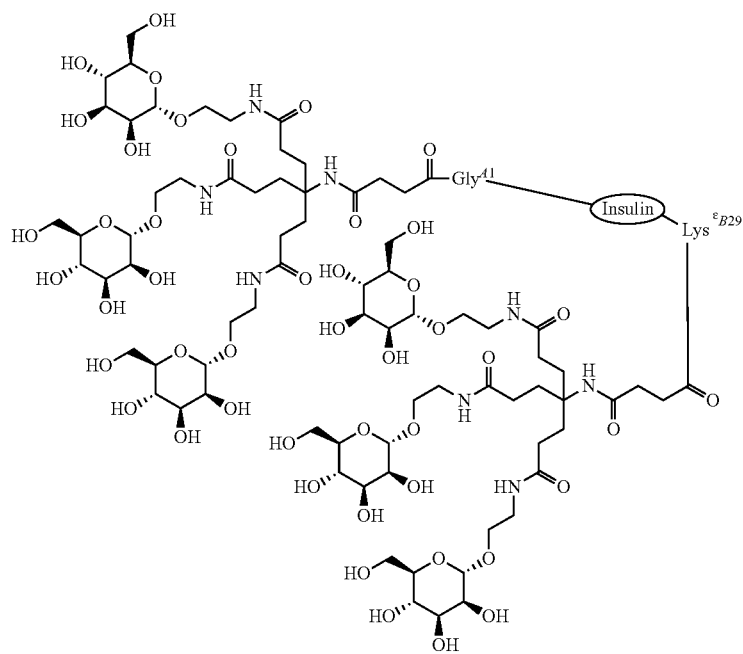
IOC-4
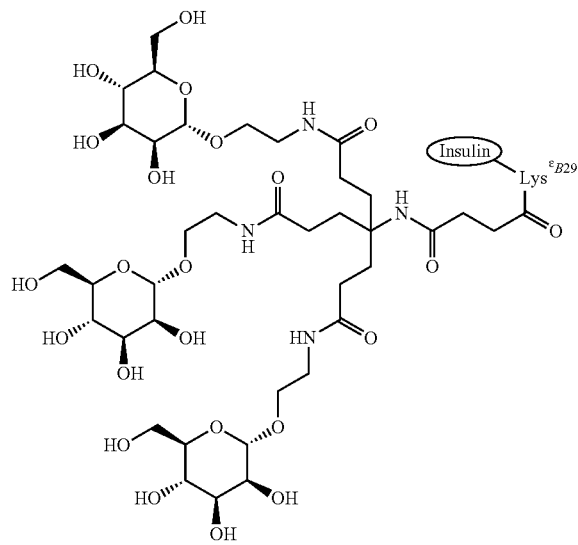
IOC-5
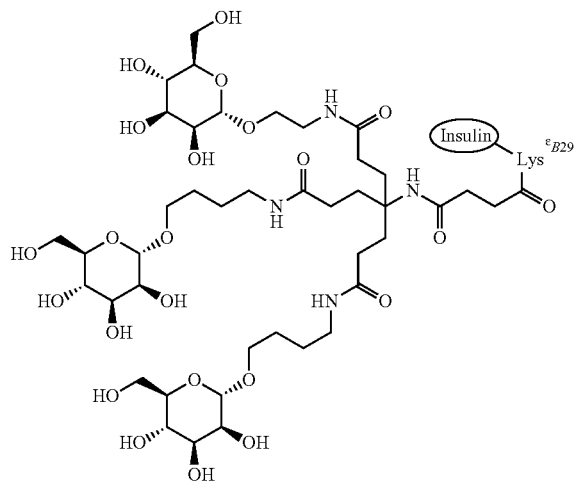

IOC-6
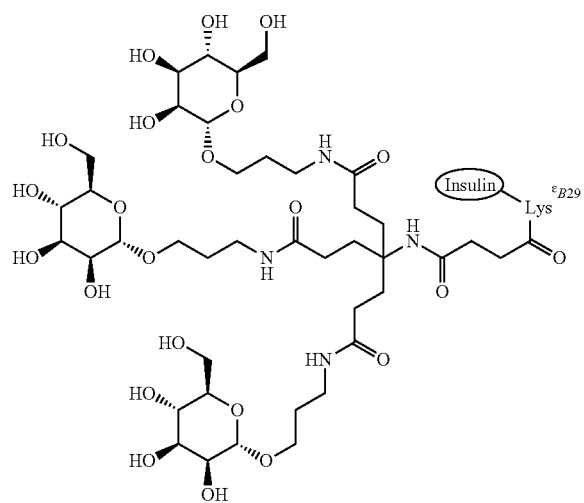
IOC-7
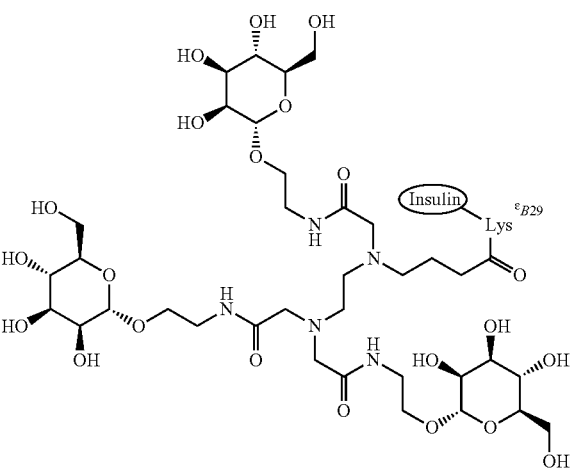
IOC-8
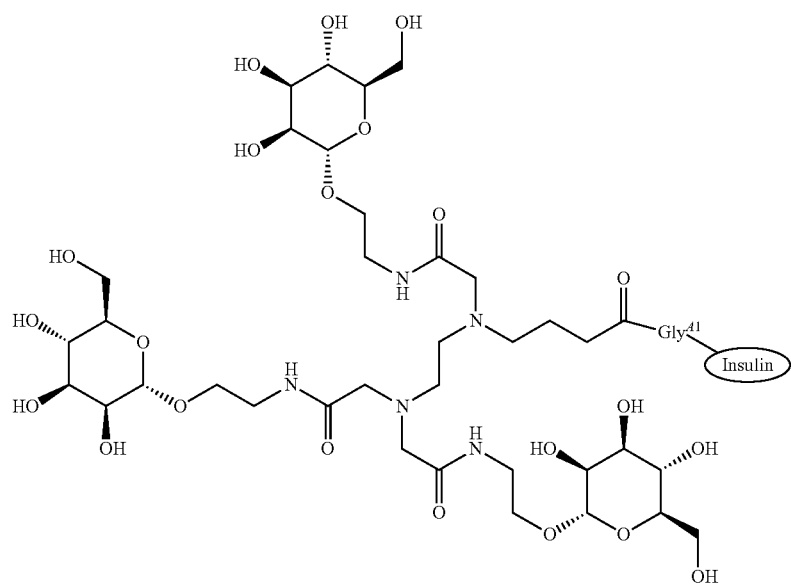

-continued
IOC-9
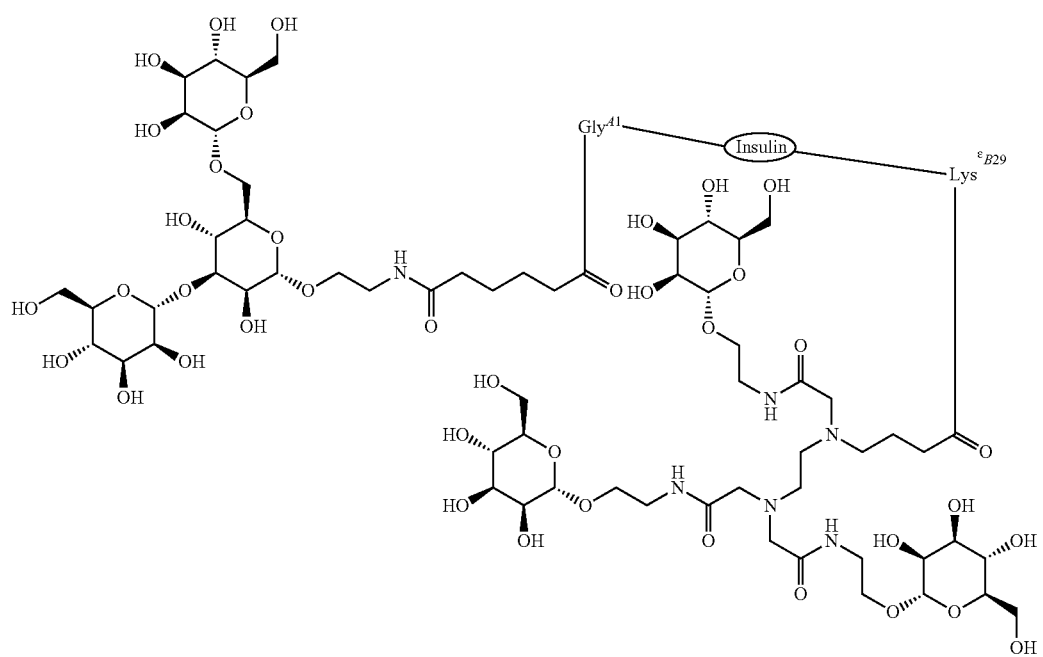
IOC-10
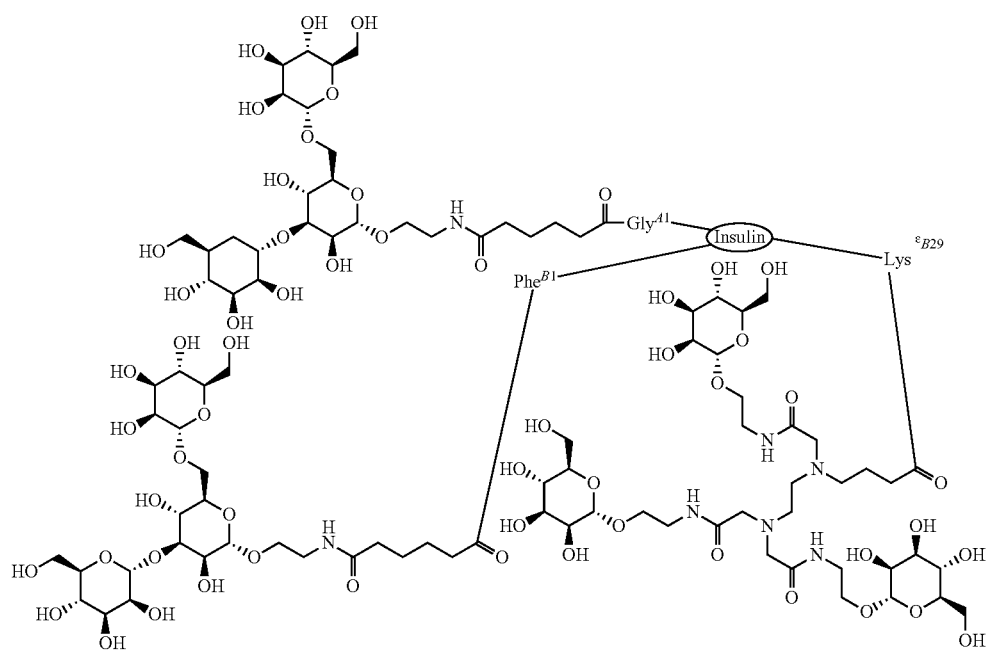

IOC-11
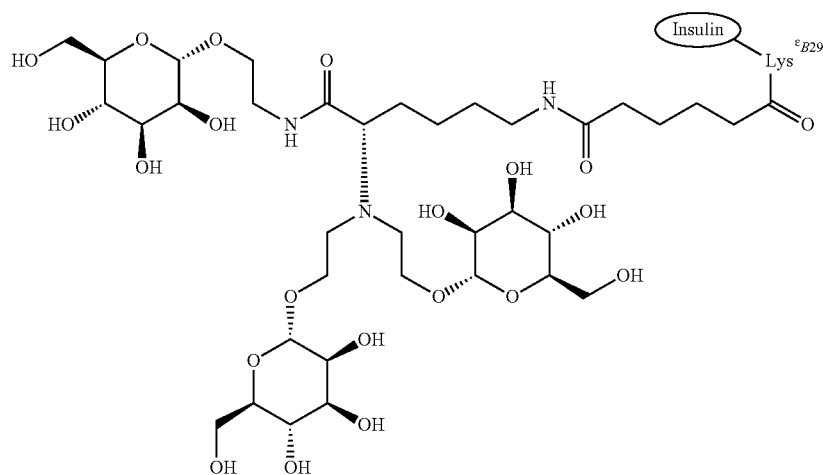
IOC-12
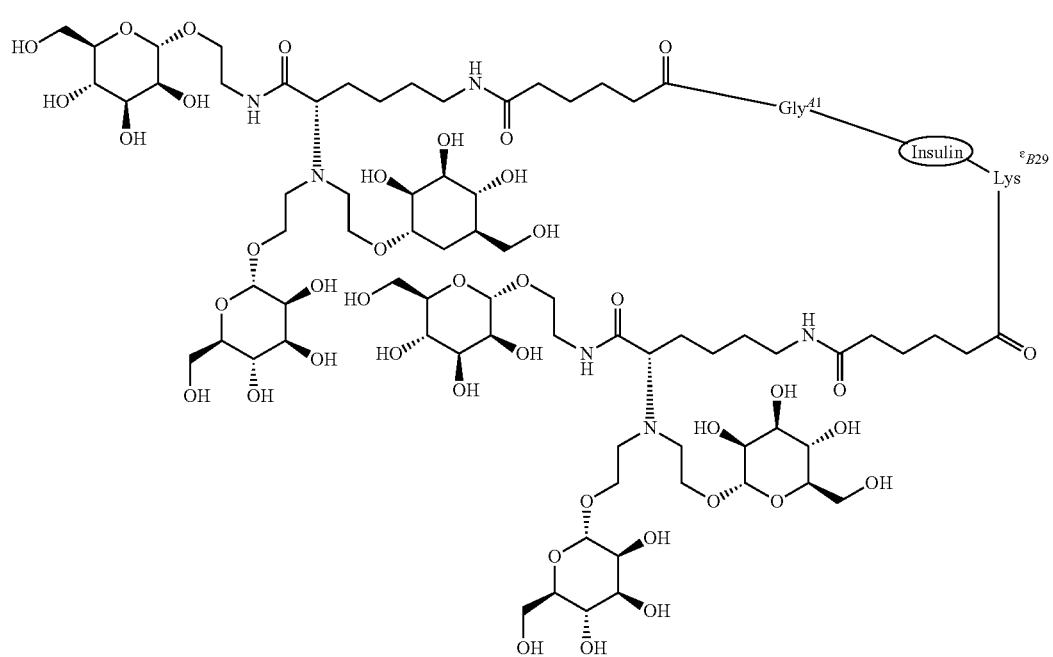

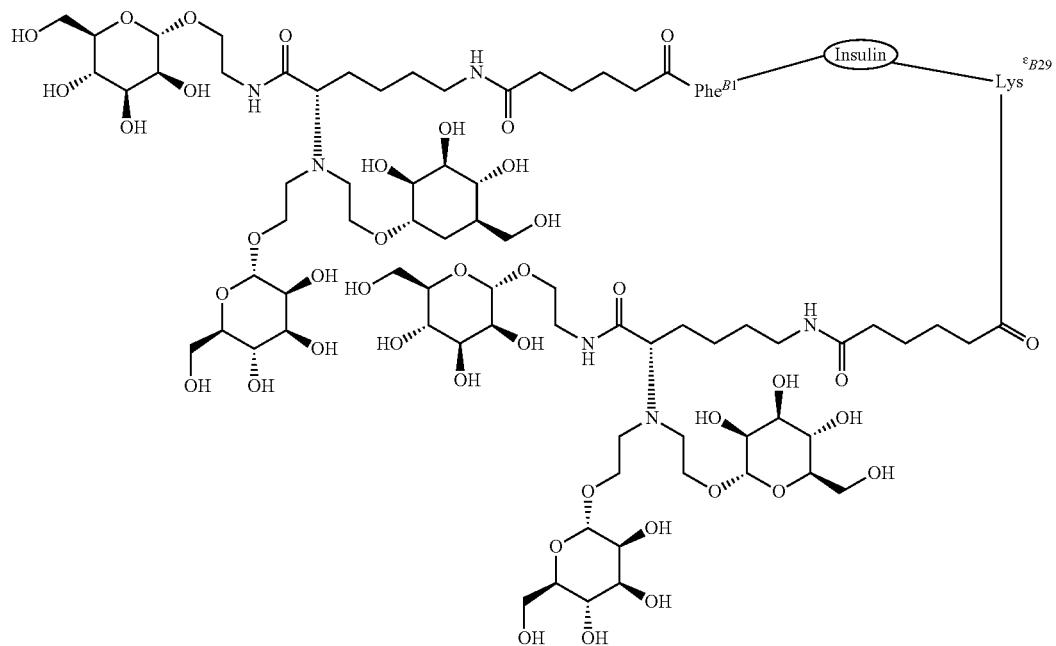
IOC-13
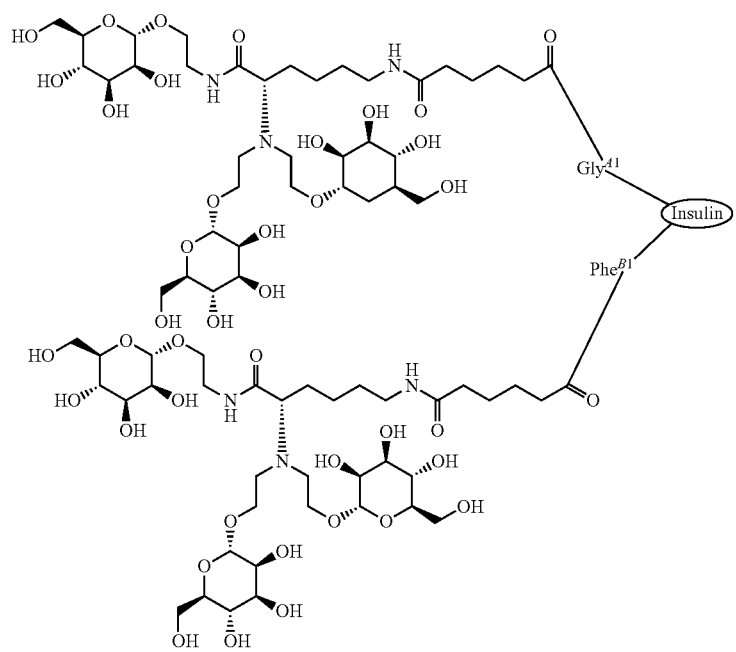
IOC-14

IOC-15
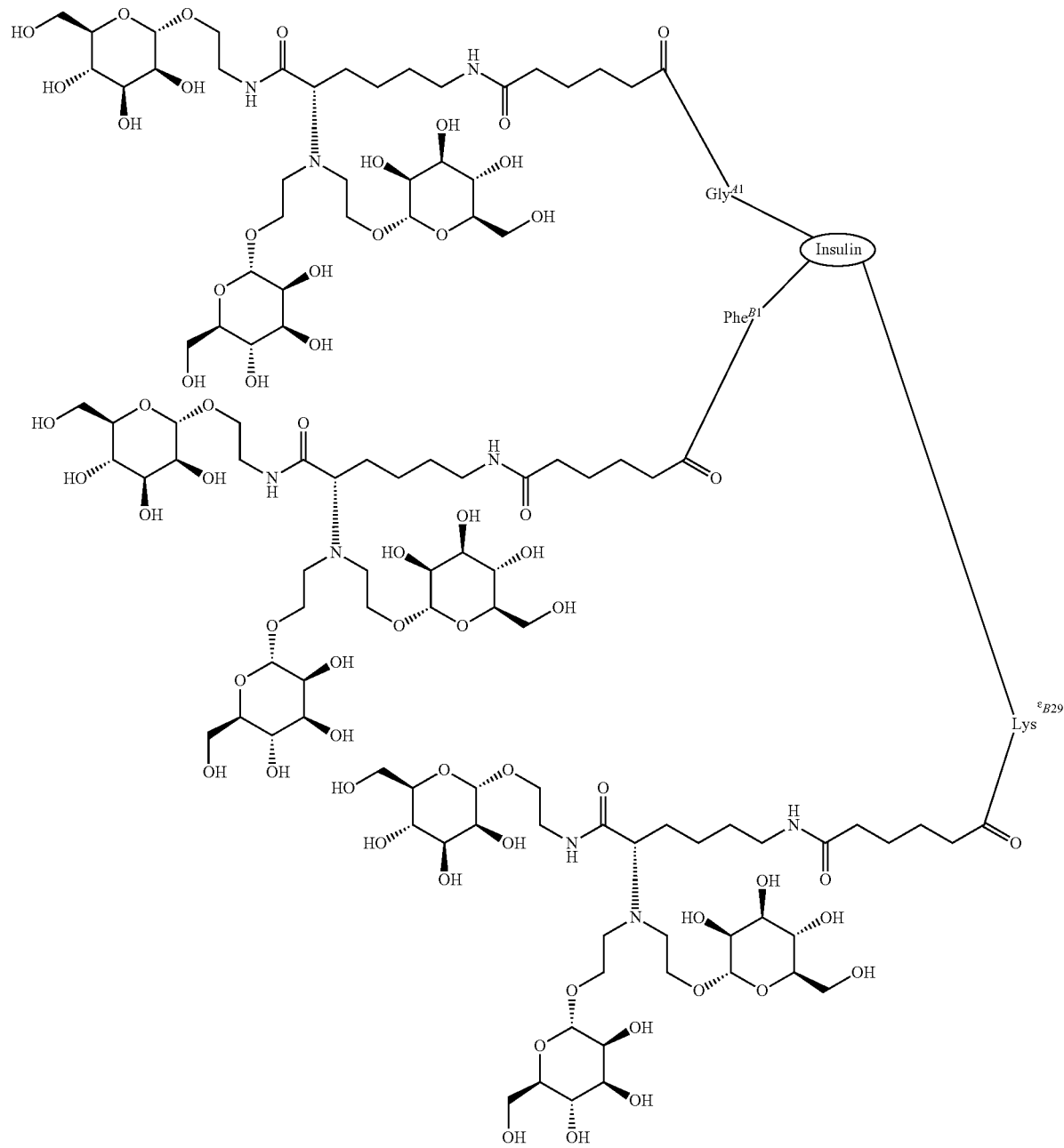

IOC-16
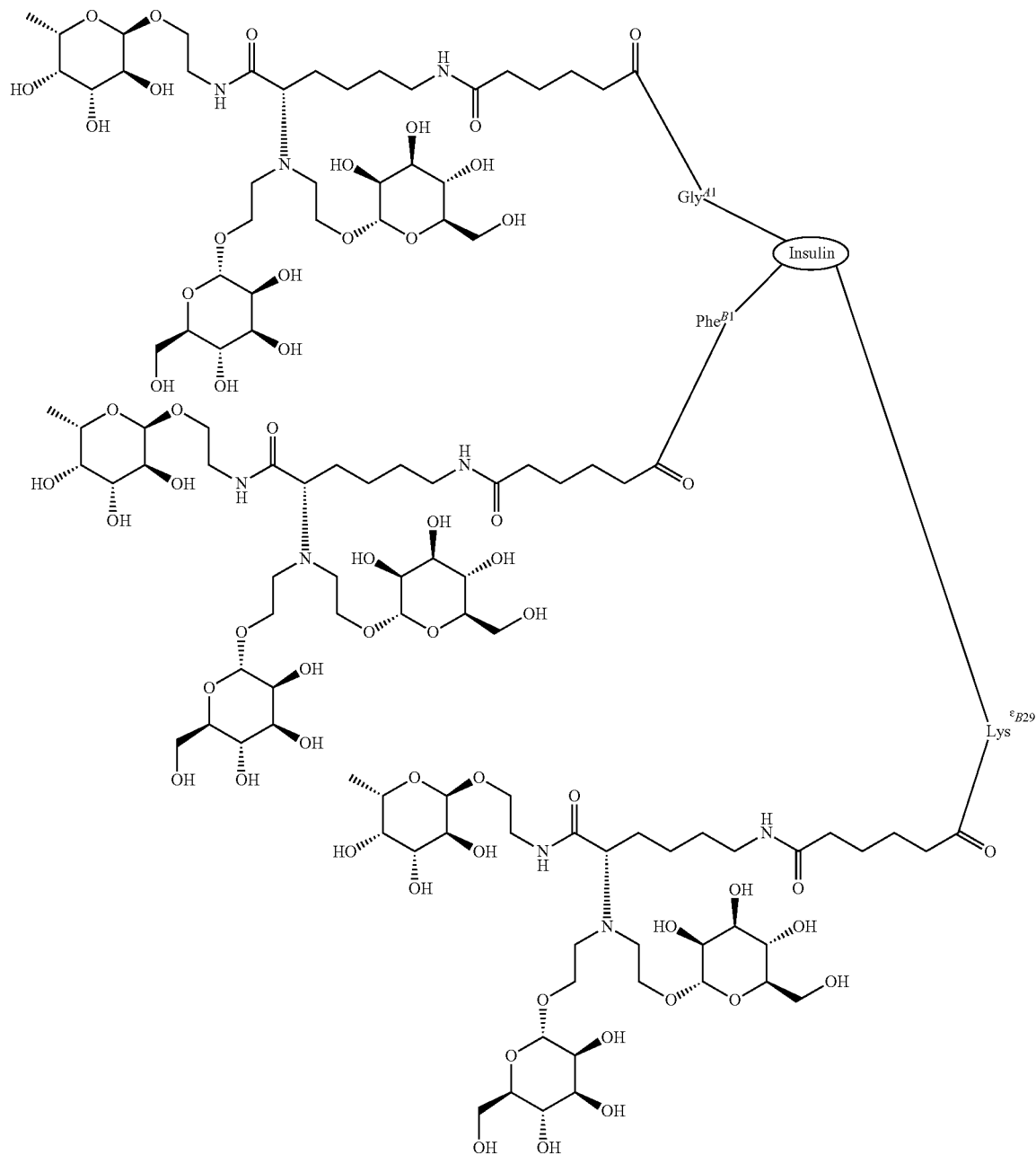

-continued
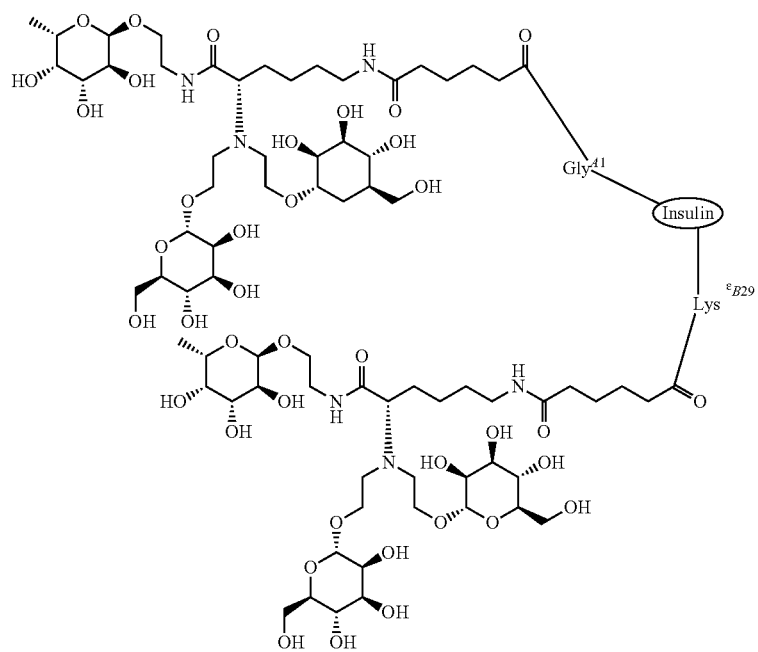
IOC-17
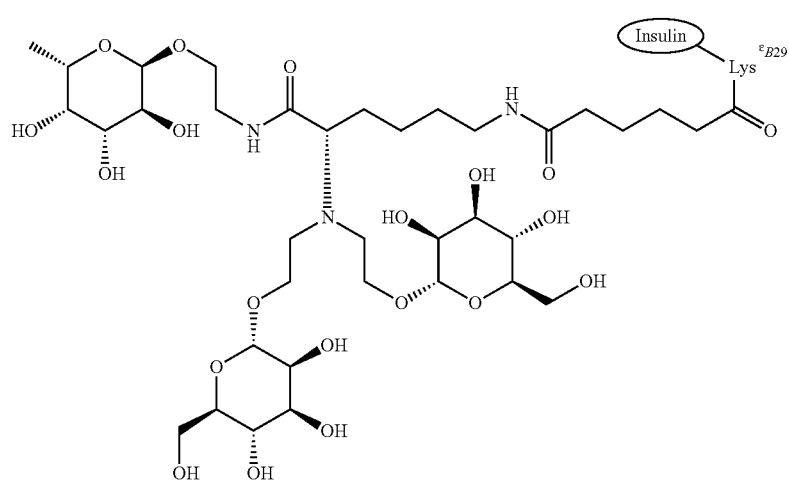
IOC-18

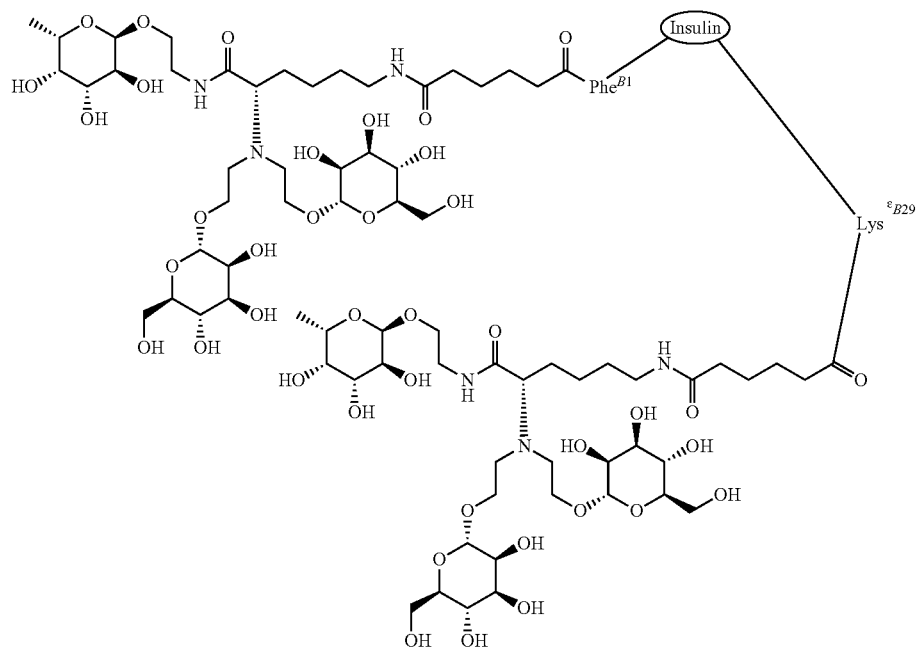
IOC-19
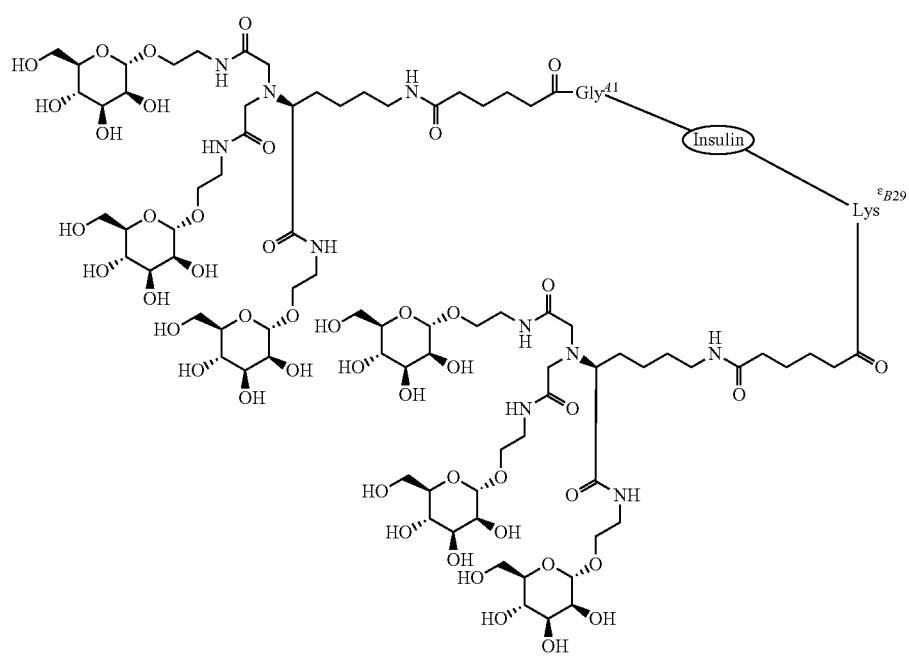
IOC-20

IOC-21
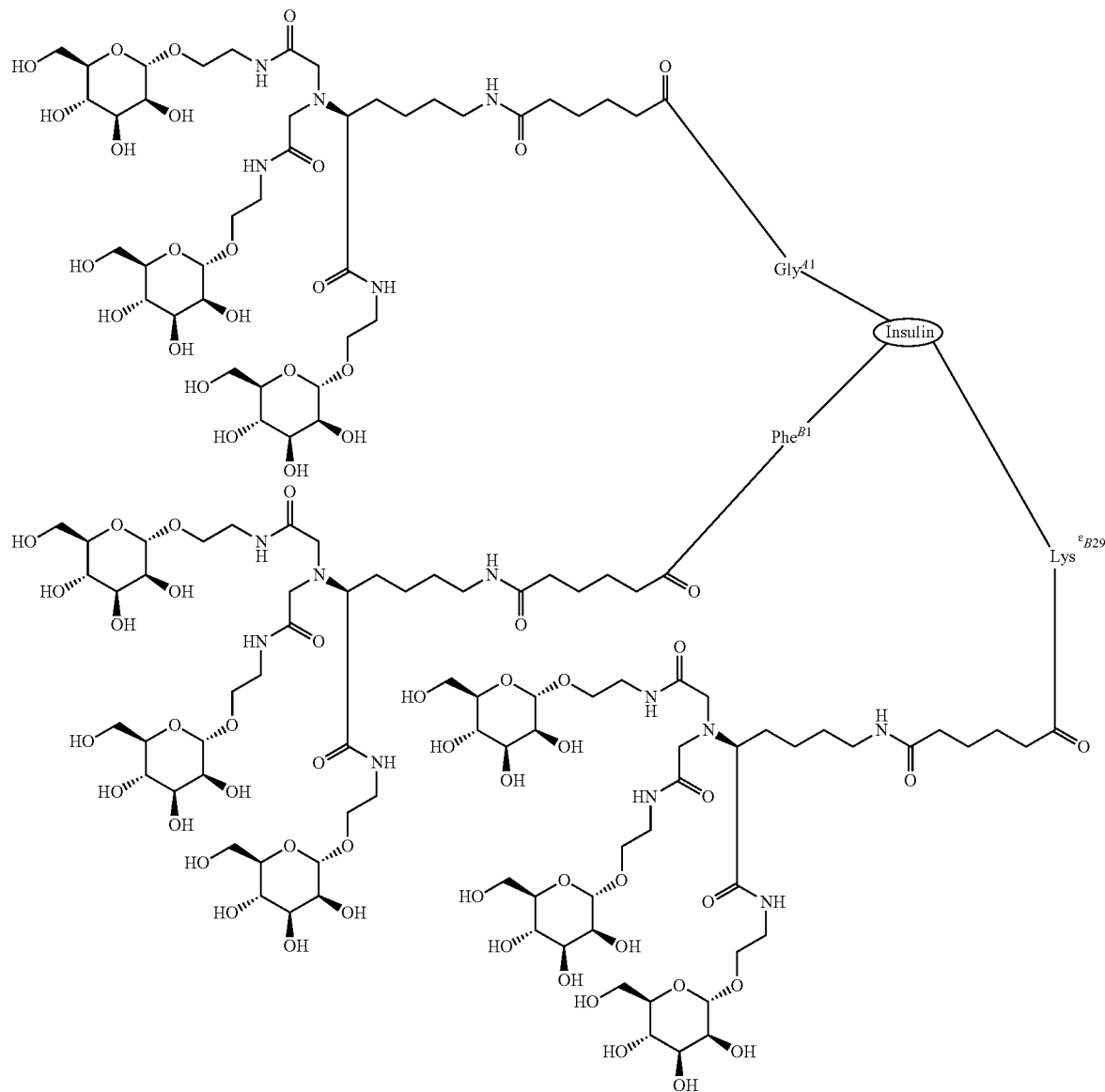

IOC-22
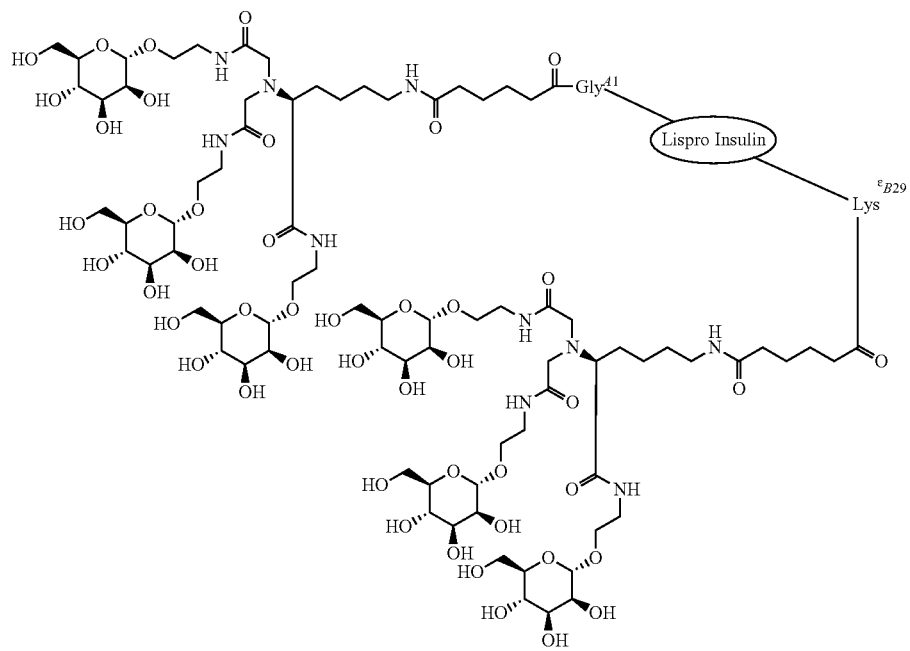
IOC-23
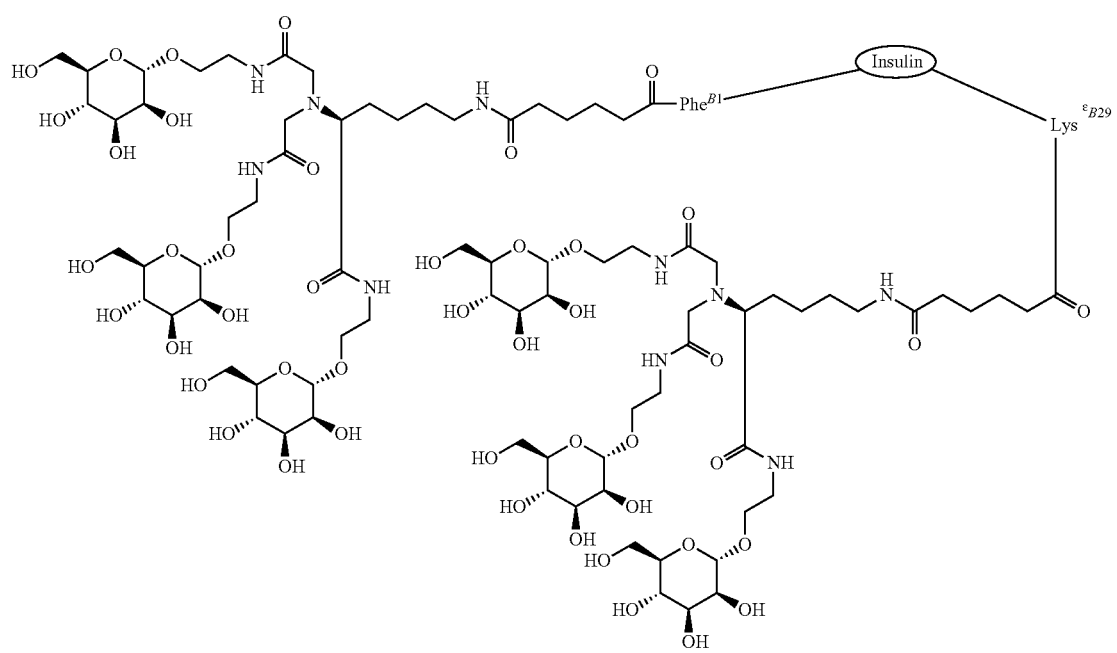

IOC-24
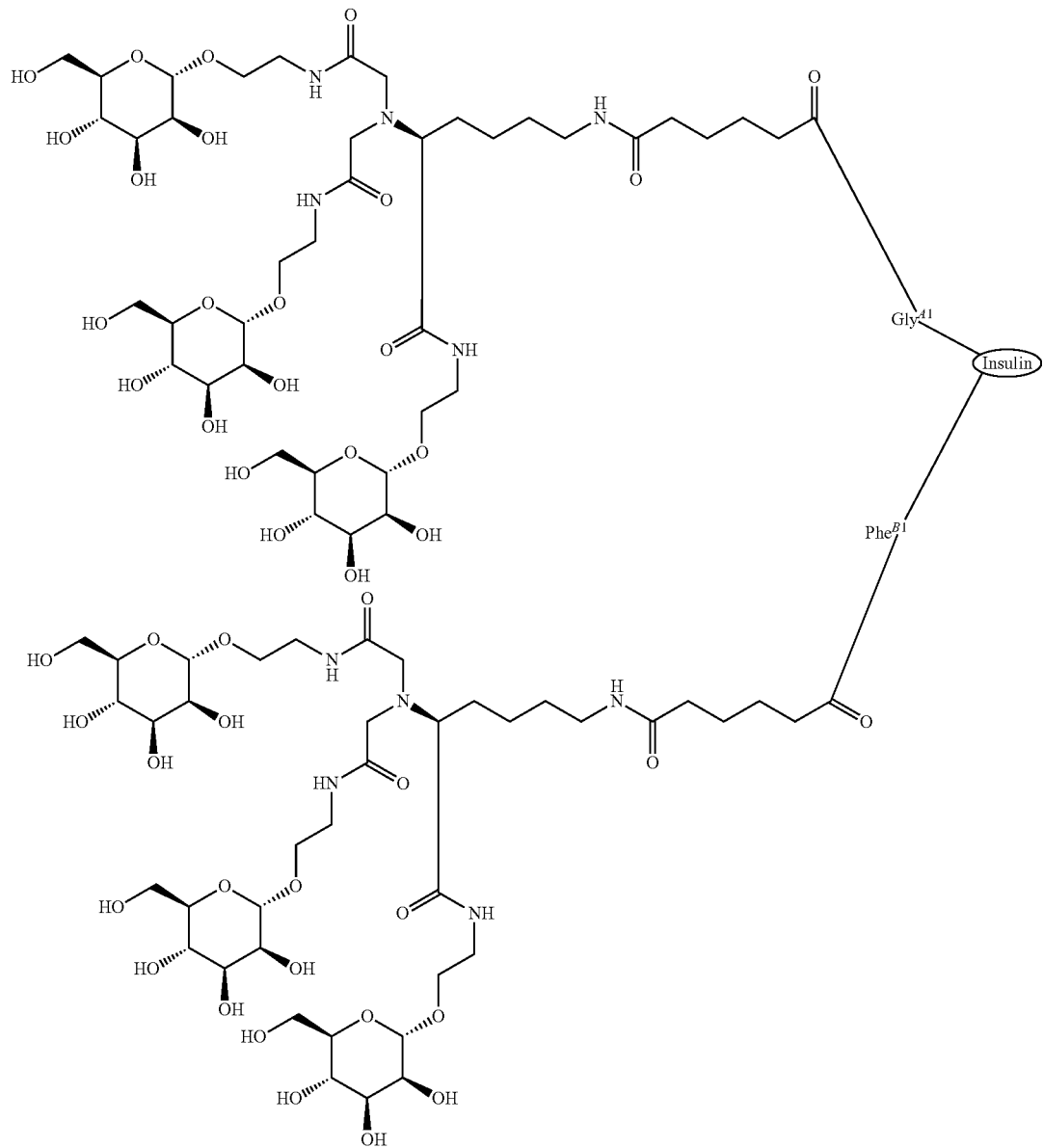

IOC-25
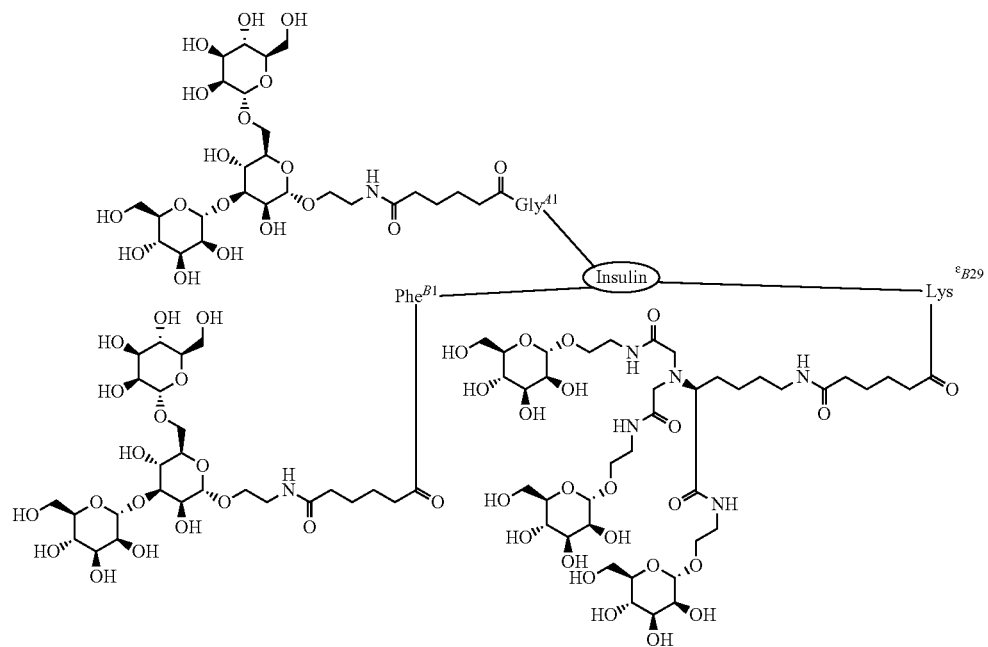
IOC-26
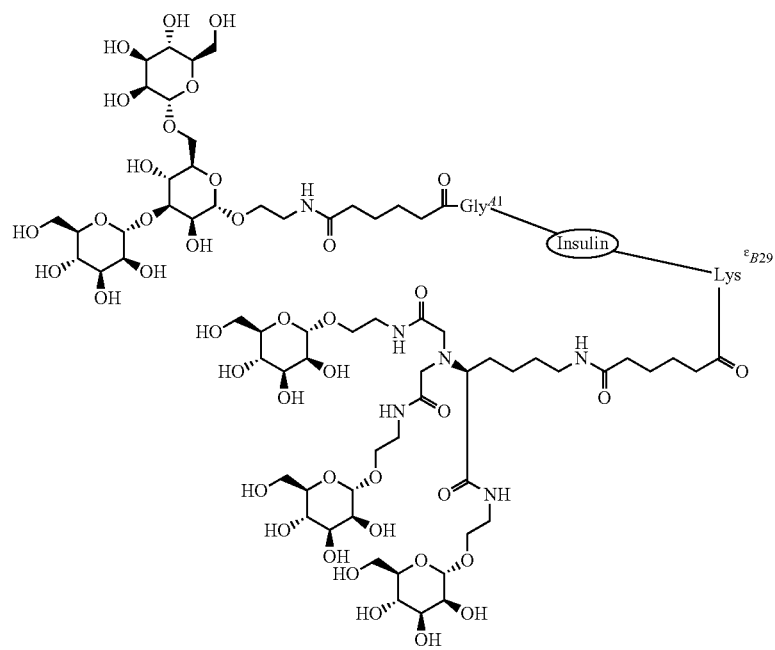

IOC-27
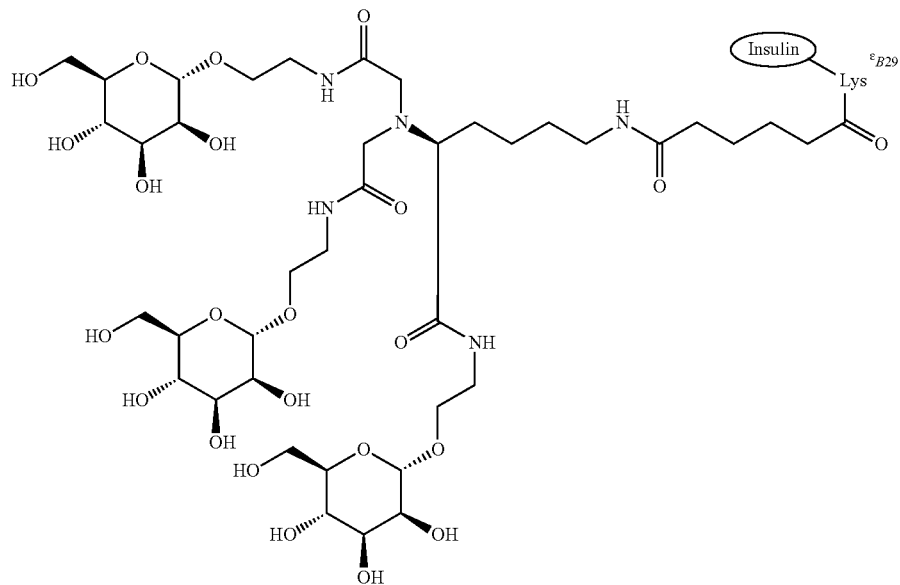
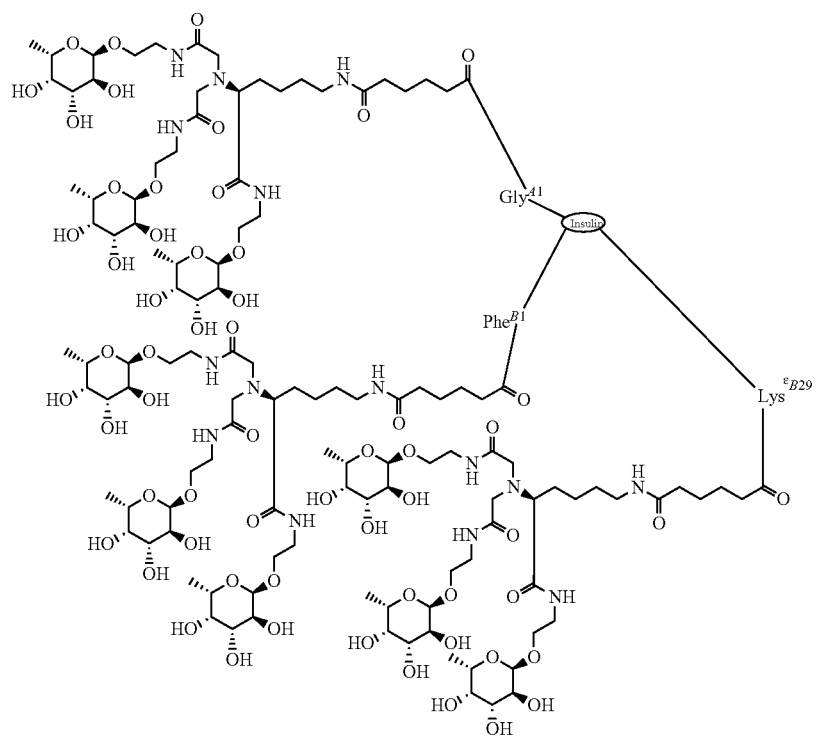

-continued
IOC-29
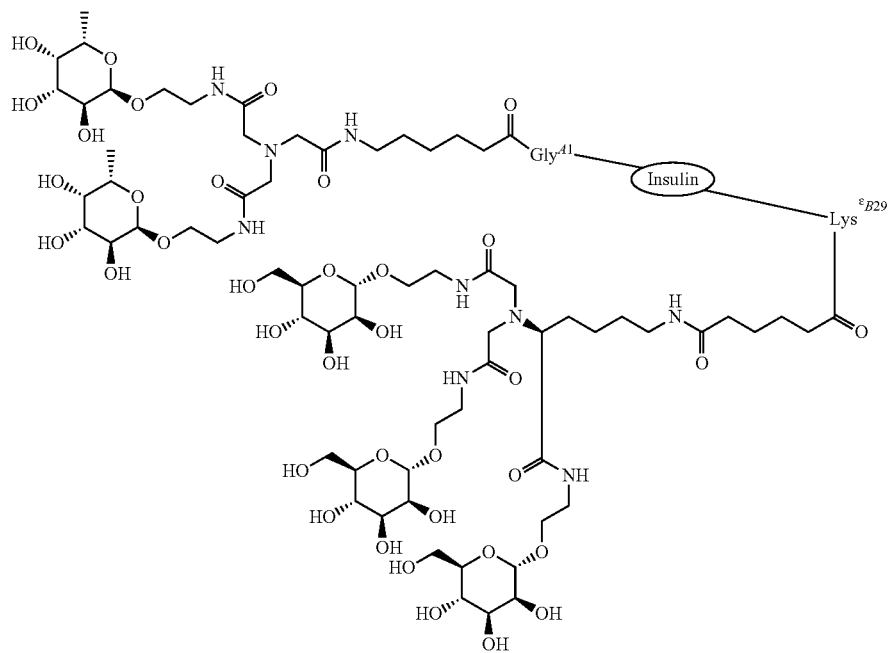
IOC-30
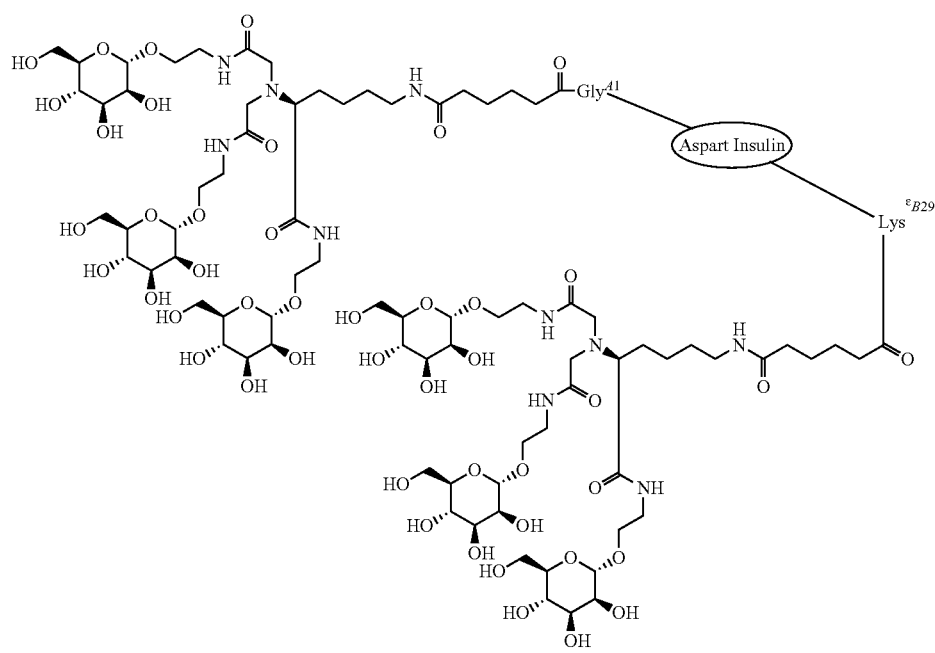

IOC-31
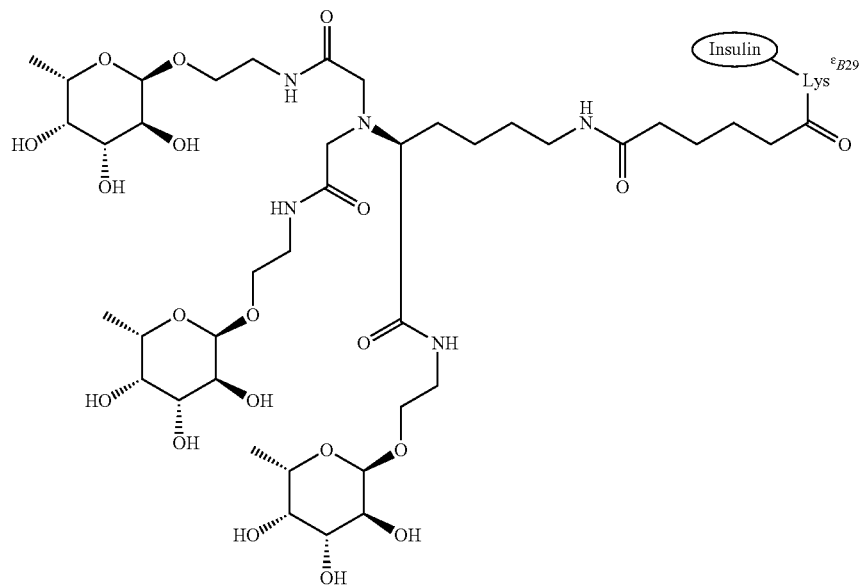
IOC-32
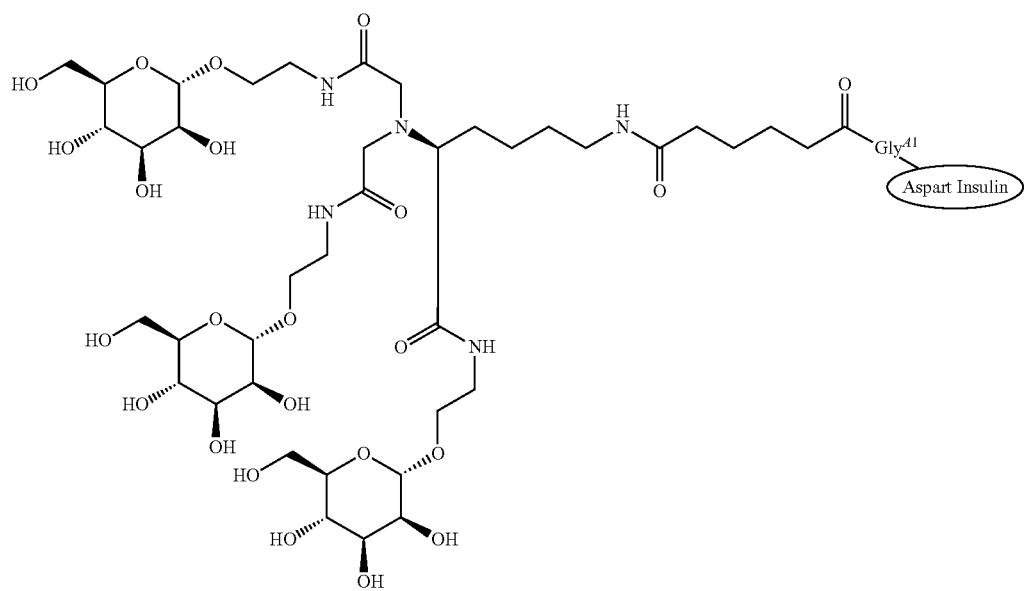

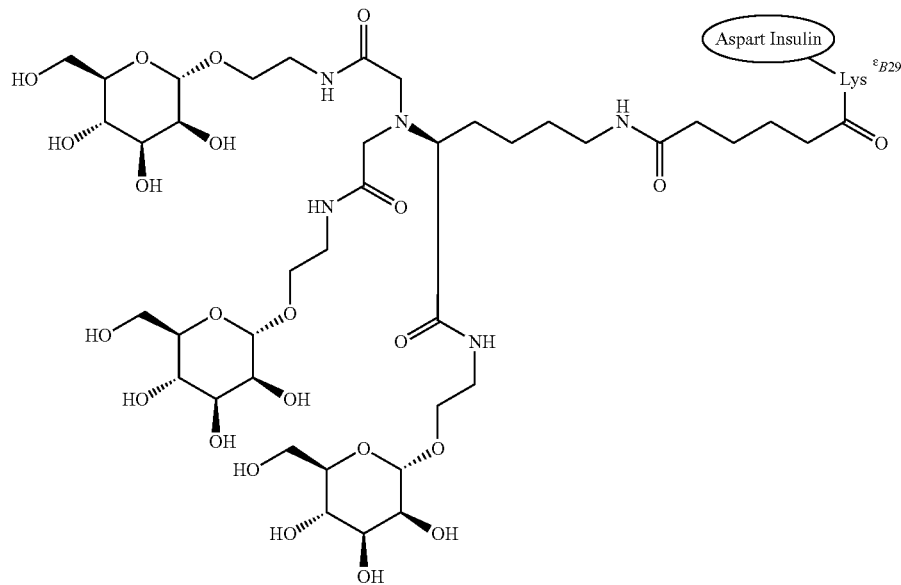
IOC-33
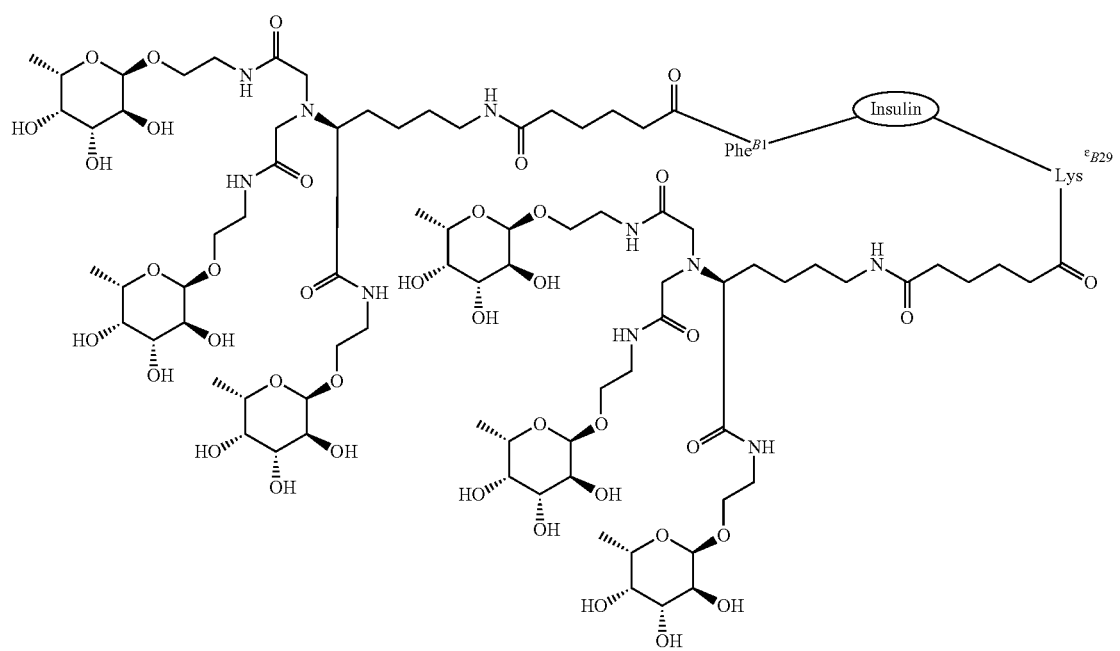
IOC-34

IOC-35
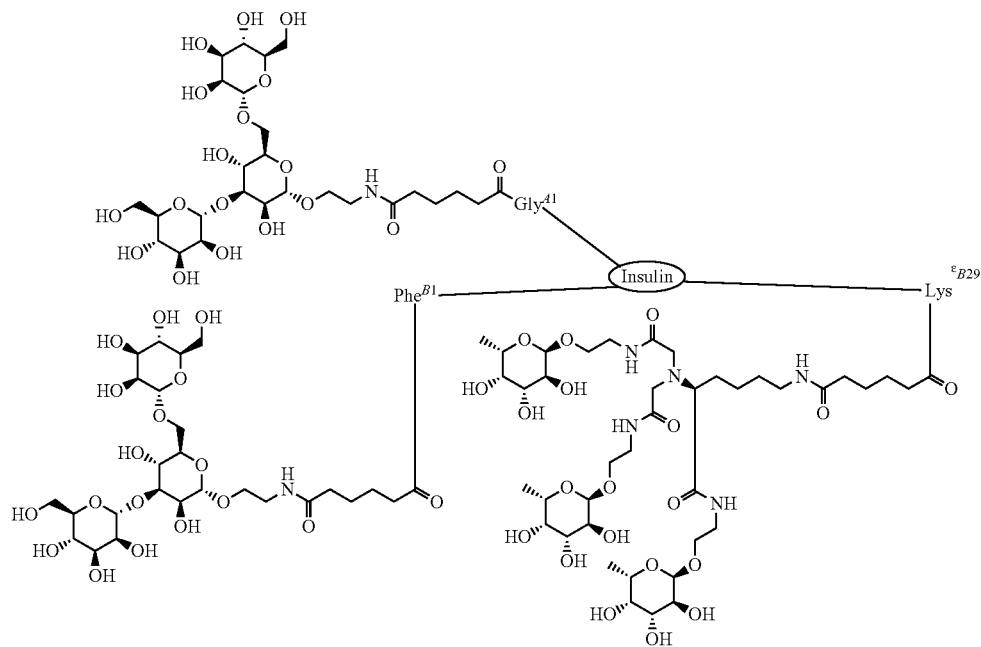
IOC-36
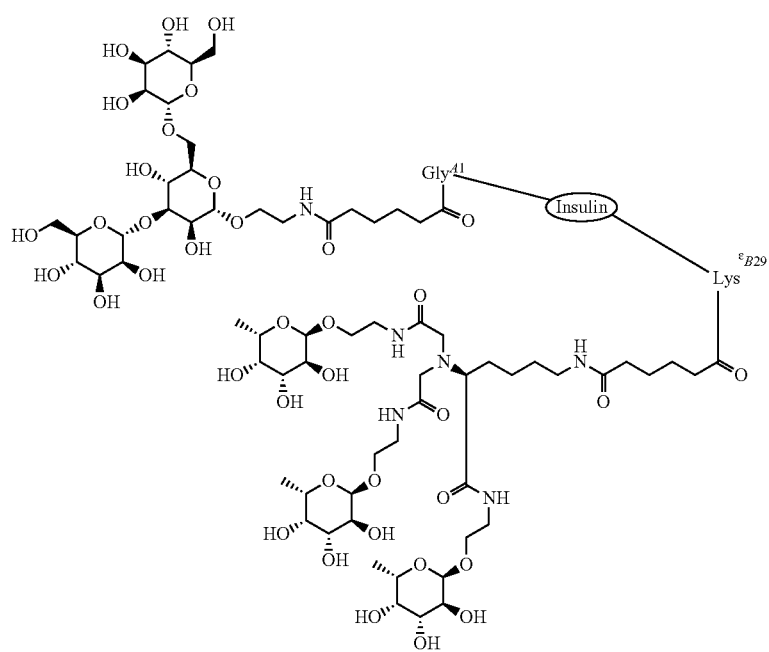

-continued
IOC-37
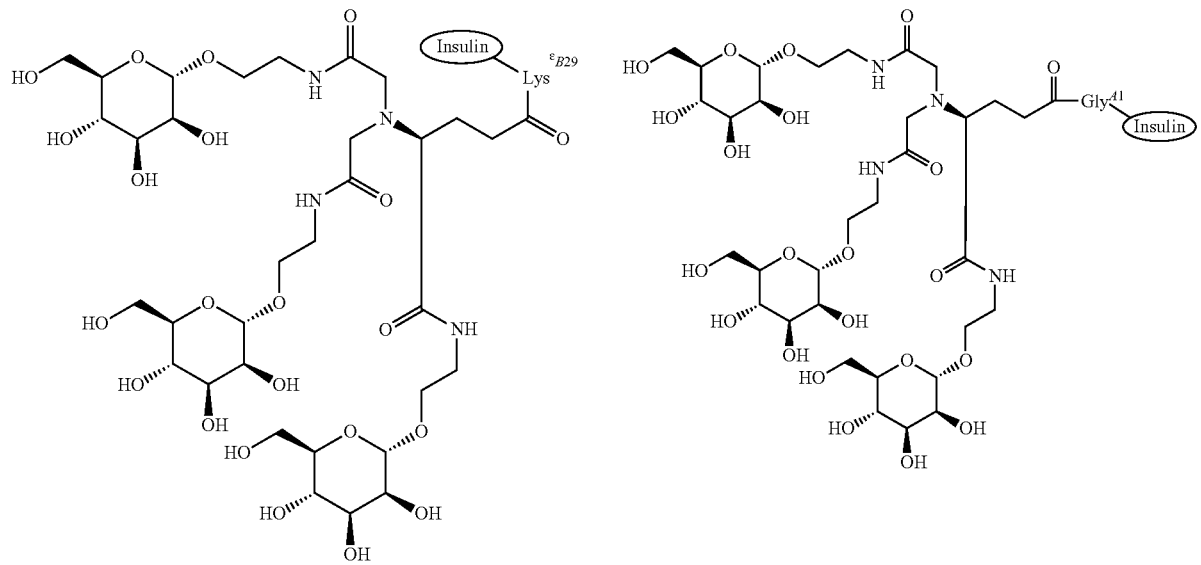
IOC-38
IOC-39
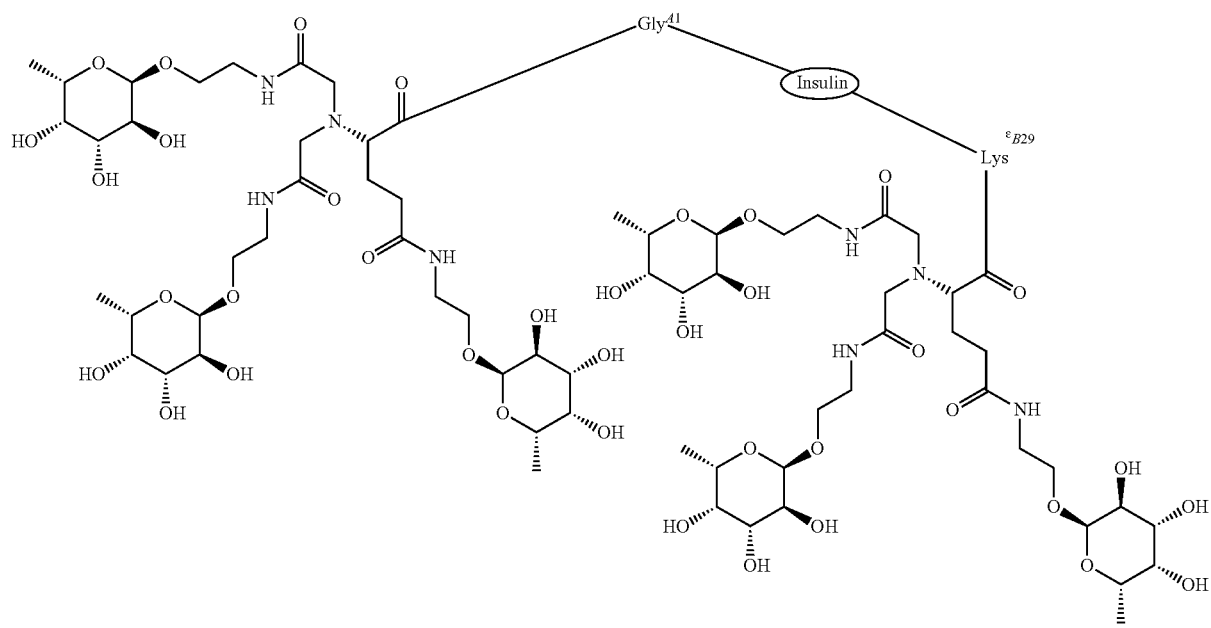

IOC-40
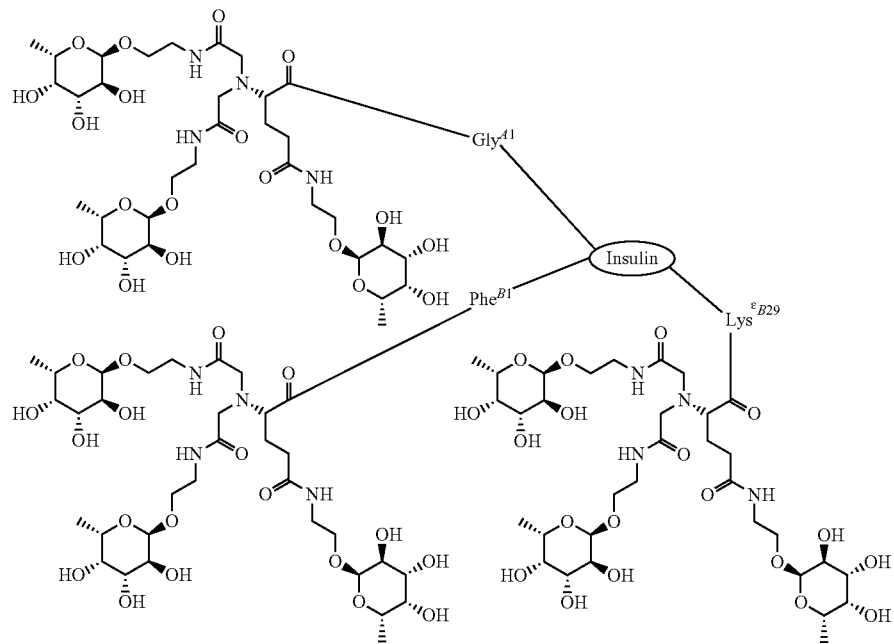
IOC-41
IOC-42
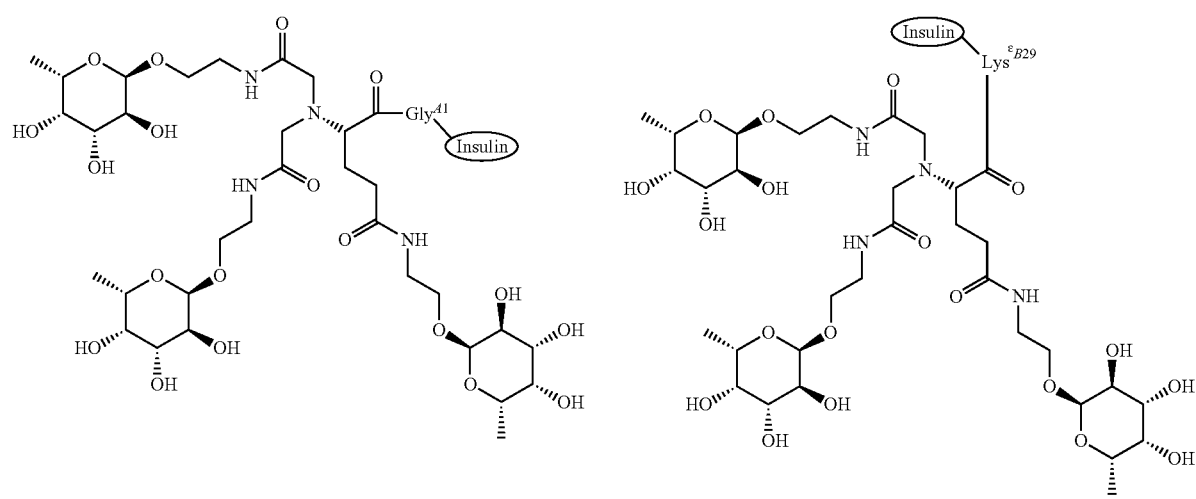

-continued
IOC-43
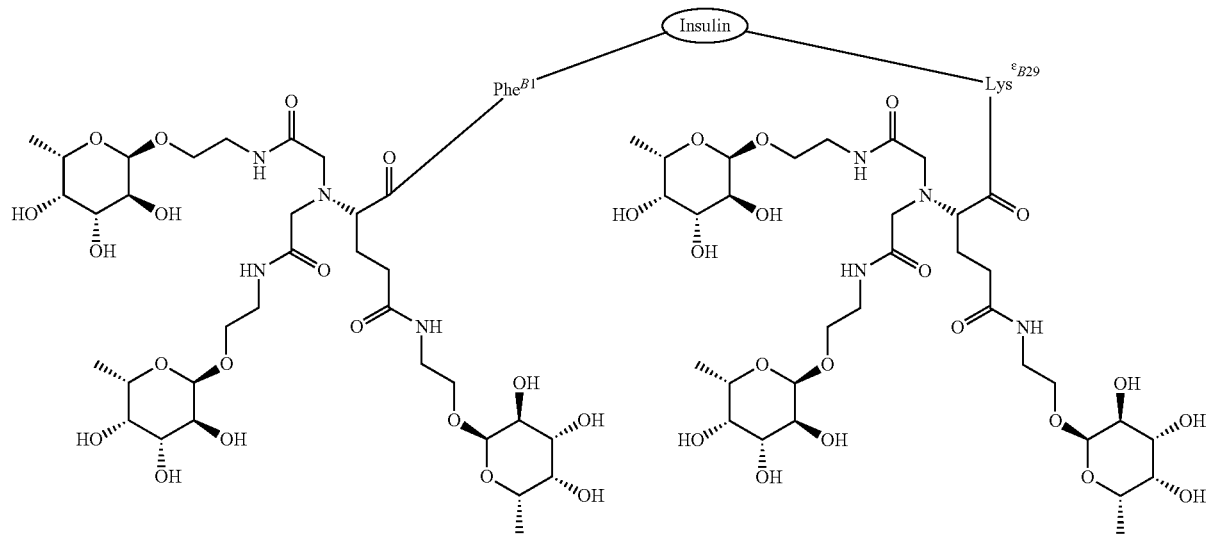
IOC-44
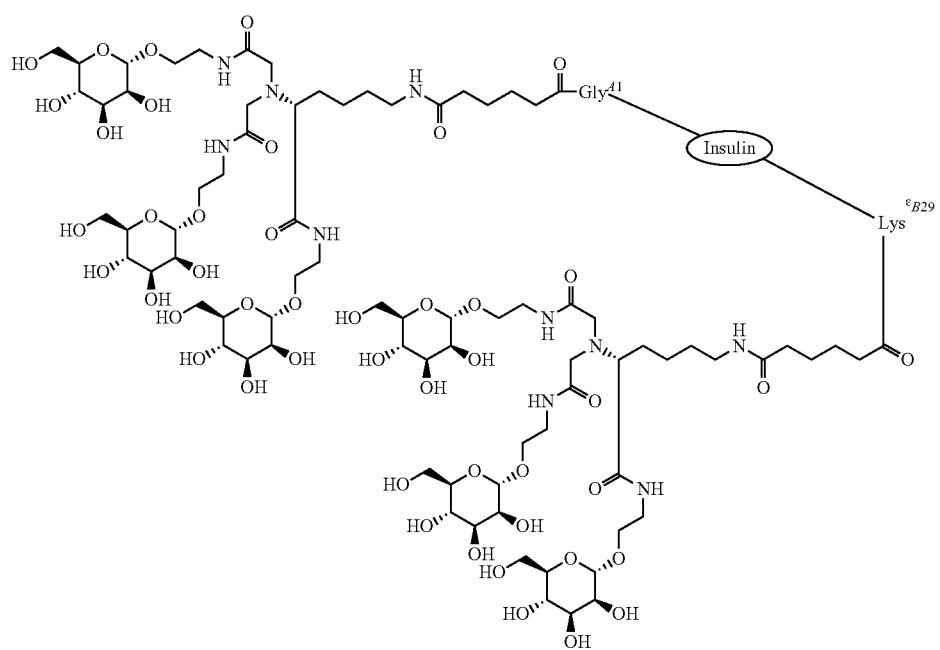

IOC-45
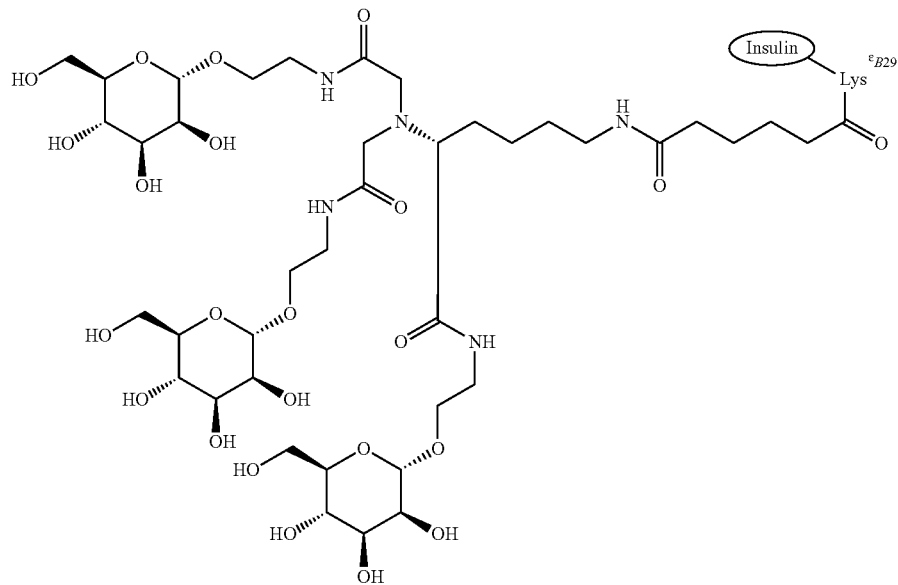
IOC-46
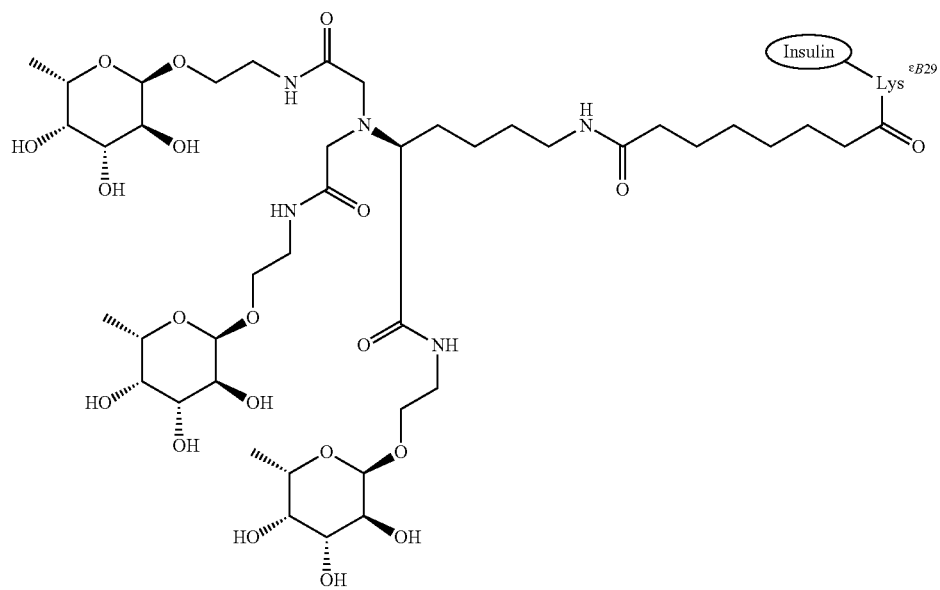

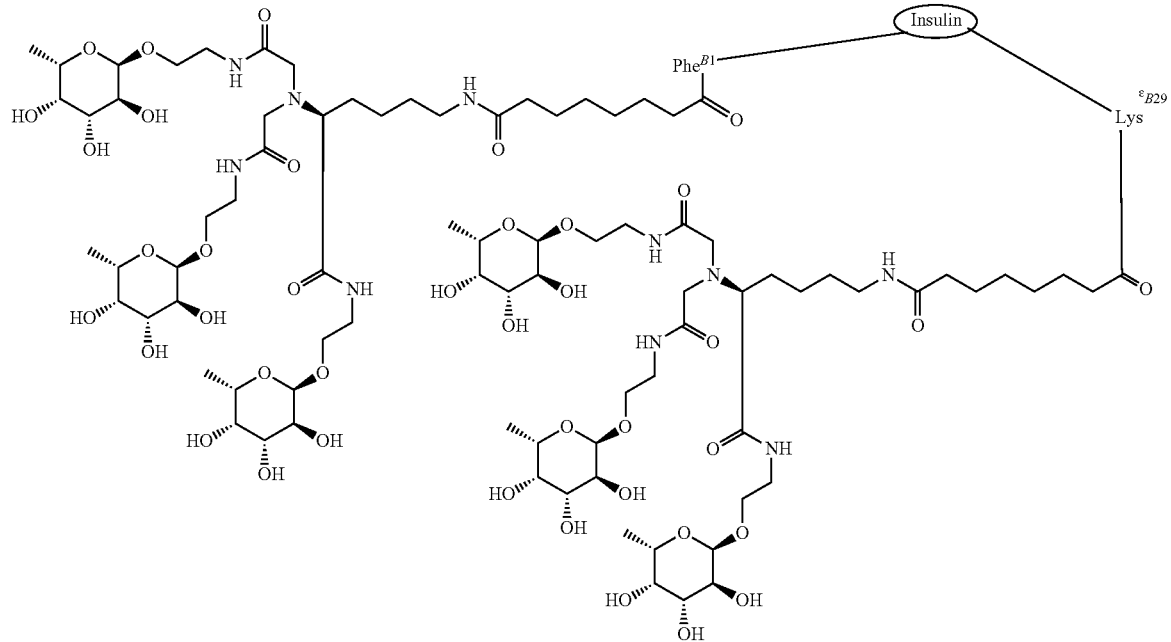
IOC-47
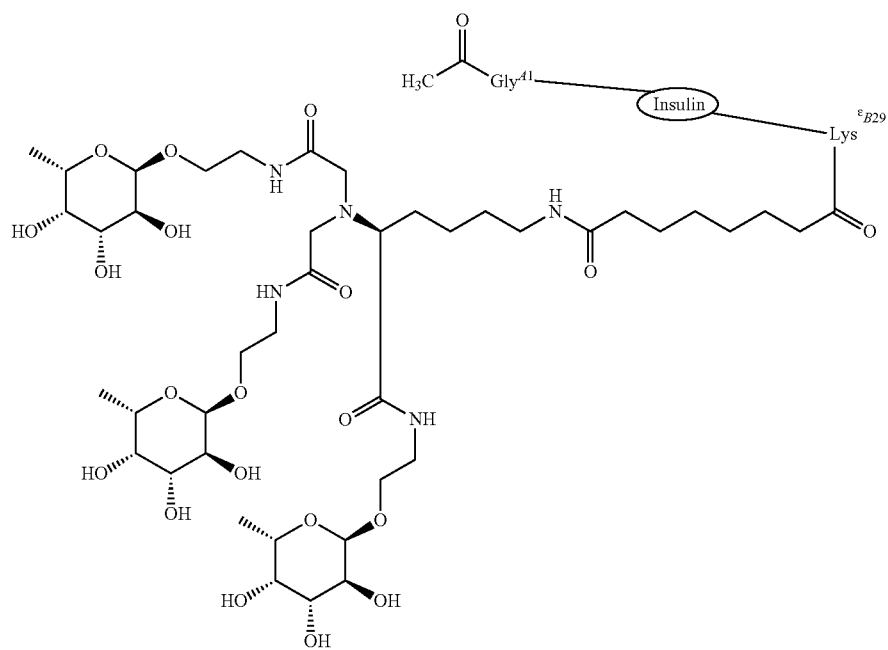
IOC-48

IOC-49
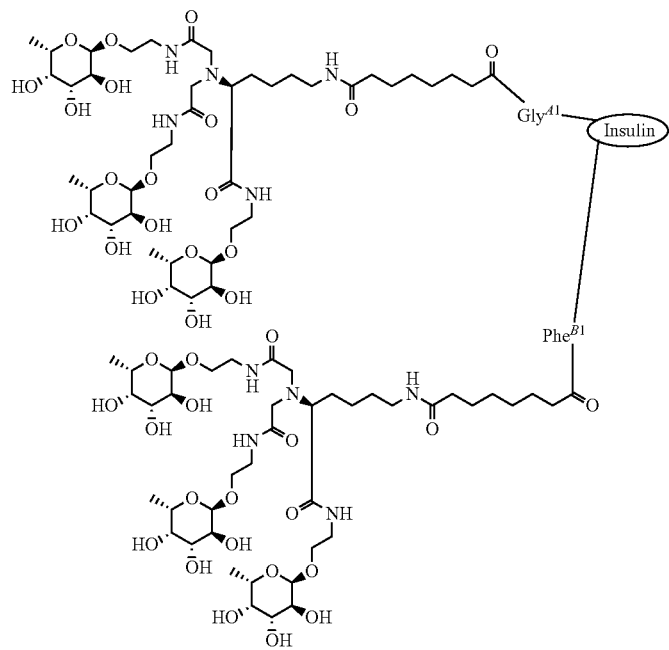
IOC-50
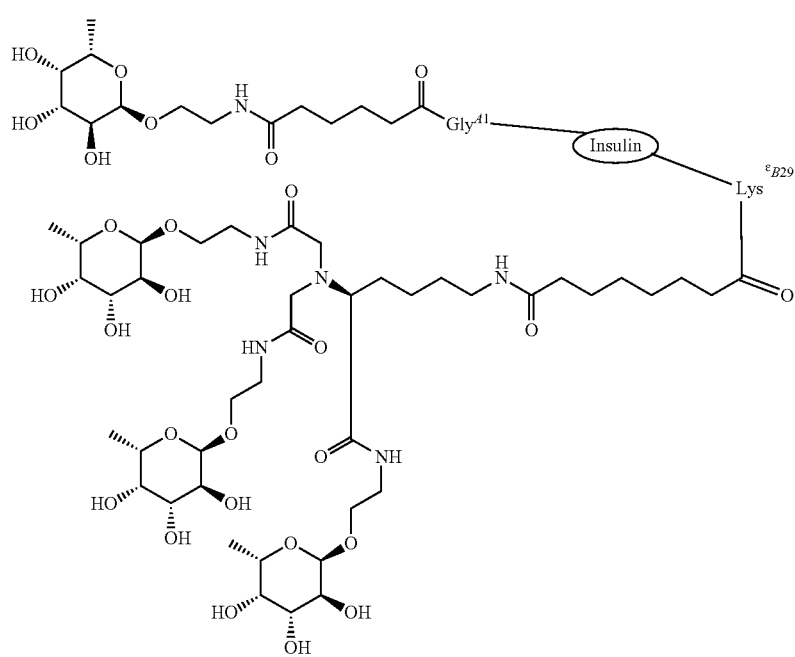

IOC-51
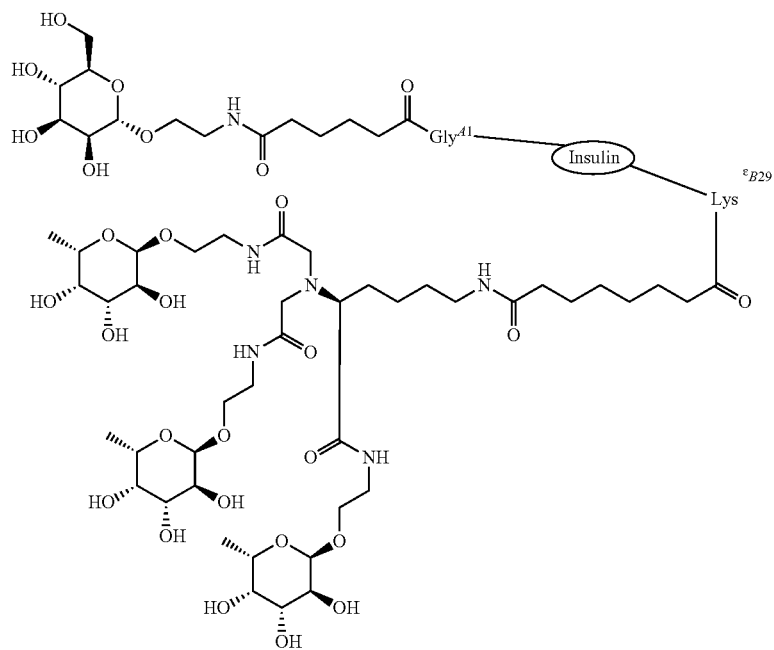
IOC-52
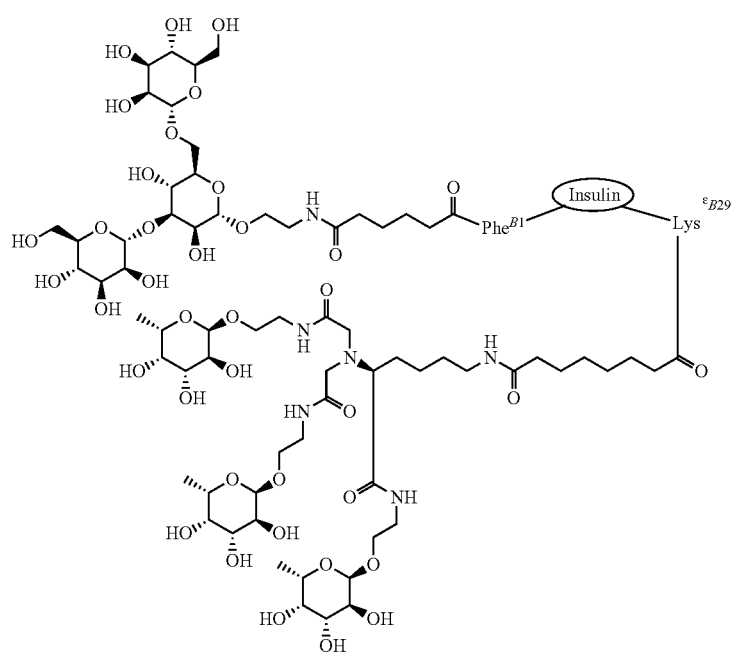

IOC-53
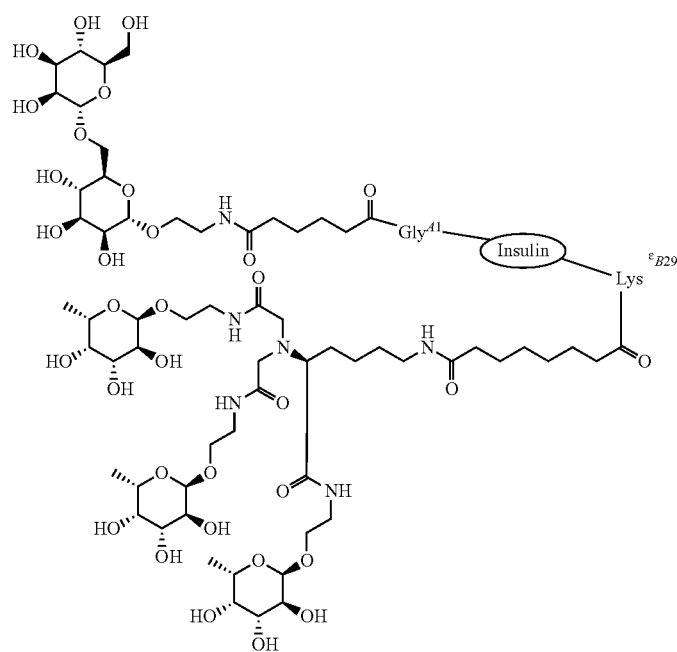
IOC-54
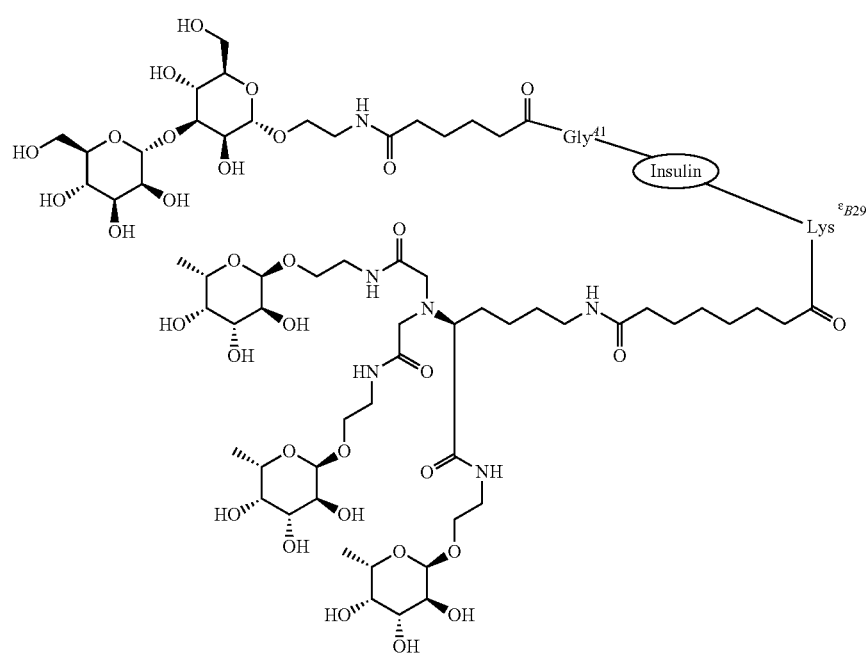

IOC-55
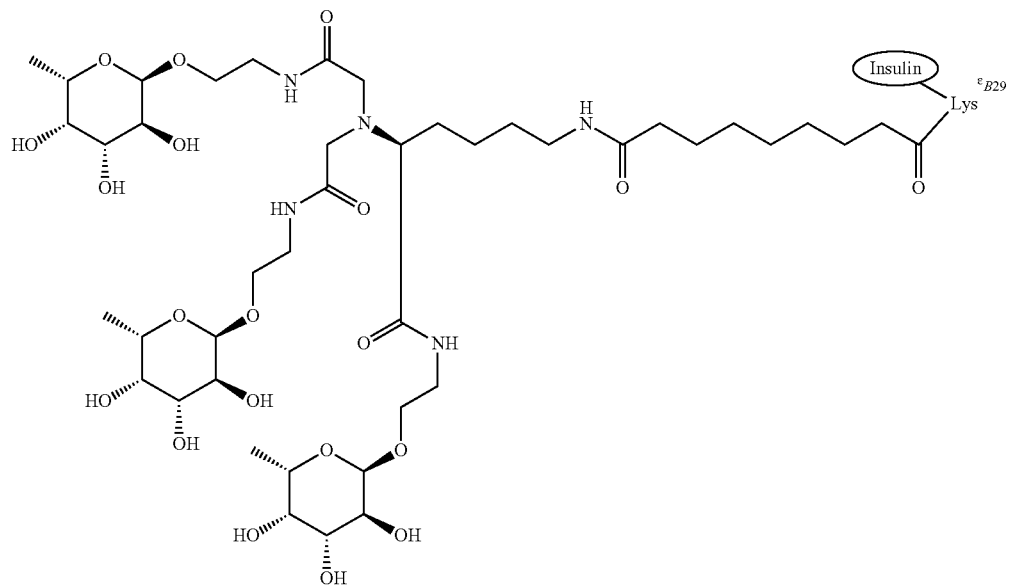
IOC-56
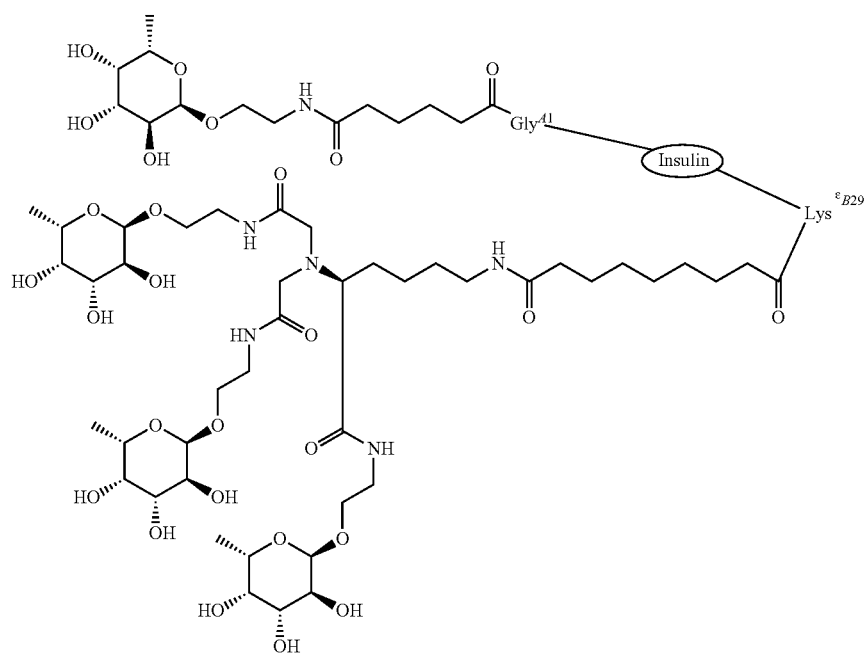

IOC-57
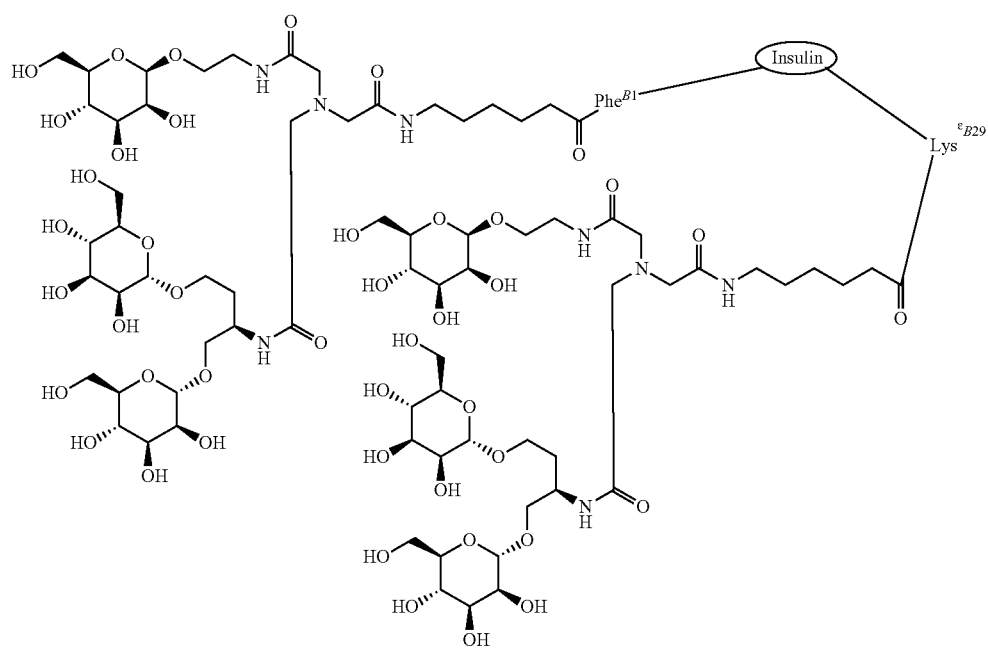
IOC-58
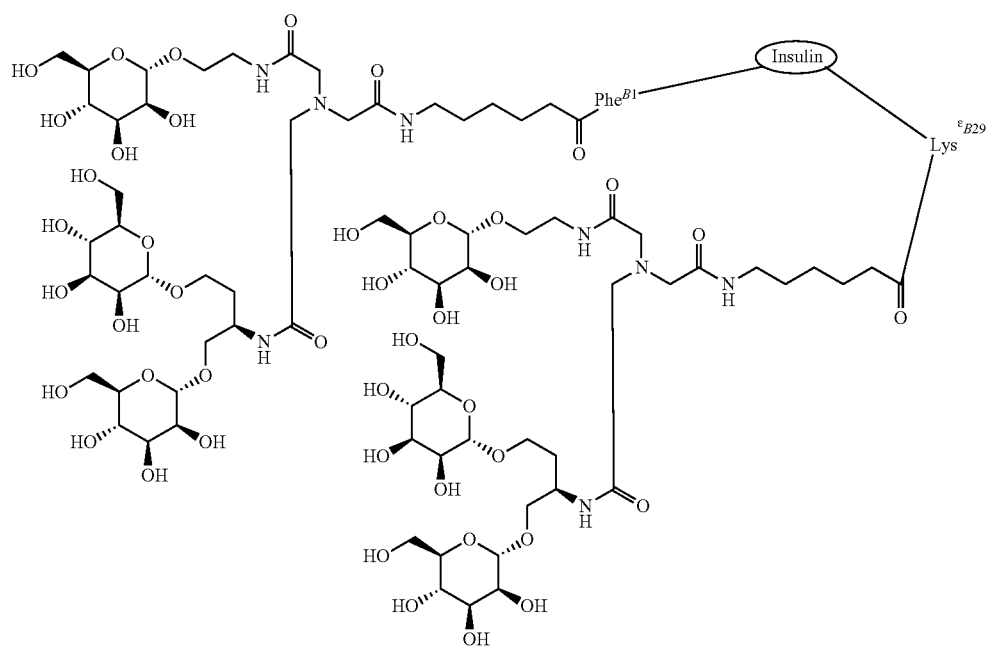

-continued
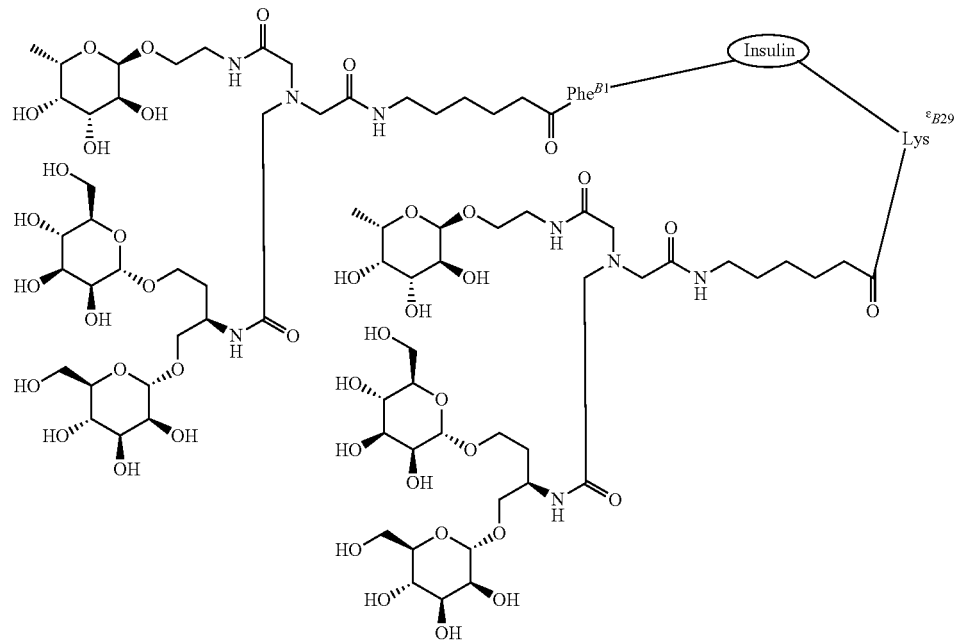
IOC-59
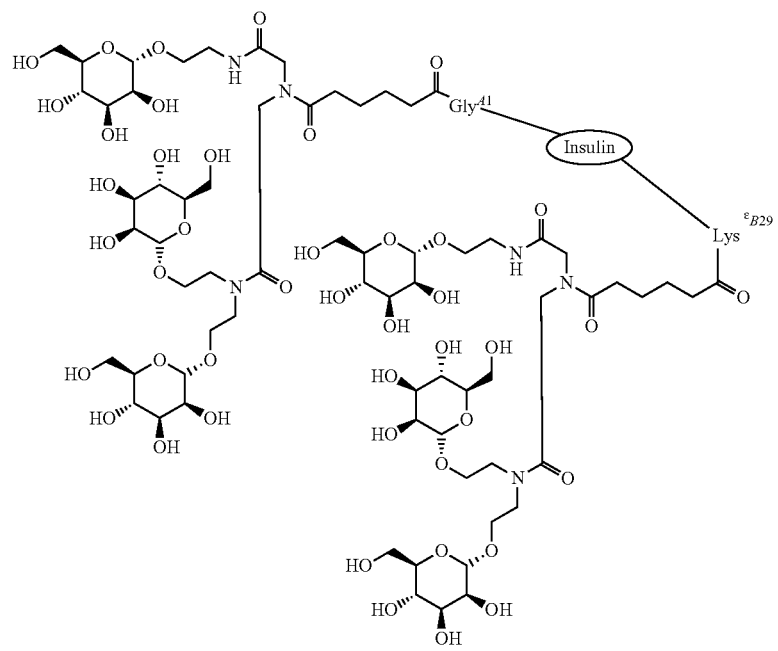
IOC-60

IOC-61
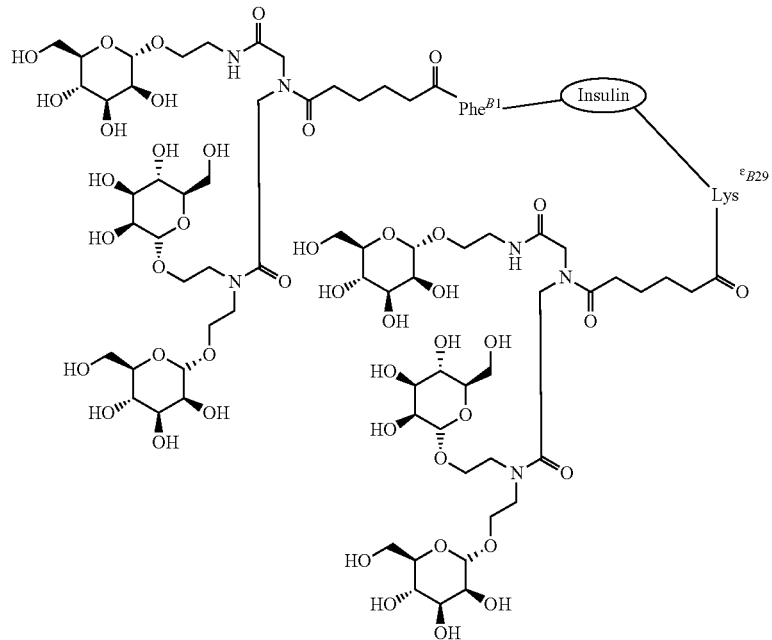
IOC-62
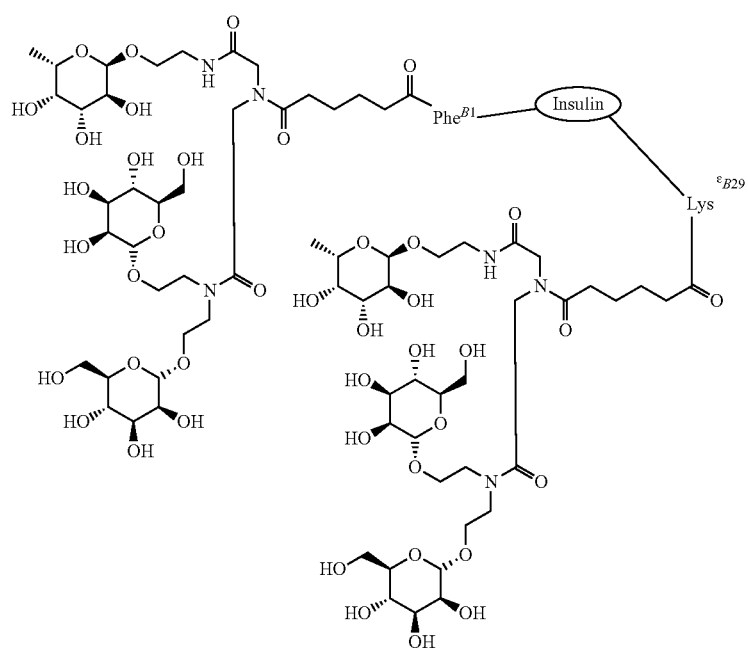

IOC-63
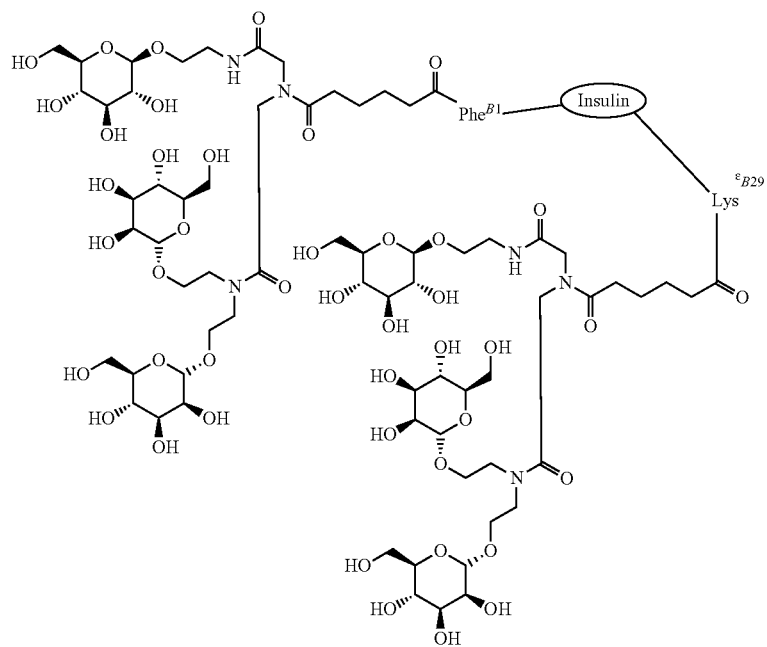

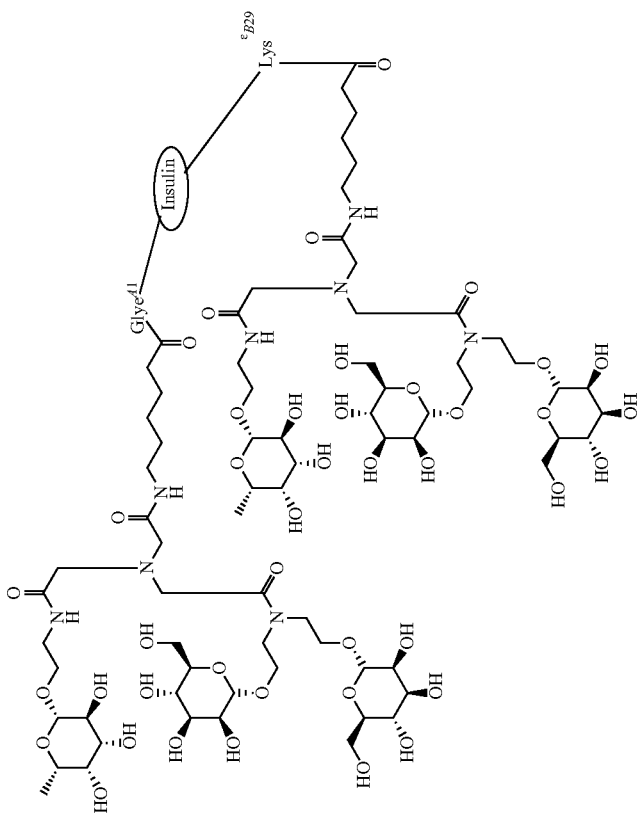
IOC-65
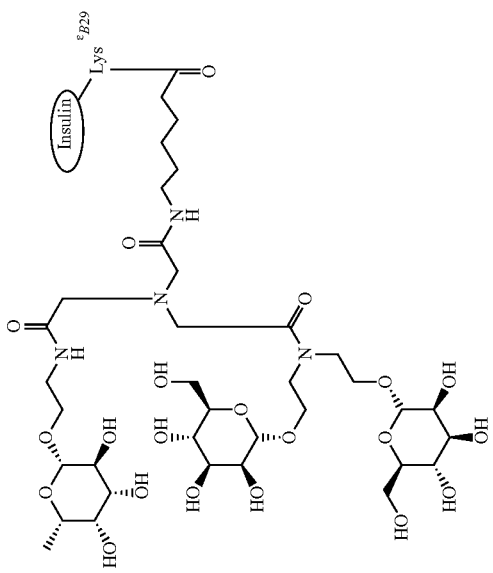
IOC-64

-continued
IOC-66
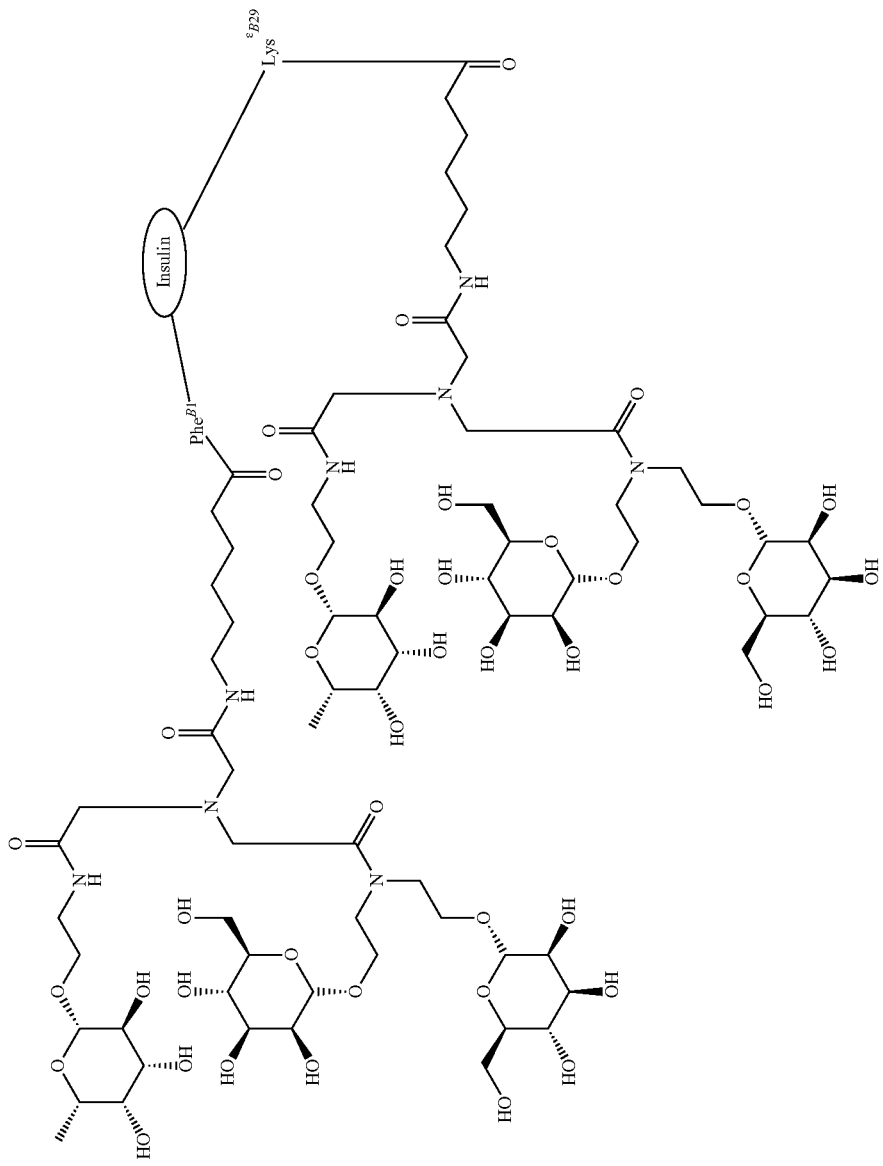

IOC-67
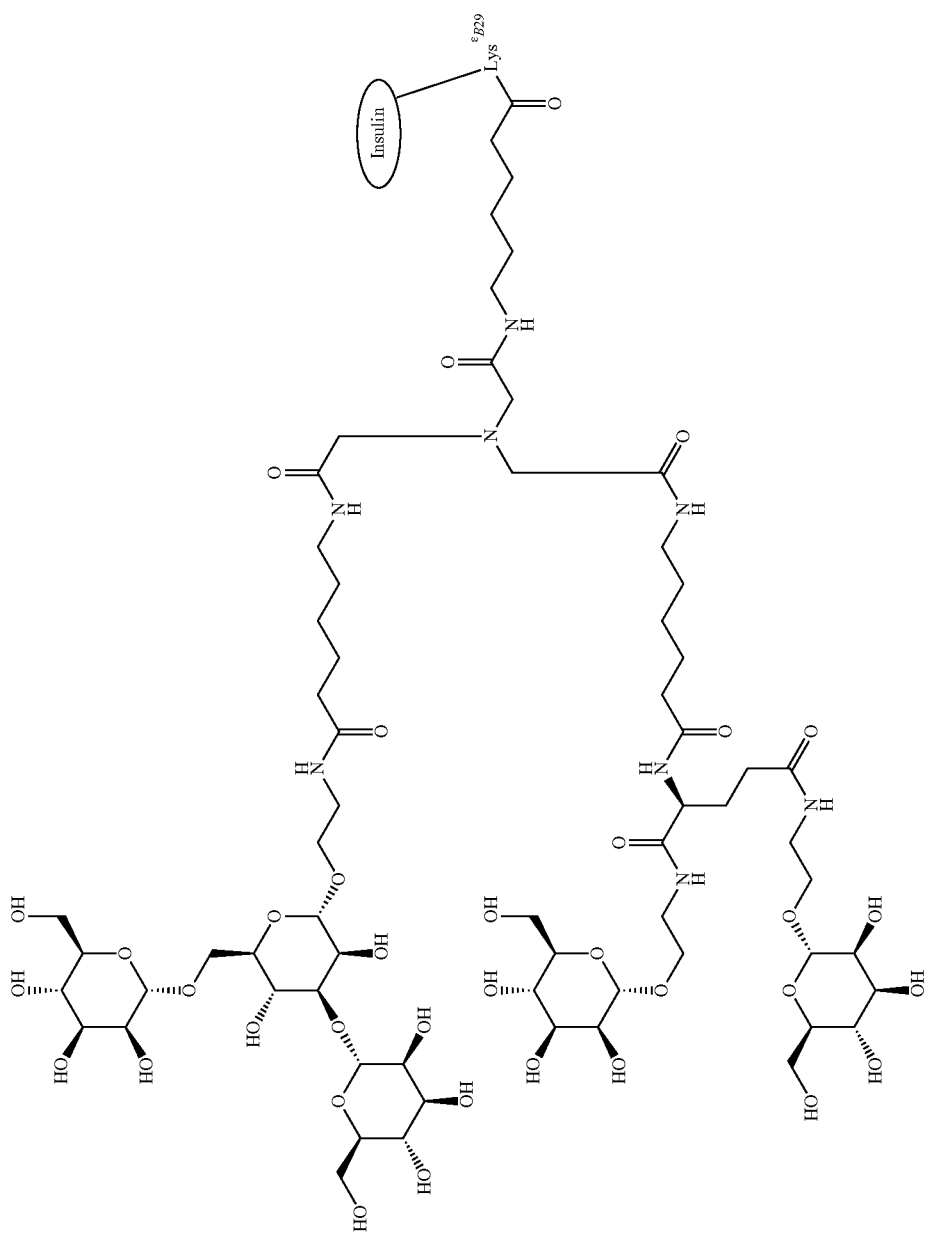

IOC-68
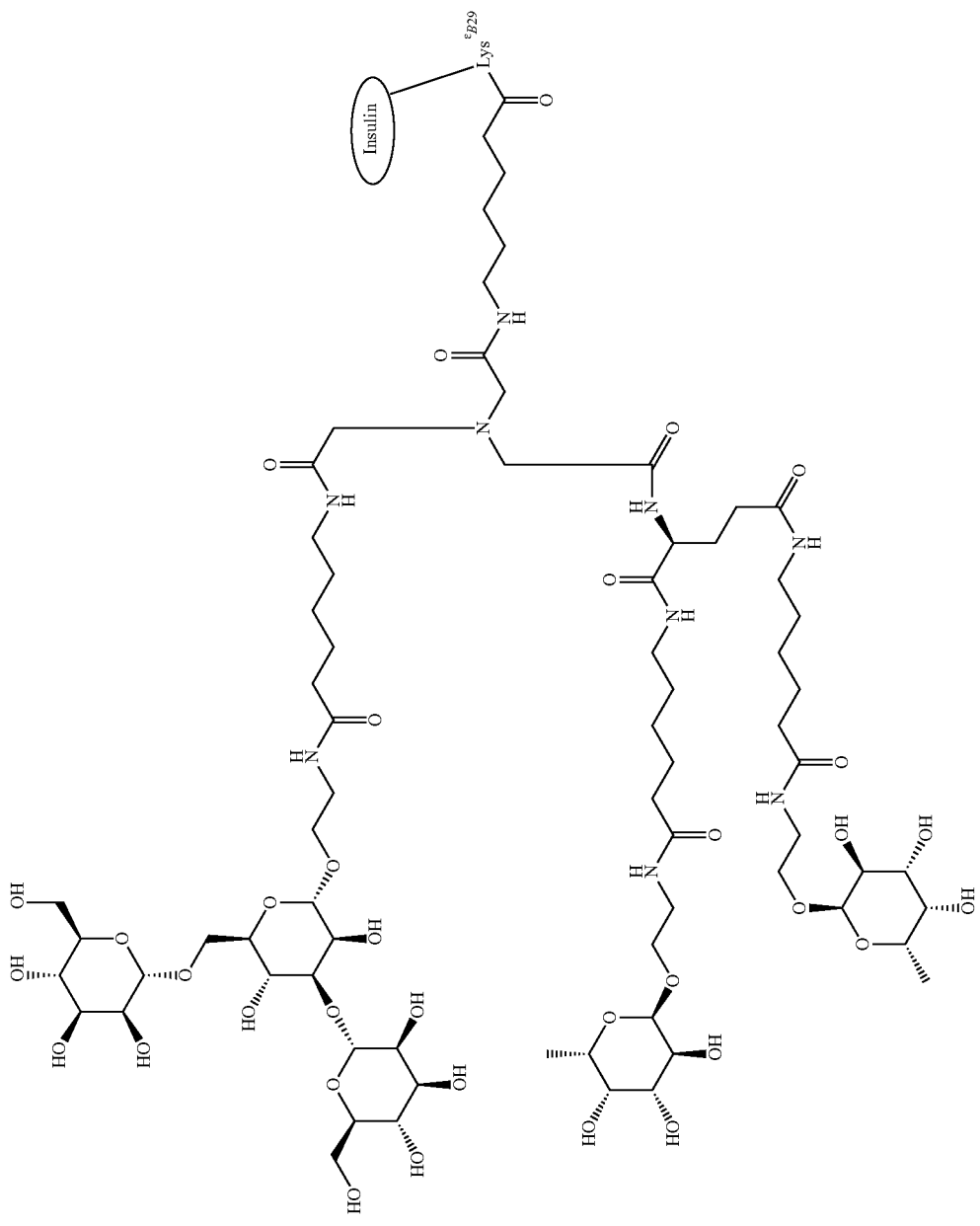

IOC-69
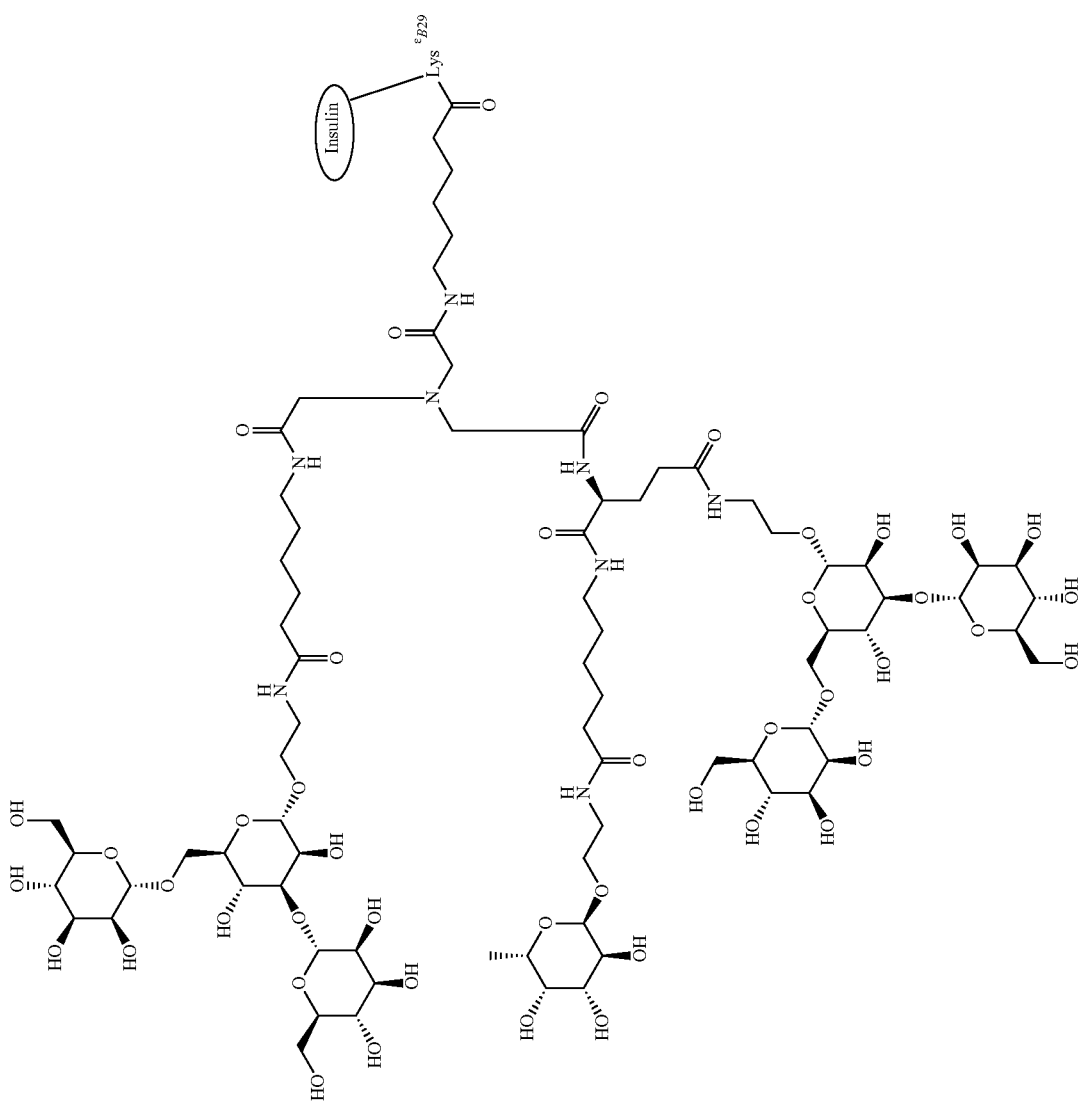

IOC-70
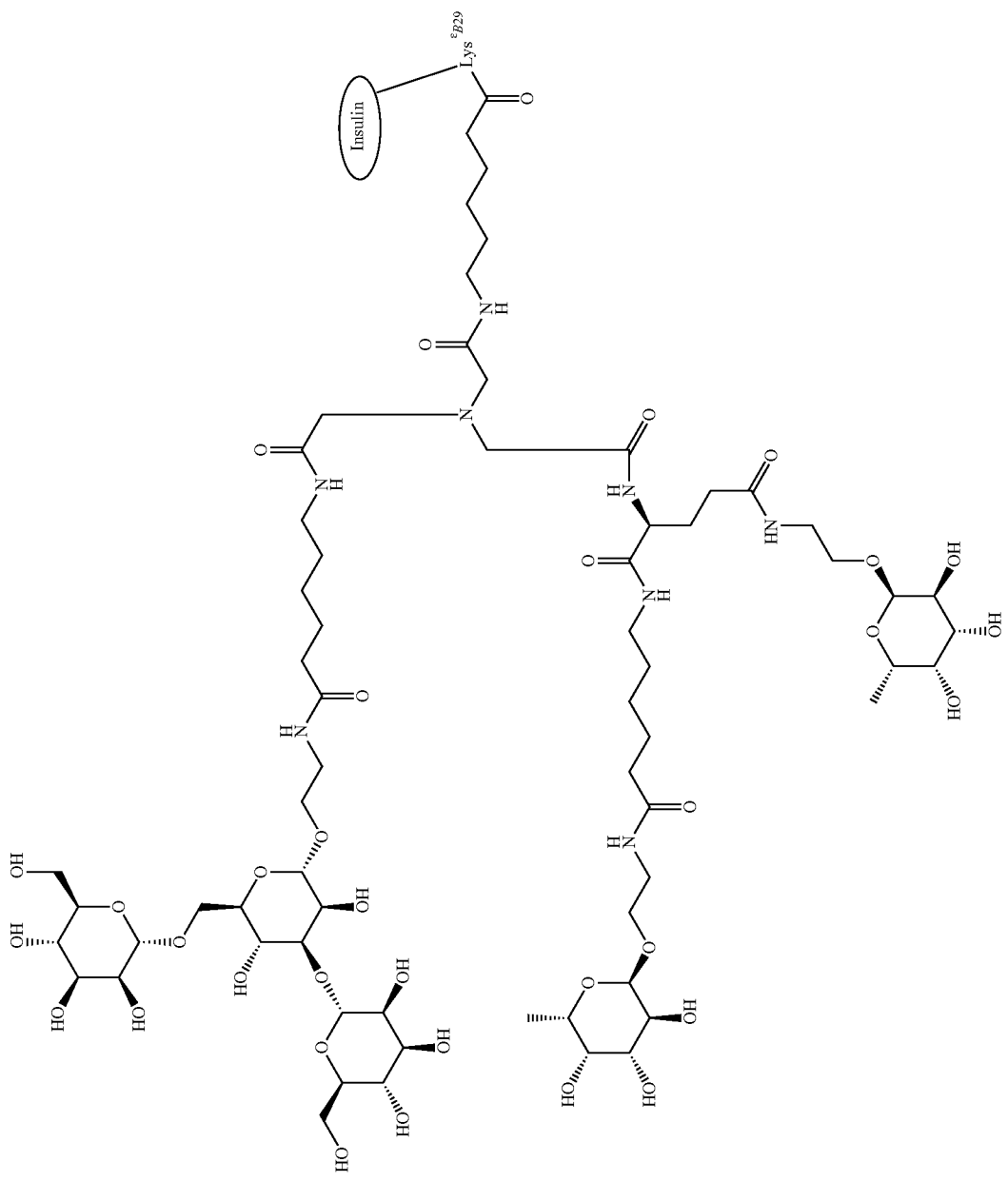

IOC-71
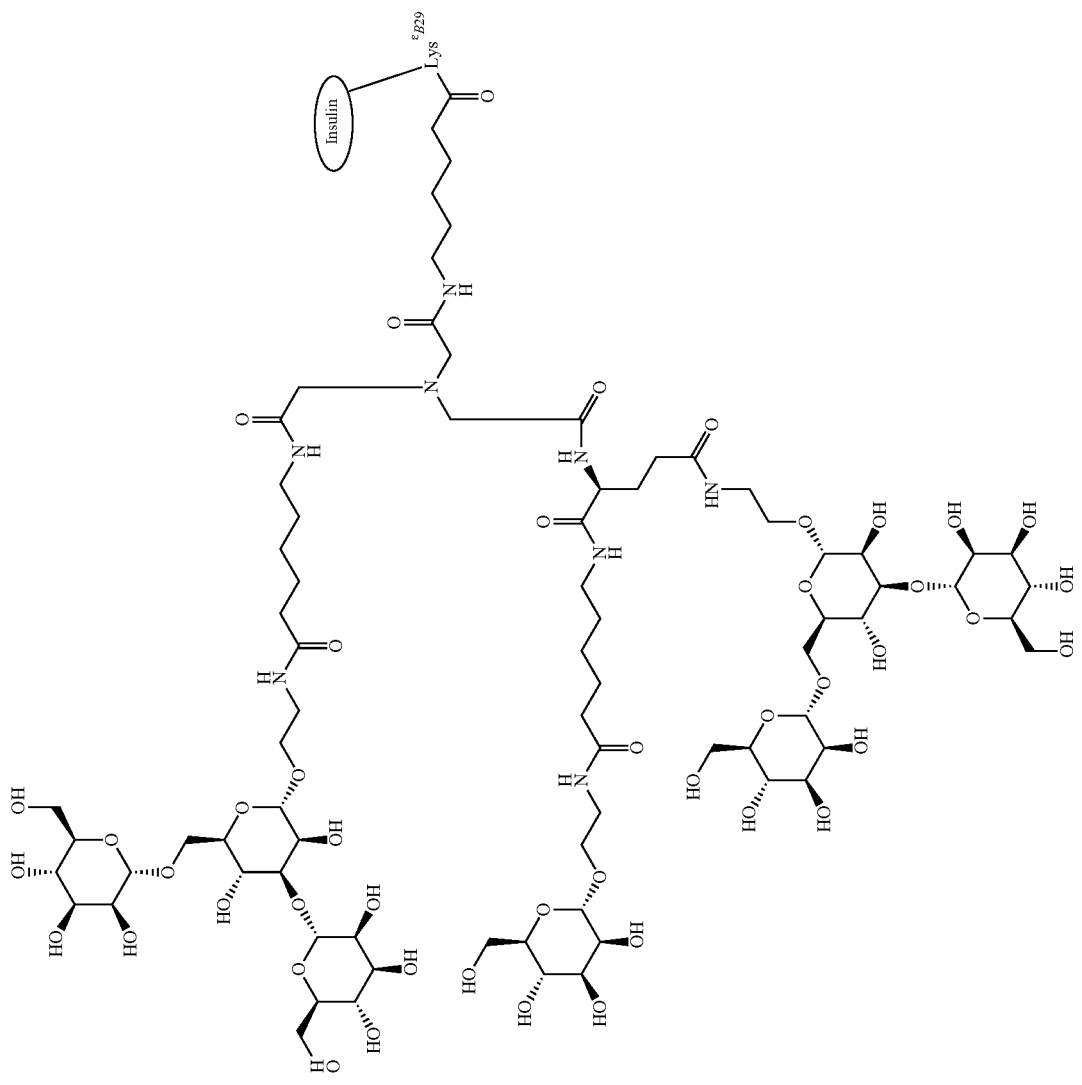

IOC-72
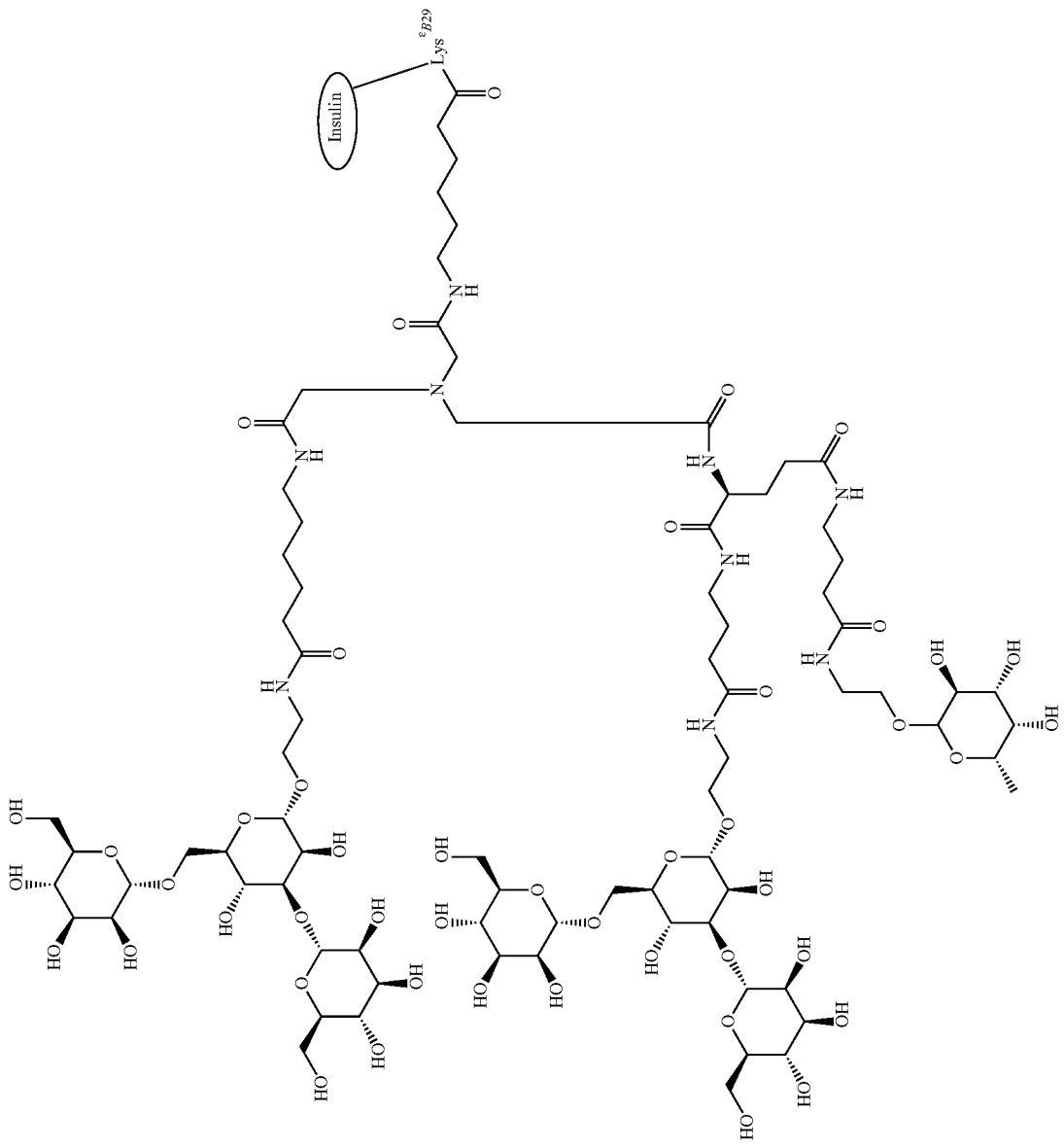

IOC-73
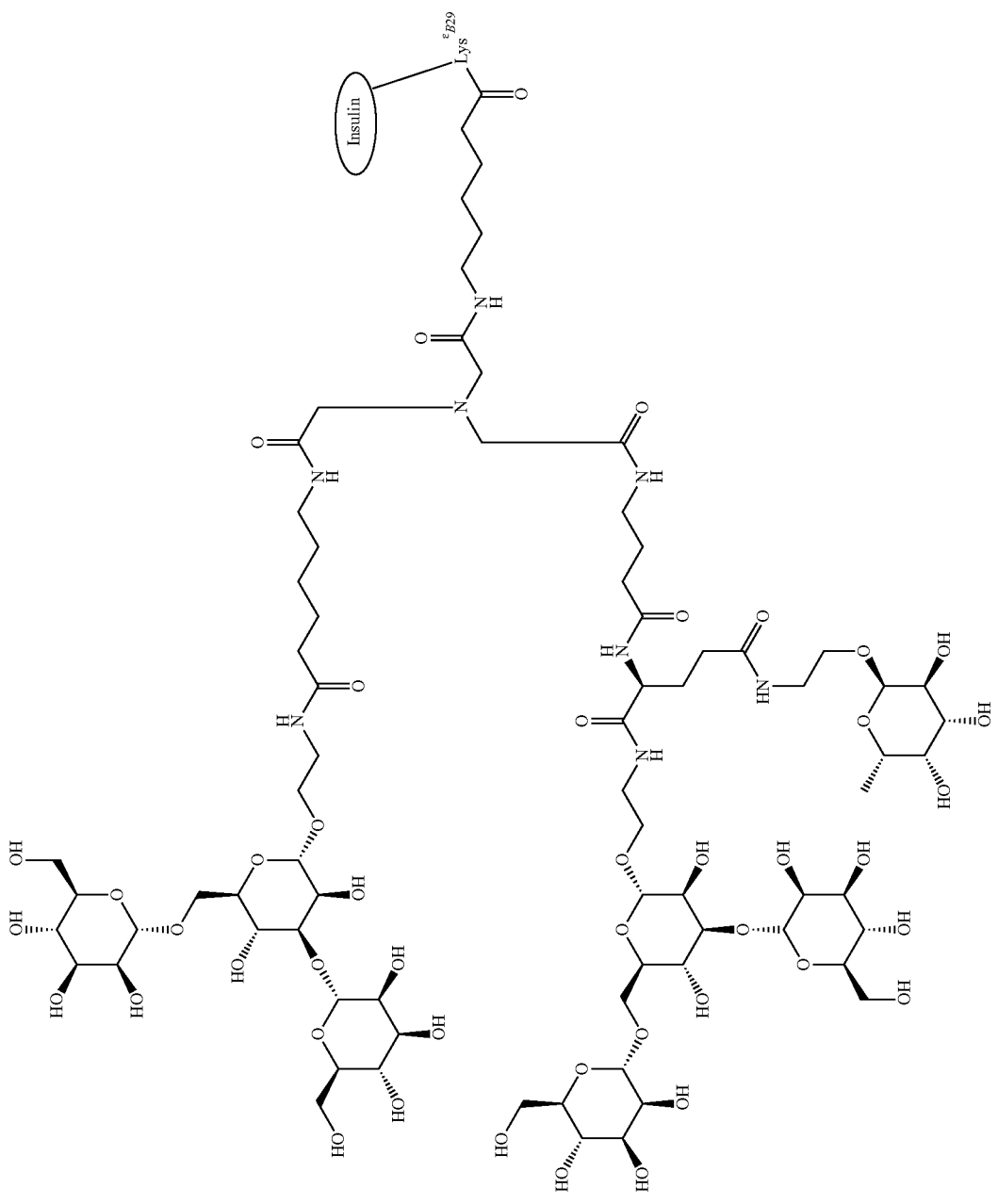

IOC-74
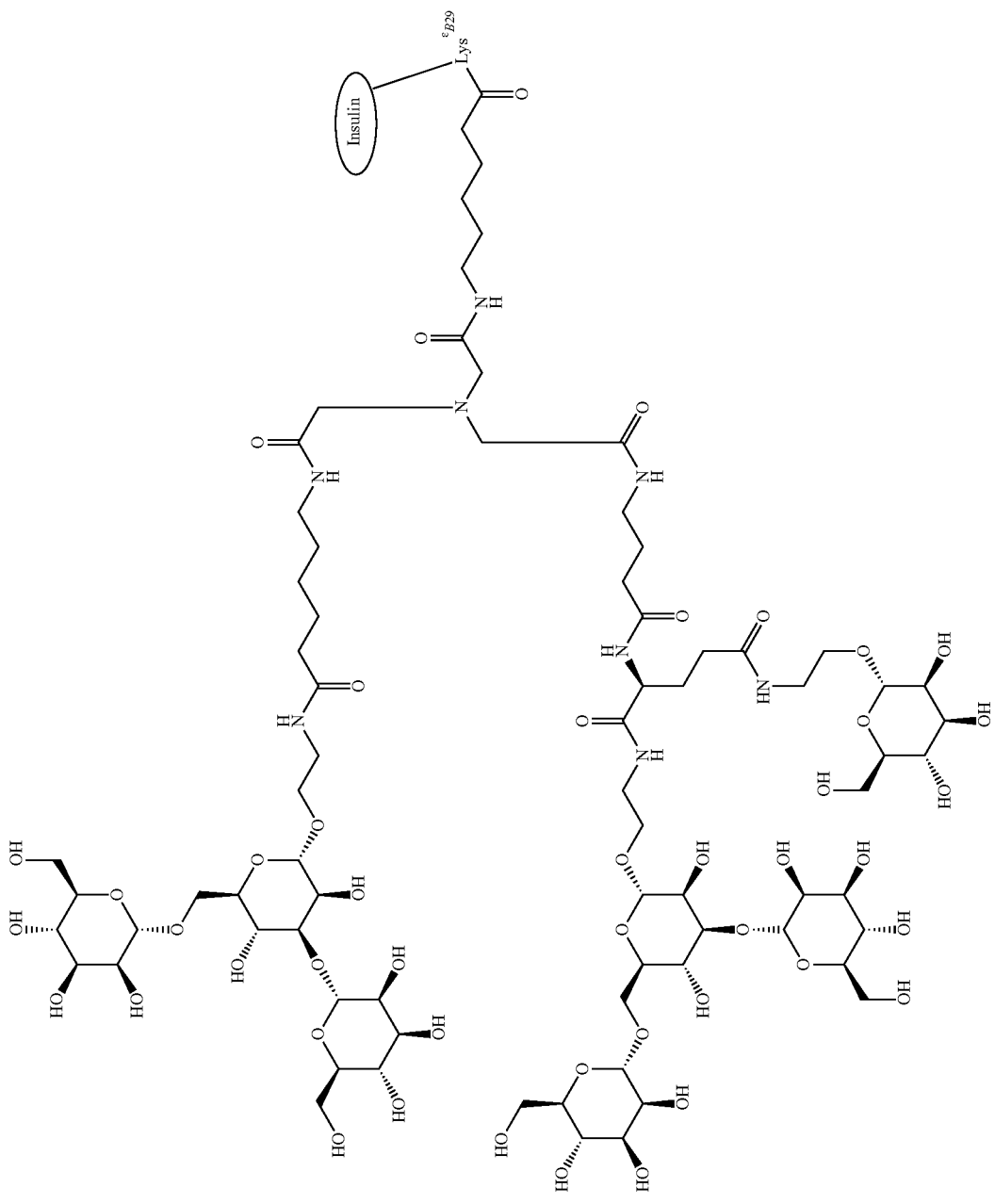

IOC-75
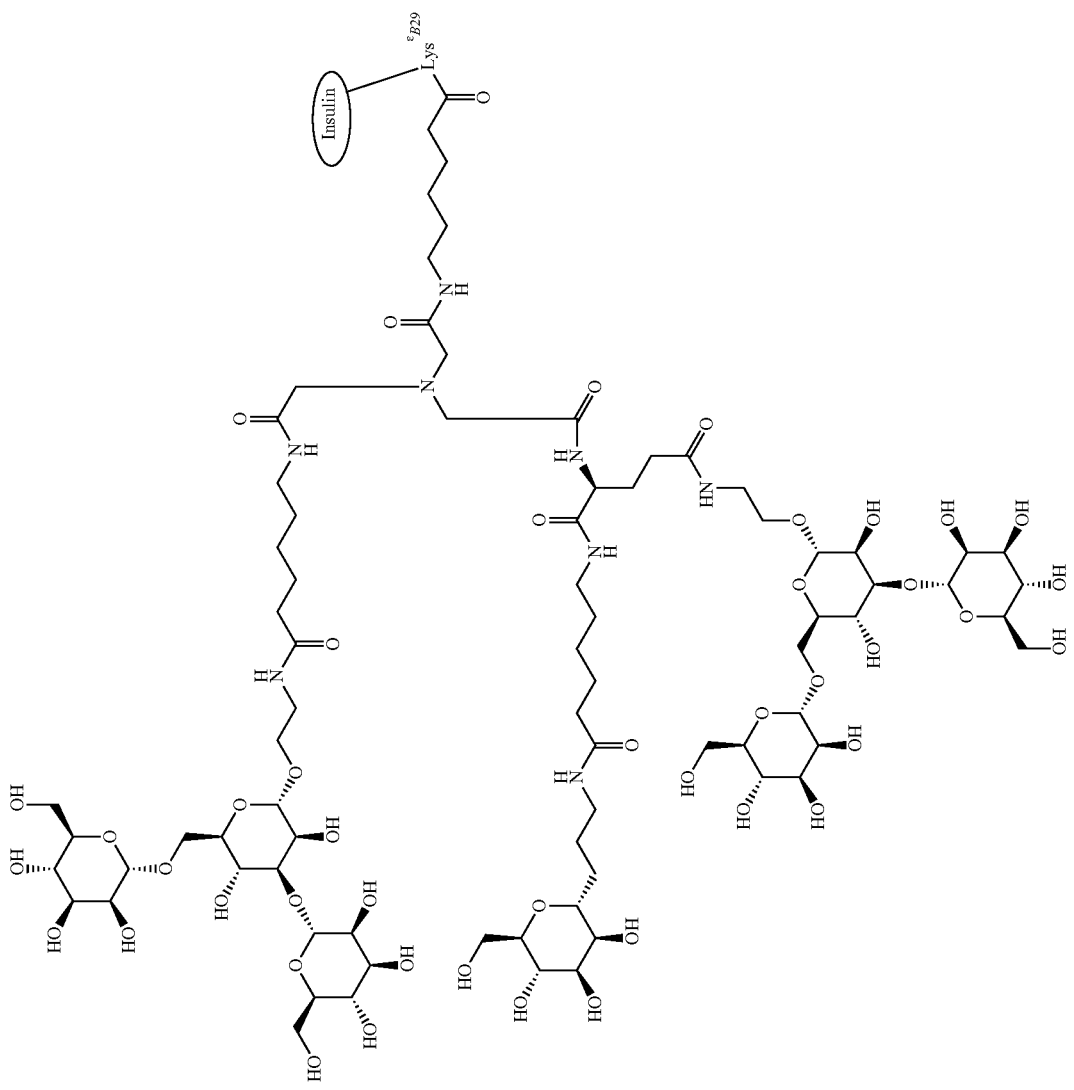

IOC-76
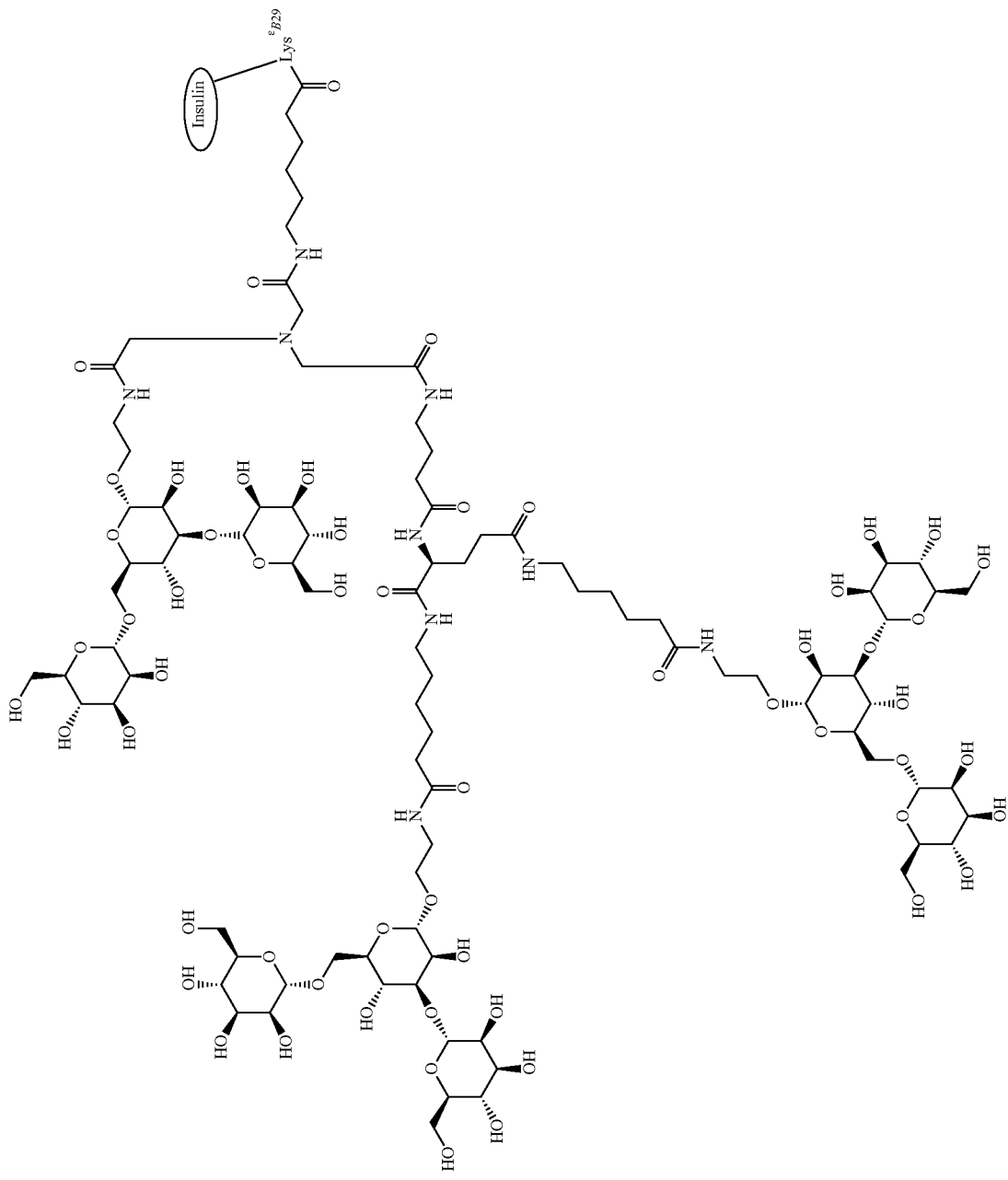

IOC-77
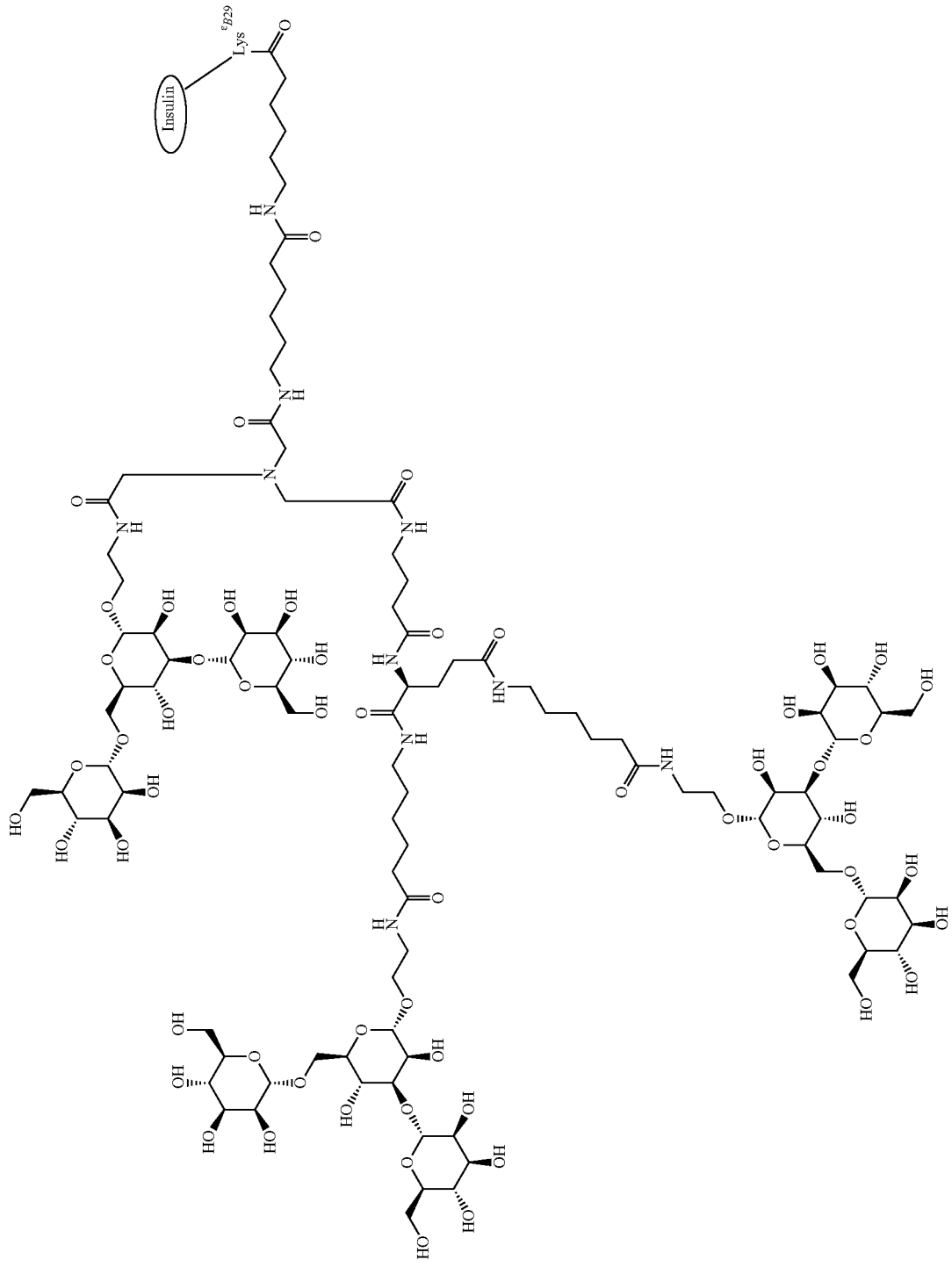

IOC-78
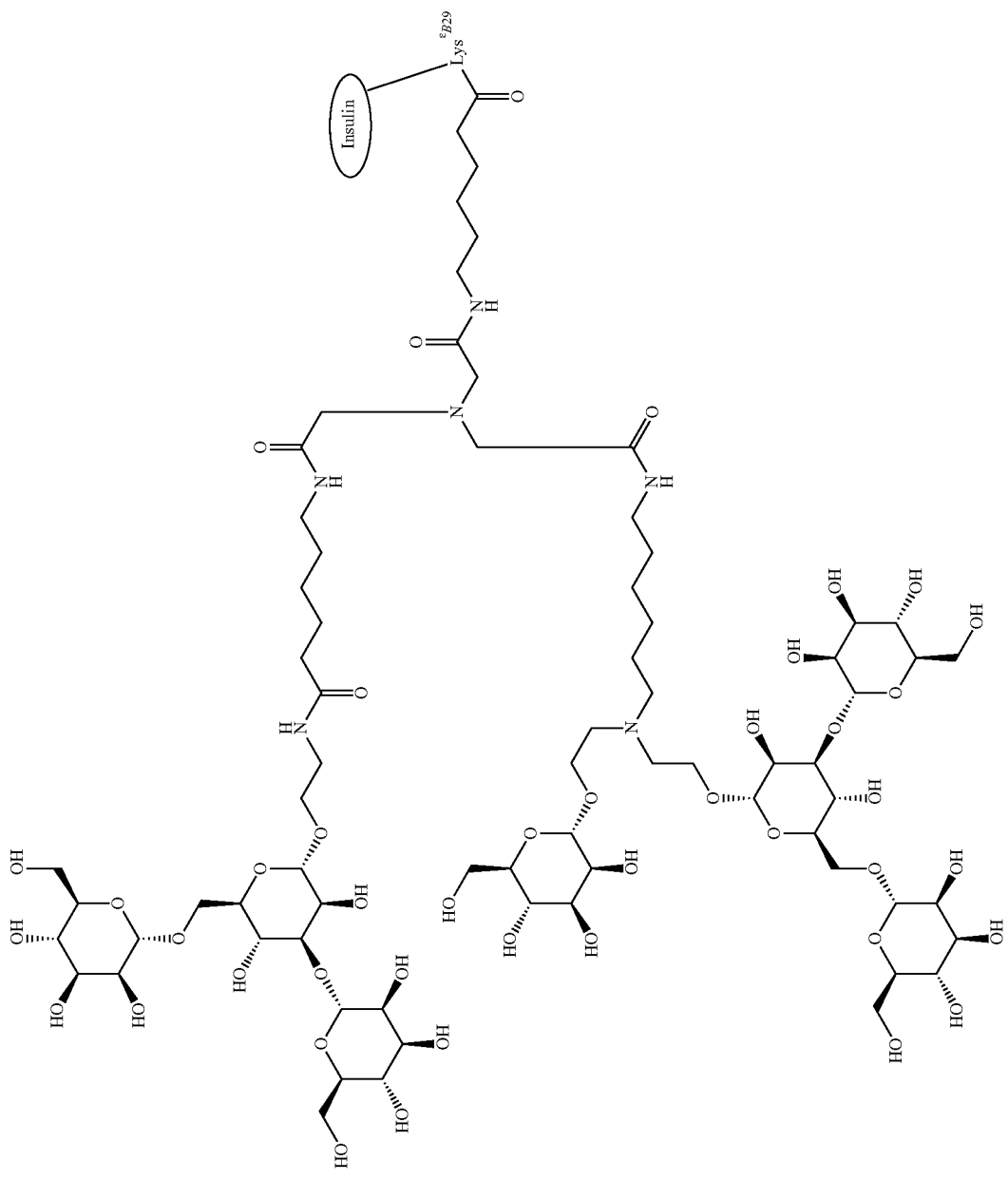

IOC-79
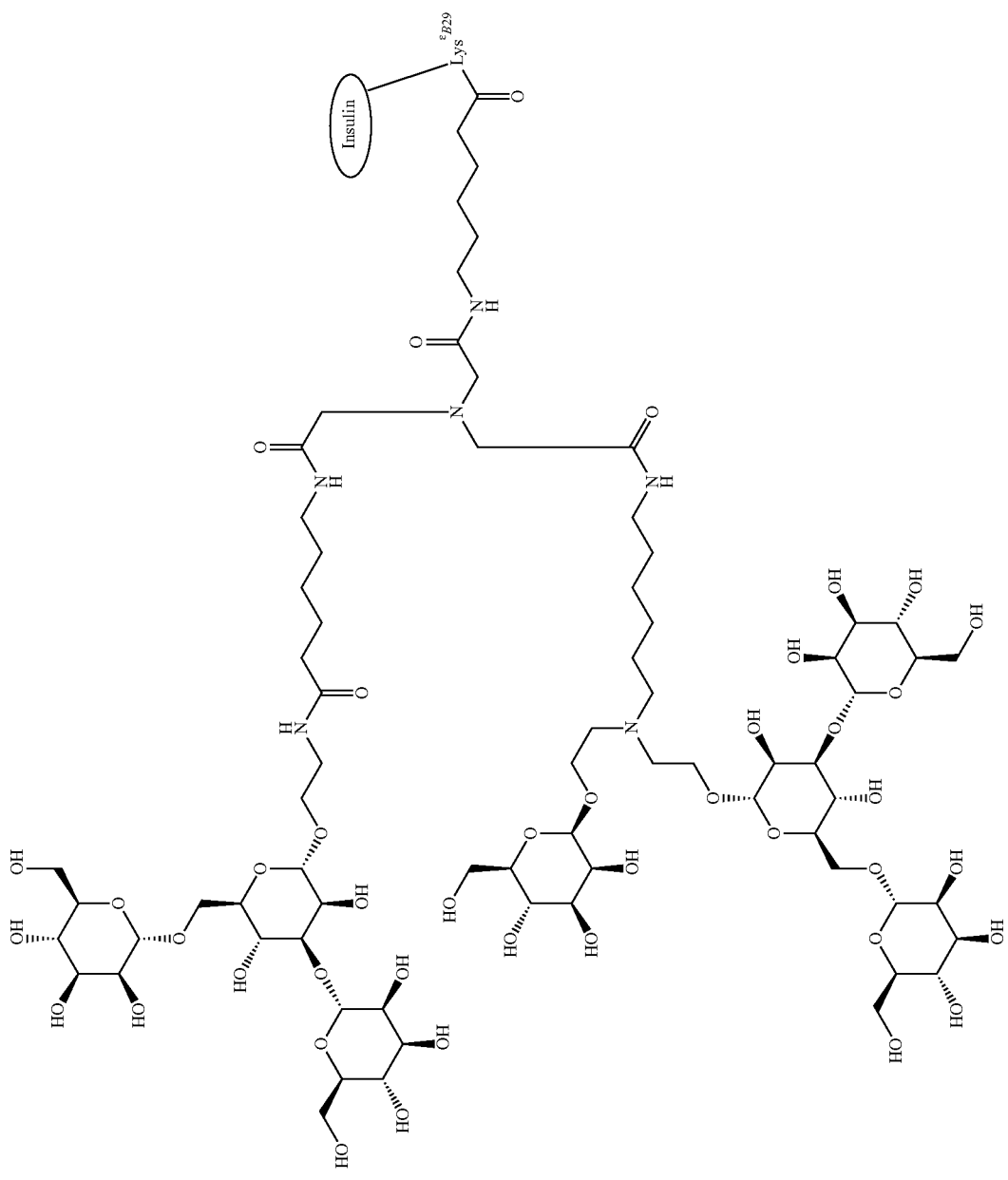

IOC-80
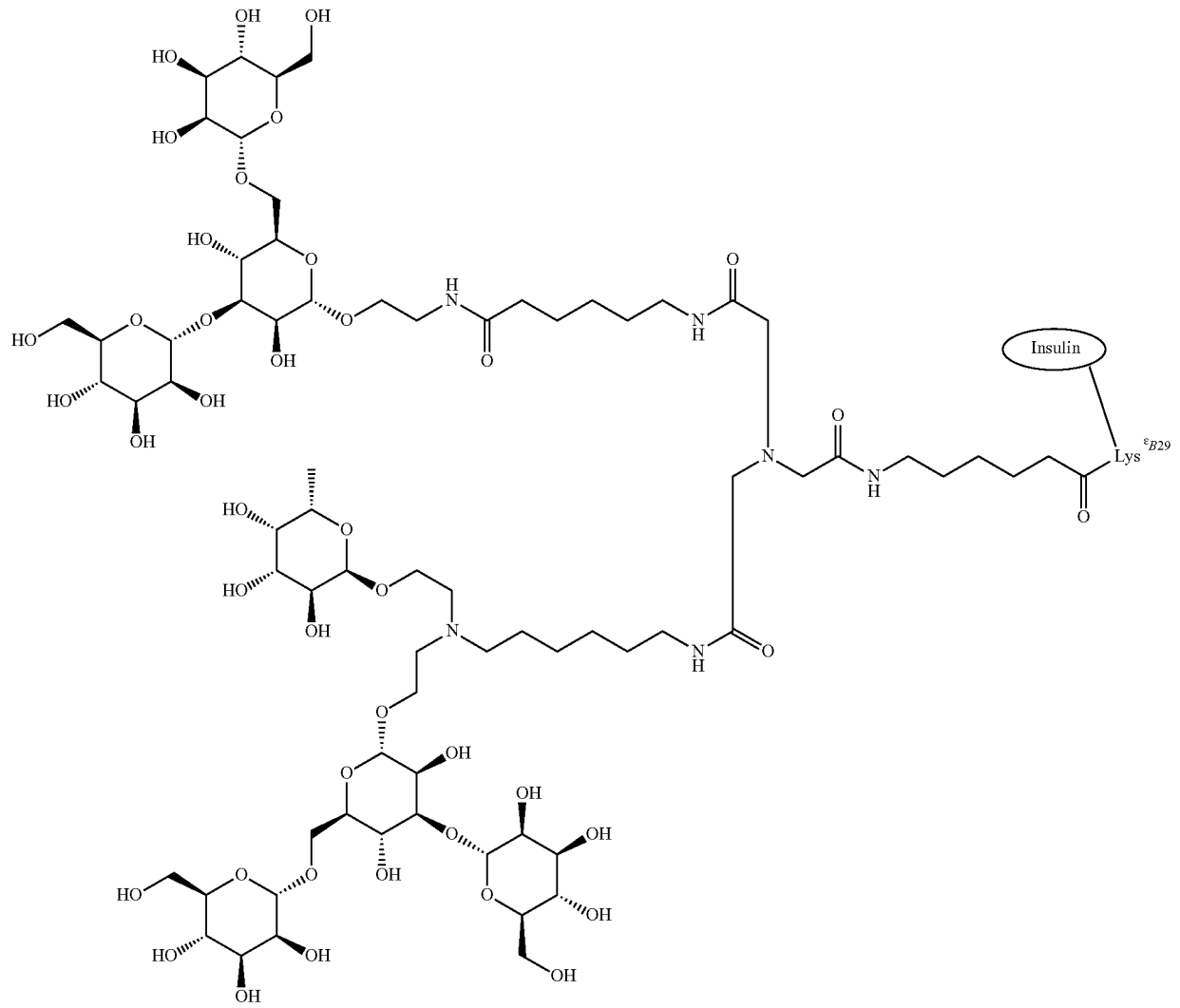

IOC-81
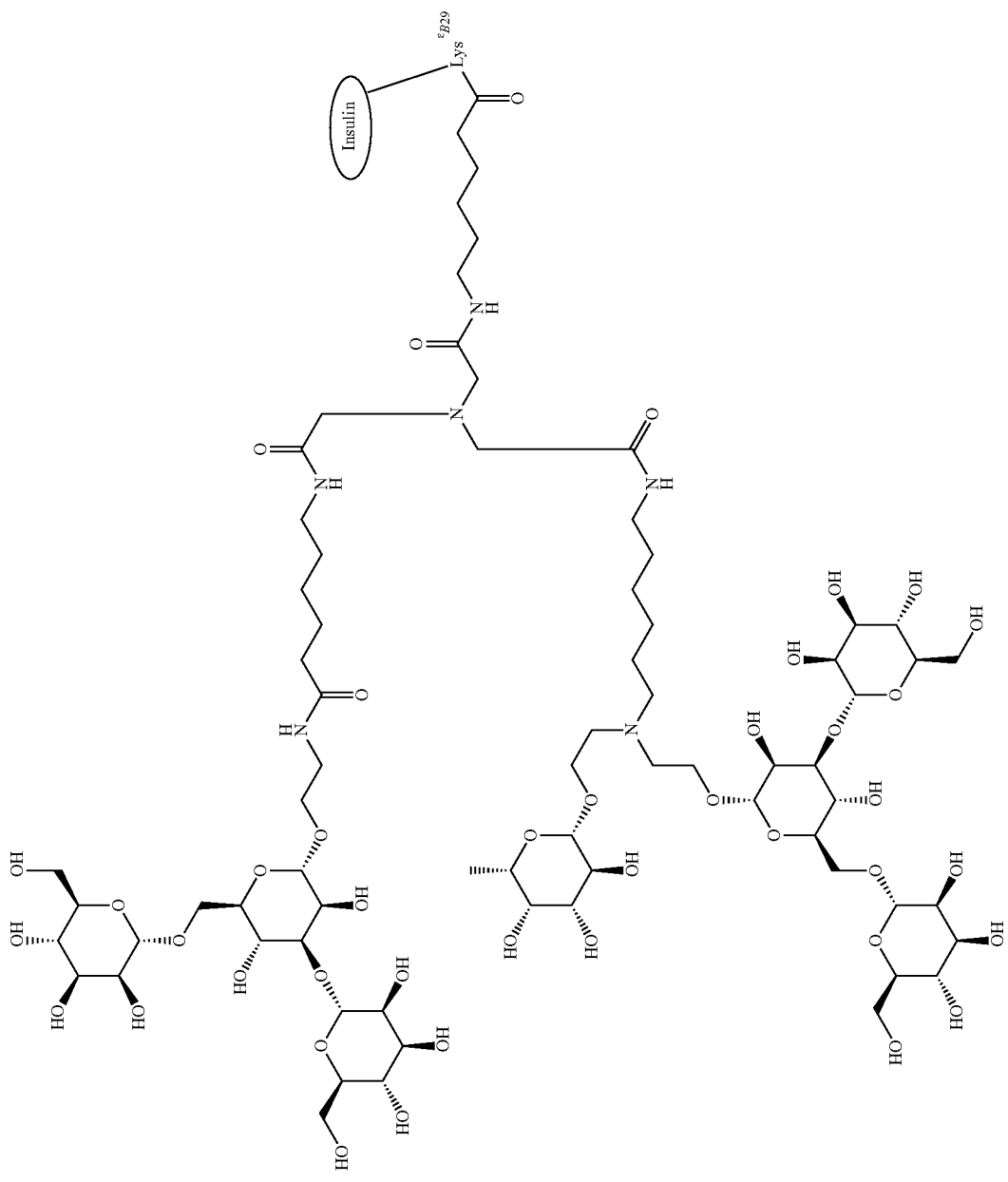

IOC-82
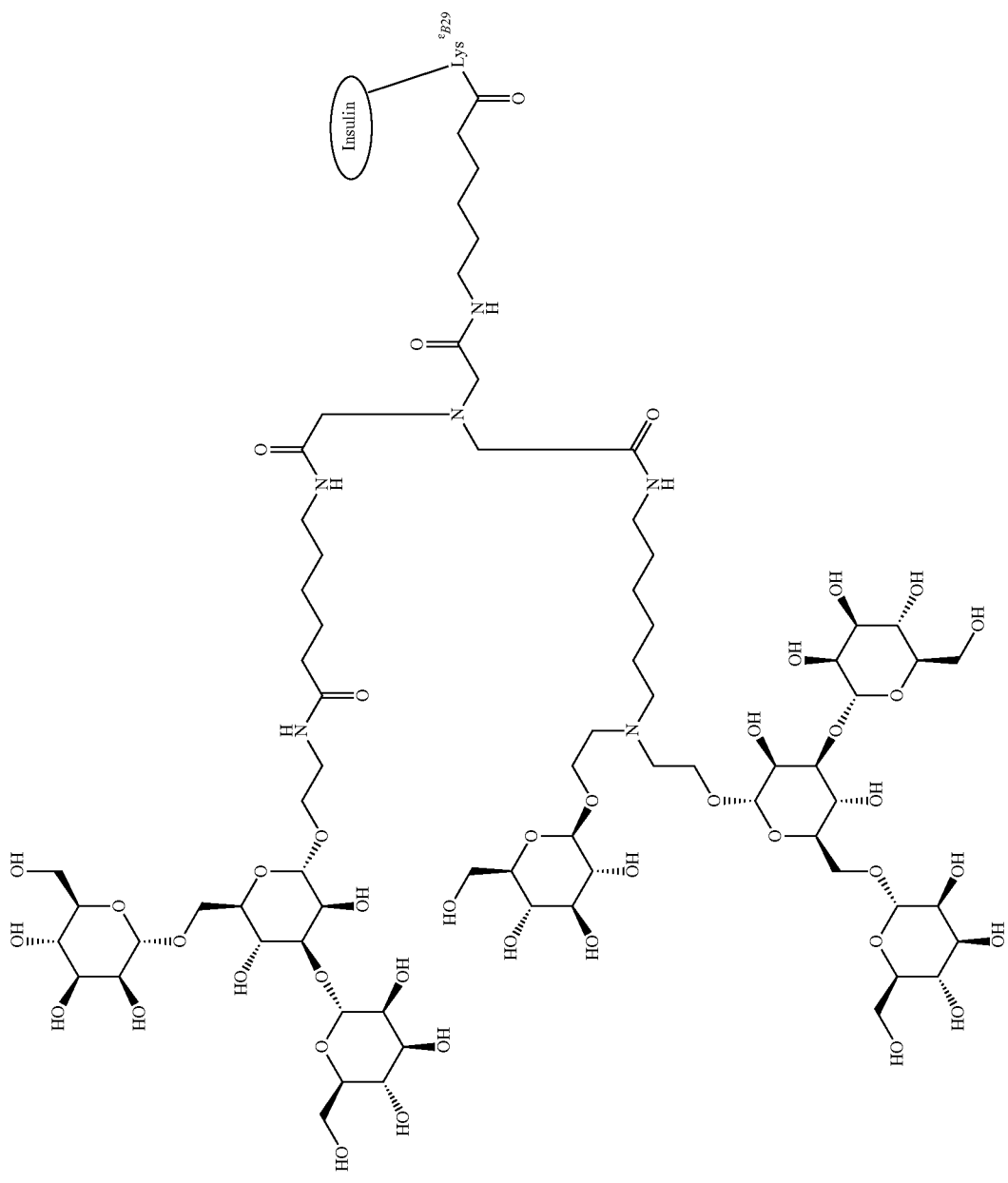

IOC-83
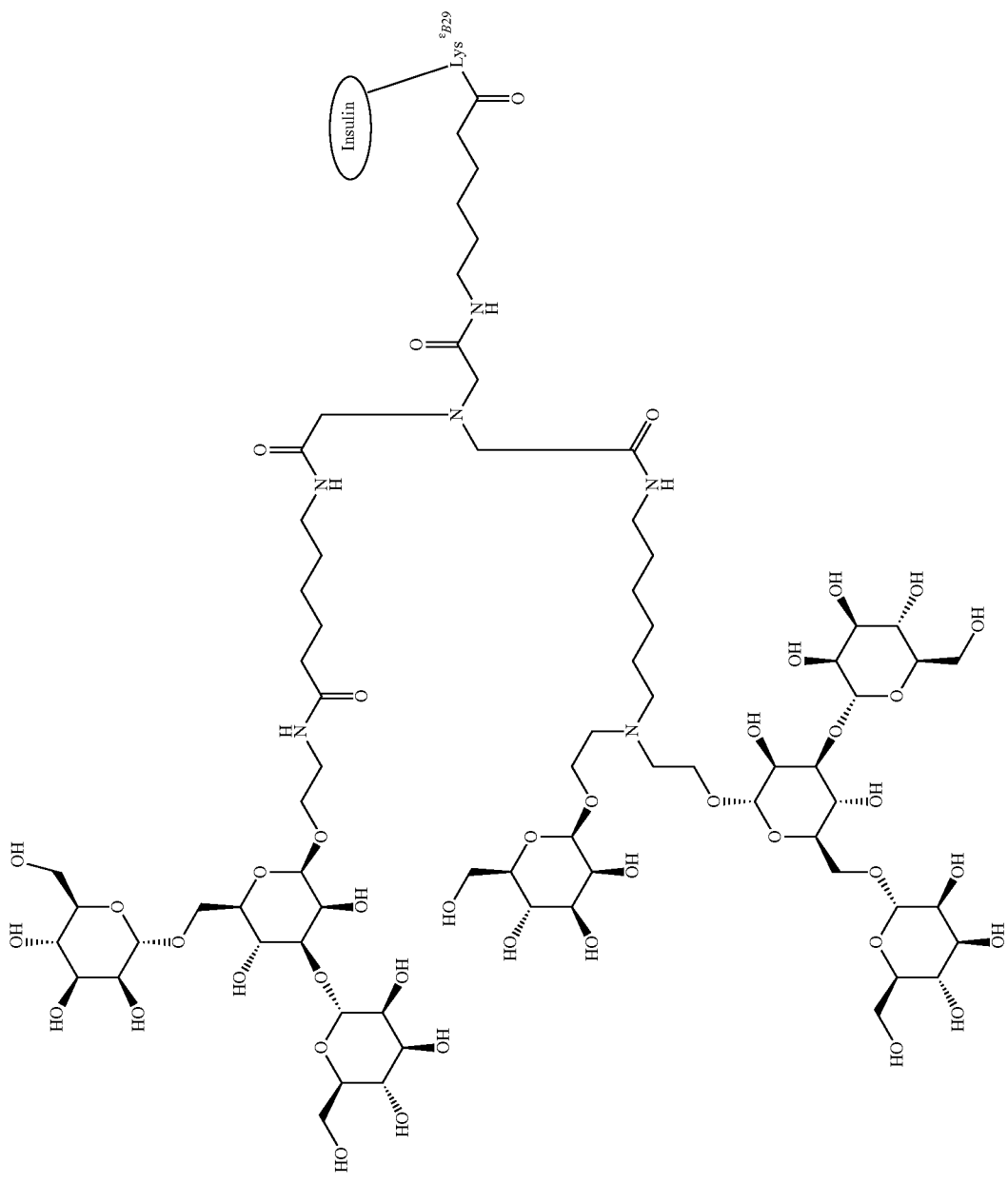

IOC-84
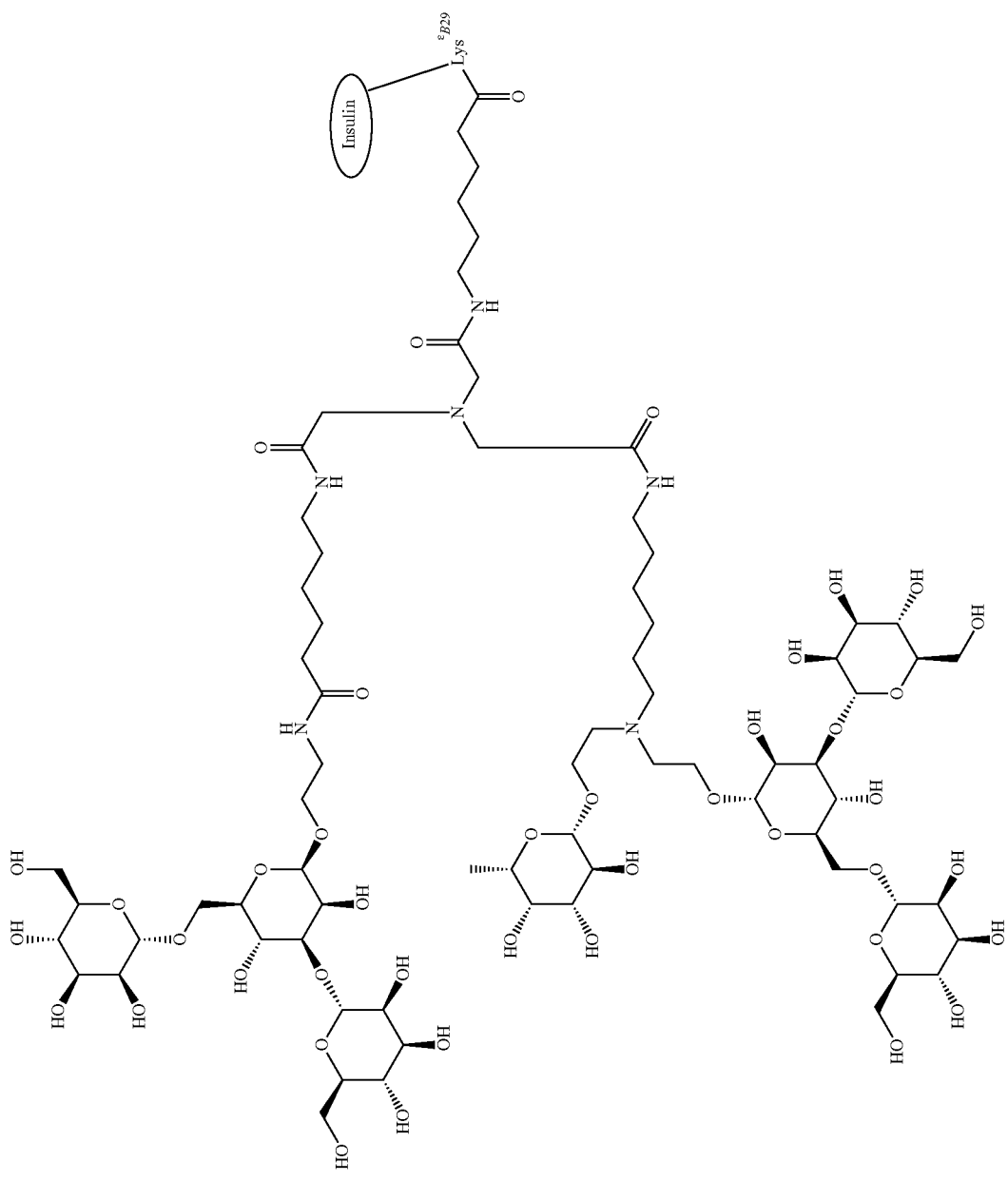

IOC-85
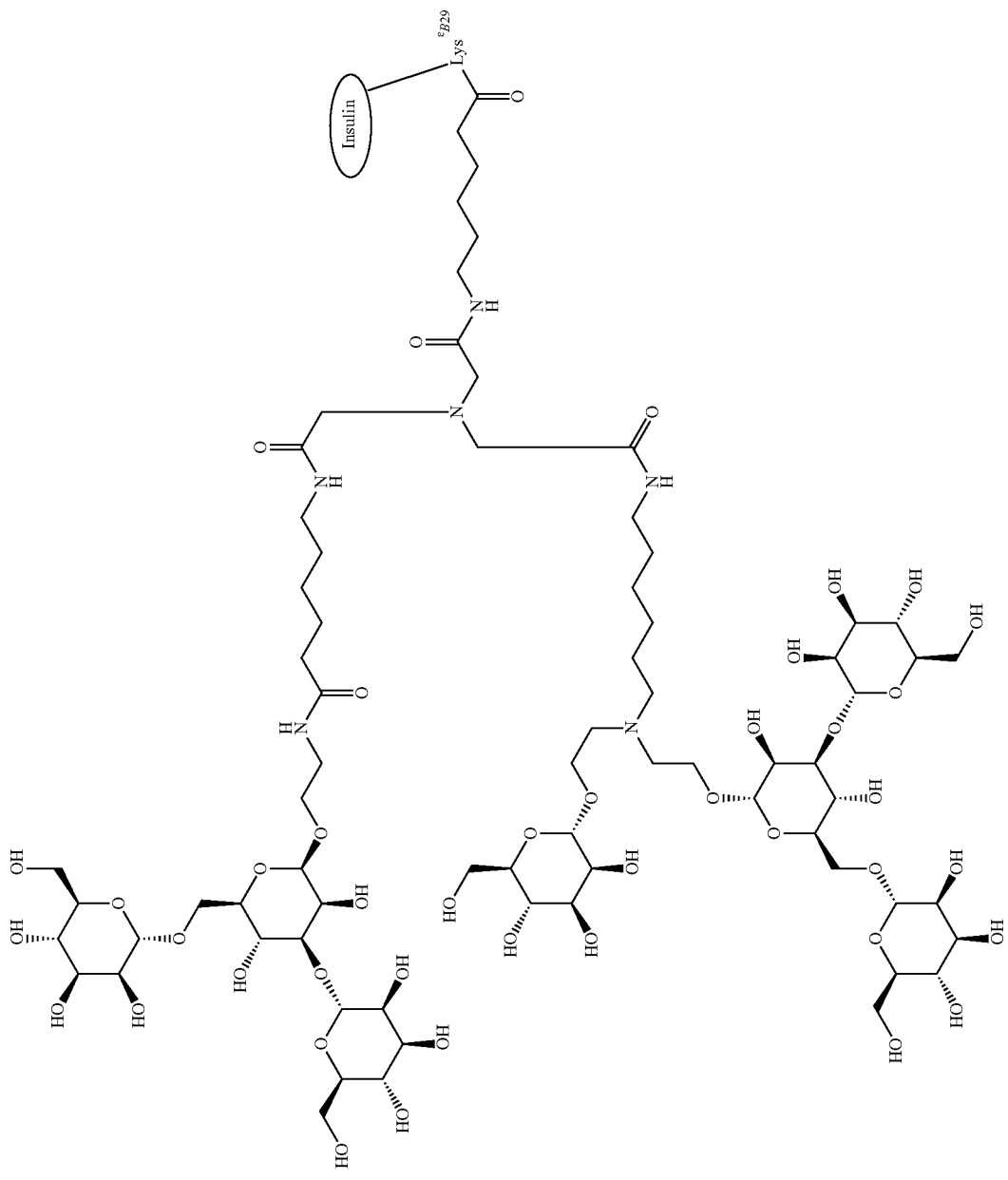

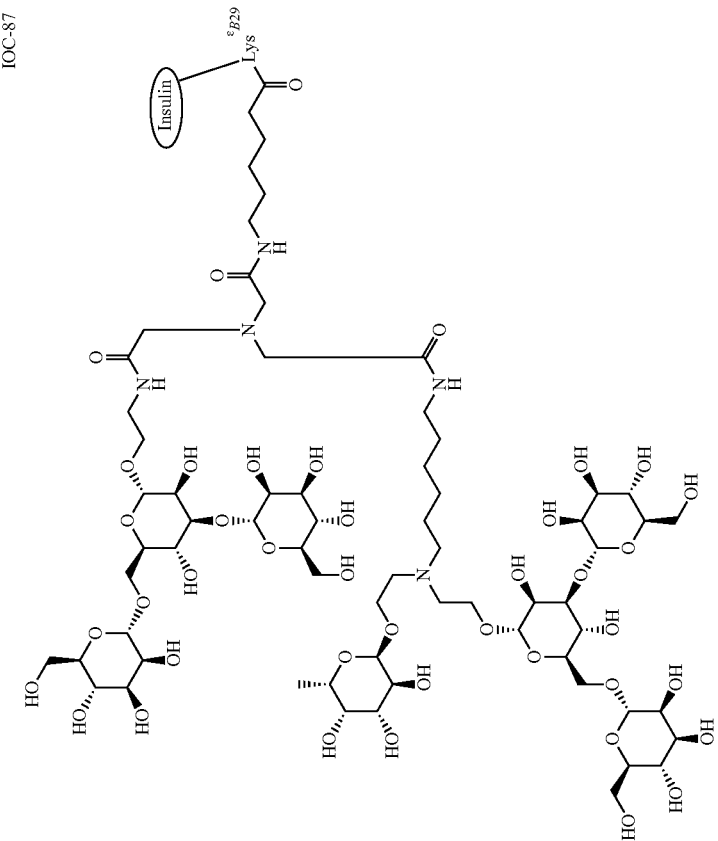
IOC-87
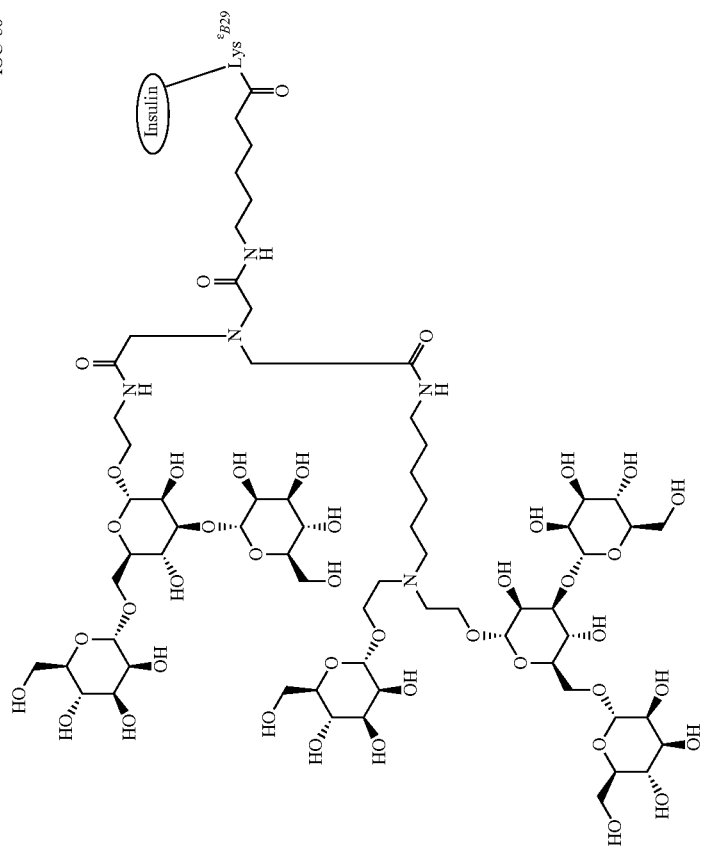
IOC-86

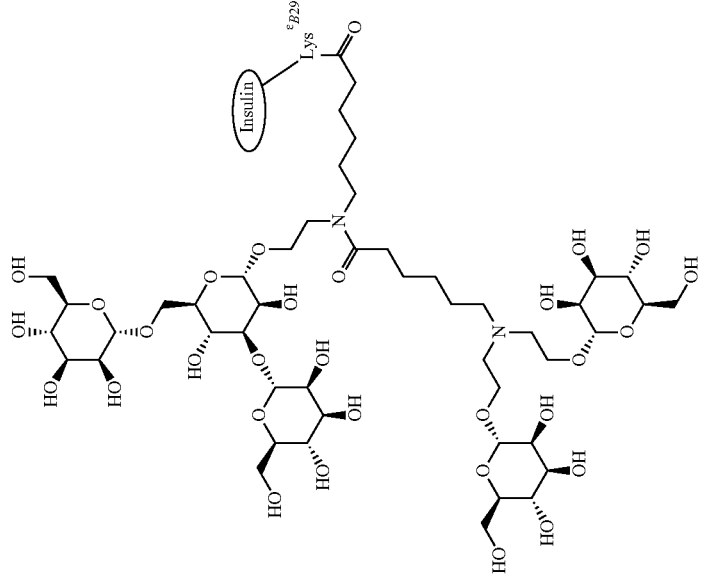
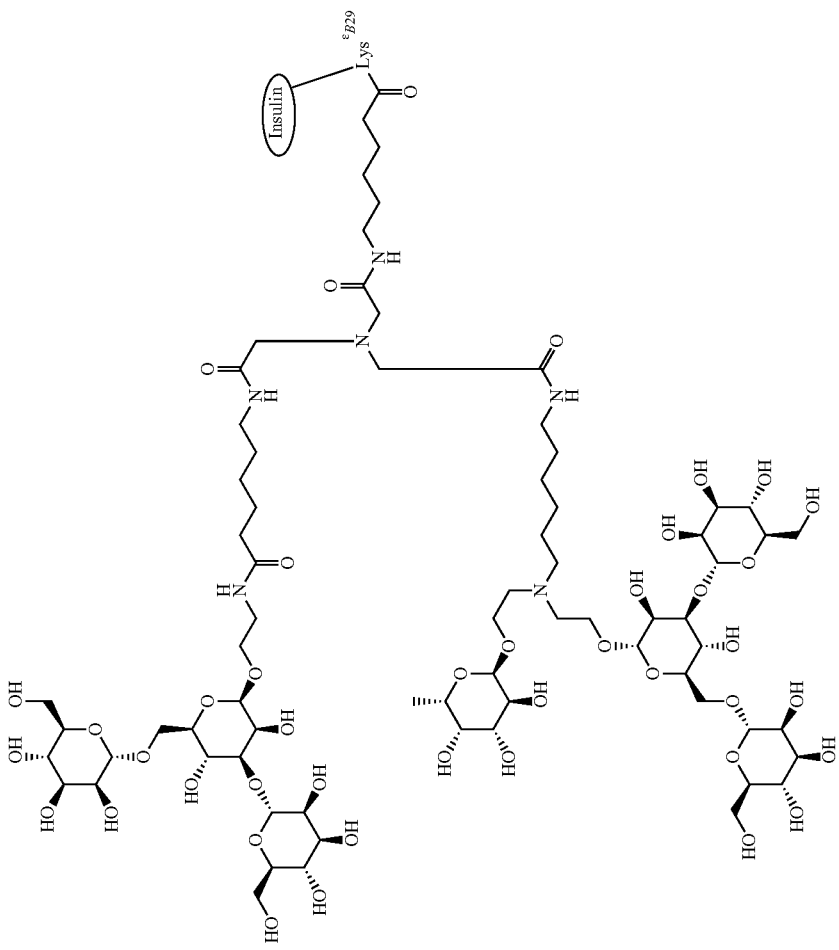

IOC-90
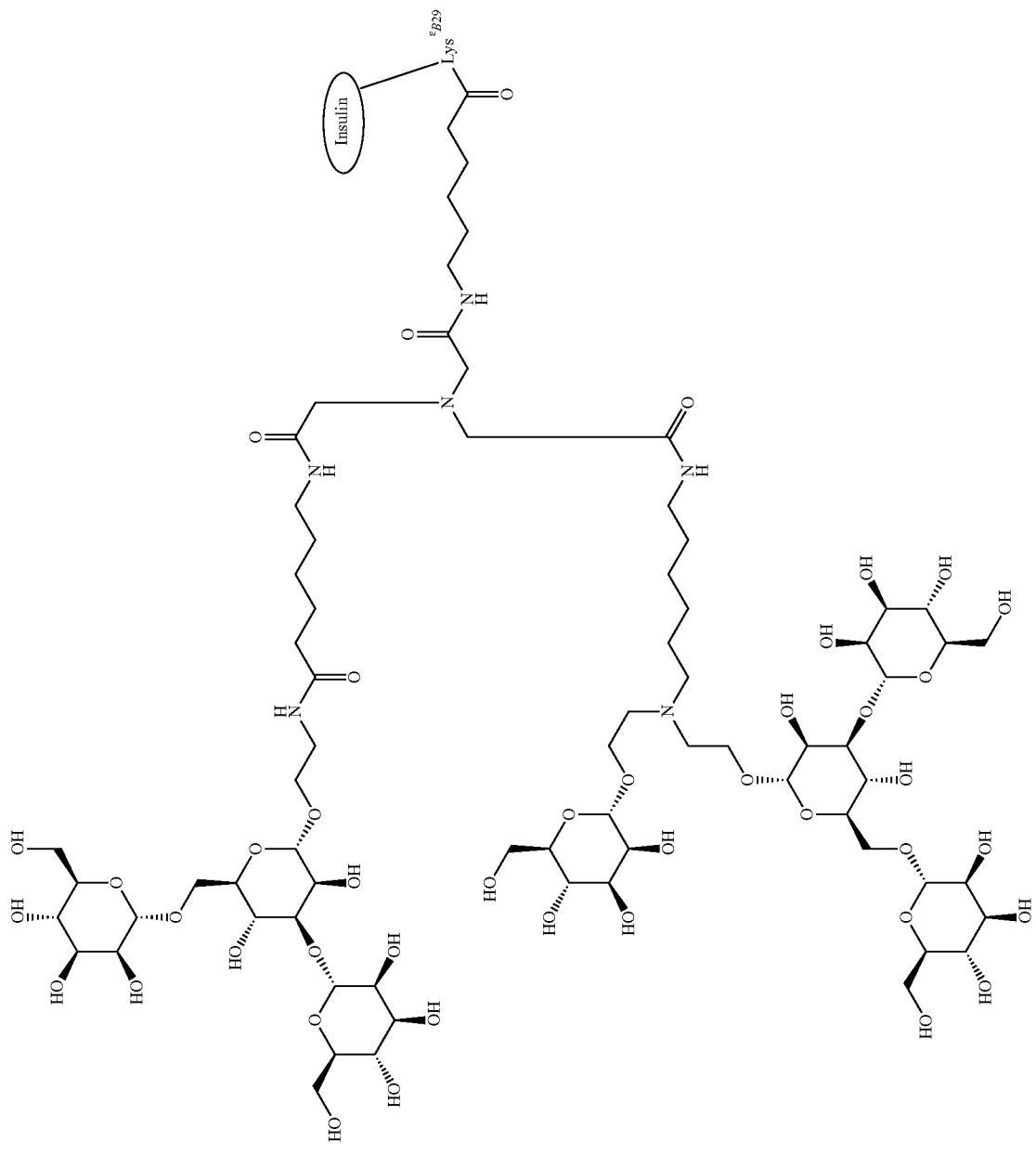

IOC-91
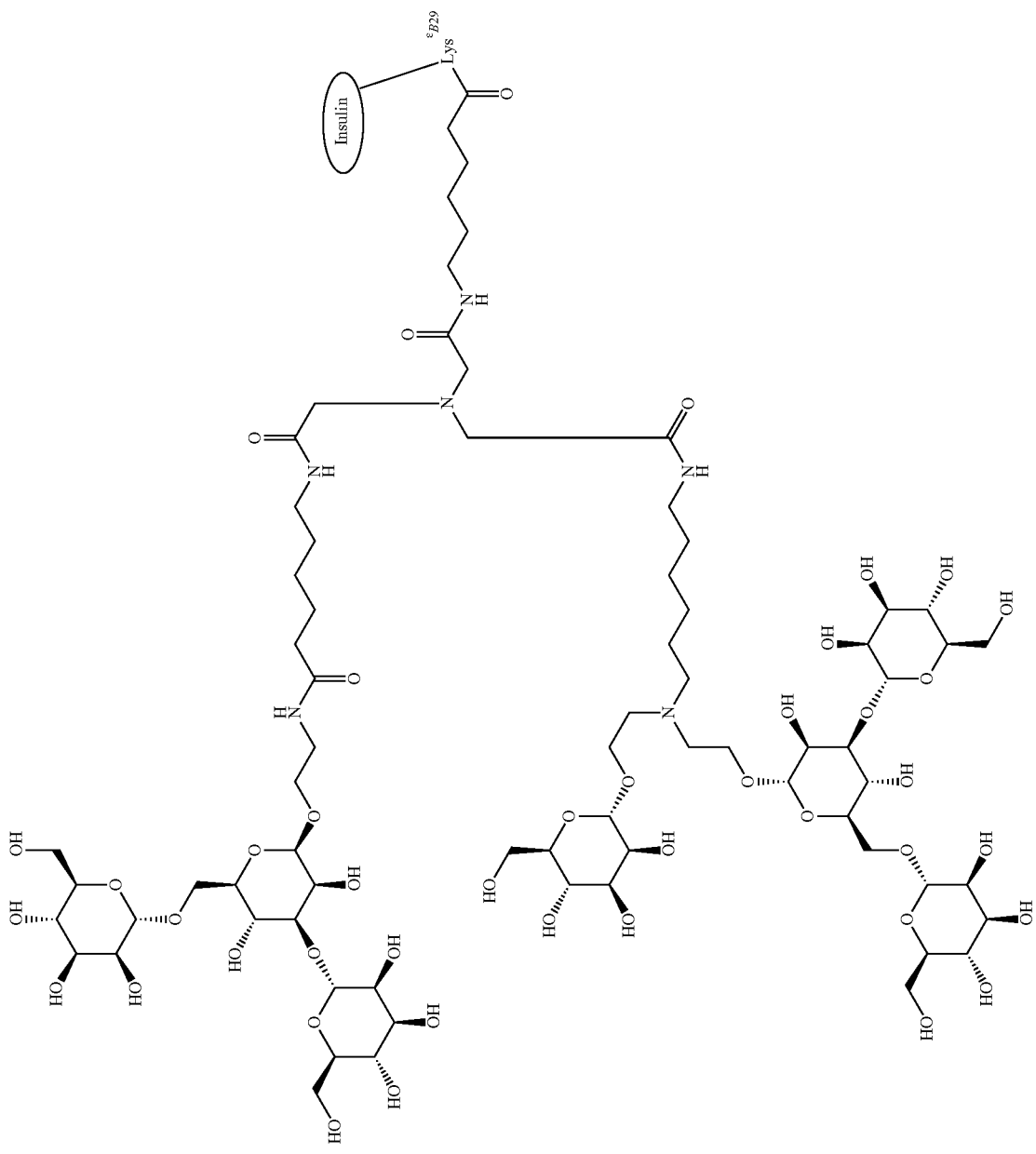

IOC-92
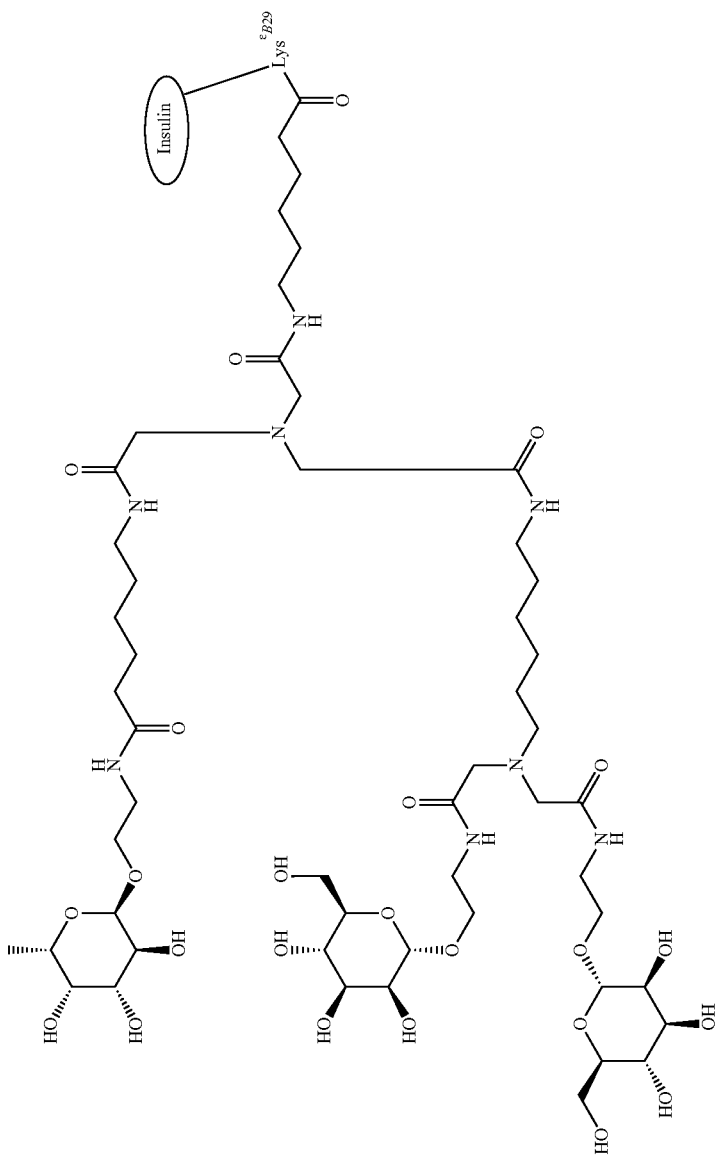

IOC-93
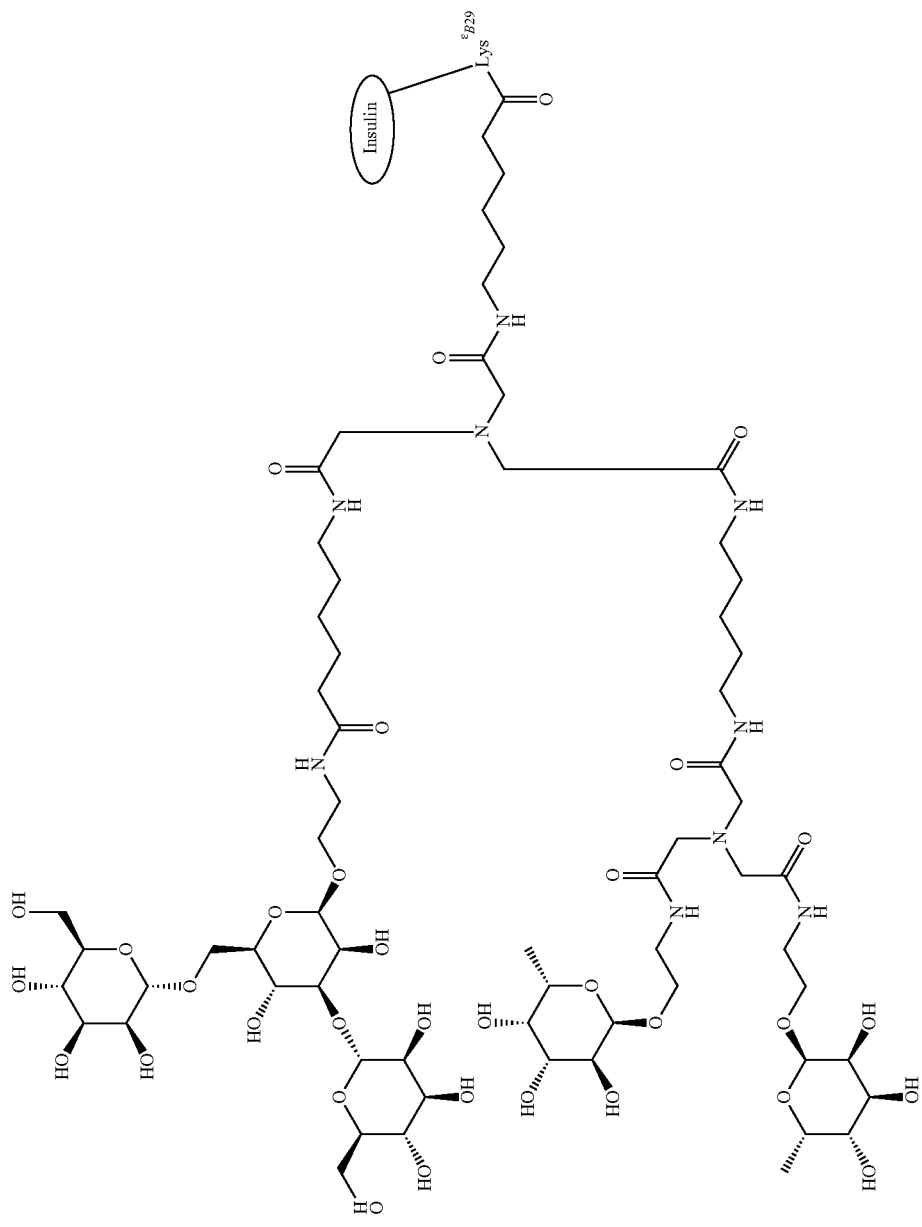

-continued
IOC-94
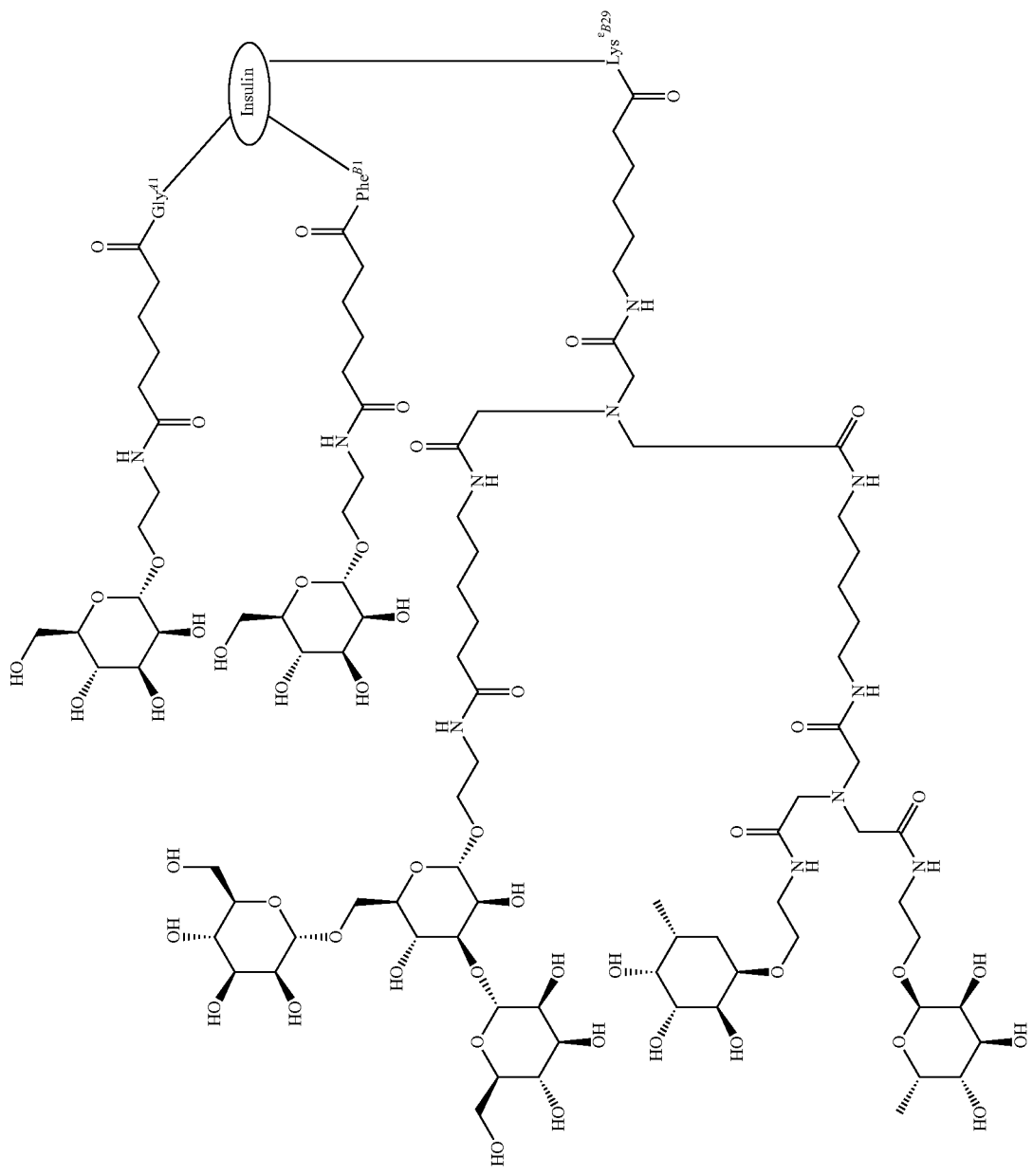

IOC-95
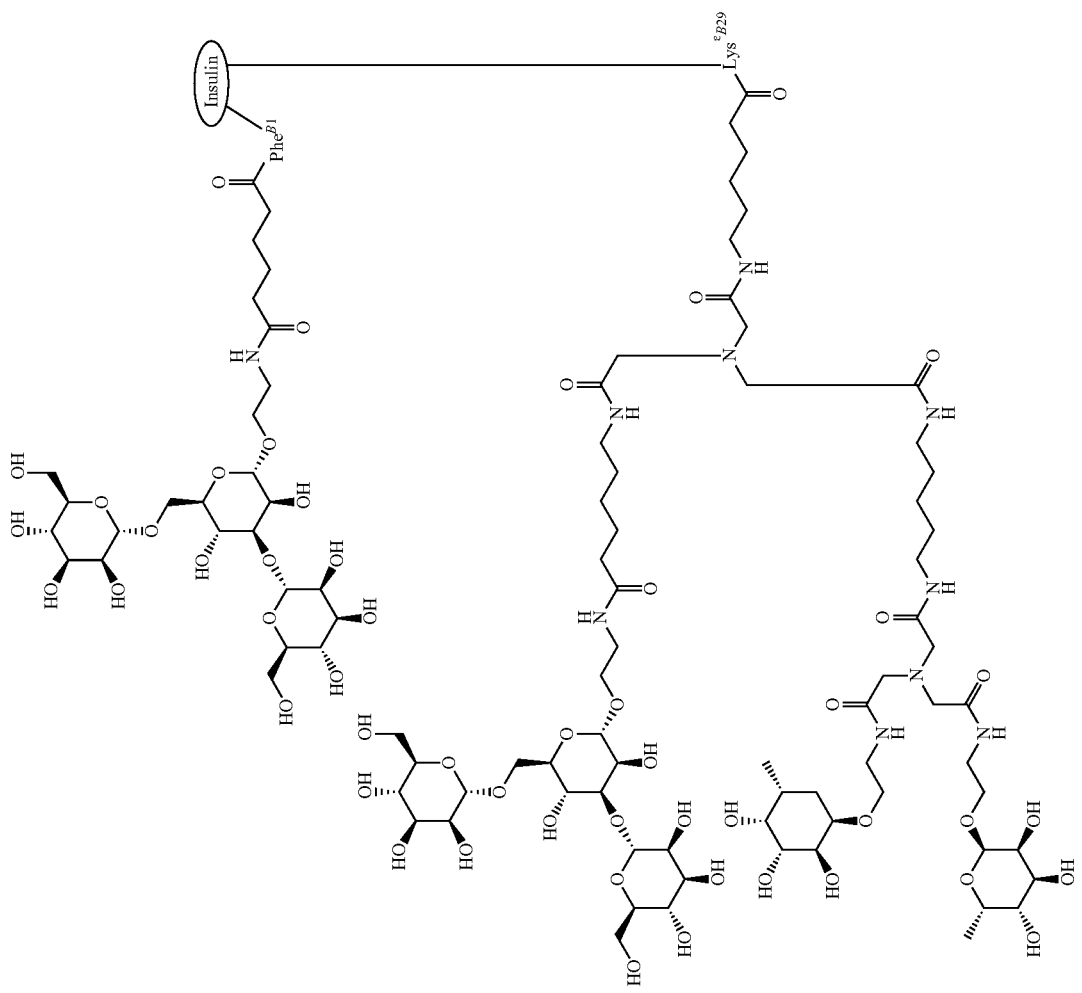

IOC-96
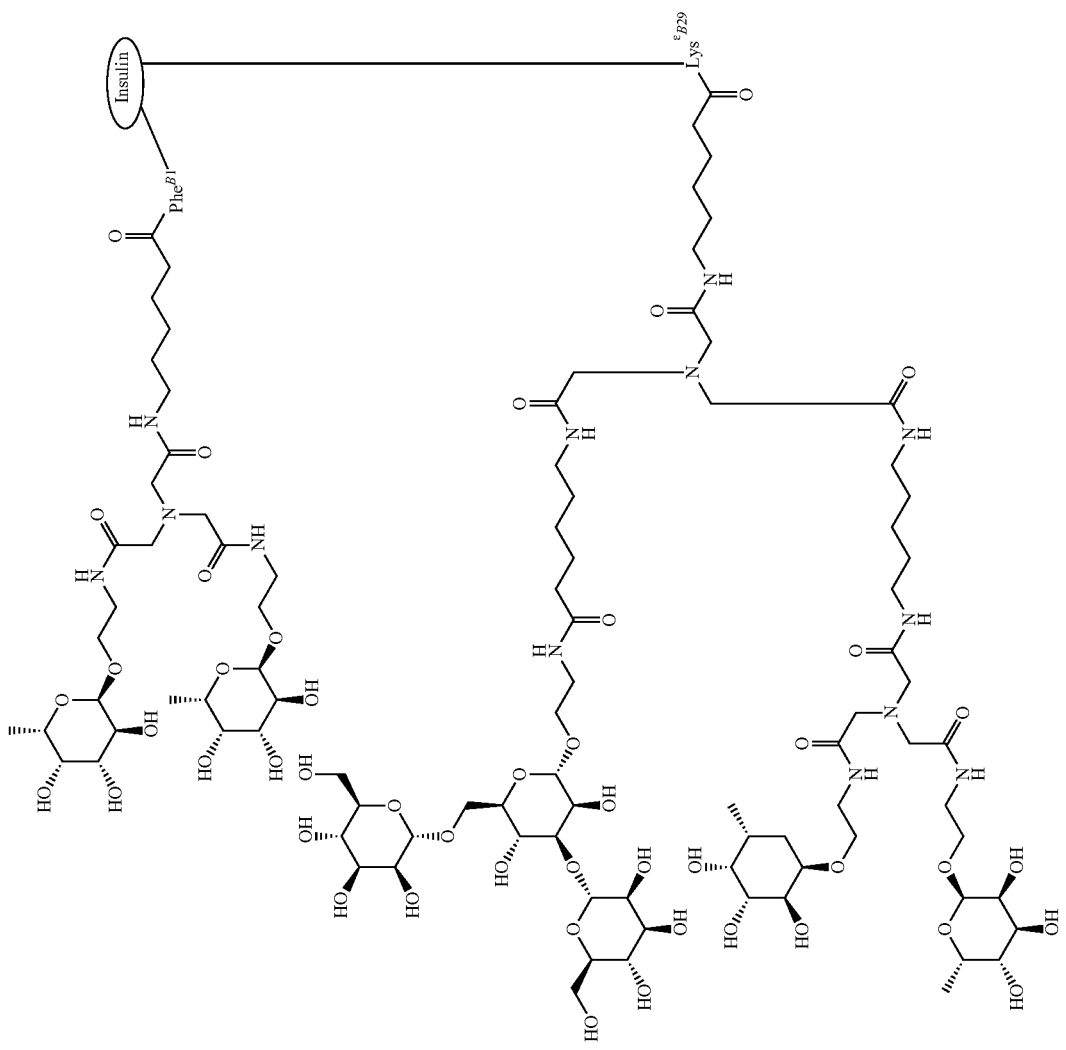

IOC-97
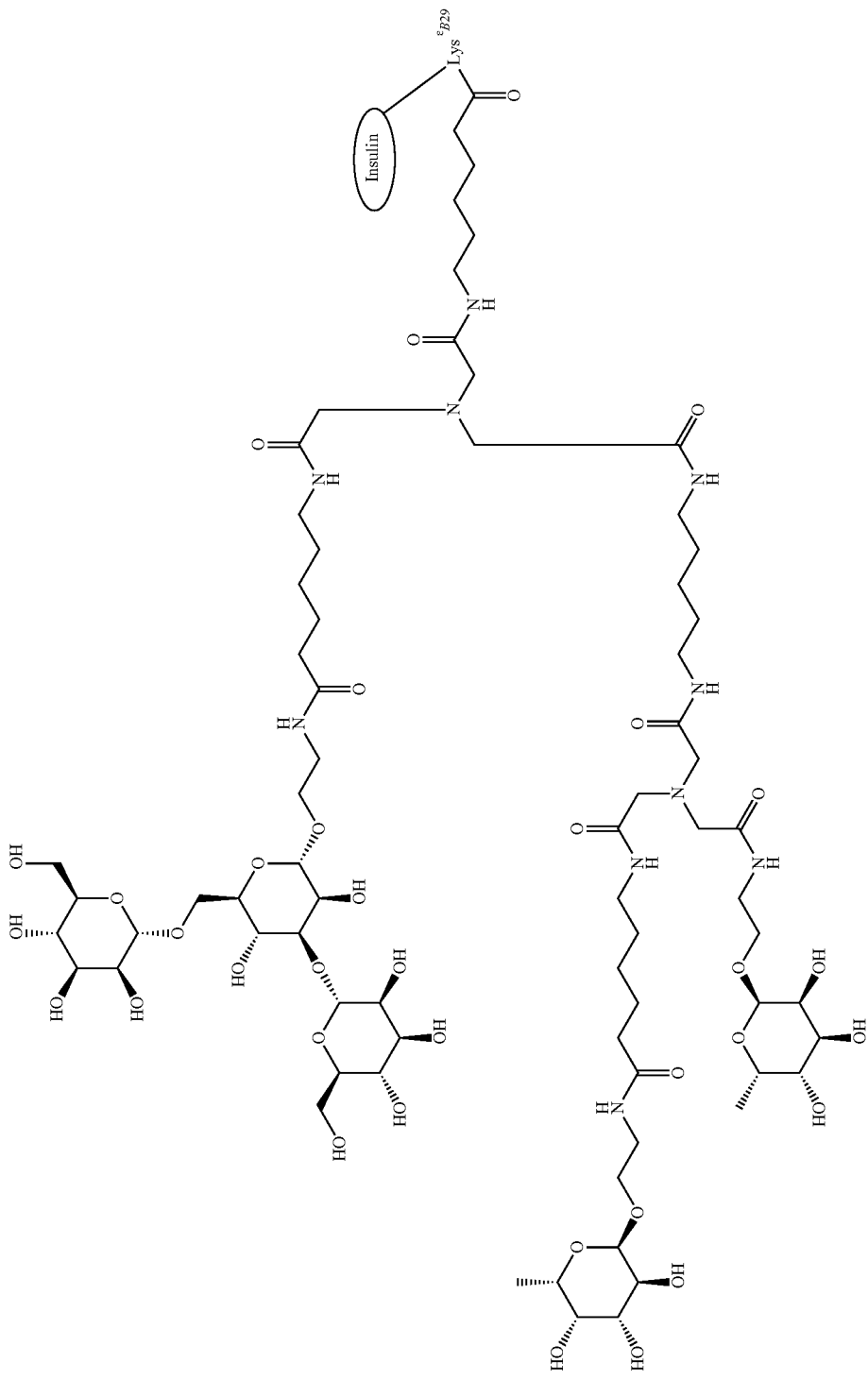

IOC-98
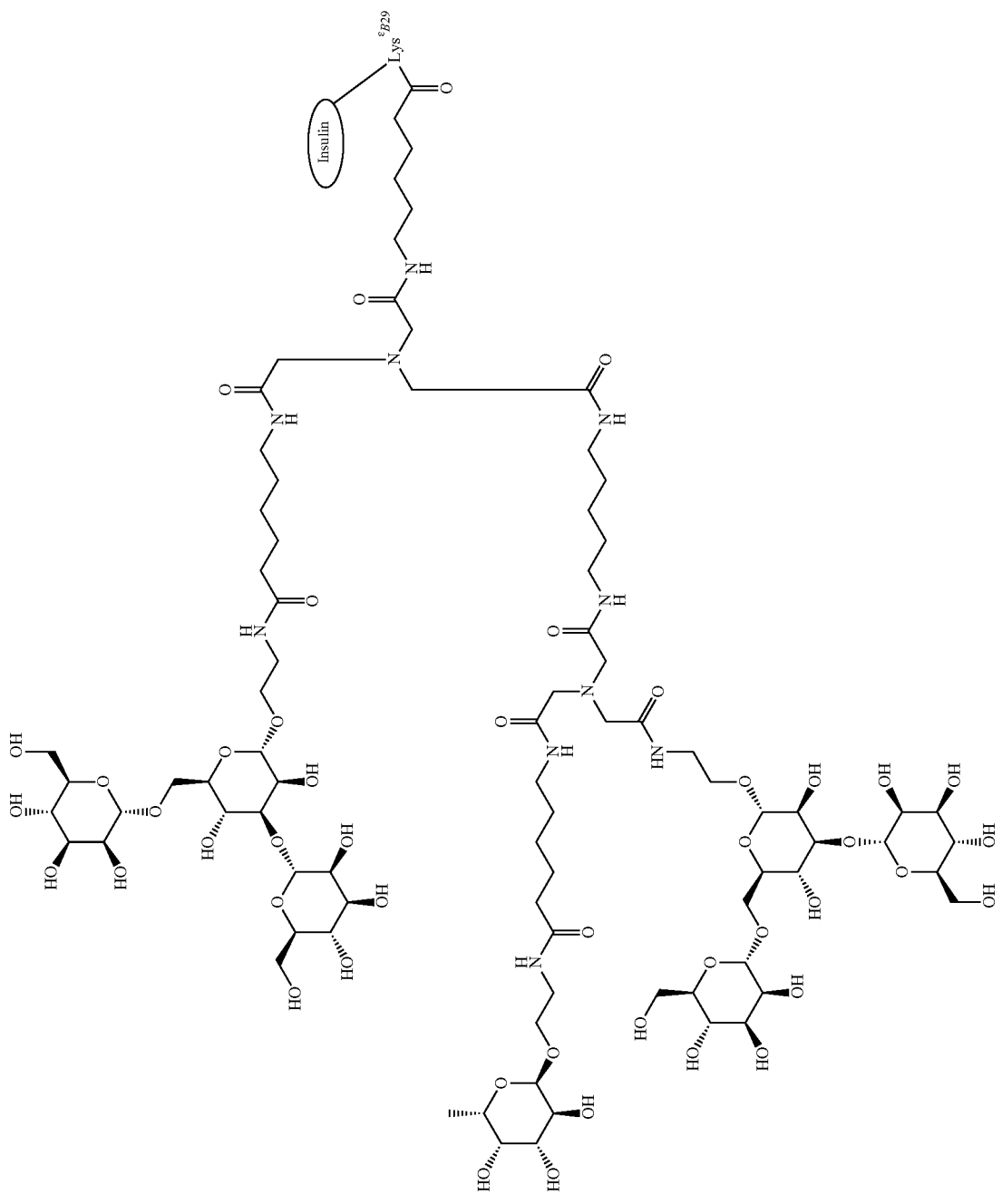

IOC-99
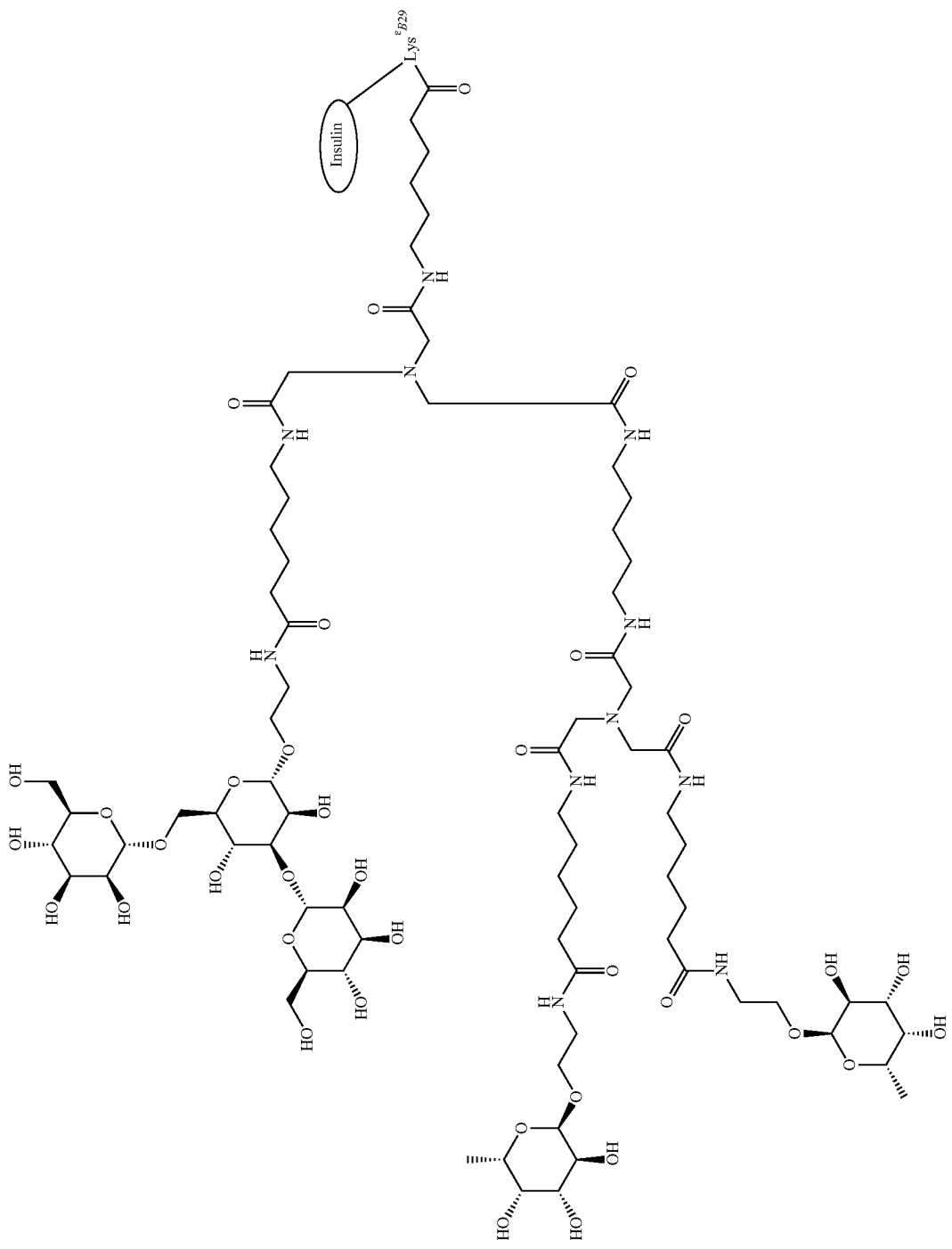

IOC-100
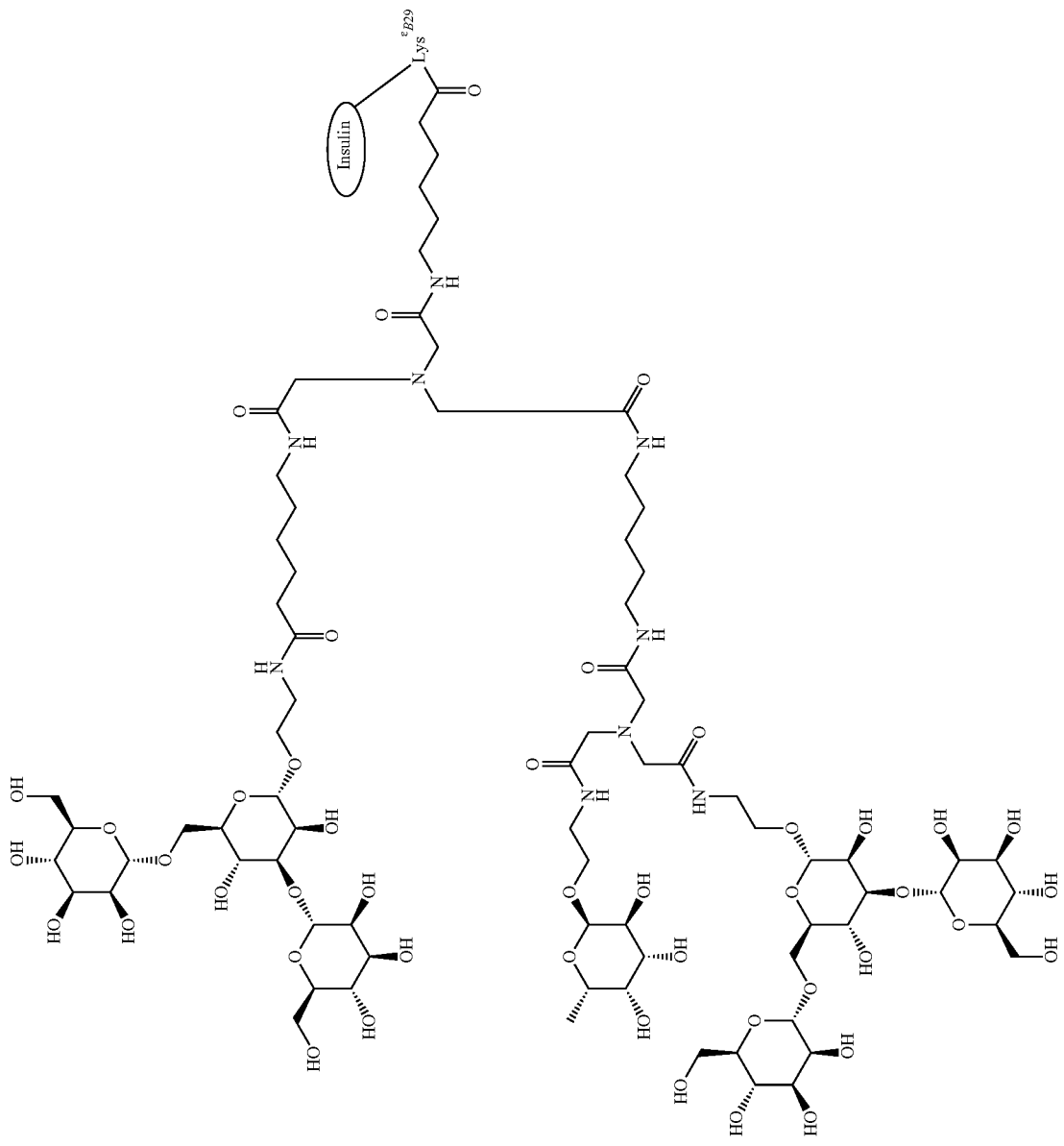

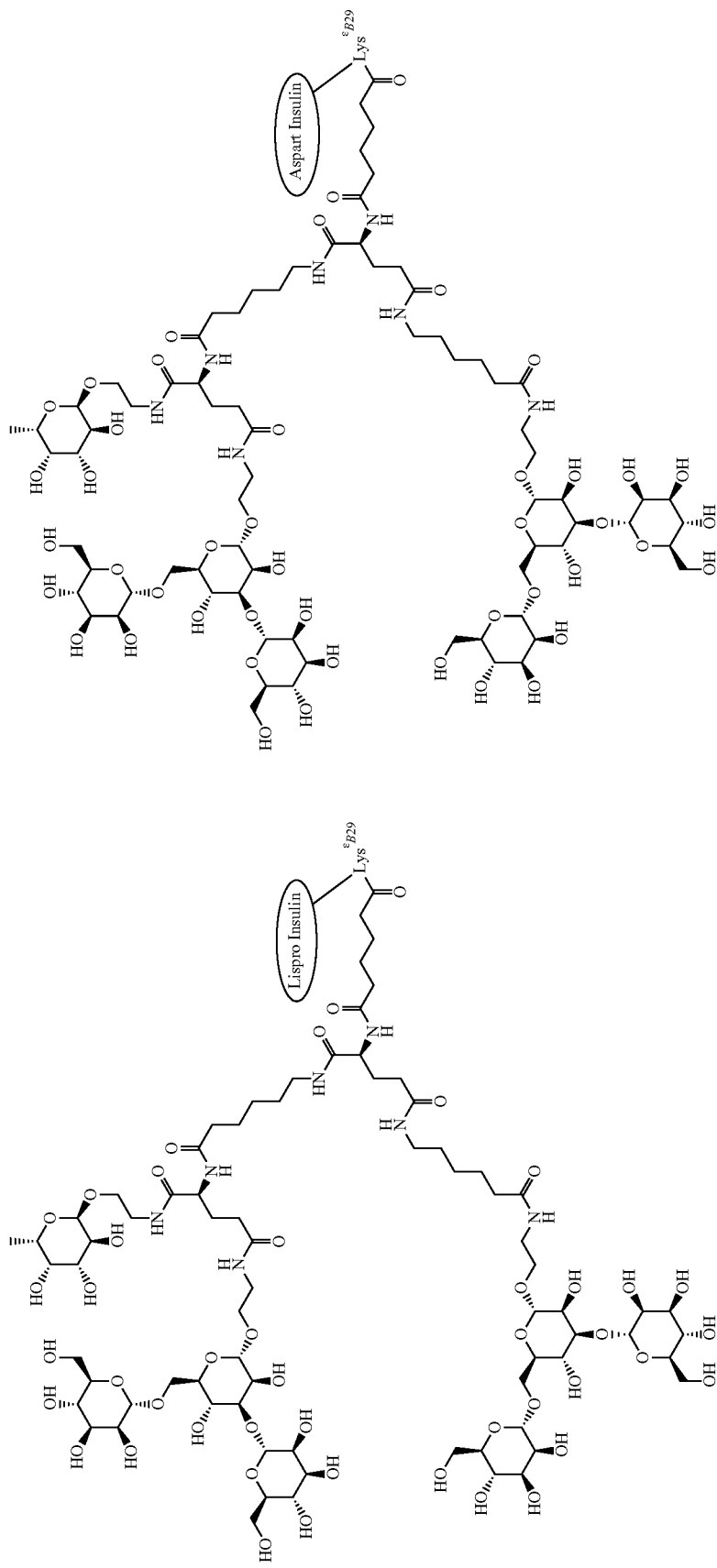

IOC-103
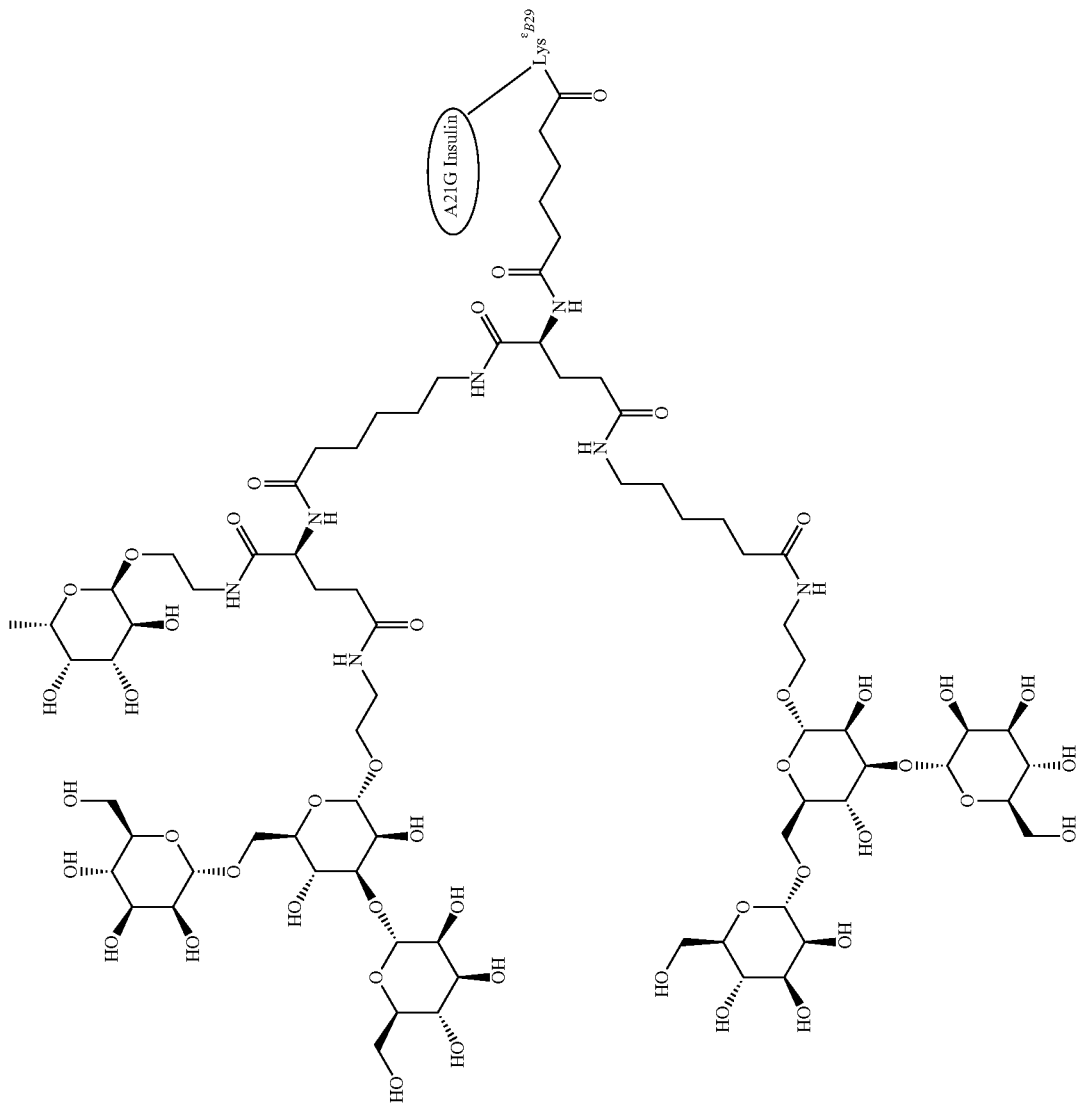

IOC-104
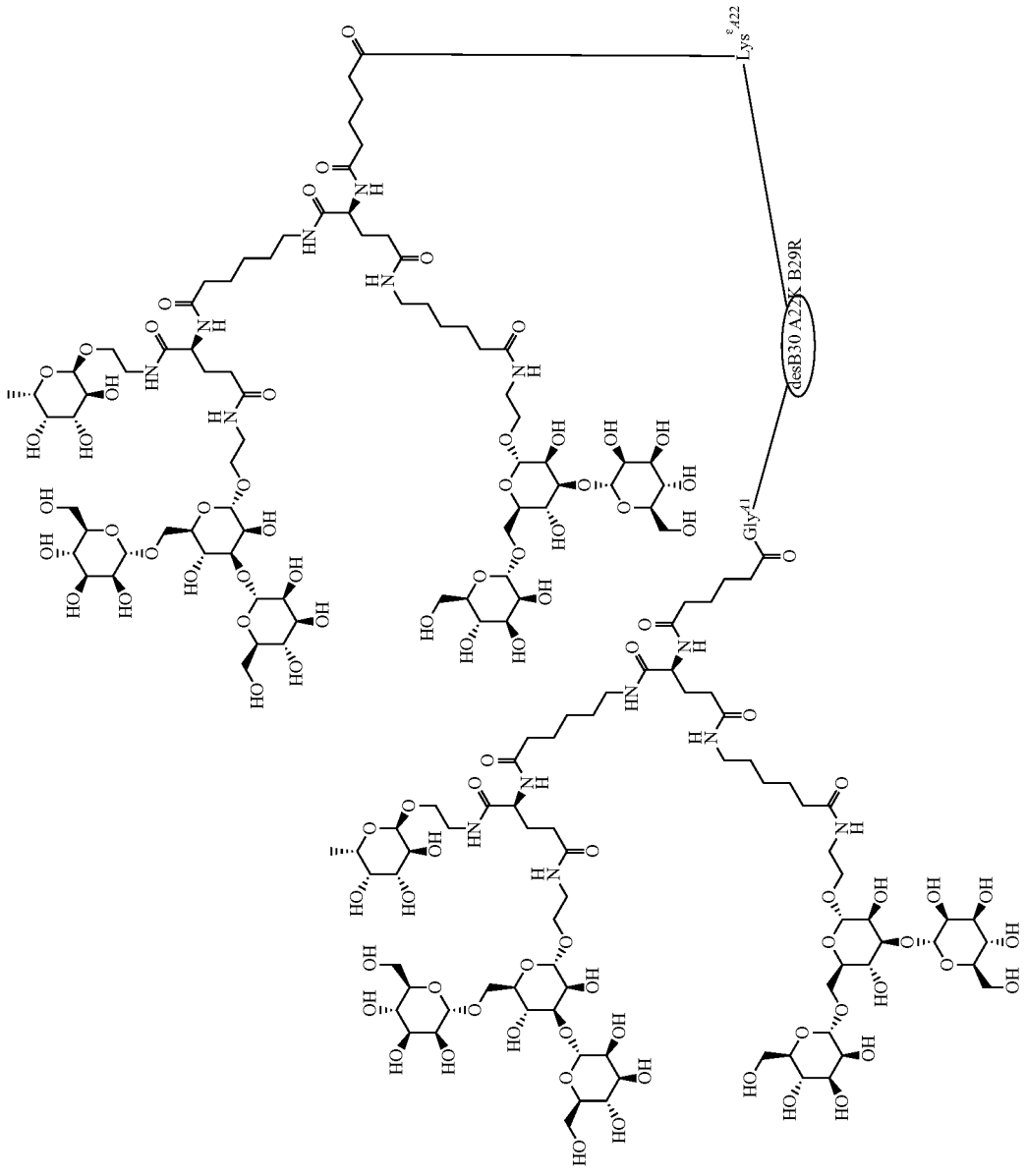

IOC-105
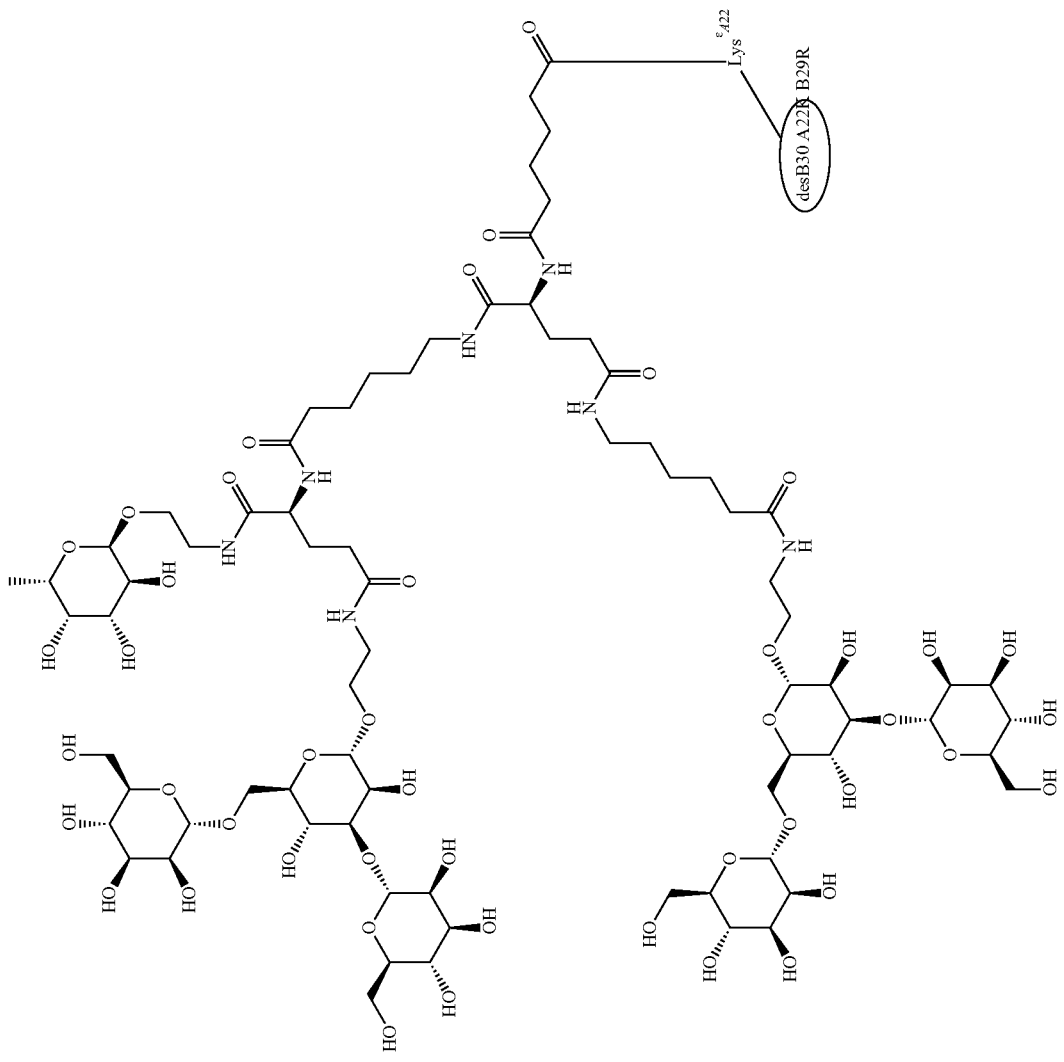

IOC-106
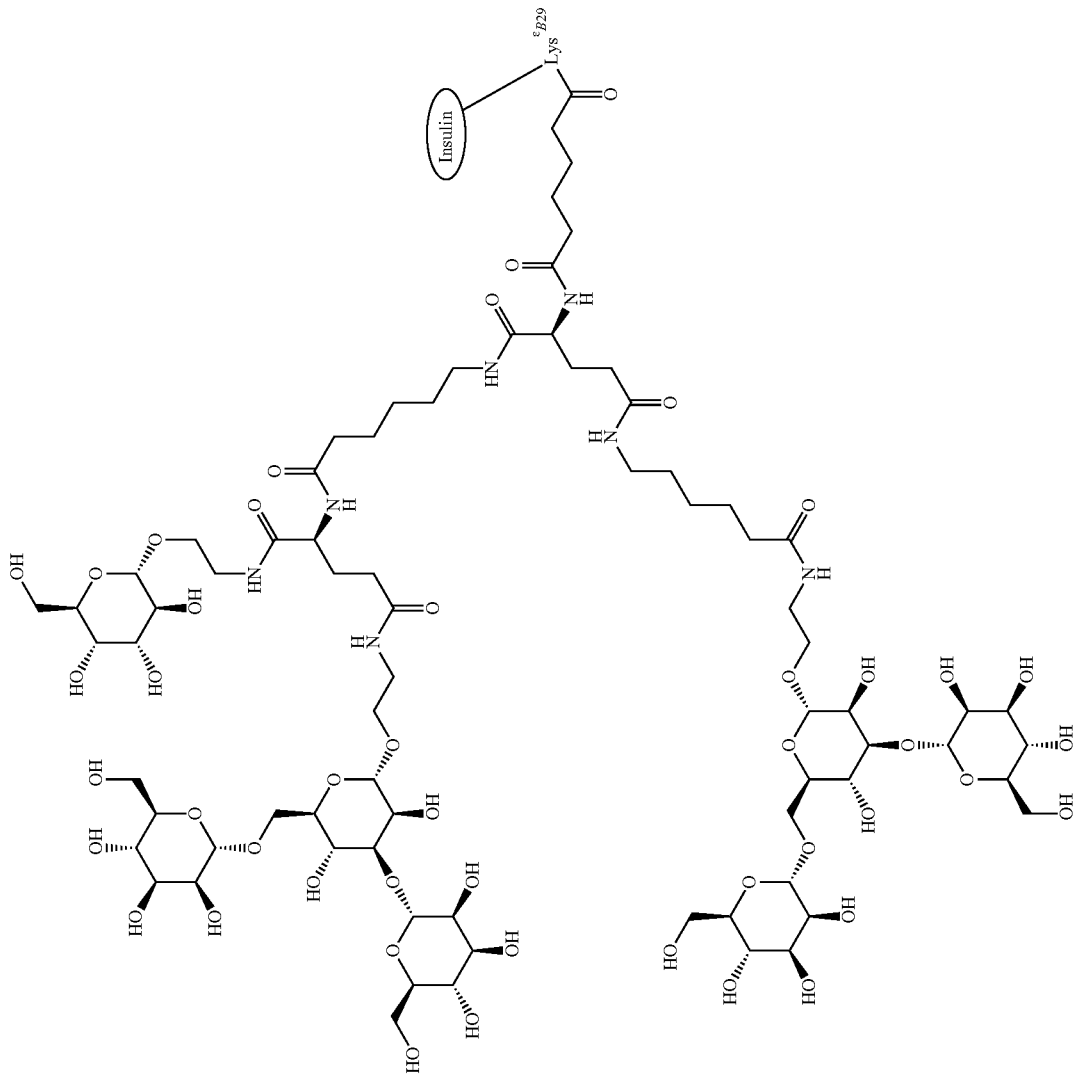

IOC-107
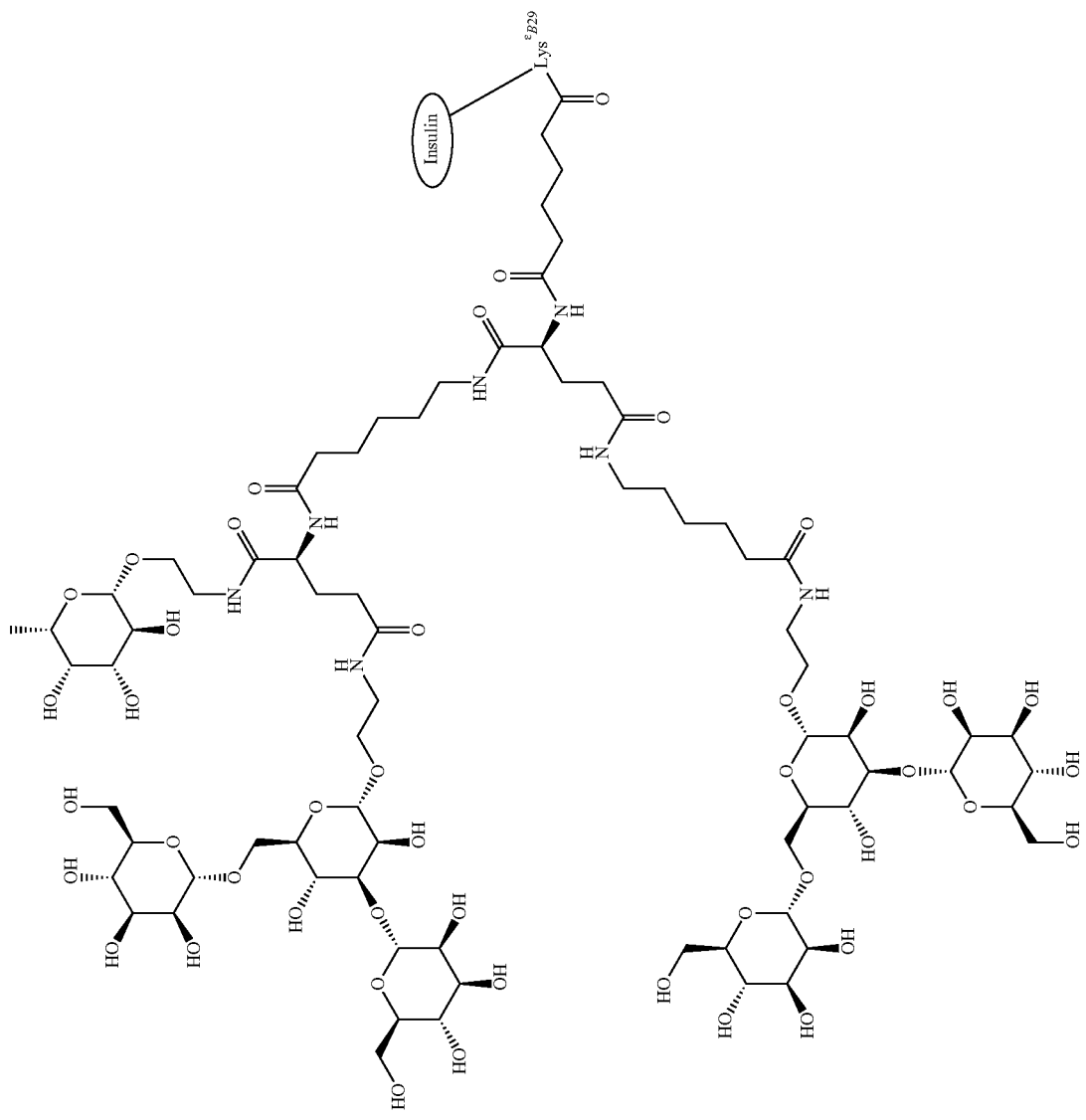

IOC-108
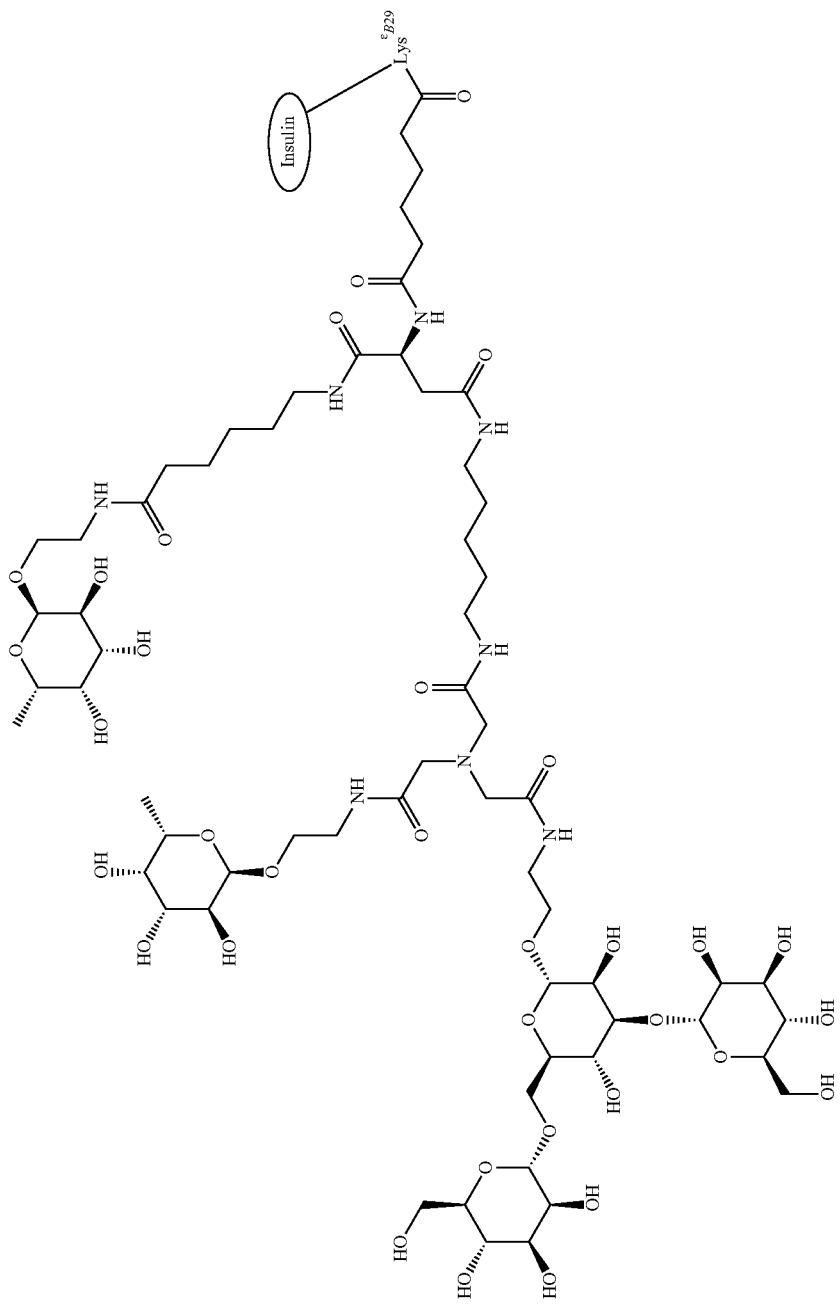

IOC-109
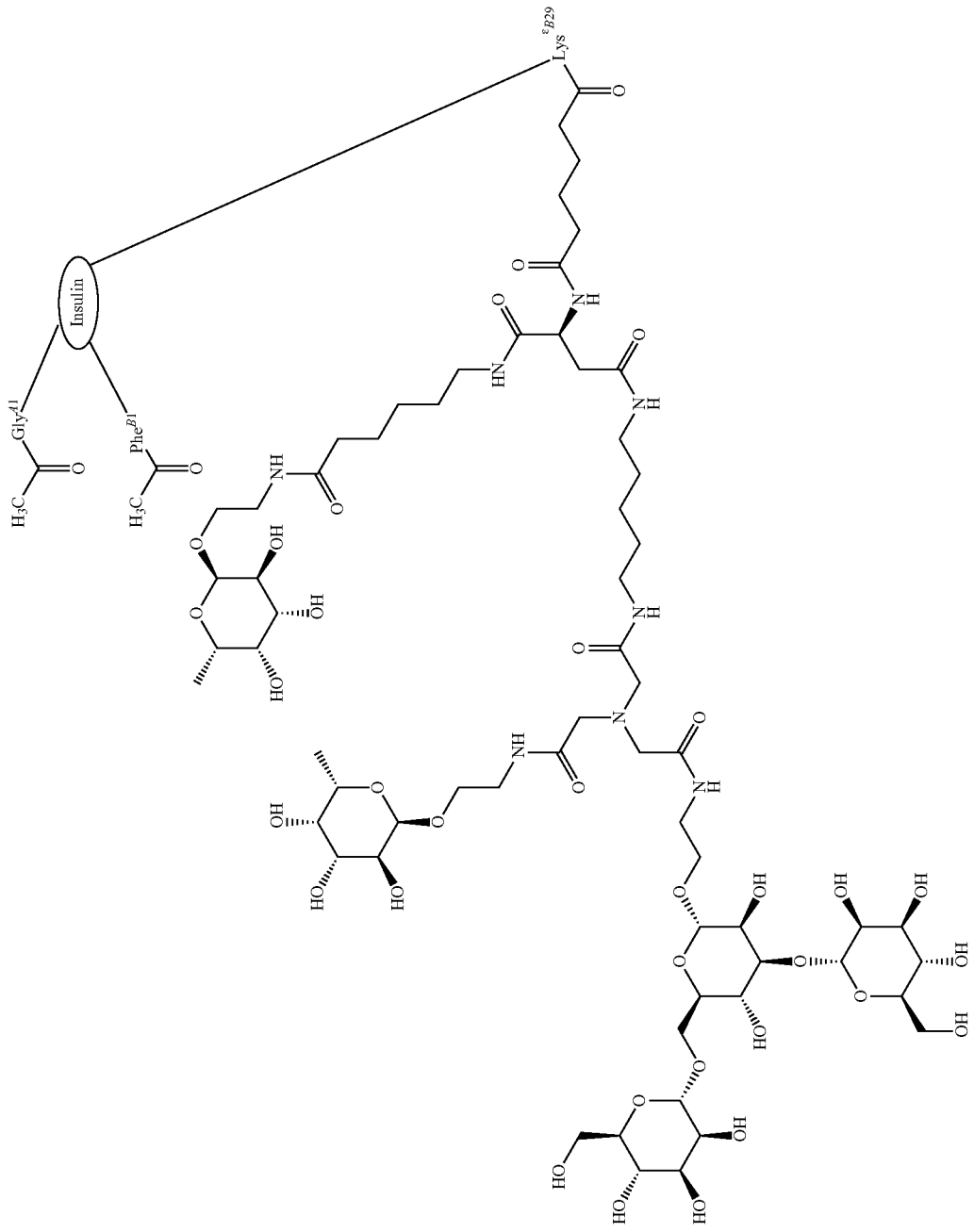

-continued
IOC-110
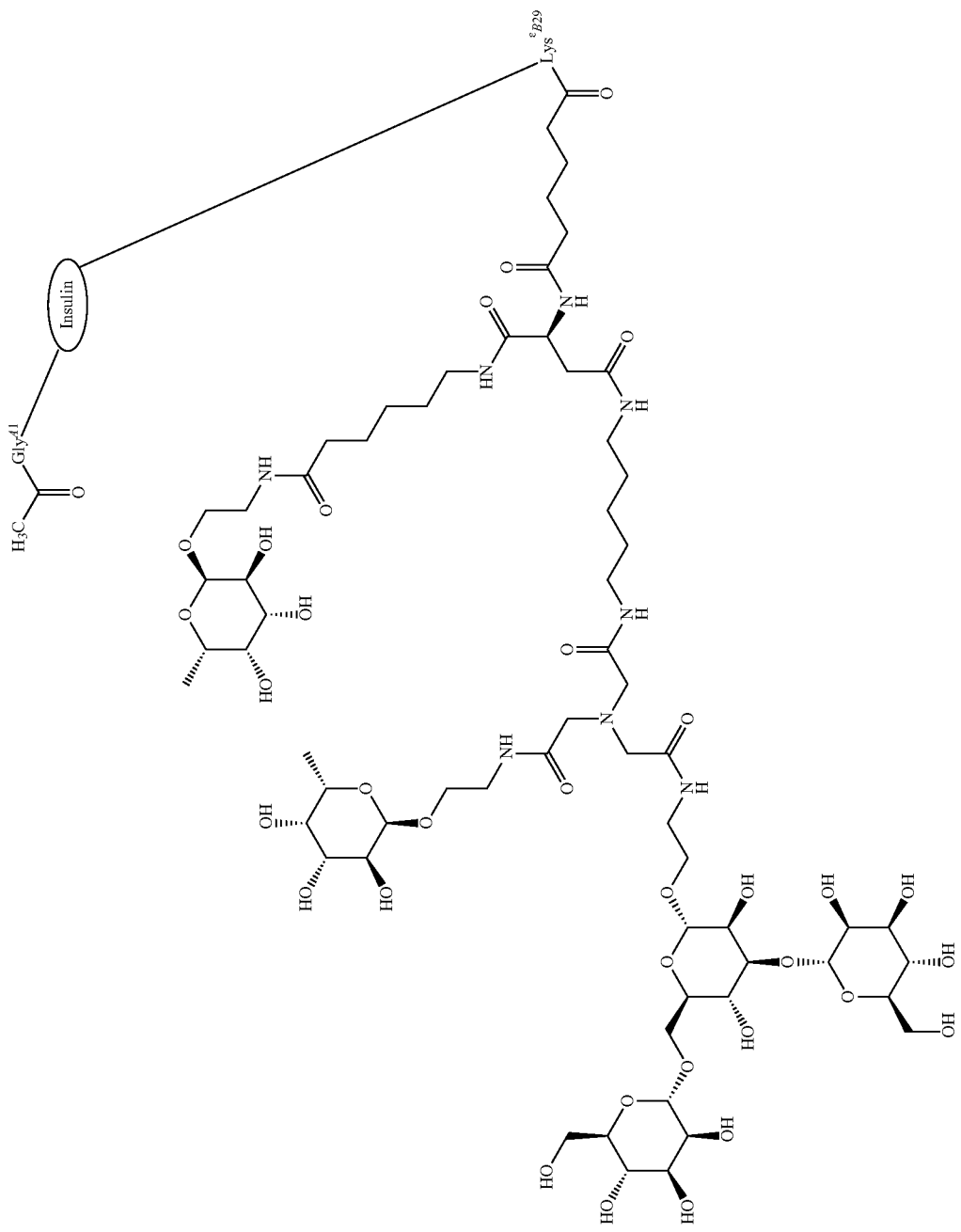

IOC-111
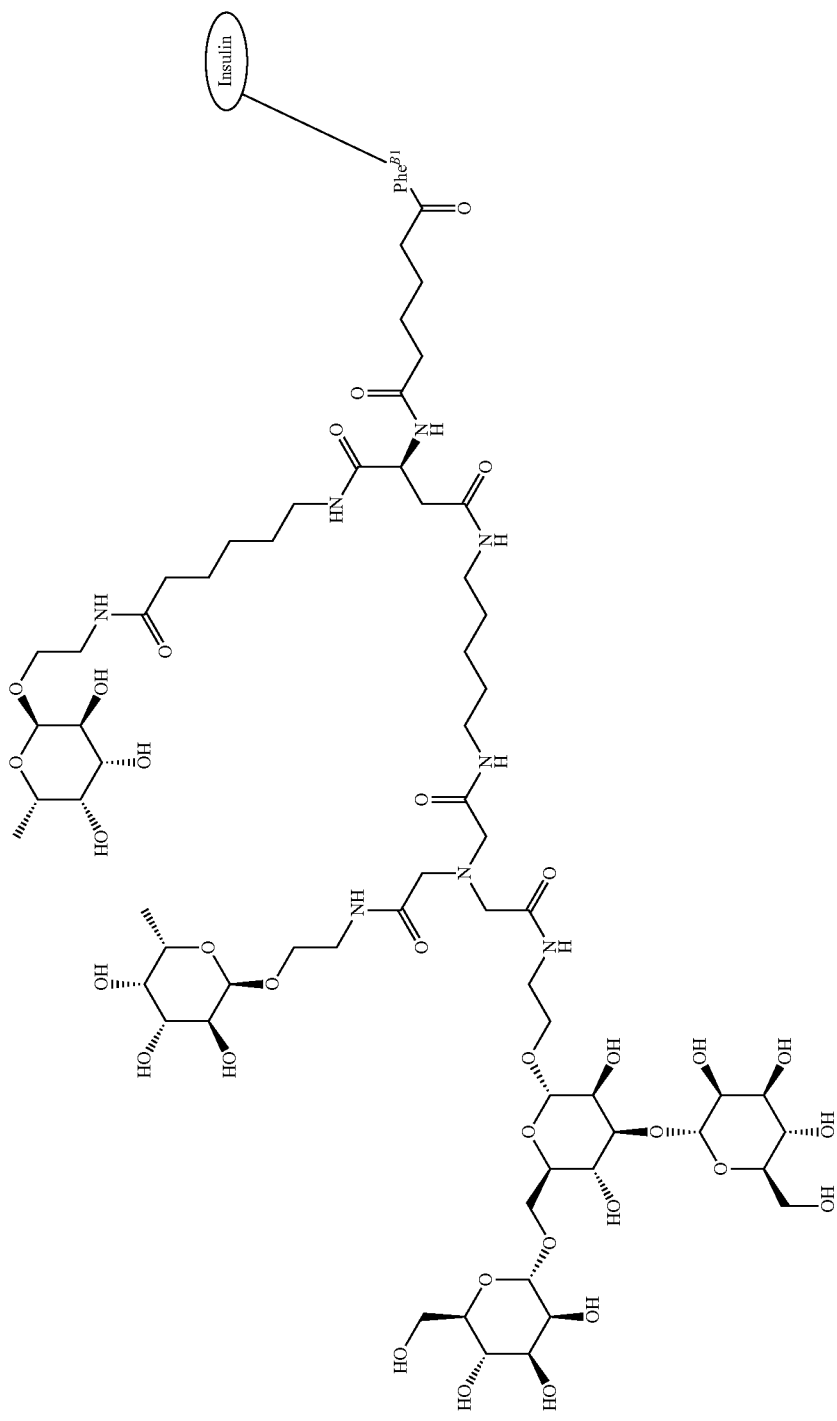

IOC-112
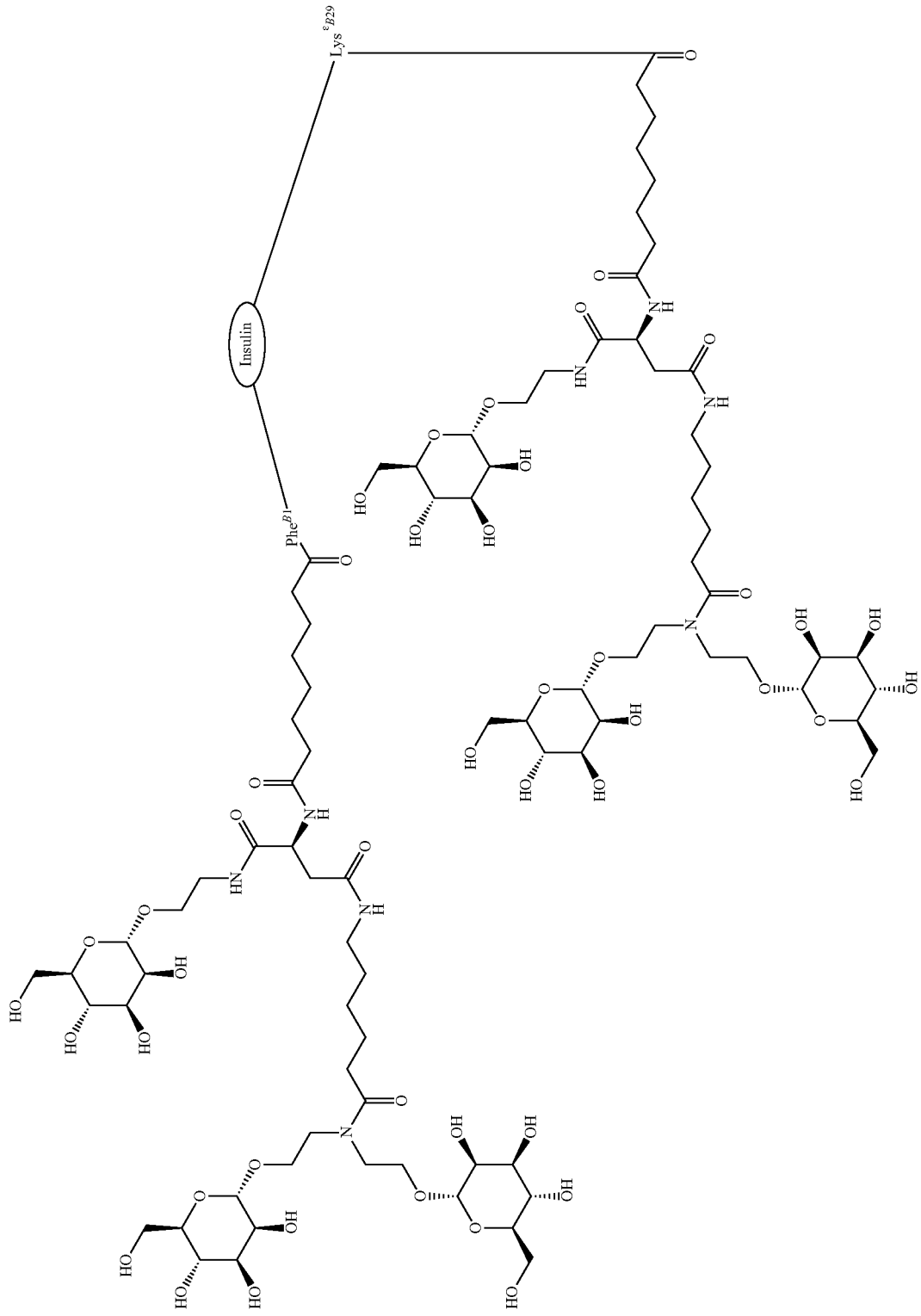

IOC-113
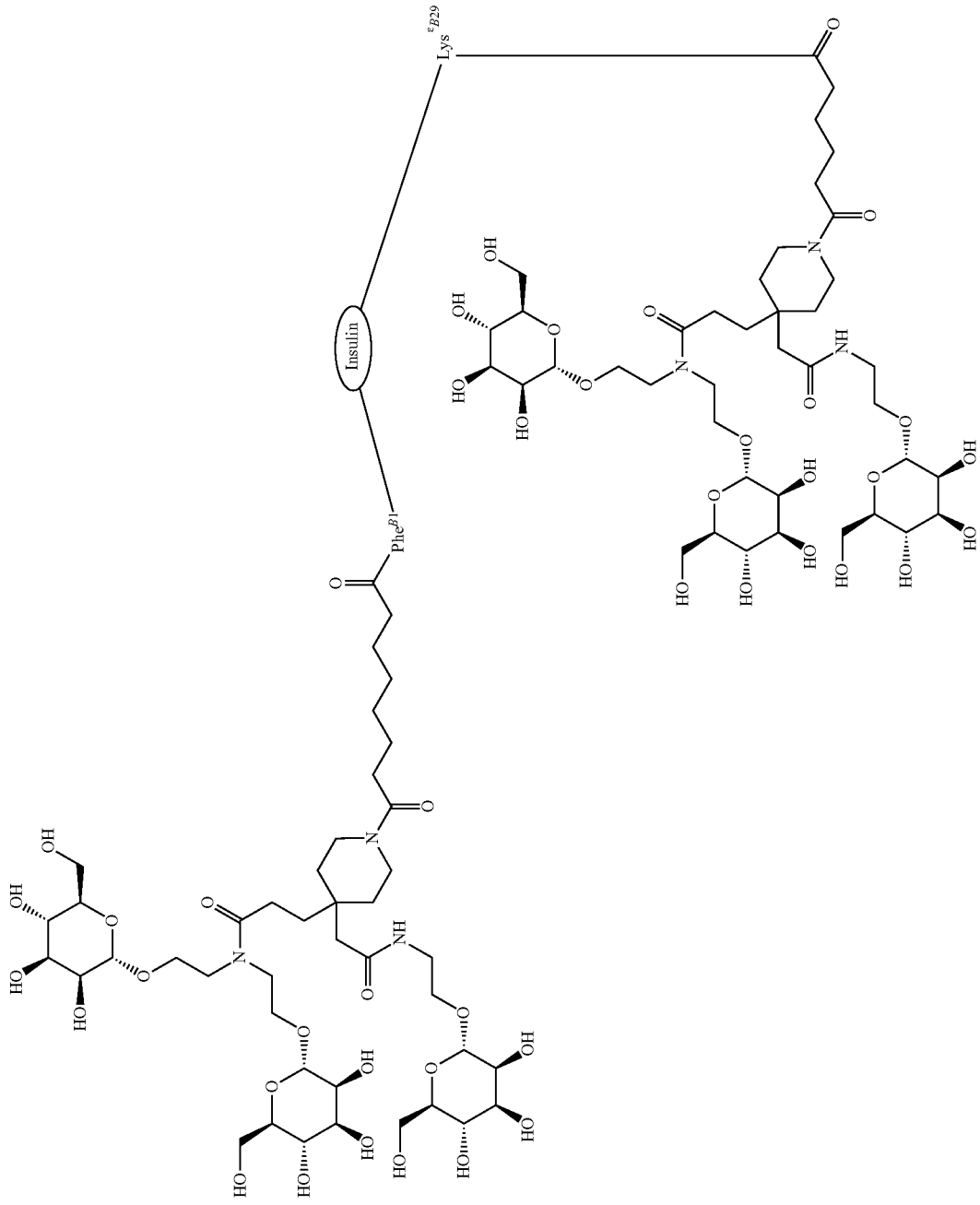

IOC-114
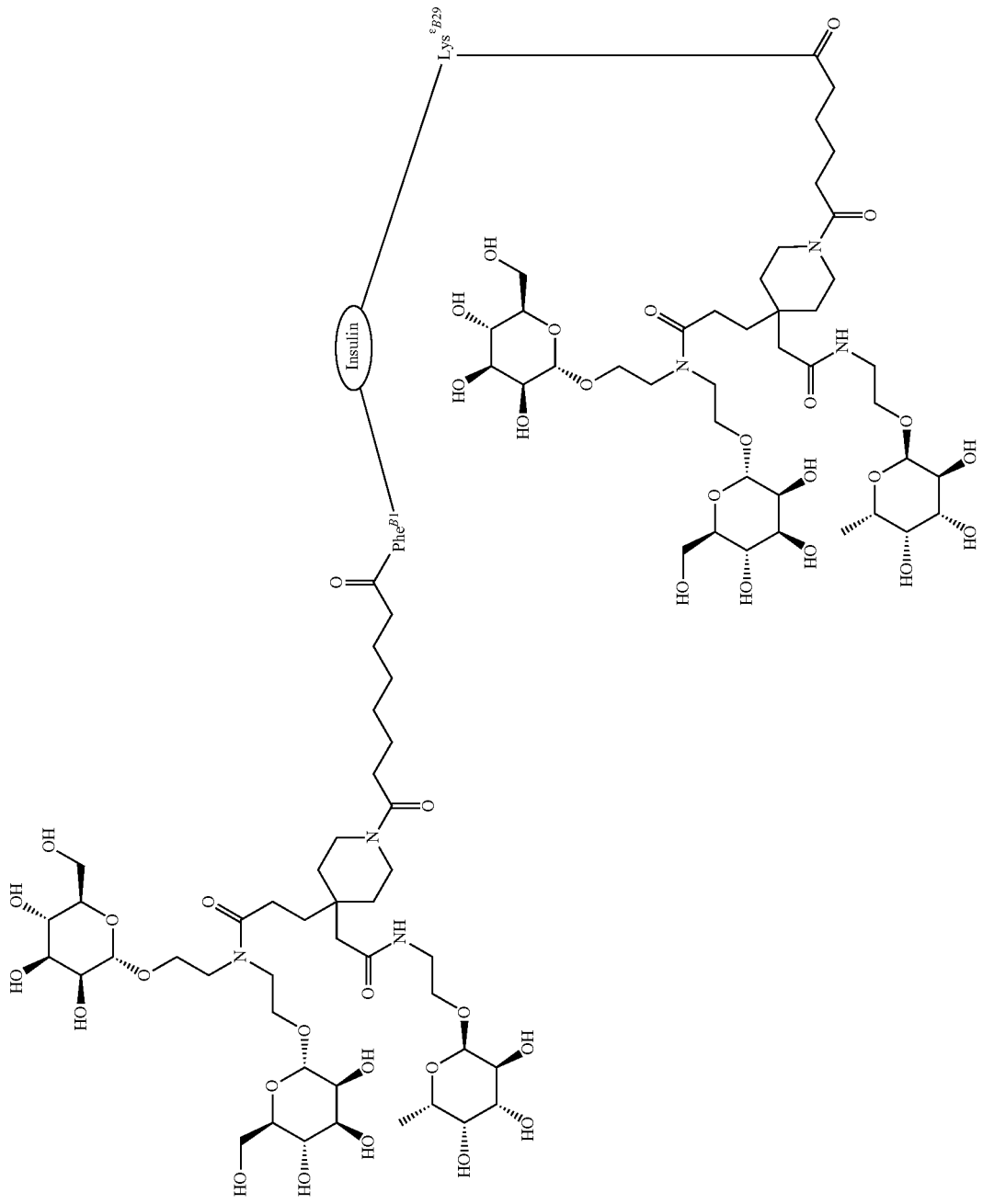

IOC-115
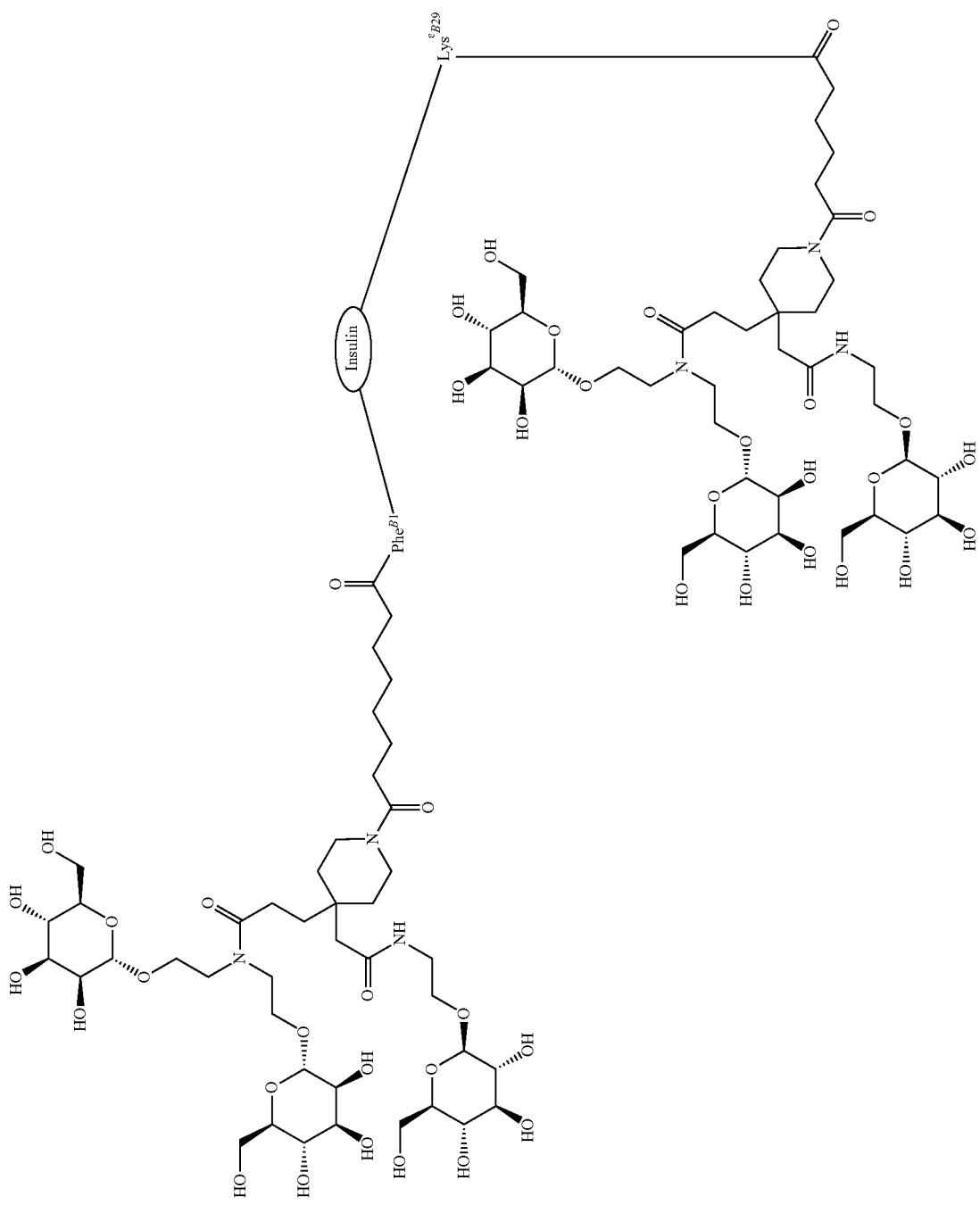

IOC-116
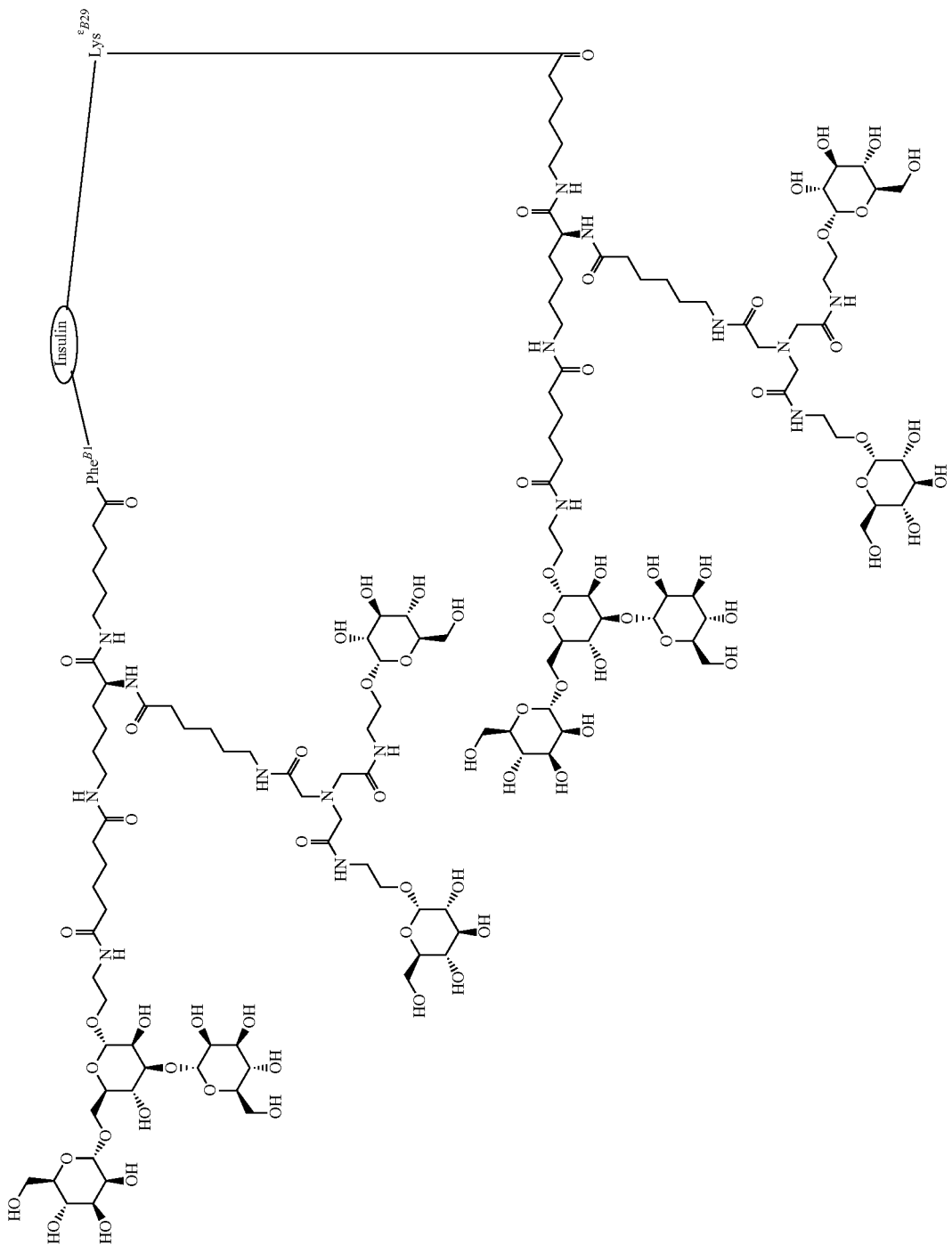

IOC-117
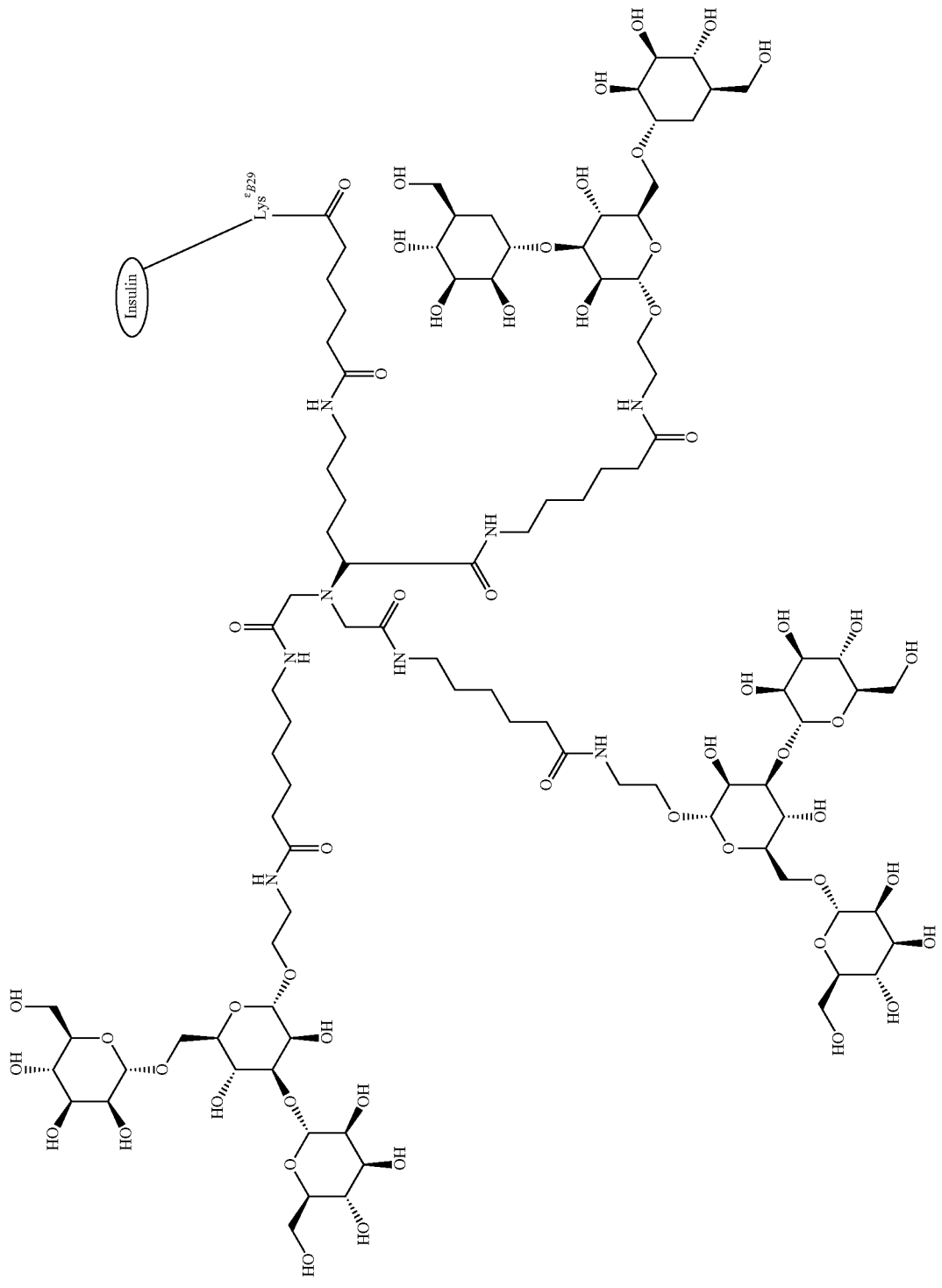

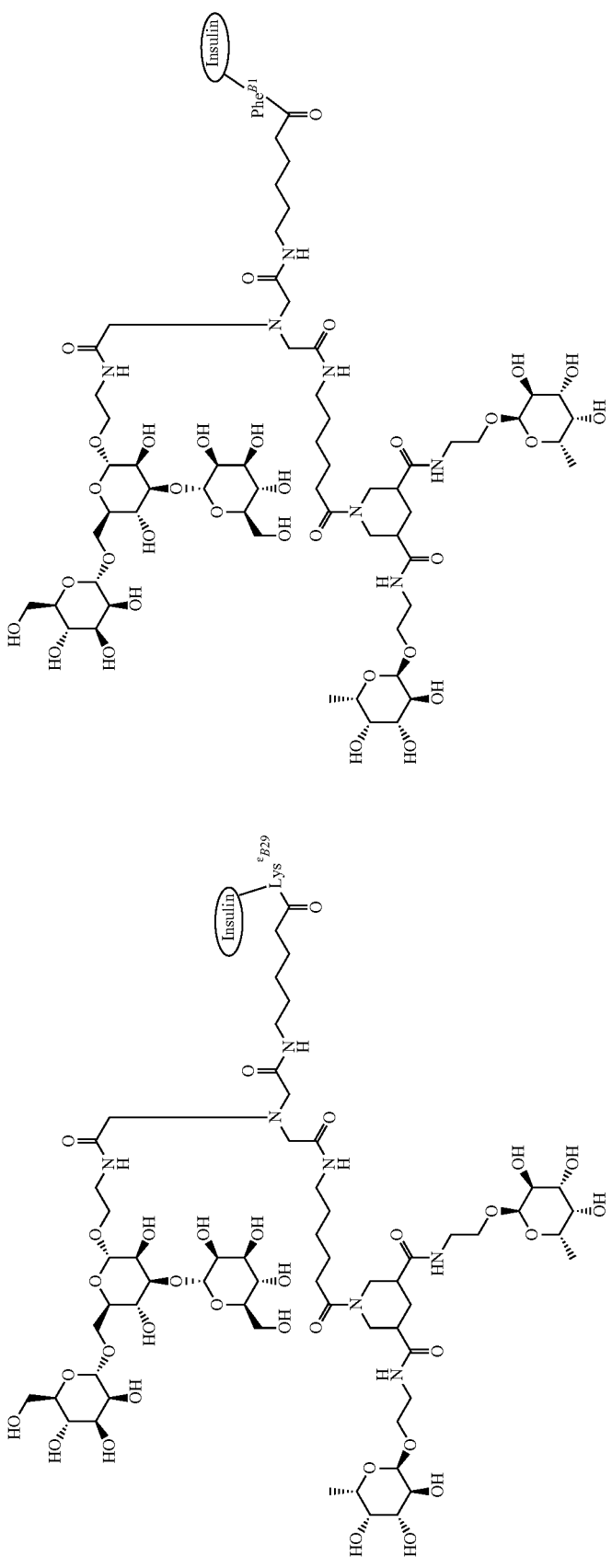

IOC-120
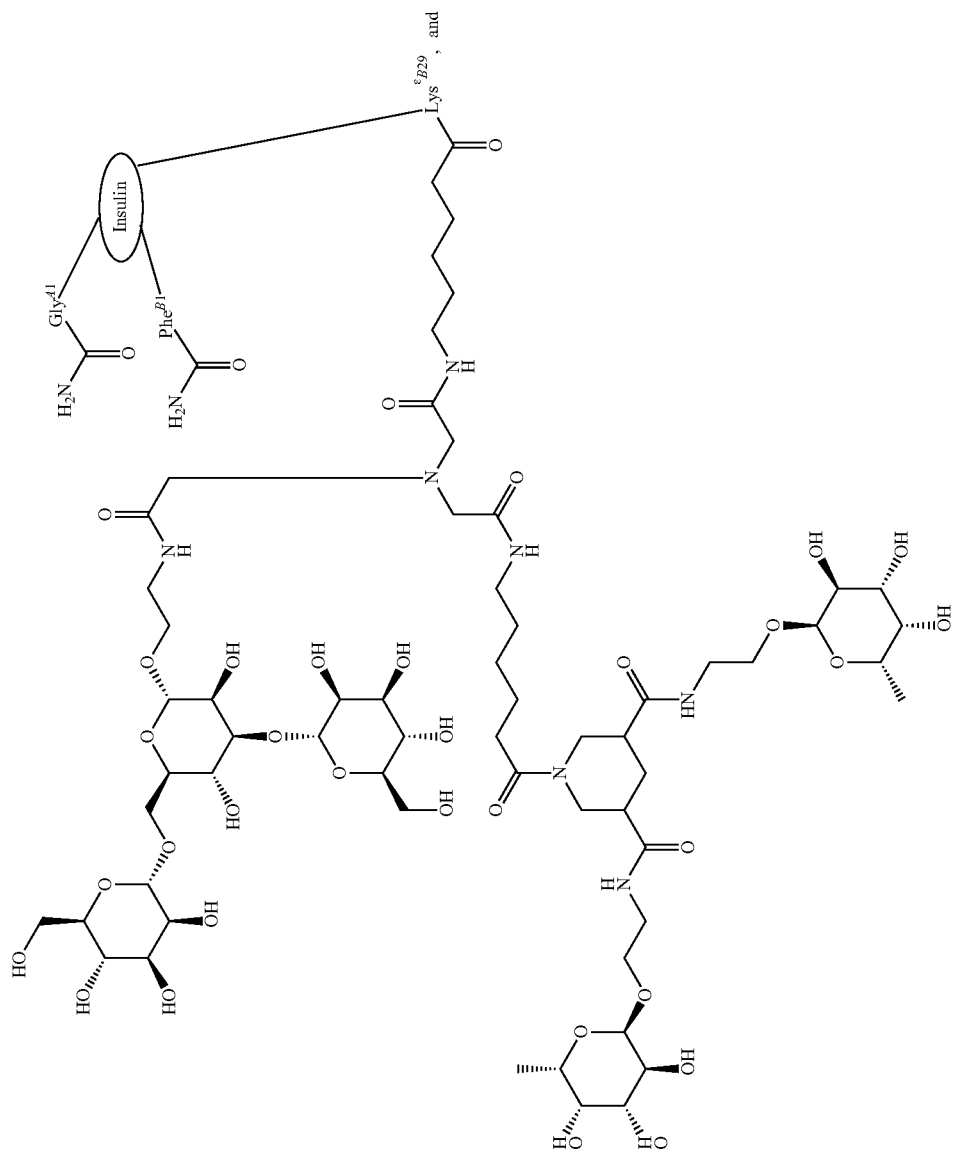

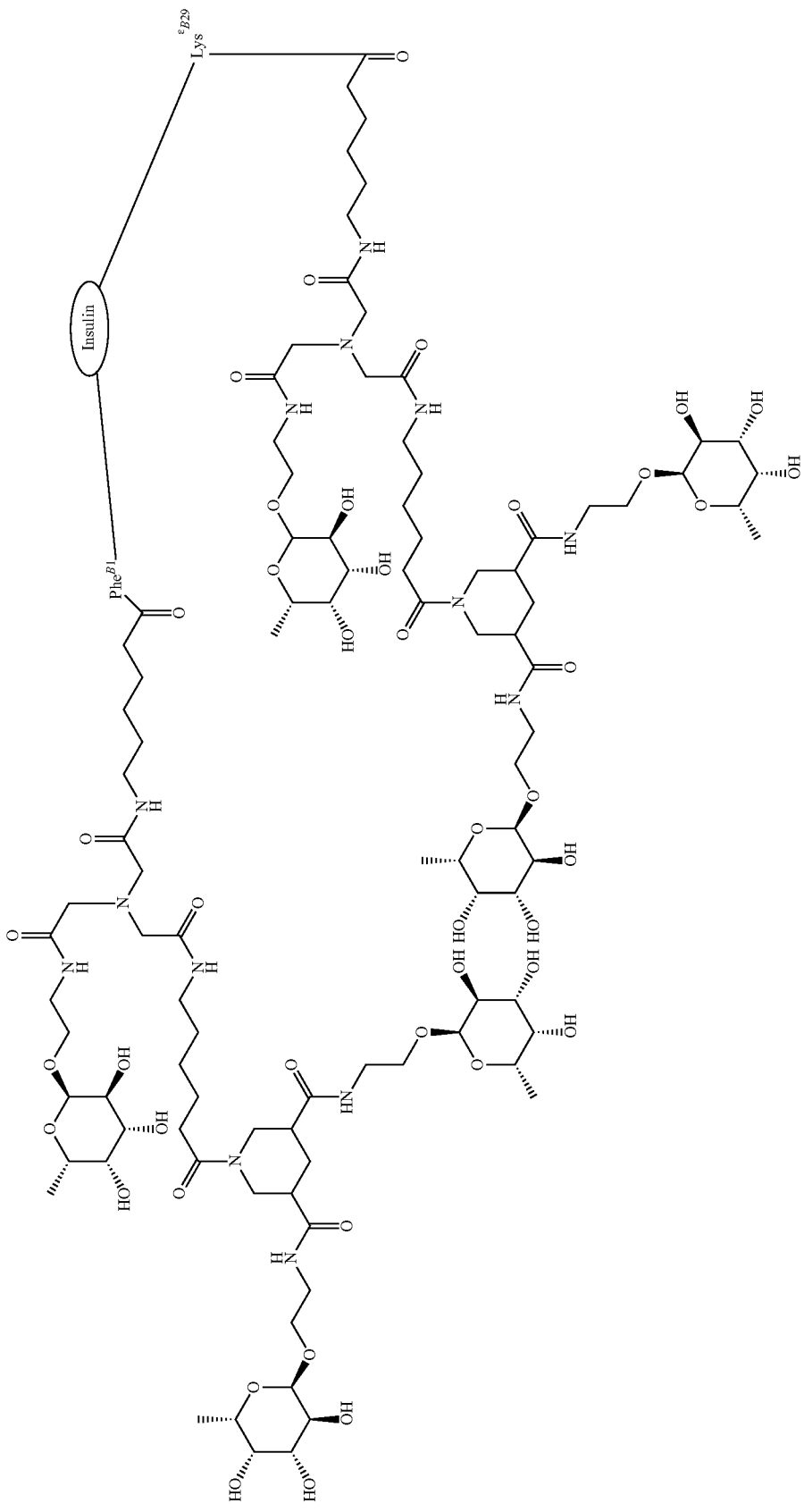

The present invention excludes insulin conjugates having the structure of IOC-212, IOC-213, or IOC-224 disclosed in U.S. Published application No. 20150105317 and shown as
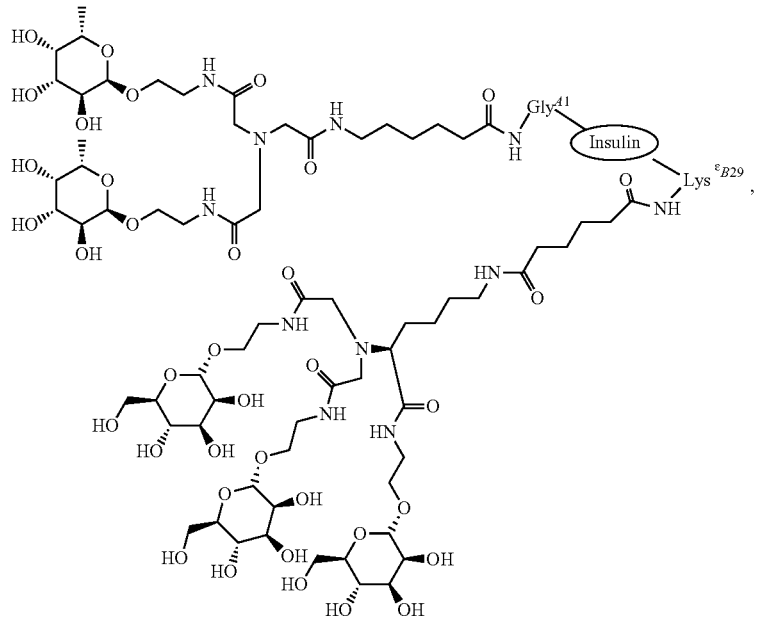
IOC-212
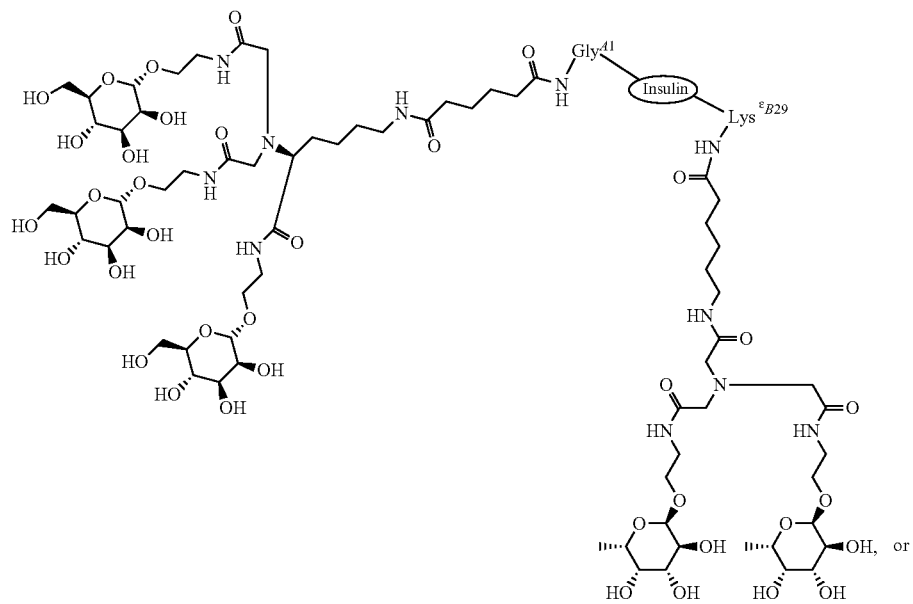
IOC-213, or IOC-224
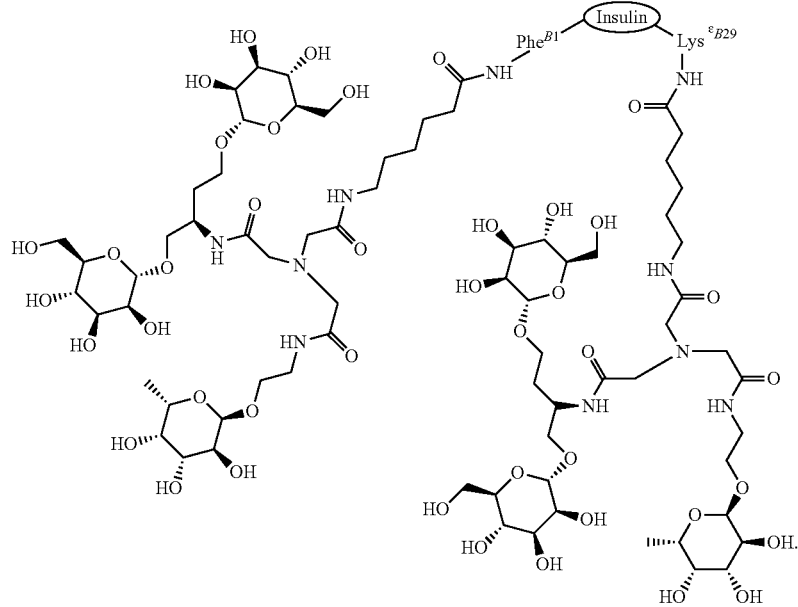
The present invention further excludes insulin conjugates having the structure of Compound A, disclosed as compound 11-6 in U.S. Patent Publication No. 20130131310 and having the structure
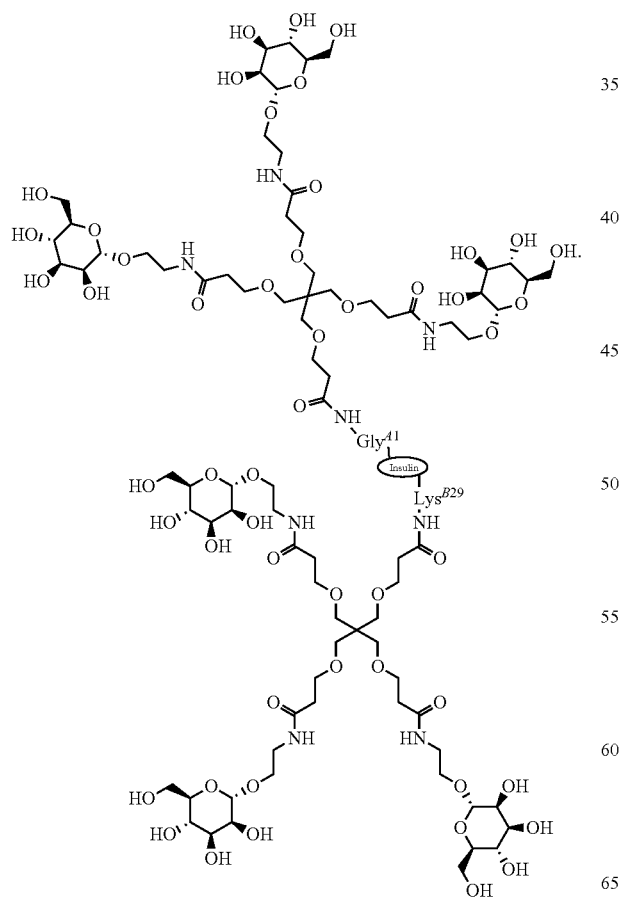

The present invention further excludes conjugates disclosed in International publication WO10088294 having a structure selected from the group consisting of

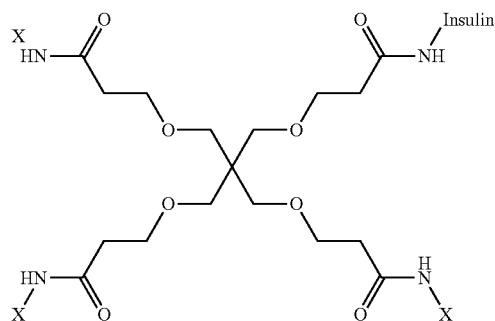

and

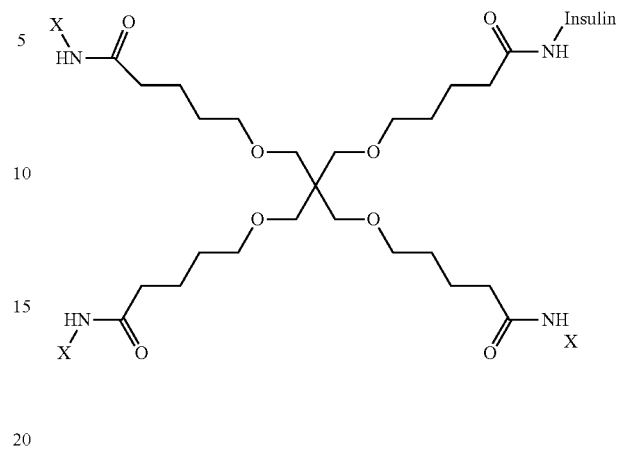

wherein each X is independently a ligand comprising or consisting of a monosaccharide, bisaccharide, trisaccharide, tetrasaccharide, or branched trisaccharide and exemplified by structures I-9, I-11, I-14, I-15, and I-16 as shown:

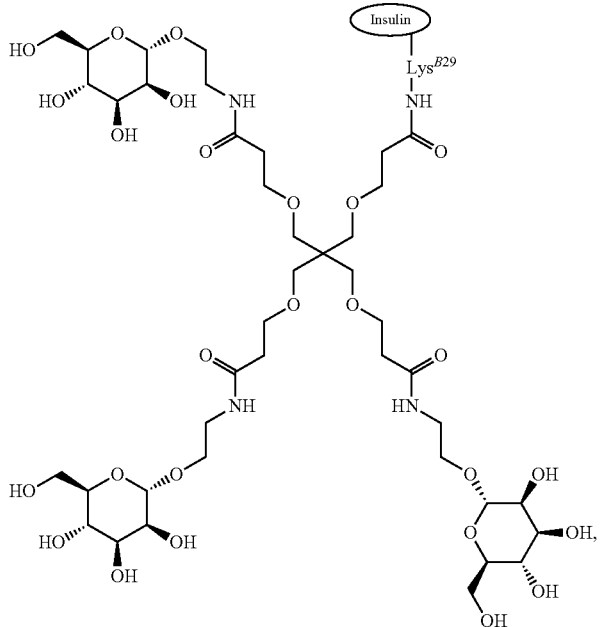

I-9

I-11
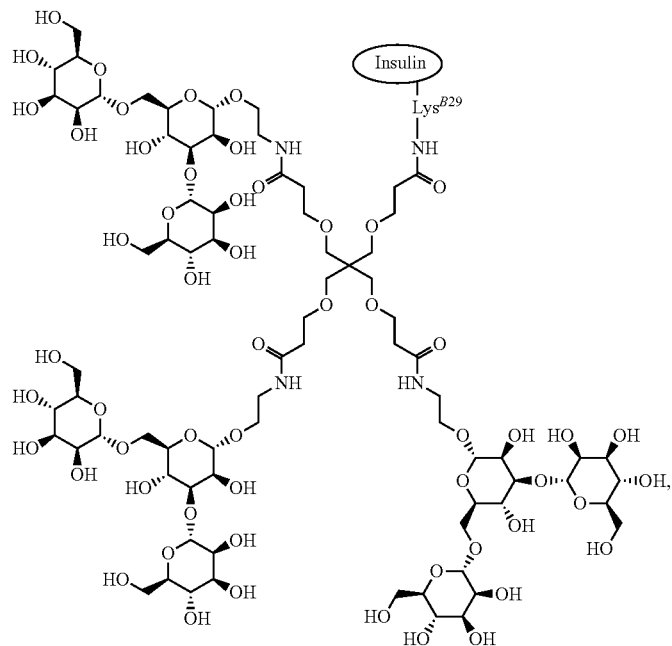
I-14
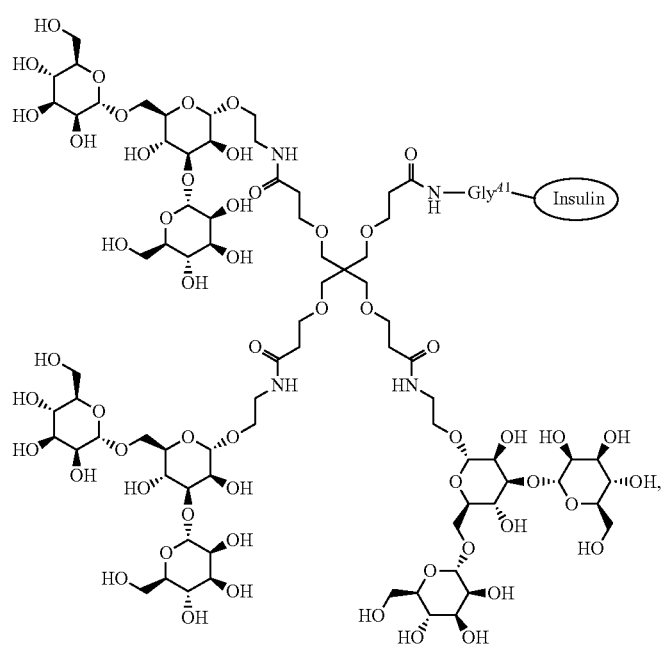

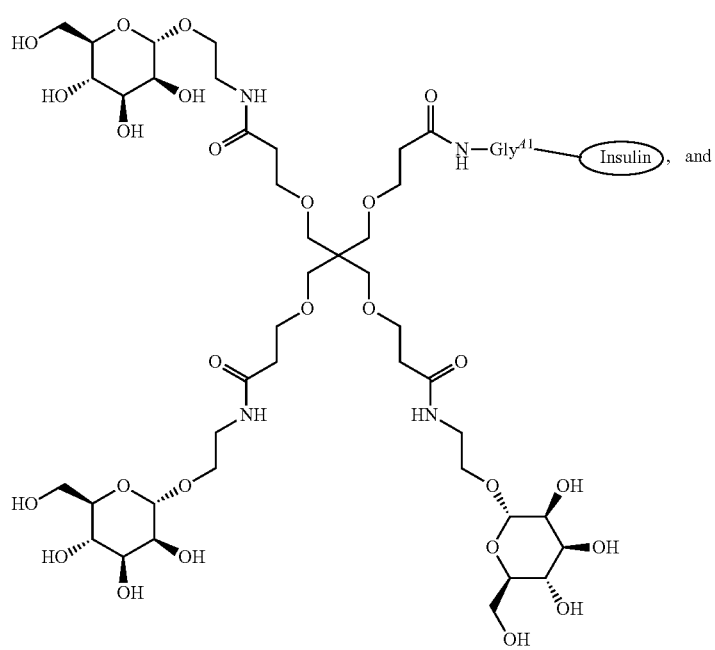

I-15

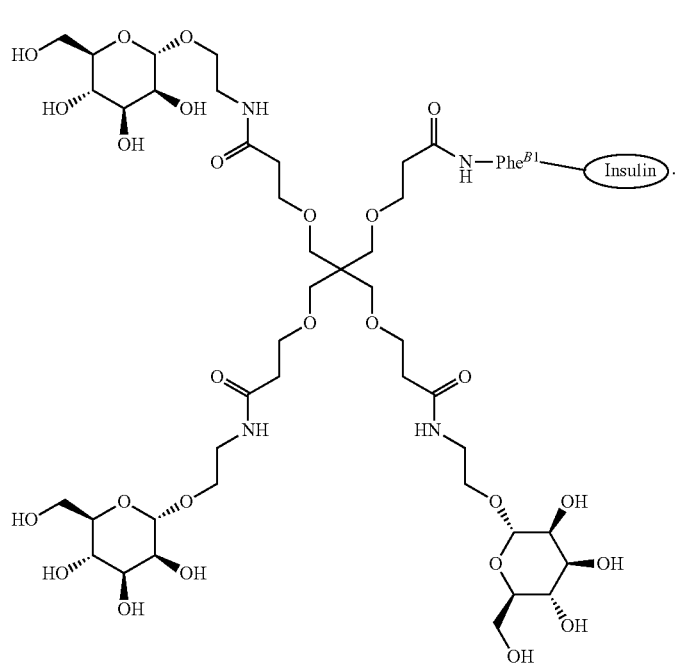

I-16

Sustained Release Formulations

In particular embodiments it may be advantageous to administer an insulin conjugate in a sustained fashion (i.e., in a form that exhibits an absorption profile that is more sustained than soluble recombinant human insulin). This will provide a sustained level of conjugate that can respond to fluctuations in glucose on a timescale that it more closely related to the typical glucose fluctuation timescale (i.e., hours rather than minutes). In particular embodiments, the sustained release formulation may exhibit a zero-order release of the conjugate when administered to a mammal under non-hyperglycemic conditions (i.e., fasted conditions).

It will be appreciated that any formulation that provides a sustained absorption profile may be used. In particular embodiments this may be achieved by combining the conjugate with other ingredients that slow its release properties into systemic circulation. For example, PZI (protamine zinc insulin) formulations may be used for this purpose. The present disclosure encompasses amorphous and crystalline forms of these PZI formulations.

Thus, in particular embodiments, a formulation of the present disclosure includes from about 0.05 to about 10 mg protamine/mg conjugate. For example, from about 0.2 to about 10 mg protamine/mg conjugate, e.g., about 1 to about 5 mg protamine/mg conjugate.

In particular embodiments, a formulation of the present disclosure includes from about 0.006 to about 0.5 mg zinc/mg conjugate. For example, from about 0.05 to about 0.5 mg zinc/mg conjugate, e.g., about 0.1 to about 0.25 mg zinc/mg conjugate.

In particular embodiments, a formulation of the present disclosure includes protamine and zinc in a ratio (w/w) in the range of about 100:1 to about 5:1, for example, from about 50:1 to about 5:1, e.g., about 40:1 to about 10:1. In particular embodiments, a PZI formulation of the present disclosure includes protamine and zinc in a ratio (w/w) in the range of about 20:1 to about 5:1, for example, about 20:1 to about 10:1, about 20:1 to about 15:1, about 15:1 to about 5:1, about 10:1 to about 5:1, about 10:1 to about 15:1.

One or more of the following components may be included in the PZI formulation: an antimicrobial preservative, an isotonic agent, and/or an unconjugated insulin molecule.

In particular embodiments, a formulation of the present disclosure includes an antimicrobial preservative (e.g., m-cresol, phenol, methylparaben, or propylparaben). In particular embodiments, the antimicrobial preservative is m-cresol. For example, in particular embodiments, a formulation may include from about 0.1 to about 1.0% v/v m-cresol. For example, from about 0.1 to about 0.5% v/v m-cresol, e.g., about 0.15 to about 0.35% v/v m-cresol.

In particular embodiments, a formulation of the present disclosure includes a polyol as isotonic agent (e.g., mannitol, propylene glycol or glycerol). In particular embodiments, the isotonic agent is glycerol. In particular embodiments, the isotonic agent is a salt, e.g., NaCl. For example, a formulation may comprise from about 0.05 to about 0.5 M NaCl, e.g., from about 0.05 to about 0.25 M NaCl or from about 0.1 to about 0.2 M NaCl.

In particular embodiments, a formulation of the present disclosure includes an amount of unconjugated insulin molecule. In particular embodiments, a formulation includes a molar ratio of conjugated insulin molecule to unconjugated insulin molecule in the range of about 100:1 to 1:1, e.g., about 50:1 to 2:1 or about 25:1 to 2:1.

The present disclosure also encompasses the use of standard sustained (also called extended) release formulations that are well known in the art of small molecule formulation (e.g., see *Remington's Pharmaceutical Sciences*, 19$^{th}$ ed., Mack Publishing Co., Easton, Pa., 1995). The present disclosure also encompasses the use of devices that rely on pumps or hindered diffusion to deliver a conjugate on a gradual basis. In particular embodiments, a long acting formulation may (additionally or alternatively) be provided by using a modified insulin molecule. For example, one could use insulin glargine (LANTUS®) or insulin detemir (LEVEMIR®) instead of wild-type human insulin in preparing the conjugate. Insulin glargine is an exemplary long acting insulin analog in which Asn at position A21 of the A-chain has been replaced by glycine and two arginine residues are at the C-terminus of the B-chain. The effect of these changes is to shift the isoelectric point, producing an insulin that is insoluble at physiological pH but is soluble at pH 4. Insulin detemir is another long acting insulin analog in which Thr at position B30 of the B-chain has been deleted and a C14 fatty acid chain has been attached to the Lys at position B29.

Uses of Conjugates

In another aspect, the present disclosure provides methods of using the insulin conjugates. In general, the insulin conjugates can be used to controllably provide insulin to an individual in need in response to a saccharide (e.g., glucose or an exogenous saccharide such as mannose, alpha-methyl mannose, L-fucose, etc.). The disclosure encompasses treating diabetes by administering an insulin conjugate of the present disclosure. Although the insulin conjugates can be used to treat any patient (e.g., dogs, cats, cows, horses, sheep, pigs, mice, etc.), they are most preferably used in the treatment of humans. An insulin conjugate may be administered to a patient by any route. In general, the present disclosure encompasses administration by oral, intravenous, intramuscular, intra-arterial, subcutaneous, intraventricular, transdermal, rectal, intravaginal, intraperitoneal, topical (as by powders, ointments, or drops), buccal, or as an oral or nasal spray or aerosol. General considerations in the formulation and manufacture of pharmaceutical compositions for these different routes may be found, for example, in *Remington's Pharmaceutical Sciences*, 19$^{th}$ ed., Mack Publishing Co., Easton, Pa., 1995. In various embodiments, the conjugate may be administered subcutaneously, e.g., by injection. The insulin conjugate may be dissolved in a carrier for ease of delivery. For example, the carrier can be an aqueous solution including, but not limited to, sterile water, saline, or buffered saline.

In general, a therapeutically effective amount of the insulin conjugate will be administered. The term "therapeutically effective amount" means a sufficient amount of the insulin conjugate to treat diabetes at a reasonable benefit/risk ratio, which involves a balancing of the efficacy and toxicity of the insulin conjugate. In various embodiments, the average daily dose of insulin is in the range of 10 to 200 U, e.g., 25 to 100 U (where 1 Unit of insulin is ~0.04 mg). In particular embodiments, an amount of conjugate with these insulin doses is administered on a daily basis. In particular embodiments, an amount of conjugate with 5 to 10 times these insulin doses is administered on a weekly basis. In particular embodiments, an amount of conjugate with 10 to 20 times these insulin doses is administered on a bi-weekly basis. In particular embodiments, an amount of conjugate with 20 to 40 times these insulin doses is administered on a monthly basis.

In particular embodiments, a conjugate of the present disclosure may be used to treat hyperglycemia in a patient (e.g., a mammalian or human patient). In particular embodiments, the patient is diabetic. However, the present methods are not limited to treating diabetic patients. For example, in particular embodiments, a conjugate may be used to treat hyperglycemia in a patient with an infection associated with impaired glycemic control. In particular embodiments, a conjugate may be used to treat diabetes.

In particular embodiments, when an insulin conjugate or formulation of the present disclosure is administered to a patient (e.g., a mammalian patient) it induces less hypoglycemia than an unconjugated version of the insulin molecule. In particular embodiments, a formulation of the present disclosure induces a lower HbA1c value in a patient (e.g., a mammalian or human patient) than a formulation comprising an unconjugated version of the insulin molecule. In particular embodiments, the formulation leads to an HbA1c value that is at least 10% lower (e.g., at least 20% lower, at least 30% lower, at least 40% lower, at least 50% lower) than a formulation comprising an unconjugated version of the insulin molecule. In particular embodiments, the formulation leads to an HbA1c value of less than 7%, e.g., in the range of about 4 to about 6%. In particular embodiments, a formulation comprising an unconjugated version of the insulin molecule leads to an HbA1c value in excess of 7%, e.g., about 8 to about 12%.

Exogenous Trigger

As mentioned previously, the methods, conjugates and compositions that are described herein are not limited to glucose responsive-conjugates. As demonstrated in the Examples, several exemplary insulin conjugates were also responsive to exogenous saccharides such as alpha-methyl mannose. It will therefore be appreciated that, in particular embodiments, an insulin conjugate may be triggered by exogenous administration of a saccharide other than glucose, such as alpha-methyl mannose or any other saccharide that can alter the PK or PD properties of the conjugate.

Once a conjugate has been administered as described above (e.g., as a sustained release formulation) it can be triggered by administration of a suitable exogenous saccharide. In a particular embodiment, a triggering amount of the exogenous saccharide is administered. As used herein, a "triggering amount" of exogenous saccharide is an amount sufficient to cause a change in at least one PK and/or PD property of the conjugate (e.g., $C_{max}$, AUC, half-life, etc. as discussed previously). It is to be understood that any of the aforementioned methods of administration for the conjugate apply equally to the exogenous saccharide. It is also be to be understood that the methods of administration for the conjugate and exogenous saccharide may be the same or different. In various embodiments, the methods of administration are different (e.g., for purposes of illustration the conjugate may be administered by subcutaneous injection on a weekly basis while the exogenous saccharide is administered orally on a daily basis). The oral administration of an exogenous saccharide is of particular value since it facilitates patient compliance. In general, it will be appreciated that the PK and PD properties of the conjugate will be related to the PK profile of the exogenous saccharide. Thus, the conjugate PK and PD properties can be tailored by controlling the PK profile of the exogenous saccharide. As is well known in the art, the PK profile of the exogenous saccharide can be tailored based on the dose, route, frequency and formulation used. For example, if a short and intense activation of the conjugate is desired then an oral immediate release formulation might be used. In contrast, if a longer less intense activation of conjugate is desired then an oral extended release formulation might be used instead. General considerations in the formulation and manufacture of immediate and extended release formulation may be found, for example, in *Remington's Pharmaceutical Sciences*, 19$^{th}$ ed., Mack Publishing Co., Easton, Pa., 1995.

It will also be appreciated that the relative frequency of administration of a conjugate of the present disclosure and an exogenous saccharide may be the same or different. In particular embodiments, the exogenous saccharide is administered more frequently than the conjugate. For example, in particular embodiment, the conjugate may be administered daily while the exogenous saccharide is administered more than once a day. In particular embodiment, the conjugate may be administered twice weekly, weekly, biweekly, or monthly, while the exogenous saccharide is administered daily. In particular embodiments, the conjugate is administered monthly, and the exogenous saccharide is administered twice weekly, weekly, or biweekly. Other variations on these schemes will be recognized by those skilled in the art and will vary depending on the nature of the conjugate and formulation used.

The following examples are intended to promote a further understanding of the present invention.

EXAMPLES

General Procedures

All chemicals were purchased from commercial sources, unless otherwise noted. Reactions sensitive to moisture or air were performed under nitrogen or argon using anhydrous solvents and reagents. The progress of reactions was monitored by analytical thin layer chromatography (TLC), high performance liquid chromatography-mass spectrometry (HPLC-MS), or ultra performance liquid chromatography-mass spectrometry (UPLC-MS). TLC was performed on E. Merck TLC plates precoated with silica gel 60E-254, layer thickness 0.25 mm. The plates were visualized using 254 nm UV and/or by exposure to cerium ammonium molybdate (CAM) orp-anisaldehyde staining solutions followed by charring. High performance liquid chromatography (HPLC) was conducted on an Agilent 1100 series HPLC using Supelco Ascentis Express C18 2.7 μm 3.0×100 mm column with gradient 10:90-99:1 v/v CH$_3$CN/H$_2$O+v 0.05% TFA over 4.0 min then hold at 98:2 v/v CH$_3$CN/H$_2$O+v 0.05% TFA for 0.75 min; flow rate 1.0 mL/min, UV range 200-400 nm (LC-MS Method A). Mass analysis was performed on a Waters Micromass® ZQTM with electrospray ionization in positive ion detection mode and the scan range of the mass-to-charge ratio was either 170-900 or 500-1500. Ultra performance liquid chromatography (UPLC) was performed on a Waters Acquity™ UPLC® system using the following methods:

UPLC-MS Method A: Waters Acquity™ UPLC® BEH C18 1.7 μm 2.1×100 mm column with gradient 10:90-70:30 v/v CH$_3$CN/H$_2$O+v 0.1% TFA over 4.0 min and 70:30-95:5 v/v CH$_3$CN/H$_2$O+v 0.1% TFA over 40 sec; flow rate 0.3 mL/min, UV wavelength 200-300 nm.

UPLC-MS Method B: Waters Acquity™ UPLC® BEH C18 1.7 μm 2.1×100 mm column with gradient 60:40-100:0 v/v CH$_3$CN/H$_2$O+v 0.1% TFA over 4.0 min and 100:0-95:5 v/v CH$_3$CN/H$_2$O+v 0.1% TFA over 40 sec; flow rate 0.3 mL/min, UV wavelength 200-300 nm.

UPLC-MS Method C: Waters Acquity™ UPLC® HSS T3 1.7 μm 2.1×100 mm column with gradient 0:100-40:60 v/v CH$_3$CN/H$_2$O+v 0.05% TFA over 8.0 min and 40:60-10:90 v/v CH$_3$CN/H$_2$O+v 0.05% TFA over 2.0 min; flow rate 0.3 mL/min, UV wavelength 200-300 nm.

UPLC-MS Method D: Waters Acquity™ UPLC® BEH C18 1.7 μm 2.1×100 mm column with gradient 0:100-60:40 v/v CH$_3$CN/H$_2$O+v 0.1% TFA over 8.0 min and 60:40-90:10 v/v CH$_3$CN/H$_2$O+v 0.1% TFA over 3.0 min and hold at 100:0 v/v CH$_3$CN/H$_2$O+v 0.1% TFA for 2 min; flow rate 0.3 mL/min, UV wavelength 200-300 nm.

UPLC-MS Method E: Waters Acquity™ UPLC® BEH C8 1.7 μm 2.1×100 mm column with gradient 10:90-55:45 v/v CH$_3$CN/H$_2$O+v 0.1% TFA over 4.2 min and 100:0-95:5 v/v CH$_3$CN/H$_2$O+v 0.1% TFA over 0.4 min; flow rate 0.3 mL/min, UV wavelength 200-300 nm.

UPLC-MS Method F: Waters Acquity™ UPLC® BEH C8 1.7 μm 2.1×100 mm column with gradient 10:90-90:10 v/v CH$_3$CN/H$_2$O+v 0.1% TFA over 4.2 min and 90:10-95:5 v/v CH$_3$CN/H$_2$O+v 0.1% TFA over 0.4 min; flow rate 0.3 mL/min, UV wavelength 200-300 nm.

UPLC-MS Method G: Waters Acquity™ UPLC® BEH300 C4 1.7 μm 2.1×100 mm column with gradient 10:90-90:10 v/v CH$_3$CN/H$_2$O+v 0.1% TFA over 4.0 min and 90:10-95:5 v/v CH$_3$CN/H$_2$O+v 0.1% TFA over 0.5 min; flow rate 0.3 mL/min, UV wavelength 200-300 nm.

Mass analysis was performed on a Waters Micromass® LCT Premier™ XE with electrospray ionization in positive ion detection mode and the scan range of the mass-to-charge ratio was 300-2000. The identification of the produced insulin conjugates was confirmed by comparing the theoretical molecular weight to the experimental value that was measured using UPLC-MS. For the determination of the position of sugar modification(s), specifically, insulin conjugates were subjected to DTT treatment (for a/b chain) or Glu-C digestion (with reduction and alkylation), and then the resulting peptides were analyzed by LC-MS. Based on the measured masses, the sugar positions were deduced.

Flash chromatography was performed using either a Biotage Flash Chromatography apparatus (Dyax Corp.) or a CombiFlash®Rf instrument (Teledyne Isco). Normal-phase chromatography was carried out on silica gel (20-70 μm, 60 Å pore size) in pre-packed cartridges of the size noted. Reverse-phase chromatography was carried out on C18-bonded silica gel (20-60 μm, 60-100 Å pore size) in pre-packed cartridges of the size noted. Preparative scale HPLC was performed on Gilson 333-334 binary system using Waters Delta Pak C4 15 μm, 300 Å, 50×250 mm column or Kromasil® C8 10 μm, 100 Å, 50×250 mm column, flow rate 85 mL/min, with gradient noted. Concentration of solutions was carried out on a rotary evaporator under reduced pressure or freeze-dried on a VirTis Freezemobile Freeze Dryer (SP Scientific).

$^1$H NMR spectra were acquired at 500 MHz (or otherwise specified) spectrometers in deuterated solvents noted. Chemical shifts were reported in parts per million (ppm). Tetramethylsilane (TMS) or residual proton peak of deutrated solvents was used as an internal reference. Coupling constant (J) were reported in hertz (Hz).

Abbreviations: acetic acid (AcOH), acetonitrile (AcCN), aqueous (aq), O-(7-azabenzotriazol-1-yl)-N,N,N',N'-tetramethyluronium hexafluorophosphate) (HATU), column volume (CV), dichloromethane (DCM), diethyl ether (ether or Et$_2$O), N,N-diisopropylethylamine or Hünig's base (DIPEA), N,N-dimethylacetamide (DMA), (4-dimethylamino)pyridine (DMAP), N,N-dimethylformamide (DMF), ethyl acetate (EtOAc), N-(3-dimethylaminopropyl)-N'-ethylcarbodiimide hydrochloride (EDC), gram(s) (g), 1-hydroxybenzotriazole hydrate (HOBt), hour(s) (h or hr), mass spectrum (ms or MS), microliter(s) (μL), milligram(s) (mg), milliliter(s) (mL), millimole (mmol), minute(s) (min), pentafluorphenol-tetramethyluronium hexafluorophosphate (PFTU), petroleum ether (PE), retention time ($t_R$), room temperature (rt), saturated (sat. or sat'd), saturated aq sodium chloride solution (brine), triethylamine (TEA), trifluoroacetic acid (TFA), trifluoroacetic anhydride (TFAA), tetrahydrofuran (THF), and N,N,N',N'-tetramethyl-O—(N-succinimidypuronium tetrafluoroborate (TSTU).

Example 1

The synthesis of oligosaccharide linker 2,5-dioxopyrrolidin-1-yl 4-[(4,14-dioxo-9-{[3-oxo-3-({2-[(α-D-mannopyranosyl)oxy]ethyl}amino)propoxy]methyl}-1,17-di[(α-D-mannopyranosyl)oxy]-7,11-dioxa-3,15-diazaheptadecan-9-yl)amino]-4-oxobutanoate (ML-1) having the following structure is described.

ML-1

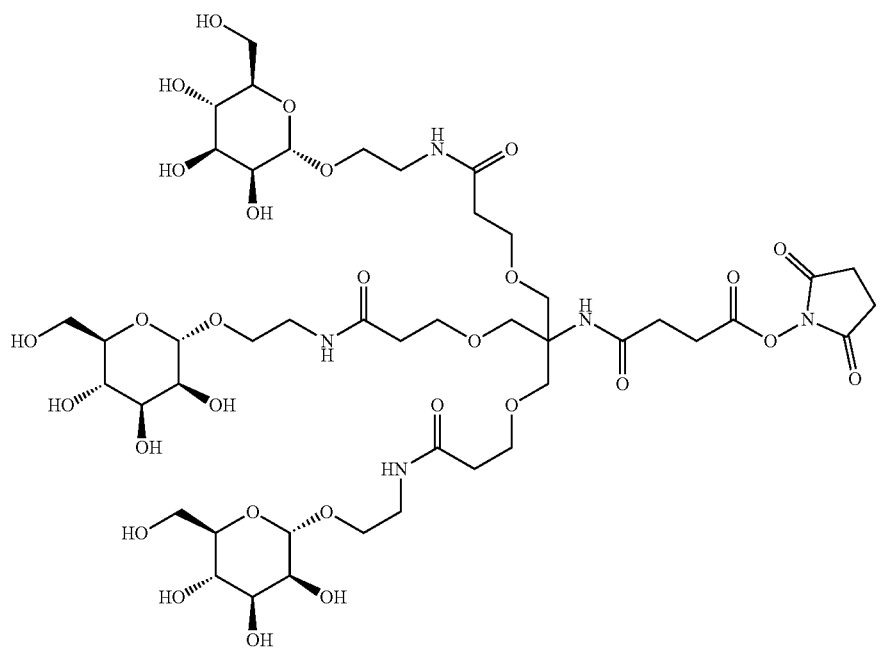

Step A. di-tert-butyl 3,3'-[(2-[4-(benzyloxy)-4-oxobutanamido]-2{[3-(tert-butoxy)-3-oxopropoxy]methyl}propane-1,3-diyl)bis(oxy)]dipropionate To a solution of di-tert-butyl 3,3'-[(2-amino-2-{[3-(tert-butoxy)-3-oxopropoxy]methyl}propane-1,3-diyl)bis(oxy)] dipropionate (2.18 g, 4.31 mmol) in DMF (28 mL) was added 4-(benzyloxy)-4-oxobutanoic acid (0.9 g, 4.32 mmol), HATU (2.0 g, 5.26 mmol), and DIPEA (1.6 ml, 9.16 mmol). The resulting mixture was stirred at rt for 16 hr. Upon completion, the reaction mixture was partitioned between H$_2$O (100 mL) and DCM (100 mL). Aqueous layer was extracted with DCM (2×50 mL). Combined organic layers were washed with 1N HCl (2×100 mL), and then with sat'd NaHCO$_3$ (2×100 mL) and finally with brine. The organic layer was dried over anhydrous Na₂SO₄ and concentrated. The residue was purified by flash chromatography on silica gel (120 g), eluting with 0-100% EtOAc in hexane, to give the title compound. ¹H NMR (CDCl₃) δ 7.38-7.28 (m, 5H), 6.17 (s, 1H), 5.12 (s, 2H), 3.69 (s, 6H), 3.65-3.61 (m, 6H), 2.69-2.64 (m, 2H), 2.54-2.49 (m, 2H), 2.48-2.41 (m, 6H), 1.47-1.41 (m, 27H).

Step B. 3,3'-[(2-[4-(benzyloxy)-4-oxobutanamido]-2-[(2-carboxyethoxy)methyl]propane-1,3-diyl)bis(oxy)]dipropionic acid Di-tert-butyl 3,3'-[(2-[4-(benzyloxy)-4-oxobutanamido]-2-{[3-(tert-butoxy)-3-oxopropoxy]methyl}propane-1,3-diyl)bis(oxy)]dipropionate (2.79 g, 4.01 mmol) was dissolved in formic acid (40 mL, 918 mmol). After stirring at rt for 48 hr, the reaction mixture was concentrated. The residue was re-dissolved in H₂O and freeze-dried to give the title compound. ¹H NMR (CDCl₃) δ 7.40-7.29 (m, 5H), 6.05 (s, 1H), 5.12 (s, 2H), 3.74-3.66 (m, 12H), 2.70-2.63 (m, 2H), 2.61-2.55 (m, 6H), 2.53-2.46 (m, 2H).

Step C. benzyl 4-[(4,14-dioxo-9-{[3-oxo-3-({2-[(α-D-mannopyranosyl)oxy]ethyl}amino)propoxy]methyl}-1,17-di[(α-D-mannopyranosyl)oxy-7,11-dioxa-3,15-diazaheptadecan-9-yl)amino]-4-oxobutanoate To a solution of 3,3'-[(2-[4-(benzyloxy)-4-oxobutanamido]-2-[(2-carboxyethoxy)methyl]propane-1,3-diyl)bis(oxy)]dipropionic acid (330 mg, 0.626 mmol) in DMF (6 mL) was added 2-aminoethyl α-D-mannopyranoside (838 mg, 3.75 mmol, *Beilstein J. Org. Chem.* 2010, 6, 699-703), HOBt (575 mg, 3.75 mmol), and EDC (720 mg, 3.75 mmol). After stirring for 16 h at rt, the reaction mixture was concentrated, and the residue was purified by flash chromatography on C18 reverse phase silica gel (50 g), eluting with 10-40% AcCN in H₂O, to give the title compound. UPLC Method A: m/z=1143.39 (z=1); $t_R$=3.71 min.

Step D. 4-[(4,14-dioxo-9-{[3-oxo-3-({2-[(α-D-mannopyranosyl)oxy]ethyl}amino)propoxy]methyl}-1,17-di[(α-D-mannopyranosyl)oxy-7,11-dioxa-3,15-diazaheptadecan-9-yl)amino]-4-oxobutanoic acid To a stirred solution of benzyl 4-[(4,14-dioxo-9-{[3-oxo-3-({2-[(α-D-mannopyranosyl)oxy]ethyl}amino)propoxy] methyl}-1,17-di[(α-D-mannopyranosyl)oxy]-7,11-dioxa-3,15-diazaheptadecan-9-yl)amino]-4-oxobutanoate (110 mg, 0.096 mmol) in H₂O (3 mL) at rt was added Pd(OH)₂ (12 mg, 0.012 mmol). The mixture was degassed and then stirred under a balloon of H₂. After stirring at rt under H₂ for 2 hr, the reaction mixture was filtered through a CELITE pad and washed with CH₃OH (3×3 mL). The filtrate was concentrated to give the title compound. ¹H NMR (CD₃OD) δ 5.49 (s, 1H), 4.78 (s, 2H), 3.87-3.82 (m, 5H), 3.80-3.74 (m, 3H), 3.74-3.65 (m, 16H), 3.64-3.52 (m, 9H), 3.50-3.43 (m, 3H), 3.41-3.34 (m, 6H), 2.51-2.41 (m, 10H).

Step E. 2,5-dioxopyrrolidin-1-yl 4-[(4,14-dioxo-9-{[3-oxo-3-({2-[(α-D-mannopyranosyl)oxy]ethyl}amino)propoxy]methyl}-1,17-di[(α-D-mannopyranosyl)oxy]-7,11-dioxa-3,15-diazaheptadecan-9-yl)amino]-4-oxobutanoate To a stirred solution of 4-[(4,14-dioxo-9-{[3-oxo-3-({2-[(α-D-mannopyranosyl)oxy]ethyl}amino)propoxy]methyl}-1,17-di[(α-D-mannopyranosyl)oxy]-7,11-di oxa-3,15-diazaheptadecan-9-yl)amino]-4-oxobutanoic acid (100 mg, 0.095 mmol) in DMF (2.0 mL) at 0° C. was added TSTU (30 mg, 0.10 mmol) and DIPEA (20 μL, 0.155 mmol). After stirring for 2 h at 0° C., the reaction was quenched with addition of TFA (15 μL, 0.199 mmol). The reaction mixture was concentrated down to half volume, and then transferred dropwise, via autopipette, to a tube containing EtOAc (45 mL). The resulting white suspension was centrifuged (4900 rpm, 20 minutes, at 4° C.) to generate a clear supernatant and a white pellet. The supernatant was drawn off, and the white pellet was re-dissolved in H₂O, which was freeze-dried to give the title product. UPLC Method A: m/z=1150.42 (z=1); $t_R$=0.92 min.

Example 2

The synthesis of oligosaccharide linker 2,5-dioxopyrrolidin-1-yl 4-[(5,15-dioxo-10-{[3-oxo-3-({[(α-D-mannopyranosyl)oxy]propyl}amino)propoxy]methyl}-1,19-di[(α-D-mannopyranosyl)oxy]-8,12-dioxa-4,16-diazanonadecan-10-yl)amino]-4-oxobutanoate (ML-2) having the following structure is described.

ML-2

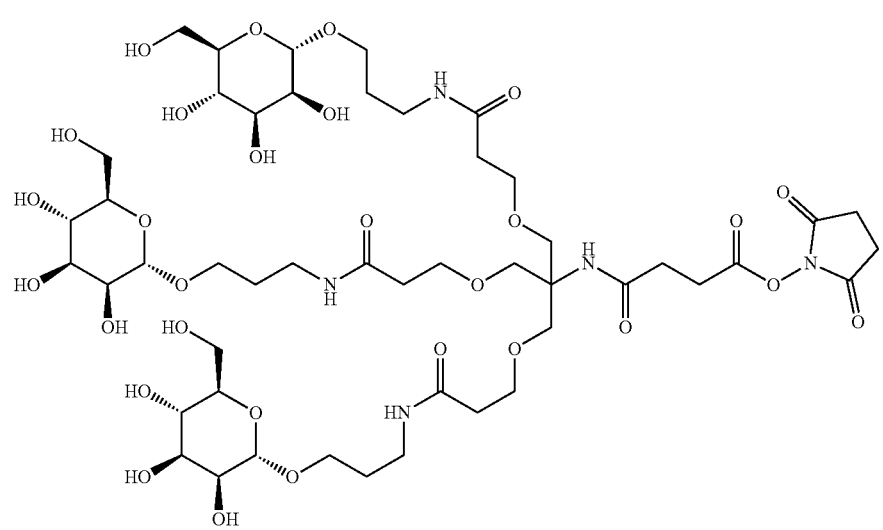

The title compound was prepared using procedures analogous to those described for ML-1 substituting 3-aminopropyl α-D-mannopyranoside (*Tetrahedron* 2003, 59, 7983) for 2-aminoethyl α-D-mannopyranoside in Step C. UPLC Method A: m/z=1192.46 (z=1); $t_R$=0.94 min.

Example 3

The synthesis of oligosaccharide linker 2,5-dioxopyrrolidin-1-yl 4-{[1,7-dioxo-4-(3-oxo-3-[({2-[(α-D-mannopyranosyl)oxy]ethyl}amino)propyl]-1,7-bis[({2-[(α-D-mannopyranosyl)oxy]ethyl}amino)heptan-4-yl]amino}-4-oxobutanoate (ML-3) having the following structure is described.

ML-3

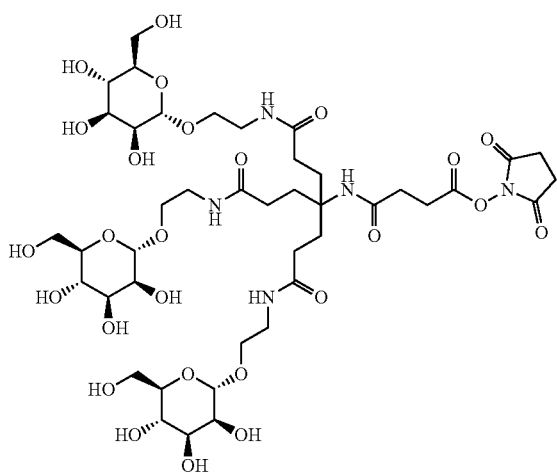

Step A. di-tert-butyl 4-[4-(benzyloxy)-4-oxobutanamido]-4-[3-(tert-butoxy)-3-oxopropyl]heptanedioate To a solution of di-tert-butyl 4-amino-4-[3-(tert-butoxy)-3-oxopropyl]heptanedioate (1.0 g, 2.406 mmol) in DMF (15 mL) was added 4-(benzyloxy)-4-oxobutanoic acid (526 mg, 2.53 mmol), DMAP (0.3 g, 2.46 mmol), and EDC (1.8 g, 9.39 mmol). The resulting mixture was stirred at rt for 16 h. Upon completion, the reaction mixture was partitioned between $H_2O$ (100 mL) and DCM (100 mL). Aqueous layer was extracted with DCM (2×50 mL). Combined organic layers were washed with 1N HCl (2×100 mL), and then with sat'd $NaHCO_3$ (2×100 mL) and finally with brine. The organic layer was dried over anhydrous $Na_2SO_4$ and concentrated. The residue was purified by flash chromatography on silica gel (120 g), eluting with 0-50% EtOAc in hexane, to give the title compound. $^1$H NMR ($CDCl_3$) δ 7.40-7.29 (m, 5H), 5.94 (s, 1H), 5.13 (s, 2H), 2.71-2.65 (m, 2H), 2.45-2.39 (m, 2H), 2.26-2.16 (m, 6H), 2.00-1.91 (m, 6H), 1.48-1.39 (m, 27H). UPLC Method B: m/z=606.21 (z=1); $t_R$=2.53 min.

Step B. 2,5-dioxopyrrolidin-1-yl 4-{[1,7-dioxo-4-(3-oxo-3-[({2-[(α-D-mannopyranosyl)oxy]ethyl}amino)propyl]-1,7-bis[({2-[(α-D-mannopyranosyl)oxy]ethyl}amino)heptan-4-yl]amino}-4-oxobutanoate The title compound was prepared using procedures analogous to those described for ML-1 substituting di-tert-butyl 4-[4-(benzyloxy)-4-oxobutanamido]-4-[3-(tert-butoxy)-3-oxopropyl]heptanedioate for di-tert-butyl 3,3'-[(2-[4-(benzyloxy)-4-oxobutanamido]-2-{[3-(tert-butoxy)-3-oxopropoxy]methyl}propane-1,3-diyl)bis(oxy)]dipropionate in Step B. UPLC Method A: m/z=1060.41 (z=1); $t_R$=1.09 min.

Example 4

The synthesis of oligosaccharide linker 2,5-dioxopyrrolidin-1-yl 4-{[1,7-dioxo-4-(3-oxo-3-[({4-[(α-D-mannopyranosyl)oxy]butyl}amino)propyl]-1,7-bis[({4-[(α-D-mannopyranosyl)oxy]butyl}amino)heptan-4-yl]amino}-4-oxobutanoate (ML-4) having the following structure is described.

ML-4

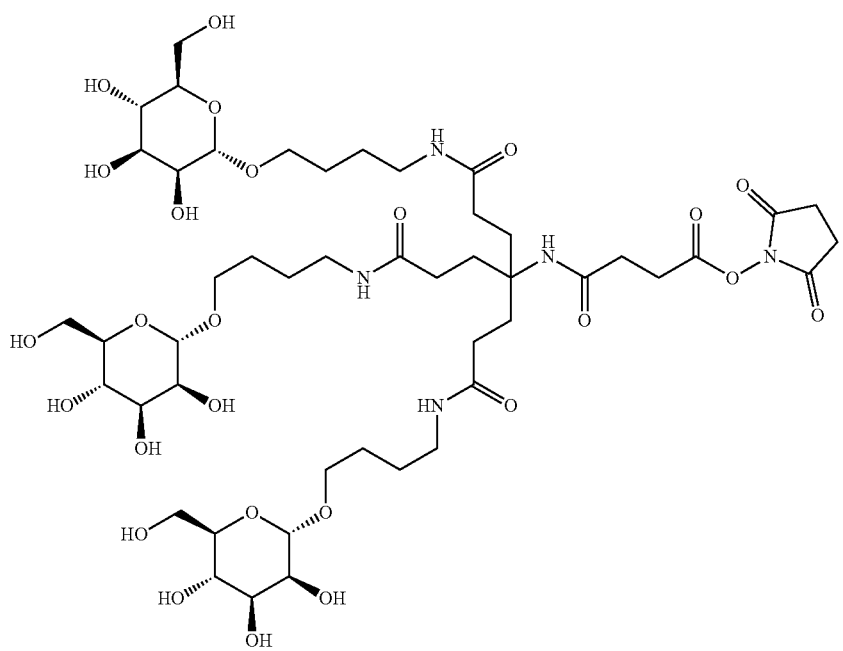

The title compound was prepared using procedures analogous to those described for ML-1 substituting di-tert-butyl 4-[4-(benzyloxy)-4-oxobutanamido]-4-[3-(tert-butoxy)-3-oxopropyl]heptanedioate for di-tert-butyl 3,3'-[(2-[4-(benzyloxy)-4-oxobutanamido]-2-{[3-(tert-butoxy)-3-oxopropoxy]methyl}propane-1,3-diyl)bis(oxy)]dipropionate in Step B and 4-aminobutyl α-D-mannopyranoside (*J. Med. Chem.* 2010, 53, 4779) for 2-aminoethyl α-D-mannopyranoside in Step C, respectively. UPLC Method A: m/z=1144.49 (z=1); t$_R$=1.20 min.

Example 5

The synthesis of oligosaccharide linker 2,5-dioxopyrrolidin-1-yl 4-{[1,7-dioxo-4-(3-oxo-3-[({3-[(α-D-mannopyranosyl)oxy]propyl}amino)propyl]-1,7-bis[({3-[(α-D-mannopyranosyl)oxy]propyl}amino)heptan-4-yl]amino}-4-oxobutanoate (ML-5) having the following structure is described.

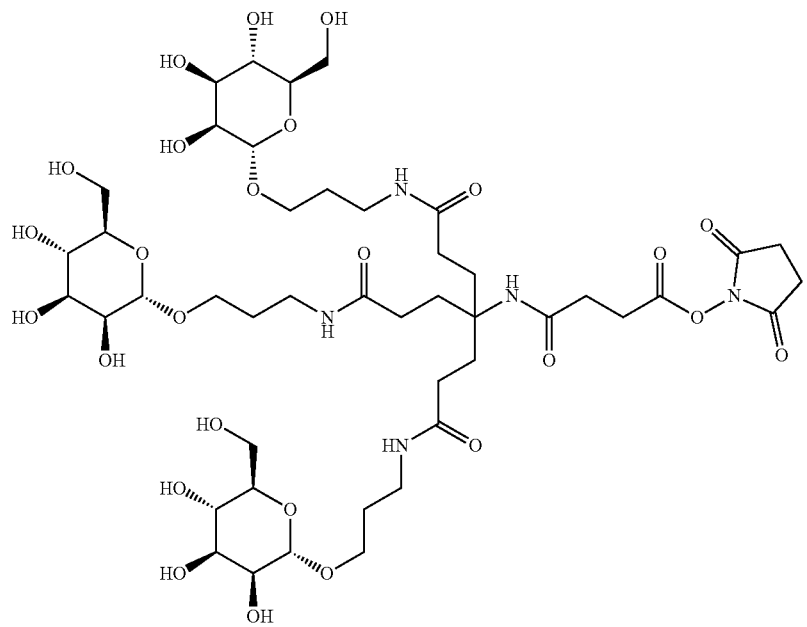

ML-5

The title compound was prepared using procedures analogous to those described for ML-1 substituting di-tert-butyl 4-[4-(benzyloxy)-4-oxobutanamido]-4-[3-(tert-butoxy)-3-oxopropyl]heptanedioate for di-tert-butyl 3,3'-[(2-[4-(benzyloxy)-4-oxobutanamido]-2-{[3-(tert-butoxy)-3-oxopropoxy]methyl}propane-1,3-diyl)bis(oxy)]dipropionate in Step B and 3-aminopropyl α-D-mannopyranoside for 2-aminoethyl α-D-mannopyranoside in Step C, respectively. UPLC Method A: m/z=1102.45 (z=1); t$_R$=1.12 min.

Example 6

The synthesis of oligosaccharide linker 2,5-dioxopyrrolidin-1-yl 4-{(2-{bis[2-oxo-2-({2-[(α-D-mannopyranosyl)oxy]ethyl}amino)ethyl]amino}ethyl)[2-oxo-2-({2-[(α-D-mannopyranosyl)oxy]ethyl}amino)ethyl]amino}butanoate (ML-6) having the following structure is described.

ML-6

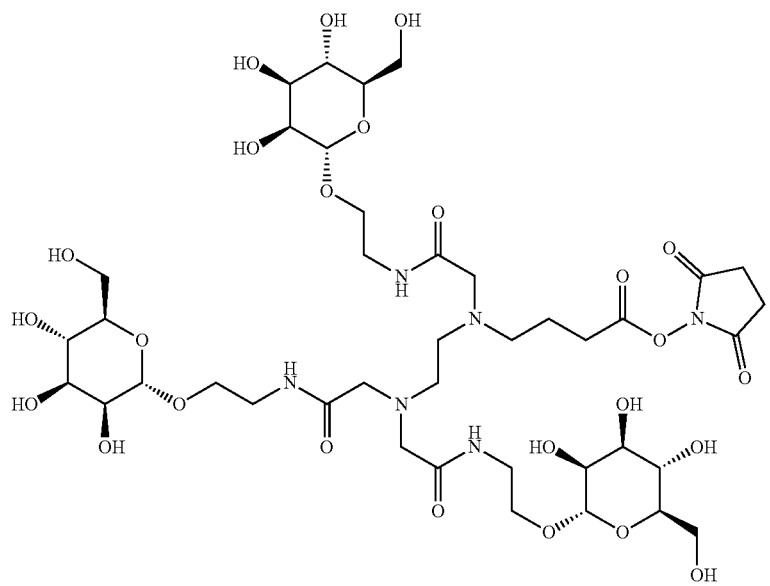

Step A. di-tert-butyl 2,2'-[(2-{[4-(benzyloxy)-4-oxobutyl][2-(tert-butoxy)-2-oxoethyl]amino}ethyl)azanediyl]diacetate To a solution of di-tert-butyl 2,2'-[(2-{[2-(tert-butoxy)-2-oxoethyl]amino}ethyl)azanediyl]diacetate (3.4 g, 8.45 mmol, *Tetrahedron Lett.*, 2006, 47, 6277) in AcCN (140 mL) was added benzyl 4-bromobutanoate (2.35 g, 9.14 mmol), and K$_2$CO$_3$ (3.50 g, 25.3 mmol). The resulting mixture was stirred at 75° C. for 16 h. Upon completion, the reaction mixture was cooled down to rt. The inorganics were removed by filtration and the filtrate was concentrated. The resulting residue was purified by flash chromatography on silica gel (40 g), eluting with 0-100% EtOAc in hexane, to give the title compound. $^1$H NMR (CDCl$_3$) δ 7.39-7.28 (m, 5H), 5.10 (s, 2H), 3.44 (s, 4H), 3.26 (s, 2H), 2.82-2.72 (m, 4H), 2.65-2.61 (m, 2H), 2.42-2.37 (m, 2H), 1.81-1.73 (m, 2H), 1.48-1.40 (m, 27H).

Step B. 2,2'-[(2-{[4-(benzyloxy)-4-oxobutyl](carboxymethyl)amino}ethyl)azanediyl]diacetic acid Di-tert-butyl 2,2'-[(2-{[4-(benzyloxy)-4-oxobutyl][2-(tert-butoxy)-2-oxoethyl]amino}ethyl)azanediyl]diacetate (2.9 g, 5.01 mmol) was dissolved in formic acid (10 mL, 1304 mmol) and stirred at rt for 48 hr. Upon completion, the mixture was concentrated and the residue was re-dissolved in H$_2$O, which was freeze-dried to give the title compound. $^1$H NMR (CD$_3$OD) δ 7.40-7.24 (m, 5H), 5.11 (s, 2H), 3.74 (s, 2H), 3.56 (s, 4H), 3.33-3.23 (m, 4H), 3.13-3.06 (m, 2H), 2.55-2.47 (m, 2H), 2.10-1.97 (m, 2H).

Step C. benzyl 4-{(2-{bis[2-oxo-2-({2-[(α-D-mannopyranosyl)oxy]ethyl}amino)ethyl]amino}ethyl)[2-oxo-2-({2-[(α-D-mannopyranosyl)oxy]ethyl}amino)ethyl]amino}butanoate To a solution of 2,2'-[(2-{[4-(benzyloxy)-4-oxobutyl](carboxymethyl)amino}ethyl)azanediyl]diacetic acid (300 mg, 0.597 mmol) in DMF (10 mL) was added 2-aminoethyl α-D-mannopyranoside (550 mg, 2.466 mmol), HOBt (549 mg, 3.58 mmol), and EDC (687 mg, 3.58 mmol). After stirring for 16 h at rt, the reaction mixture was concentrated and the residue was purified by flash chromatography on C18 reverse phase silica gel (50 g), eluting with 10-40% AcCN in H$_2$O, to give the title compound. UPLC Method A: m/z=1026.40 (z=1); t$_R$=2.28 min.

Step D. 2,5-dioxopyrrolidin-1-yl 4-{(2-{bis[2-oxo-2-({2-[(α-D-mannopyranosyl)oxy]ethyl}amino)ethyl]amino}ethyl)[2-oxo-2-({2-[(α-D-mannopyranosyl)oxy]ethyl}amino)ethyl]amino}butanoate The title compound was prepared using procedures analogous to those described for ML-1 substituting benzyl 4-{(2-{bis[2-oxo-2-({2-[(α-D-mannopyranosyl)oxy]ethyl}amino)ethyl]amino}ethyl)[2-oxo-2-({2-[(α-D-mannopyranosyl)oxy]ethyl}amino)ethyl]amino}butanoate for benzyl 4-[(4,14-dioxo-9-{[3-oxo-3-({2-[(α-D-mannopyranosyl)oxy]ethyl}amino)propoxy]methyl}-1,17-di[(α-D-mannopyranosyl)oxy]-7,11-dioxa-3,15-diazaheptadecan-9-yl)amino]-4-oxobutanoate in Step D. UPLC Method A: m/z=1033.31 (z=1); t$_R$=0.91 min.

Example 7

The synthesis of oligosaccharide linker 2,5-dioxopyrrolidin-1-yl (S)-6-{[5-(bis{2-[(α-D-mannopyranosyl)oxy]ethyl}amino)-6-oxo-6-({2-[(α-L-fucopyranosyl)oxy]ethyl}amino)hexyl]amino}-6-oxohexanoate (ML-7) having the following structure is described.

ML-7

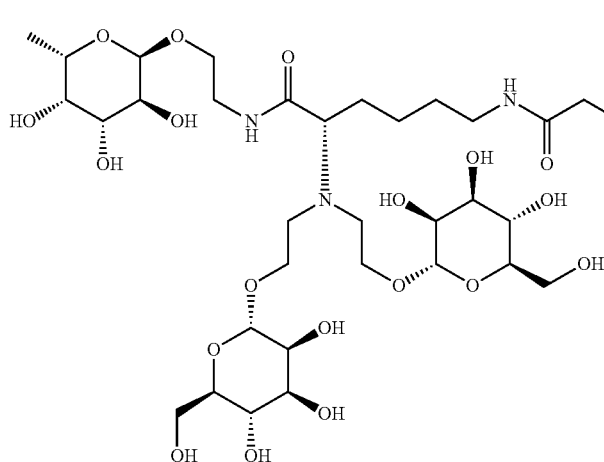

Step A. $N^6$-[6-(benzyloxy)-6-oxohexanoyl]-$N^2$-[(benzyloxy)carbonyl]-L-lysine To a solution of 6-(benzyloxy)-6-oxohexanoic acid (3.20 g, 13.5 mmol) in DMF (30 mL) at 0° C. was added TSTU (4.08 g, 13.5 mmol) and, after 5 min, DIPEA (2.36 mL, 13.5 mmol) dropwise. After stirring for 1 hr at 0° C., to the resulting mixture was added [(benzyloxy)carbonyl]-L-lysine (2.53 g, 9.03 mmol) as a solid and DIPEA (3.15 mL, 18.1 mmol). The suspension was allowed to stir overnight while the temperature gradually warmed up to rt. The reaction mixture was concentrated, and the title compound was isolated by chromatography on C-18 column (ISCO 130 g), flow rate 50 mL/min; gradient 0-50% AcCN in $H_2O$ over 40 min). UPLC Method A: m/z=499.26 (z=1); $t_R$=4.22 min.

Step B. benzyl (S)-6-[(5-{(benzyloxy)carbonyl] amino}-6-oxo-6-[(α-L-fucopyranosyl)oxy]hexyl) amino]-6-oxohexanoate To a solution of $N^6$-[6-(benzyloxy)-6-oxohexanoyl]-$N^2$-[(benzyloxy)carbonyl]-L-lysine (5.4 g, 10.8 mmol) and 2-aminoethyl α-L-fucopyranoside (2.24 g, 10.83 mmol) in DMF (54 mL) at rt was added DIPEA (5.68 mL, 32.5 mmol) and HOBt (1.66 g, 10.83 mmol) and EDC (3.11 g, 16.3 mmol). The reaction mixture was allowed to stir overnight and then concentrated. The title material was isolated by chromatography on C18 column (ISCO 130 g), flow rate 50 mL/min; gradient 0-50% AcCN/$H_2O$ over 40 min, and then re-purified by chromatography on 130 g $SiO_2$ column (flow 100 mL/min, gradient 0-30% in 30 min followed by hold, where solvent A was EtOAc and solvent B was EtOAc/$CH_3OH$/AcCN/$H_2O$ (v/v/v/v=6/1/1/1). UPLC Method A: m/z=688.34 (z=1); $t_R$=3.76 min.

Step C. (S)-6-({5-amino-6-oxo-6-[(α-L-fucopyranosyl)oxy]hexyl}amino)-6-oxohexanoic acid A suspension of benzyl (S)-6-[(5-{[(benzyloxy)carbonyl]amino}-6-oxo-6-[(α-L-fucopyranosyl)oxy]hexyl)amino]-6-oxohexanoate (1.32 g, 1.919 mmol) and Pearlman's catalyst (337 mg, 0.480 mmol) in a mixture of $H_2O$ (48 mL) and $CH_3OH$ (48 mL) was stirred under a balloon of $H_2$ for 18 hr. The catalyst was removed by filtration through a pack of CELITE and the filtrate was concentrated and freeze-dried to give the title compound. UPLC Method A: m/z=464.28 (z=1); $t_R$=0.92 min.

Step D. (S)-6-({5-(bis{2-[(2',3',4',6'-tetra-O-acetyl-α-D-mannopyranosyl)oxy]ethyl}amino)-6-oxo-6-[(α-L-fucopyranosyl)oxy]hexyl}amino)-6-oxohexanoic acid To a mixture of 2-(2',3',4',6'-tetra-O-acetyl-α-D-mannopyranosyl)acetaldehyde (2.02 g, 5.18 mmol; *Eur. J. Org. Chem.* 2010, 36, 6974) and (S)-6-({5-amino-6-oxo-6-[(α-L-fucopyranosyl)oxy]hexyl}amino)-6-oxohexanoic acid (800 mg, 1.73 mmol) in 20 mL of a mixture of $H_2O$/$CH_3OH$ (v/v=1/1) was added $NaCNBH_3$ (130 mg, 2.071 mmol). Stirred the mixture overnight, concentrated on rotovap, and isolated the title material by chromatography (330 g $SiO_2$ column, flow rate 100 mL/min, solvent A was EtOAc/$CH_3OH$/AcCN/$H_2O$ (v/v/v/v=6/1/1/1), Solvent B was EtOAc/$CH_3OH$/AcCN/$H_2O$ (v/v/v/v=2/1/1/1), gradient 0-50% solvent B in solvent A over 40 min followed by hold. UPLC Method A: m/z=1212.52 (z=1); $t_R$=3.28 min.

Step E. (S)-6-({5-(bis{2-[(α-D-mannopyranosyl)oxy]ethyl}amino)-6-oxo-6-[(α-L-fucopyranosyl)oxy]hexyl}amino)-6-oxohexanoic acid A solution of (S)-6-({5-(bis{2-[(2',3',4',6'-tetra-O-acetyl-α-D-mannopyranosyl)oxy]ethyl}amino)-6-oxo-6-[(α-L-fucopyranosyl)oxy]hexyl}amino)-6-oxohexanoic acid (1.36 g, 1.12 mmol) in water (10.0 mL) was treated with 5M NaOH solution (1.9 mL, 9.5 mmol). The reaction mixture was stirred for 2 hr, neutralized with 5M HCl, and freeze-dried. The title compound was isolated by chromatography on C18 ISCO column using gradient 0-40% AcCN in $H_2O$. UPLC Method A: m/z=876.46 (z=1); $t_R$=1.39 min.

Step F. 2,5-dioxopyrrolidin-1-yl (S)-6-{[5-(bis{2-[(α-D-mannopyranosyl)oxy]ethyl}amino)-6-oxo-6-({2-[(α-L-fucopyranosyl)oxy]ethyl}amino)hexyl]amino}-6-oxohexanoate The title compound was prepared using procedures analogous to that described for ML-1 substituting (S)-6-({5-(bis 2-[(α-D-mannopyranosyl)oxy]ethyl}amino)-6-oxo-6-[(α-L-fucopyranosyl)oxy]hexyl}amino)-6-oxohexanoic acid for 4-[(4,14-dioxo-9-{[3-oxo-3-({2-[(α-D-mannopyranosyl)oxy]ethyl}amino)propoxy]methyl}-1,17-di[(α-D-mannopyranosyl)oxy]-7,11-dioxa-3,15-diazaheptadecan-9-yl)amino]-4-oxobutanoic acid in Step E. UPLC Method A: m/z=973.45 (z=1); $t_R$=1.82 min.

Example 8

The synthesis of oligosaccharide linker 2,5-dioxopyrrolidin-1-yl (S)-6-{[5-(bis{2-[(α-D-mannopyranosyl)oxy]ethyl}amino)-6-oxo-6-({2-[(α-D-mannopyranosyl)oxy]ethyl}amino)hexyl]amino}-6-oxohexanoate (ML-8) having the following structure is described.

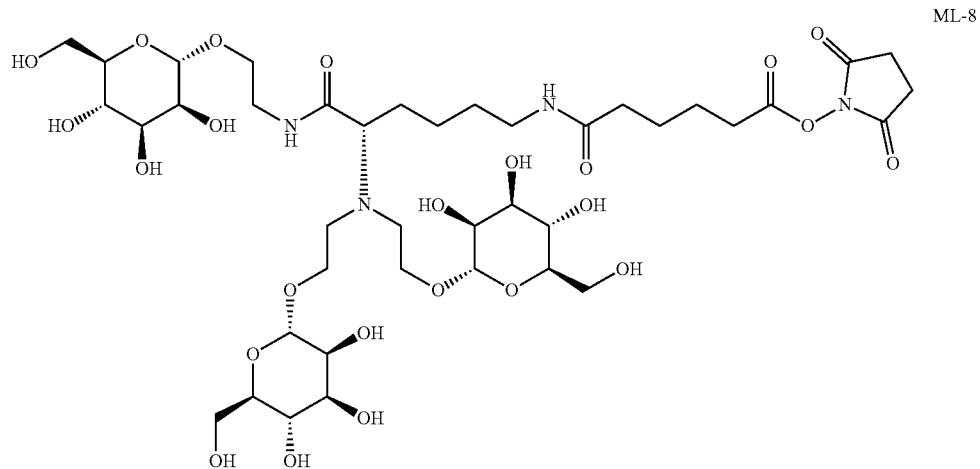 [SMILES: O=C(CCCCC(=O)ON1C(=O)CCC1=O)NCCCC[C@@H](C(=O)NCCO[C@H]1O[C@H](CO)[C@@H](O)[C@H](O)[C@@H]1O)N(CCO[C@H]1O[C@H](CO)[C@@H](O)[C@H](O)[C@@H]1O)CCO[C@H]1O[C@H](CO)[C@@H](O)[C@H](O)[C@@H]1O]

The title compound was prepared using procedures analogous to those described for ML-7 substituting 2-aminoethyl α-D-mannopyranoside for 2-aminoethyl α-L-fucopyranoside in Step B. UPLC Method A: m/z=989.56 (z=1); $t_R$=2.69 min.

Example 9

The synthesis of oligosaccharide linker 2,5-dioxopyrrolidin-1-yl (S)-6-{[5-{bis[2-oxo-2-({2-[(α-D-mannopyranosyl)oxy]ethyl}amino)ethyl]amino}-6-oxo-6-({2-[(α-D-mannopyranosyl)oxy]ethyl}amino)hexyl]amino}-6-oxohexanoate (ML-9) having the following structure is described.

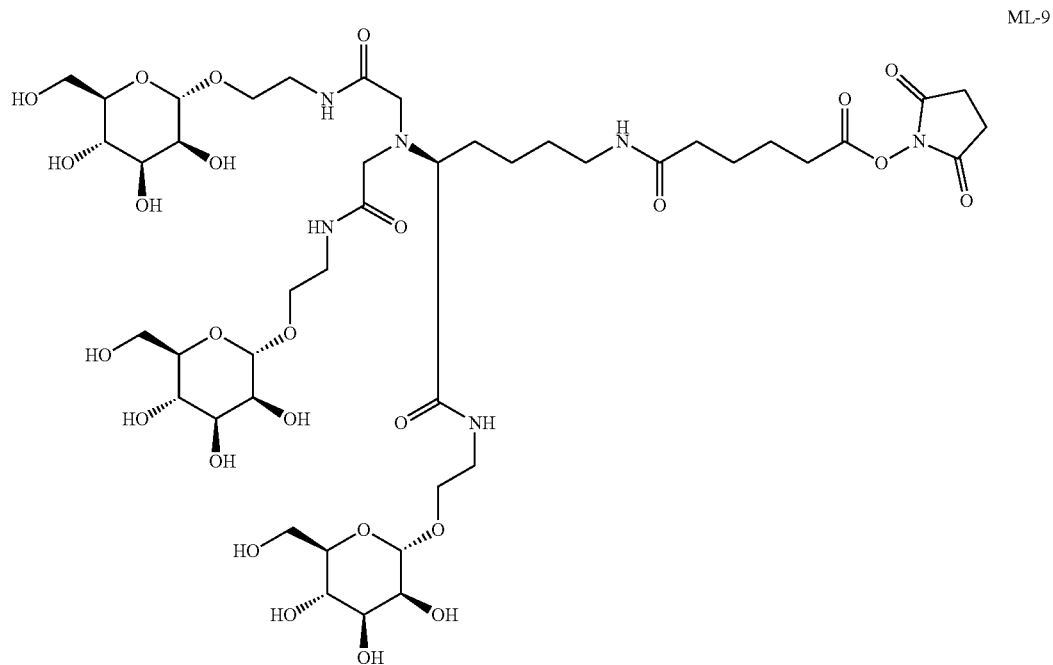 [SMILES: O=C(CCCCC(=O)ON1C(=O)CCC1=O)NCCCC[C@@H](C(=O)NCCO[C@H]1O[C@H](CO)[C@@H](O)[C@H](O)[C@@H]1O)N(CC(=O)NCCO[C@H]1O[C@H](CO)[C@@H](O)[C@H](O)[C@@H]1O)CC(=O)NCCO[C@H]1O[C@H](CO)[C@@H](O)[C@H](O)[C@@H]1O]

Step A. N⁶-[(benzyloxy)carbonyl]-N-[2-(α-D-mannopyranosyloxy)ethyl]-N²,N²-bis[2-({2-[(α-D-mannopyranosyl)oxy]ethyl}amino)-2-oxoethyl]-L-lysinamide To a solution of N⁶-[(benzyloxy)carbonyl]-N²,N²-bis(carboxymethyl)-L-lysine (1.0 g, 2.52 mmol) in DMF (15 mL) at rt was added a solution of 2-aminoethyl α-D-mannopyranoside (2.48 g, 11.10 mmol) in H₂O (2 mL) and HOBt (1.78 g, 11.60 mmol). The mixture was cooled to 0° C. and EDC (2.23 g, 11.60 mmol) was added. After stirring at 0° C. for 1.5 hr, the resulting solution was allowed to stir at rt for 48 hr. The mixture was concentrated and the residue was purified by Biotage Snap On 120 g C18 column, eluting with 0-30% AcCN in H₂O. The desired fractions were combined and freeze-dried to afford the title compound. UPLC Method D: m/z=1012.32 (z=1); $t_R$=3.78 min.

Step B. N-(2-[(α-D-mannopyranosyl)oxy]ethyl}-N², N²-bis[2-({2-[(α-D-mannopyranosyl)oxy]ethyl}amino)-2-oxoethyl]-L-lysinamide To a solution of N⁶-[(benzyloxy)carbonyl]-N-{2-[(α-D-mannopyranosyl)oxy]ethyl}-N²,N²-bis[2-({2-[(α-D-mannopyranosyl)oxy]ethyl}amino)-2-oxoethyl]-L-lysinamide (700 mg, 0.69 mmol) in H₂O (15 mL) was added Pd/C (150 mg, 0.14 mmol). The mixture was allowed to stir under a balloon of H₂ at rt for 16 hr. The catalyst was filtered off through a CELITE pad, and the filtrate was freeze-dried to afford the title product. UPLC Method D: m/z=878.28 (z=1); $t_R$=3.64 min.

Step C. benzyl 6-{[(5S)-5-{bis[2-({2-[(α-D-mannopyranosyl)oxy]ethyl}amino)-2-oxoethyl]amino}-6-({2-[(α-D-mannopyranosyl)oxy]ethyl}amino)-6-oxohexyl]amino}-6-oxohexanoate To a solution of N-{2-[(α-D-mannopyranosyl)oxy]ethyl}-N²,N²-bis[2-({2-[(α-D-mannopyranosyl)oxy]ethyl}amino)-2-oxoethyl]-L-lysinamide (291 mg, 0.873 mmol) in DMF (15 mL) at 0° C. was added benzyl (2,5-dioxopyrrolidin-1-yl) adipate (730 mg, 0.832 mmol) and TEA (122 µl, 0.873 mmol). After stirring at 0° C. for 30 min, the mixture was allowed to gradually warm up to rt. After stirring at rt for 2 hr, the mixture was concentrated and the residue was purified by Biotage snap on 120 g C18 column, eluting with 0-30% AcCN in H₂O. The desired fractions were combined and lyophilized to afford the title compound. UPLC Method D: m/z=1096.77 (z=1); $t_R$=4.78 min.

Step D. 2,5-dioxopyrrolidin-1-yl (S)-6-{[5-{bis[2-oxo-2-({2-[(α-D-mannopyranosyl)oxy]ethyl}amino)ethyl]amino}-6-oxo-6-({2-[(α-D-mannopyranosyl)oxy]ethyl}amino)hexyl]amino}-6-oxohexanoate The title compound was prepared using procedures analogous to those described for ML-1 substituting benzyl 6-{[(5S)-5-{bis[2-({2-[(α-D-mannopyranosyl)oxy]ethyl}amino)-2-oxoethyl]amino}-6-({2-[(α-D-mannopyranosyl)oxy]ethyl}amino)-6-oxohexyl]amino}-6-oxohexanoate for benzyl 4-[(4,14-dioxo-9-{[3-oxo-3-({2-[(α-D-mannopyranosyl)oxy]ethyl}amino)propoxy]methyl}-1,17-di[(α-D-mannopyranosyl)oxy]-7,11-dioxa-3,15-diazaheptadecan-9-yl)amino]-4-oxobutanoate in Step D. UPLC Method A: m/z=1103.79 (z=1); $t_R$=1.68 min.

Example 10

The synthesis of oligosaccharide linker 2,5-dioxopyrrolidin-1-yl (S)-6-{[5-{bis[2-oxo-2-({2-[(α-L-fucopyranosyl)oxy]ethyl}amino)ethyl]amino}-6-oxo-6-({2-[(α-L-fucopyranosyl)oxy]ethyl}amino)hexyl]amino}-6-oxohexanoate (ML-10) having the following structure is described.

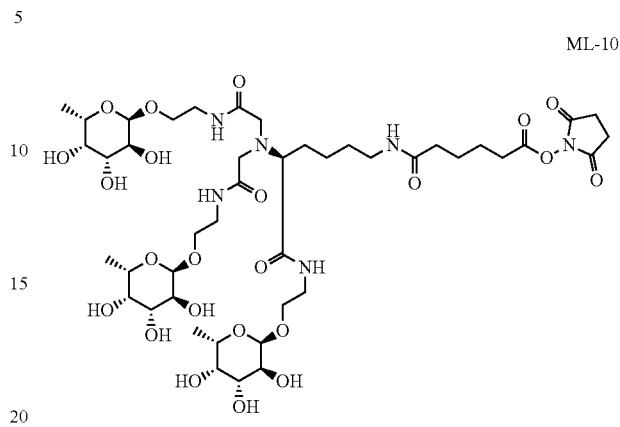

ML-10

The title compound was prepared using procedures analogous to those described for ML-9 substituting 2-aminoethyl α-L-fucopyranoside for 2-aminoethyl α-D-mannopyranoside in Step A.

Example 11

The synthesis of oligosaccharide linker 2,5-dioxopyrrolidin-1-yl (S)-4-{bis[2-oxo-2-({2-[(α-D-mannopyranosyl)oxy]ethyl}amino)ethyl]amino}-5-oxo-5-({2-[(α-D-mannopyranosyl)oxy]ethyl}amino)pentanoate (ML-11) having the following structure is described.

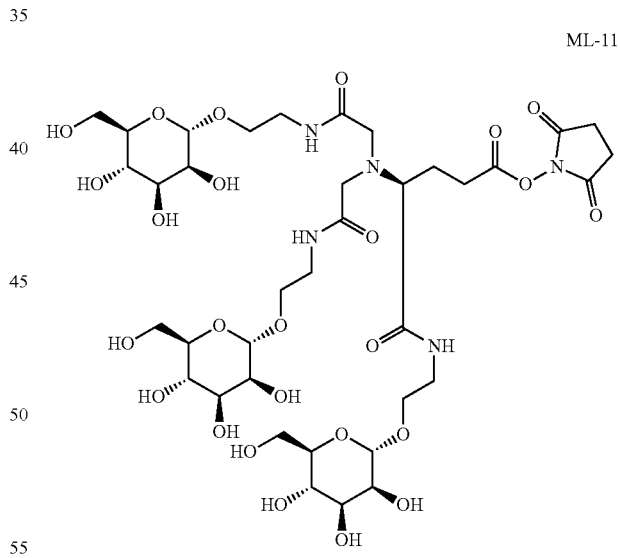

ML-11

Step A. benzyl (S)-4-{bis-[2-oxo-2-({2-[(α-D-mannopyranosyl)oxy]ethyl}amino)ethyl]amino}-5-oxo-5-({2-[(α-D-mannopyranosyl)oxy]ethyl}amino)pentanoate To a solution of (S)-2,2'-((4-(benzyloxy)-1-carboxy-4-oxobutyl)azanediyl)diacetic acid (1.0 g, 2.83 mmol) in DMF (40 mL) at 0° C. was added EDC (2.71 g, 14.15 mmol) and HOBt (217 mg, 1.415 mmol). The resulting mixture was stirred at 0° C. for 30 min and then transferred to a suspension of 2-aminoethyl α-D-mannopyranoside (2.84 g, 12.74 mmol) in DMF (15 mL). The mixture was gradually warmed up to rt. After stirring overnight, the reaction mixture was concentrated and the residue was purified by reverse phase prep HPLC (C4 column, 50×250 mm, 85 mL/min, gradient from 8% to 25.5% of AcCN in H$_2$O with 0.1% TFA over 15 min) to give the title compound. UPLC-MS Method A: m/z=969.26 (z=1); t$_R$=2.09 min.

Step B. (S)-4-{bis-[2-oxo-2-({2-[(α-D-mannopyranosyl)oxy]ethyl}amino)ethyl]amino}-5-oxo-5-({2-[(α-D-mannopyranosyl)oxy]ethyl}amino)pentanoic acid To a solution of benzyl (S)-4-{bis-[2-oxo-2-({2-[(α-D-mannopyranosyl)oxy]ethyl}amino)ethyl]amino}-5-oxo-5-({2-[(α-D-mannopyranosyl)oxy]ethyl}amino)pentanoate (1.36 g, 1.404 mmol) in H$_2$O (25 mL) was added Pd/C (224 mg, 0.211 mmol). The resulting suspension was stirred under a balloon of H$_2$ at rt for 4 hr. The catalyst was filtered off through a CELITE pad, washed with water and freeze-dried to give the title compound. UPLC-MS Method A: m/z=879.3 (z=1); t$_R$=1.04 min.

Step C. 2,5-dioxopyrrolidin-1-yl (S)-4-{bis-[2-oxo-2-({2-[(α-D-mannopyranoyl)oxy]ethyl}amino)ethyl]amino}-5-oxo-5-({2-[(α-D-mannopyranosyl)oxy]ethyl}amino)pentanoate To a solution of (S)-4-{bis-[2-oxo-2-({2-[(α-D-mannopyranosyl)oxy]ethyl}amino)ethyl]amino}-5-oxo-5-({2-[(α-D-mannopyranosyl)oxy]ethyl}amino)pentanoic acid (1.03 g, 1.177 mmol) in DMF (27 mL) at 0° C. was added TSTU (0.567 g, 1.883 mmol) and DIPEA (360 µl, 2.059 mmol). The reaction mixture was stirred at 0° C. for 2 hr and then concentrated. The resulting residue was added dropwise to AcCN (40 mL). Precipitate was formed and collected by filtration and dried to give the title compound. UPLC-MS Method A: m/z=976.3 (z=1); t$_R$=1.12 min.

Example 12

The synthesis of oligosaccharide linker 2,5-dioxopyrrolidin-1-yl N$^2$,N$^2$-bis[2-oxo-2-(}2-[(α-L-fucopyranosyl)oxy]ethyl}amino)ethyl]-N$^5$-{2-[(α-L-fucopyranosyl)oxy]ethyl}-L-glutaminate (ML-12) having the following structure is described.

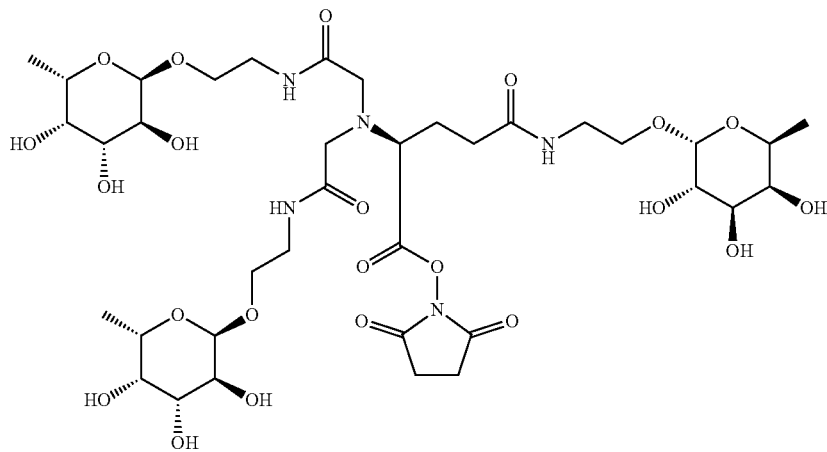

ML-12

The title compound was prepared using procedures analogous to those described for ML-11 substituting (S)-2,2'-((4-(benzyloxy)-1-carboxy-4-oxobutyl)azanediyl)diacetic acid for (S)-2,2'-((1-(benzyloxy)-4-carboxy-1-oxobutan-2-yl)azanediyl)diacetic acid and 2-aminoethyl α-D-mannopyranoside for 2-aminoethyl α-L-fucopyranoside, respectively, in Step A. UPLC Method A: m/z=928.3 (z=1); t$_R$=1.90 min.

Example 13

The synthesis of oligosaccharide linker 2,5-dioxopyrrolidin-1-yl (R)-6-{[5-{bis[2-oxo-2-({2-[(α-D-mannopyranosyl)oxy]ethyl}amino)ethyl]amino}-6-oxo-6-({2-[(α-D-mannopyranosyl)oxy]ethyl}amino)hexyl]amino}-6-oxohexanoate (ML-13) having the following structure is described.

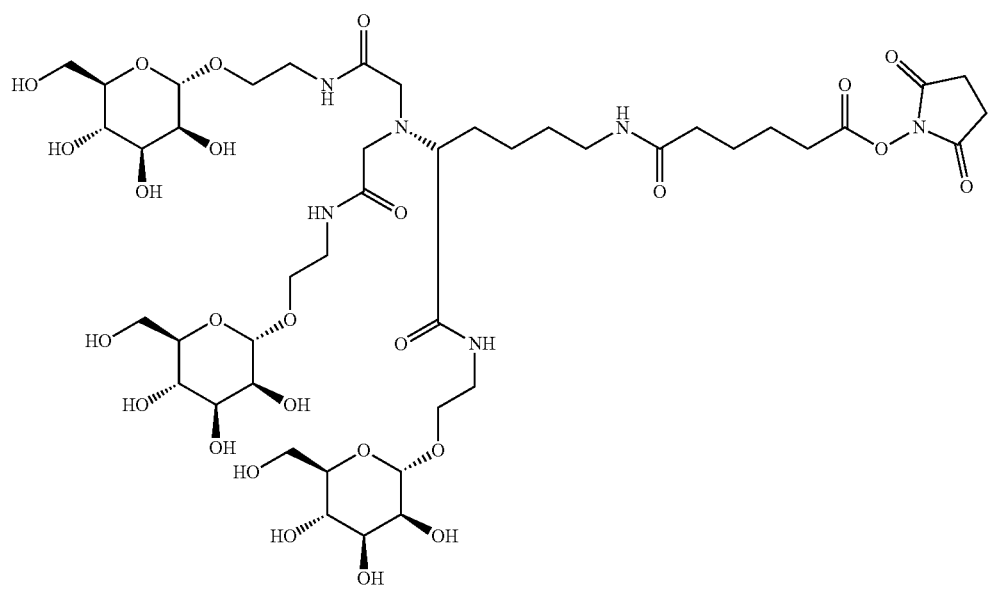

ML-13

The title compound was prepared using procedures analogous to those described for ML-9 substituting $N^6$-[(benzyloxy)carbonyl]-$N^2,N^2$-bis(carboxymethyl)-D-lysine for $N^6$-[(benzyloxy)carbonyl]-$N^2,N^2$-bis(carboxymethyl)-L-lysine in Step A. UPLC-MS Method A: m/z=1103.65 (z=1); $t_R$=1.13 min.

Example 14

The synthesis of oligosaccharide linker 2,5-dioxopyrrolidin-1-yl (S)-8-{[5-{bis[2-oxo-2-({2-[(α-L-fucopyranosyl)oxy]ethyl}amino)ethyl]amino}-6-oxo-6-({2-[(α-L-fucopyranosyl)oxy]ethyl}amino)hexyl]amino}-8-oxooctanoate (ML-14) having the following structure is described.

The title compound was prepared using procedures analogous to those described for ML-9 substituting 1-benzyl 8-(2,5-dioxopyrrolidin-1-yl) octanedioate for benzyl (2,5-dioxopyrrolidin-1-yl) adipate in Step C. UPLC-MS Method A: m/z=1083.34 (z=1); $t_R$=2.74 min.

Example 15

The synthesis of oligosaccharide linker 2,5-dioxopyrrolidin-1-yl (S)-9-{[5-{bis[2-oxo-2-({2-[(α-L-fucopyranosyl)oxy]ethyl}amino)ethyl]amino}-6-oxo-6-({2-[(α-L-fucopyranosyl)oxy]ethyl}amino)hexyl]amino}-9-oxononanoate (ML-15) having the following structure is described.

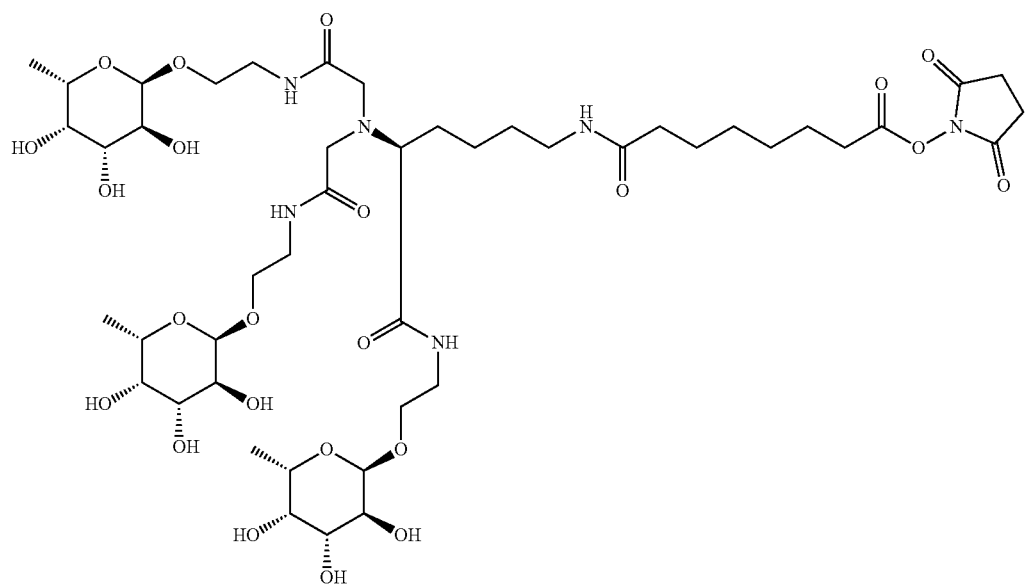

ML-14

ML-15

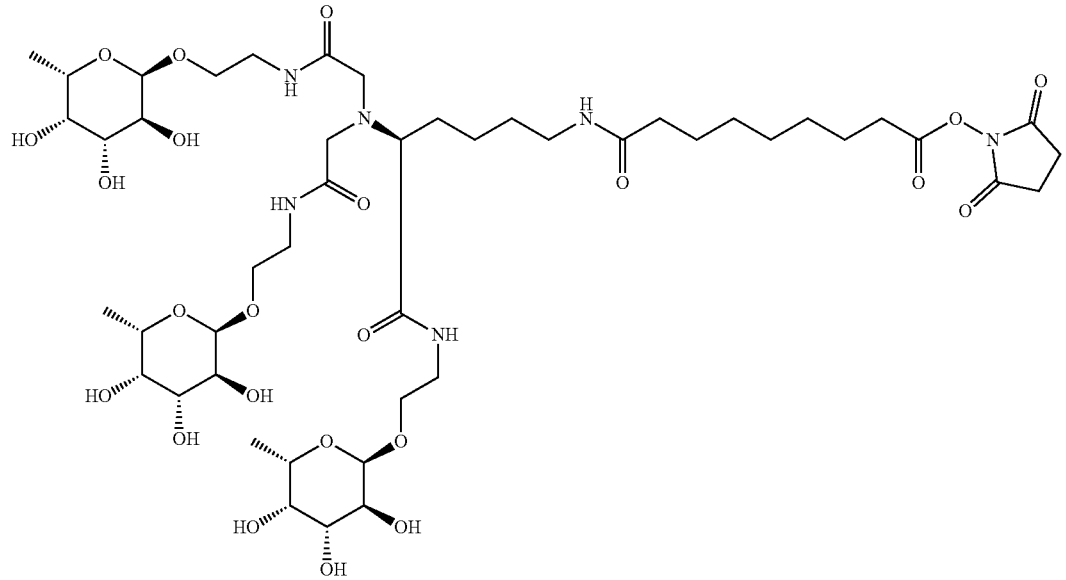

The title compound was prepared using procedures analogous to those described for ML-9 substituting 1-benzyl 9-(2,5-dioxopyrrolidin-1-yl) nonanedioate for benzyl (2,5-oxopyrrolidin-1-yl) adipate in Step C. UPLC-MS Method A: m/z=1083.37 (z=1); $t_R$=2.85 min.

Example 16

The synthesis of oligosaccharide linker 2,5-dioxopyrrolidin-1-yl (R)-6-(2-{[2-({1,4-di[(α-D-mannopyranosyl)oxy]butan-2-yl}amino)-2-oxoethyl][2-oxo-2-({2-[((β-D-mannopyranosyl)oxy]ethyl}amino)ethyl]amino}acetamido)hexanoate (ML-16) having the following structure is described.

ML-16

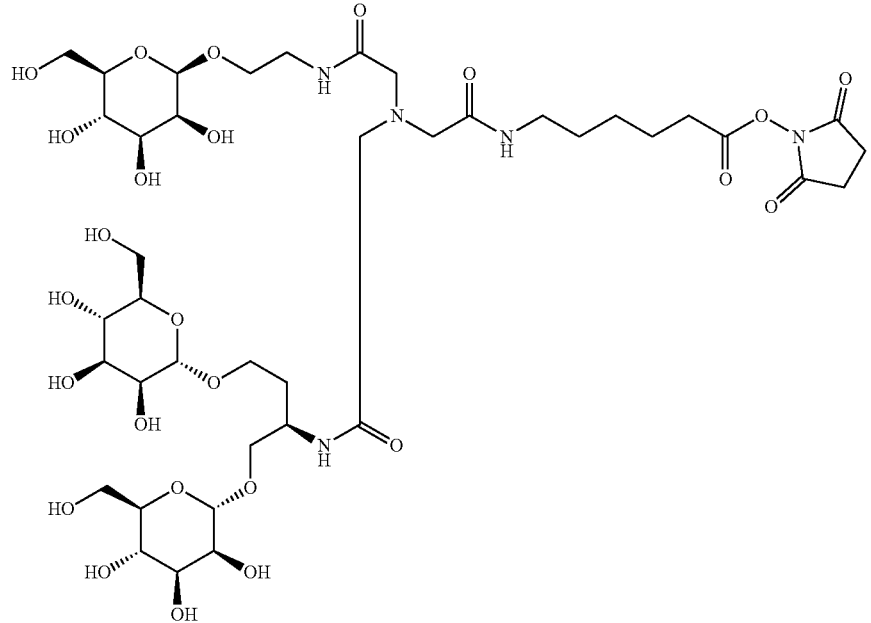

Step A. (R)-N-(2-{[6-(benzyloxy)-6-oxohexyl]amino}-2-oxoethyl)-N-[2-({1,4-di[(α-D-mannopyranosyl)oxy]butan-2-yl}amino)-2-oxoethyl]glycine To a suspension of 2,2'-[(2-{[6-(benzyloxy)-6-oxohexyl]amino}-2-oxoethyl)azanediyl]diacetic acid (0.3 g, 0.761 mmol) in DCM (2 mL) at 0° C. was added TFAA (150 μL, 1.062 mmol). After stirring at 0° C. for 3 hr, the mixture was cooled to −30° C., to which a solution of TEA (260 μL, 1.865 mmol) in DMF (1.0 mL) was added dropwise over 5 mins. After stirring at −30° C. for 30 min, a solution of (R)-1,4-di[(α-D-mannopyranosyl)oxy]butan-2-amine (355 mg, 0.827 mmol, WO 2015051052 A2) in DMF (2 mL) was added and the resulting mixture was allowed to stir at rt. After stirring for 16 hr, the mixture was concentrated and the residue was purified by flash chromatography on C18 reverse phase silica gel (50 g), eluting with 0-40% AcCN in $H_2O$, to produce the title compound. UPLC-MS Method A: m/z=806.38 (z=1); $t_R$=3.00 min.

Step B. benzyl (R)-6-(2-{[2-({1,4-di[(α-D-mannopyranosyl)oxy]butan-2-yl}amino)-2-oxoethyl][2-oxo-2-({2-[(β-D-mannopyranosyl)oxy]ethyl}amino)ethyl]amino}acetamido)hexanoate To a solution of (R)-N-(2-{[6-(benzyloxy)-6-oxohexyl]amino}-2-oxoethyl)-N-[2-({1,4-di[(α-D-mannopyranosyl)oxy]butan-2-yl}amino)-2-oxoethyl]glycine (100 mg, 0.124 mmol) in DMF (3 mL) was added 2-aminoethyl β-D-mannopyranoside (29 mg, 0.130 mmol, WO 2015051052 A2), DMAP (17 mg, 0.139 mmol), and EDC (95 mg, 0.496 mmol). After stirring for 16 h at rt, the reaction mixture was concentrated and the residue was purified by flash chromatography on C18 reverse phase silica gel (50 g), eluting with 5-60% AcCN in $H_2O$, to give the title compound. UPLC-MS Method A: m/z=1011.50 (z=1); $t_R$=2.81 min.

Step C. (R)-6-(2-{[2-({1,4-di[(α-D-mannopyranosyl)oxy]butan-2-yl}amino)-2-oxoethyl][2-oxo-2-({2-[(β-D-mannopyranosyl)oxy]ethyl}amino)ethyl]amino}acetamido)hexanoate To a stirred solution of benzyl (R)-6-(2-{[2-({1,4-di[(α-D-mannopyranosyl)oxy]butan-2-yl}amino)-2-oxoethyl][2-oxo-2-({2-[(β-D-mannopyranosyl)oxy]ethyl}amino)ethyl]amino}acetamido)hexanoate (92 mg, 0.091 mmol) in $H_2O$ (5 mL) at rt was added Pd(OH)$_2$ (5 mg, 4.70 μmol). The mixture was degassed and then stirred under a balloon of $H_2$. After stirring for 2 hr, the reaction mixture was filtered through a CELITE pad and washed with $CH_3OH$ (3×10 mL). The filtrate was concentrated to give the title compound. UPLC-MS Method A: m/z=921.44 (z=1); $t_R$=1.09 min.

Step D. 2,5-dioxopyrrolidin-1-yl (R)-6-(2-{[2-({1,4-di[(α-D-mannopyranosyl)oxy]butan-2-yl}amino)-2-oxoethyl][2-oxo-2-({2-[(β-D-mannopyranosyl)oxy]ethyl}amino)ethyl]amino}acetamido)hexanoate To a stirred solution of ®-6-(2-{[2-({1,4-di[(α-D-mannopyranosyl)oxy]butan-2-yl}amino)-2-oxoethyl][2-oxo-2-({2-[(β-D-mannopyranosyl)oxy]ethyl}amino)ethyl]amino}acetamido)hexanoate (84 mg, 0.091 mmol) in DMF (2.0 mL) at 0° C. was added TSTU (33 mg, 0.109 mmol) and DIPEA (25 μL, 0.146 mmol). After stirring for 2 h at 0° C., the crude reaction was quenched with TFA (15 μL, 0.192 mmol), and then concentrated down to half volume. The desired product was isolated via precipitation as follows: The reaction solution was transferred, via autopipette, to a tube containing EtOAc (45 mL). The addition was made dropwise. The resulting white suspension was centrifuged (3500 rpm, 20 min, at 4° C.) to generate a clear supernatant and a white pellet. The supernatant was drawn off, and white pellet was dissolved in $H_2O$, which was freeze-dried to give the title product. UPLC-MS Method A: m/z=1018.48 (z=1); $t_R$=1.10 min.

Example 17

The synthesis of oligosaccharide linker 2,5-dioxopyrrolidin-1-yl (R)-6-(2-{[2-({1,4-di[(α-D-mannopyranosyl)oxy]butan-2-yl}amino)-2-oxoethyl][2-oxo-2-({2-[(α-D-mannopyranosyl)oxy]ethyl}amino)ethyl]amino}acetamido)hexanoate (ML-17) having the following structure is described.

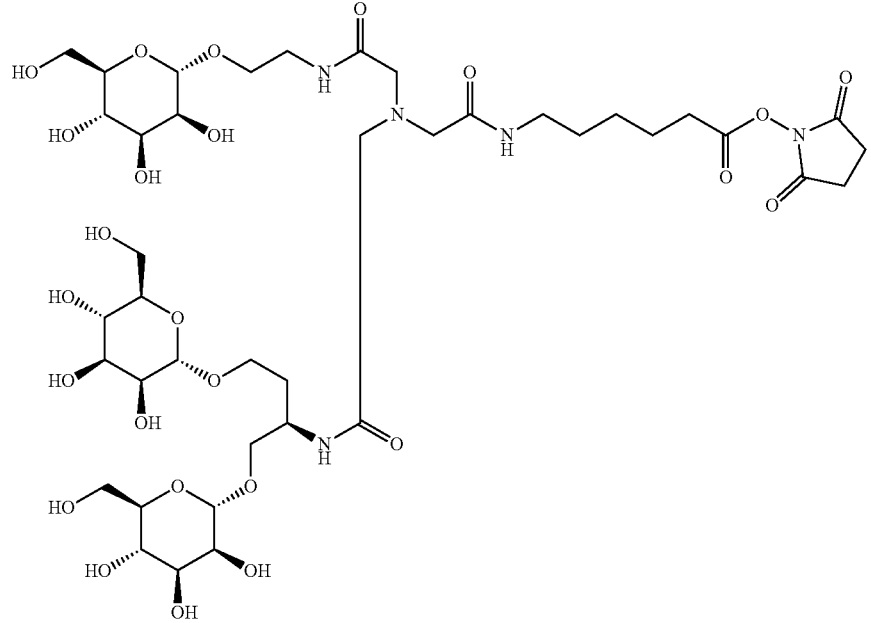

ML-17

The title compound was prepared using procedures analogous to those described for ML-16 substituting 2-aminoethyl α-D-mannopyranoside for 2-aminoethyl β-D-mannopyranoside in Step B. UPLC-MS Method A: m/z=1018.47 (z=1); $t_R$=1.10 min.

Example 18

The synthesis of oligosaccharide linker 2,5-dioxopyrrolidin-1-yl (R)-6-(2-{[2-({1,4-di[(α-D-mannopyranosyl)oxy]butan-2-yl}amino)-2-oxoethyl][2-oxo-2-({2-[(α-L-fucopyranosyl)oxy]ethyl}amino)ethyl]amino}acetamido)hexanoate (ML-18) having the following structure is described.

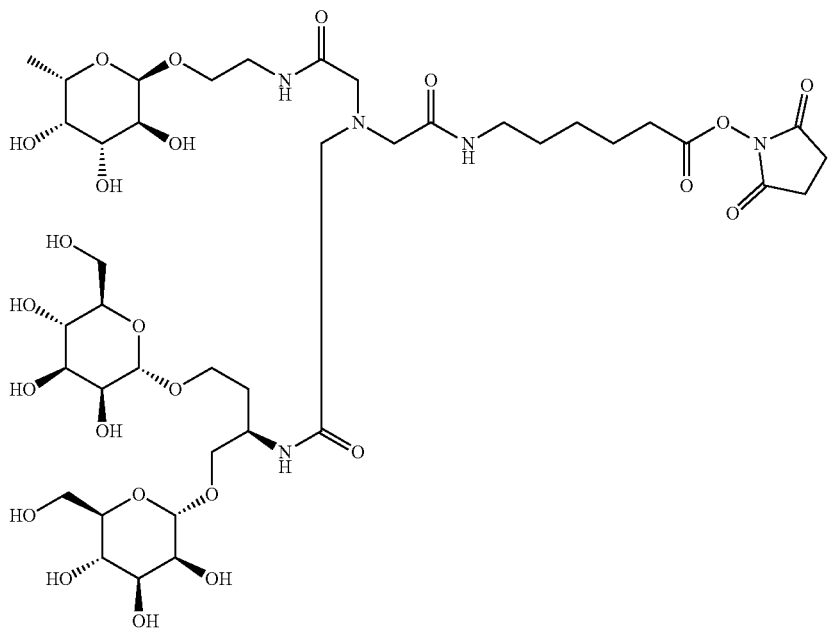

ML-18

The title compound was prepared using procedures analogous to those described for ML-16 substituting 2-aminoethyl α-L-fucopyranoside for 2-aminoethyl β-D-mannopyranoside in Step B. UPLC-MS Method A: m/z=1002.48 (z=1); $t_R$=2.05 min.

Example 19

The synthesis of oligosaccharide linker 2,5-dioxopyrrolidin-1-yl 6-(2-{[2-(bis{2-[(α-D-mannopyranosyl)oxy]ethyl}amino)-2-oxoethyl][2-oxo-2-({2-[(α-L-fucopyranosyl)oxy]ethyl}amino)ethyl]amino}acetamido)hexanoate (ML-19) having the following structure is described.

ML-19

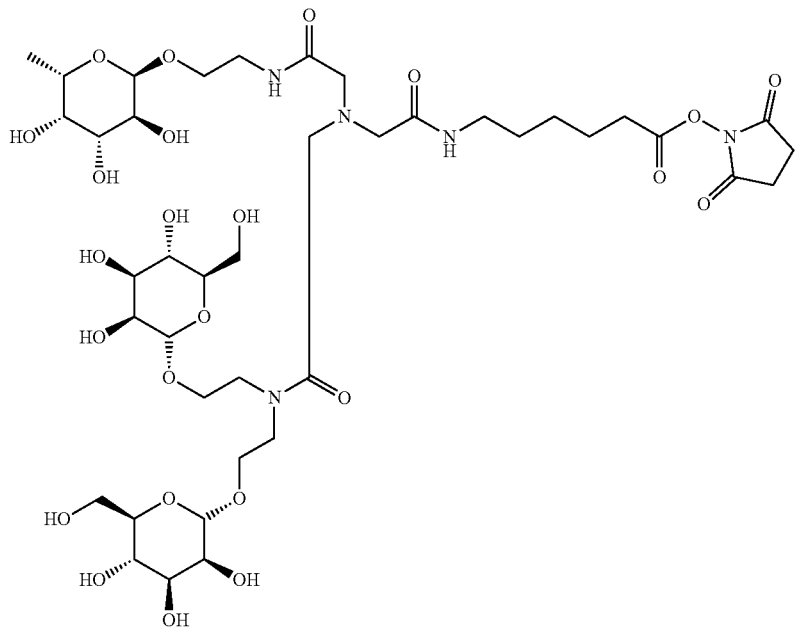

Step A. N-benzyl-2-[(2,3,4,6-tetra-O-acetyl-α-D-mannopyranosyl)oxy]-N-(2-[(2,3,4,6-tetra-O-acetyl-α-D-mannopyranosyl)oxy]ethyl}ethan-1-amine To a solution of 2-(2',3',4',6'-tetra-O-acetyl-α-D-mannopyranosyl)acetaldehyde (1.82 g, 4.67 mmol, *Eur. J. Org. Chem.* 2010, 6974-6980) and benzylamine (200 mg, 1.87 mmol) in DCM was added HOAc (32.1 µL, 0.560 mmol) followed by sodium triacetoxyborohydride (1.187 g, 5.60 mmol) in one lot. After stirred overnight, the reaction mixture was partitioned between DCM (100 mL) and sat'd NaHCO₃ (100 mL). After formation of bubbles ceased (20 min), the organic layer was separated, and the aq. layer was re-extracted with DCM (2×50 mL). Combined org. layers were dried over Na₂SO₄, concentrated, and the title compound was isolated by chromatography (120 g SiO₂ column, flow rate 100 mL/min, gradient 0-50% EtOAc/Hex (30 min) followed by 1 hr. hold). ¹H NMR (CDCl₃) δ 7.3-7.2 (m, 5H), 5.3-5.2 (ser m, 3H), 4.8 (s, 1H), 4.20 (m, 1H), 4.05 (m, 1H), 3.95 (m, 1H), 3.75 (m, 2H), 3.55 (m, 1H), 2.80 (m, 2H), 2.19 (s, 6H), 2.10 (s, 6H), 2.05 (s, 3H), 1.95 (s, 6H). LC-MS Method A: m/z=856.4 (z=1); $t_R$=1.70 min.

Step B. bis(2-[(2,3,4,6-tetra-O-acetyl-α-D-mannopyranosyl)oxy]ethyl}amine

A 500 mL high-pressure bottle was flushed with nitrogen, and a Pearlman's catalyst (476 mg, 0.678 mmol) was placed in it, followed by addition of a solution of N-benzyl-2-[(2,3,4,6-tetra-O-acetyl-α-D-mannopyranosyl)oxy]-N-{2-[(2,3,4,6-tetra-O-acetyl-α-D-mannopyranosyl)oxy]ethyl}ethan-1-amine (2.90 g, 3.39 mmol) in MeOH (67.8 mL). the reaction mixture was hydrogenated over a period of 24 hrs at 50 psi of hydrogen on a Parr shaker. The catalyst was filtered out through CELITE. The title compound was isolated by chromatography (40 g SiO₂ column, flow rate=40 mL/min, Solvent A: EtOAc, and Solvent B: 10% of MeOH/EtOAc, gradient 0-50% in 30 min followed by 30 min hold with 50% Solvent B). LC-MS Method A: m/z=766.3 (z=1); $t_R$=1.51 min.

Step C. N-(2-{[6-(benzyloxy)-6-oxohexyl]amino}-2-oxoethyl)-N-[2-(bis{2-[(2,3,4,6-tetra-O-acetyl-α-D-mannopyranosyl)oxy]ethyl}amino)-2-oxoethyl]glycine To a suspension of 2,2'-((2-((6-benzyloxy)-6-oxohexyl)amino)-2-oxethyl)azanediyl)diacetic acid (0.50 g, 1.27 mmol) in DCM (4.0 mL) at 0° C. was added TFAA (213 µL, 1.585 mmol), and the mixture was stirred at 0° C. for 3 hr. The mixture was cooled to −30° C., and a solution of TEA (424 µL, 3.04 mmol) in DMF (2.0 mL) was added, and stirring was continued at −30° C. for 30 min. Added a solution of bis{2-[(2,3,4,6-tetra-O-acetyl-α-D-mannopyranosyl)oxy]ethyl}amine (971 mg, 1.268 mmol) in DMF (8.0 mL). The reaction mixture was constantly cooled to −30° C. After addition was complete, the mixture was allowed to warm over a period of 2 hr to rt. The reaction mixture was concentrated and the title compound was isolated by chromatography (120 g SiO₂ column, flow rate 100 mL/min, gradient A-B of 0-30% B in 30 min followed by hold, where solvent A was EtOAc/MeOH/AcCN/H₂O (v/v/v/v=6/1/1/1), and solvent B was EtOAc/MeOH/AcCN/H₂O (v/v/v/v=2/1/1/1) to give the title material. UPLC-MS Method A: m/z=1142.24 (z=1); $t_R$=4.49 min.

Step D. benzyl 6-[2-([2-(bis{2-[(2,3,4,6-tetra-O-acetyl-α-D-mannopyranosyl)oxy]ethyl}amino)-2-oxoethyl](2-oxo-2-[(α-L-fucopyranosyl)oxy]ethyl}amino)acetamidoihexanoate To a mixture of N-(2-{[6-(benzyloxy)-6-oxohexyl]amino}-2-oxoethyl)-N-[2-(bis{2-[(2,3,4,6-O-acetyl-α-D- mannopyranosyl)oxy]ethyl}amino)-2-oxoethyl]glycine (1.26 g, 1.103 mmol) and 2-aminoethyl α-L-fucopyranoside (297 mg, 1.434 mmol) in DMF (15.8 mL) was added DIPEA (578 μL, 3.31 mmol), HOBt (169 mg, 1.103 mmol), and EDC (317 mg, 1.655 mmol). After stirring overnight, the reaction mixture was concentrated. The title material was isolated by chromatography (120 g ISCO C18 column, flow rate 50 mL/min; gradient 0-80% AcCN/H₂O in 40 min). UPLC-MS Method A: m/z=1331.54 (z=1); $t_R$=3.31 min.

Step E. 6-[2-([2-(bis{2-[(2,3,4,6-tetra-O-acetyl-α-D-mannopyranosyl)oxy]ethyl}amino)-2-oxoethyl][2-oxo-2-[(α-L-fucopyranosyl)oxy]ethyl}amino)acetamido]hexanoic acid To a solution of benzyl 6-[2-([2-(bis{2-[(2,3,4,6-tetra-O-α-D-mannopyranosyl)oxy]ethyl}amino)-2-oxoethyl]{2-oxo-2-[(α-L-fucopyranosyl)oxy]ethyl}amino)acetamido] hexanoate (980 mg, 0.736 mmol) in CH₃OH (10.0 mL) was added sodium methoxide (30% wt in CH₃OH) (39.8 mg, 0.221 mmol). The reaction mixture was allowed to stir overnight. UPLC-MS analysis of the reaction mixture indicated removal of acyl groups and transesterification of benzyl ester to methyl ester (UPLC-MS Method A: m/z=919.45 (z=1); $t_R$=1.75 min). The reaction mixture was concentrated and the residue was re-dissolved the in H₂O (5.0 mL) and followed by addition of 5M NaOH (294 μl, 1.472 mmol). After stirring for 2 hr, the reaction mixture was neutralized using 1M HCl to pH=6.0 and freeze-dried to give the title compound. UPLC-MS Method A: m/z=905.43 (z=1); $t_R$=1.40 min.

Step D. 2,5-dioxopyrrolidin-1-yl 6-(2-{[2-(bis{2-[(α-D-mannopyranosyl)oxy]ethyl}amino)-2-oxoethyl][2-oxo-2-({2-[(α-L-fucopyranosyl)oxy] ethyl}amino)ethyl]amino}acetamido)hexanoate The title compound was prepared using procedures analogous to that described for ML-1 substituting 6-[2-([2-(bis{2-[(α-D-mannopyranosyl)oxy]ethyl}amino)-2-oxoethyl]{2-oxo-2-[(α-L-fucopyranosyl)oxy]ethyl}amino)acetamido] hexanoic acid for 4-[(4,14-dioxo-9-{[3-oxo-3-({2-[(α-D-mannopyranosyl)oxy]ethyl}amino)propoxy]methyl}-1,17-di[(α-D-mannopyranosyl)oxy]-7,11-dioxa-3,15-diazaheptadecan-9-yl)amino]-4-oxobutanoic acid in Step E. UPLC-MS Method A: m/z=1002.55 (z=1); $t_R$=1.74 min.

Example 20

The synthesis of oligosaccharide linker 2,5-dioxopyrrolidin-1-yl 6-{[2-(bis{2-[(α-D-mannopyranosyl)oxy] ethyl}amino)-2-oxoethyl][2-oxo-2-({2-[(α-D-mannopyranosyl)oxy]ethyl}amino)ethyl]amino}-6-oxohexanoate (ML-20) having the following structure is described.

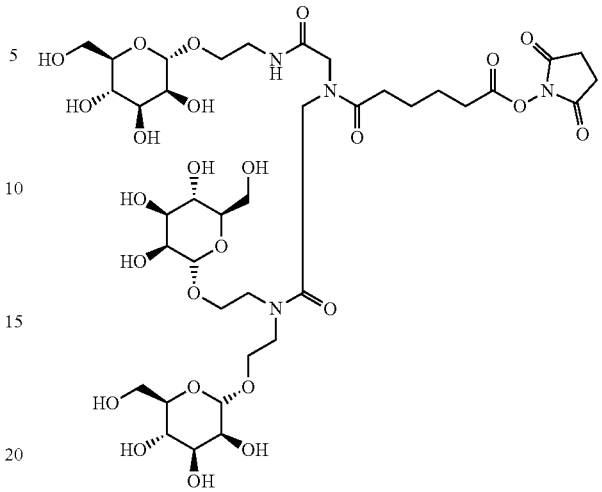

ML-20

Step A. N-{6-[(α-D-mannopyranosyl)oxy]-6-oxo-hexanoyl}-N-[2-(bis{2-[(α-D-mannopyranosyl)oxy] ethyl}amino)-2-oxoethyl]glycine To a suspension of 2,2'-{[6-(benzyloxy)-6-oxohexanoyl] imino}diacetic acid (560 mg, 1.594 mmol) in DCM (14 mL) at 0° C. was added TFAA (282 μL, 1.994 mmol) slowly, and the resulting mixture was allowed to stir at 0° C. for 3 hr. The resulting mixture was then cooled to −30° C., and a solution of TEA (534 μL, 3.83 mmol) in DMF (7 mL) was added dropwise over 25 min. The mixture was stirred at −30° C. for 30 min, and then a solution of bis{2-[(α-D-mannopyranosyl) oxy]ethyl}amine (685 mg, 1.595 mmol) in DMF (14.0 mL) was added. After stirring at rt over weekend, the reaction mixture was concentrated, and the residue was purified by column chromatography on Gold 100 g C18 reverse phase silica gel, eluting with AcCN in H₂O (gradient from 0% to 50% in 25 CV) to give the title compound. UPLC-MS Method A: m/z=763.35 (z=1); $t_R$=2.76 min.

Step B: benzyl 6-([2-(bis{2-[(α-D-mannopyranosyl) oxy]ethyl}amino)-2-oxoethyl]{2-oxo-2-[(α-D-mannopyranosyl)oxy]ethyl}amino)-6-oxohexanoate To a solution of N-{6-[(α-D-mannopyranosyl)oxy]-6-oxo-hexanoyl}-N-[2-(bis{2-[(α-D-mannopyranosyl)oxy] ethyl}amino)-2-oxoethyl]glycine (270 mg, 0.354 mmol) in DMF (13 mL) at 0° C. was added EDC (115 mg, 0.602 mmol) and HOBt (16 mg, 0.106 mmol) and 30 min later 2-aminoethyl α-D-mannopyranoside (119 mg, 0.531 mmol). The mixture was allowed to gradually warm up to rt, stirred overnight, and then concentrated. The resulting residue was purified by column chromatography on Gold 100 g C18 reverse phase silica gel, eluting with AcCN in H₂O (gradient from 0% to 50% in 25 CV) to give the title compound. UPLC-MS Method A: m/z=968.48 (z=1); $t_R$=2.50 min.

Step C. 6-([2-(bis{2-[(α-D-mannopyranosyl)oxy] ethyl}amino)-2-oxoethyl](2-oxo-2-[(α-D-mannopyranosyl)oxy]ethyl}amino)-6-oxohexanoic acid A solution of benzyl 6-([2-(bis{2-[(α-D-mannopyranosyl) oxy]ethyl}amino)-2-oxoethyl]{2-oxo-2-[(α-D-mannopyranosyl)oxy]ethyl}amino)-6-oxohexanoate (120 mg, 0.124 mmol) in water (20 mL) was added Pd/C (20 mg, 0.019 mmol). The resulting suspension was stirred under a balloon of H₂ at rt for 2 hr. The catalyst was filtered off through a CELITE pad, washed with H₂O and freeze-dried to give the title compound. UPLC-MS Method A: m/z=878.45 (z=1); $t_R$=1.22 min.

Step D: 2,5-dioxopyrrolidin-1-yl 6-{[2-(bis{2-[(α-D-mannopyranosyl)oxy]ethyl}amino)-2-oxoethyl][2-oxo-2-({2-[(α-D-mannopyranosyl)oxy]ethyl}amino)ethyl]amino}-6-oxohexanoate To a solution of 6-([2-(bis{2-[(α-D-mannopyranosyl)oxy]ethyl}amino)-2-oxoethyl]{2-oxo-2-[(α-D-mannopyranosyl)oxy]ethyl}amino)-6-oxohexanoic acid (106 mg, 0.121 mmol) in DMF (25 mL) at 0° C. was added TSTU (63.6 mg, 0.211 mmol) and DIPEA (39 μl, 0.223 mmol). After stirring at 0° C. for 2 hr, the mixture was concentrated and the residue was purified by column chromatography on 40 g Grace C18 reverse phase silica gel, eluting with AcCN in H₂O (gradient from 0% to 40% in 20 CV), to give the title compound. UPLC-MS Method G: m/z=975.48 (z=1); $t_R$=1.47 min.

Example 21

The synthesis of oligosaccharide linker 2,5-dioxopyrrolidin-1-yl 6-{[2-(bis{2-[(α-D-mannopyranosyl)oxy]ethyl}amino)-2-oxoethyl][2-oxo-2-({2-[(α-L-fucopyranosyl)oxy]ethyl}amino)ethyl]amino}-6-oxohexanoate (ML-21) having the following structure is described.

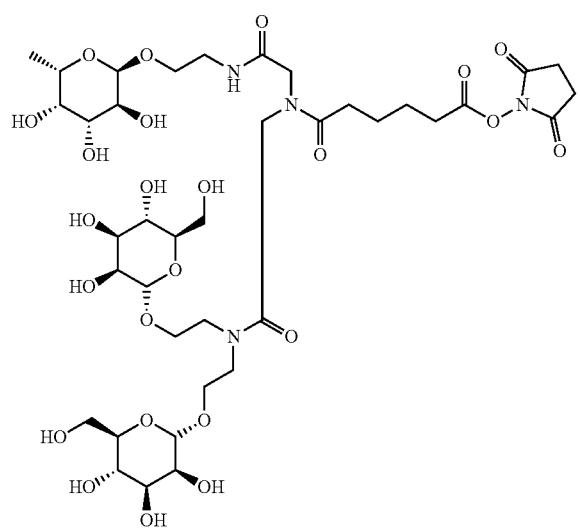

ML-21

The title compound was prepared using procedures analogous to those described for ML-20 substituting 2-aminoethyl α-L-fucopyranoside for 2-aminoethyl α-D-mannopyranoside in Step B. UPLC-MS Method G: m/z=959.47 (z=1); $t_R$=1.72 min.

Example 22

The synthesis of oligosaccharide linker 2,5-dioxopyrrolidin-1-yl 6-{[2-(bis{2-[(α-D-mannopyranosyl)oxy]ethyl}amino)-2-oxoethyl][2-oxo-2-({2-[(β-D-glucopyranosyl)oxy]ethyl}amino)ethyl]amino}-6-oxohexanoate (ML-22) having the following structure is described.

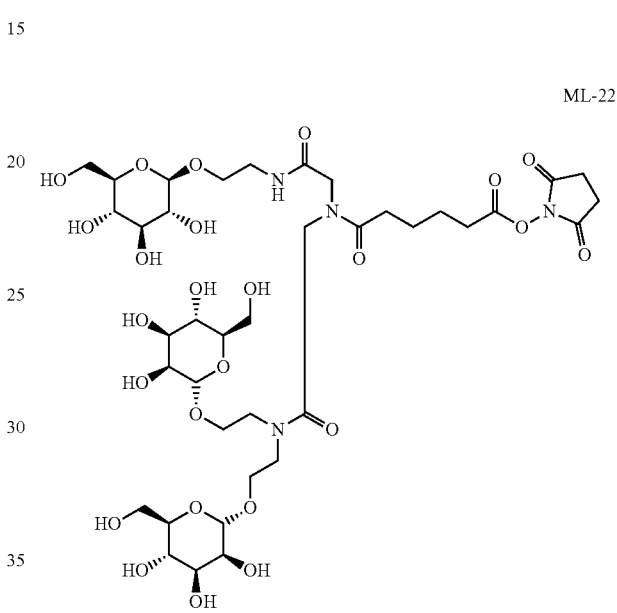

ML-22

The title compound was prepared using procedures analogous to those described for ML-20 substituting 2-aminoethyl β-D-glucopyranoside for 2-aminoethyl α-D-mannopyranoside in Step B. UPLC-MS Method A: m/z=975.46 (z=1); $t_R$=2.11 min.

Example 23

The synthesis of oligosaccharide linker 2,5-dioxopyrrolidin-1-yl (S)-4,9,16,20-tetraoxo-18-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-1-[(α-D-mannopyranosyl)oxy]-7-({2-[(α-D-mannopyranosyl)oxy]ethyl}carbamoyl)-3,8,15,18,21-pentaazaheptacosan-27-oate (ML-23) having the following structure is described.

ML-23

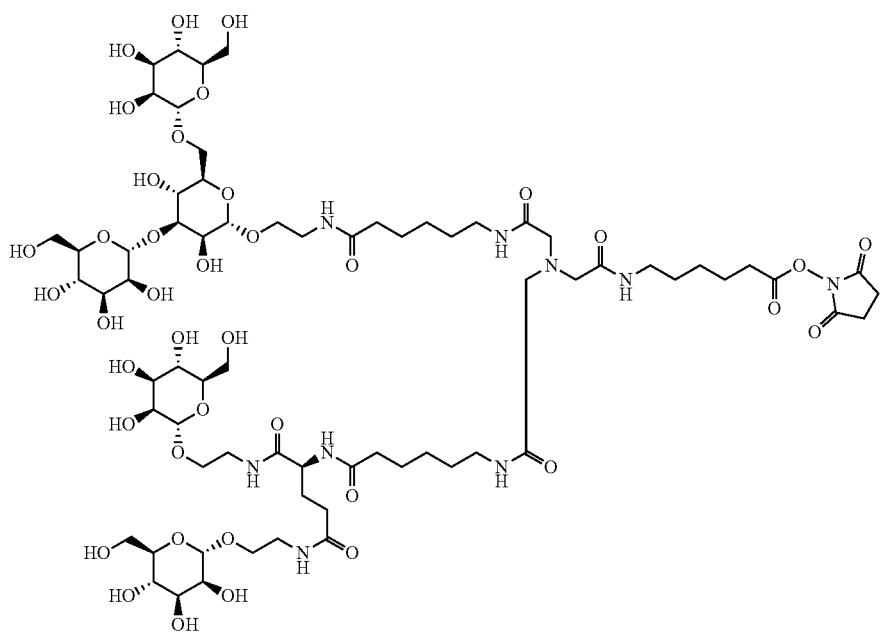

Step A. benzyl (6-oxo-6-{[2-({α-D-mannopyranosyl-(1→3)-[α-D-mannopyranosyl-(1→6)]-α-D-mannopyranosyl}oxy)ethyl]amino})hexyl)carbamate To a solution of 2-({α-D-mannopyranosyl-(1→3)-[α-D-mannopyranosyl-(1→6)]-α-D-mannopyranosyl}oxy)ethan-1-amine (720 mg, 1.32 mmol) in anhydrous DMA (9 mL) at 0° C. was added a solution of 2,5-dioxopyrrolidin-1-yl 6-{[(benzyloxy)carbonyl]amino}hexanoate (572 mg, 1.58 mmol) in DMA (3.0 mL) over 10 min and followed by slow addition of TEA (275 μL, 1.97 mmol). The resulting mixture was stirred at rt for 16 hr and concentrated. The residue was purified by silica gel column chromatography (BCombiFlash Teldyne ISCO: 40 g RediSep column) eluent: gradient EtOAc/MeOH/AcCN (v/v/v=6/2/2) to EtOAc/MeOH/AcCN/H$_2$O (v/v/v/v=6/2/2/2) over 20 CV to give the title compound. UPLC-MS Method A: m/z=795.7 (z=1); $t_R$=1.14 min.

Step B. 6-amino-N-[2-({α-D-mannopyranosyl-(1→3)-[α-D-mannopyranosyl-(1→6)]-α-D-mannopyranosyl}oxy)ethyl]hexanamide To a N$_2$-flushed solution of benzyl (6-oxo-6-{[2-({α-D-mannopyranosyl-(1→3)-[α-D-mannopyranosyl-(1→6)]-α-D-mannopyranosyl}oxy)ethyl]amino})hexyl)carbamate (890 mg, 1.12 mmol) in a mixture of ethanol (14 mL) and water (7 mL) was added 10% Pd/C (120 mg). The resulting mixture was stirred under a balloon of H$_2$ overnight. The catalyst was filtered off through a Celite pad and washed with methanol. The filtrate was evaporated to give the title compound. UPLC-MS Method A: m/z=661.6 (z=1); $t_R$=0.27 min.

Step C. N-(2-{[6-(benzyloxy)-6-oxohexyl]amino}-2-oxoethyl)-N-{2-[(6-{[2-({α-D-mannopyranosyl-(1→3)-[α-D-mannopyranosyl-(1→6)]-α-D-mannopyranosyl}oxy)ethyl]amino}-6-oxohexyl)amino]-2-oxoethyl}glycine To a suspension 2,2'-[(2-{[6-(benzyloxy)-6-oxohexyl]amino}-2-oxoethyl) azanediyl]diacetic acid (450 mg, 1.14 mmol) in anhydrous DCM (4 mL) at 0° C. was added TFAA (0.2 mL, 1.43 mol). After stirring at 0° C. for 3 hr, the resulting mixture was cooled down to −30° C. To the reaction mixture at −30° C. was added a solution of TEA (0.38 mL, 2.74 mmol) in anhydrous DMF (2 mL) dropwise over 30 min, and after another 30 min a suspension of 6-amino-N-[2-({α-D-mannopyranosyl-(1→3)-[α-D-mannopyranosyl-(1→6)]-α-D-mannopyranosyl}oxy)ethyl]hexanamide (754 mg, 1.14 mmol) in DMF (4 mL). The resulting mixture was allowed to stir at rt for 16 hr. The solution was decanted from flask and evaporated. The residue was purified by silica gel column chromatography (CombiFlash Teldyne ISCO: 40 g RediSep column) eluent: gradient EtOAc/MeOH/AcCN (v/v/v=6/2/2) to EtOAc/MeOH/AcCN/H$_2$O (v/v/v/v=6/2/2/2) over 20 CV then to EtOAc/MeOH/AcCN/H$_2$O (v/v/v/v=6/2/2/2) over 10 CV to give the title compound. UPLC-MS Method A: m/z=1038.1 (z=1); $t_R$=1.40 min.

Step D. benzyl [(S)-1,5-dioxo-1,5-bis({2-[(α-D-mannopyranosyl)oxy]ethyl}amino)pentan-2-yl]carbamate To a solution of Z-glutamic acid (600 mg, 2.13 mmol) and 2-aminoethyl α-D-mannopyranoside (1.19 g, 5.33 mmol) in DMF (12 mL) at rt was added EDC (1.64 g, 8.53 mmol) and DMAP (261 mg, 2.13 mmol). After stirring for 48 hr, the reaction mixture was evaporated, and the residue was added slowly to AcCN (180 mL). The resulting suspension was centrifuged 2× (3500 rpm 8 min). The supernatent was decanted off, and the residual white pellets was dissolved in MeOH, combined and evaporated. The residue was purified by silica gel column chromatography (CombiFlash Teldyne ISCO: 80 g RediSep column) eluent: gradient EtOAc/:MeOH/AcCN (v/v/v=6/2/2) to EtOAc/MeOH/AcCN/H$_2$O (v/v/v/v=6/2/2/2) over 12 CV then to EtOAc/:MeOH/AcCN/H$_2$O (v/v/v/v=6/2/2/2) over 5 CV to give the title compound. UPLC-MS Method A: m/z=691.5 (z=1); $t_R$=0.40 min.

Step E. (S)-2-amino-N¹,N⁵-bis{2-[(α-D-mannopyranosyl)oxy]ethyl}pentanediamide To a nitrogen flushed solution of benzyl [(S)-1,5-dioxo-1,5-bis({2-[(α-D-mannopyranosyl)oxy]ethyl}amino)pentan-2-yl]carbamate (850 mg, 1.23 mmol) in a mixture of EtOH (12 mL) and water (6 mL) was added 10% Pd/C (131 mg, 0.12 mmol). The resulting mixture was stirred under a balloon of hydrogen overnight. The catalyst was filtered off through a CELITE pad and washed with MeOH. The combined filtrates were evaporated to give the title compound. UPLC-MS Method A: m/z=558.5 (z=1); $t_R$=0.52 min.

Step F. benzyl (6-{[(S)-1,5-dioxo-1,5-bis({2-[(α-D-mannopyranosyl)oxy]ethyl}amino)pentan-2-yl]amino}-6-oxohexyl)carbamate To a solution of (S)-2-amino-N¹,N⁵-bis{2-[(α-D-mannopyranosyl)oxy]ethyl}pentanediamide (685 mg, 1.23 mmol) in DMF (5 mL) at 0° C. was added a solution of 2,5-dioxopyrrolidin-1-yl 6-{[(benzyloxy)carbonyl]amino}hexanoate (445 mg, 1.23 mmol) in DMA (5 mL) over 10 mins followed by slow addition of TEA (257 μL, 1.84 mmol). The resulting mixture was stirred at rt overnight and evaporated. The residue was purified by silica gel column chromatography (CombiFlash Teldyne ISCO: 40 g RediSep column) eluent: gradient EtOAc/MeOH/AcCN (v/v/v=6/1/1) to EtOAc/MeOH/AcCN/H₂O (v/v/v/v=6/2/2/2) over 30 CV to give the title compound. UPLC-MS Method A: m/z=805.7 (z=1); $t_R$=0.51 min.

Step G. (S)-2-(6-aminohexanamido)-N¹,N⁵-bis{2-[(α-D-mannopyranosyl)oxy]ethyl}pentanediamide To a nitrogen flushed solution of benzyl (6-{[(S)-1,5-dioxo-1,5-bis({2-[(α-D-mannopyranosyl)oxy]ethyl}amino)pentan-2-yl]amino}-6-oxohexyl)carbamate (768 mg, 0.954 mmol) in a mixture of EtOH (5 mL) and H₂O (2.5 mL) was added 10% Pd/C (102 mg, 0.095 mmol). The resulting mixture was stirred under a balloon of hydrogen overnight. The catalyst was filtered off through a CELITE pad and washed with MeOH (10 mL) to afford the title compound. UPLC-MS Method A: m/z=671.6 (z=1); $t_R$=0.24 min.

Step H. benzyl (S)-4,9,16,20-tetraoxo-18-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-1-[(α-D-mannopyranosyl)oxy]-7-({2-[(α-D-mannopyranosyl)oxy]ethyl}carbamoyl)-3,8,15,18,21-pentaazaheptacosan-27-oate To a solution of N-(2-{[6-(benzyloxy)-6-oxohexyl]amino}-2-oxoethyl)-N-{2-[(6-{[2-({α-D-mannopyranosyl-(1→3)-[α-D-mannopyranosyl-(1→6)]-α-D-mannopyranosyl}oxy)ethyl]amino}-6-oxohexyl)amino]-2-oxoethyl}glycine (200 mg, 0.193 mmol) and (S)-2-(6-aminohexanamido)-N¹,N⁵-bis{2-[(α-D-mannopyranosyl)oxy]ethyl}pentanediamide (194 mg, 0.289 mmol) in DMF (4 mL) at 0° C. was added EDC (74 mg, 0.386 mmol) and DMAP (47 mg, 0.386 mmol). After stirring at rt for 3 days, the reaction mixture was concentrated and the residue was added dropwise to AcCN (50 mL). The resulting precipitate formed was spun down on centrifuge at 3500 rpm for 8 min. The supernatant was decanted and the solid pellet was dissolved in MeOH, combined, evaporated, and purified by silica gel column chromatography with a gradient EtOAc/MeOH/AcCN (v/v/v=6/1/1) to EtOAc/MeOH/AcCN/H₂O (v/v/v/v=6/2/2/2) over 20 CV then to EtOAc/:MeOH/AcCN/H₂O (v/v/v/v=6/2/2/2) over 10 CV to provide the title product. UPLC-MS Method D: m/z=1688 (z=1); $t_R$=4.68.

Step I. (S)-4,9,16,20-tetraoxo-18-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-1-[(α-D-mannopyranosyl)oxy]-7-({2-[(α-D-mannopyranosyl)oxy]ethyl}carbamoyl)-3,8,15,18,21-pentaazaheptacosan-27-oic acid To a nitrogen flushed solution of benzyl (S)-4,9,16,20-tetraoxo-18-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-1-[(α-D-mannopyranosyl)oxy]-7-({2-[(α-D-mannopyranosyl)oxy]ethyl}carbamoyl)-3,8,15,18,21-pentaazaheptacosan-27-oate (180 mg, 0.107 mmol) in water (2 mL) was added 10% palladium on carbon (11 mg). The resulting mixture was stirred under a balloon of hydrogen for 2 hr. The catalyst was filtered off through a 0.2 micron syringe filter, and the filtrate was freeze-dried to give the title compound. UPLC-MS Method D: m/z=1599 (z=1); $t_R$=3.01 min.

Step J. 2,5-dioxopyrrolidin-1-yl (S)-4,9,16,20-tetraoxo-18-(2-oxo-2-[(6-oxo-6-[2-({α-D-mannopyranosyl-(1→3)-[α-D-mannopyranosyl-(1→6)]-α-D-mannopyranosyl}oxy)ethyl]amino}hexyl)amino]ethyl}-1-[(α-D-mannopyranosyl)oxy]-7-({2-[(α-D-mannopyranosyl)oxy]ethyl}carbamoyl)-3,8,15,18,21-pentaazaheptacosan-27-oate To a solution of (S)-4,9,16,20-tetraoxo-18-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-1-[(α-D-mannopyranosyl)oxy]-7-({2-[(α-D-mannopyranosyl)oxy]ethyl}carbamoyl)-3,8,15,18,21-pentaazaheptacosan-27-oic acid (161 mg, 0.101 mmol) in DMF (2 mL) at 0° C. was added dipyrrolidino(N-succinimidyloxy)carbenium hexafluorophosphate (50 mg, 0.1121 mmol) and DIPEA (0.023 mL, 0.13 mmol). The resulting mixture was stirred at 0° C. for 90 min and then quenched with TFA (11 μL, 0.141 mmol). The mixture was added dropwise into AcCN (40 mL), and the precipitate was collected by centrifugation at 3500 rpm for 15 min. The supernatant was decanted off, and the pellet was re-dissolved in DMF (1.5 mL) and then added dropwise to AcCN (40 mL) and centrifuged at 3500 rpm for 15 min again. The supernatant was decanted off and the pellet was re-dissolved in H₂O (2 mL) and freeze-dried to give the title compound. UPLC-MS Method D: m/z=1696 (z=1); $t_R$=3.36 min.

Example 24

The synthesis of oligosaccharide linker 2,5-dioxopyrrolidin-1-yl (S)-4,11,16,20-tetraoxo-18-{2-oxo-2-[(6-oxo-6-{[2-(α-D-mannopyranosyl-(1→3)-[α-D-mannopyranosyl-(1→6)]-α-D-mannopyranosyl}oxy)ethyl]amino}hexyl)amino]ethyl}-14-{[6-oxo-6-({2-[(α-L-fucopyranosyl)oxy]ethyl}amino)hexyl]carbamoyl}-1-[(α-L-fucopyranosyl)oxy]-3,10,15,18,21-pentaazaheptacosan-27-oate (ML-24) having the following structure is described.

ML-24

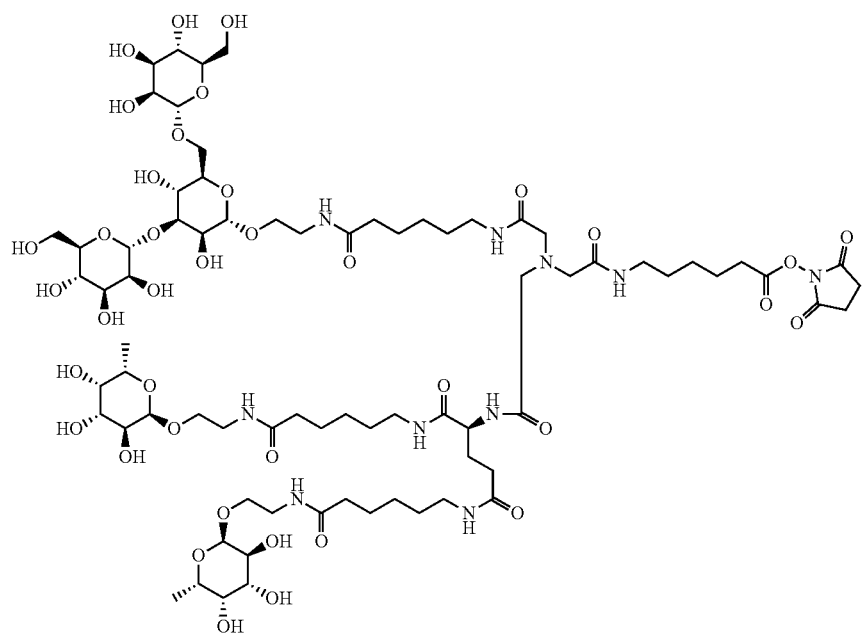

Step A. benzyl [6-oxo-6-({2-[(α-L-fucopyranosyl)oxy]ethyl}amino)hexyl]carbamate

The title compound was prepared using the procedure analogous to that described for ML-23 substituting 2-aminoethyl α-L-fucopyranoside for 2-({α-D-mannopyranosyl-(1→3)-[α-D-mannopyranosyl-(1→6)]-α-D-mannopyranosyl}oxy)ethan-1-amine in Step A. UPLC-MS Method D: m/z=455.18 (z=1); $t_R$=3.73 min.

Step B. 6-amino-N-(2-[(α-L-fucopyranosyl)oxy]ethyl}hexanamide

The title compound was prepared using the procedure analogous to that described for ML-23 substituting benzyl [6-oxo-6-({2-[(α-L-fucopyranosyl)oxy]ethyl}amino)hexyl]carbamate for benzyl (6-oxo-6-{[2-({α-D-mannopyranosyl-(1→3)-[α-D-mannopyranosyl-(1→6)]-α-D-mannopyranosyl}oxy)ethyl]amino})hexyl)carbamate in Step B. UPLC-MS Method A: m/z=321 (z=1); $t_R$=1.10 min.

Step C. 2,5-dioxopyrrolidin-1-yl (S)-4,11,16,20-tetraoxo-18-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-14-{[6-oxo-6-({2-[(α-L-fucopyranosyl)oxy]ethyl}amino)hexyl]carbamoyl}-1-[(α-L-fucopyranosyl)oxy]-3,10,15,18,21-pentaazaheptacosan-27-oate The title compound was prepared using procedures analogous to those described for ML-23 substituting 6-amino-N-[2-[(α-L-fucopyranosyl)oxy]ethyl}hexanamide for 2-aminoethyl α-D-mannopyranoside in Step D. UPLC-MS Method A: m/z=1778 (z=1); $t_R$=2.47 min.

Example 25

The synthesis of oligosaccharide linker 2,5-dioxopyrrolidin-1-yl (S)-4,11,14,18-tetraoxo-16-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-12-(3-oxo-3-{[2-({α-D-mannopyranosyl-(1→3)-[α-D-mannopyranosyl-(1→6)]-α-D-mannopyranosyl}oxy)ethyl]amino}propyl)-1-[(α-L-fucopyranosyl)oxy]-3,10,13,16,19-pentaazapentacosan-25-oate (ML-25) having the following structure is described.

ML-25

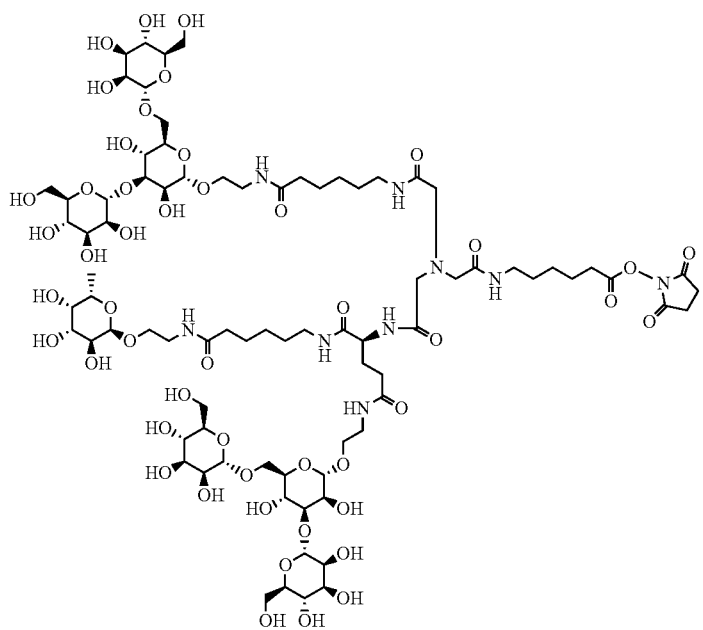

Step A. benzyl (S)-4{[(benzyloxy)carbonyl]amino}-5-oxo-5-{[6-oxo-6-({2-[(α-L-fucopyranosyl)oxy]ethyl}amino)hexyl]amino}pentanoate To a mixture of 6-amino-N-[2-[(α-L-fucopyranosyl)oxy]ethyl}hexanamide (518 mg, 1.62 mmol) and Z-L-glutamic acid γ-benzyl ester (500 mg, 1.35 mmol) in DMF (8 mL) was added EDC (645 mg, 3.37 mmol), HOBt (20 mg, 0.135 mmol) and TEA (0.019 mL, 0.135 mmol). The resulting mixture was stirred at rt for 16 hr and then evaporated. The residue was purified by silica gel column chromatography, eluting with gradient 0-60% AcCN in water, to give the title compound. UPLC-MS Method D: m/z=674 (z=1); $t_R$=5.11 min.

Step B. (S)-4-{[(benzyloxy)carbonyl]amino}-5-oxo-5-{[6-oxo-6-({2-[(α-L-fucopyranosyl)oxy]ethyl}amino)hexyl]amino}pentanoic acid To a solution of benzyl (S)-4-{[(benzyloxy)carbonyl]amino}-5-oxo-5-{[6-oxo-6-({2-[(α-L-fucopyranosyl)oxy]ethyl}amino)hexyl]amino}pentanoate (669 mg, 0.993 mmol) in a mixture of THF (5 mL), MeOH (2 mL) and water (2 mL) was added 1N NaOH soln (1.192 mL, 1.19 mmol). The reaction mixture was stirred at rt for 3 hr, and then the reaction was quenched by addition of HOAc (80 μL, 1.39 mmol). The resulting mixture was evaporated, and the residue was purified by C18 reverse phase silica gel chromatography with gradient 0-40% AcCN in water to isolate the title compound. UPLC-MS Method D: m/z=584 (z=1); $t_R$=3.32 min.

Step C. benzyl (S)-(1,5-dioxo-1-{[6-oxo-6-({2-[(α-L-fucopyranosyl)oxy]ethyl}amino)hexyl]amino}-5-{[2-({α-D-mannopyranosyl-(1→3)-[α-D-mannopyranosyl-(1→6)]-α-D-mannopyranosyl}oxy)ethyl]amino}pentan-2-yl)carbamate To a solution of (S)-4-{[(benzyloxy)carbonyl]amino}-5-oxo-5-{[6-oxo-6-({2-[(α-L-fucopyranosyl)oxy]ethyl}amino)hexyl]amino}pentanoic acid (415 mg, 0.71 mmol) and 2-({α-D-mannopyranosyl-(1→3)-[α-D-mannopyranosyl-(1→6)]-α-D-mannopyranosyl}oxy)ethan-1-amine (506 mg, 0.924 mmol) in DMF (5 mL) was added EDC (341 mg, 1.78 mmol) and DMAP (87 mg, 0.71 mmol). The resulting mixture was stirred at rt overnight, and then evaporated. The residue was purified by C18 reverse phase silica gel chromatography with gradient 0-40% AcCN in water to isolate the title compound. UPLC-MS Method D: m/z=1114 (z=1); $t_R$=2.61 min.

Step D. (S)-2-amino-$N^1$-[6-oxo-6-({2-[(α-L-fucopyranosyl)oxy]ethyl}amino)hexyl]-$N^5$-[2-({α-D-mannopyranosyl-(1→3)-[α-D-mannopyranosyl-(1→6)]-α-D-mannopyranosyl}oxy)ethyl]pentanediamide The title compounds was prepared using the procedure analogous to that described for ML-23 substituting benzyl (S)-(1,5-dioxo-1-{[6-oxo-6-({2-[(α-L-fucopyranosyl)oxy]ethyl}amino)hexyl]amino}-5-{[2-({α-D-mannopyranosyl-(1→3)-[α-D-mannopyranosyl-(1→6)]-α-D-mannopyranosyl}oxy)ethyl]amino}pentan-2-yl)carbamate for benzyl (6-oxo-6-{[2-({α-D-mannopyranosyl-(1→3)-[α-D-mannopyranosyl-(1→6)]-α-D-mannopyranosyl}oxy)ethyl]amino})hexyl)carbamate in Step B. UPLC-MS Method D: m/z=978 (z=1); $t_R$=1.25 min.

Step E. 2,5-dioxopyrrolidin-1-yl (S)-4,11,14,18-tetraoxo-16-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-12-(3-oxo-3-{[2-({α-D-mannopyranosyl-(1→3)-[α-D-mannopyranosyl-(1→6)]-α-D-mannopyranosyl}oxy)ethyl]amino}propyl)-1-[(α-L-fucopyranosyl)oxy]-3,10,13,16,19-pentaazapentacosan-25-oate The title compounds was prepared using the procedure analogous to those described for ML-23 substituting (S)-2-amino-N$^1$-[6-oxo-6-({2-[(α-L-fucopyranosyl)oxy]ethyl}amino)hexyl]-N$^5$-[2-({α-D-mannopyranosyl-(1→3)-[α-D-mannopyranosyl-(1→6)]-α-D-mannopyranosyl}oxy)ethyl]pentanediamide for (S)-2-(6-aminohexanamido)-N$^1$,N$^5$-bis{2-[(α-D-mannopyranosyl)oxy]ethyl}pentanediamide in Step H. UPLC-MS Method A: m/z=1003.28 (z=2); t$_R$=2.33 min.

Example 26

The synthesis of oligosaccharide linker 2,5-dioxopyrrolidin-1-yl (S)-4,11,14,18-tetraoxo-16-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-12-[3-oxo-3-({2-[(α-L-fucopyranosyl)oxy]ethyl}amino)propyl]-1-[(α-L-fucopyranosyl)oxy]-3,10,13,16,19-pentaazapentacosan-25-oate (ML-26) having the following structure is described.

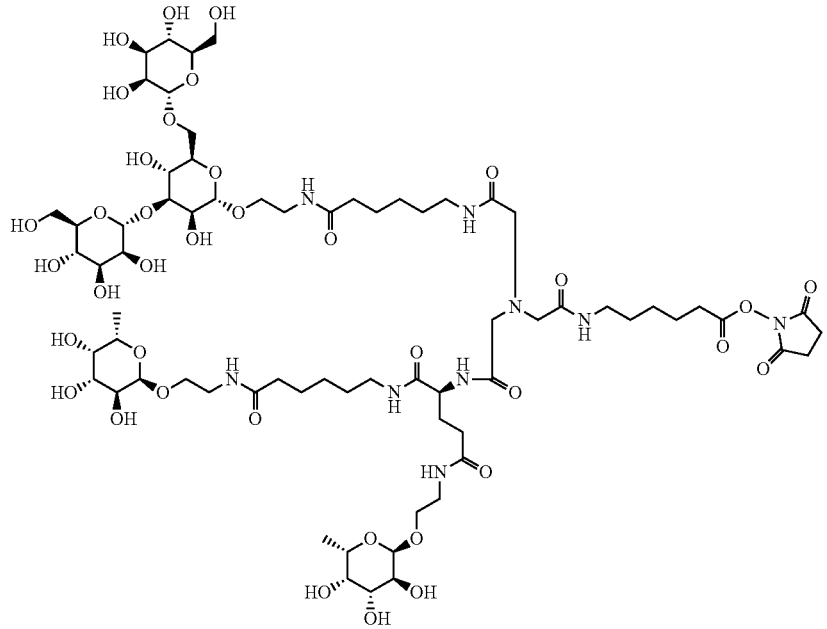

ML-26

The title compounds was prepared using the procedure analogous to those described for ML-25 substituting 2-aminoethyl α-L-fucopyranoside for 2-aminoethyl α-D-mannopyranosyl-(1→3)-[α-D-mannopyranosyl-(1→6)]-α-D-mannopyranoside in Step C. UPLC-MS Method A: m/z=1664.56 (z=2); t$_R$=2.39 min.

Example 27

The synthesis of oligosaccharide linker 2,5-dioxopyrrolidin-1-yl (S)-4,11,14,18-tetraoxo-16-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl -12-(3-oxo-3-{[2-({α-D-mannopyranosyl-(1→3)-[α-D-mannopyranosyl-(1→6)]-α-D-mannopyranosyl}oxy)ethyl]amino}propyl)-1-[(α-D-mannopyranosyl)oxy]-3,10,13,16,19-pentaazapentacosan-25-oate (ML-27) having the following structure is described.

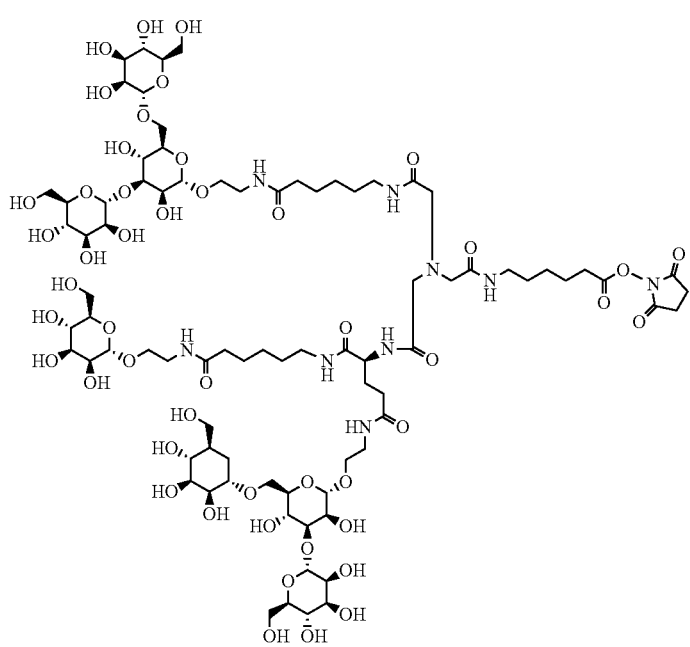

ML-27

The title compounds was prepared using the procedure analogous to those described for ML-25 substituting 6-amino-N-{2-[(α-D-mannopyranosyl)oxy]ethyl}hexanamide for 6-amino-N-{2-[(α-L-fucopyranosyl)oxy]ethyl}hexanamide in Step A. UPLC-MS Method A: m/z=1010.8 (z=2); $t_R$=2.27 min.

Example 28

The synthesis of oligosaccharide linker 2,5-dioxopyrrolidin-1-yl (S)-4,9,14,18-tetraoxo-16-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl -12-[(4-oxo-4-{[2-({α-D-mannopyranosyl-(1→3)-[α-D-mannopyranosyl-(1→6)]-α-D-mannopyranosyl}oxy)ethyl]amino}butyl)carbamoyl]-1-[(α-L-fucopyranosyl)oxy]-3,8,13,16,19-pentaazapentacosan-25-oate (ML-28) having the following structure is described.

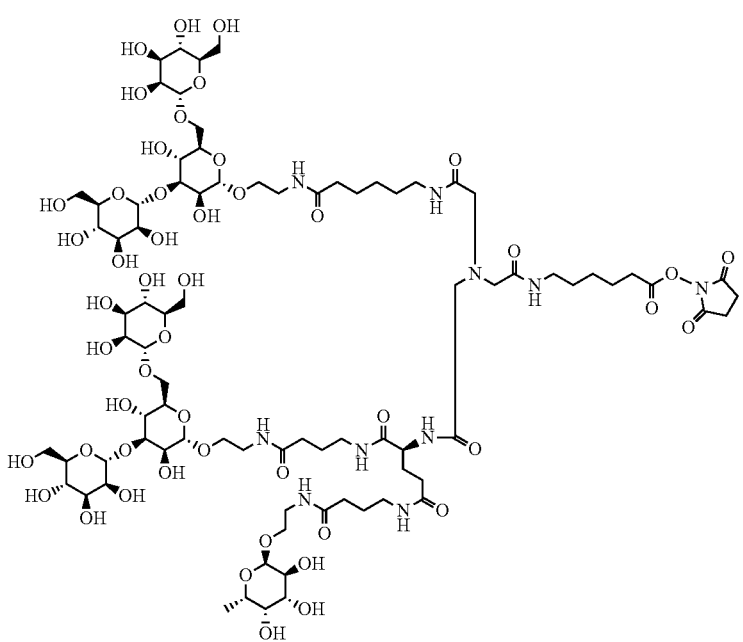

ML-28

Step A. benzyl (4-oxo-4-{[2-({α-D-mannopyrano-syl-(1→3)-[α-D-mannopyranosyl-(1→6)]-α-D-mannopyranosyl}oxy)ethyl]amino}butyl)carbamate The title compounds was prepared using the procedure analogous to that described for ML-23 substituting 2,5-dioxopyrrolidin-1-yl 4-{[(benzyloxy)carbonyl]amino}butanoate for 2,5-dioxopyrrolidin-1-yl 6-{[(benzyloxy)carbonyl]amino}hexanoate in Step A. UPLC-MS Method A: m/z=767.2 (z=1); $t_R$=2.74 min.

Step B. 4-amino-N-[2-({α-D-mannopyranosyl-(1→3)-[α-D-mannopyranosyl-(1→6)]-α-D-mannopyranosyl}oxy)ethyl]butanamide The title compounds was prepared using the procedure analogous to that described for ML-23 substituting benzyl (4-oxo-4-{[2-({α-D-mannopyranosyl-(1→3)-[α-D-mannopyranosyl-(1→6)]-α-D-mannopyranosyl}oxy)ethyl]amino}butyl)carbamate for benzyl (6-oxo-6-{[2-({α-D-mannopyranosyl-(1→3)-[α-D-mannopyranosyl-(1→6)]-α-D-mannopyranosyl}oxy)ethyl]amino})hexyl)carbamate in Step B. UPLC-MS Method A: m/z=633.2 (z=1); $t_R$=0.87 min.

Step C. benzyl [4-oxo-4-({2-[(α-L-fucopyranosyl)oxy]ethyl}amino)butyl]carbamate

The title compounds was prepared using the procedure analogous to that described for ML-23 substituting 2-aminoethyl α-L-fucopyranoside and 2,5-dioxopyrrolidin-1-yl 4-{[(benzyloxy)carbonyl]amino}butanoate for 2-({α-D-mannopyranosyl-(1→3)-[α-D-mannopyranosyl-(1→6)]-α-D-mannopyranosyl}oxy)ethan-1-amine and 2,5-dioxopyrrolidin-1-yl 6-{[(benzyloxy)carbonyl]amino}hexanoate, respectively, in Step A. UPLC-MS Method A: m/z=427.18 (z=1); $t_R$=3.29 min.

Step D. 4-amino-N-{2-[(α-L-fucopyranosyl)oxy]ethyl}butanamide

The title compounds was prepared using the procedure analogous to that described for ML-23 substituting benzyl [4-oxo-4-({2-[(α-L-fucopyranosyl)oxy]ethyl}amino)butyl]carbamate for benzyl (6-oxo-6-{[2-({α-D-mannopyranosyl-(1→3)-[α-D-mannopyranosyl-(1→6)]-α-D-mannopyranosyl}oxy)ethyl]amino})hexyl)carbamate in Step B. UPLC-MS Method A: m/z=583.32 (z=1); $t_R$=0.95 min.

Step E. 2,5-dioxopyrrolidin-1-yl (S)-4,9,14,18-tetraoxo-16-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-12-[(4-oxo-4-{[2-({α-D-mannopyranosyl-(1→3)-[α-D-mannopyranosyl-(1→6)]-α-D-mannopyranosyl}oxy)ethyl]amino}butyl)carbamoyl]-1-[(α-L-fucopyranosyl)oxy]-3,8,13,16,19-pentaazapentacosan-25-oate The title compounds was prepared using procedures analogous to those described for ML-25 substituting 4-amino-N-[2-({α-D-mannopyranosyl-(1→3)-[α-D-mannopyranosyl-(1→6)]-α-D-mannopyranosyl}oxy)ethyl]butanamide for 6-amino-N-{2-[(α-L-fucopyranosyl)oxy]ethyl}hexanamide in Step A, and 4-amino-N-{2-[(α-L-fucopyranosyl)oxy]ethyl}butanamide for 2-({α-D-mannopyranosyl-(1→3)-[α-D-mannopyranosyl-(1→6)]-α-D-mannopyranosyl}oxy)ethan-1-amine in Step C, respectively. UPLC-MS Method A: m/z=1031.37 (z=2); $t_R$=2.18 min.

Example 29

The synthesis of oligosaccharide linker 2,5-dioxopyrrolidin-1-yl (S)-4,9,14,18-tetraoxo-16-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-1-[(α-L-fucopyranosyl)oxy]-7-{[2-({α-D-mannopyranosyl-(1→3)-[α-D-mannopyranosyl-(1→6)]-α-D-mannopyranosyl}oxy)ethyl]carbamoyl}-3,8,13,16,19-pentaazapentacosan-25-oate (ML-29) having the following structure is described.

ML-29

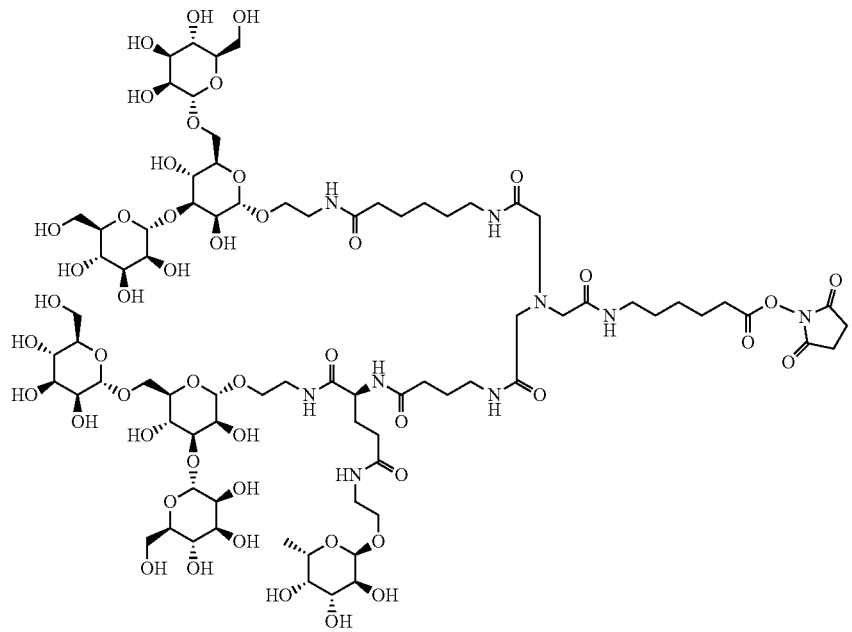

The title compounds was prepared using procedures analogous to those described for ML-25 substituting 2-({α-D-mannopyranosyl-(1→3)-[α-D-mannopyranosyl-(1→6)]-α-D-mannopyranosyl}oxy)ethan-1-amine for 6-amino-N-{2-[(α-L-fucopyranosyl)oxy]ethyl}hexanamide in Step A, and 2-aminoethyl α-L-fucopyranoside for 2-({α-D-mannopyranosyl-(1→3)-[α-D-mannopyranosyl-(1→6)]-α-D-mannopyranosyl}oxy)ethan-1-amine in Step C, respectively. UPLC-MS Method A: m/z=1010.89 (z=2); $t_R$=2.26 min.

Example 30

The synthesis of oligosaccharide linker 2,5-dioxopyrrolidin-1-yl (S)-4,9,14,18-tetraoxo-16-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-1-[(α-D-mannopyranosyl)oxy]-7-{[2-({α-D-mannopyranosyl-(1→3)-[α-D-mannopyranosyl-(1→6)]-α-D-mannopyranosyl}oxy)ethyl]carbamoyl}-3,8,13,16,19-pentaazapentacosan-25-oate (ML-30) having the following structure is described.

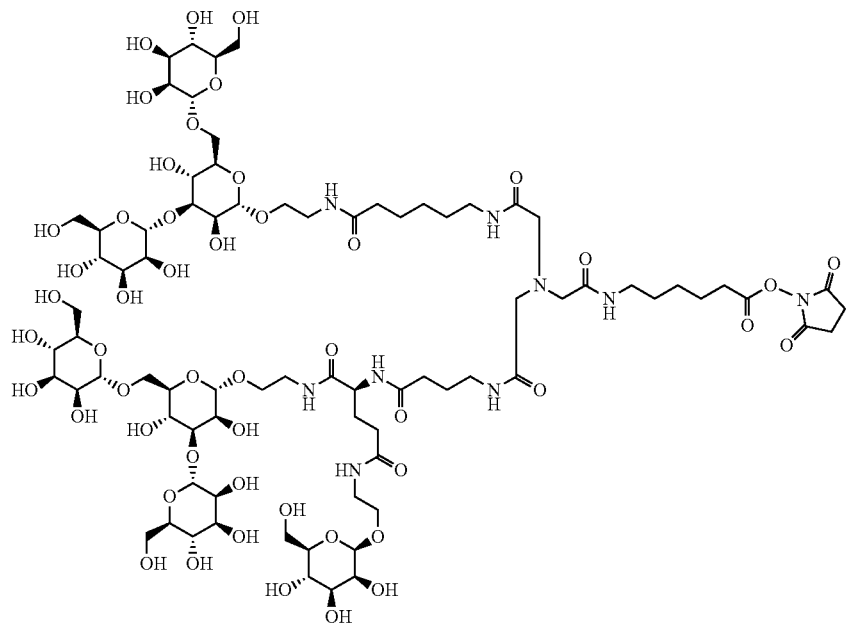

ML-30

The title compounds was prepared using procedures analogous to those described for ML-25 substituting 2-({α-D-mannopyranosyl-(1→3)-[α-D-mannopyranosyl-(1→6)]-α-D-mannopyranosyl}oxy)ethan-1-amine for 6-amino-N-{2-[(α-L-fucopyranosyl)oxy]ethyl}hexanamide in Step A, and 2-aminoethyl α-D-mannopyranoside for 2-({α-D-mannopyranosyl-(1→3)-[α-D-mannopyranosyl-(1→6)]-α-D-mannopyranosyl}oxy)ethan-1-amine in Step C, respectively. UPLC-MS Method A: m/z=1992.63 (z=1); $t_R$=2.29 min.

Example 31

The synthesis of oligosaccharide linker 2,5-dioxopyrrolidin-1-yl (S)-5,12,15,19-tetraoxo-17-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-13-(3-oxo-3-{[2-({α-D-mannopyranosyl-(1→3)-[α-D-mannopyranosyl-(1→6)]-α-D-mannopyranosyl}oxy)ethyl]amino}propyl)-1-[3-(α-D-mannopyranosyl)propyl]-4,11,14,17,20-pentaazahexacosan-26-oate (ML-31) having the following structure is described.

ML-31

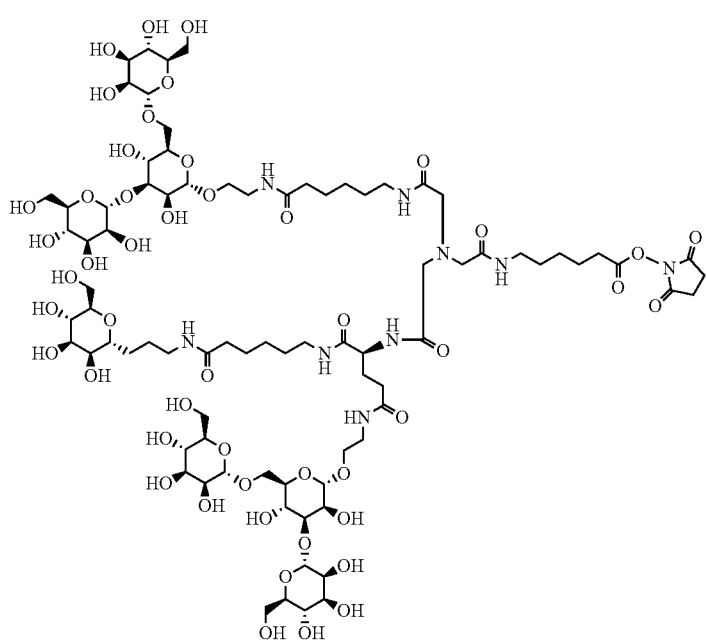

Step A. benzyl (6-{[3-(α-D-mannopyranosyl)propyl]amino}-6-oxohexyl)carbamate

The title compound was prepared using the procedure analogous to that described for ML-23 substituting 3-(α-D-mannopyranosyl)propan-1-amine for 2-({α-D-mannopyranosyl-(1→3)-[α-D-mannopyranosyl-(1→6)]-α-D-mannopyranosyl}oxy)ethan-1-amine in Step A. UPLC-MS Method D: m/z=469.29 (z=1); $t_R$=4.75 min.

Step B. 6-amino-N-[3-(α-D-mannopyranosyl)propyl]hexanamide

The title compound was prepared using the procedure analogous to that described for ML-23 substituting benzyl (6-{[3-(α-D-mannopyranosyl)propyl]amino}-6-oxohexyl)carbamate for benzyl (6-oxo-6-{[2-({α-D-mannopyranosyl-(1→3)-[α-D-mannopyranosyl-(1→6)]-α-D-mannopyranosyl}oxy)ethyl]amino})hexyl)carbamate in Step B. UPLC-MS Method D: m/z=335.26 (z=1); $t_R$=4.10 min.

Step C. 2,5-dioxopyrrolidin-1-yl (S)-5,12,15,19-tetraoxo-17-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-13-(3-oxo-3-{[2-({α-D-mannopyranosyl-(1→3)-[α-D-mannopyranosyl-(1→6)]-α-D-mannopyranosyl}oxy)ethyl]amino}propyl)-1-[3-(α-D-mannopyranosyl)propyl]-4,11,14,17,20-pentaazahexacosan-26-oate The title compounds was prepared using procedures analogous to those described for ML-25 substituting 6-amino-N-[3-(α-D-mannopyranosyl)propyl]hexanamide for 6-amino-N-{2-[(α-L-fucopyranosyl)oxy]ethyl}hexanamide in Step A. UPLC-MS Method D: m/z=1009.95 (z=2); $t_R$=3.91 min.

Example 32

The synthesis of oligosaccharide linker 2,5-dioxopyrrolidin-1-yl (S)-4,11,16,23,27-pentaoxo-25-(2-oxo-2-{[3-({α-D-mannopyranosyl-(1→3)-[α-D-mannopyranosyl-(1→6)]-α-D-mannopyranosyl}oxy)propyl]amino}ethyl)-14-[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl]-1-({α-D-mannopyranosyl-(1→3)-[α-D-mannopyranosyl-(1→6)]-α-D-mannopyranosyl}oxy)-3,10,15,22,25,28-hexaazatetratriacontan-34-oate (ML-32) having the following structure is described.

ML-32

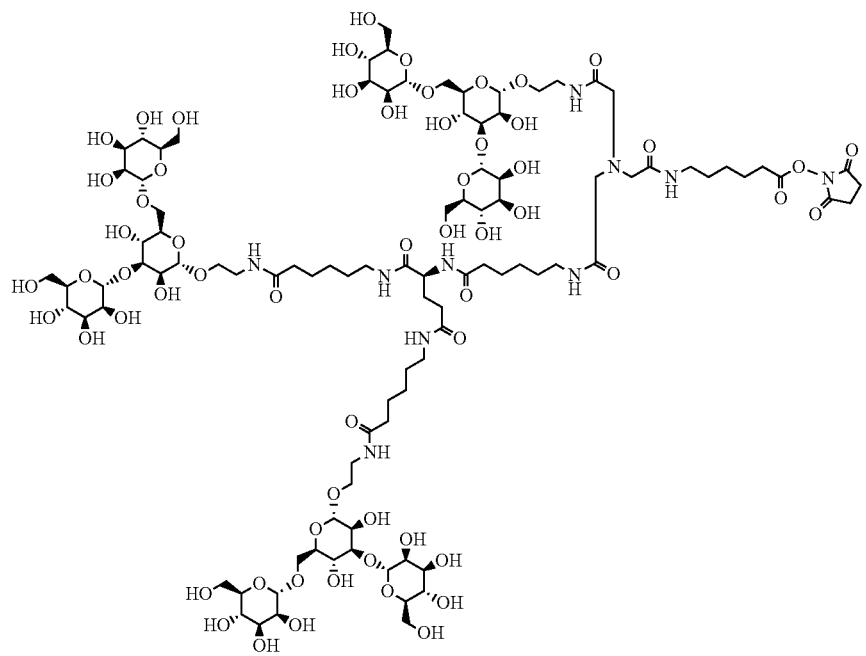

The title compounds was prepared using procedures analogous to those described for ML-23 substituting 2-({α-D-mannopyranosyl-(1→3)-[α-D-mannopyranosyl-(1→6)]-α-D-mannopyranosyl}oxy)ethan-1-amine for 6-amino-N-[2-({α-D-mannopyranosyl-(1→3)-[α-D-mannopyranosyl-(1→6)]-α-D-mannopyranosyl}oxy)ethyl]hexanamide in Step C, and 6-amino-N-[2-({α-D-mannopyranosyl-(1→3)-[α-D-mannopyranosyl-(1→6)]-α-D-mannopyranosyl}oxy) ethyl]hexanamide for 2-aminoethyl α-D-mannopyranoside in Step D, respectively. UPLC-MS Method D: m/e=1230.03 (z=2); $t_R$=4.20 min.

Example 33

The synthesis of oligosaccharide linker 2,5-dioxopyrrolidin-1-yl (S)-4,11,16,23,27,34-hexaoxo-25-(2-oxo-2-{[2-({α-D-mannopyranosyl-(1→3)-[α-D-mannopyranosyl-(1→6)]-α-D-mannopyranosyl}oxy)ethyl]amino}ethyl)-14-[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl]-1-({α-D-mannopyranosyl-(1→3)-[α-D-mannopyranosyl-(1→6)]-α-D-mannopyranosyl}oxy)-3,10,15,22,25,28,35-heptaazahentetracontan-41-oate (ML-33) having the following structure is described.

ML-33

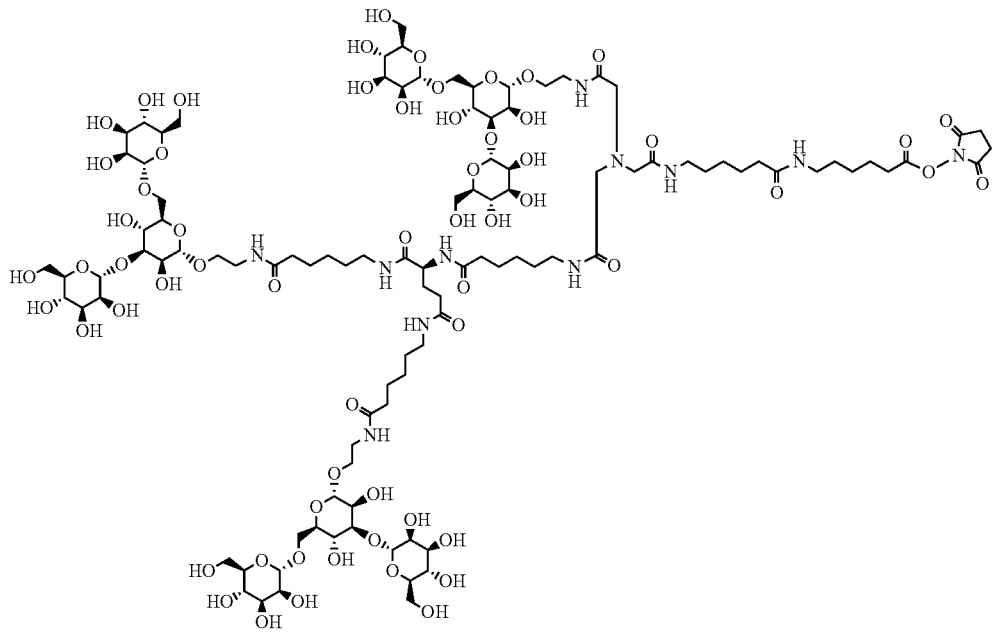

Step A. benzyl (S)-4,11,16,23,27,34-hexaoxo-25-(2-oxo-2-{[2-({α-D-mannopyranosyl-(1→3)-[α-D-mannopyranosyl-(1→6)]-α-D-mannopyranosyl}oxy)ethyl]amino}ethyl)-14-[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl]-1-({α-D-mannopyranosyl-(1→3)-[α-D-mannopyranosyl-(1→6)]-α-D-mannopyranosyl}oxy)-3,10,15,22,25,28,35-heptaazahentetracontan-41-oate To a solution of ML-32 (110 mg, 0.045 mmol) and benzyl 6-aminohexanoate 4-methylbenzenesulfonate (25 mg, 0.063 mmol) in DMF (2 mL) at rt was added DIPEA (19 µL, 0.107 mmol). After stirring for 2 hours, the reaction was quenched by addition of TFA (8.6 µL, 0.112 mmol). After 190 min, the mixture was added dropwise to AcCN (40 mL), and the resulting mixture spun in a centrifuge at 3500 rpm for 15 mins. The supernatent was decanted, and the solid pellet was re-suspended in AcCN (40 mL) and spun in a centrifuge at 3500 rpm for 15 min. Supernatant was decanted, and the residue was dissolved in H$_2$O (4 mL), to which 10% palladium on carbon (4 mg) was added. The mixture was stirred under a balloon of H$_2$ for 1 hr. The catalyst was filtered off through a cake of CELITE, and the filtrate was freeze-dried to give the title compound. UPLC-MS Method D: m/z=1238.11 (z=2); t$_R$=3.39 min.

Step B. 2,5-dioxopyrrolidin-1-yl (S)-4,11,16,23,27,34-hexaoxo-25-(2-oxo-2-{[2-({α-D-mannopyranosyl-(1→3)-[α-D-mannopyranosyl-(1→6)]-α-D-mannopyranosyl}oxy)ethyl]amino}ethyl)-14-[(6oxo-6-{[2-({α-D-mannopyranosyl-(1→3)-[α-D-mannopyranosyl-(1→6)]-α-D-mannopyranosyl}oxy)ethyl]amino}hexyl)carbamoyl]-1-({α-D-mannopyranosyl-(1→3)-[α-D-mannopyranosyl-(1→6)]-α-D-mannopyranosyl}oxy)-3,10,15,22,25,28,35-heptaazahentetracontan-41-oate The title compounds was prepared using procedures analogous to those described for ML-1 substituting benzyl (S)-4,11,16,23,27,34-hexaoxo-25-(2-oxo-2-{[2-({α-D-mannopyranosyl-(1→3)-[α-D-mannopyranosyl-(1→6)]-α-D-mannopyranosyl}oxy)ethyl]amino}ethyl)-14-[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl]-1-({α-D-mannopyranosyl-(1→3)-[α-D-mannopyranosyl-(1→6)]-α-D-mannopyranosyl}oxy)-3,10,15,22,25,28,35-heptaazahentetracontan-41-oate for benzyl 4-[(4,14-dioxo-9-{[3-oxo-3-({2-[(α-D-mannopyranosyl)oxy]ethyl}amino)propoxy]methyl}-1,17-di[(α-D-mannopyranosyl)oxy]-7,11-dioxa-3,15-diazaheptadecan-9-yl)amino]-4-oxobutanoate in Step D. UPLC-MS Method D: m/z=1286.65 (z=2); t$_R$=3.40 min.

Example 34

The synthesis of oligosaccharide linker 2,5-dioxopyrrolidin-1-yl 4,11,15-trioxo-13-(2-oxo-2-{[6-({2-[(α-D-mannopyranosyl)oxy]ethyl}[2-({α-D-mannopyranosyl-(1→3)-[α-D-mannopyranosyl-(1→6)]-α-D-mannopyranosyl}oxy)ethyl]amino)hexyl]amino}ethyl)-1-({α-D-mannopyranosyl-(1→3)-[α-D-mannopyranosyl-(1→6)]-α-D-mannopyranosyl}oxy)-3, 10,13,16-tetraazadocosan-22-oate (ML-34) having the following structure is described.

ML-34

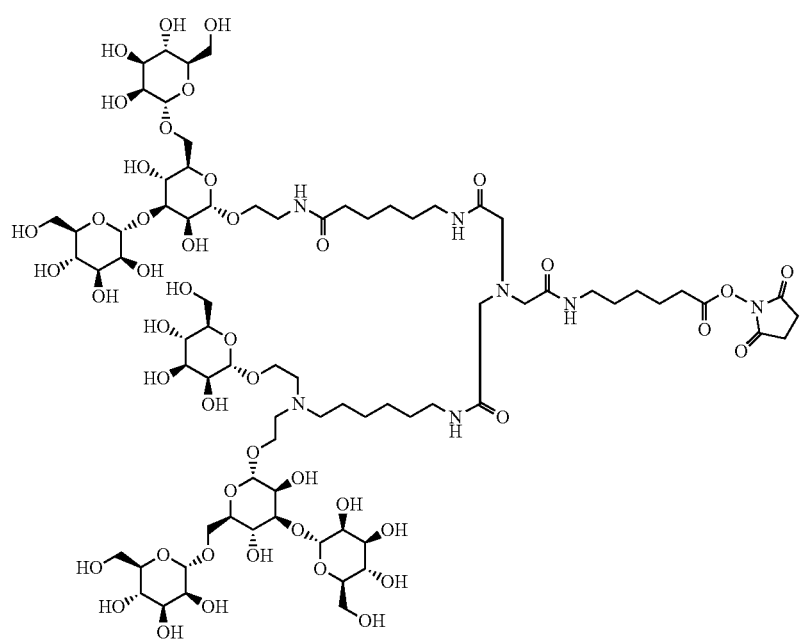

Step A. perbenzoylated 2-aminoethyl α-D-mannopyranosyl-(1→3)-[α-D-mannopyranosyl-(1→6)]-α-D-mannopyranoside To a nitrogen flushed solution of perbenzoylated-man(α-1,3)-man(α-1,6)-a-1-azidoethylmannopyranoside (25 g, 15.5 mmol, U.S. Pat. No. 9,050,370 B2) in EtOAc (300 mL) was added 10% Pd/C (1.65 g). The resulting mixture was stirred at rt under a balloon of $H_2$ overnight. The catalyst was filtered off through a CELITE pad, and the filtrate was concentrated. The residue was purified by silica gel column chromatography (Teledyne Isco: Gold SNAP 330 g) eluent: gradient 2-5% MeOH in DCM over 8 CV to give the title compound. UPLC-MS Method B: m/z=1588.64 (z=1); $t_R$=4.06 min.

Step B. benzyl (6-{[2-({(2,3,4,6-tetra-O-benzoyl-α-D-mannopyranosyl)-(1→3)-[2,3,4,6-tetra-O-benzoyl-α-D-mannopyranosyl-(1→6)]-4-O-benzoyl-α-D-mannopyranosyl}oxy)ethyl]amino}hexyl)carbamate To a solution of perbenzoylated 2-aminoethyl α-D-mannopyranosyl-(1→3)-[α-D-mannopyranosyl-(1→6)]-α-D-mannopyranoside (15.9 g, 10.03 mmol) and benzyl (6-oxohexyl) carbamate (1 g, 4.01 mmol) in DCM (150 mL) was added HOAc (230 µL, 4.01 mmol) and sodium triacetoxyborohydride (2.12 g, 10.03 mmol). The resulting mixture was stirred at rt overnight. The reaction mixture was concentrated, and the residue was re-dissolved in EtOAc (300 mL) and washed with sat'd $NaHCO_3$ (2×300 mL) and brine (200 mL). The organic layer was dried over $Na_2SO_4$, filtered, and evaporated. The residue was purified by silica gel column chromatography (Teledyne Isco: 2×SNAP Gold 330 g) eluent: gradient 2-5% MeOH in DCM over 8 CV to give the title compound. UPLC-MS Method B: m/z=1822.79 (z=1); $t_R$=4.48 min.

Step C. benzyl (6-{(2-[(2,3,4,6-tetra-O-acetyl-α-D-mannopyranosyl)oxy]ethyl)[2-({(2,3,4,6-tetra-O-benzoyl-α-D-mannopyranosyl)-(1→3)-[2,3,4,6-tetra-O-benzoyl-α-D-mannopyranosyl-(1→6)]-4-O-benzoyl-α-D-mannopyranosyl}oxy)ethyl]amino}hexyl)carbamate A solution of benzyl (6-{[2-({(2,3,4,6-tetra-O-benzoyl-α-D-mannopyranosyl)-(1→3)-[2,3,4,6-tetra-O-benzoyl-α-D-mannopyranosyl-(1→6)]-4-O-benzoyl-α-D-mannopyranosyl}oxy)ethyl]amino}hexyl)carbamate (2 g, 1.1 mmol) and 2-oxoethyl 2,3,4,6-tetra-O-acetyl-α-D-mannopyranoside (1.29 g, 3.3 mmol, WO 2015051052 A2) in DCM (15 mL) at rt was added acetic acid (63 µL, 1.1 mmol). After stirring for 10 min, to the resulting mixture was added sodium triacetoxyborohydride (465 mg, 2.2 mmol). After stirring overnight, the mixture was concentrated, and the residue was taken up in EtOAc (100 mL), washed with sat'd $NaHCO_3$ (100 mL), brine (50 mL), dried over $Na_2SO_4$, and concentrated. The residue was purified by silica gel column chromatography (Teledyne Isco: SNAP 80 g GOLD) eluent: gradient 30-100% EtOAc in Hexanes to give the title compound.

Step D. benzyl (6-{(2-[(α-D-mannopyranosyl)oxy]ethyl)[2-({α-D-mannopyranosyl-(1→3)-[α-D-mannopyranosyl-(1→6)]-α-D-mannopyranosyl}oxy)ethyl]amino}hexyl)carbamate To a solution of benzyl (6-{(2-[(2,3,4,6-tetra-O-acetyl-α-D-mannopyranosyl)oxy]ethyl)[2-({(2,3,4,6-tetra-O-benzoyl-α-D-mannopyranosyl)-(1→3)-[2,3,4,6-tetra-O-benzoyl-α-D-mannopyranosyl-(1→6)]-4-O-benzoyl-α-D-mannopyranosyl}oxy)ethyl]amino}hexyl)carbamate (2.4 g, 1.09 mmol) in a mixture of DCM (15 mL) and MeOH (15 mL) was added sodium methoxide (2.7 mL of a 0.5M soln in MeOH, 1.34 mmol). The resulting mixture was stirred at rt over the weekend, while a white precipitate formed. The mixture was concentrated to ~4 mL and added dropwise to stirred AcCN (80 mL) to form a white precipitate. The suspension was centrifuged at 3500 rpm for 15 min. The supernatant was removed and the white pellet was re-suspended in AcCN (80 mL) and centrifuged at 3500 rpm for a further 15 min. The supernatant was decanted, and the remaining solid was dried to give the title compound. UPLC-MS Method D: m/z=987.55 (z=1); $t_R$=3.27 min.

Step E. $N^1$-(2-[(α-D-mannopyranosyl)oxy]ethyl)-$N^1$-(2-({α-D-mannopyranosyl-(1→3)-[α-D-mannopyranosyl-(1→6)]-α-D-mannopyranosyl}oxy)ethyl) hexane-1,6-diamine To a solution of benzyl (6-{(2-[(α-D-mannopyranosyl)oxy]ethyl)[2-({α-D-mannopyranosyl-(1→3)-[α-D-mannopyranosyl-(1→6)]-α-D-mannopyranosyl}oxy)ethyl]amino}hexyl)carbamate (1.05 g, 1.06 mmol) in water (15 mL) was added 10% Pd/C (113 mg). The resulting mixture was stirred under a balloon of $H_2$ for 2 hrs. The catalyst was filtered off through a pack of CELITE, and 5M HCl (638 µL, 3.19 mmol) was added to the filtrate followed by 10% Pd/C (113 mg). The resulting mixture was stirred under a balloon of $H_2$ for 2 hrs. The mixture was filtered through a pack of CELITE, and the filtrate was freeze-dried give the title compound. UPLC-MS Method D: m/z=853.49 (z=1); $t_R$=1.00 min.

Step F. 2,5-dioxopyrrolidin-1-yl 4,11,15-trioxo-13-(2-oxo-2-{[6-({2-[(α-D-mannopyranosyl)oxy]ethyl}[2-({α-D-mannopyranosyl-(1→3)-[α-D-mannopyranosyl-(1→6)]-α-D-mannopyranosyl}oxy)ethyl]amino)hexyl]amino}ethyl)-1-({α-D-mannopyranosyl-(1→3)-[α-D-mannopyranosyl-(1→6)]-α-D-mannopyranosyl}oxy)-3,10,13,16-tetraazadocosan-22-oate The title compounds was prepared using procedures analogous to those described for ML-23 substituting $N^1$-(2-[(α-D-mannopyranosyl)oxy]ethyl)-$N^1$-(2-({α-D-mannopyranosyl-(1→3)-[α-D-mannopyranosyl-(1→6)]-α-D-mannopyranosyl}oxy)ethyl)hexane-1,6-diamine for (S)-2-(6-aminohexanamido)-$N^1$,$N^5$-bis{2-[(α-D-mannopyranosyl)oxy]ethyl}pentanediamide in Step H. UPLC-MS Method D: m/z=1879.94 (z=1); $t_R$=4.19 min.

Example 35

The synthesis of oligosaccharide linker 2,5-dioxopyrrolidin-1-yl 4,11,15-trioxo-13-(2-oxo-2-{[6-({2-[(β-D-mannopyranosyl)oxy]ethyl}[2-({α-D-mannopyranosyl-(1→3)-[α-D-mannopyranosyl-(1→6)]-α-D-mannopyranosyl}oxy)ethyl]amino)hexyl]amino}ethyl)-1-({α-D-mannopyranosyl-(1→3)-[α-D-mannopyranosyl-(1→6)]-α-D-mannopyranosyl}oxy)-3,10,13,16-tetraazadocosan-22-oate (ML-35) having the following structure is described.

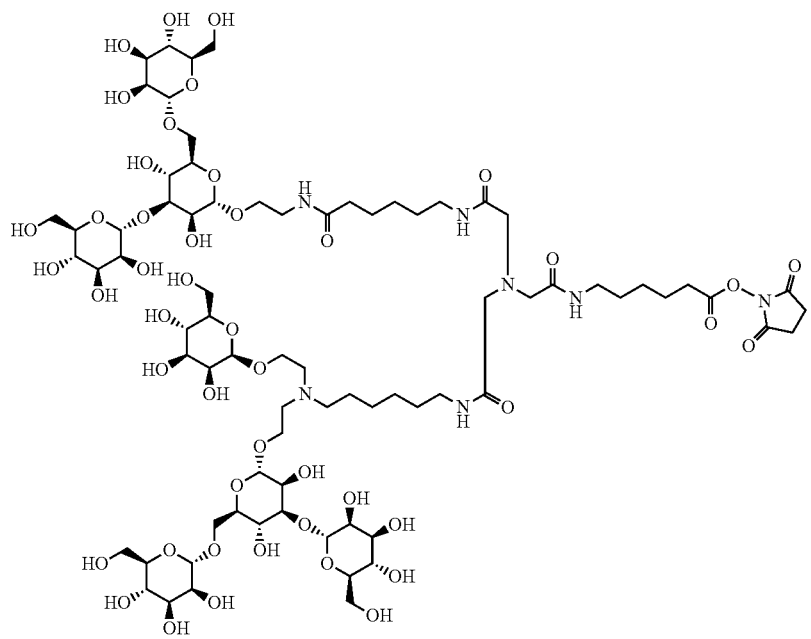

ML-35

The title compounds was prepared using procedures analogous to those described for ML-34 substituting 2-oxoethyl 2,3,4,6-tetra-O-acetyl-β-D-mannopyranoside for 2-oxoethyl 2,3,4,6-tetra-O-acetyl-α-D-mannopyranoside in Step C. UPLC-MS Method D: m/z=1880.06 (z=1); $t_R$=4.29 min.

Example 36

The synthesis of oligosaccharide linker 2,5-dioxopyrrolidin-1-yl 4,11,15-trioxo-13-(2-oxo-2-{[6-({2-[(α-L-fucopyranosyl)oxy]ethyl}[2-({α-D-mannopyranosyl-(1→3)-[α-D-mannopyranosyl-(1→6)]-α-D-mannopyranosyl}oxy)ethyl]amino)hexyl]amino}ethyl)-1-({α-D-mannopyranosyl-(1→3)-[α-D-mannopyranosyl-(1→6)]-α-D-mannopyranosyl}oxy)-3,10,13,16-tetraazadocosan-22-oate (ML-36) having the following structure is described.

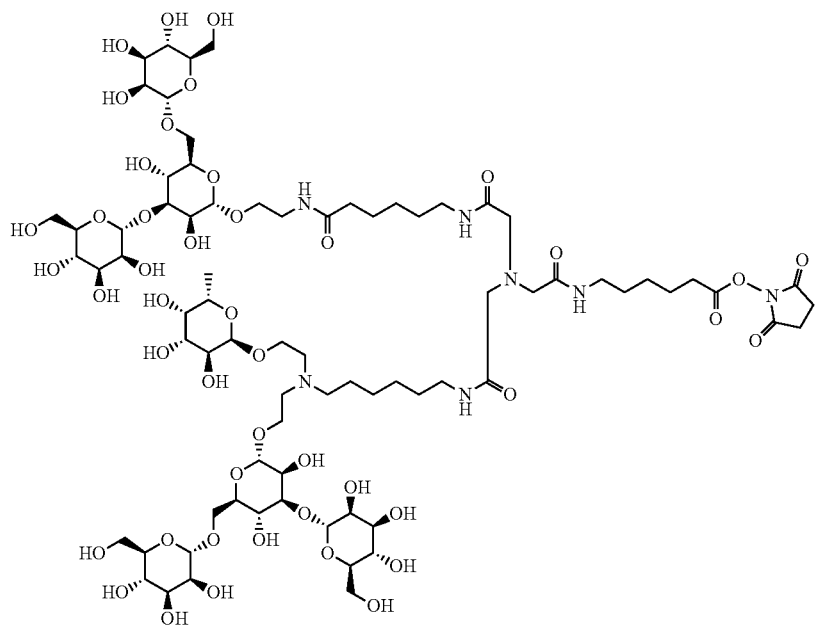

ML-36

The title compounds was prepared using procedures analogous to those described for ML-34 substituting 2-oxoethyl 2,3,4-tri-O-acetyl-α-L-fucopyranoside for 2-oxoethyl 2,3,4,6-tetra-O-acetyl-α-D-mannopyranoside in Step C. UPLC-MS Method D: m/z=1864.01 (z=1); $t_R$=4.21 min.

Example 37

The synthesis of oligosaccharide linker 2,5-dioxopyrrolidin-1-yl 4,11,15-trioxo-13-(2-oxo-2-{[6-({2-[(β-L-fucopyranosyl)oxy]ethyl}[2-({α-D-mannopyranosyl-(1→3)-[α-D-mannopyranosyl-(1→6)]-α-D-mannopyranosyl}oxy)ethyl]amino)hexyl]amino}ethyl)-1-({α-D-mannopyranosyl-(1→3)-[α-D-mannopyranosyl-(1→6)]-α-D-mannopyranosyl}oxy)-3,10,13,16-tetraazadocosan-22-oate (ML-37) having the following structure is described.

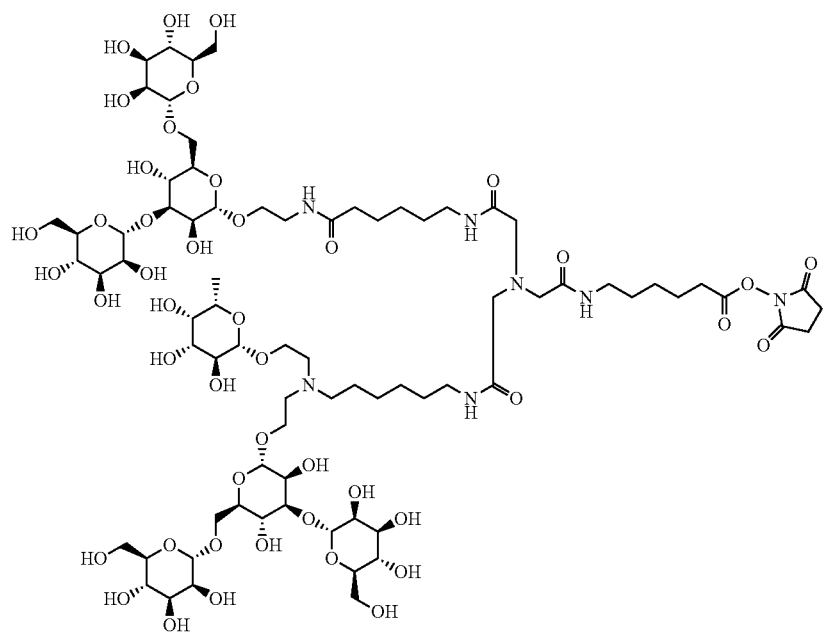

ML-37

The title compounds was prepared using procedures analogous to those described for ML-34 substituting 2-oxoethyl 2,3,4-tri-O-acetyl-β-L-fucopyranoside for 2-oxoethyl 2,3,4,6-tetra-O-acetyl-α-D-mannopyranoside in Step C. UPLC-MS Method D: m/z=1864.06 (z=1); $t_R$=3.93 min.

Example 38

The synthesis of oligosaccharide linker 2,5-dioxopyrrolidin-1-yl 4,11,15-trioxo-13-(2-oxo-2-{[6-({2-[(β-D-glucopyranosyl)oxy]ethyl}[2-({α-D-mannopyranosyl-(1→3)-[α-D-mannopyranosyl-(1→6)]-α-D-mannopyranosyl}oxy)ethyl]amino)hexyl]amino}ethyl)-1-({α-D-mannopyranosyl-(1→3)-[α-D-mannopyranosyl-(1→6)]-α-D-mannopyranosyl}oxy)-3,10,13,16-tetraazadocosan-22-oate (ML-38) having the following structure is described.

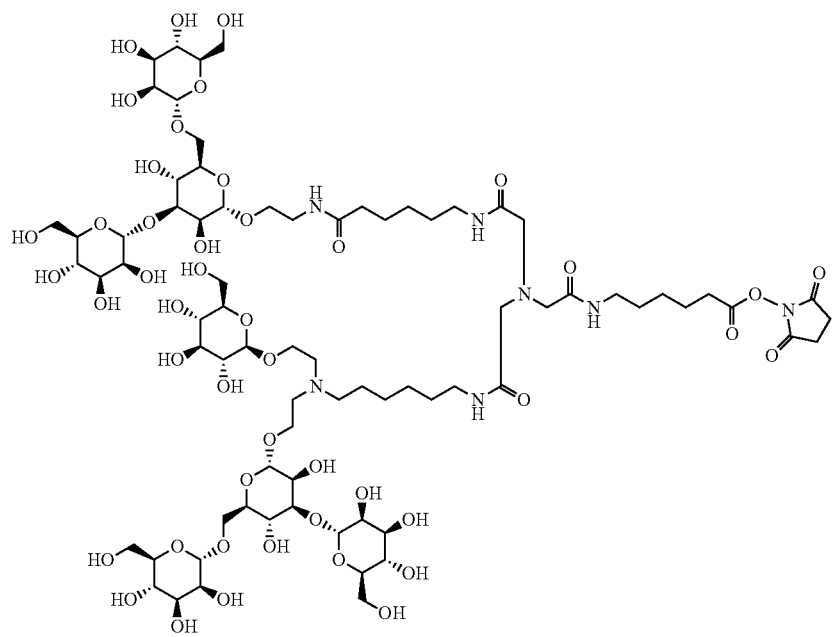

ML-38

The title compounds was prepared using procedures analogous to those described for ML-34 substituting 2-oxoethyl 2,3,4,6-tetra-O-acetyl-β-D-glucopyranoside for 2-oxoethyl 2,3,4,6-tetra-O-acetyl-α-D-mannopyranoside in Step C. UPLC-MS Method D: m/z=1878.92 (z=1); $t_R$=4.07 min.

Example 39

The synthesis of oligosaccharide linker 2,5-dioxopyrrolidin-1-yl 4,11,15-tri oxo-13-(2-oxo-2-{[6-({2-[(β-D-mannopyranosyl)oxy]ethyl}[2-({α-D-mannopyranosyl-(1→3)-[α-D-mannopyranosyl-(1→6)]-α-D-mannopyranosyl}oxy)ethyl]amino)hexyl]amino}ethyl)-1-({α-D-mannopyranosyl-(1→3)-[α-D-mannopyranosyl-(1→6)]-β-D-mannopyranosyl}oxy)-3,10,13,16-tetraazadocosan-22-oate (ML-39) having the following structure is described.

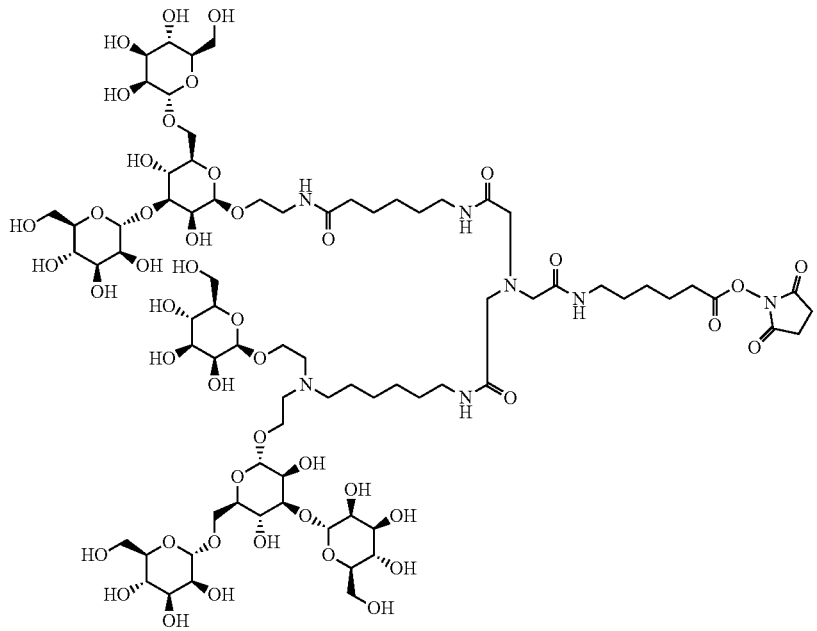

ML-39

The title compounds was prepared using procedures analogous to those described for ML-23 substituting 2-({α-D-mannopyranosyl-(1→3)-[α-D-mannopyranosyl-(1→6)]-β-D-mannopyranosyl}oxy)ethan-1-amine for 2-({α-D-mannopyranosyl-(1→3)-[α-D-mannopyranosyl-(1→6)]-α-D-mannopyranosyl}oxy)ethan-1-amine in Step A, and substituting $N^1$-(2-[(β-D-mannopyranosyl)oxy]ethyl)-$N^1$-(2-({α-D-mannopyranosyl-(1→3)-[α-D-mannopyranosyl-(1→6)]-α-D-mannopyranosyl}oxy)ethyl)hexane-1,6-diamine for (S)-2-(6-aminohexanamido)-$N^1$,$N^5$-bis{2-[(α-D-mannopyranosyl)oxy]ethyl}pentanediamide in Step H, respectively. UPLC-MS Method D: m/z=1879.91 (z=1); $t_R$=3.95 min.

Example 40

The synthesis of oligosaccharide linker 2,5-dioxopyrrolidin-1-yl 4,11,15-trioxo-13-(2-oxo-2-{[6-({2-[(β-L-fucopyranosyl)oxy]ethyl [2-({α-D-mannopyranosyl-(1→3)-[α-D-mannopyranosyl-(1→6)]-α-D-mannopyranosyl}oxy)ethyl]amino)hexyl]amino}ethyl)-1-({α-D-mannopyranosyl-(1→3)-[α-D-mannopyranosyl-(1→6)]-β-D-mannopyranosyl}oxy)-3,10,13,16-tetraazadocosan-22-oate (ML-40) having the following structure is described.

ML-40

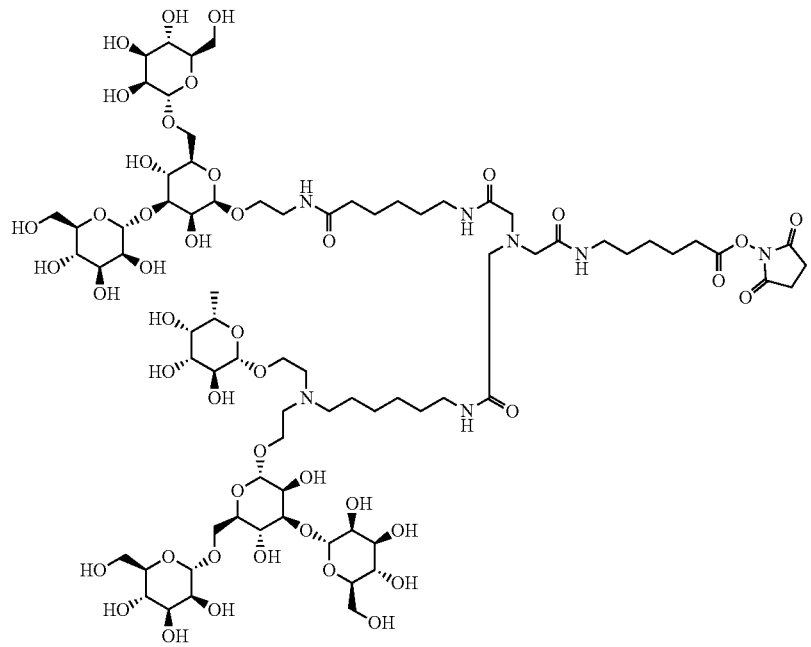

The title compounds was prepared using procedures analogous to those described for ML-23 substituting 2-({α-D-mannopyranosyl-(1→3)-[α-D-mannopyranosyl-(1→6)]-β-D-mannopyranosyl}oxy)ethan-1-amine for 2-({α-D-mannopyranosyl-(1→3)-[α-D-mannopyranosyl-(1→6)]-α-D-mannopyranosyl}oxy)ethan-1-amine in Step A, and substituting $N^1$-(2-[(β-L-fucopyranosyl)oxy]ethyl)40-(2-({α-D-mannopyranosyl-(1→3)-[α-D-mannopyranosyl-(1→6)]-α-D-mannopyranosyl}oxy)ethyl)hexane-1,6-diamine for (S)-2-(6-aminohexanamido)-$N^1$,$N^5$-bis{2-[(α-D-mannopyranosyl)oxy]ethyl}pentanediamide in Step H, respectively. UPLC-MS Method D: m/z=1864.02 (z=1); $t_R$=3.64 min.

Example 41

The synthesis of oligosaccharide linker 2,5-dioxopyrrolidin-1-yl 4,11,15-trioxo-13-(2-oxo-2-{[6-({2-[(α-D-mannopyranosyl)oxy]ethyl}[2-({α-D-mannopyranosyl-(1→3)-[α-D-mannopyranosyl-(1→6)]-α-D-mannopyranosyl}oxy)ethyl]amino)hexyl]amino}ethyl)-1-({α-D-mannopyranosyl-(1→3)-[α-D-mannopyranosyl-(1→6)]-β-D-mannopyranosyl}oxy)-3,10,13,16-tetraazadocosan-22-oate (ML-41) having the following structure is described.

ML-41

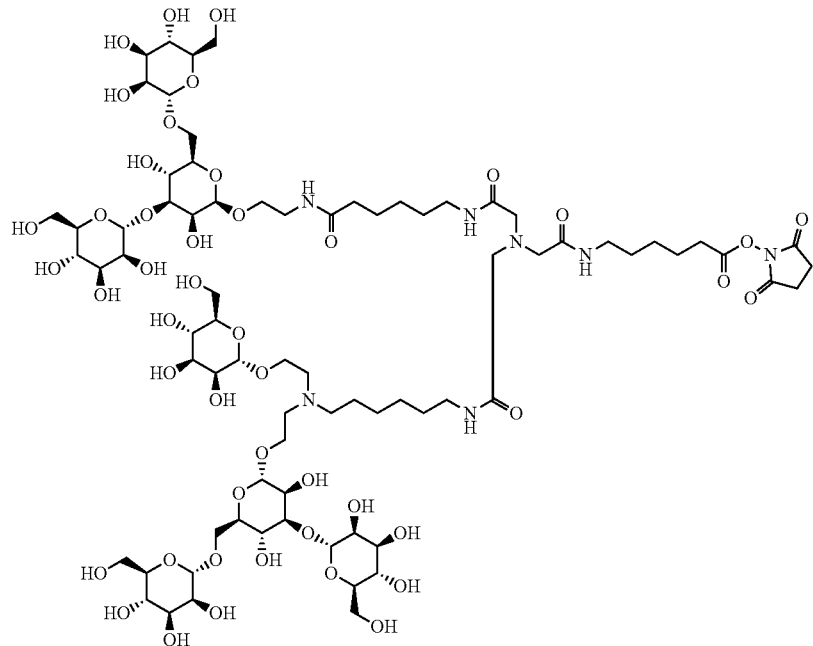

The title compounds was prepared using procedures analogous to those described for ML-23 substituting 2-({α-D-mannopyranosyl-(1→3)-[α-D-mannopyranosyl-(1→6)]-β-D-mannopyranosyl}oxy)ethan-1-amine (WO 2015051052 A2) for 2-({α-D-mannopyranosyl-(1→3)-[α-D-mannopyranosyl-(1→6)]-α-D-mannopyranosyl}oxy)ethan-1-amine in Step A, and substituting $N^1$-(2-[(α-D-mannopyranosyl)oxy]ethyl)40-(2-({α-D-mannopyranosyl-(1→3)-[α-D-mannopyranosyl-(1→6)]-α-D-mannopyranosyl}oxy)ethyl)hexane-1,6-diamine for (S)-2-(6-aminohexanamido)-$N^1$,$N^5$-bis{2-[(α-D-mannopyranosyl)oxy]ethyl}pentanediamide in Step H, respectively. UPLC-MS Method A: m/z=1879.86 (z=1); $t_R$=1.72 min.

Example 42

The synthesis of oligosaccharide linker 2,5-dioxopyrrolidin-1-yl 11,15-dioxo-13-(2-oxo-2-{[2-({α-D-mannopyranosyl-(1→3)-[α-D-mannopyranosyl-(1→6)]-α-D-mannopyranosyl}oxy)ethyl]amino}ethyl)-1-[(α-D-mannopyranosyl)oxy]-3-[2-(α-D-mannopyranosyl-(1→3)-[α-D-mannopyranosyl-(1→6)]-α-D-mannopyranosyl}oxy)ethyl]-3,10,13,16-tetraazadocosan-22-oate (ML-42) having the following structure is described.

ML-42

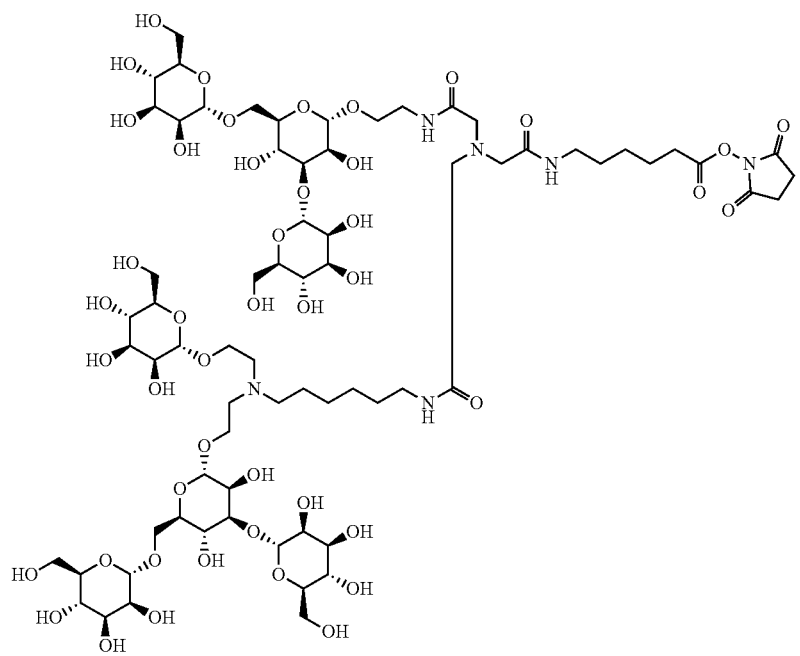

The title compounds was prepared using procedures analogous to those described for ML-23 substituting 2-aminoethyl α-D-mannopyranosyl-(1→3)-[α-D-mannopyranosyl-(1→6)]-α-D-mannopyranoside for 6-amino-N-[2-({α-D-mannopyranosyl-(1→3)-[α-D-mannopyranosyl-(1→6)]-α-D-mannopyranosyl}oxy)ethyl]hexanamide in Step C, and substituting $N^1$-(2-[(α-D-mannopyranosyl)oxy]ethyl)-$N^1$-(2-({α-D-mannopyranosyl-(1→3)-[α-D-mannopyranosyl-(1→6)]-α-D-mannopyranosyl}oxy)ethyl)hexane-1,6-diamine for (S)-2-(6-aminohexanamido)-$N^1$,$N^5$-bis{2-[(α-D-mannopyranosyl)oxy]ethyl}pentanediamide in Step H, respectively. UPLC-MS Method A: m/z=1766.32 (z=1); $t_R$=1.55 min.

Example 43

The synthesis of oligosaccharide linker 2,5-dioxopyrrolidin-1-yl 11,15-dioxo-13-(2-oxo-2-{[2-({α-D-mannopyranosyl-(1→3)-[α-D-mannopyranosyl-(1→6)]-α-D-mannopyranosyl}oxy)ethyl]amino}ethyl)-1-[(α-D-mannopyranosyl)oxy]-3-[2-(α-D-mannopyranosyl-(1→3)-[α-D-mannopyranosyl-(1→6)]-α-D-mannopyranosyl}oxy)ethyl]-3,10,13,16-tetraazadocosan-22-oate (ML-43) having the following structure is described.

ML-43

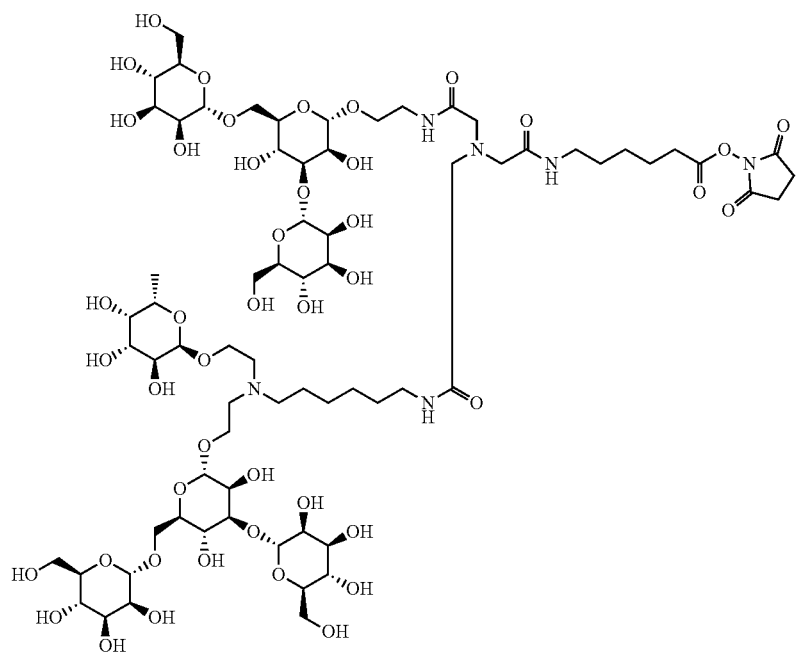

The title compounds was prepared using procedures analogous to those described for ML-23 substituting 2-aminoethyl α-D-mannopyranosyl-(1→3)-[α-D-mannopyranosyl-(1→6)]-α-D-mannopyranoside for 6-amino-N-[2-({α-D-mannopyranosyl-(1→3)-[α-D-mannopyranosyl-(1→6)]-α-D-mannopyranosyl}oxy)ethyl]hexanamide in Step C, and substituting $N^1$-(2-[(α-L-fucopyranosyl)oxy]ethyl)-$N^1$-(2-({α-D-mannopyranosyl-(1→3)-[α-D-mannopyranosyl-(1→6)]-α-D-mannopyranosyl}oxy)ethyl)hexane-1,6-diamine for (S)-2-(6-aminohexanamido)-$N^1$,$N^5$-bis{2-[(α-D-mannopyranosyl)oxy]ethyl}pentanediamide in Step H, respectively. UPLC-MS Method A: m/z=1750.85 (z=1); $t_R$=1.67 min.

Example 44

The synthesis of oligosaccharide linker 2,5-dioxopyrrolidin-1-yl 4,11,15-tri oxo-13-(2-oxo-2-{[6-({2-[(α-L-fucopyranosyl)oxy]ethyl}[2-({α-D-mannopyranosyl-(1→3)-[α-D-mannopyranosyl-(1→6)]-α-D-mannopyranosyl}oxy)ethyl]amino)hexyl]amino}ethyl)-1-({α-D-mannopyranosyl-(1→3)-[α-D-mannopyranosyl-(1→6)]-β-D-mannopyranosyl}oxy)-3,10,13,16-tetraazadocosan-22-oate (ML-44) having the following structure is described.

ML-44

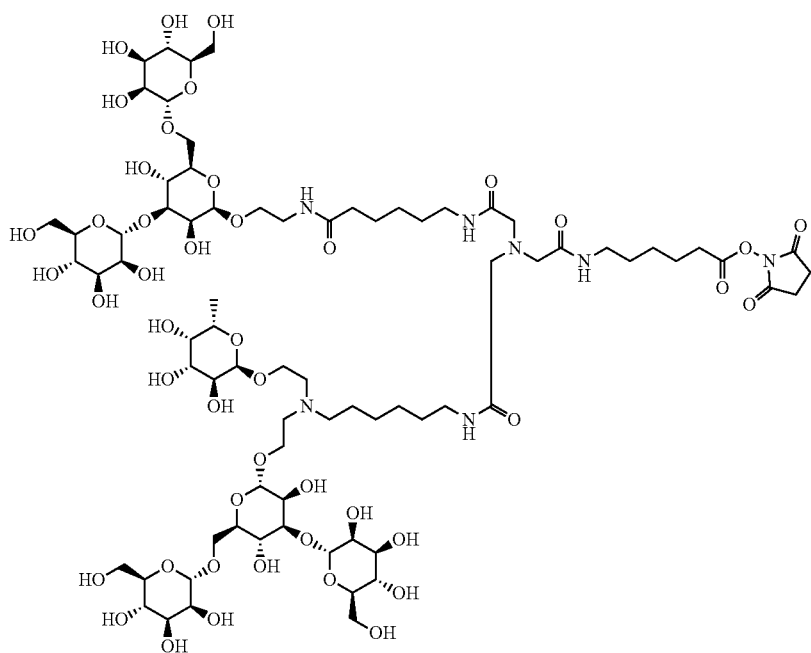

The title compounds was prepared using procedures analogous to those described for ML-23 substituting 2-({α-D-mannopyranosyl-(1→3)-[α-D-mannopyranosyl-(1→6)]-β-D-mannopyranosyl}oxy)ethan-1-amine for 2-({α-D-mannopyranosyl-(1→3)-[α-D-mannopyranosyl-(1→6)]-α-D-mannopyranosyl}oxy)ethan-1-amine in Step A, and substituting $N^1$-(2-[(α-L-fucopyranosyl)oxy]ethyl)-$N^1$-(2-({α-D-mannopyranosyl-(1→3)-[α-D-mannopyranosyl-(1→6)]-α-D-mannopyranosyl}oxy)ethyl)hexane-1,6-diamine for (S)-2-(6-aminohexanamido)-$N^1$,$N^5$-bis{2-[(α-D-mannopyranosyl)oxy]ethyl}pentanediamide in Step H, respectively. UPLC-MS Method A: m/z=1863.99 (z=1); $t_R$=1.80 min.

Example 45

The synthesis of oligosaccharide linker 2,5-dioxopyrrolidin-1-yl 6-{6-(bis{2-[(α-D-mannopyranosyl)oxy]ethyl}amino)-N-[2-({α-D-mannopyranosyl-(1→3)-[α-D-mannopyranosyl-(1→6)]-α-D-mannopyranosyl}oxy)ethyl]hexanamido}hexanoate (ML-45) having the following structure is described.

ML-45

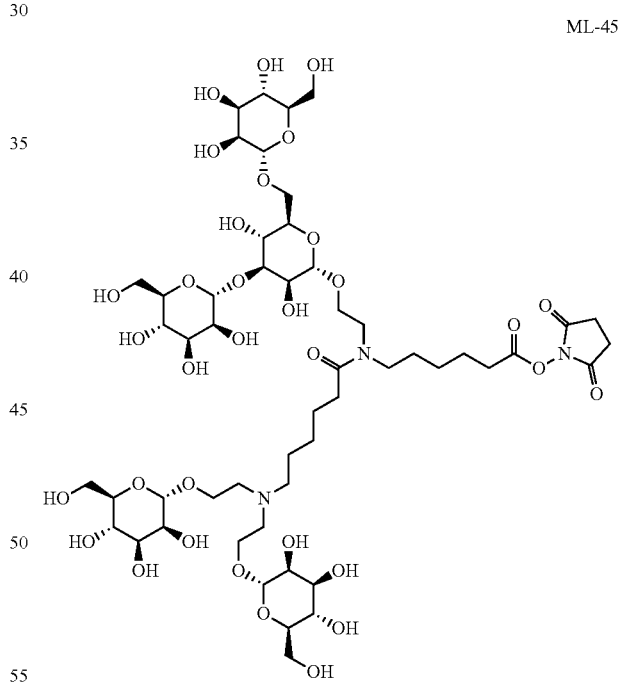

The title compounds was prepared using procedures analogous to those described for ML-23 substituting 2-({α-D-mannopyranosyl-(1→3)-[α-D-mannopyranosyl-(1→6)]-β-D-mannopyranosyl}oxy)ethan-1-amine for 2-({α-D-mannopyranosyl-(1→3)-[α-D-mannopyranosyl-(1→6)]-α-D-mannopyranosyl}oxy)ethan-1-amine in Step A, and substituting $N^1$-(2-[(α-L-fucopyranosyl)oxy]ethyl)-$N^1$-(2-({α-D-mannopyranosyl-(1→3)-[α-D-mannopyranosyl-(1→6)]-α-D-mannopyranosyl}oxy)ethyl)hexane-1,6-diamine for (S)-2-(6-aminohexanamido)-$N^1$,$N^5$-bis{2-[(α-D- mannopyranosyl)oxy]ethyl}pentanediamide in Step H, respectively. UPLC-MS Method A: m/z=1863.99 (z=1); t$_R$=1.80 min.

Example 46

The synthesis of oligosaccharide linker 2,5-dioxopyrrolidin-1-yl 4,11,15-trioxo-13-(2-oxo-2-((6-oxo-6-((2-({α-D-mannopyranosyl-(1→3)-[α-D-mannopyranosyl-(1→6)]-α-D-mannopyranosyl}oxy)ethyl)amino)hexyl)amino)ethyl)-1-[(β-D-mannopyranosyl)oxy]-3-(2-({α-D-mannopyranosyl-(1→3)-[α-D-mannopyranosyl-(1→6)]-α-D-mannopyranosyl}oxy)ethyl)-3,10,13,16-tetraazadocosan-22-oate (ML-46) having the following structure is described.

Step B. benzyl [6-oxo-6-({2-[(2,3,4,6-tetra-O-acetyl-β-D-mannopyranosyl)oxy]ethyl}[2-({(2,3,4,6-tetra-O-benzoyl-α-D-mannopyranosyl)-(1→3)-[2,3,4,6-tetra-O-benzoyl-α-D-mannopyranosyl-(1→6)1-4-O-benzoyl-α-D-mannopyranosyl}oxy)ethyl]amino)hexyl]carbamate To a solution of 2-[(2,3,4,6-tetra-O-acetyl-β-D-mannopyranosyl)oxy]-N-(2-({(2,3,4,6-tetra-O-benzoyl-α-D-mannopyranosyl)-(1→3)-[2,3,4,6-tetra-O-benzoyl-α-D-mannopyranosyl-(1→6)]-4-O-benzoyl-α-D-mannopyranosyl}oxy)ethyl)ethan-1-amine (550 mg, 0.28 mmol) and 2,5-dioxopyrrolidin-1-yl 6-{[(benzyloxy)carbonyl]amino}hexanoate (244 mg, 0.672 mmol) in DMF (3 mL)

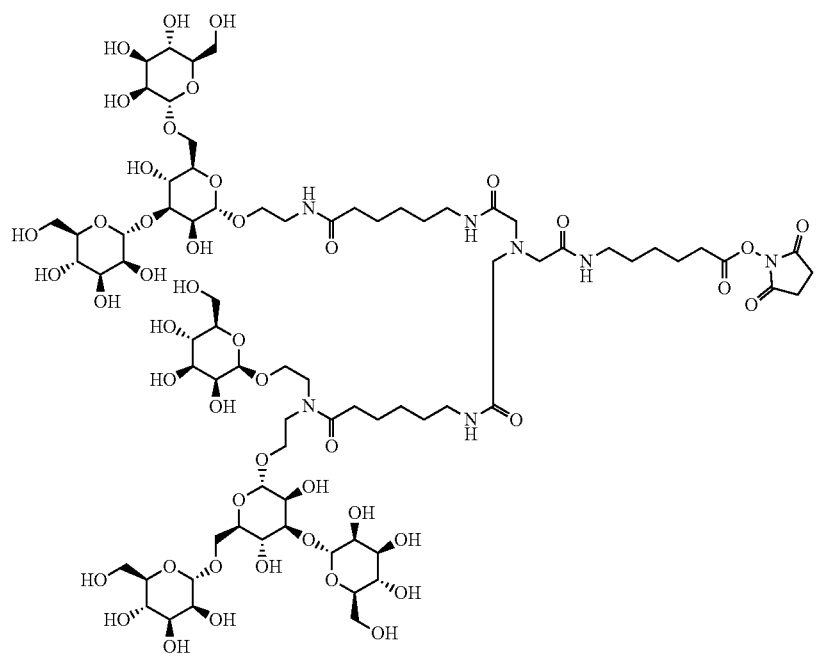

ML-46

Step A. 2-[(2,3,4,6-tetra-O-acetyl-β-D-mannopyranosyl)oxy]-N-(2-({(2,3,4,6-tetra-O-benzoyl-α-D-mannopyranosyl)-(1→3)-[2,3,4,6-tetra-O-benzoyl-α-D-mannopyranosyl-(1→6)1-4-O-benzoyl-α-D-mannopyranosyl}oxy)ethyl)ethan-1-amine To a solution of 2-oxoethyl 2,3,4,5-tetra-O-acetyl-β-D-mannopyranoside (450 mg, 1.153 mmol) and perbenzoylated 2-aminoethyl α-D-mannopyranosyl-(1→3)-[α-D-mannopyranosyl-(1→6)]-α-D-mannopyranoside (3.29 g, 2.08 mmol) in DCM (5 mL) was added HOAc (66 µL, 1.15 mmol) followed by sodium triacetoxyborohydride (367 mg, 1.73 mmol). The resulting mixture was stirred at rt overnight and then concentrated. The residue was partitioned between EtOAc (25 mL) and sat'd NaHCO₃ (30 mL); organic layer was washed with brine (15 mL), dried over Na₂SO₄, filtered and evaporated. The resulting residue was purified by silica gel column chromatography (Teledyne Isco: SNAP 80 g Gold) eluent: gradient 2-5% MeOH in DCM over 8 CV to give the title compound.

was added DIPEA (138 µL, 784 µmol). The resulting mixture was stirred at rt overnight. The mixture was partitioned between EtOAc (15 mL) and water (30 mL). The aqueous layer was separated and extracted with EtOAc (3×15 mL). The organic layers were combined and washed with brine (15 mL), dried over Na₂SO₄, filtered and evaporated. The residue was purified by silica gel column chromatography (Teledyne Isco: SNAP 40 g gold) eluent: gradient 30-100% EtOAc in Hexanes (8 CV) to give the title compound.

Step C. benzyl [6-oxo-6-({2-[(β-D-mannopyranosyl)oxy]ethyl}[2-({α-D-mannopyranosyl-(1→3)-[α-D-mannopyranosyl-(1→6)]-α-D-mannopyranosyl}oxy)ethyl]amino)hexyl]carbamate To a solution of benzyl [6-oxo-6-({2-[(2,3,4,6-tetra-O-acetyl-(3-D-mannopyranosyl)oxy]ethyl}[2-(1(2,3,4,6-tetra-O-benzoyl-α-D-mannopyranosyl)-(1→3)-[2,3,4,6-tetra-O-benzoyl-α-D-mannopyranosyl-(1→6)]-4-O-benzoyl-α-D-mannopyranosyl}oxy)ethyl]amino)hexyl]carbamate (460 mg, 0.208 mmol) in a mixture of MeOH (3 mL) and DCM (3 mL) was added sodium methoxide (39 µL, 30% in MeOH, 0.208 mmol). The resulting solution was stirred for 2 hr, and a white precipitate started to form. The mixture was concentrated to remove the DCM and more MeOH (3 mL) was added. After stirring at rt overnight, the mixture was neutralized by the addition of Dowex 50W resin. The resin was filtered off, and the filtrate was concentrated down to 1 mL volume, which was added dropwise to AcCN (40 mL) to give a white precipitate. The suspension was centrifuged at 3500 rpm 4° C. for 20 min. The supernatant was decanted, and the solid pellet was re-suspended in AcCN (40 mL). The resulting suspension was centrifuged at 3500 rpm 4° C. for 20 min, and then the supernatant was decanted, and the solid pellet was dried under a stream of $N_2$ and purified by reverse phase silica gel column chromatography (Teledyne Isco: C18 40 g) eluent: gradient 5-35% AcCN in water to give the title compound. UPLC-MS Method A: m/z=1001.51 (z=1); $t_R$=2.30 min.

Step D. 6-amino-N-{2-[(β-D-mannopyranosyl)oxy]ethyl}-N-(2-({α-D-mannopyranosyl-(1→3)-[α-D-mannopyranosyl-(1→6)]-α-D-mannopyranosyl}oxy)ethyl)hexanamide To a solution of benzyl [6-oxo-6-({2-[(β-D-mannopyranosyl)oxy]ethyl}[2-({α-D-mannopyranosyl-(1→3)-[α-D-mannopyranosyl-(1→6)]-α-D-mannopyranosyl}oxy)ethyl]amino)hexyl]carbamate (185 mg, 0.185 mmol) in water (5 mL) was added 10% Pd/C (19 mg). The resulting mixture was stirred under a balloon of $H_2$ for 5 hr. The catalyst was filtered off through a 0.45 μm filter, and the filtrate was freeze-dried to give the title compound. UPLC-MS Method A: m/z=867.46 (z=1); $t_R$=0.84 min.

Step E. 2,5-dioxopyrrolidin-1-yl 4,11,15-trioxo-13-(2-oxo-2-((6-oxo-6-((2-({α-D-mannopyranosyl-(1→3)-[α-D-mannopyranosyl-(1→6)]-α-D-mannopyranosyl}oxy)ethyl)amino)hexyl)amino)ethyl)-1-[(β-D-mannopyranosyl)oxy]-3-(2-({α-D-mannopyranosyl-(1→3)-[α-D-mannopyranosyl-(1→6)]-α-D-mannopyranosyl}oxy)ethyl)-3,10,13,16-tetraazadocosan-22-oate The title compounds was prepared using procedures analogous to those described for ML-23 substituting 6-amino-N-{2-[(β-D-mannopyranosyl)oxy]ethyl}-N-(2-({α-D-mannopyranosyl-(1→3)-[α-D-mannopyranosyl-(1→6)]-α-D-mannopyranosyl}oxy)ethyl)hexanamide for (S)-2-(6-aminohexanamido)-$N^1$,$N^5$-bis{2-[(α-D-mannopyranosyl)oxy]ethyl}pentanediamide in Step H. UPLC-MS Method A: m/z=1893.75 (z=1); $t_R$=1.75 min.

Example 47

The synthesis of oligosaccharide linker 2,5-dioxopyrrolidin-1-yl 4,11,15-trioxo-13-(2-oxo-2-((6-oxo-6-((2-({α-D-mannopyranosyl-(1→3)-[α-D-mannopyranosyl-(1→6)]-β-D-mannopyranosyl}oxy)ethyl)amino)hexyl)amino)ethyl)-1-[(β-D-mannopyranosyl)oxy]-3-(2-({α-D-mannopyranosyl-(1→3)-[α-D-mannopyranosyl-(1→6)]-α-D-mannopyranosyl}oxy)ethyl)-3,10,13,16-tetraazadocosan-22-oate (ML-47) having the following structure is described.

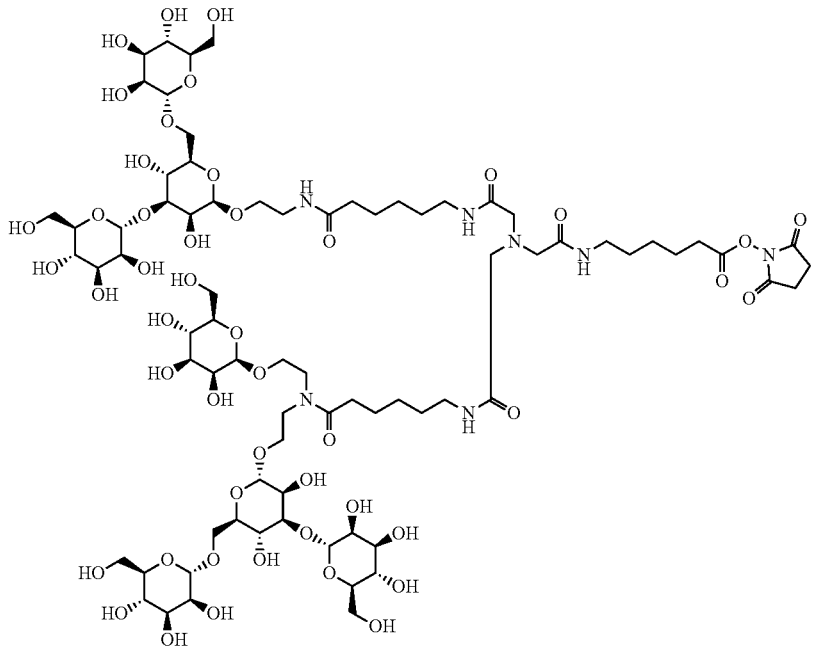

ML-47

The title compounds was prepared using procedures analogous to those described for ML-23 substituting 2-({α-D-mannopyranosyl-(1→3)-[α-D-mannopyranosyl-(1→6)]-β-D-mannopyranosyl}oxy)ethan-1-amine for 2-({α-D-mannopyranosyl-(1→3)-[α-D-mannopyranosyl-(1→6)]-α-D-mannopyranosyl}oxy)ethan-1-amine in Step A, and substituting 6-amino-N-{2-[(β-D-mannopyranosyl)oxy]ethyl}-N-(2-({α-D-mannopyranosyl-(1→3)-[α-D-mannopyranosyl-(1→6)]-α-D-mannopyranosyl}oxy)ethyl)hexanamide for (S)-2-(6-aminohexanamido)-N$^1$,N$^5$-bis{2-[(α-D-mannopyranosyl)oxy]ethyl}pentanediamide in Step H, respectively. UPLC-MS Method A: m/z=1893.75 (z=1); $t_R$=1.73 min.

Example 48

The synthesis of oligosaccharide linker 2,5-dioxopyrrolidin-1-yl 4,8,16,20-tetraoxo-6-[2-oxo-2-({2-[(α-D-mannopyranosyl)oxy]ethyl}amino)ethyl]-18-(2-oxo-2-{[6-oxo-6-({2-[(α-L-fucopyranosyl)oxy]ethyl}amino)hexyl]amino}ethyl)-1-[(α-D-mannopyranosyl)oxy]-3,6,9,15,18,21-hexaazaheptacosan-27-oate (ML-48) having the following structure is described.

which was further purified by reverse phase silica gel column chromatography (CombiFlash Teldyne ISCO: 26 g C18 column) gradient: 0-60% AcCN in $H_2O$ to give the title compound. UPLC-MS Method C: m/z=819 (z=1); $t_R$=4.58.

Step B. 2,2'-({2-[(5-aminopentyl)amino]-2-oxoethyl}azanediyl)bis(N-{2-[(α-D-mannopyranosyl)oxy]ethyl}acetamide)

To a solution of benzyl [5-(2-{bis[2-oxo-2-({2-[(α-D-mannopyranosyl)oxy]ethyl}amino)ethyl]amino}acetamido)pentyl]carbamate (500 mg, 0.61 mmol) in a mixture of EtOH (6 mL) and water (3 mL) was added 10% Pd/C (65 mg). The resulting mixture was stirred under a balloon of $H_2$ for 2 hrs. The catalyst was filtered off through a cake of CELITE, washing with MeOH. The combined filtrates were concentrated, and the residue was freeze-dried to give the title compound. UPLC-MS Method C: m/z=685 (z=1); $t_R$=2.08.

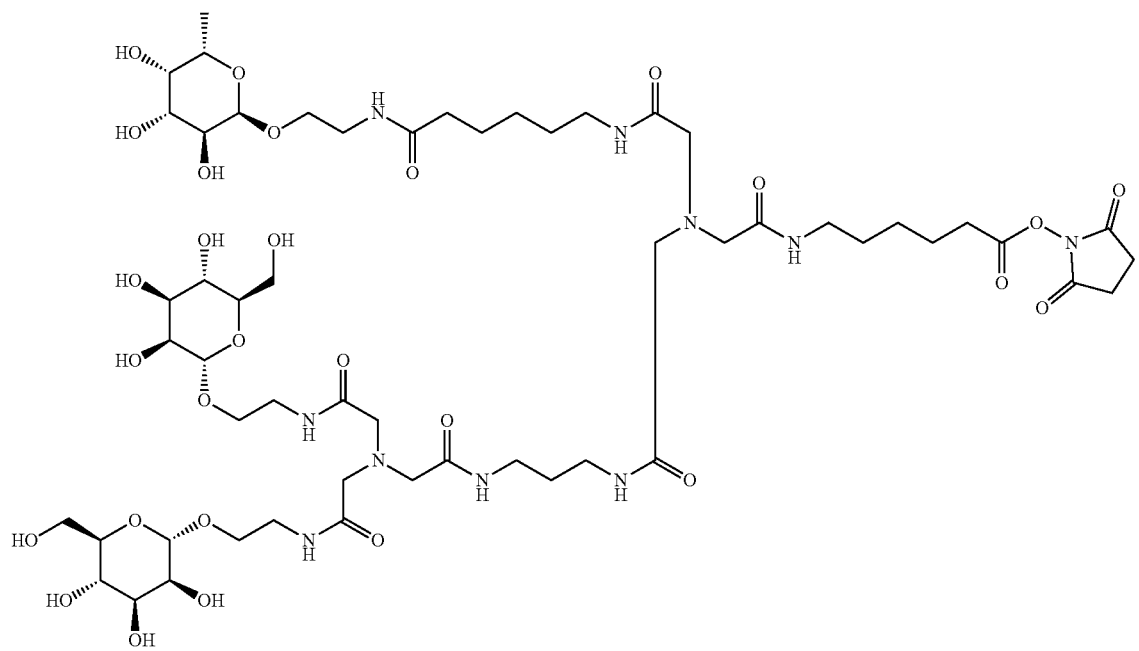

ML-48

Step A. benzyl [5-(2-{bis[2-oxo-2-({2-[(α-D-mannopyranosyl)oxy]ethyl}amino)ethyl]amino}acetamido)pentyl]carbamate To a solution of 13-(carboxymethyl)-3,11-dioxo-1-phenyl-2-oxa-4,10,13-triazapentadecan-15-oic acid (400 mg, 0.98 mmol) and 2-aminoethyl α-D-mannopyranoside (545 mg, 2.44 mmol) in DMF (8 mL) was added EDC (749 mg, 3.91 mmol) and DMAP (358 mg, 2.93 mmol). The resulting mixture was stirred at rt for 3 days and then evaporated. The residue was purified by silica gel column chromatography (CombiFlash Teldyne ISCO: 24 g RediSep column), eluting 0-66% solvent A: EtOAc/MeOH/AcCN (v/v/v=6/1/1) in buffer B EtOAc/MeOH/AcCN/$H_2O$ (v/v/v/v=6/3/3/3) over 30 CV then hold for 5 CV to give the crude title product,

Step C. 2,5-dioxopyrrolidin-1-yl 4,8,16,20-tetraoxo-6-[2-oxo-2-({2-[(α-D-mannopyranosyl)oxy]ethyl}amino)ethyl]-18-(2-oxo-2-{[6-oxo-6-({2-[(α-L-fucopyranosyl)oxy]ethyl}amino)hexyl]amino}ethyl)-1-[(α-D-mannopyranosyl)oxy]-3,6,9,15,18,21-hexaazaheptacosan-27-oate The title compound was prepared using procedures analogous to those described for ML-16 substituting 6-amino-N-{2-[(α-L-fucopyranosyl)oxy]ethyl}hexanamide for (R)-1,4-di[(α-D-mannopyranosyl)oxy]butan-2-amine in Step A, and 2,2'-({2-[(5-aminopentyl)amino]-2-oxoethyl}azanediyl)bis(N-{2-[(α-D-mannopyranosyl)oxy]ethyl}acetamide) for 2-aminoethyl α-D-mannopyranoside in Step B, respectively. UPLC-MS Method C: m/z=1371 (z=1); $t_R$=2.17 min.

Example 49

The synthesis of oligosaccharide linker 2,5-dioxopyrrolidin-1-yl 4,8,16,20-tetraoxo-6-[2-oxo-2-({2-[(α-L-fucopyranosyl)oxy]ethyl}amino)ethyl]-18-(2-oxo-2-{[6-oxo-6-({2-({α-D-mannopyranosyl-(1→3)-[α-D-mannopyranosyl-(1→6)]-α-D-mannopyranosyl}oxy)ethyl}amino)hexyl]amino}ethyl)-1-[(α-L-fucopyranosyl)oxy]-3,6,9,15,18,21-hexaazaheptacosan-27-oate (ML-49) having the following structure is described.

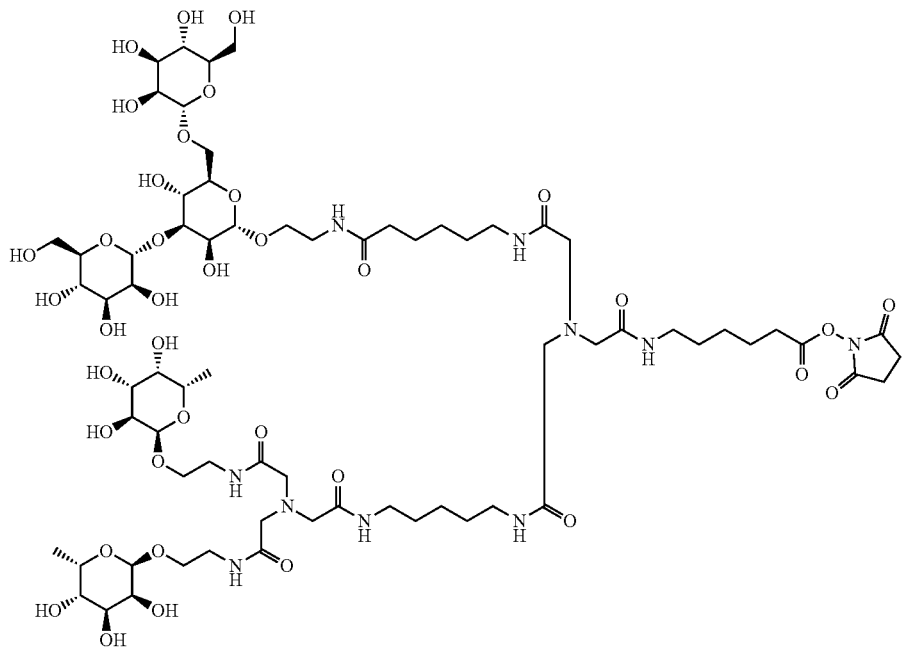

ML-49

Step A. 2,2'-({2-[(5-aminopentyl)amino]-2-oxoethyl}azanediyl)bis(N-(2-[(α-L-fucopyranosyl)oxy]ethyl}acetamide)

The title compound was prepared using procedures analogous to those described for ML-48 substituting 2-aminoethyl α-L-fucopyranoside for 2-aminoethyl α-D-mannopyranoside in Step B. UPLC-MS Method C: m/z=654 (z=1); $t_R$=2.45.

Step B. 2,5-dioxopyrrolidin-1-yl 4,8,16,20-tetraoxo-6-[2-oxo-2-({2-[(α-L-fucopyranosyl)oxy]ethyl}amino)ethyl]-18-(2-oxo-2-{[6-oxo-6-({2-({α-D-mannopyranosyl-(1→3)-[α-D-mannopyranosyl-(1→6)]-α-D-mannopyranosyl}oxy)ethyl}amino)hexyl]amino}ethyl)-1-[(α-L-fucopyranosyl)oxy]-3,6,9,15,18,21-hexaazaheptacosan-27-oate The title compound was prepared using procedures analogous to those described for ML-23 substituting 2,2'-({2-[(5-aminopentyl)amino]-2-oxoethyl}azanediyl)bis(N-{2-[(α-L-fucopyranosyl)oxy]ethyl}acetamide) for (S)-2-(6-aminohexanamido)-N¹,N⁵-bis{2-[(α-D-mannopyranosyl)oxy]ethyl}pentanediamide in Step H. UPLC-MS Method C: m/z=1680 (z=1); $t_R$=2.07 min.

Example 50

The synthesis of oligosaccharide linker 2,5-dioxopyrrolidin-1-yl 4,11,15,23,27-pentaoxo-13-(2-oxo-2-((2-[(α-L-fucopyranosyl)oxy]ethyl)amino)ethyl)-25-(2-oxo-2-((6-oxo-6-((2-({α-D-mannopyranosyl-(1→3)-[α-D-mannopyranosyl-(1→6)]-α-D-mannopyranosyl}oxy)ethyl)amino)hexyl)amino)ethyl)-1-[(α-L-fucopyranosyl)oxy]-3,10,13,16,22,25,28-heptaazatetratriacontan-34-oate (ML-50) having the following structure is described.

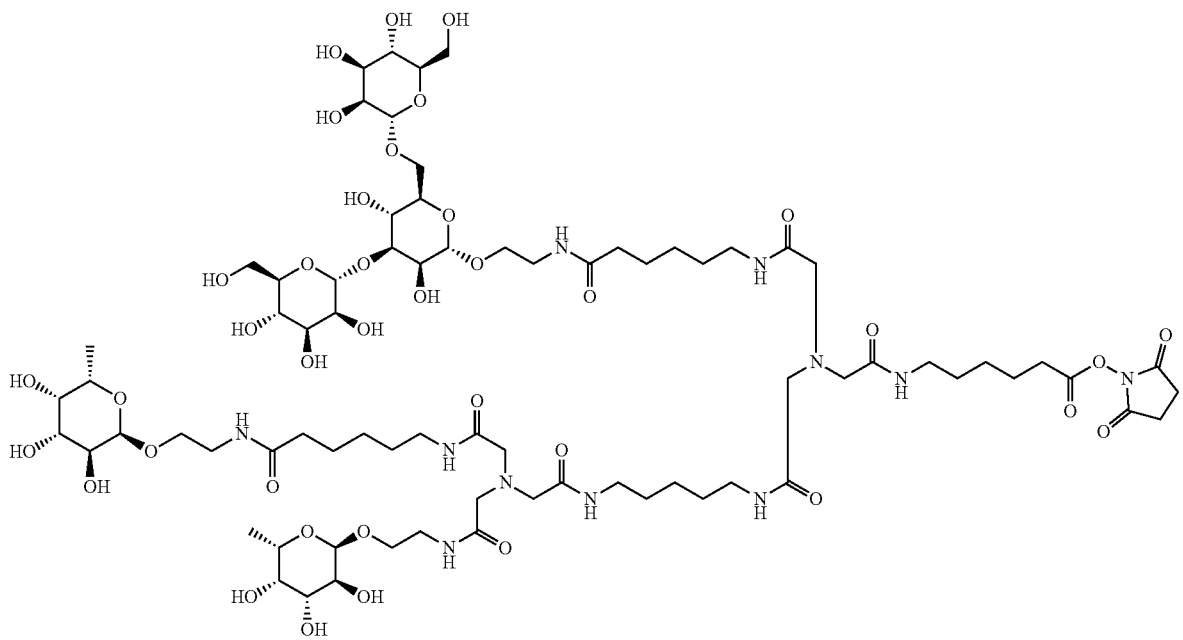 [SMILES: C[C@@H]1O[C@@H](OCCNC(=O)CCCCCNC(=O)CN(CC(=O)NCCCCCNC(=O)CN(CC(=O)NCCCCCC(=O)NCCO[C@H]2O[C@H](CO[C@H]3O[C@H](CO)[C@@H](O)[C@H](O)[C@@H]3O)[C@@H](O)[C@H](O[C@H]3O[C@H](CO)[C@@H](O)[C@H](O)[C@@H]3O)[C@@H]2O)CC(=O)NCCCCCC(=O)ON2C(=O)CCC2=O)CC(=O)NCCO[C@@H]2O[C@@H](C)[C@@H](O)[C@@H](O)[C@@H]2O)[C@@H](O)[C@H](O)[C@@H]1O]

ML-50

Step A. 3,11-dioxo-13-(2-oxo-2-{[6-oxo-6-({2-[(α-L-fucopyranosyl)oxy]ethyl}amino)hexyl]amino}ethyl)-1-phenyl-2-oxa-4,10,13-triazapentadecan-15-oic acid To a solution of 6-amino-N-{[(2-α-L-fucopyranosyl)oxy]ethyl}hexanamide (200 mg, 0.506 mmol) in DMF (3 mL) at rt was added 13-(carboxymethyl)-3,11-dioxo-1-phenyl-2-oxa-4,10,13-triazapentadecan-15-oic acid, TEA (0.106 mL, 0.759 mmol), and HATU (212 mg, 0.556 mmol) was added slowly. After stirring for 16 h, the reaction mixture was concentrated and the residue was purified on reverse phase chromatography to isolate the title compound. UPLC-MS Method A: m/z=712.34 (z=1); $t_R$=3.68 min.

Step B. benzyl (4,11,15-trioxo-13-[2-oxo-2-({2-[(α-L-fucopyranosyl)oxy]ethyl}amino)ethyl]-1-[(α-L-fucopyranosyl)oxy]-3,10,13,16-tetraazahenicosan-21-yl}carbamate To a solution of 3,11-dioxo-13-(2-oxo-2-{[6-oxo-6-({2-[(α-L-fucopyranosyl)oxy]ethyl}amino)hexyl]amino}ethyl)-1-phenyl-2-oxa-4,10,13-triazapentadecan-15-oic acid (45 mg, 0.063 mmol) in DMF (3 mL) at rt was added EDC (14.54 mg, 0.076 mmol), HOBt (11.62 mg, 0.076 mmol), TEA (0.022 mL, 0.158 mmol), and 2-aminoethyl α-L-fucopyranoside (19.65 mg, 0.095 mmol). After stirring for 16 h, the reaction mixture was concentrated and the residue was purified on reverse phase chromatography to isolate the title compound. UPLC-MS Method A: m/z=901.40 (z=1); $t_R$=3.55 min.

Step C. 6-(2-({2-[(5-aminopentyl)amino]-2-oxoethyl}[2-oxo-2-({2-[(α-L-fucopyranosyl)oxy]ethyl}amino)ethyl]amino)acetamido)-N-(2-[(α-L-fucopyranosyl)oxy]ethyl)hexanamide To a solution of benzyl{4,11,15-trioxo-13-[2-oxo-2-({2-[(α-L-fucopyranosyl) oxy]ethyl}amino)ethyl]-1-[(α-L-fucopyranosyl)oxy]-3,10,13,16-tetraazahenicosan-21-yl}carbamate (28.5 mg, 0.032 mmol) in water (3 mL) was added catalytic amount of Pd/C. The mixture was 3× with $H_2$ and then stirred for 1 hr. The catalyst was filtered off through a cake of CELITE and washed with water. The filtrate was freeze-dried to give the title compound. UPLC-MS Method A: m/z=767.38 (z=1); $t_R$=1.72 min.

Step D. 2,5-dioxopyrrolidin-1-yl 4,11,15,23,27-pentaoxo-13-(2-oxo-2-((2-[(α-L-fucopyranosyl)oxy]ethyl)amino)ethyl)-25-(2-oxo-2-((6-oxo-6-((2-({α-D-mannopyranosyl-(1→3)-[α-D-mannopyranosyl-(1→6)]-α-D-mannopyranosyl}oxy)ethyl)amino)hexyl)amino)ethyl)-1-[(α-L-fucopyranosyl)oxy]-3,10,13,16,22,25,28-heptaazatetratriacontan-34-oate The title compound was prepared using procedures analogous to those described for ML-23 substituting 6-(2-({2-[(5-aminopentyl)amino]-2-oxoethyl}[2-oxo-2-({2-[(α-L-fucopyranosyl)oxy]ethyl}amino)ethyl]amino)acetamido)-N-(2-[(α-L-fucopyranosyl)oxy]ethyl)hexanamide for (S)-2-(6-aminohexanamido)-$N^1$,$N^5$-bis{2-[(α-D-mannopyranosyl)oxy]ethyl}pentanediamide in Step H. UPLC-MS Method C: m/z=1793.62 (z=1); $t_R$=2.57 min.

Example 51

The synthesis of oligosaccharide linker 2,5-dioxopyrrolidin-1-yl 4,11,15,23,27-pentaoxo-13-(2-oxo-2-((2-({α-D-mannopyranosyl-(1→3)-[α-D-mannopyranosyl-(1→6)]-α-D-mannopyranosyl{oxy)ethyl)amino)ethyl)-25-(2-oxo-2-((6-oxo-6-((2-({α-D-mannopyranosyl-(1→3)-[α-D-mannopyranosyl-(1→6)]-α-D-mannopyranosyl}oxy)ethyl)amino)hexyl)amino)ethyl)-1-[(α-L-fucopyranosyl)oxy]-3,10,13,16,22,25,28-heptaazatetratriacontan-34-oate (ML-51) having the following structure is described.

ML-51

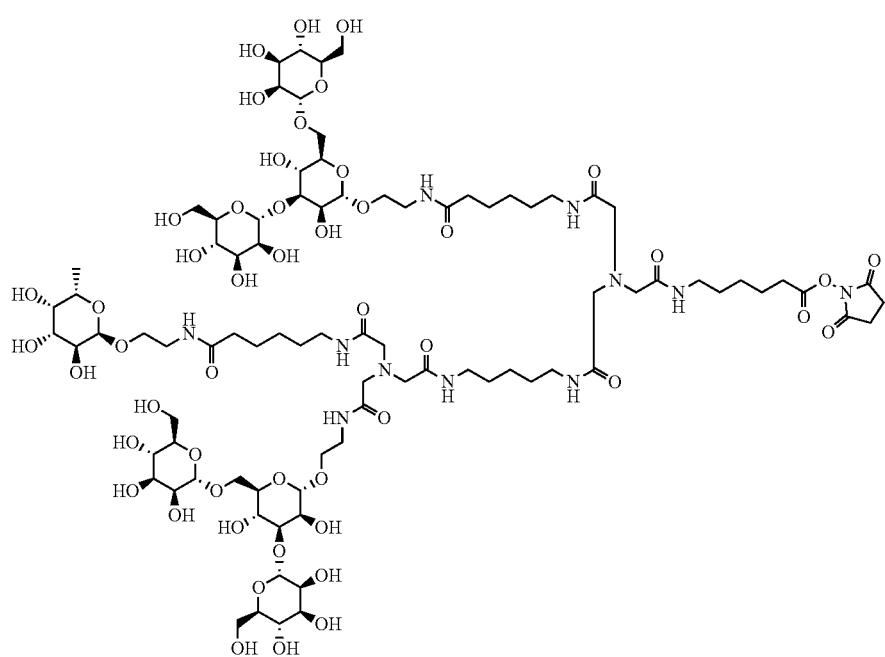

The title compound was prepared using procedures analogous to those described for ML-50 substituting 2-aminoethyl α-D-mannopyranosyl-(1→3)-[α-D-mannopyranosyl-(1→6)]-α-D-mannopyranoside for 2-aminoethyl α-L-fucopyranoside in Step B. UPLC-MS Method C: m/z=1067.40 (z=2); $t_R$=2.31 min.

Example 52

The synthesis of oligosaccharide linker 2,5-dioxopyrrolidin-1-yl 4,11,15,23,27-pentaoxo-25-{(2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl) amino]ethyl}-13-(2-oxo-2-[6-oxo-6-({2-[(α-L-fucopyranosyl)oxy]ethyl}amino)hexyl]amino}ethyl)-1-[(α-L-fucopyranosyl)oxy]-3,10,13,16,22,25,28-heptaazatetratriacontan-34-oate (ML-52) having the following structure is described.

ML-52

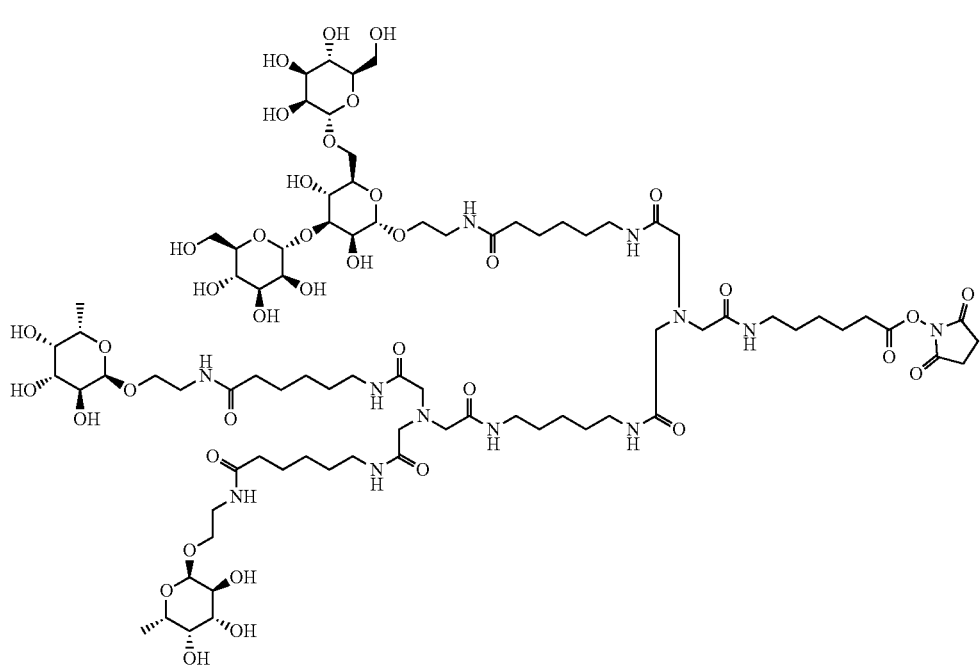

The title compound was prepared using procedures analogous to those described for ML-49 substituting 6-amino-N-{[(2-α-L-fucopyranosyl)oxy]ethyl}hexanamide for 2-aminoethyl α-L-fucopyranoside in Step A. UPLC-MS Method C: m/z=953.35 (z=2); $t_R$=2.59 min.

Example 53

The synthesis of oligosaccharide linker 2,5-dioxopyrrolidin-1-yl 4,8,16,20-tetraoxo-6-(2-oxo-2-{[2-({α-D-mannopyranosyl-(1→3)-[α-D-mannopyranosyl-(1→6)]-α-D-mannopyranosyl}oxy)ethyl]amino}ethyl)-18-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-1-[(α-L-fucopyranosyl)oxy]-3,6,9,15,18,21-hexaazaheptacosan-27-oate (ML-53) having the following structure is described.

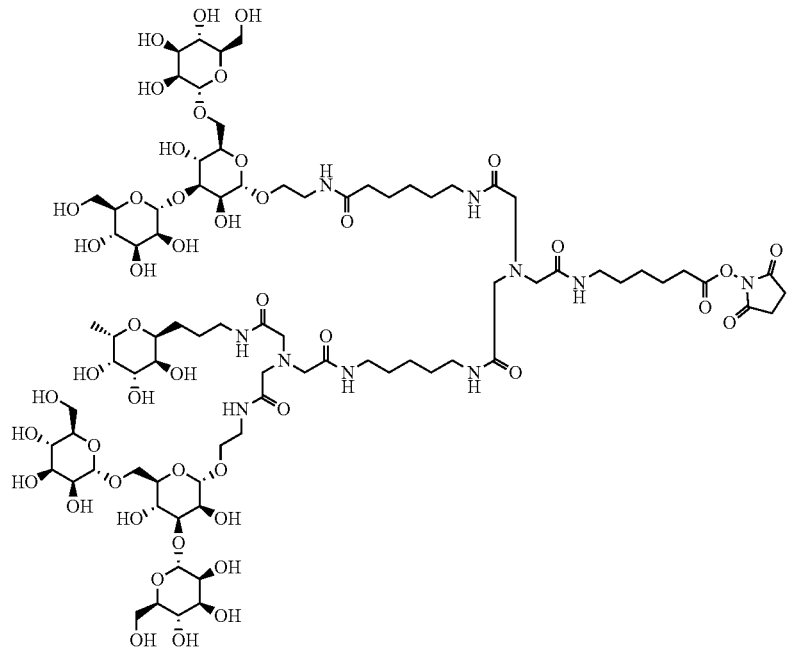

ML-53

The title compound was prepared using procedures analogous to those described for ML-50 substituting 2-aminoethyl α-L-fucopyranoside for 6-amino-N-{[(2-α-L-fucopyranosyl)oxy]ethyl}hexanamide in Step A, and 2-aminoethyl α-D-mannopyranosyl-(1→3)-[α-D-mannopyranosyl-(1→6)]-α-D-mannopyranoside for 2-aminoethyl α-L-fucopyranoside in Step B, respectively. UPLC-MS Method A: m/z=1011.06 (z=2); $t_R$=1.52 min.

Example 54

The synthesis of oligosaccharide linker 2,5-dioxopyrrolidin-1-yl (7R,17S)-4,9,16,19-tetraoxo-17-{3-oxo-3-[(6-oxo-6-{[2-({α-D-mannopyranosyl-(1→3)-[α-D-mannopyranosyl-(1→6)]-α-D-mannopyranosyl}oxy)ethyl]amino}hexyl)amino]propyl -7-({2-[(α-L-fucopyranosyl)oxy]ethyl}carbamoyl)-1-({α-D-mannopyranosyl-(1→3)-[α-D-mannopyranosyl-(1→6)]-α-D-mannopyranosyl}oxy)-3,8,15,18-tetraazatetracosan-24-oate (ML-54) having the following structure is described.

ML-54

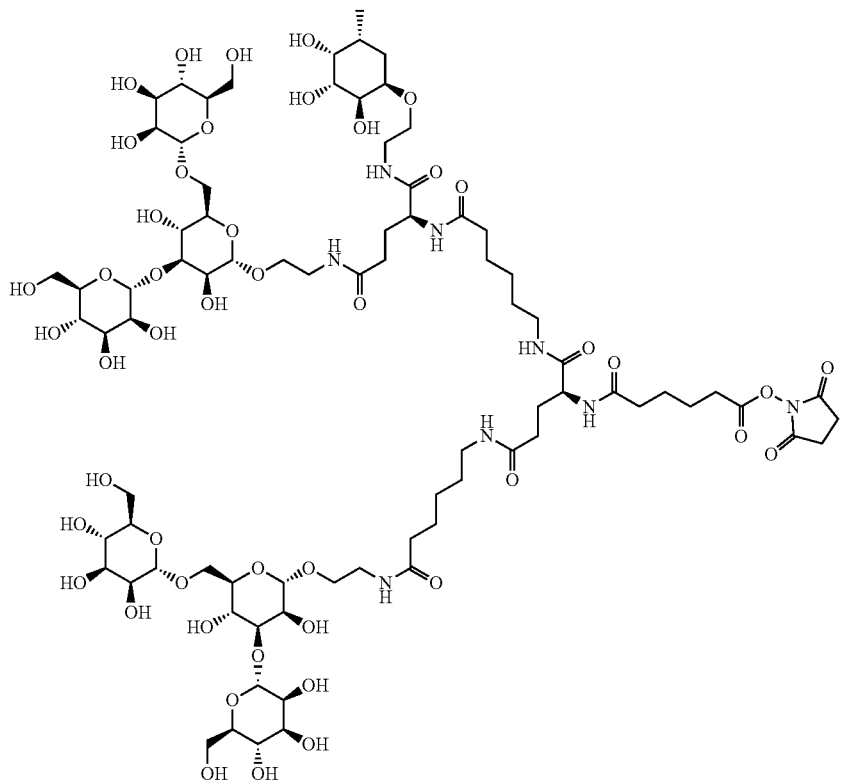

Step A. benzyl N²-[(benzyloxy)carbonyl]-N⁵-[2-({α-D-mannopyranosyl-(1→3)-[α-D-mannopyranosyl-(1→6)]-α-D-mannopyranosyl}oxy)ethyl]-L-glutaminate To a mixture of 2-aminoethyl α-D-mannopyranosyl-(1→3)-[α-D-mannopyranosyl-(1→6)]-α-D-mannopyranoside (4.0 g, 7.31 mmol) and (S)-5-(benzyloxy)-4-{[(benzyloxy)carbonyl]amino}-5-oxopentanoic acid (2.98 g, 8.04 mmol) in DMF (30 mL) at rt was added EDC (2.10 g, 10.96 mmol) and HOBt (112 mg, 0.731 mmol). The mixture was allowed to stir at rt. After overnight, the reaction mixture was concentrated, and the residue was purified on C18 reverse phase cartridge on Biotage (0-65% AcCN in water). The desired fractions were combined and freeze-dried to give the title compound. UPLC-MS Method D: m/z=901.01 (z=1); $t_R$=4.04 min.

Step B. N⁵-[2-({α-D-mannopyranosyl-(1→3)-[α-D-mannopyranosyl-(1→6)]-α-D-mannopyranosyl}oxy)ethyl]-L-glutaminate To a solution of benzyl N²-[(benzyloxy)carbonyl]-N⁵-[2-({α-D-mannopyranosyl-(1→3)-[α-D-mannopyranosyl-(1→6)]-α-D-mannopyranosyl}oxy)ethyl]-L-glutaminate (3.92 g, 4.36 mmol) in water (50 mL) at rt was added Pd(OH)₂ (153 mg, 0.218 mmol). The mixture was allowed to shaken by Parr hydrogenator under 60 psi of H₂ at rt for 4 hrs. The catalyst was filtered off through a cake of CELITE and washed with water (3×20 mL). The filtrates were combined and freeze-dried to give the title compound.

Step C. N²-(6-{[(benzyloxy)carbonyl]amino}hexanoyl)-N⁵-[2-({α-D-mannopyranosyl-(1→3)-[α-D-mannopyranosyl-(1→6)]-α-D-mannopyranosyl}oxy)ethyl]-L-glutaminate To a mixture of N⁵-[2-({α-D-mannopyranosyl-(1→3)-[α-D-mannopyranosyl-(1→6)]-α-D-mannopyranosyl}oxy)ethyl]-L-glutaminate (2.98 g, 4.40 mmol) in DMF (30 ml) at rt was added 2,5-dioxopyrrolidin-1-yl 6-{[(benzyloxy)carbonyl]amino}hexanoate (1.76 g, 4.84 mmol, Step A, ML-7) and TEA (1.228 mL, 8.81 mmol). The mixture was allowed to stir at rt. After overnight, the reaction mixture was concentrated, and the residue was purified on C18 240 g 0-50% AcCN in water. The desired fractions were combined and freeze-dried to give the title compound. UPLC-MS Method D: m/z=924.46 (z=1); $t_R$=3.89 min.

Step D. benzyl (S)-(6-{[1,5-dioxo-1-({2-[(α-L-fucopyranosyl)oxy]ethyl}amino)-5-{[2-({α-D-mannopyranosyl-(1→3)-[α-D-mannopyranosyl-(1→6)]-α-D-mannopyranosyl}oxy)ethyl]amino}pentan-2-yl]amino}-6-oxohexyl)carbamate To a mixture of N²-(6-{[(benzyloxy)carbonyl]amino}hexanoyl)-N⁵-[2-({α-D-mannopyranosyl-(1→3)-[α-D-mannopyranosyl-(1→6)]-β-D-mannopyranosyl}oxy)ethyl]-L-glutaminate (2.383 g, 2.58 mmol) and 2-aminoethyl α-L-fucopyranoside (641 mg, 3.10 mmol) in DMF (40 mL) at rt was added EDC (742 mg, 3.87 mmol) and HOBt (39.5 mg, 0.258 mmol). The mixture was allowed to stir at rt. After overnight, the reaction mixture was concentrated, and the residue was purified on C18 240 g gradient 0-50% AcCN in water. The desired fractions were combined and lyophilized Step E. (S)-2-(6-aminohexanamido)-N$^1$-{2-[(α-L-fucopyranosyl)oxy]ethyl}-N$^5$-[2-({α-D-mannopyranosyl-(1→3)-[α-D-mannopyranosyl-(1→6)]-α-D-mannopyranosyl}oxy)ethyl]pentanediamide To a solution of benzyl (S)-(6-{[1,5-dioxo-1-({2-[(α-L-fucopyranosyl)oxy]ethyl}amino)-5-{[2-({α-D-mannopyranosyl-(1→3)-[α-D-mannopyranosyl-(1→6)]-α-D-mannopyranosyl}oxy)ethyl]amino}pentan-2-yl]amino}-6-oxohexyl)carbamate (1.79 g, 1.610 mmol) in water (40 mL) at rt was added Pd(OH)$_2$ (56.5 mg, 0.081 mmol). The mixture was allowed to be shaken in a Parr hydrogenator under 60 Psi of H$_2$ for 2 hrs at rt. After overnight, the catalyst was filtered off, and the filtrate was lyophilized to give the title compound. UPLC-MS Method D: m/z=979.54 (z=1); t$_R$=3.82 min.

Step F. benzyl N$^2$-[(benzyloxy)carbonyl]-N$^5$-(6-oxo-6-{[2-({α-D-mannopyranosyl-(1→3)-[α-D-mannopyranosyl-(1→6)]-α-D-mannopyranosyl}oxy)ethyl]amino}hexyl)-L-glutaminate To a solution of 6-amino-N-[2-({α-D-mannopyranosyl-(1→3)-[α-D-mannopyranosyl-(1→6)]-α-D-mannopyranosyl}oxy)ethyl]hexanamide (2.96 g, 4.48 mmol) and Z-GLU-OBZL (1.83 g, 4.93 mmol) in DMF (30 mL) was added EDC (1.288 g, 6.72 mmol) and HOBt (0.069 g, 0.448 mmol). The mixture was allowed to stir at rt overnight. After overnight, the reaction mixture was concentrated, and the residue was purified on 120 g C18 using Biotage (0-50% AcCN in water) to give the title compound. UPLC-MS Method D: m/z=1014.49 (z=1); t$_R$=4.26 min.

Step G. N$^5$-(6-oxo-6-{[2-({α-D-mannopyranosyl-(1→3)-[α-D-mannopyranosyl-(1→6)]-α-D-mannopyranosyl}oxy)ethyl]amino}hexyl)-L-glutamine A suspension of benzyl N$^2$-[(benzyloxy)carbonyl]-N$^5$-(6-oxo-6-{[2-({α-D-mannopyranosyl-(1→3)-[α-D-mannopyranosyl-(1→6)]-α-D-mannopyranosyl}oxy)ethyl]amino}hexyl)-L-glutaminate (3.5 g, 3.45 mmol) and Pd(OH)$_2$ (100 mg, 0.142 mmol) in water (100 mL) was added using a Parr shaker under 50 Psi of H$_2$ at rt overnight. After overnight, catalyst was filtered off, and the filtrate was freeze-dried to give the title compound. UPLC-MS Method D: m/z=790.40 (z=1); t$_R$=3.80 min.

Step H. benzyl (7R,17S)-4,9,16,19-tetraoxo-17-{3-oxo-3-[(6-oxo-6-{[2-({α-D-mannopyranosyl-(1→3)-[α-D-mannopyranosyl-(1→6)]-α-D-mannopyranosyl}oxy)ethyl]amino}hexyl)amino]propyl}-7-({2-[(α-L-fucopyranosyl)oxy]ethyl}carbamoyl)-1-({α-D-mannopyranosyl-(1→3)-[α-D-mannopyranosyl-(1→6)]-α-D-mannopyranosyl}oxy)-3,8,15,18-tetraazatetracosan-24-oate To a solution of (S)-2-(6-aminohexanamido)-N$^1$-{2-[(α-L-fucopyranosyl)oxy]ethyl}-N$^5$-[2-({α-D-mannopyranosyl-(1→3)-[α-D-mannopyranosyl-(1→6)]-α-D-mannopyranosyl}oxy)ethyl]pentanediamide (1.017 g, 1.039 mmol) and N$^2$-(6-(benzyloxy)-6-oxohexanoyl)-N$^5$-(6-oxo-6-{[2-({α-D-mannopyranosyl-(1→3)-[α-D-mannopyranosyl-(1→6)]-α-D-mannopyranosyl}oxy)ethyl]amino}hexyl)-L-glutamine (1.047 g, 1.039 mmol) in DMF (30 mL) at rt was added EDC (299 mg, 1.558 mmol) and HOBt (15.91 mg, 0.104 mmol). The mixture was allowed to stir at rt overnight. After overnight, the mixture was concentrated, and the residue was purified on C18 275 g 0-45% AcCN in water. The desired fractions were combined and lyophilized to give the title compound. UPLC-MS Method B: m/z=1970.07 (z=1); t$_R$=3.26 min.

Step I. 2,5-dioxopyrrolidin-1-yl (7R,17S)-4,9,16,19-tetraoxo-17-{3-oxo-3-[(6-oxo-6-{[2-({α-D-mannopyranosyl-(1→3)-[α-D-mannopyranosyl-(1→6)]-α-D-mannopyranosyl}oxy)ethyl]amino}hexyl)amino]propyl}-7-({2-[(α-L-fucopyranosyl)oxy]ethyl}carbamoyl)-1-({α-D-mannopyranosyl-(1→3)-[α-D-mannopyranosyl-(1→6)]-α-D-mannopyranosyl}oxy)-3,8,15,18-tetraazatetracosan-24-oate The title compound was prepared using procedures analogous to those described for ML-1 substituting benzyl (7R,17S)-4,9,16,19-tetraoxo-17-{3-oxo-3-[(6-oxo-6-{[2-({α-D-mannopyranosyl-(1→3)-[α-D-mannopyranosyl-(1→6)]-α-D-mannopyranosyl}oxy)ethyl]amino}hexyl)amino]propyl}-7-({2-[(α-L-fucopyranosyl)oxy]ethyl}carbamoyl)-1-({α-D-mannopyranosyl-(1→3)-[α-D-mannopyranosyl-(1→6)]-α-D-mannopyranosyl}oxy)-3,8,15,18-tetraazatetracosan-24-oate for benzyl 4-[(4,14-dioxo-9-{[3-oxo-3-({2-[(α-D-mannopyranosyl)oxy]ethyl}amino)propoxy]methyl}-1,17-di[(α-D-mannopyranosyl)oxy]-7,11-dioxa-3,15-diazaheptadecan-9-yl)amino]-4-oxobutanoate in Step D. UPLC-MS Method D: m/z=1977.05 (z=1); t$_R$=4.05 min.

Example 55

The synthesis of oligosaccharide linker 2,5-dioxopyrrolidin-1-yl (7R,17S)-4,9,16,19-tetraoxo-17-{3-oxo-3-[(6-oxo-6-{[2-({α-D-mannopyranosyl-(1→3)-[α-D-mannopyranosyl-(1→6)]-α-D-mannopyranosyl}oxy)ethyl]amino}hexyl)amino]propyl}-7-({2-[(α-L-fucopyranosyl)oxy]ethyl}carbamoyl)-1-({α-D-mannopyranosyl-(1→3)-[α-D-mannopyranosyl-(1→6)]-α-D-mannopyranosyl}oxy)-3,8,15,18-tetraazatetracosan-24-oate (ML-55) having the following structure is described.

ML-55

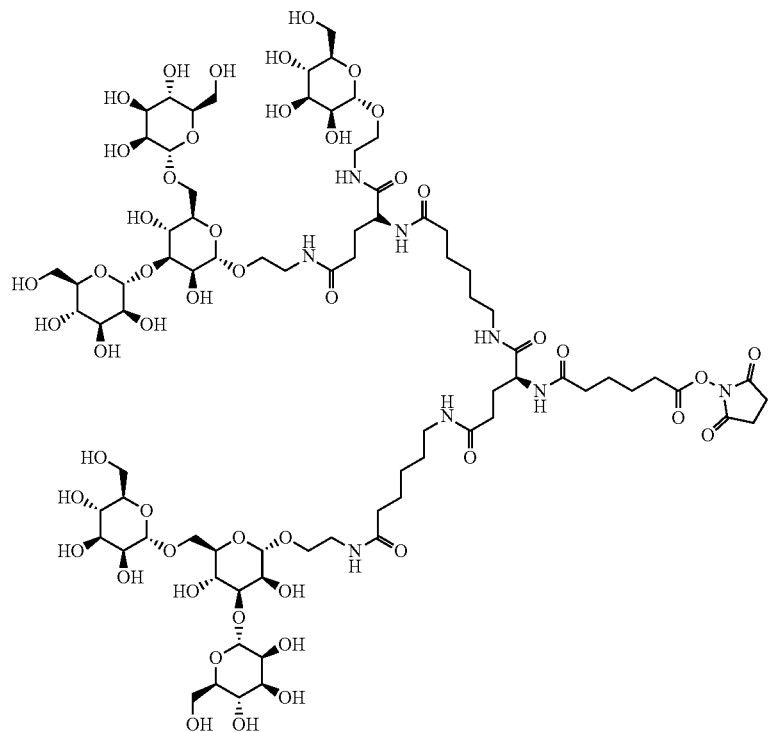

The title compound was prepared using procedures analogous to those described for ML-54 substituting 2-aminoethyl α-D-mannopyranoside for 2-aminoethyl α-L-fucopyranoside in Step D. UPLC-MS Method D: m/z=1992.99 (z=1); $t_R$=4.56 min.

Example 56

The synthesis of oligosaccharide linker 2,5-dioxopyrrolidin-1-yl (S)-4,8,16,20-tetraoxo-6-(2-oxo-2-{[2-({α-D-mannopyranosyl-(1→3)-[α-D-mannopyranosyl-(1→6)]-α-D-mannopyranosyl}oxy)ethyl]amino}ethyl)-18-{[6-oxo-6-({2-[(α-L-fucopyranosyl)oxy]ethyl)amino]hexyl}carbamoyl)-1-[(α-L-fucopyranosyl)oxy]-3,6,9,15,19-pentaazapentacosan-25-oate (ML-56) having the following structure is described.

ML-56

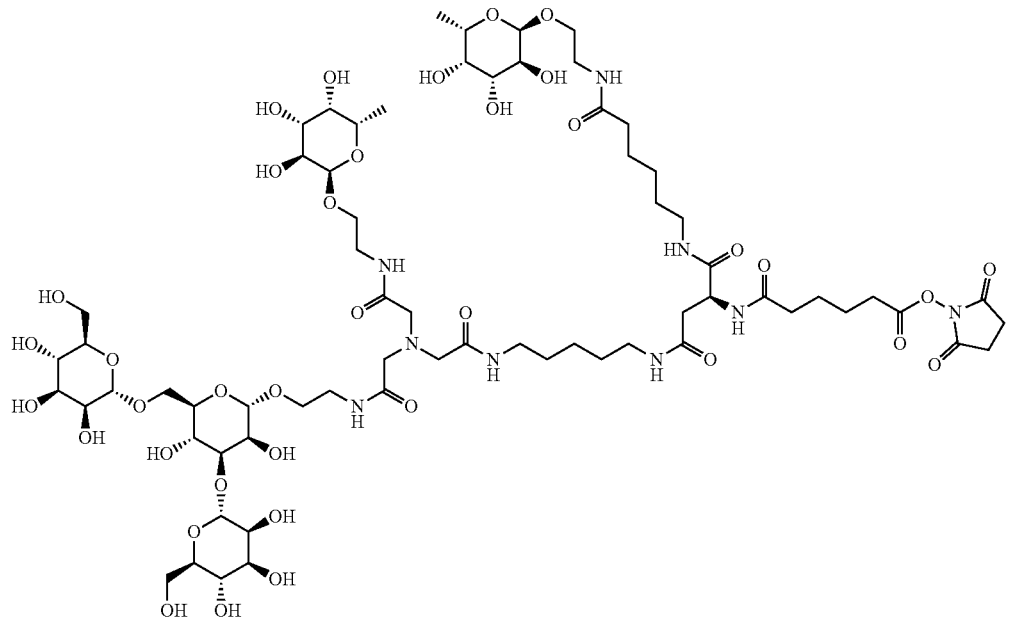

Step A. N-(5-aminopentyl)-2-{(2-oxo-2-{[2-({α-D-mannopyranosyl-(1→3)-[α-D-mannopyranosyl-(1→6)]-α-D-mannopyranosyl}oxy)ethyl]amino}ethyl)[2-oxo-2-({2-[(α-L-fucopyranosyl)oxy]ethyl}amino)ethyl]amino}acetamide The title compound was prepared using procedures analogous to those described for ML-50 substituting 2-aminoethyl α-L-fucopyranoside for 6-amino-N-{[(2-α-L-fucopyranosyl)oxy]ethyl}hexanamide in Step A, and 2-aminoethyl α-D-mannopyranosyl-(1→3)-[α-D-mannopyranosyl-(1→6)]-α-D-mannopyranoside for in 2-aminoethyl α-L-fucopyranoside Step B, respectively. UPLC-MS Method A: m/z=994.36 (z=1); $t_R$=0.93 min.

Step B. benzyl (S)-3-{[(benzyloxy)carbonyl]amino}-4-oxo-4-{[6-oxo-6-({2-[(α-L-fucopyranosyl)oxy]ethyl}amino)hexyl]amino}butanoate To a solution of 6-amino-N-{[(2-α-L-fucopyranosyl)oxy]ethyl}hexanamide (2.3 g, 7.18 mmol) in water (2 mL) was added a solution of Z-ASP(OBZL)-OH (2.57 g, 7.18 mmol) in DMF (4 mL), HOBt (1.649 g, 10.77 mmol) and EDC (2.064 g, 10.77 mmol). The mixture was stirred at rt overnight and concentrated. The residue was purified by Biotage snap on 120 g C18 column, elute with 0-60% AcCN in water to give the title compound. UPLC-MS Method C: m/z=660.22 (z=1); $t_R$=4.79 min.

Step C. (S)-3-amino-4-oxo-4-{[6-oxo-6-({2-[(α-L-fucopyranosyl)oxy]ethyl}amino)hexyl]amino}butanoic acid To a solution of benzyl (S)-3-{[(benzyloxy)carbonyl]amino}-4-oxo-4-{[6-oxo-6-({2-[(α-L-fucopyranosyl)oxy]ethyl}amino)hexyl]amino}butanoate (2.65 g, 4.02 mmol) in a mix solvent of AcCN (10 mL) and water (20 mL) was added Pd/C (43 mg, 0.402 mmol). The suspension was stirred at rt under a balloon of $H_2$ overnight. The catalyst was filtered off, and the filtrate was freeze-dried to give the title compound.

Step D. (S)-3-[6-(benzyloxy)-6-oxohexanamido)-4-oxo-4-{[6-oxo-6-({2-[(α-L-fucopyranosyl)oxy]ethyl}amino)hexyl]amino}butanoic acid To a solution of (S)-3-amino-4-oxo-4-{[6-oxo-6-({2-[(α-L-fucopyranosyl)oxy]ethyl}amino)hexyl]amino}butanoic acid (1.5 g, 3.44 mmol) in DMF (10 mL) was added benzyl (2,5-dioxopyrrolidin-1-yl) adipate (1.263 g, 3.79 mmol) and TEA (528 μL, 3.79 mmol). The mixture was stirred at rt overnight and concentrated. The residue was purified by Biotage snap on 120 g C18 column. elute with 0-50% AcCN in water to give the title compound. UPLC-MS Method A: m/z=654.26 (z=1); $t_R$=3.78 min.

Step E. 2,5-dioxopyrrolidin-1-yl (S)-4,8,16,20-tetraoxo-6-(2-oxo-2-{[2-({α-D-mannopyranosyl-(1→3)-[α-D-mannopyranosyl-(1→6)]-α-D-mannopyranosyl}oxy)ethyl]amino}ethyl)-18-{[6-oxo-6-({2-[(α-L-fucopyranosyl)oxy]ethyl}amino]hexyl}carbamoyl]-1-[(α-L-fucopyranosyl)oxy]-3,6,9,15,19-pentaazapentacosan-25-oate The title compound was prepared using procedures analogous to those described for ML-16 substituting (S)-3-[6-(benzyloxy)-6-oxohexanamido)-4-oxo-4-{[6-oxo-6-({2-[(α-L-fucopyranosyl)oxy]ethyl}amino)hexyl]amino}butanoic acid for (R)-N-(2-{[6-(benzyloxy)-6-oxohexyl]amino}-2-oxoethyl)-N-[2-({1,4-di[(α-D-mannopyranosyl)oxy]butan-2-yl}amino)-2-oxoethyl]glycine and N-(5-aminopentyl)-2-{(2-oxo-2-{[2-({α-D-mannopyranosyl-(1→3)-[α-D-mannopyranosyl-(1→6)]-α-D-mannopyranosyl}oxy)ethyl]amino}ethyl)[2-oxo-2-({2-[(α-L-fucopyranosyl)oxy]ethyl}amino)ethyl]amino}acetamide for 2-aminoethyl β-D-Mannopyranoside, respectively, in Step B. UPLC-MS Method A: m/z=1636.49 (z=1); $t_R$=2.18 min.

Example 57

The synthesis of oligosaccharide linker 2,5-dioxopyrrolidin-1-yl (S)-6-{[4-{[6-(bis{2-[(α-D-mannopyranosyl)oxy]ethyl}amino)-6-oxohexyl]amino}-1,4-dioxo-1-({2-[(α-D-mannopyranosyl)oxy]ethyl}amino)butan-2-yl]amino}-6-oxohexanoate (ML-57) having the following structure is described.

in water, 25 CV. The desired fractions were combined and freeze-dried to give the title compound. $^1$H NMR δ(ppm) (CD$_3$OD): 1.40 (3H, d, J=9.06 Hz), 1.58-1.52 (2H, m), 1.68-1.62 (2H, m), 2.06 (0H, s), 2.49 (2H, t, J=7.56 Hz), 3.15 (2H, t, J=6.94 Hz), 3.51-3.47 (2H, m), 3.74-3.59 (12H, m), 3.94-3.80 (6H, m), 5.09 (2H, s), 7.32 (1H, d, J=6.30 Hz), 7.37-7.36 (3H, m). UPLC-MS Method A: m/z=677.35 (z=1); t$_R$=2.78 min.

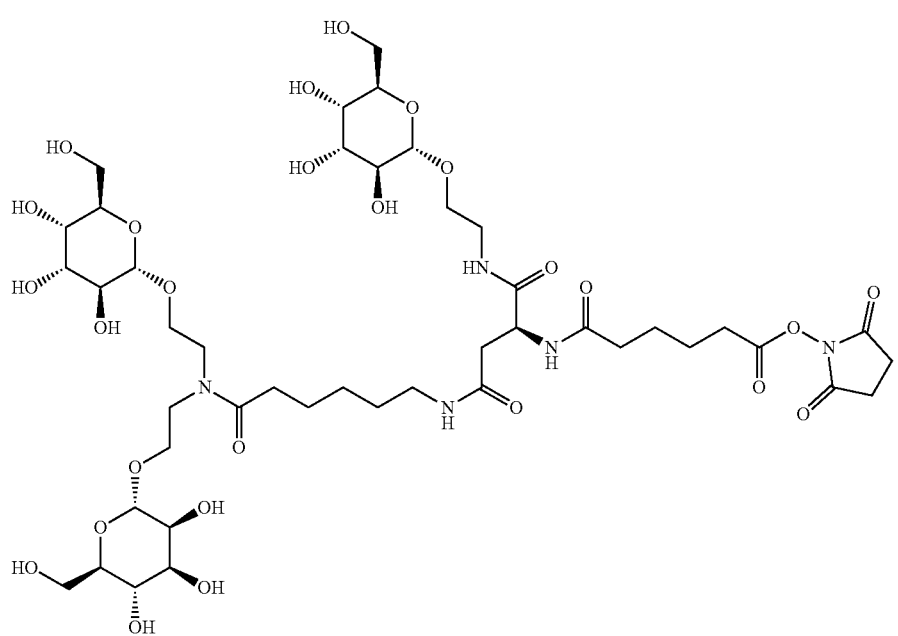

ML-57

Step A. benzyl [6-(bis{2-[(2,3,4,6-tetra-O-acetyl-α-D-mannopyranosyl)oxy]ethyl}amino)-6-oxohexyl]carbamate To a solution of bis{2-[(2,3,4,6-tetra-O-acetyl-α-D-mannopyranosyl)oxy]ethyl}amine (4.0 g, 5.22 mmol) in DMF (6 mL) at 0° C. was added 2,5-dioxopyrrolidin-1-yl 6-{[(benzyloxy)carbonyl]amino}hexanoate (4.73 g, 13.06 mmol), followed by DIPEA (1.095 mL, 6.27 mmol). The mixture was gradually warmed up to rt, stirred overnight, and concentrated. The resulting residue was purified by Biotage snap on 120 g C18 column, (two times) elute with 0-40% AcCN in water, 20 CV to give the title compound. UPLC-MS Method D: m/z=1013.42 (z=1); t$_R$=4.16 min.

Step B. benzyl [6-(bis{2-[(α-D-mannopyranosyl)oxy]ethyl}amino)-6-oxohexyl]carbamate To a solution of benzyl [6-(bis{2-[(2,3,4,6-tetra-O-acetyl-α-D-mannopyranosyl)oxy]ethyl}amino)-6-oxohexyl]carbamate (4.18 g, 4.13 mmol) in MeOH (20 mL) at rt was added NaOCH$_3$ (825 μl, 0.413 mmol). After stirring at rt overnight, to the mixture was added pre-washed DOWEX 50WX-200(H) ion-exchange resin (5.7 g), shaken then filter. the filtrate was concentrated and the residue was purified by Biotage snap on 120 g C18 column, elute with 0-15% AcCN

Step C. 6-amino-N,N-bis(2-[(α-D-mannopyranosyl)oxy]ethyl}hexanamide

To a solution of benzyl [6-(bis{2-[(α-D-mannopyranosyl)oxy]ethyl}amino)-6-oxohexyl]carbamate (2.4 g, 3.55 mmol) in water (10 ml) was added Pd/C (189 mg, 0.177 mmol). The suspension was stirred under a balloon of H$_2$ at rt overnight. The catalyst was filtered off through a cake of CELITE, and the filtrate was freeze-dried to give the title compound. UPLC-MS Method A: m/z=543.2951 (z=1); t$_R$=1.35 min.

Step D. (S)-3-[6-(benzyloxy)-6-oxohexanamido]-4-oxo-4-({2-[(α-D-mannopyranosyl)oxy]ethyl}amino)butanoic acid The title compound was prepared using procedures analogous to Step B-D described for ML-56 substituting (S)-3-[6-(benzyloxy)-6-oxohexanamido]-4-oxo-4-({2-[(α-D-mannopyranosyl)oxy]ethyl}amino)butanoic acid for 6-amino-N-{[(2-α-L-fucopyranosyl)oxy]ethyl}hexanamide in Step B. UPLC-MS Method A: m/z=557.26 (z=1); t$_R$=2.92 min.

Step E. 2,5-dioxopyrrolidin-1-yl (S)-6-{[4-{[6-(bis(2-[(α-D-mannopyranosyl)oxy]ethyl}amino)-6-oxohexyl]amino}-1,4-dioxo-1-({2-[(α-D-mannopyranosyl)oxy]ethyl}amino)butan-2-yl]amino}-6-oxohexanoate The title compound was prepared using procedures analogous to those described for ML-16 substituting (S)-3-[6-

(benzyloxy)-6-oxohexanamido]-4-oxo-4-({2-[(α-D-manno-pyranosyl)oxy]ethyl}amino)butanoic acid for (R)-N-(2-{[6-(benzyloxy)-6-oxohexyl]amino}-2-oxoethyl)-N-[2-({1,4-di[(α-D-mannopyranosyl)oxy]butan-2-yl}amino)-2-oxoethyl] glycine and 6-amino-N,N-bis{2-[(α-D-mannopyranosyl)oxy]ethyl}hexanamide for 2-aminoethyl β-D-mannopyranoside, respectively, in Step B. UPLC-MS Method A: m/z=1088.60 (z=1); $t_R$=1.91 min.

Example 58

The synthesis of oligosaccharide linker 2,5-dioxopyrrolidin-1-yl 6-{4-[3-(bis{2-[(α-D-mannopyranosyl)oxy]ethyl}amino)-3-oxopropyl]-4-[2-oxo-2-({2-[(α-L-fucopyranosyl)oxy]ethyl}amino)ethyl]piperidin-1-yl}-6-oxohexanoate (ML-58) having the following structure is described.

1.240 mmol) in DCM (14 mL) at 0° C. was added TFAA (219 μL, 1.550 mmol) slowly. After stirring at 0° C. for 3 hrs, the mixture was cooled to −30° C., to which a solution of TEA (415 μL, 2.98 mmol) in DMF (7 mL) added dropwise over 25 mins. After stirring at −30° C. for additional 30 min, to the reaction mixture was added a solution of bis{2-[(2,3,4,6-tetra-O-acetyl-α-D-mannopyranosyl)oxy]ethyl}amine (532 mg, 1.240 mmol) in DMF (14 mL). The reaction mixture was allowed to stir at rt over the weekend, and then concentrated. The residue was purified by column chromatography on Grace 120 g C18 Reverse phase, eluting with AcCN/water (gradient from 0% to 50% in 25 CV), give the title compound. UPLC-MS Method A: m/z=831.44 (z=1); $t_R$=2.86 min.

ML-58

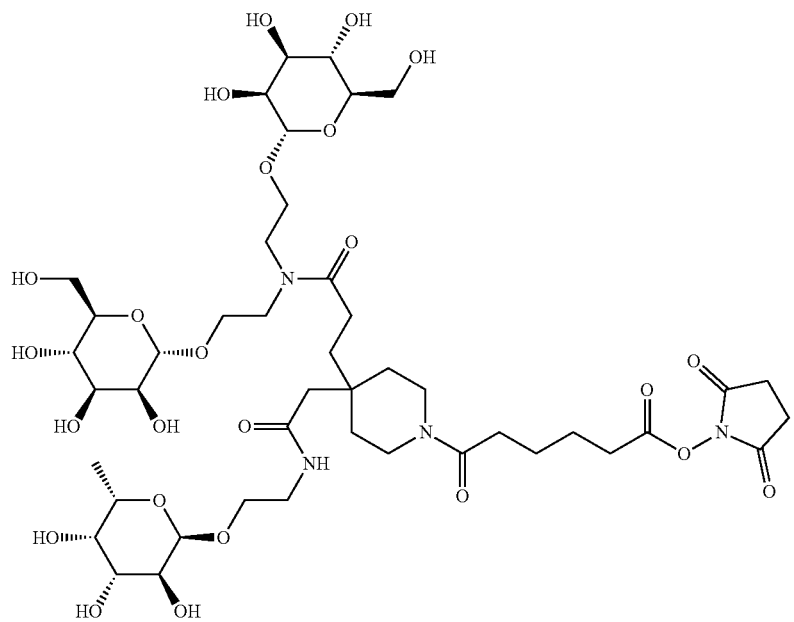

Step A. 3-{1-[6-(benzyloxy)-6-oxohexanoyl]-4-(carboxymethyl)piperidin-4-yl}propanoic acid To a solution of 2,2'-(piperidine-4,4-diyl)diacetic acid (1.019 g, 5.06 mmol) in DMF (25 mL) at 0° C. was added 2,5-dioxopyrrolidin-1-yl 6-{[(benzyloxy)carbonyl]amino}hexanoate (1.857 g, 5.57 mmol) in DMF (3 mL) portionwise over a period of 15 min and then TEA (1.694 ml, 12.15 mmol) dropwise over a period of 10 min. The resulting mixture was stirred at rt overnight. The mixture was concentrated, and the residue was purified by column chromatography on Grace 120 g C18 Reverse phase, eluting with AcCN/water (gradient from 0% to 50% in 25 CV), to give the title compound. UPLC-MS Method A: m/z=420.22 (z=1); $t_R$=3.65 min.

Step B. 2-{1-[6-(benzyloxy)-6-oxohexanoyl]-4-[3-(bis{2-[(α-D-mannopyranosyl)oxy]ethyl}amino)-3-oxopropyl]piperidin-4-yl}acetic acid To a suspension of 3-{1-[6-(benzyloxy)-6-oxohexanoyl]-4-(carboxymethyl)piperidin-4-yl}propanoic acid (520 mg, Step C. benzyl 6-{4-[3-(bis{2-[(α-D-mannopyranosyl)oxy]ethyl}amino)-3-oxopropyl]-4-(2-oxo-2-[(α-L-fucopyranosyl)oxy]ethyl)piperidin-1-yl}-6-oxohexanoate To a solution of 2-{1-[6-(benzyloxy)-6-oxohexanoyl]-4-[3-(bis{2-[(α-D-mannopyranosyl)oxy]ethyl}amino)-3-oxopropyl]piperidin-4-yl}acetic acid (219 mg, 0.264 mmol) in DMF (13 mL) at 0° C. was added EDC (86 mg, 0.448 mmol), HOBt (12 mg, 0.079 mmol), and 30 min later and 2-aminoethyl α-L-fucopyranoside (88 mg, 0.395 mmol). The mixture then was gradually warmed up to rt and stirred overnight. The mixture was concentrated, and the residue was purified by column chromatography on Gold 50 g C18 reverse phase silica gel, eluting with AcCN in H₂O (gradient from 0% to 50% in 25 CV), to give the title compound. UPLC-MS Method A: m/z=1036.57 (z=1); $t_R$=2.76 min.

Step C. 2,5-dioxopyrrolidin-1-yl 6-{4-[3-(bis{2-[(α-D-mannopyranosyl)oxy]ethyl}amino)-3-oxopropyl]-4-[2-oxo-2-({2-[(α-D-mannopyranosyl)oxy]ethyl}amino)ethyl]piperidin-1-yl}-6-oxohexanoate The title compound was prepared using procedures analogous to those described for ML-16 substituting 2-{1-[6-(benzyloxy)-6-oxohexanoyl]-4-[3-(bis{2-[(α-D-mannopyranosyl)oxy]ethyl}amino)-3-oxopropyl]piperidin-4-yl}acetic acid for (R)-N-(2-{[6-(benzyloxy)-6-oxohexyl]amino-2-oxoethyl)-N-[2-({1,4-di[(α-D-mannopyranosyl)oxy]butan-2-yl}amino)-2-oxoethyl]glycine and bis{2-[(2,3,4,6-tetra-O-acetyl-α-D-mannopyranosyl)oxy]ethyl}amine for 2-aminoethyl β-D-mannopyranoside, respectively, in Step B. UPLC-MS Method A: m/z=1027.54 (z=1); $t_R$=1.91 min.

Example 59

The synthesis of oligosaccharide linker 2,5-dioxopyrrolidin-1-yl 6-{4-[3-(bis{2-[(α-D-mannopyranosyl)oxy]ethyl}amino)-3-oxopropyl]-4-[2-oxo-2-({2-[(α-D-mannopyranosyl)oxy]ethyl}amino)ethyl]piperidin-1-yl}-6-oxohexanoate (ML-59) having the following structure is described.

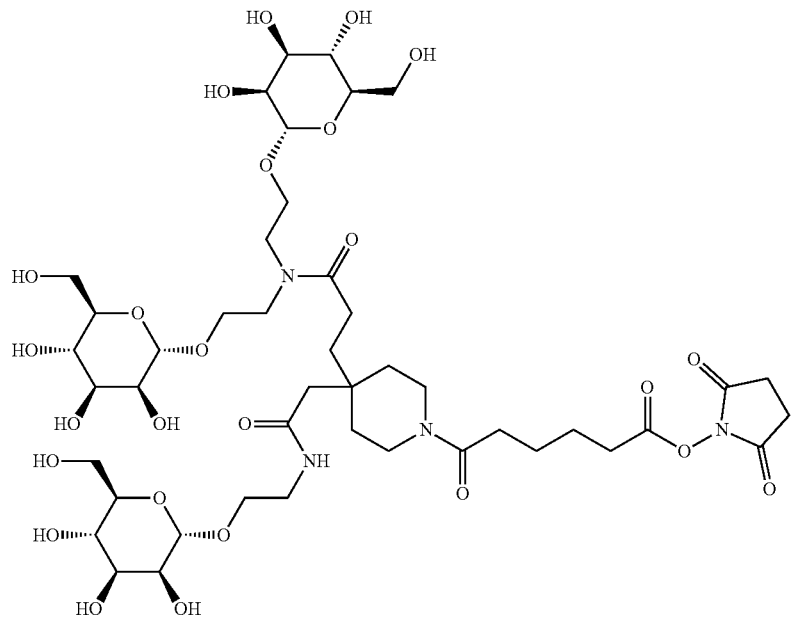

ML-59

The title compound was prepared using procedures analogous to those described for ML-58 substituting 2-aminoethyl α-D-mannopyranoside for 2-aminoethyl α-L-fucopyranoside in Step C. UPLC-MS Method A: m/z=1043.52 (z=1); $t_R$=1.80 min.

Example 60

The synthesis of oligosaccharide linker 2,5-dioxopyrrolidin-1-yl 6-{4-[3-(bis{2-[(α-D-mannopyranosyl)oxy]ethyl}amino)-3-oxopropyl]-4-[2-oxo-2-({2-[(β-D-glucopyranosyl)oxy]ethyl}amino)ethyl]piperidin-1-yl}-6-oxohexanoate (ML-60) having the following structure is described.

ML-60

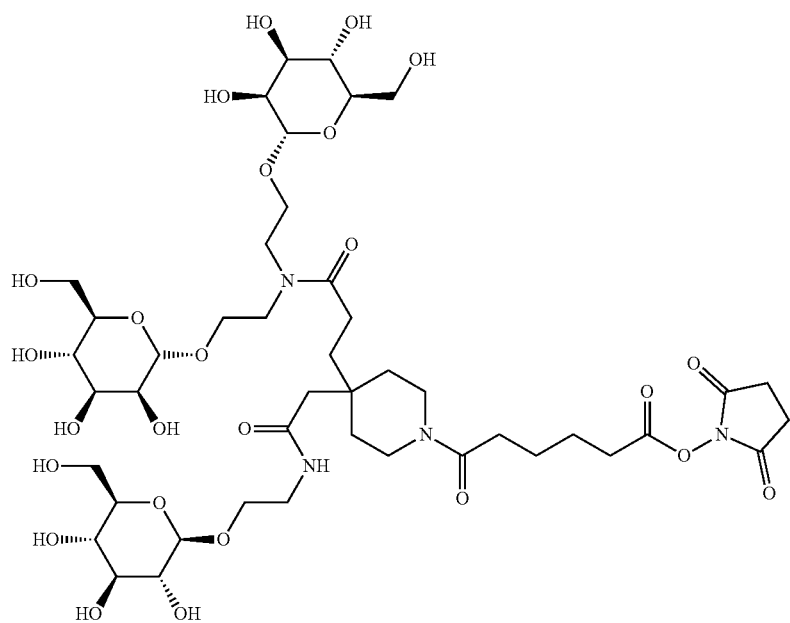

The title compound was prepared using procedures analogous to those described for ML-58 substituting 2-aminoethyl β-D-glucopyranoside for 2-aminoethyl α-L-fucopyranoside in Step C. UPLC-MS Method A: m/z=1043.52 (z=1); $t_R$=1.97 min.

Example 61

The synthesis of oligosaccharide linker 2,5-dioxopyrrolidin-1-yl (S)-4,8,15,18-tetraoxo-6-[2-oxo-2-({2-[(α-D-glucopyranosyl)oxy]ethyl}amino)ethyl]-17-[4-(6-oxo-6-{[2-({α-D-mannopyranosyl-(1→3)-[α-D-mannopyranosyl-(1→6)]-α-D-mannopyranosyl}oxy)ethyl]amino}hexanamido)butyl]-1-[(α-D-glucopyranosyl)oxy]-3,6,9,16,19-pentaazapentacosan-25-oate (ML-61) having the following structure is described.

ML-61

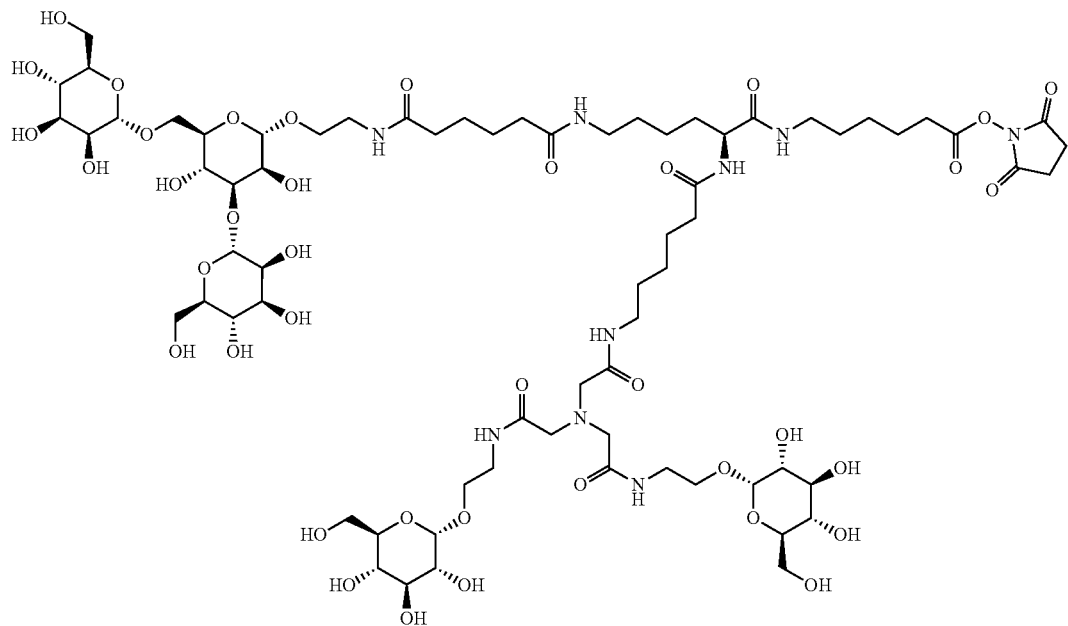

Step A. N²-[(benzyloxy)carbonyl]-N⁶-(6-oxo-6-{[2-({α-D-mannopyranosyl-(1→3)-[α-D-mannopyranosyl-(1→6)]-α-D-mannopyranosyl}oxy)ethyl]amino}hexanoyl)-L-lysine To a solution of Z-Lys-OH (363 mg, 1.294 mmol) in DMF (10 mL) at 0° C. was added 6-[(2,5-Dioxopyrrolidin-1-yl)oxy]-N-(2-{[α-D-mannopyranosyl-(1→3)-[α-D-mannopyranosyl-(1→6)]-α-D-mannopyranosyl]oxy}ethyl)-6-oxohexanamide (1.0 g, 1.294 mmol) dropwise followed DIPEA (226 µL, 1.294 mmol). The mixture was gradually warmed to rt, stirred at rt for 18 hr and concentrated. The residue was purified by C18 column (ISCO 130 g) eluted with AcCN/H₂O (0-30% in 18 CV), flow rate 85 mL/min. The desired fractions were combined and freeze-dried to give the title compound. UPLC-MS Method A: m/z=938.34 (z=1); $t_R$=3.83 min.

Step B. N⁶-(6-oxo-6-{[2-({α-D-mannopyranosyl-(1→3)-[α-D-mannopyranosyl-(1→6)]-α-D-mannopyranosyl}oxy)ethyl]amino}hexanoyl)-L-lysine To a solution of N²-[(benzyloxy)carbonyl]-N⁶-(6-oxo-6-{[2-({α-D-mannopyranosyl-(1→3)-[α-D-mannopyranosyl-(1→6)]-α-D-mannopyranosyl}oxy)ethyl]amino}hexanoyl)-L-lysine (600 mg, 0.640 mmol) in H₂O (10 mL) was added Pd/C (68.1 mg, 0.064 mmol). The resulting mixture was degassed and filled with N₂ (3×), and then degassed and stirred under a balloon H₂ for 18 hr. The reaction mixture was diluted with MeOH (10 mL). The catalyst was filtered off through a pad of CELITE, washed with MeOH (2×10 mL). The filtrate was concentrated and freeze-dried to give the title product. UPLC-MS Method A: m/z=804.41 (z=1); $t_R$=4.01 min.

Step C. 6-(2-{bis[2-oxo-2-({2-[(α-D-glucopyranosyl)oxy]ethyl}amino)ethyl]amino}acetamido)hexanoic acid To a solution of 2,2'-[(2-{[6-(benzyloxy)-6-oxohexyl]amino}-2-oxoethyl)azanediyl]diacetic acid (400 mg, 1.014 mmol) in DMF (10 mL) at rt was added EDC (486 mg, 2.54 mmol) and HOBt (388 mg, 2.54 mmol). After stirring for 30 min, to the mixture was added 2-aminoethyl α-D-glucopyranoside (498 mg, 2.231 mmol). The reaction mixture was stirred at rt for 18 hr and then concentrated. The residue was purified by C18 column chromatography (86 g column, eluted with 0-30% AcCN/H₂O in 16 CV) to give the corresponding benzyl ester of the title compound.

The resulting benzyl ester (318 mg, 0.396 mmol) was dissolved in H₂O (10 mL). To the resulting solution was added Pd/C (108 mg, 0.101 mmol), degassed and filled with N₂ (3×), then degassed and stirred under a balloon of H₂ for 18 hr. The suspension was then diluted with MeOH (10 mL), filtered through a pad of CELITE. The catalyst was washed with MeOH (3×10 mL). The filtrate was concentrated and freeze-dried to give the title compound. UPLC-MS Method A: m/z=715.39 (z=1); $t_R$=3.96 min.

Step D. N²-[6-(2-{bis[2-oxo-2-({2-[(α-D-glucopyranosyl)oxy]ethyl}amino)ethyl]amino}acetamido)hexanoyl]-N⁶-(6-oxo-6-{[2-({α-D-mannopyranosyl-(1→3)-[α-D-mannopyranosyl-(1→6)]-α-D-mannopyranosyl}oxy)ethyl]amino}hexanoyl)-L-lysine To a solution of 6-(2-{bis[2-oxo-2-({2-[(α-D-glucopyranosyl)oxy]ethyl}amino)ethyl]amino}acetamido)hexanoic acid (200 mg, 0.280 mmol) in DMF (2 mL) at 0° C. was added TSTU (84 mg, 0.280 mmol) followed by DIPEA (49 µL, 0.280 mmol). After the mixture was warmed up gradually to rt and stirred at rt for 2 hr. UPLC-MS analysis of an aliquot of the reaction mixture indicated the clean formation of the activated ester: UPLC-MS Method: m/z=812.20 (z=1); $t_R$=3.224 min. The crude product was used without purification.

To a solution of 6-(2-{bis[2-oxo-2-({2-[(α-D-glucopyranosyl)oxy]ethyl}amino)ethyl]amino}acetamido)hexanoic acid (160 mg, 0.199 mmol) in DMSO (2 mL) at rt was added the aforementioned crude activated ester (226 mg, 0.279 mmol) in DMF (2 mL) and DIPEA (49 µL, 0.279 mmol). After stirring for 18 hr, the reaction mixture was added dropwise to acetone (35 mL), and a white precipitate formed, which was separated by centrifugation (3500 rpm, 20 min). The solid was redissolved in AcCN/H₂O and purified by C18 column (eluted with AcCN/H₂O 0-50% in 16 CV, 43 g column). The desired fractions were combined and freeze-dried to give the title compound. UPLC-MS Method B: m/z=151.63 (z=1); $t_R$=3.02 min.

Step E. benzyl (S)-4,8,15,18-tetraoxo-6-[2-oxo-2-({2-[(α-D-glucopyranosyl) oxy]ethyl}amino)ethyl]-17-[4-(6-oxo-6-{[2-({α-D-mannopyranosyl-(1 →3)-[α-D-mannopyranosyl-(1 →6)]-α-D-mannopyranosyl}oxy)ethyl]amino}hexanamido)butyl]-1-[(α-D-glucopyranosyl)oxy]-3,6,9,16,19-pentaazapentacosan-25-oate To a solution of N²-[6-(2-{bis[2-oxo-2-({2-[(α-D-glucopyranosyl)oxy]ethyl}amino)ethyl]amino}acetamido)hexanoyl]-N⁶-(6-oxo-6-{[2-({α-D-mannopyranosyl-(1→3)-[α-D-mannopyranosyl-(1→6)]-α-D-mannopyranosyl}oxy)ethyl]amino}hexanoyl)-L-lysine (150 mg, 0.100 mmol) in DMF (3 mL) at 0° C. was added TSTU (30 mg, 0.100 mmol) followed by DIPEA (1 eq). The reaction mixture was warmed up to rt and stirred at rt for 2 hr. To the resulting solution was added 6-(benzyloxy)-6-oxohexan-1-aminium tosylate (59.0 mg, 0.150 mmol) in DMF (5 mL) portionwise over 15 min and followed by addition of DIPEA (1.5 eq). The resulting mixture was stirred at rt overnight and concentrated. The residue was purified by column chromatography on 86 g C18 reverse phase silica gel, eluting with AcCN/H₂O (gradient from 0% to 50% in 16 CV). The desired fractions were combined and freeze-dried to give the title compound. UPLC-MS Method B: m/z=1704.31 (z=1); $t_R$=3.84 min.

Step F. 2,5-dioxopyrrolidin-1-yl (S)-4,8,15,18-tetraoxo-6-[2-oxo-2-({2-[(α-D-glucopyranosyl)oxy]ethyl}amino)ethyl]-17-[4-(6-oxo-6-{[2-({α-D-mannopyranosyl-(1→3)-[α-D-mannopyranosyl-(1→6)]-α-D-mannopyranosyl}oxy)ethyl]amino}hexanamido)butyl]-1-[(α-D-glucopyranosyl)oxy]-3,6,9,16,19-pentaazapentacosan-25-oate The title compound was prepared using procedures analogous to those described for ML-1 substituting benzyl (S)-4,8,15,18-tetraoxo-6-[2-oxo-2-({2-[(α-D-glucopyranosyl)oxy]ethyl}amino)ethyl]-17-[4-(6-oxo-6-{[2-({α-D-mannopyranosyl-(1→3)-[α-D-mannopyranosyl-(1→6)]-α-D-mannopyranosyl}oxy)ethyl]amino}hexanamido)butyl]-1-[(α-D-glucopyranosyl)oxy]-3,6,9,16,19-pentaazapentacosan-25-oate for benzyl 4-[(4,14-dioxo-9-{[3-oxo-3-({2-[(α-D-mannopyranosyl)oxy]ethyl}amino)propoxy]methyl}-1,17-di[(α-D-mannopyranosyl)oxy]-7,11- dioxa-3,15-diazaheptadecan-9-yl)amino]-4-oxobutanoate in Step D. UPLC-MS Method B: m/z=1711.80 (z=1); $t_R$=3.33 min.

Example 62

The synthesis of oligosaccharide linker 2,5-dioxopyrrolidin-1-yl (S)-4,8,15,18-tetraoxo-6-(2-oxo-2-{[2-({α-D-mannopyranosyl-(1→3)-[α-D-mannopyranosyl-(1→6)]-α-D-mannopyranosyl}oxy)ethyl]amino}ethyl)-17-[4-(6-oxo-6-{[2-({α-D-mannopyranosyl-(1→3)-[α-D-mannopyranosyl-(1→6)]-α-D-mannopyranosyl}oxy)ethyl]amino}hexanamido)butyl]-1-({α-D-mannopyranosyl-(1→3)-[α-D-mannopyranosyl-(1→6)]-α-D-mannopyranosyl}oxy)-3,6,9,16,19-pentaazapentacosan-25-oate (ML-62) having the following structure is described.

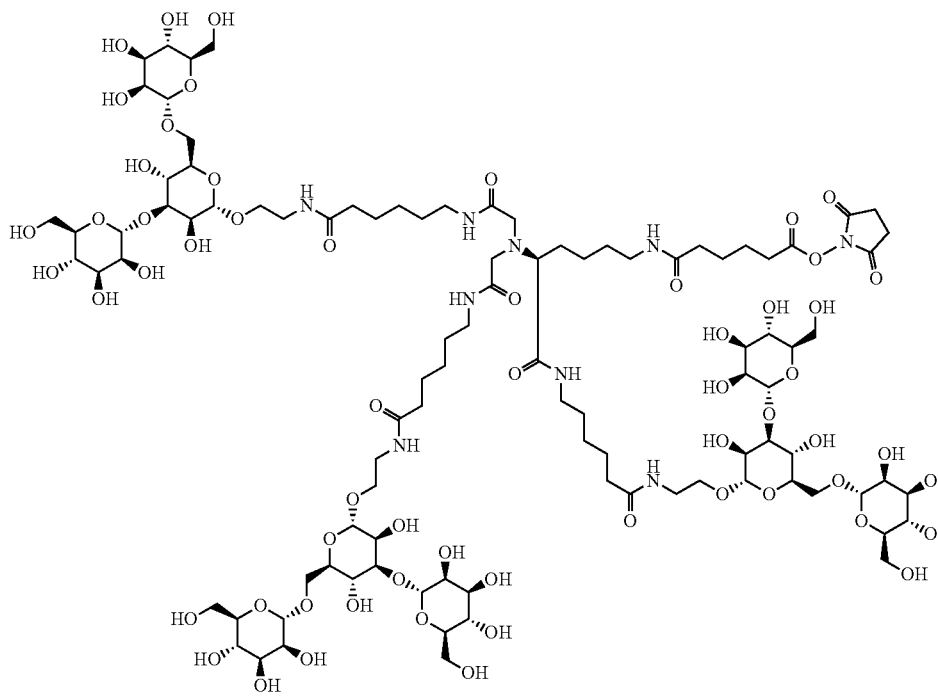

ML-62

The title compound was prepared using procedures analogous to those described for ML-9 substituting 6-amino-N-[2-({α-D-mannopyranosyl-(1→3)-[α-D-mannopyranosyl-(1→6)]-α-D-mannopyranosyl}oxy)ethyl]hexanamide for 2-aminoethyl α-D-mannopyranoside in Step A. UPLC-MS Method B: m/z=1208.18 (z=2); $t_R$=3.49 min.

Example 63

The synthesis of oligosaccharide linker 2,5-dioxopyrrolidin-1-yl 6-(2-{[2-({6-[3,5-bis({2-[(α-L-fucopyranosyl)oxy]ethyl}carbamoyl)piperidin-1-yl]-6-oxohexyl}amino)-2-oxoethyl](2-oxo-2-{[2-({α-D-mannopyranosyl-(1 →3)4α-D-mannopyranosyl-(1→6)]-α-D-mannopyranosyl}oxy)ethyl]amino}ethyl)amino}acetamido)hexanoate (ML-63) having the following structure is described.

ML-63

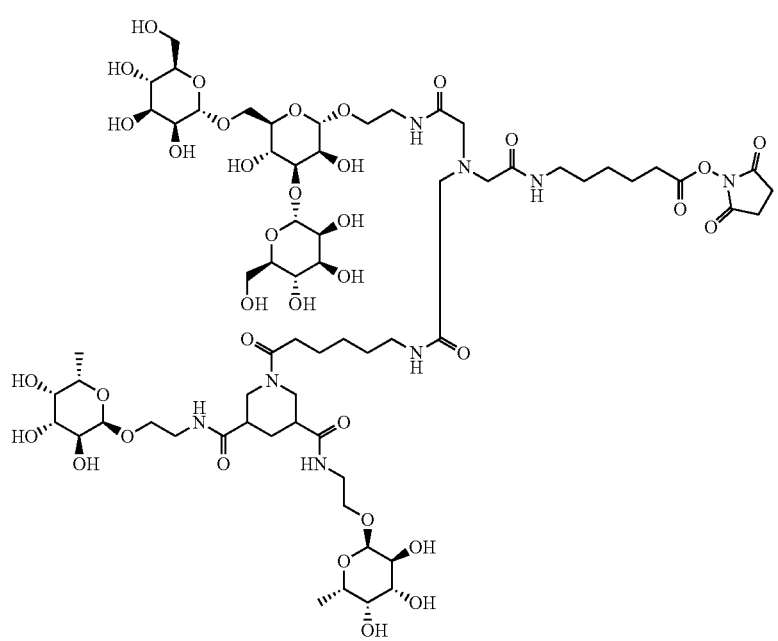

Step A. N³,N⁵-bis{2-[(α-L-fucopyranosyl)oxy]ethyl}pyridine-3,5-dicarboxamide To a stirred solution of pyridine-3,5-dicarboxylic acid (400 mg, 2.394 mmol) in DMF (30 mL) at rt was added 2-aminoethyl α-L-fucopyranoside (1.488 g, 7.18 mmol), DMAP (731 mg, 5.98 mmol) and EDC (2.294 g, 11.97 mmol). After stirring overnight, the reaction mixture was diluted with H₂O (30 mL) and extracted with EtOAc (30× mL). The aqueous phase was separated and concentrated, and the residue was purified on a C18 column (300 g), eluting with 0-30% AcCN/H₂O in 50 min. The desired fractions were collected and freeze-dried to give the title compound. LC-MS Method A: m/z=546 (z=1); $t_R$=1.79 min.

Step B. N³,N⁵-bis{2-[(α-L-fucopyranosyl)oxy]ethyl}piperidine-3,5-dicarboxamide To a stirred solution of N³,N⁵-bis{2-[(α-L-fucopyranosyl)oxy]ethyl}pyridine-3,5-dicarboxamide (677 mg, 1.241 mmol) in H₂O (5 mL) at rt was added PtO₂ (85 mg, 0.372 mmol). The mixture solution was degassed and refilled with N₂, and then stirred under a balloon of H₂ at rt for 2 hr. The reaction mixture was concentrated and re-dissolved in MeOH. The remaining solid was collected after centrifugation, and washed with MeOH once more. The supernatant was concentrated to give the title product. LC-MS Method A: m/z=552 (z=1); $t_R$=0.20 min.

Step C. benzyl (6-13,5-bis({2-[(α-L-fucopyranosyl)oxy]ethyl}carbamoyl)piperidin-1-yl]-6-oxohexyl}carbamate To a stirred solution of 2,5-dioxopyrrolidin-1-yl 6-{[(benzyloxy)carbonyl]amino}hexanoate (948 mg, 2.54 mmol) in DMF (4 mL) at rt was added N³,N⁵-bis{2-[(α-L-fucopyranosyl)oxy]ethyl}piperidine-3,5-dicarboxamide (560 mg, 1.015 mmol) in DMF (6 mL) and TEA (354 μL, 2.54 mmol). The reaction mixture was stirred at rt overnight and then concentrated. The residue was purified by C18 reverse phase column, eluting with 0-50% AcCN/H₂O, to give the title compound. UPLC Method A: m/z=799 (z=1); $t_R$=3.06 min.

Step D. 1-(6-aminohexanoyl)-N³,N⁵-bis{2-[(α-L-fucopyranosyl)oxy]ethyl}piperidine-3,5-dicarboxamide To a stirred solution of benzyl{6-[3,5-bis({2-[(α-L-fucopyranosyl)oxy]ethyl}carbamoyl)piperidin-1-yl]-6-oxohexyl}carbamate (220 mg, 0.275 mmol) in H₂O (5 mL) at rt was added Pd(OH)₂ (58.0 mg, 0.083 mmol). The resulting suspension was degassed and then refilled with N₂, and then stirred under a balloon of H₂ at rt for 2 hr. The catalyst was filtered off through a pad of CELITE and washed with H₂O. The filtrate was freeze-dried to give the title compound. UPLC Method A: m/z=665 (z=1); $t_R$=1.13 min.

Step E. 2,5-dioxopyrrolidin-1-yl 6-(2-{[2-({6-[3,5-bis({2-[(α-L-fucopyranosyl)oxy]ethyl}carbamoyl)piperidin-1-yl]-6-oxohexyl}amino)-2-oxoethyl](2-oxo-2-{[2-({α-D-mannopyranosyl-(1→3)-[α-D-mannopyranosyl-(1→6)]-α-D-mannopyranosyl}oxy)ethyl]amino}ethyl)amino}acetamido)hexanoate The title compound was prepared using procedures analogous to those described for ML-23 substituting 1-(6-aminohexanoyl)-N³,N⁵-bis{2-[(α-L-fucopyranosyl)oxy]ethyl}piperidine-3,5-dicarboxamide for (S)-2-(6-aminohexanamido)-N¹,N⁵-bis{2-[(α-D-mannopyranosyl)oxy]ethyl}pentanediamide in Step H. UPLC Method A: m/z=1577 (z=1); $t_R$=2.18 min.

Example 64

The synthesis of oligosaccharide linker 2,5-dioxopyrrolidin-1-yl 6-(2-{[2-({6-[3,5-bis({2-[(α-L-fucopyranosyl)oxy]ethyl}carbamoyl)piperidin-1-yl]-6-oxohexyl}amino)-2-oxoethyl][2-oxo-2-({2-[(α-L-fucopyranosyl)oxy]

ethyl}amino)ethyl]amino}acetamido)hexanoate (ML-64) having the following structure is described.

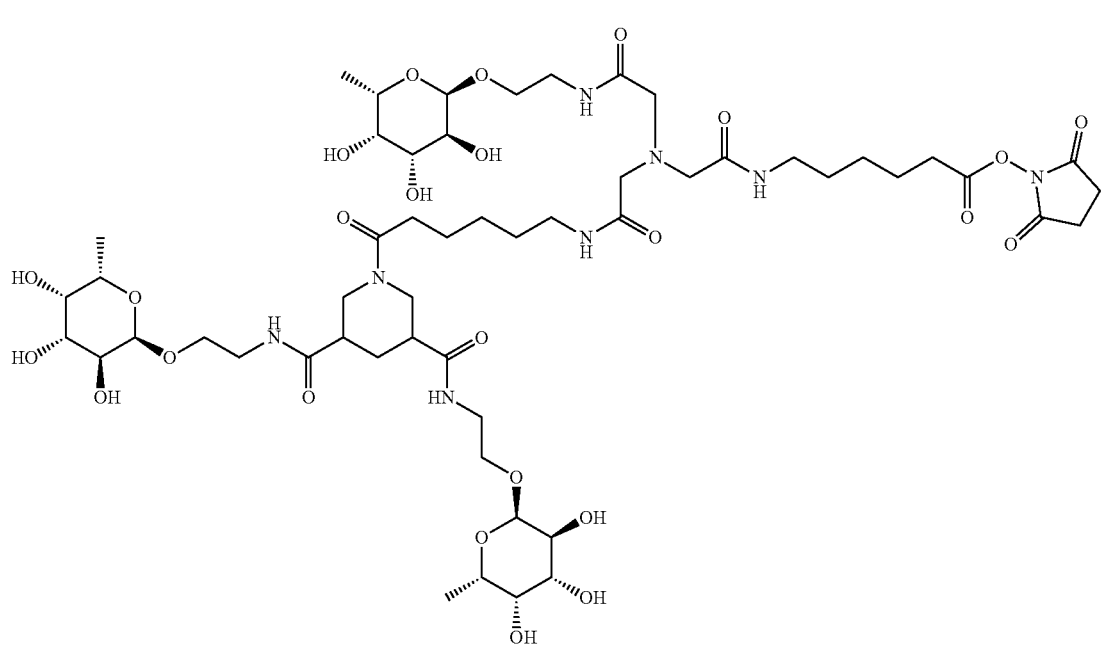

ML-64

The title compound was prepared using procedures analogous to those described for ML-23 substituting 2-aminoethyl α-L-fucopyranoside for 6-amino-N-[2-({α-D-mannopyranosyl-(1→3)-[α-D-mannopyranosyl-(1→6)]-α-D-mannopyranosyl}oxy)ethyl]hexanamide in Step C and 1-(6-aminohexanoyl)-N³,N⁵-bis{2-[(α-L-fucopyranosyl)oxy]ethyl}piperidine-3,5-dicarboxamide for (S)-2-(6-aminohexanamido)-N¹,N⁵-bis{2-[(α-D-mannopyranosyl)oxy]ethyl}pentanediamide in Step H, respectively. UPLC Method A: m/z=1124 (z=1); $t_R$=2.21 min.

Example 65

Synthesis of Conjugates with Same Linker-Oligosaccharides on $N^{A1}$ and $N^{B29}$ of Insulin In an appropriate sized container, insulin is suspended at rt in an organic solvent, e.g., DMSO, in the presence of a base, e.g., TEA. The mixture is allowed to stir gently until insulin completely dissolved. In a separate vial, an activated ester intermediate is dissolved in an organic solvent, e.g., DMSO, at rt. Aliquots of the solution of the activated ester is added over a period of time to the solution containing insulin until UPLC chromatogram shows that all of the unmodified insulin has reacted and that a substantial portion of the reaction mixture has converted into A1,B29-conjugated insulin. The reaction is quenched by the addition of an amine nucleophile, e.g., 2-aminoethanol. The reaction solution is stirred at rt for 30 min. The resulting solution is carefully diluted with cold H₂O (20×) at 0° C., and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (Poly-SULFOETHYL A column, PolyLC Inc., 250×21 mm, 5 m, 1000 Å; Buffer A: 0.1% (v/v)H₃PO₄/25% AcCN; Buffer B: 0.1% (v/v)H₃PO₄/25% AcCN/0.5 M NaCl). Fractions containing A1,B29-conjugate with desired purity are combined and concentrated using TFF system or Amicon Ultra-15. The resulting solution is then further purified by reverse phase HPLC (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 66

Synthesis of Conjugates with Linker-Oligosaccharide on $N^{A1}$ of Insulin

In an appropriate sized container, insulin is suspended at rt in an organic solvent, e.g., DMSO, in the presence of a base, e.g., TEA. The mixture is allowed to stir gently until insulin completely dissolved. In a separate vial, an activated ester intermediate is dissolved in an organic solvent, e.g., DMSO, at rt. Aliquots of the solution of the activated ester is added over a period of time to the solution containing insulin until UPLC chromatogram shows that most of the unmodified insulin has reacted and that a substantial portion of the reaction mixture has converted into A1-conjugated insulin. The reaction is quenched by the addition of an amine nucleophile, e.g., 2-aminoethanol. The reaction solution is stirred at rt for 30 min. The resulting solution is carefully diluted with cold H₂O (20×) at 0° C., and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (Poly-SULFOETHYL A column, PolyLC Inc., 250×21 mm, 5 μm, 1000 Å; Buffer A: 0.1% (v/v)H₃PO₄/25% AcCN; Buffer B: 0.1% (v/v)H₃PO₄/25% AcCN/0.5 M NaCl). Fractions containing A1-conjugate with desired purity are combined and concentrated using TFF system or Amicon Ultra-15. The resulting solution is then further purified by reverse phase HPLC (Waters C4 250×50 mm column, 10 µm, 1000 Å column or Kromasil C8 250×50 mm, 10 µm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 67

Synthesis of Conjugates with Linker-Oligosaccharide on $N^{B1}$ of Insulin

In an appropriate sized container, protected insulin, e.g., $N^{A1},N^{\epsilon B29}$-bis[(9H-fluoren-9-ylmethoxy)carbonyl]- or $N^{A1}$, $N^{\epsilon B29}$-bis(trifluoroacetyl)human insulin (WO 2015051052 A2) is suspended at rt in an organic solvent, e.g., DMSO, in the presence of a base, e.g., TEA. The mixture is allowed to stir gently until protected insulin completely dissolved. In a separate vial, an activated ester intermediate is dissolved in an organic solvent, e.g., DMSO, at rt. Aliquots of the solution of the activated ester is added over a period of time to the solution containing insulin until UPLC chromatogram shows that all of the unmodified insulin has reacted and that a substantial portion of the reaction mixture has converted into B1-conjugated protected insulin. The reaction is quenched at low temperature by the addition of excess amount of an amine nucleophile, e.g., 2-aminoethanol or ammonia. The reaction solution is stirred at low temperature until UPLC chromatogram indicated complete removal of the protecting group. The resulting solution is carefully diluted with cold H₂O (20×) at 0° C., and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 µm, 1000 Å; Buffer A: 0.1% (v/v)H₃PO₄/25% AcCN; Buffer B: 0.1% (v/v)H₃PO₄/25% AcCN/0.5 M NaCl). Fractions containing B1-conjugate with desired purity are combined and concentrated using TFF system or Amicon Ultra-15. The resulting solution is then further purified by reverse phase HPLC (Waters C4 250×50 mm column, 10 µm, 1000 Å column or Kromasil C8 250×50 mm, 10 µm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 68

Synthesis of Conjugates with Linker-Oligosaccharide on $N^{\epsilon B29}$ of Insulin In an appropriate sized container, insulin is dissolved, with gentle stirring, at rt in a mixed solvent: 2:3 v/v 0.1 M Na₂CO₃:AcCN. After the mixture cleared, the pH is adjusted to the value of 10.5-10.8 using alkaline solution, e.g., 0.1 N NaOH. In a separate vial, an activated ester intermediate is dissolved in an organic solvent, e.g., DMSO, at rt. Aliquots of the solution of the activated ester is added over a period of time to the solution containing insulin until UPLC chromatogram shows that most of the unmodified insulin has reacted and that a substantial portion of the reaction mixture has converted into B29-conjugated insulin. The reaction is quenched by the addition of an amine nucleophile, e.g., 2-aminoethanol. The reaction solution is stirred at rt for 30 min. The resulting solution is carefully diluted with cold H₂O (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 µm, 1000 Å; Buffer A: 0.1% (v/v) H₃PO₄/25% AcCN; Buffer B: 0.1% (v/v)H₃PO₄/25% AcCN/0.5 M NaCl). Fractions containing B29-conjugate with desired purity are combined and concentrated using TFF system or Amicon Ultra-15. The resulting solution is then further purified by reverse phase HPLC (Waters C4 250×50 mm column, 10 µm, 1000 Å column or Kromasil C8 250×50 mm, 10 µm, 100 Å column; Buffer A: 0.05-0.1% TFA in water; Buffer B: 0.05-0.1% TFA in AcCN). Fractions containing the title conjugate are combined and freeze-dried or buffer exchanged using TFF system and/or Amicon Ultra-15 to give the title product.

Example 69

Synthesis of Conjugates with Same Linker-Oligosaccharides on $N^{B1}$ and $N^{\epsilon B29}$ of Insulin In an appropriate sized container, protected insulin, e.g., $N^{A1}$-(9H-fluoren-9-ylmethoxy)carbonyl- or $N^{A1}$-(trifluoroacetyl)human insulin is suspended at rt in an organic solvent, e.g., DMSO, in the presence of a base, e.g., TEA. The mixture is allowed to stir gently until protected insulin completely dissolved. In a separate vial, an activated ester intermediate is dissolved in an organic solvent, e.g., DMSO, at rt. Aliquots of the solution of the activated ester are added over a period of time to the solution containing insulin until UPLC chromatogram shows that all of the unmodified protected insulin has reacted and that a substantial portion of the reaction mixture has converted into B1,B29-conjugated protected insulin. The reaction is quenched at low temperature by the addition of excess amount of an amine nucleophile, e.g., 2-piperidine, aminoethanol, or ammonia. The reaction solution is stirred at low temperature until UPLC chromatogram indicated complete removal of the protecting group. The resulting solution is carefully diluted with cold H₂O (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 µm, 1000 Å; Buffer A: 0.1% (v/v)H₃PO₄/25% AcCN; Buffer B: 0.1% (v/v)H₃PO₄/25% AcCN/0.5 M NaCl). Fractions containing B1,B29-conjugate with desired purity are combined and concentrated using TFF system or Amicon Ultra-15. The resulting solution is then further purified by reverse phase HPLC (Waters C4 250×50 mm column, 10 µm, 1000 Å column or Kromasil C8 250×50 mm, 10 µm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 70

Synthesis of Conjugates with Same Linker-Oligosaccharides on $N^{A1}$, $N^{B1}$, and $N^{\epsilon B29}$ of Insulin In an appropriate sized container, insulin is suspended at rt in an organic solvent, e.g., DMSO, in the presence of a base, e.g., TEA. The mixture is allowed to stir gently until insulin completely dissolved. In a separate vial, an activated ester intermediate is dissolved in an organic solvent, e.g., DMSO, at rt. Aliquots of the solution of the activated ester are added over a period of time to the solution containing insulin until UPLC chromatogram shows that all of the unmodified insulin has reacted and that a substantial portion of the reaction mixture has converted into A1-, B1-, and B29-conjugated insulin. The reaction is quenched by the addition of an amine nucleophile, e.g., 2-aminoethanol. The reaction solution is stirred at rt for 30 min. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 μm, 1000 Å; Buffer A: 0.1% (v/v)$H_3PO_4$/25% AcCN; Buffer B: 0.1% (v/v)$H_3PO_4$/25% AcCN/0.5 M NaCl).

Fractions containing A1, B1, B29-conjugate with desired purity are combined and concentrated using TFF system or Amicon Ultra-15. The resulting solution is then further purified by reverse phase HPLC (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 71

Synthesis of Conjugates with Different Linker-Oligosaccharides on $N^{A1}$ (and same on $N^{B1}$) and $N^{\epsilon B29}$ of Insulin In an appropriate sized container, $N^{\epsilon B29}$-conjugated insulin is suspended at rt in an organic solvent, e.g., DMSO, in the presence of a base, e.g., TEA. The mixture is allowed to stir gently until insulin completely dissolved. In a separate vial, an activated ester intermediate was dissolved in an organic solvent, e.g., DMSO, at rt. Aliquots of the solution of the activated ester are added over a period of time to the solution containing insulin until UPLC chromatogram shows that all of the starting insulin had been reacted and that a substantial portion of the reaction mixture had been converted into A1,B29-conjugated insulin (or A1,B1,B29-conjugated insulin). The reaction is quenched by the addition of an amine nucleophile, e.g., 2-aminoethanol. The reaction solution is stirred at rt for 30 min. The resulting solution is carefully diluted with cold $H_2O$ (20×) at 0° C. and its pH was adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution may be first subjected to ion exchange chromatography (PolySULFOETHYL A column, PolyLC Inc., 250×21 mm, 5 μm, 1000 Å; Buffer A: 0.1% (v/v)$H_3PO_4$/25% AcCN; Buffer B: 0.1% (v/v)$H_3PO_4$/25% AcCN/0.5 M NaCl). Fractions containing A1,B29-conjugate or A1,B1,B29-conjugate with desired purity are combined and concentrated using TFF system or Amicon Ultra-15. The resulting solution is then further purified by reverse phase HPLC (Waters C4 250×50 mm column, 10 μm, 1000 Å column or Kromasil C8 250×50 mm, 10 μm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 72

Insulin Receptor Phosphorylation Assays were performed as follows.

CHO cells stably expressing human IR(B) were in grown in F12 cell media containing 10% FBS and antibiotics (G418, Penicillin/Strepavidin) for at least 8 hours and then serum starved by switching to F12 media containing 0.5% BSA (insulin-free) in place of FBS for overnight growth. Cells were harvested and frozen in aliquots for use in the MSD pIR assay. Briefly, the frozen cells were plated in either 96-well (40,000 cells/well, Method A) or 384-well (10,000 cells/well, Method B) clear tissue culture plates and allowed to recover. IOC molecules at the appropriate concentrations were added and the cells incubated for 8 min at 37° C. The media was aspirated and chilled MSD cell lysis buffer was added as per MSD kit instructions. The cells were lysed on ice for 40 min and the lysate then mixed for 10 minutes at room temperature. The lysate was transferred to the MSD kit pIR detection plates. The remainder of the assay was carried out following the MSD kit recommended protocol.

Example 73

Insulin Receptor Binding Assays were performed as follows.

Two competition binding assays were utilized to determine IOC affinity for the human insulin receptor type B (IR(B)) against the endogenous ligand, insulin, labeled with $^{125}$[I].

Method C: IR binding assay was a whole cell binding method using CHO cells overexpressing human IR(B). The cells were grown in F12 media containing 10% FBS and antibiotics (G418, Penicillin/Strepavidin), plated at 40,000 cells/well in a 96-well tissue culture plate for at least 8 hrs. The cells were then serum starved by switching to DMEM media containing 1% BSA (insulin-free) overnight. The cells were washed twice with chilled DMEM media containing 1% BSA (insulin-free) followed by the addition of IOC molecules at appropriate concentration in 90 μL of the same media. The cells were incubated on ice for 60 min. The $^{125}$[I]-insulin (10 μL) was added at 0.015 nM final concentration and incubated on ice for 4 hrs. The cells were gently washed three times with chilled media and lysed with 30 μL of Cell Signaling lysis buffer (cat #9803) with shaking for 10 min at room temperature. The lysate was added to scintillation liquid and counted to determine $^{125}$[I]-insulin binding to IR and the titration effects of IOC molecules on this interaction.

Method D: IR binding assay was run in a scintillation proximity assay (SPA) in 384-well format using cell membranes prepared from CHO cells overexpressing human IR(B) grown in F12 media containing 10% FBS and antibiotics (G418, Penicillin/Strepavidin). Cell membranes were prepared in 50 mM Tris buffer, pH 7.8 containing 5 mM $MgCl_2$. The assay buffer contained 50 mM Tris buffer, pH 7.5, 150 mM NaCl, 1 mM $CaCl_2$, 5 mM MgCl2, 0.1% BSA and protease inhibitors (Complete-Mini-Roche). Cell membranes were added to WGA PVT PEI SPA beads (5 mg/ml final concentration) followed by addition of IOC molecules at appropriate concentrations. After 5-15 min incubation at room temperature, $^{125}$[I]-insulin was added at 0.015 nM final concentration for a final total volume of 50 µL. The mixture was incubated with shaking at room temperature for 1 to 12 hours followed by scintillation counting to determine $^{125}$[I]-insulin binding to IR and the titration effects of IOC molecules on this interaction.

Example 74

Human macrophage mannose receptor 1 (MRC1) Binding Assays were performed as follows.

The competition binding assay for MRC1 utilized a ligand, mannosylated-BSA labeled with the DELFIA Eu-N1-ITC reagent, as reported in the literature. Assay was performed either in a 96-well plate with 100 µL well volume (Method E) or in a 384-well plate with 25 µL well volume (Method F). Anti-MRC1 antibody (2 ng/µl) in PBS containing 1% stabilizer BSA was added to a Protein G plate that had been washed three times with 100 µl of 50 mM Tris buffer, pH 7.5 containing 100 mM NaCl, 5 mM $CaCl_2$, 1 mM $MgCl_2$ and 0.1% Tween-20 (wash buffer). The antibody was incubated in the plate for 1 hr at room temperature with shaking. The plate was washed with wash buffer 3-5 times followed by addition of MRC1 (2 ng/µl final concentration) in PBS containing 1% stabilizer BSA. The plate was incubated at room temperature with gentle shaking for 1 hr. The plate was washed three times with wash buffer. The IOC molecules in 12.5 µL (or 50 µL depending on plate format) buffer at appropriate concentrations were added followed by 12.5 µL (or 50 µL) Eu-mannosylated-BSA (0.1 nM final concentration) in 50 mM Tris, pH 7.5 containing 100 mM NaCl, 5 mM $CaCl_2$, 1 mM $MgCl_2$ and 0.2% stabilizer BSA. The plate was incubated for 2 hrs at room temperature with shaking followed by washing three times with wash buffer. Perkin Elmer Eu-inducer reagent was added and incubated for 30 min at room temperature prior to detection of the Eu signal (Excitation=340 nm: Emission=615 nm).

Example 75

The following table lists conjugates that were prepared using appropriate intermediates following one of the General Methods described above. These conjugates were characterized using UPLC Method E or UPLC Method F noted by an asterisk (*), exhibiting either four charged, i.e. [(M+4)/4], (or five charged, i.e. [(M+5)/5]) species of parent compound at certain retention time ($t_R$). The in vitro biological activities towards insulin receptor (IR) were measured by either ligand competition assays or functional phosphorylation assays, as described above, labeled as following: Method A: IR phosphorylation assay based on 96-well; Method B: IR phosphorylation assay based on 384-well with automated liquid dispense; Method C: cell-based IR binding assay; Method D: SPA IR binding assay method E; Method E: MRC1 assay was performed in a 96-well plate; Method F: MRC I assay was performed in a 384-well plate. The results are shown in Table 1.

| | | UPLC-MS | | | | | | |
|---|---|---|---|---|---|---|---|---|
| | | Mass [(m + 4)/4 | IR Activation | | IR Binding | | MRC1 Binding | |
| IOC # | $t_R$ (min) | or (m + 5)/5] | IP† (nM) | Method | IP‡ (nM) | Method | IP‡ (nM) | Method |
| IOC-1 | 3.41 | 1711.62 | 1.93 | A | 1.06 | C | NA | |
| IOC-2 | 3.42 | 1721.86 | 0.48 | A | 0.88 | C | NA | |
| IOC-3 | 3.36 | 1924.10 | 8.44 | B | 4.83 | C | 51.34 | F |
| IOC-4 | 3.39 | 1689.01 | 1.04 | A | 1.01 | C | NA | |
| IOC-5 | 3.39 | 1709.95 | 2.67 | A | 0.84 | C | NA | |
| IOC-6 | 3.38 | 1699.41 | 1.47 | A | 0.86 | C | NA | |
| IOC-7 | 3.45 | 1682.26 | 0.89 | A | 0.50 | C | 113.7 | E |
| IOC-8 | 3.42 | 1682.25 | 6.08 | A | 0.38 | C | 60.0 | E |
| IOC-9 | 3.33 | 1846.64 | 18.14 | A | 1.57 | C | 19.98 | E |
| IOC-10 | 3.32 | 1608.85 | 14.91 | A | 1.98 | C | 4.89 | E |
| IOC-11 | 3.36 | 1671.47 | 2.75 | A | 0.75 | C | 174.90 | E |
| IOC-12 | 3.23 | 1889.97 | 1.63 | B | 5.35 | C | 12.79 | F |
| IOC-13 | 3.25 | 1890.01 | 4.69 | A | 1.20 | C | 9.34 | E |
| IOC-14 | 3.24 | 1889.98 | 10.72 | A | 1.36 | C | 15.77 | E |
| IOC-15 | 3.16 | 1687.87 | 6.12 | A | 1.78 | C | 3.58 | E |
| IOC-16 | 3.2 | 1677.26 | 7.57 | B | 5.43 | D | 5.19 | F |
| IOC-17 | 3.33 | 1881.70 | 7.62 | B | 4.05 | D | 23.42 | F |
| IOC-18 | 3.48 | 1666.87 | 0.33 | B | 0.19 | D | 84.45 | F |
| IOC-19 | 3.36 | 1881.70 | 0.50 | B | 0.53 | D | 10.82 | F |
| IOC-20 | 3.35 | 1946.58 | 3.31 | B | 3.16 | D | 31.87 | F |
| IOC-21 | 2.55 | 1755.00 | 17.06 | A | 4.50 | C | NA | |
| IOC-22 | 3.63 | 1557.81 | 25.93 | A | 1.80 | C | 14.69 | E |
| IOC-23 | 3.77 | 1577.53 | 4.90 | A | 1.17 | D | 11.81 | E |
| IOC-24 | 3.49 | 1557.48 | 9.75 | A | 1.37 | C | 10.92 | E |
| IOC-25 | 3.67 | 1623.00 | 17.51 | A | 1.83 | C | 7.13 | E |
| IOC-26 | 3.68 | 1491.51 | 5.86 | B | 6.55 | D | 40.55 | F |
| IOC-27 | 3.39 | 1699.58 | NA | | 2.11 | C | NA | |
| IOC-28 | 3.38 | 1726.68 | 22.32 | A | 9.94 | C | 0.32 | E |
| IOC-29 | 3.82 | 1492.19 | 9.41 | B | 11.41 | D | 8.96 | E |
| IOC-30 | 3.68 | 1560.83 | 10.87 | A | 1.56 | C | 14.52 | E |
| IOC-31 | 4.00 | 1687.69 | 1.82 | A | 0.37 | C | 31.68 | E |

-continued

| | UPLC-MS | | IR Activation | | IR Binding | | MRC1 Binding | |
|---|---|---|---|---|---|---|---|---|
| | $t_R$ | Mass [(m + 4)/4 or (m + 5)/5] | IP† | | IP‡ | | IP‡ | |
| IOC # | (min) | | (nM) | Method | (nM) | Method | (nM) | Method |
| IOC-32 | 3.77 | 1704.22 | 4.44 | A | 0.38 | C | 341.30 | E |
| IOC-33 | 3.77 | 1704.22 | 0.46 | A | 0.16 | C | 288.60 | E |
| IOC-34 | 4.38 | 1538.25 | 1.06 | B | 1.47 | C | 0.80 | E |
| IOC-35 | 3.72 | 1613.24 | 21.22 | A | 2.06 | C | 2.30 | E |
| IOC-36 | 3.83 | 1481.69 | 22.39 | A | 2.58 | C | 9.21 | E |
| IOC-37 | 3.43 | 1668.00 | 3.70 | A | 0.43 | C | 227.90 | E |
| IOC-38 | 3.45 | 1668.00 | 12.69 | A | 0.22 | C | 116.00 | E |
| IOC-39 | 3.42 | 1859.00 | 20.72 | A | 7.23 | C | 2.17 | E |
| IOC-40 | 3.37 | 1650.10 | 13.16 | A | 13.80 | C | 1.29 | E |
| IOC-41 | 3.45 | 1655.84 | 2.67 | A | 1.40 | C | 47.97 | E |
| IOC-42 | 3.52 | 1655.65 | 0.45 | A | 0.21 | C | 52.57 | E |
| IOC-43 | 3.44 | 1859.06 | 0.62 | B | 0.90 | D | 1.25 | F |
| IOC-44 | 3.69 | 1557.29 | 32.52 | A | 2.01 | C | 17.59 | E |
| IOC-45 | 3.77 | 1698.78 | 0.69 | A | 0.33 | C | 90.75 | E |
| IOC-46 | 4.04 | 1694.13 | 1.07 | A | 0.28 | C | 12.00 | E |
| IOC-47 | 3.99 | 1936.61 | 1.13 | A | 1.44 | C | 0.57 | E |
| IOC-48 | 3.57 | 1704.85 | 23.10 | A | 1.41 | C | 45.96 | E |
| IOC-49 | 3.89 | 1936.45 | 14.94 | A | 3.17 | C | 0.90 | E |
| IOC-50 | 4.03 | 1773.45 | 1.69 | B | 5.85 | C | 35.18 | E |
| IOC-51 | 3.52 | 1777.83 | 20.20 | A | 2.01 | C | 34.61 | E |
| IOC-52 | 4.14 | 1859.33 | 4.70 | A | 1.33 | C | 2.23 | E |
| IOC-53 | 3.87 | 1818.46 | 22.05 | A | 2.06 | C | 50.94 | E |
| IOC-54 | 3.85 | 1817.71 | 11.87 | A | 1.03 | C | 44.13 | E |
| IOC-55 | 3.99 | 1698.31 | 0.49 | B | 4.03 | C | 49.72 | E |
| IOC-56 | 3.34 | 1777.68 | 2.19 | B | 6.86 | D | 65.57 | E |
| IOC-57 | 3.39 | 1904.30 | 1.43 | B | 2.21 | D | 3.66 | F |
| IOC-58 | 3.41 | 1904.02 | 1.77 | B | 0.55 | D | 17.86 | F |
| IOC-59 | 3.43 | 1896.34 | 1.26 | B | 0.94 | D | 2.28 | F |
| IOC-60 | 3.77 | 1882.41 | 1.85 | B | 2.31 | D | 33.09 | F |
| IOC-61 | 3.77 | 1882.41 | 1.13 | B | 1.97 | D | 17.87 | F |
| IOC-62 | 3.79 | 1875.19 | 0.77 | B | 2.25 | D | 5.12 | F |
| IOC-63 | 4.04 | 1882.04 | 0.63 | B | 1.65 | D | 70.25 | F |
| IOC-64 | 3.51 | 1674.17 | 0.45 | B | 0.44 | D | 54.84 | F |
| IOC-65 | 3.27 | 1896.42 | 1.73 | B | 1.48 | D | 9.55 | F |
| IOC-66 | 3.47 | 1895.72 | 1.41 | B | 0.89 | D | 4.24 | F |
| IOC-67 | 3.36 | 1478.35 | 3.44 | A | 1.42 | C | NA | |
| IOC-68 | 3.36 | 1868.32 | 2.70 | A | 0.85 | C | 10.16 | E |
| IOC-69 | 3.34 | 1925.42 | 5.84 | A | 1.53 | C | 3.28 | E |
| IOC-70 | 3.36 | 1840.07 | 5.35 | A | 1.42 | C | 11.30 | E |
| IOC-71 | 3.32 | 1929.40 | 2.02 | A | 0.65 | C | 4.44 | E |
| IOC-72 | 3.33 | 1939.84 | 5.58 | A | 1.09 | C | 1.81 | E |
| IOC-73 | 3.32 | 1918.40 | 4.58 | A | 1.03 | C | 3.41 | E |
| IOC-74 | 3.33 | 1922.41 | 14.07 | A | 1.05 | C | 8.96 | E |
| IOC-75 | 3.33 | 1543.03 | 1.03 | B | 0.88 | C | 5.37 | E |
| IOC-76 | 3.31 | 1630.86 | 0.97 | B | 0.98 | C | 13.36 | E |
| IOC-77 | 3.32 | 1653.72 | 1.46 | B | 2.09 | C | 9.94 | E |
| IOC-78 | 3.31 | 1515.39 | 2.30 | B | 6.86 | D | 3.66 | F |
| IOC-79 | 3.31 | 1262.72 | 2.38 | B | 4.94 | D | 11.43 | F |
| IOC-80 | 3.32 | 1890.01 | 2.61 | B | 8.56 | D | 4.53 | F |
| IOC-81 | 3.32 | 1511.80 | 2.13 | B | 6.56 | D | 13.74 | F |
| IOC-82 | 3.32 | 1514.73 | 2.78 | B | 8.18 | D | 24.11 | F |
| IOC-83 | 3.31 | 1894.11 | 2.70 | B | 3.24 | D | 8.27 | F |
| IOC-84 | 3.32 | 1889.07 | 4.23 | B | 2.17 | D | 7.23 | F |
| IOC-85 | 3.31 | 1515.52 | 2.43 | B | 1.59 | D | 9.05 | F |
| IOC-86 | 3.32 | 1492.58 | 7.44 | B | 5.44 | D | 9.80 | F |
| IOC-87 | 3.32 | 1489.01 | 1.78 | B | 0.92 | D | 10.33 | F |
| IOC-88 | 3.31 | 1512.08 | 2.04 | B | 0.48 | D | 3.97 | F |

-continued

| | | UPLC-MS | | | | | | |
|---|---|---|---|---|---|---|---|---|
| | | Mass [(m + 4)/4 | IR Activation | | IR Binding | | MRC1 Binding | |
| IOC # | $t_R$ (min) | or (m + 5)/5] | IP† (nM) | Method | IP‡ (nM) | Method | IP‡ (nM) | Method |
| IOC-89 | 3.34 | 1744.70 | 1.04 | B | 2.13 | D | 94.54 | F |
| IOC-90 | 3.33 | 1518.00 | 4.82 | B | 2.26 | D | 11.46 | F |
| IOC-91 | 3.33 | 1517.49 | 4.82 | B | 2.72 | D | 4.71 | F |
| IOC-92 | 3.45 | 1766.99 | 1.11 | A | 1.13 | C | NA | |
| IOC-93 | 3.36 | 1844.09 | 2.55 | A | 2.30 | C | 8.73 | E |
| IOC-94 | 3.4 | 1608.54 | 23.64 | A | 3.04 | C | 16.14 | E |
| IOC-95 | 3.36 | 1606.40 | 8.68 | A | 1.16 | C | 0.81 | E |
| IOC-96 | 3.3 | 1607.95 | 10.11 | A | 1.49 | C | 0.94 | E |
| IOC-97 | 2.26 | 1871.71 | 1.37 | A | 0.86 | C | 3.41 | E |
| IOC-98 | 2.24 | 1956.56 | 1.53 | A | 1.22 | C | 2.25 | E |
| IOC-99 | 2.27 | 1900.54 | 2.07 | A | 0.57 | C | 5.84 | E |
| IOC-100 | 3.7 | 1928.82 | 4.56 | A | 1.20 | C | 1.23 | E |
| IOC-101* | 3.38 | 1917.99 | 2.22 | B | 5.79 | D | 14.22 | F |
| IOC-102* | 3.33 | 1922.59 | 1.79 | B | 0.68 | D | 1.20 | F |
| IOC-103* | 3.83 | 1903.06 | 1.65 | B | 2.55 | D | 4.90 | F |
| IOC-104* | 3.58 | 1917.18 | 1.52 | B | 2.28 | D | 0.59 | F |
| IOC-105* | 3.7 | 1931.08 | 0.44 | B | 0.56 | D | 7.76 | F |
| IOC-106 | 3.32 | 1922.15 | 1.94 | B | 2.96 | D | 9.56 | F |
| IOC-107 | 3.39 | 1917.61 | 1.56 | B | 2.85 | D | 4.69 | F |
| IOC-108 | 3.61 | 1832.91 | 3.83 | A | 0.41 | C | 5.58 | E |
| IOC-109 | 3.2 | 1853.76 | 2.87 | B | 4.44 | C | 21.73 | E |
| IOC-110 | 3.08 | 1843.26 | 3.09 | B | 5.61 | C | 14.10 | E |
| IOC-111 | 3.2 | 1833.67 | 1.15 | B | 0.63 | D | 23.58 | F |
| IOC-112 | 3.94 | 1551.45 | 0.94 | B | 5.18 | D | 52.33 | F |
| IOC-113 | 3.75 | 1916.78 | 2.66 | B | 3.26 | D | 8.29 | F |
| IOC-114 | 3.8 | 1909.07 | 1.24 | B | 2.30 | D | 1.24 | F |
| IOC-115 | 4.07 | 1917.14 | 0.69 | B | 1.93 | D | 10.8 | F |
| IOC-116 | 4.01 | 1800.65 | 1.29 | B | 0.74 | D | 24.31 | F |
| IOC-117 | 4.19 | 1622.79 | 2.01 | B | 5.41 | D | 7.47 | F |
| IOC-118 | 3.51 | 1817 | 1.94 | B | 2.60 | D | 37.02 | F |
| IOC-119 | 3.51 | 1817 | 0.56 | B | 0.89 | D | 39.10 | F |
| IOC-120 | 3.51 | 1840 | 3.92 | B | 6.56 | D | 64.54 | F |
| IOC-121 | 3.38 | 1957 | 1.31 | B | 0.01 | D | 1.68 | F |

Example 76

Effect of Methyl α-D-Mannopyranoside (αMM) on PK and PD of various IOCs in Non-Diabetic Minipigs was evaluated.

Male Yucatan miniature pigs, non-diabetic, instrumented with two Jugular vein vascular access ports (VAP), are used in these studies. Animals are fasted overnight prior to the study. On the day of the study, animals are restrained in slings, and VAPs accessed for infusion and sampling. At t=−60 minutes, a constant infusion of PBS (n=3) or 21.2% α-methyl mannose (αMM) (n=3) is started, at a rate of 2.67 mL/kg/hr. This infusion will be maintained for the duration of the study. At t=0 min, and after collecting a baseline blood sample for plasma glucose measurement, animals are administered IOC as a single bolus IV. Sampling continues for 90 minutes, with final readouts of plasma glucose and compound levels.

IOCs are formulated at 17-69 nmol/mL in sodium chloride (87 mM), phenol (21 mM), dibasic sodium phosphate (26.5 mM), Osmolality=275 mOsm, pH=7.4; QS with Water for Injection.

Time points for sample collection: −60 min, 0 min, 1 min, 2 min, 4 min, 6 min, 8 min, 10 min, 15 min, 20 min, 25 min, 30 min, 35 min, 45 min, 60 min, and 90 min.

Blood is collected in K3-EDTA tubes, supplemented with 10 μg/ml Aprotinin, and kept on an ice bath until processing, within 30 minutes of collection. After centrifugation at 3000 rpm, 4° C., for 8 min, plasma is collected and aliquoted for glucose measurement using a Beckman Coulter AU480 Chemistry analyzer and for compound levels measurement by LC-MS.

The IOCs evaluated were IOC-3, IOC-9, IOC-12, IOC-13, IOC-14, IOC-15, IOC-20, IOC-22, IOC-23, IOC-24, IOC-28, IOC-30, IOC-36, IOC-56, IOC-57, IOC-58, IOC-59, IOC-60, IOC-61, IOC-62, IOC-65, IOC-69, IOC-70, IOC-71, IOC-78, IOC-80, IOC-81, IOC-93, IOC-101, IOC-102, IOC-107, IOC-108, IOC-111, IOC-112, IOC-113, IOC-114, IOC-115, IOC-116, IOC-118, IOC-120, IOC-121, and Compound A. Compound A is an IOC disclosed as compound 11-6 in U.S. Patent Publication No. 20130131310 and having the structure

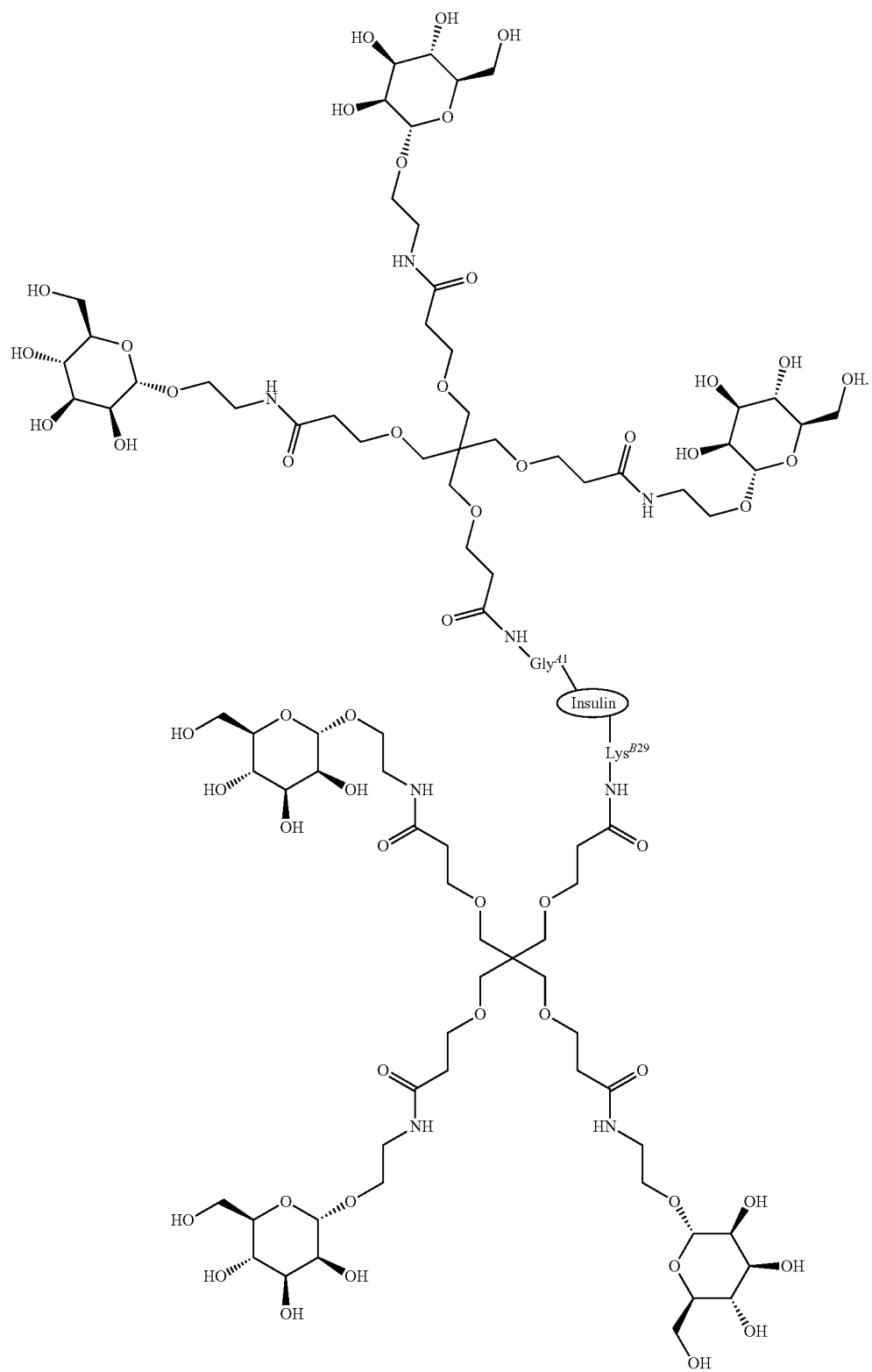

Glucose results are expressed as % changes over baseline values at t=0 minutes, and the results are shown in FIG. 1A through FIG. 11D.

FIG. 1A shows blood glucose depression curves in non-diabetic male Yucatan minipigs equipped with dual vascular access ports (n=3 per study) following i.v. injection of conjugate IOC-3 at 0.69 nmol/kg under conditions of PBS infusion or i.v. alpha methyl mannose (αMM) infusion.

FIG. 1B shows blood glucose depression curves in non-diabetic male Yucatan minipigs equipped with dual vascular access ports (n=3 per study) following i.v. injection of conjugate IOC-9 at 0.35 nmol/kg under conditions of PBS infusion or i.v. alpha methyl mannose (αMM) infusion.

FIG. 1C shows blood glucose depression curves in non-diabetic male Yucatan minipigs equipped with dual vascular access ports (n=3 per study) following i.v. injection of conjugate IOC-12 at 0.17 nmol/kg under conditions of PBS infusion or i.v. alpha methyl mannose (αMM) infusion.

FIG. 1D shows blood glucose depression curves in non-diabetic male Yucatan minipigs equipped with dual vascular access ports (n=3 per study) following i.v. injection of conjugate IOC-13 at 0.17 nmol/kg under conditions of PBS infusion or i.v. alpha methyl mannose (αMM) infusion.

FIG. 2A shows blood glucose depression curves in non-diabetic male Yucatan minipigs equipped with dual vascular access ports (n=3 per study) following i.v. injection of conjugate IOC-14 at 0.17 nmol/kg under conditions of PBS infusion or i.v. alpha methyl mannose (αMM) infusion.

Figure 2B:
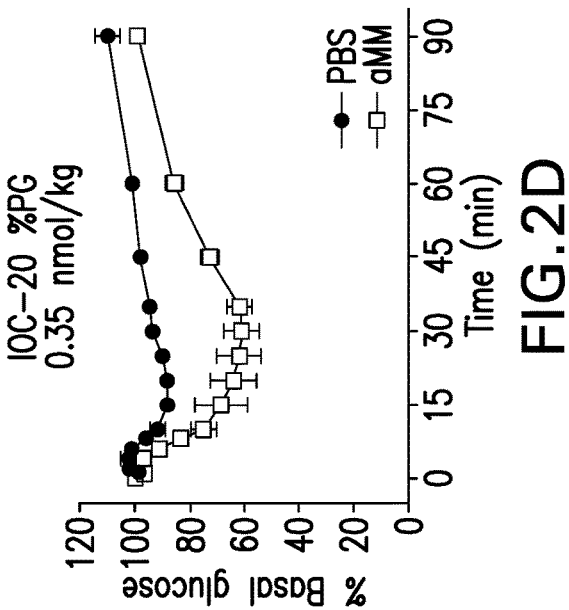
FIG. 2B shows plasma glucose depression curves in non-diabetic male Yucatan minipigs equipped with dual vascular access ports (n=3 per study) following i.v. injection of conjugate IOC-15 at 0.17 nmol/kg under conditions of PBS infusion or i.v. alpha methyl mannose (αMM) infusion.

FIG. 2B shows blood glucose depression curves in non-diabetic male Yucatan minipigs equipped with dual vascular access ports (n=3 per study) following i.v. injection of conjugate IOC-15 at 0.17 nmol/kg under conditions of PBS infusion or i.v. alpha methyl mannose (αMM) infusion.

Figure 2C:
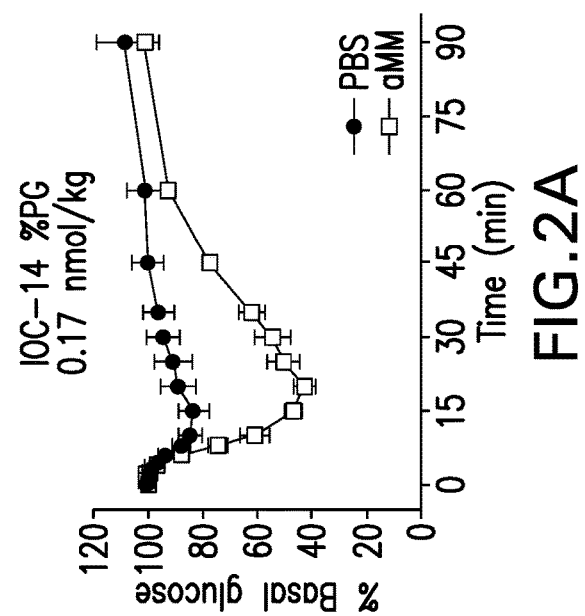
FIG. 2C shows plasma glucose depression curves in non-diabetic male Yucatan minipigs equipped with dual vascular access ports (n=3 per study) following i.v. injection of conjugate IOC-20 at 0.69 nmol/kg under conditions of PBS infusion or i.v. alpha methyl mannose (αMM) infusion.

FIG. 2C shows blood glucose depression curves in non-diabetic male Yucatan minipigs equipped with dual vascular access ports (n=3 per study) following i.v. injection of conjugate IOC-20 at 0.69 nmol/kg under conditions of PBS infusion or i.v. alpha methyl mannose (αMM) infusion.

Figure 2D:
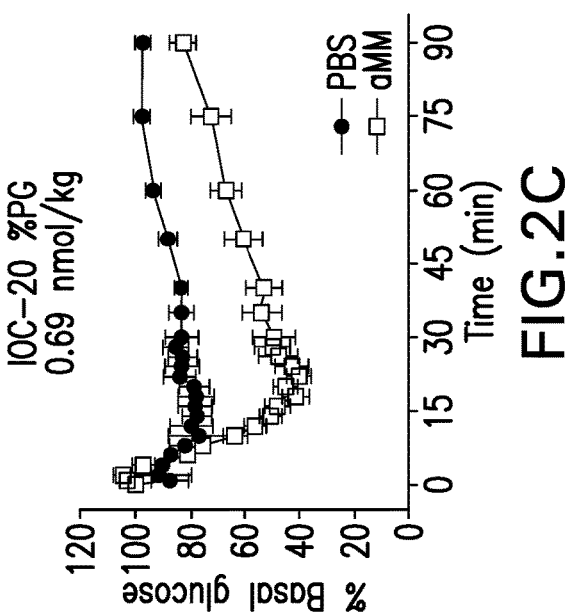
FIG. 2D shows plasma glucose depression curves in non-diabetic male Yucatan minipigs equipped with dual vascular access ports (n=3 per study) following i.v. injection of conjugate IOC-20 at 0.35 nmol/kg under conditions of PBS infusion or i.v. alpha methyl mannose (αMM) infusion.

FIG. 2D shows blood glucose depression curves in non-diabetic male Yucatan minipigs equipped with dual vascular access ports (n=3 per study) following i.v. injection of conjugate IOC-20 at 0.35 nmol/kg under conditions of PBS infusion or i.v. alpha methyl mannose (αMM) infusion.

Figure 3A:
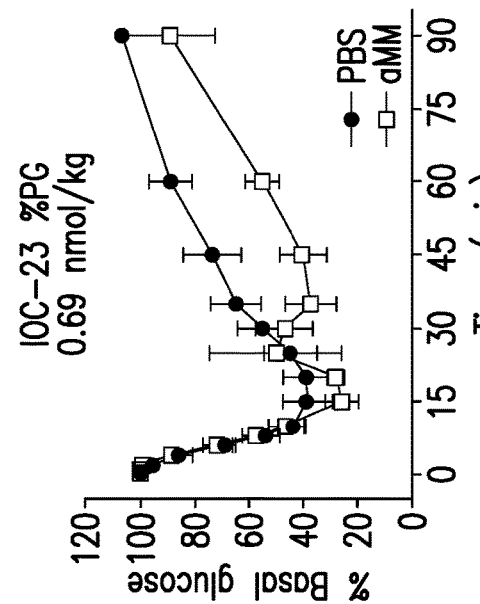
FIG. 3A shows plasma glucose depression curves in non-diabetic male Yucatan minipigs equipped with dual vascular access ports (n=3 per study) following i.v. injection of conjugate IOC-22 at 0.69 nmol/kg under conditions of PBS infusion or i.v. alpha methyl mannose (αMM) infusion.

FIG. 3A shows blood glucose depression curves in non-diabetic male Yucatan minipigs equipped with dual vascular access ports (n=3 per study) following i.v. injection of conjugate IOC-22 at 0.69 nmol/kg under conditions of PBS infusion or i.v. alpha methyl mannose (αMM) infusion.

Figure 3B:
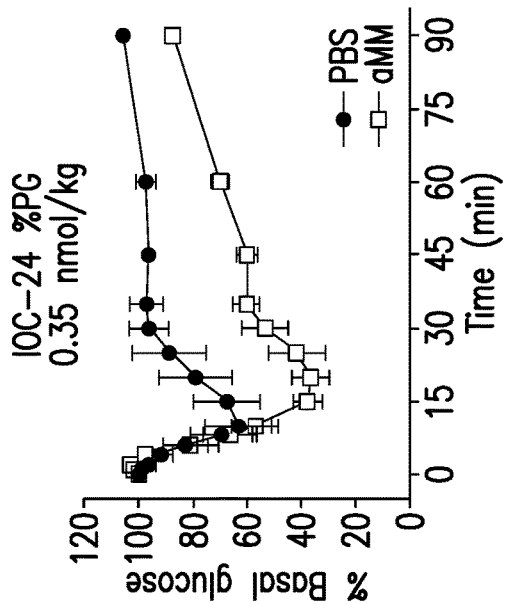
FIG. 3B shows plasma glucose depression curves in non-diabetic male Yucatan minipigs equipped with dual vascular access ports (n=3 per study) following i.v. injection of conjugate IOC-23 at 0.69 nmol/kg under conditions of PBS infusion or i.v. alpha methyl mannose (αMM) infusion.

FIG. 3B shows blood glucose depression curves in non-diabetic male Yucatan minipigs equipped with dual vascular access ports (n=3 per study) following i.v. injection of conjugate IOC-23 at 0.69 nmol/kg under conditions of PBS infusion or i.v. alpha methyl mannose (αMM) infusion.

Figure 3C:
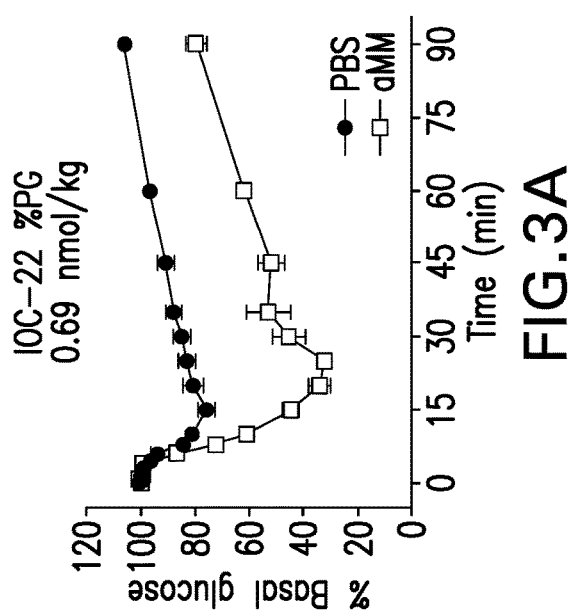
FIG. 3C shows plasma glucose depression curves in non-diabetic male Yucatan minipigs equipped with dual vascular access ports (n=3 per study) following i.v. injection of conjugate IOC-23 at 0.17 nmol/kg under conditions of PBS infusion or i.v. alpha methyl mannose (αMM) infusion.

FIG. 3C shows blood glucose depression curves in non-diabetic male Yucatan minipigs equipped with dual vascular access ports (n=3 per study) following i.v. injection of conjugate IOC-23 at 0.17 nmol/kg under conditions of PBS infusion or i.v. alpha methyl mannose (αMM) infusion.

Figure 3D:
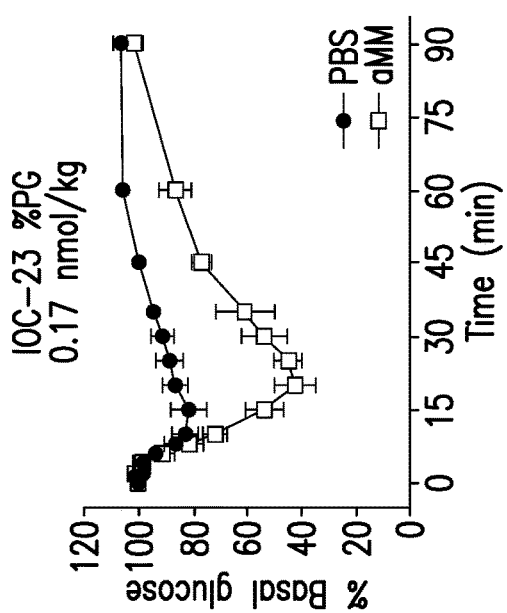
FIG. 3D shows plasma glucose depression curves in non-diabetic male Yucatan minipigs equipped with dual vascular access ports (n=3 per study) following i.v. injection of conjugate IOC-24 at 0.35 nmol/kg under conditions of PBS infusion or i.v. alpha methyl mannose (αMM) infusion.

FIG. 3D shows blood glucose depression curves in non-diabetic male Yucatan minipigs equipped with dual vascular access ports (n=3 per study) following i.v. injection of conjugate IOC-24 at 0.35 nmol/kg under conditions of PBS infusion or i.v. alpha methyl mannose (αMM) infusion.

Figure 4A:
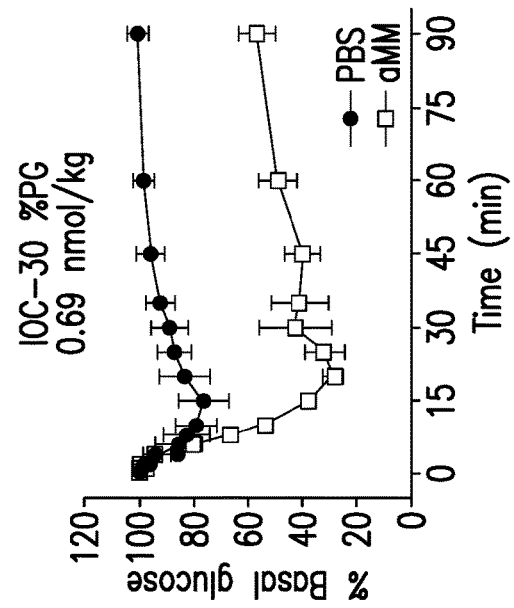
FIG. 4A shows plasma glucose depression curves in non-diabetic male Yucatan minipigs equipped with dual vascular access ports (n=3 per study) following i.v. injection of conjugate IOC-28 at 0.69 nmol/kg under conditions of PBS infusion or i.v. alpha methyl mannose (αMM) infusion.

FIG. 4A shows blood glucose depression curves in non-diabetic male Yucatan minipigs equipped with dual vascular access ports (n=3 per study) following i.v. injection of conjugate IOC-28 at 0.69 nmol/kg under conditions of PBS infusion or i.v. alpha methyl mannose (αMM) infusion.

Figure 4B:
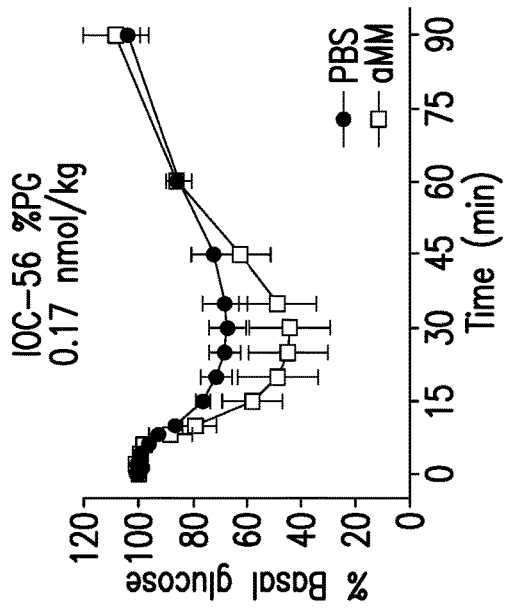
FIG. 4B shows plasma glucose depression curves in non-diabetic male Yucatan minipigs equipped with dual vascular access ports (n=3 per study) following i.v. injection of conjugate IOC-30 at 0.69 nmol/kg under conditions of PBS infusion or i.v. alpha methyl mannose (αMM) infusion.

FIG. 4B shows blood glucose depression curves in non-diabetic male Yucatan minipigs equipped with dual vascular access ports (n=3 per study) following i.v. injection of conjugate IOC-30 at 0.69 nmol/kg under conditions of PBS infusion or i.v. alpha methyl mannose (αMM) infusion.

Figure 4C:
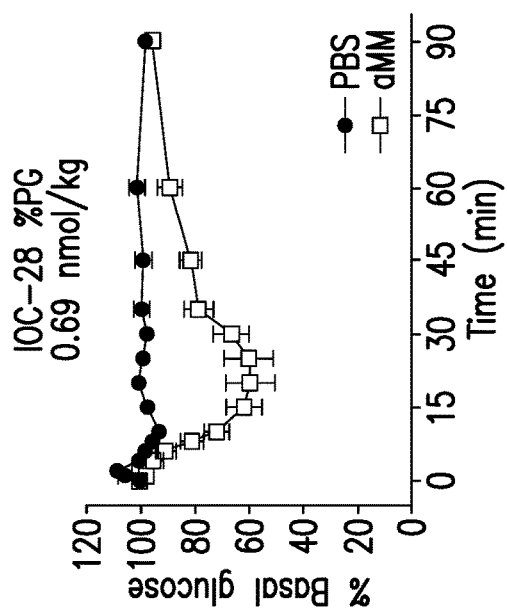
FIG. 4C shows plasma glucose depression curves in non-diabetic male Yucatan minipigs equipped with dual vascular access ports (n=3 per study) following i.v. injection of conjugate IOC-36 at 0.35 nmol/kg under conditions of PBS infusion or i.v. alpha methyl mannose (αMM) infusion.

FIG. 4C shows blood glucose depression curves in non-diabetic male Yucatan minipigs equipped with dual vascular access ports (n=3 per study) following i.v. injection of conjugate IOC-36 at 0.35 nmol/kg under conditions of PBS infusion or i.v. alpha methyl mannose (αMM) infusion.

Figure 4D:
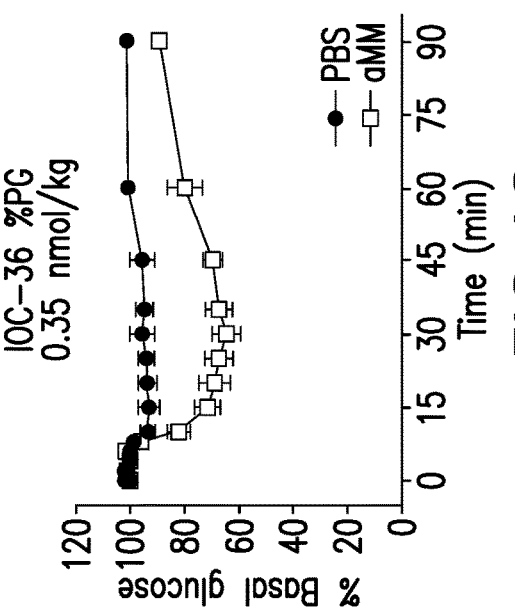
FIG. 4D shows plasma glucose depression curves in non-diabetic male Yucatan minipigs equipped with dual vascular access ports (n=3 per study) following i.v. injection of conjugate IOC-56 at 0.17 nmol/kg under conditions of PBS infusion or i.v. alpha methyl mannose (αMM) infusion.

FIG. 4D shows blood glucose depression curves in non-diabetic male Yucatan minipigs equipped with dual vascular access ports (n=3 per study) following i.v. injection of conjugate IOC-56 at 0.17 nmol/kg under conditions of PBS infusion or i.v. alpha methyl mannose (αMM) infusion.

Figure 5A:
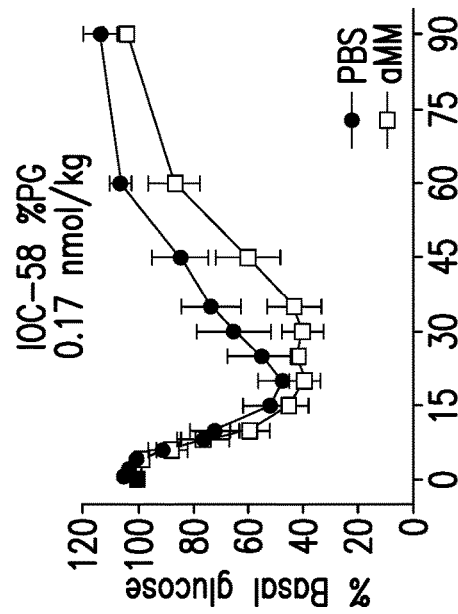
FIG. 5A shows plasma glucose depression curves in non-diabetic male Yucatan minipigs equipped with dual vascular access ports (n=3 per study) following i.v. injection of conjugate IOC-57 at 0.17 nmol/kg under conditions of PBS infusion or i.v. alpha methyl mannose (αMM) infusion.

FIG. 5A shows blood glucose depression curves in non-diabetic male Yucatan minipigs equipped with dual vascular access ports (n=3 per study) following i.v. injection of conjugate IOC-57 at 0.17 nmol/kg under conditions of PBS infusion or i.v. alpha methyl mannose (αMM) infusion.

Figure 5B:
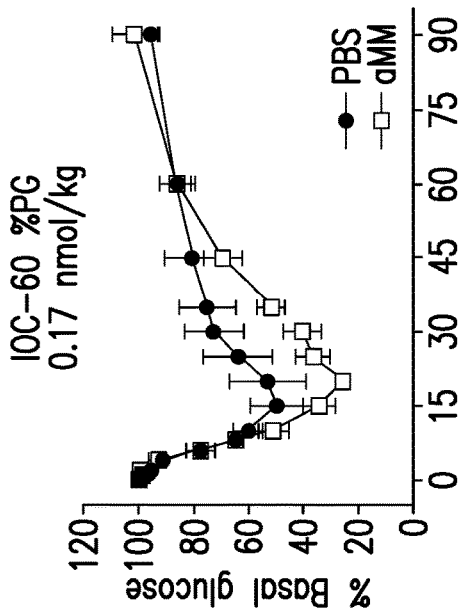
FIG. 5B shows plasma glucose depression curves in non-diabetic male Yucatan minipigs equipped with dual vascular access ports (n=3 per study) following i.v. injection of conjugate IOC-58 at 0.17 nmol/kg under conditions of PBS infusion or i.v. alpha methyl mannose (αMM) infusion.

FIG. 5B shows blood glucose depression curves in non-diabetic male Yucatan minipigs equipped with dual vascular access ports (n=3 per study) following i.v. injection of conjugate IOC-58 at 0.17 nmol/kg under conditions of PBS infusion or i.v. alpha methyl mannose (αMM) infusion.

Figure 5C:
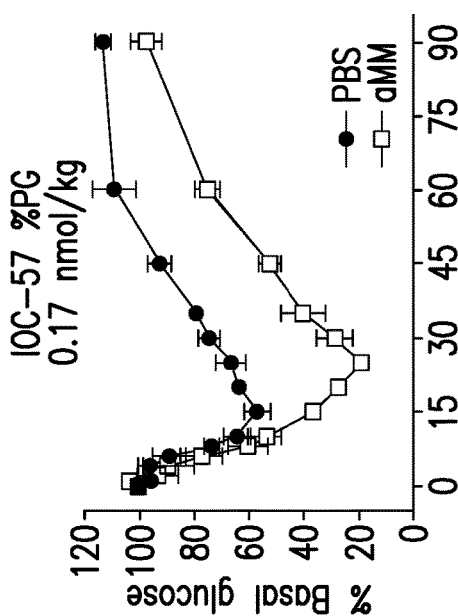
FIG. 5C shows plasma glucose depression curves in non-diabetic male Yucatan minipigs equipped with dual vascular access ports (n=3 per study) following i.v. injection of conjugate IOC-59 at 0.17 nmol/kg under conditions of PBS infusion or i.v. alpha methyl mannose (αMM) infusion.

FIG. 5C shows blood glucose depression curves in non-diabetic male Yucatan minipigs equipped with dual vascular access ports (n=3 per study) following i.v. injection of conjugate IOC-59 at 0.17 nmol/kg under conditions of PBS infusion or i.v. alpha methyl mannose (αMM) infusion.

Figure 5D:
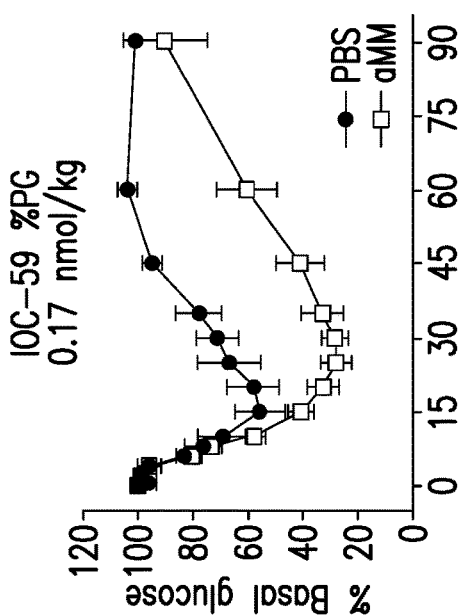
FIG. 5D shows plasma glucose depression curves in non-diabetic male Yucatan minipigs equipped with dual vascular access ports (n=3 per study) following i.v. injection of conjugate IOC-60 at 0.17 nmol/kg under conditions of PBS infusion or i.v. alpha methyl mannose (αMM) infusion.

FIG. 5D shows blood glucose depression curves in non-diabetic male Yucatan minipigs equipped with dual vascular access ports (n=3 per study) following i.v. injection of conjugate IOC-60 at 0.17 nmol/kg under conditions of PBS infusion or i.v. alpha methyl mannose (αMM) infusion.

FIG. 6A shows blood glucose depression curves in non-diabetic male Yucatan minipigs equipped with dual vascular access ports (n=3 per study) following i.v. injection of conjugate IOC-61 at 0.17 nmol/kg under conditions of PBS infusion or i.v. alpha methyl mannose (αMM) infusion.

FIG. 6B shows blood glucose depression curves in non-diabetic male Yucatan minipigs equipped with dual vascular access ports (n=3 per study) following i.v. injection of conjugate IOC-62 at 0.17 nmol/kg under conditions of PBS infusion or i.v. alpha methyl mannose (αMM) infusion.

FIG. 6C shows blood glucose depression curves in non-diabetic male Yucatan minipigs equipped with dual vascular access ports (n=3 per study) following i.v. injection of conjugate IOC-65 at 0.17 nmol/kg under conditions of PBS infusion or i.v. alpha methyl mannose (αMM) infusion.

FIG. 6D shows blood glucose depression curves in non-diabetic male Yucatan minipigs equipped with dual vascular access ports (n=3 per study) following i.v. injection of conjugate IOC-69 at 0.17 nmol/kg under conditions of PBS infusion or i.v. alpha methyl mannose (αMM) infusion.

Figure 7A:
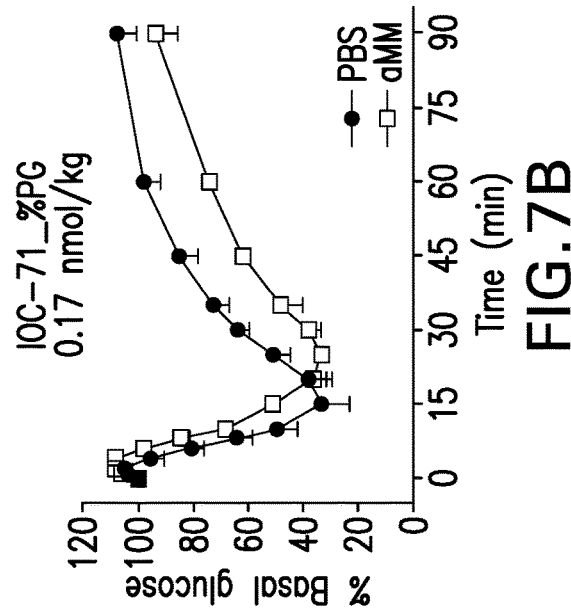
FIG. 7A shows plasma glucose depression curves in non-diabetic male Yucatan minipigs equipped with dual vascular access ports (n=3 per study) following i.v. injection of conjugate IOC-70 at 0.17 nmol/kg under conditions of PBS infusion or i.v. alpha methyl mannose (αMM) infusion.

FIG. 7A shows blood glucose depression curves in non-diabetic male Yucatan minipigs equipped with dual vascular access ports (n=3 per study) following i.v. injection of conjugate IOC-70 at 0.17 nmol/kg under conditions of PBS infusion or i.v. alpha methyl mannose (αMM) infusion.

Figure 7B:
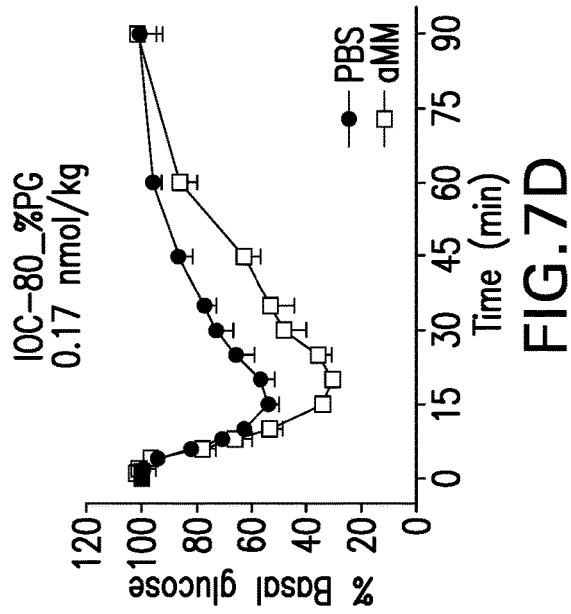
FIG. 7B shows plasma glucose depression curves in non-diabetic male Yucatan minipigs equipped with dual vascular access ports (n=3 per study) following i.v. injection of conjugate IOC-71 at 0.17 nmol/kg under conditions of PBS infusion or i.v. alpha methyl mannose (αMM) infusion.

FIG. 7B shows blood glucose depression curves in non-diabetic male Yucatan minipigs equipped with dual vascular access ports (n=3 per study) following i.v. injection of conjugate IOC-71 at 0.17 nmol/kg under conditions of PBS infusion or i.v. alpha methyl mannose (αMM) infusion.

Figure 7C:
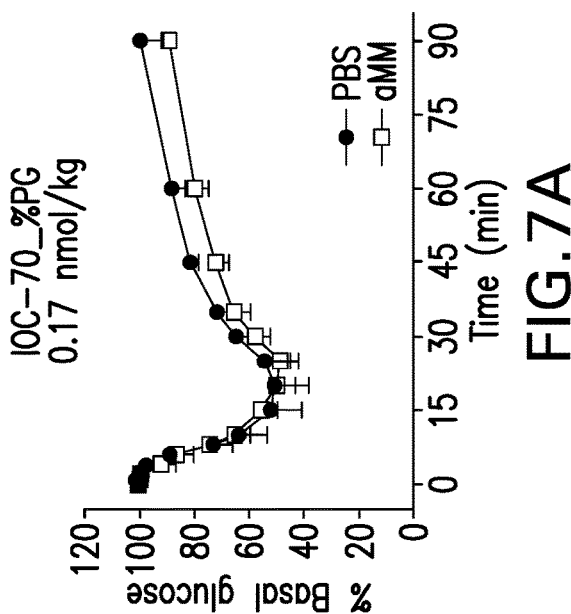
FIG. 7C shows plasma glucose depression curves in non-diabetic male Yucatan minipigs equipped with dual vascular access ports (n=3 per study) following i.v. injection of conjugate IOC-78 at 0.17 nmol/kg under conditions of PBS infusion or i.v. alpha methyl mannose (αMM) infusion.

FIG. 7C shows blood glucose depression curves in non-diabetic male Yucatan minipigs equipped with dual vascular access ports (n=3 per study) following i.v. injection of conjugate IOC-78 at 0.17 nmol/kg under conditions of PBS infusion or i.v. alpha methyl mannose (αMM) infusion.

Figure 7D:
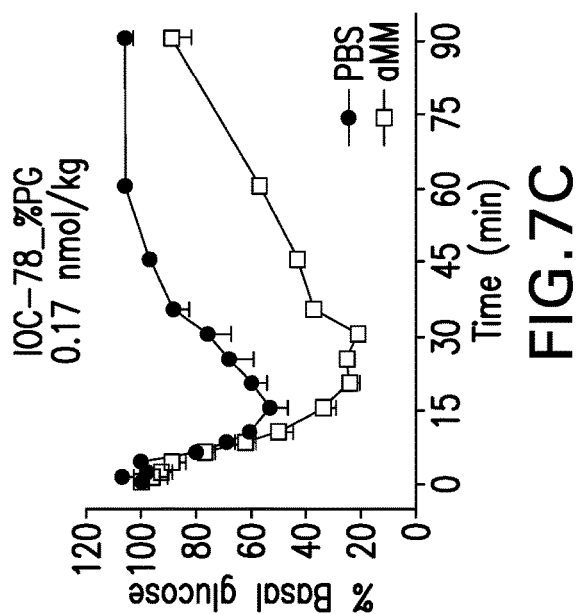
FIG. 7D shows plasma glucose depression curves in non-diabetic male Yucatan minipigs equipped with dual vascular access ports (n=3 per study) following i.v. injection of conjugate IOC-80 at 0.17 nmol/kg under conditions of PBS infusion or i.v. alpha methyl mannose (αMM) infusion.

FIG. 7D shows blood glucose depression curves in non-diabetic male Yucatan minipigs equipped with dual vascular access ports (n=3 per study) following i.v. injection of conjugate IOC-80 at 0.17 nmol/kg under conditions of PBS infusion or i.v. alpha methyl mannose (αMM) infusion.

FIG. 8A shows blood glucose depression curves in non-diabetic male Yucatan minipigs equipped with dual vascular access ports (n=3 per study) following i.v. injection of conjugate IOC-81 at 0.17 nmol/kg under conditions of PBS infusion or i.v. alpha methyl mannose (αMM) infusion.

FIG. 8B shows blood glucose depression curves in non-diabetic male Yucatan minipigs equipped with dual vascular access ports (n=3 per study) following i.v. injection of conjugate IOC-93 at 0.69 nmol/kg under conditions of PBS infusion or i.v. alpha methyl mannose (αMM) infusion.

FIG. 8C shows blood glucose depression curves in non-diabetic male Yucatan minipigs equipped with dual vascular access ports (n=3 per study) following i.v. injection of conjugate IOC-101 at 0.17 nmol/kg under conditions of PBS infusion or i.v. alpha methyl mannose (αMM) infusion.

FIG. 8D shows blood glucose depression curves in non-diabetic male Yucatan minipigs equipped with dual vascular access ports (n=3 per study) following i.v. injection of conjugate IOC-102 at 0.17 nmol/kg under conditions of PBS infusion or i.v. alpha methyl mannose (αMM) infusion.

Figure 9A:
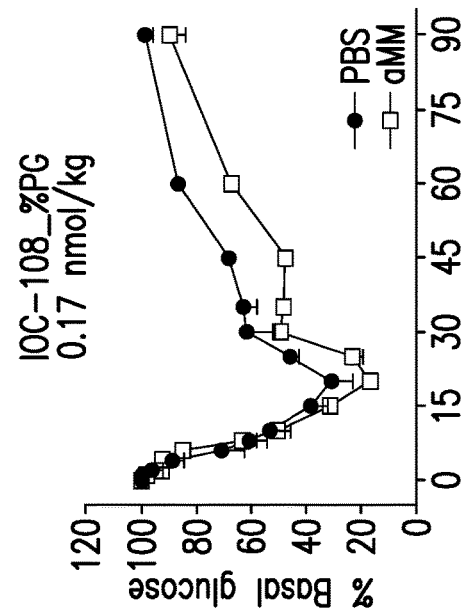
FIG. 9A shows plasma glucose depression curves in non-diabetic male Yucatan minipigs equipped with dual vascular access ports (n=3 per study) following i.v. injection of conjugate IOC-107 at 0.17 nmol/kg under conditions of PBS infusion or i.v. alpha methyl mannose (αMM) infusion.

FIG. 9A shows blood glucose depression curves in non-diabetic male Yucatan minipigs equipped with dual vascular access ports (n=3 per study) following i.v. injection of conjugate IOC-107 at 0.17 nmol/kg under conditions of PBS infusion or i.v. alpha methyl mannose (αMM) infusion.

Figure 9B:
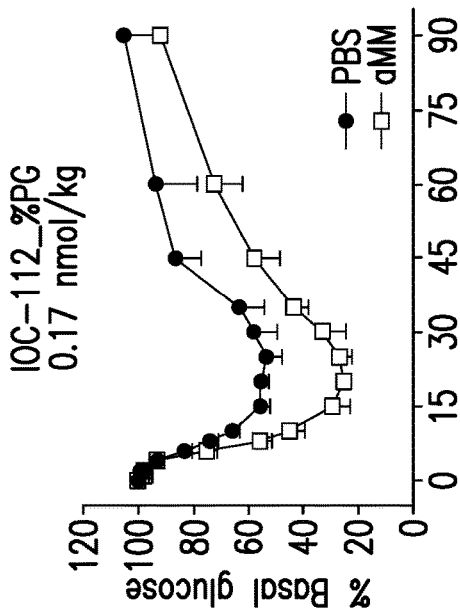
FIG. 9B shows plasma glucose depression curves in non-diabetic male Yucatan minipigs equipped with dual vascular access ports (n=3 per study) following i.v. injection of conjugate IOC-108 at 0.17 nmol/kg under conditions of PBS infusion or i.v. alpha methyl mannose (αMM) infusion.

FIG. 9B shows blood glucose depression curves in non-diabetic male Yucatan minipigs equipped with dual vascular access ports (n=3 per study) following i.v. injection of conjugate IOC-108 at 0.17 nmol/kg under conditions of PBS infusion or i.v. alpha methyl mannose (αMM) infusion.

Figure 9C:
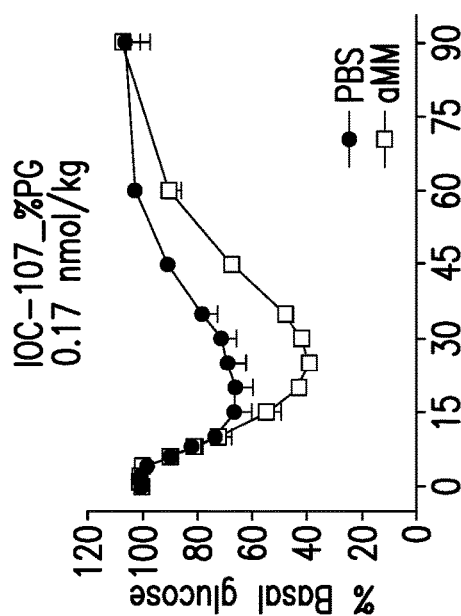
FIG. 9C shows plasma glucose depression curves in non-diabetic male Yucatan minipigs equipped with dual vascular access ports (n=3 per study) following i.v. injection of conjugate IOC-111 at 0.17 nmol/kg under conditions of PBS infusion or i.v. alpha methyl mannose (αMM) infusion.

FIG. 9C shows blood glucose depression curves in non-diabetic male Yucatan minipigs equipped with dual vascular access ports (n=3 per study) following i.v. injection of conjugate IOC-111 at 0.17 nmol/kg under conditions of PBS infusion or i.v. alpha methyl mannose (αMM) infusion.

Figure 9D:
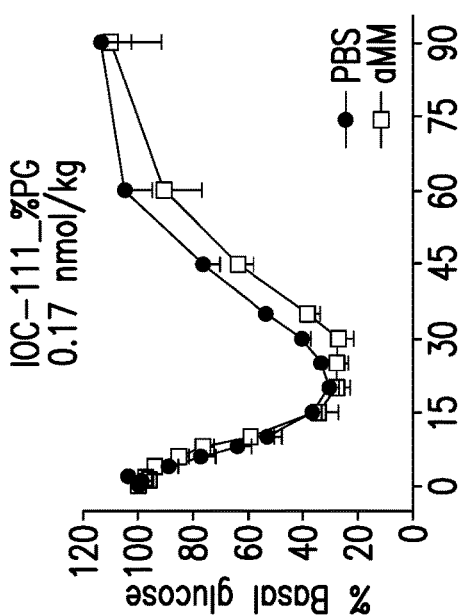
FIG. 9D shows plasma glucose depression curves in non-diabetic male Yucatan minipigs equipped with dual vascular access ports (n=3 per study) following i.v. injection of conjugate IOC-112 at 0.17 nmol/kg under conditions of PBS infusion or i.v. alpha methyl mannose (αMM) infusion.

FIG. 9D shows blood glucose depression curves in non-diabetic male Yucatan minipigs equipped with dual vascular access ports (n=3 per study) following i.v. injection of conjugate IOC-112 at 0.17 nmol/kg under conditions of PBS infusion or i.v. alpha methyl mannose (αMM) infusion.

Figure 10A:
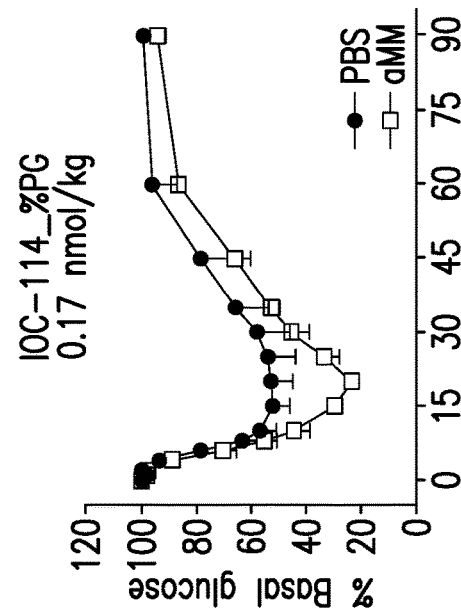
FIG. 10A shows plasma glucose depression curves in non-diabetic male Yucatan minipigs equipped with dual vascular access ports (n=3 per study) following i.v. injection of conjugate IOC-113 at 0.17 nmol/kg under conditions of PBS infusion or i.v. alpha methyl mannose (αMM) infusion.

FIG. 10A shows blood glucose depression curves in non-diabetic male Yucatan minipigs equipped with dual vascular access ports (n=3 per study) following i.v. injection of conjugate IOC-113 at 0.17 nmol/kg under conditions of PBS infusion or i.v. alpha methyl mannose (αMM) infusion.

Figure 10B:
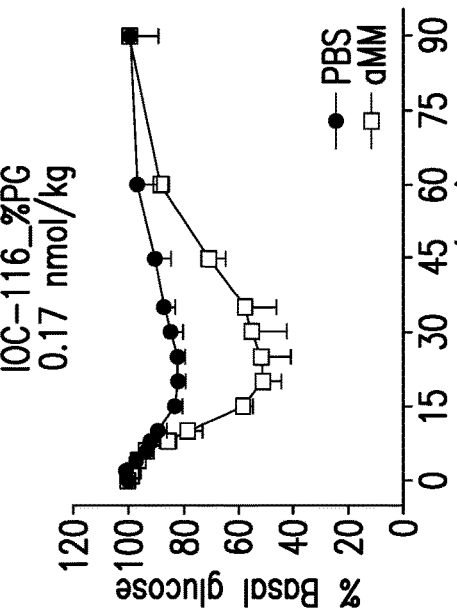
FIG. 10B shows plasma glucose depression curves in non-diabetic male Yucatan minipigs equipped with dual vascular access ports (n=3 per study) following i.v. injection of conjugate IOC-114 at 0.17 nmol/kg under conditions of PBS infusion or i.v. alpha methyl mannose (αMM) infusion.

FIG. 10B shows blood glucose depression curves in non-diabetic male Yucatan minipigs equipped with dual vascular access ports (n=3 per study) following i.v. injection of conjugate IOC-114 at 0.17 nmol/kg under conditions of PBS infusion or i.v. alpha methyl mannose (αMM) infusion.

Figure 10C:
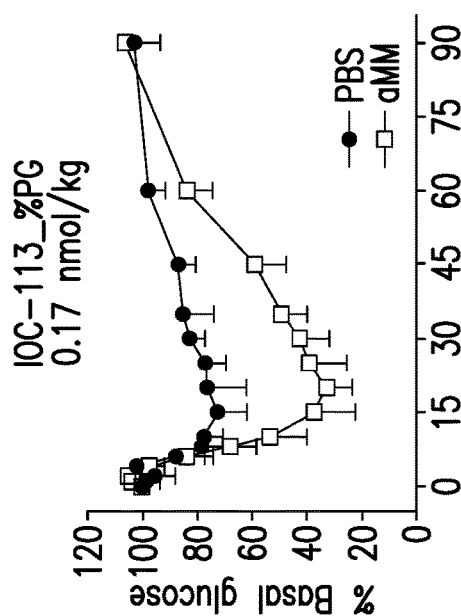
FIG. 10C shows plasma glucose depression curves in non-diabetic male Yucatan minipigs equipped with dual vascular access ports (n=3 per study) following i.v. injection of conjugate IOC-115 at 0.17 nmol/kg under conditions of PBS infusion or i.v. alpha methyl mannose (αMM) infusion.

FIG. 10C shows blood glucose depression curves in non-diabetic male Yucatan minipigs equipped with dual vascular access ports (n=3 per study) following i.v. injection of conjugate IOC-115 at 0.17 nmol/kg under conditions of PBS infusion or i.v. alpha methyl mannose (αMM) infusion.

Figure 10D:
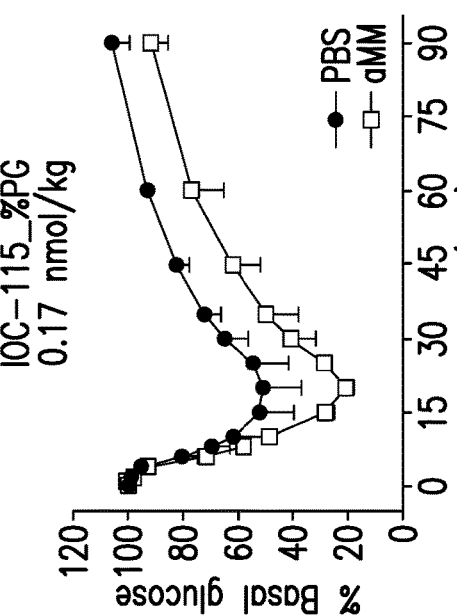
FIG. 10D shows plasma glucose depression curves in non-diabetic male Yucatan minipigs equipped with dual vascular access ports (n=3 per study) following i.v. injection of conjugate IOC-116 at 0.17 nmol/kg under conditions of PBS infusion or i.v. alpha methyl mannose (αMM) infusion.

FIG. 10D shows blood glucose depression curves in non-diabetic male Yucatan minipigs equipped with dual vascular access ports (n=3 per study) following i.v. injection of conjugate IOC-116 at 0.17 nmol/kg under conditions of PBS infusion or i.v. alpha methyl mannose (αMM) infusion.

FIG. 11A shows blood glucose depression curves in non-diabetic male Yucatan minipigs equipped with dual vascular access ports (n=3 per study) following i.v. injection of conjugate IOC-118 at 0.17 nmol/kg under conditions of PBS infusion or i.v. alpha methyl mannose (αMM) infusion.

FIG. 11B shows blood glucose depression curves in non-diabetic male Yucatan minipigs equipped with dual vascular access ports (n=3 per study) following i.v. injection of conjugate IOC-120 at 0.35 nmol/kg under conditions of PBS infusion or i.v. alpha methyl mannose (αMM) infusion.

FIG. 11C shows blood glucose depression curves in non-diabetic male Yucatan minipigs equipped with dual vascular access ports (n=3 per study) following i.v. injection of conjugate IOC-121 at 0.17 nmol/kg under conditions of PBS infusion or i.v. alpha methyl mannose (αMM) infusion.

FIG. 11D shows blood glucose depression curves in non-diabetic male Yucatan minipigs equipped with dual vascular access ports (n=3 per study) following i.v. injection of Compound A at 0.69 nmol/kg under conditions of PBS infusion or i.v. alpha methyl mannose (αMM) infusion.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

---

What is claimed is:
1. A conjugate selected from the group consisting of

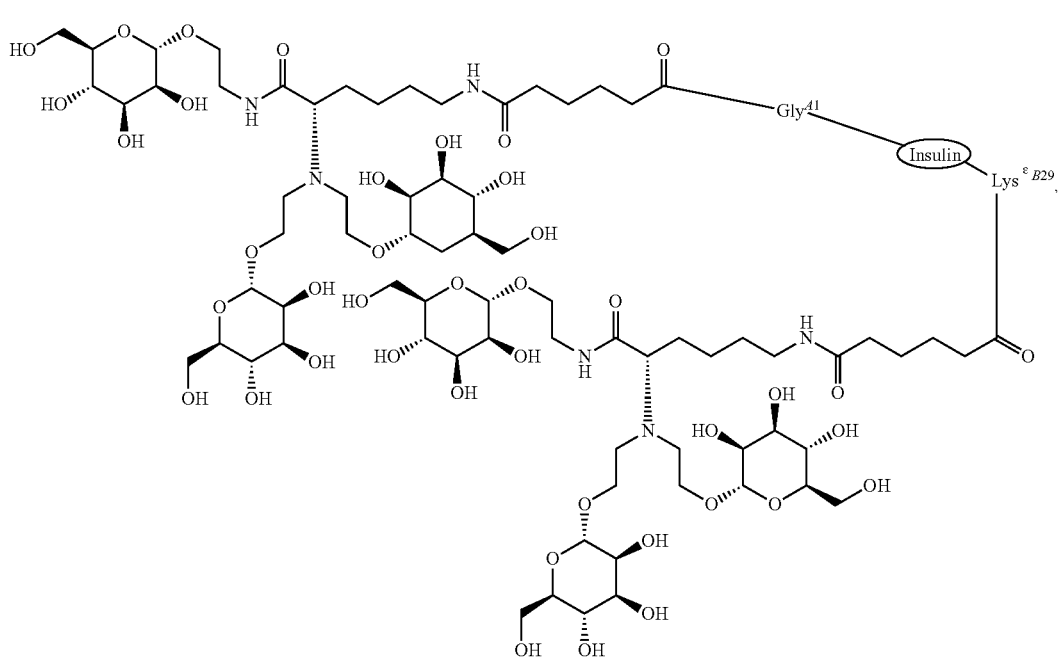

IOC-12

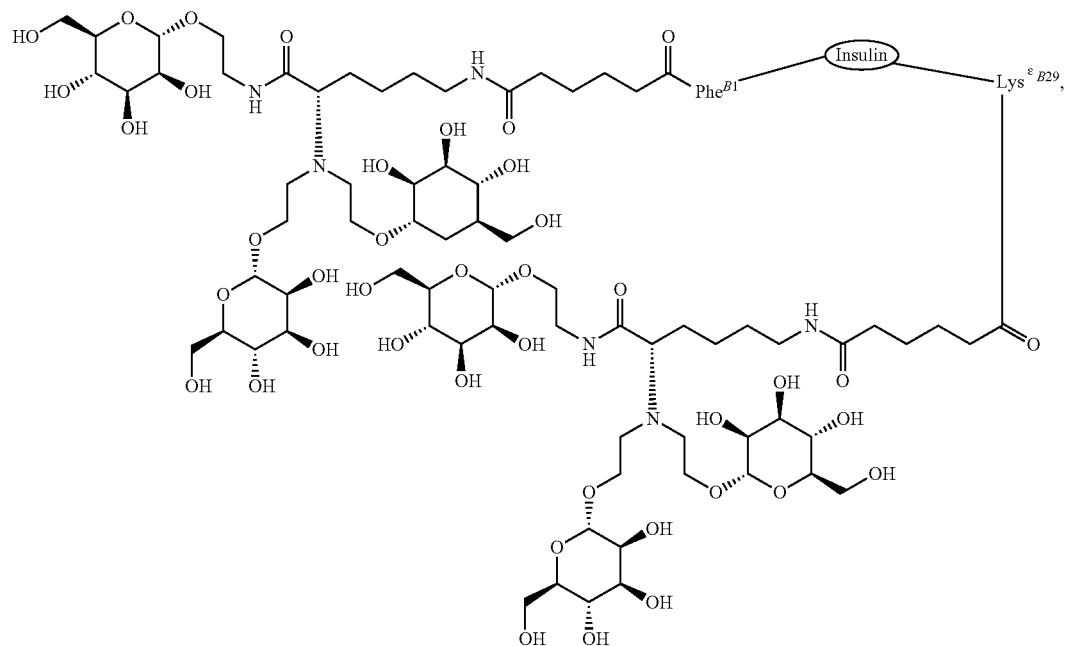
IOC-13
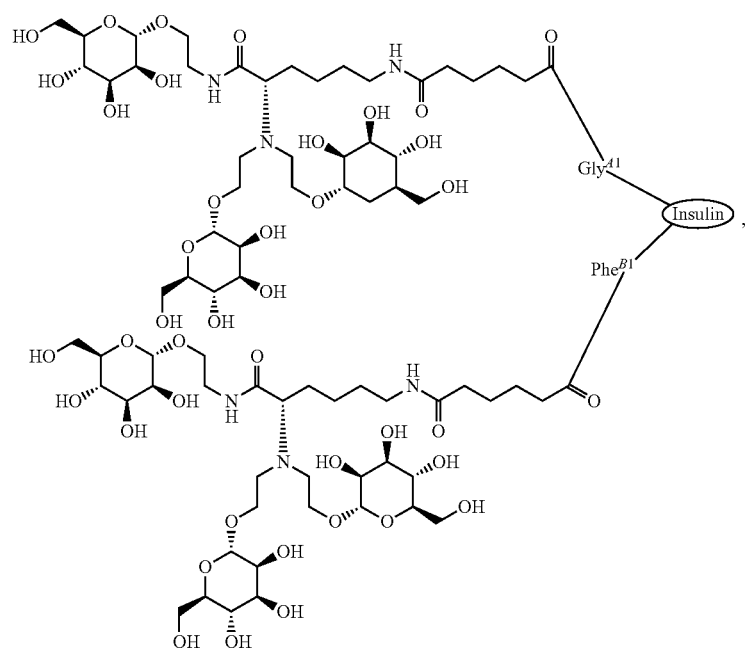
IOC-14

IOC-15
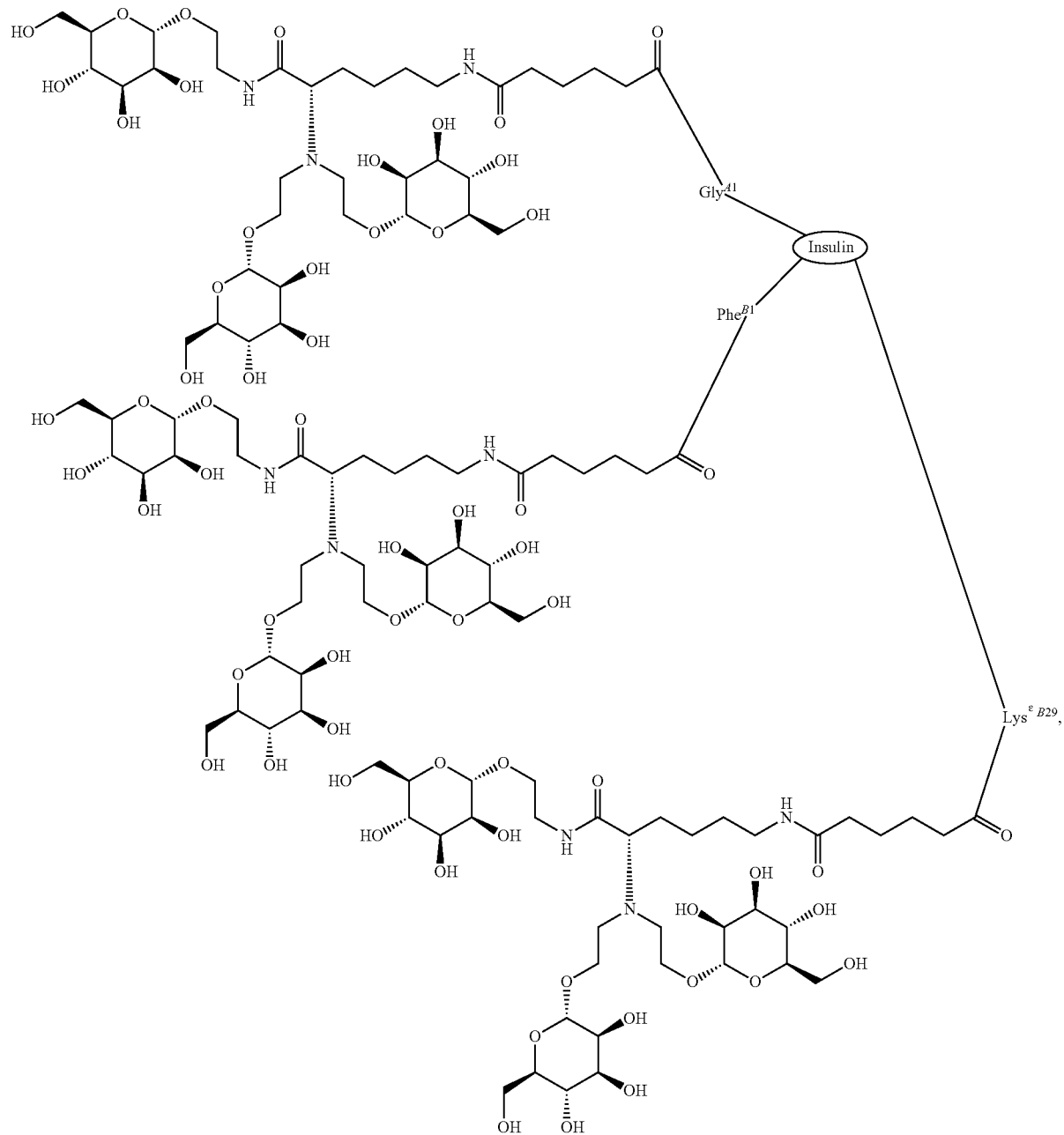

-continued
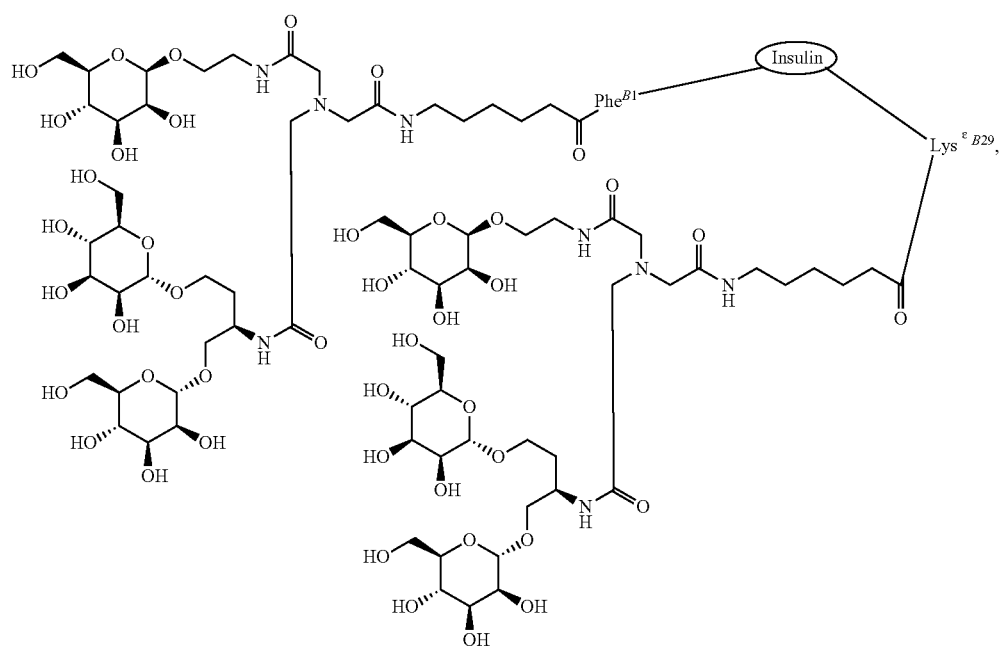
IOC-57
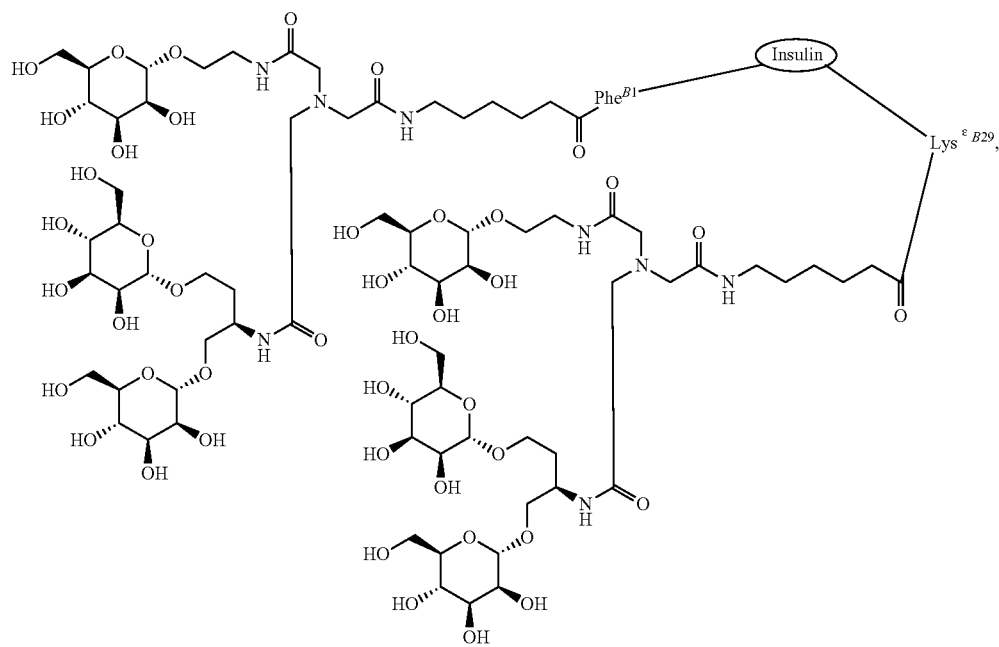
IOC-58

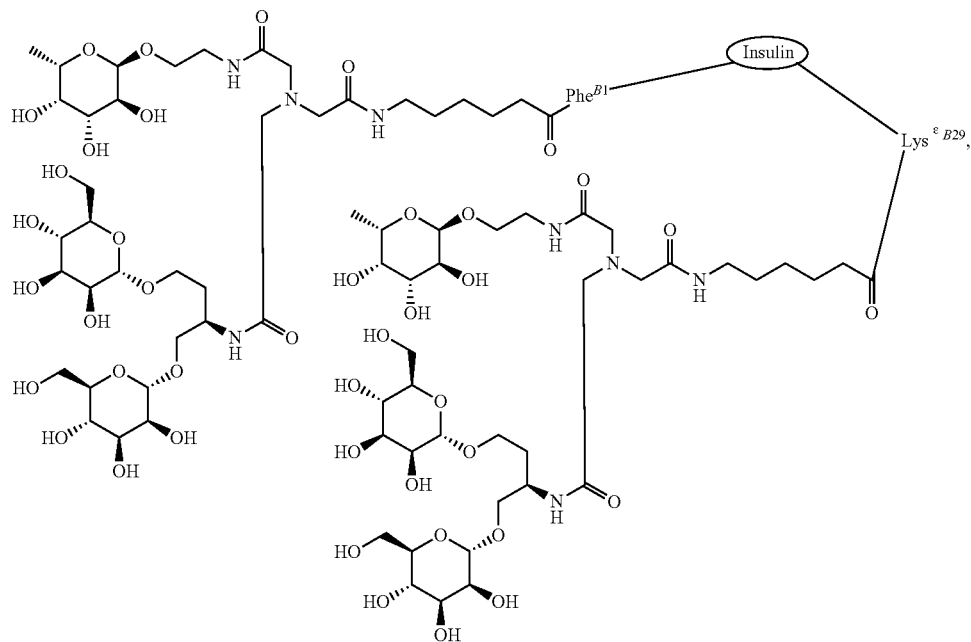
IOC-59
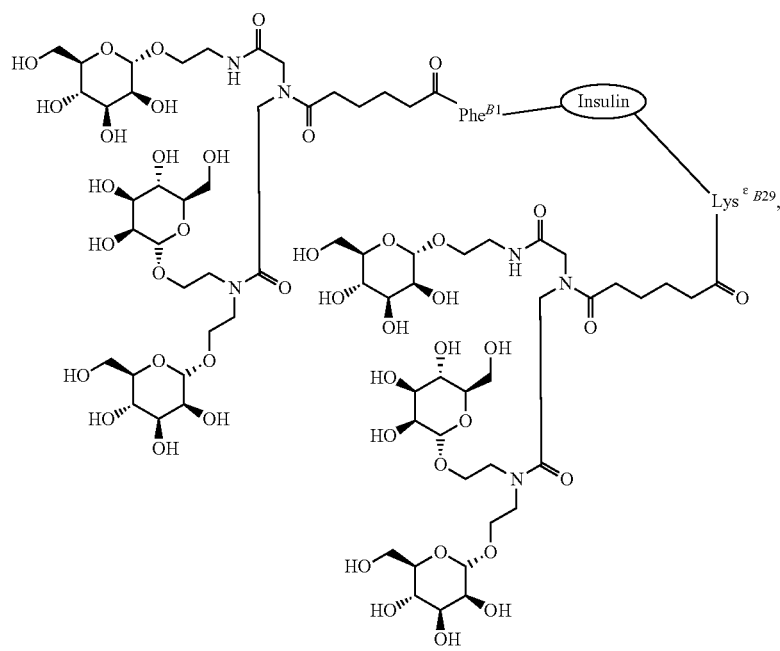
IOC-61

-continued
IOC-62
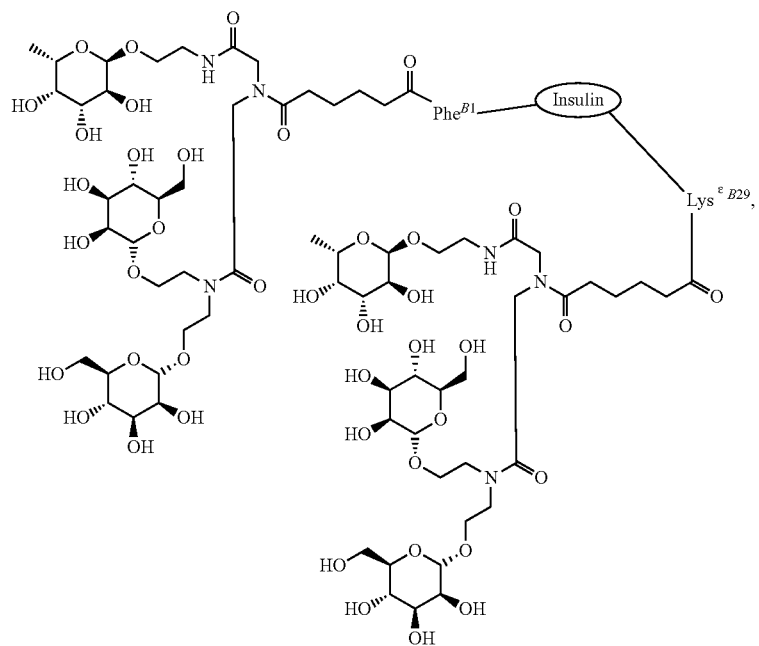
IOC-65
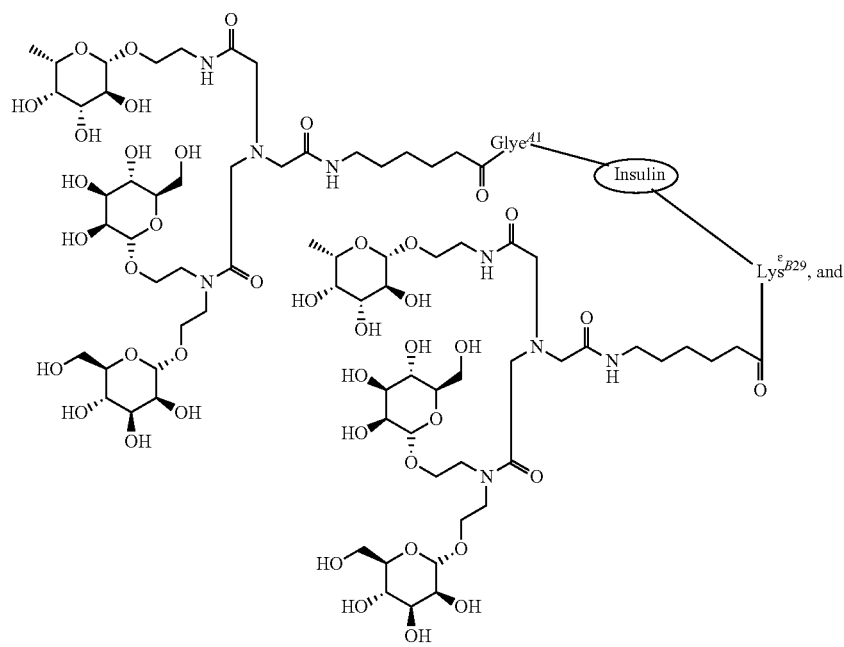

-continued

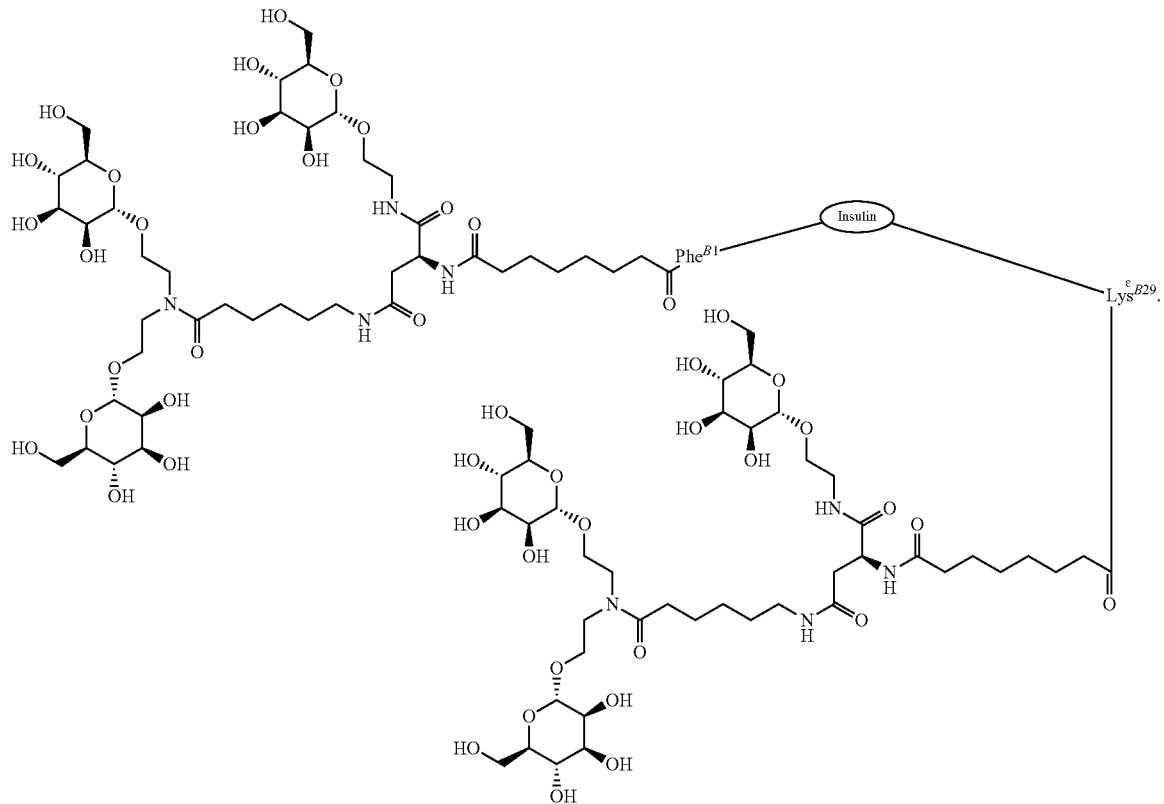

IOC-112

2. A composition comprising a conjugate of claim 1 and a pharmaceutically acceptable carrier.

3. A method for treating diabetes comprising administering to an individual in need thereof a therapeutically effective amount of the conjugate of claim 1 to treat the diabetes.

4. The method of claim 3, wherein the diabetes is Type I diabetes, Type II diabetes, or gestational diabetes.

5. A method for treating diabetes comprising administering to an individual in need thereof a therapeutically effective amount of the composition of claim 2 to treat the diabetes.

6. The method of claim 5, wherein the diabetes is Type I diabetes, Type II diabetes, or gestational diabetes.

* * * * *

UNITED STATES PATENT AND TRADEMARK OFFICE
CERTIFICATE OF CORRECTION

PATENT NO. : 11,041,009 B2
APPLICATION NO. : 16/495703
DATED : June 22, 2021
INVENTOR(S) : Danqing Feng et al.

Page 1 of 1

It is certified that error appears in the above-identified patent and that said Letters Patent is hereby corrected as shown below:

On the Title Page

Inventors item (72) Lines 4-6, delete "Christopher R. Moyes, Westfield, NJ (US)" and "Ravi Nargund, Skillman, NJ (US)"

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*